(12) United States Patent
Zhou et al.

(10) Patent No.: US 7,790,747 B2
(45) Date of Patent: Sep. 7, 2010

(54) CHEMOKINE RECEPTOR BINDING COMPOUNDS

(75) Inventors: Yuanxi Zhou, Richmond (CA); Elyse Bourque, Langley (CA); Yongbao Zhu, Langley (CA); Jonathan Langille, Langley (CA); Markus Metz, Delta (CA); Wen Yang, Aldergrove (CA); Ernest J. McEachern, Vancouver (CA); Curtis Harwig, Vancouver (CA); Ian R. Baird, Abbotsford (CA); Tong-Shuang Li, Langley (CA); Renato T. Skerlj, Vancouver (CA)

(73) Assignee: Genzyme Corporation, Cambridge, MA (US)

( * ) Notice: Subject to any disclaimer, the term of this patent is extended or adjusted under 35 U.S.C. 154(b) by 1101 days.

(21) Appl. No.: 11/453,221

(22) Filed: Jun. 14, 2006

(65) Prior Publication Data
US 2009/0099205 A1    Apr. 16, 2009

Related U.S. Application Data

(60) Provisional application No. 60/792,359, filed on Apr. 14, 2006, provisional application No. 60/691,269, filed on Jun. 15, 2005.

(51) Int. Cl.
*A61K 31/4545* (2006.01)
*C07D 409/14* (2006.01)

(52) U.S. Cl. .................. 514/318; 514/273.2; 514/256; 514/326; 544/129; 544/333; 546/194; 546/210; 546/212

(58) Field of Classification Search ............... 514/273.2, 514/256, 318, 326; 544/129, 333; 546/194, 546/210, 212
See application file for complete search history.

(56) References Cited

U.S. PATENT DOCUMENTS

| | | | |
|---|---|---|---|
| 5,021,409 A | 6/1991 | Murrer | |
| 5,583,131 A | 12/1996 | Bridger | |
| 5,698,546 A | 12/1997 | Bridger | |
| 5,817,807 A | 10/1998 | Bridger | |
| 6,001,826 A | 12/1999 | Murrer | |
| 6,245,773 B1 * | 6/2001 | Wong et al. ............ | 514/272 |
| 6,319,932 B1 | 11/2001 | Nerenberg et al. | |
| 6,365,583 B1 | 4/2002 | Macfarland | |

FOREIGN PATENT DOCUMENTS

| | | | |
|---|---|---|---|
| WO | WO-97/42956 | 11/1997 | |
| WO | WO-00/56729 | 9/2000 | |
| WO | WO-01/87839 | 11/2001 | |
| WO | WO-02/22599 | 3/2002 | |
| WO | WO-02/22600 | 3/2002 | |
| WO | WO-02/34745 | 5/2002 | |
| WO | WO 03/042178 | * 5/2003 | |
| WO | WO-03/042178 | 5/2003 | |
| WO | WO 2004/018425 | * 3/2004 | |

OTHER PUBLICATIONS

Amara et al. "G protein-dependent CCR% . . . " J. Virology Feb. p. 2550-2558 (2003).*
Margolis et al. "Blockade of CC . . . " J. Clin. Investigation p. 1876-1880 (1998).*
Margolis et al. "Blockade of CC chemokine receptor 5 . . . " CA 129:80536 (1998).*
Database CAPLUS, accession No. 1997:752840, DN 128:61520, Wong et al. (1997).
Invitation to Pay Additional Fees and, Where Applicable, Protest Fee for PCT/US06/23125, mailed on Oct. 19, 2006, 2 pages.
Database CAPLUS on STN, accession No. 49:17187, Rose et al. (1955).
International Search Report and Written Opinion for PCT/US06/23125, mailed Apr. 3, 2007, 6 pages.
Mensonides-Harsema et al., J. Med. Chem. (2000) 43:432-439.
Supplementary Partial European Search Report for EP 06773133.1, mailed Jul. 23, 2009, 6 pages.
Abi-Younes et al., Circ. Res. (2000) 86:131-138.
Aiuti et al., J. Exp. Med. (1997) 185:111-120.
Alkhatib et al., Science (1996) 272:1955-1958.
Arai et al., Eur. J. Haematol. (2000) 64:323-332.
Arenburg et al., J. Leukocyte Biol. (1997) 62:554-562.
Balashov et al., PNAS USA (1999) 96:6873-6878.
Blaak et al., Proc. Natl. Acad. Sci. USA (2000) 97:1269-1274.
Blanco et al., Antimircrobial. Agents and Chemother. (2000) 44:51-56.
Bleul et al., J. Exp. Med. (1998) 187:753-762.
Bleul et al., Nature (1996) 382:829-833.
Bradstock et al., Leukemia (2000) 14:882-888.
Bridger et al., Advances in Antiviral Drug Design, vol. 3, E. De Clercq (Ed.), JAI press (1999) pp. 161-229.
Bridger et al., J. Med. Chem. (1999) 42:3971-3981.
Burger et al., Blood (1999) 94:3658-3667.
Carroll et al., Science (1997) 276:273-276.
Cocchi et al., Science (1995) 270:1811-1815.
Connor and Ho, J. Virol. (1994) 68:4400-4408.
Deng et al., Nature (1996) 381:661-666.
Donzella et al., Nature Medicine (1998) 4:72-77.
Dragic et al., Nature (1996) 381:667-673.
Egberink et al., J. Virol. (1999) 73:6346-6352.
Eitner et al., Transplantation (1998) 66:1551-1557.
Fedyk et al., J. Leukocyte Biol. (1999) 66:667-673.
Feng et al., Science (1996) 272:872-877.
Gerard et al., Natl. Immunol. (2001) 2(2):108-115.

(Continued)

*Primary Examiner*—Celia Chang
(74) *Attorney, Agent, or Firm*—Morrison & Foerster LLP

(57) ABSTRACT

The present invention relates to chemokine receptor binding compounds, pharmaceutical compositions and their use. More specifically, the present invention relates to modulators of chemokine receptor activity, preferably modulators of CCR5. These compounds demonstrate protective effects against infection of target cells by a human immunodeficiency virus (HIV).

14 Claims, No Drawings

OTHER PUBLICATIONS

Gonzalo et al., J. Immunol. (2000) 165:499-508.
Gupta et al., J. Biolog. Chem. (1998) 7:4282-4287.
Ishii et al., J. Immunol. (1999) 163:3612-3620.
Lataillade et al., Blood (1999) 95:756-768.
Liu et al., Cell (1996) 86:367-377.
Luster, New Eng. J. Med. (1998) 338(7):436-445.
Ma et al., Immunity (1999) 10:463-471.
Maekawa et al., Internal Medicine (2000) 39:90-100.
Michael et al., J. Virol. (1998) 72:6040-6047.
Michael et al., Nature Med. (1997) 3:338-340.
Miedema et al., Immune, Rev. (1994) 140:35.
Moore et al., J. of Invest. Med. (1998) 46:113-120.
Moore et al., Trends Cardiovasc. Med. (1998) 8:51-58.
Murdoch et al., Blood (2000) 95:3032-3043.
Murphy et al., Pharmacol. Rev. (2000) 52(1):145-176.
Nagasawa et al., Nature (1996) 382:635-638.
Nagase et al., J. Immunol. (2000) 164:5935-5943.
Nanki et al., J. Immunol. (2000) 164:5010-5014.
Oberlin et al., Nature (1996) 382:833-835.
Obrien et al., Lancet (1997) 349:1219.
Panzer et al., Transplantation (2004) 78(9):1341-1350.
Peled et al., Blood (2000) 95:3289-3296.
Peled et al., Science (1999) 283:845-848.
Ponath, Exp. Opin. Invest. Drugs (1998) 7:1-18.
Rana et al., J. Virol. (1997) 71:3219-3227.
Robinson et al., Cancer Res. (2003) 63(23):8360-8365.
Salcedo et al., Am. J. Pathol. (1999) 154:1125-1135.
Samson et al., Nature (1996) 382:722-725.
Schols et al., Anitviral Research (1997) 35:147-156.
Schols et al., J. Exp. Med. (1997) 186:1383-1388.
Schuitemaker et al., J. Virol. (1992) 66:1354-1360.
Seghal et al., J. Surg. Oncol. (1998) 69:99-104.
Simmons et al., J. Virol. (1996) 70:8355-8360.
Simmons et al., J. Virol. (1998) 72:8453-8457.
Szekanecz et al., Seminars in Immunology (2003) 15:15-21.
Tachibana et al., Nature (1998) 393:591-594.
Tan et al., Expert Opin. Investig. Drugs (2003) 12(11):1765-1776.
Tersmette et al., J. Virol. (1988) 62:2026-2032.
Theodorou et al., Lancet (1997) 349:1219-1220.
Viardot et al., Ann. Hematol. (1998) 77:195-197.
Wyatt et al., Science (1998) 280:1884-1888.
Xia et al., J. Neurovirology (1999) 5:32-41.
Yssel et al., Clinical and Experimental Allergy (1998) 28:104-109.
Yun et al., Circulation (2004) 109(7):932-937.
Zhang et al., AIDS Res. Hum. Retroviruses (1997) 13:1357-1366.
Zhang et al., J. Virol. (1998) 72:9307-9312.
Zhang et al., J. Virol. (1999) 73:3443-3448.
Zou et al., Nature (1998) 393:591-594.

* cited by examiner

CHEMOKINE RECEPTOR BINDING COMPOUNDS

CROSS-REFERENCE TO RELATED APPLICATIONS

This application claims the benefit of U.S. provisional application Ser. No. 60/792,359, filed Apr. 14, 2006, and U.S. provisional application Ser. No. 60/691,269, filed Jun. 15, 2005. These applications are incorporated herein by reference.

TECHNICAL FIELD

This invention generally relates to novel compounds, pharmaceutical compositions and their use. More specifically, these novel compounds may be modulators of chemokine receptor activity, preferably modulators of chemokine receptor CCR5, and may further demonstrate protective effects against infection in target cells by a human immunodeficiency virus (HIV). In another aspect, the compounds in the present invention may be useful in the treatment and prevention of various inflammatory and autoimmune diseases.

BACKGROUND OF THE INVENTION

Approximately 40 human chemokines have been described that function at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1-18, 1998). These chemotactic cytokines, or chemokines, constitute a family of proteins, approximately 8-10 kDa in size, that are released by a wide variety of cells, to attract macrophages, T cells, eosinophils, basophils, and neutrophils to sites of inflammation and also play a role in the maturation of cells of the immune system. Chemokines appear to share a common structural motif that consists of 4 conserved cysteines involved in maintaining tertiary structure. There are two major subfamilies of chemokines: the "CC" or β-chemokines and the "CXC" or α-chemokines, depending on whether the first two cysteines are separated by a single amino acid, i.e., CXC or are adjacent, i.e., CC.

These chemokines bind specifically to cell-surface receptors belonging to the family of G-protein-coupled seven-transmembrane proteins which are referred to as "chemokine receptors", and mediate biological activity through these receptors. The chemokine receptor is classified based upon the chemokine that constitutes the receptor's natural ligand. Chemokine receptors of the β-chemokines are designated "CCR"; while those of the α-chemokines are designated "CXCR." These chemokine receptors include but are not limited to CCR1, CCR2, CCR2A, CCR2B, CCR3, CCR4, CCR5, CCR6, CXCR3 and CXCR4 (see for a complete review, Murphy et al. *Pharmacol. Rev.* 52(1), 145-176 (2000)).

Chemokines are considered to be principal mediators in the initiation and maintenance of inflammation (see *Chemokines in Disease* published by Humana Press (1999), Edited by C. Herbert; Murdoch et al. *Blood* 95, 3032-3043 (2000)). More specifically, chemokines have been found to play an important role in the regulation of endothelial cell function, including proliferation, migration and differentiation during angiogenesis and re-endothelialization after injury (Gupta et al., *J. Biolog. Chem.*, 7:4282-4287, 1998). Both chemokine receptors CXCR4 and CCR5 have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR5 (Wyatt et al., *Science*, 280:1884-1888 (1998)). HIV-1 isolates arising subsequently in the infection bind to the CXCR4 chemokine receptor. The observed binding of another related retrovirus, feline immunodeficiency virus, to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. *Nature* 381, 661-666 (1996); Alkhatib et al. *Science* 272, 1955-1958, (1996)). During the course of infection within a patient, it appears that a majority of HIV particles shift from the M-tropic to the more aggressive pathogenic T-tropic viral phenotype (Miedema et al., *Immune. Rev.*, 140:35 (1994); Blaak et al. *Proc. Natl. Acad. Sci.* 97, 1269-1274 (2000); Simmonds et al. *J. Virol.* 70, 8355-8360 (1996); Tersmette et al. *J. Virol.* 62, 2026-2032, (1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus' ability to enter the cell following binding of the CCR5 receptor, while the T-tropic viral phenotype correlates with viral entry into the cell following binding and membrane fusion with the CXCR4 receptor. Clinically, observations suggest that patients who possess genetic mutations in the CCR5 or CXCR4 appear resistant or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997)).

Despite the number of chemokine receptors which have been reported to mediate HIV entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1 (SDF-1). On the other hand, fusion and entry of M-tropic viruses that use CCR5 are inhibited by the natural CC-chemokines namely, Regulated on Activation Normal T-cell Expressed and Secreted (RANTES or CCL5) and Macrophage Inflammatory proteins (MIP-1 alpha and MIP-1 beta or CCL3 and CCL4, respectively). SDF-1 is known as CXCL12 or Pre B-cell stimulating factor (PBSF).

However, the binding of chemokine receptors to their natural ligands appears to serve a more evolutionary and central role than only as mediators of HIV infection. The binding of the natural ligand, PBSF/SDF-1 to the CXCR4 chemokine receptor provides an important signaling mechanism.

CXCR4 or SDF-1 knock-out mice exhibit cerebellar, cardiac and gastrointestinal tract abnormalities and die in utero (Zou et al., *Nature*, 393:591-594 (1998); Tachibana et al., *Nature*, 393:591-594 (1998); Nagasawa et al. *Nature* 382, 635-638 (1996)). CXCR4-deficient mice also display hematopoietic defects (Nagasawa et al. *Nature* 382, 635-638 (1996)). Furthermore, the migration of CXCR4 expressing leukocytes and hematopoietic progenitors to SDF-1 appears to be important for maintaining B-cell lineage and localization of CD34+ progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)). Known angiogenic growth factors VEG-F and bFGF, up-regulated levels of CXCR4 in endothelial cells, and SDF-1 can induce neovascularization in vivo (Salcedo et al. *Am. J. Pathol.* 154, 1125-1135 (1999)). Furthermore, leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimer's disease (Xia et al. *J. Neurovirology* 5, 32-41 (1999)) and arthritis (Nanki et al. *J. Immunol.* 164, 5010-5014 (2000)).

Platelets have also been shown to secrete the chemokine RANTES upon activation, and that the presence of RANTES on the endothelium promotes the arrest of monocytes on the inflamed endothelium, an important step in atherogenesis as the conversion of macrophages into foam cells in the subendothelium is a central process in atheroma formation (Tan, et al., *Expert Opin. Investig. Drugs*, 12(11):1765-1776 (2003)). Hence, the inhibition or prevention of the binding of RANTES, directly or indirectly, to the CCR5 receptor could potentially attenuate the development of atherosclerosis. For example, Met_RANTES has also been shown to inhibit the binding of monocytes to the activated endothelium (Tan, et al., supra).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design* Volume 3, p 161-229; Published by JAI press (1999); Edited by E. De Clercq). Small molecules, such as bicyclams, appear to specifically bind to CXCR4 and not CCR5 (Donzella et al., *Nature Medicine*, 4:72-77 (1998)). These experiments demonstrated interference with HIV entry and membrane fusion into the target cell in vitro.

Bicyclams were also shown to inhibit fusion and replication of feline immunodeficiency virus (FIV) that uses CXCR4 for entry (Egberink et al. *J. Virol.* 73, 6346-6352 (1999)). CCR5 blocking agents include monoclonal antibodies, some which selectively block HIV coreceptor activity but not chemokine binding, and chemokine derivatives, such as truncated versions of RANTES, Met-RANTES, and AOP-RANTES and the viral chemokine KSHV vMIP-II, all which block both chemokine and HIV interaction with CCR5 but are not selective (reviewed by Murphy et al. *Pharmacol. Rev.* 52(1), 145-176 (2000)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

Passive immunization with anti-MIP-1 alpha has been shown to delay the onset and reduce the severity of collagen-induced-arthritis (CIA) in mice, where the CIA model is an established murine model representing human rheumatoid arthritis (Szekanecz, Z., et al., *AP, Seminars in Immunology*, 15 (2003), p. 15-21). Other studies have also shown that agents that block the CCR5 receptor may provide a rational approach to the treatment of multiple sclerosis. Administration of anti-MIP-1 alpha antiserum has been shown to prevent CNS infiltration by PBMC in mice with experimental allergic encephalomyelitis, a rodent model of multiple sclerosis (Balashov, K. E., et al., *Proc. Natl. Acad. Sci. USA*, Vol. 96 (1999), p. 6873-6878).

Other studies involving chronic rejection of transplanted hearts or cardiac allograft vasculopathy (CAV) and acute renal allograft rejection have shown that blocking chemokine receptors such as CCR5 may provide unique therapeutic approaches in the treatment or prevention of such diseases (Yun J J, et al., *Circulation*, 2004, Vol. 109(7), p. 932-7, Panzer U., et al., *Transplantation*, 2004, Vol. 78(9), p. 1341-50). For example, antagonism of the chemokine receptors CCR1 and CCR5 with Met-RANTES attenuated CAV development by reducing mononuclear cell recruitment to the transplanted heart. Met-CCL5, an antagonist of CCR1 and CCR5, had been tested and shown to inhibit the growth of breast tumors (Robinson S C. et al, *Cancer Res.*, 2003, Vol. 63(23), p. 8360-5).

Chemokines, as indicated above, play an important role and are implicated in a wide variety of human disease such as in autoimmune disease, allograft rejection, infection, allergies, neoplasia, and vascular abnormalities. In addition to its contributory role in HIV infection, the chemokine receptor CCR5 has been associated with diseases such as the inflammatory demyelinating diseases of the central nervous system, including multiple sclerosis and experimental autoimmune encephalomyelitis, rheumatoid arthritis, intestinal inflammation, allograft rejection, asthma, and cardiovascular disease (reviewed in Gerard et al. *Natl. Immunol.* 2(2), 108-115 (2001) and Luster, A., N. *Eng. J. Med.*, 338 (7), 436-445

(1998)). The CCR5 receptor is expressed on T-lymphocytes, and macrophages and reports of CCR5 on neurons, astrocytes, capillary endothelial cells, epithelium, vascular smooth muscle, and fibroblast have been published. The natural ligands that bind to the CCR5 receptor, in addition to RANTES and MIP-1 alpha/beta, are monocyte chemoattractant protein 2 (MCP-2 or CCL8).

U.S. Pat. Nos. 5,583,131; 5,698,546; 5,817,807; 5,021,409; and 6,001,826 which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 and/or CCR5 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). Furthermore, these compounds demonstrate protective effects against HIV infection of target cells by binding in vitro to the CCR5 receptor.

Additionally, U.S. Pat. No. 6,365,583 discloses that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

PCT WO 00/56729, PCT WO 02/22600, PCT WO 02/22599, and PCT WO 02/34745 describe a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR4 has been found to be associated with the vascularization of the gastrointestinal tract (Tachibana et al., *Nature*, 393:591-594 (1998)) as well as in hematopoiesis and cerebellar development (Zou et al., *Nature*, 393:591-594 (1998)). Interference with any of these important functions served by the binding of pre-B-cell growth-stimulating factor/stromal derived factor (PBSF/SDF-1) to the CXCR4 chemokine receptor results in lethal deficiencies in vascular development, hematopoiesis and cardiogenesis. Similarly, fetal cerebellar development appears to rely upon the effective functioning of CXCR4 in neuronal cell migration and patterning in the central nervous system. This G-protein-coupled chemokine receptor appears to play an important role in ensuring the necessary patterns of migration of granule cells in the cerebellar analogue.

Herein, we disclose compounds that have unique chemical attributes and that exhibit protective effects against HIV infection of target cells by binding to chemokine receptor CCR5. In addition, these compounds antagonize the binding, signaling and chemotactic effects of the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that may modulate chemokine receptors and interfere with the binding of the natural ligand thereto. More particularly, the present invention relates to novel piperidine derivatives that may bind to chemokine receptors, preferably CCR5 receptors.

The compounds of the present invention may be useful as agents demonstrating protective effects on target cells from HIV infection. The compounds of the present invention may also be useful for the treatment and prevention of inflammatory and autoimmune diseases. Embodiments of the present invention are compounds that may act as antagonists or agonists of chemokine receptors, which may be useful as agents capable of reconstituting the immune system by increasing the level of CD4$^+$ cells; as antagonist agents of apoptosis in immune cells, such as CD8$^+$ cells, and neuronal cells; as antagonist agents of migration of human bone marrow B lineage cells to stromal-derived factor 1, as well as other biological activities related to the ability of these compounds to inhibit the binding of chemokines to their receptors.

In one aspect, the invention provides a compound having formula (1)

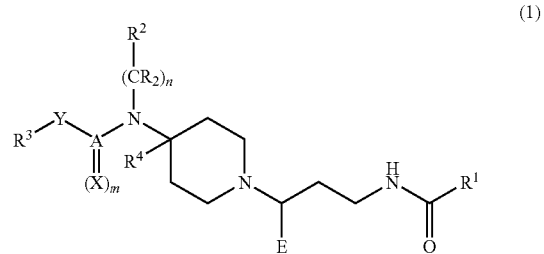

and pharmaceutically acceptable salts thereof, wherein A is carbon or sulfur;

X is oxygen, sulfur, NR$^2$, NOR$^2$, NCN, NSO$_2$R$^2$, NAc, NNO$_2$, CRNO$_2$, NCOR$^2$, C(CN)$_2$ or CRCN, provided X is oxygen if A is sulfur;

Y is a bond, O(CR$_2$)$_p$, S(CR$_2$)$_p$, NR(CR$_2$)$_p$ or (CR$_2$)$_p$ wherein one carbon in (CR$_2$)$_p$ may optionally be substituted and/or replaced with N, O or S; or Y together with (CR$_2$)$_m$ may form a 5-6 membered ring;

n and p are independently 0 to 6;

m is 1 to 2, provided m is 1 if A is carbon;

E is H or methyl;

R$^1$ is an optionally substituted aryl or heteroaryl;

R$^2$ is H, an optionally substituted alkyl, a carbocyclic ring, a heterocyclic ring, an aryl, or a heteroaryl; and R$^3$ is H; an optionally substituted alkyl, alkenyl or alkynyl; hydroxy, alkoxy, cyano, amino, amido, carboxyl, CO$_2$R$^2$, S=(O)$_p$R$^2$, CR=N—OR, O(CR$_2$)CN, NR—COR$^2$, SR$^2$; a carbocyclic ring, a heterocyclic ring, an aryl, or a heteroaryl;

R and R$^4$ are independently H, C$_{1-6}$ alkyl, or C$_{3-6}$ cycloalkyl;

wherein in each said optionally substituted alkyl, alkenyl or alkynyl, a carbon may be optionally substituted with halo, N, O, or S, and/or replaced with N, O or S; and each carbocyclic ring, heterocyclic ring, aryl or heteroaryl may be optionally substituted and/or fused with a carbocyclic, aryl, heterocyclic, or heteroaryl ring.

In one embodiment of the above formula (1), $R^1$ is phenyl, pyrimidinyl, pyridinyl, pyridine N-oxide, thienyl, isoxazolyl or pyrazolyl, each of which is optionally substituted by one or more halo, cyano, alkyl, alkoxy, amine, amide, cycloalkyl, heterocyclyl, aryl, heteroaryl, or N-oxide.

In another embodiment of the above formula (1), $R^2$ is H, an optionally substituted alkyl, cycloalkyl, aryl or heteroaryl, each of which is optionally linked to one or more $C_{1-6}$ alkyl, alkoxy, trifluoromethyl, carboxylalkyl, cyano, halo, cycloalkyl, heterocyclyl, aryl, heteroaryl, or N-oxide. In some examples, $R^2$ is phenyl, pyridiminyl, pyridinyl, thiazolyl, furanyl, thienyl, or imidazolyl.

In yet another embodiment of the above formula (1), $R^3$ is H, OH, cyano, $NR_2$, SR, SOR, $SO_2R$, $CO_2R$, $CONR_2$, or an optionally substituted alkyl or alkoxy, wherein R is independently H or $C_{1-6}$ alkyl; or $R^3$ may be a carbocyclic ring, a heterocyclic ring, an aryl, or a heteroaryl, each of which may be optionally substituted with halo, cyano, alkyl, alkoxy, cycloalkyl, heterocyclyl, aryl, heteroaryl, or N-oxide and/or fused with a carbocyclic, aryl, heterocyclic, or heteroaryl ring. In some examples, $R^3$ is cyclohexyl, tetrahydropyran, morpholine, phenyl optionally fused with a 5-6 membered heterocyclic ring, pyridinyl, thienyl, $C_{1-6}$ straight or branched alkyl, bicyclo[4.2.0]octa-1,3,5-triene, indolyl, benzodioxolyl, dihydrobenzofuranyl, dihydroisobenzofuranyl, benzofuranyl, dihydrobenzodioxinyl, pyrrolidin-2-one, tetrazole, imidazole, dioxolane, or isoxazole.

In another embodiment of the above formula (1), each $R^4$ is hydrogen. In other examples, n is 1. In some examples, A and Y are not both heteroatoms.

In another aspect, the present invention provides a compound having formula (2) or a pharmaceutically acceptable salt thereof:

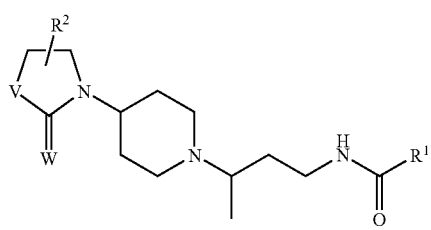

(2)

and pharmaceutically acceptable salts thereof;
wherein W is oxygen, sulfur, $NR^2$, $NOR^2$, NCN, $NSO_2R^2$, NAc, $NNO_2$, $CRNO_2$, $NCOR^2$, $C(CN)_2$ or CRCN;
V is O, S, N-L-$R^3$, or CR-L-$R^3$;
L is a bond or a $(CR_2)_m$ linker optionally having one carbon of $(CR_2)_m$ replaced by a group selected from O, S, and NR, and m is 1-3;
$R^1$ is an optionally substituted aryl or heteroaryl;
$R^2$ is H, an optionally substituted alkyl, a carbocyclic ring, a heterocyclic ring, an aryl, or a heteroaryl;
$R^3$ is H; an optionally substituted alkyl, alkenyl or alkynyl; hydroxy, alkoxy, cyano, amino, amido, $COR^2$, $CO_2R^2$, $S=(O)_pR^2$, CR=N—OR, $O(CR_2)CN$, NR—$COR^2$, $SR^2$; a carbocyclic ring, a heterocyclic ring, an aryl, or a heteroaryl; and
R is H, $C_{1-6}$ alkyl, or $C_{3-6}$ cycloalkyl;
wherein in each said optionally substituted alkyl, alkenyl or alkynyl, a carbon may be optionally substituted with halo, N, O, or S, and/or replaced with N, O or S; and each carbocyclic ring, heterocyclic ring, aryl or heteroaryl may be optionally substituted and/or fused with a carbocyclic, aryl, heterocyclic, or heteroaryl ring.

In one embodiment of the above formula (2), $R^1$ is phenyl, pyrimidinyl or pyridinyl, each optionally substituted with halo, cyano, alkyl, alkoxy, cycloalkyl, heterocyclyl, aryl, heteroaryl, or N-oxide.

In another embodiment of the above formula (2), $R^2$ is phenyl, thienyl, or imidazolyl each optionally substituted with halo, cyano, alkoxy, heterocyclyl, aryl, heteroaryl, or N-oxide; or alkyl or cycloalkyl, each of which may be optionally substituted with halo, cyano, OR, SR, or $N(R)_m$, or in which one carbon may be optionally replaced with N, O, or S.

In yet another embodiment of the above formula (2), $R^3$ is H, $C_{1-10}$ straight or branched alkyl; or $R^3$ is a $C_{3-7}$ cycloalkyl, a 5-6 membered aryl, heteroaryl or heterocyclic ring, each optionally substituted with halo, cyano, alkyl, alkoxy, cycloalkyl, heterocyclyl, aryl, heteroaryl, or fused with a carbocyclic or heterocyclic ring. In some examples, $R^3$ is H, cyclopentyl, cyclohexyl, cycloheptyl, tetrahydropyran, morpholine, phenyl optionally fused to a 5-6 membered heterocyclic ring, pyridinyl, imidazole, furan, pyrimidine, thienyl, $C_{1-6}$ straight or branched alkyl, or bicyclo[4.2.0]octa-1,3,5-triene.

In some embodiments of the above formula (1) or (2), each R is independently selected, and each can be H or alkyl. In some embodiments each R is H. In other embodiments one or more occurrences of R is an alkyl group, typically a $C_1$-$C_6$ alkyl group, or a cycloalkyl group, typically a $C_3$-$C_6$ cycloalkyl group. In other embodiments at least one R is a $C_1$-$C_6$ alkyl or cycloalkyl group. Where two R groups appear on a single atom such as in a $(CR_2)$ unit, they may optionally be linked to form a 3-8 membered ring. Where two R groups occur on adjacent atoms they may also be linked to form a 3-8 membered ring. In some embodiments, each optional substituent include but are not limited to halogen, alkyl, amine, cyano, amide or heteroaryl.

The present invention also provides pharmaceutical compositions comprising compounds having formula (1) or (2), and a pharmaceutically acceptable carrier. Furthermore, the present invention provides methods for treating a CCR5 mediated disease in a cell, tissue or organ, comprising contacting a compound having formula (1) or (2) with the system, thereby treating a CCR5-mediated disease. The present invention also provides methods for treating a CCR5 mediated-disease in a human or animal subject, comprising administering a compound having formula (1) or (2) with the subject, thereby treating a CCR5-mediated disease.

Examples of CCR5-mediated diseases that may be treated using the compounds of the present invention include but are not limited to HIV, an inflammatory demyelinating disease of the central nervous system, an autoimmune disease, multiple sclerosis, experimental autoimmune encephalomyelitis, psoriatic or rheumatoid arthritis, intestinal inflammation, allograft rejection, asthma, cardiovascular disease, atherosclerosis, allergic disease, allergic rhinitis, dermatitis, conjunctivitis, hypersensitivity lung disease, hypersensitivity pneumonitis, eosinophilic pneumonia, delayed-type hypersensitivity, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis, dermatomyositis, systemic anaphylaxis, myasthenia gravis, juvenile onset diabetes, glomerulonephritis, autoimmune thyroiditis, graft rejection, allograft rejection, graft-versus-host disease, inflammatory bowel disease, Crohn's disease, ulcerative colitis, spondyloarthropathy, scleroderma; psoriasis, inflammatory dermatosis, dermatitis, eczema, atopic dermatitis, allergic contact dermatitis, urticaria, vasculitis, eosinophilic myotis, eosinophilic fascitis, tumor or cancer.

The compounds of formula (1) or (2) may form hydrates or solvates, and may be in any stereoisomeric forms and mixtures of stereoisomeric forms thereof. Racemate compounds may be separated into individual isomers using known separation and purification methods. Individual optical isomers and a mixture thereof, are included in the scope of the present invention.

MODES OF CARRYING OUT THE INVENTION

In one aspect, the invention provides compounds having formula (1) or (2) described above, which may be chemokine modulators of chemokine receptors.

In more detail, the compounds may bind chemokine receptors and interfere with the binding of the natural ligand thereto, and may demonstrate protective effects on target cells from HIV infection. The compounds may be useful as antagonists or agonists of chemokine receptors, and are thus capable of reconstituting the immune system by increasing the level of $CD4^+$ cells; as antagonist agents of apoptosis in immune cells, such as $CD8^+$ cells, and neuronal cells; as antagonist agents of migration of human bone marrow B lineage cells to stromal-derived factor 1, as well as other biological activities related to the ability of these compounds to inhibit the binding of chemokines to their receptors.

Chemokine antagonists that interfere in the binding of a chemokine to its receptor are useful to reconstitute the immune system by increasing the level of $CD4^+$ cells (Biard-Piechaczyk, et al., *Immunol. Lett.*, 70:1-3 (1999)); as antagonist agents of apoptosis in immune cells, such as $CD8^+$ cells (Herbin, et al., *Nature* 395: 189-193, (1998)), and as antagonist agents of apoptosis in neuronal cells (Ohagen et al., *J. of Virol.*, 73: 897-906, (1999); and Hesselgesser, et al., *Curr. Biol.* 8: 595-598, (1998)). Chemokine receptor antagonist agents also inhibit the migration of human bone marrow B lineage cells to stromal-derived factor 1 (See e.g., E. Fedyk, et al., *J of Leukocyte Biol.*, 66:667-783, (1999)).

The invention includes pharmaceutical compositions comprising a therapeutically effective amount of a compound of formula (1) or (2) along with at least one excipient, and methods of treating diseases of the human body or the bodies of other mammals with such compositions. As used herein, the term "therapeutically effective amount" refers to the amount of a compound of formula (1) or (2) that will elicit the biological or medical response of a cell, tissue, organ, system, animal or human that is being sought by the researcher, veterinarian, medical doctor, or other clinician.

The invention provides a method for blocking or interfering with the binding by a chemokine receptor with its natural ligand, comprising contacting of the chemokine receptor with an effective amount of the compound according to formula (1) or (2). The present invention also provides methods of protecting target cells possessing chemokine receptors, which binding to a pathogenic agent results in disease or pathology, comprising administering to a mammalian subject a pharmaceutical composition comprising a therapeutically effective amount of the compound according to formula (1) or (2).

Furthermore, the invention provides the use of a compound of formula (1) or (2) in the manufacture of a medicament for the treatment of a disease in which blocking or interfering with binding of a chemokine receptor with its natural ligand is advantageous. The compound is formulated into a composition in an amount corresponding to a therapeutically effective amount of a compound of formula (1) or (2).

The Invention Compounds

The invention compounds are described generally by formula (1) or formula (2).

In one aspect, the invention provides compounds having formula (1):

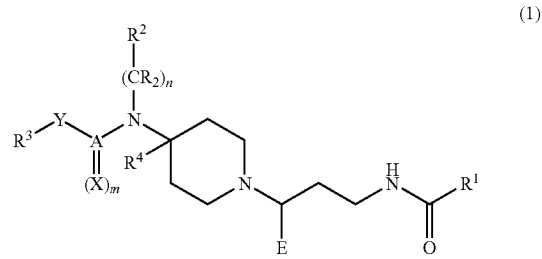

and pharmaceutically acceptable salts thereof, wherein A is carbon or sulfur;

X is oxygen, sulfur, $NR^2$, $NOR^2$, NCN, $NSO_2R^2$, NAc, $NNO_2$, $CRNO_2$, $NCOR^2$, $C(CN)_2$ or CRCN, provided X is oxygen if A is sulfur;

Y is a bond, $O(CR_2)_p$, $S(CR_2)_p$, $NR(CR_2)_p$ or $(CR_2)_p$ wherein one carbon in $(CR_2)_p$ may optionally be substituted and/or replaced with N, O or S; or Y together with $(CR_2)_m$ may form a 5-6 membered ring;

n and p are independently 0 to 6;

m is 1 to 2, provided m is 1 if A is carbon;

E is H or methyl;

$R^1$ is an optionally substituted aryl or heteroaryl;

$R^2$ is H, an optionally substituted alkyl, a carbocyclic ring, a heterocyclic ring, an aryl, or a heteroaryl; and $R^3$ is H; an optionally substituted alkyl, alkenyl or alkynyl; hydroxy, alkoxy, cyano, amino, amido, carboxyl, $CO_2R^2$, $S=(O)_pR^2$, CR=N—OR, $O(CR_2)CN$, NR—$COR^2$, $SR^2$; a carbocyclic ring, a heterocyclic ring, an aryl, or a heteroaryl;

R and $R^4$ are independently H, $C_{1-6}$ alkyl, or $C_{3-6}$ cycloalkyl;

wherein in each said optionally substituted alkyl, alkenyl or alkynyl, a carbon may be optionally substituted with halo, N, O, or S, and/or replaced with N, O or S; and each carbocyclic ring, heterocyclic ring, aryl or heteroaryl may be optionally substituted and/or fused with a carbocyclic, aryl, heterocyclic, or heteroaryl ring.

In formula (1), each occurrence of R is independently determined, and each may be H, C1-C6 alkyl, C3-C6 cycloalkyl, or C4-C10 cycloalkylalkyl; furthermore, one or more $CR_2$ members in a group described as $(CR_2)_m$ or $(CR_2)_n$, may be replaced with a group selected from O, S, SO, $SO_2$, NCOR, and NR. For example, $(CR_2)_n$ where n is 3 can be $CH_2OCH_2$, for example.

In the above formula (1), R may be hydrogen, $C_{1-6}$ alkyl, $C_3$-$C_8$ cycloalkyl, or $C_4$-$C_{10}$ cycloalkylalkyl. In some examples, R and $R^4$ are independently H, $C_{1-6}$ alkyl, or $C_3$-$C_8$ cycloalkyl. In particular examples, R and $R^4$ are each H.

In the above formula (1), $R^1$ may be phenyl, pyrimidinyl, pyridinyl, pyridine N-oxide, thienyl, isoxazolyl or pyrazolyl, each of which is optionally substituted by one or more halo, cyano, alkyl, alkoxy, amine, amide, cycloalkyl, heterocyclyl, aryl, heteroaryl, or N-oxide.

In other embodiments, $R^1$ in formula (1) may be an optionally substituted cyclic or acyclic alkyl or 5- or 6-membered non-aromatic heterocyclic ring, each of which is optionally substituted by one or more of cyclic alkyl, acyclic alkyl, alkene, alkyne, halogen, CN, OH, $NH_2$, $NHR^5$, or $OR^5$; or phenyl, pyridine, pyridine N-oxide or heteroaryl, each of which is optionally substituted by one or more of cyclic or acyclic alkyl, alkene, alkyne, OH, OMe, $NH_2$, $NH(C_{1-6}$ alkyl), $N(C_{1-6}$ alkyl$)_2$, halogen, CN, $CF_3$, $OCF_3$, NHC(O) $(C_{1-6}$ alkyl), $C(O)(C_{1-6}$ alkyl), $C(O)O(C_{1-6}$ alkyl), OC(O) $(C_{1-6}$ alkyl), C(O)OH, $C(O)NH(C_{1-6}$ alkyl), $C(O)N(C_{1-6}$ alkyl$)_2$, $S(C_{1-6}$ alkyl), $SO_nR^6$, $NHS(O)_n(C_{1-6}$ alkyl) where n is 1 or 2; or an N-linked phenyl, pyridine, pyridine N-oxide or heteroaryl ring, each of which is optionally substituted by one or more of cyclic or acyclic alkyl, alkene, alkyne, halogen, CN, $NH_2$, $NH(C_{1-6}$ alkyl), $N(C_{1-6}$ alkyl$)_2$, $C(O)NH(C_{1-6}$ alkyl), $C(O)N(C_{1-6}$ alkyl$)_2$, or $C(O)O(C_{1-6}$ alkyl).

In the above formula (1), $R^2$ may be H, an optionally substituted alkyl, cycloalkyl, aryl or heteroaryl, each of which is optionally linked to one or more $C_{1-6}$ alkyl, alkoxy, trifluoromethyl, carboxylalkyl, cyano, halo, cycloalkyl, heterocyclyl, aryl, heteroaryl, or N-oxide. In some examples, $R^2$ is phenyl, pyridiminyl, pyridinyl, thiazolyl, furanyl, thienyl, or imidazolyl.

In other embodiments, $R^2$ in formula (1) may be phenyl, pyridine or heteroaryl, each of which is optionally substituted by one or more of cyclic or acyclic alkyl, alkene, alkyne, halogen, CN, $NO_2$, OH, $NH_2$, $CF_3$, $CH_2OH$, $C(O)O(C_{1-6}$ alkyl), $OR^7$, or 5- or 6-membered non aromatic heterocyclic ring; or a $C_{1-6}$ alkyl, alkene or alkyne, $OC(O)(C_{1-6}$ alkyl), $NHC(O)(C_{1-6}$ alkyl), $NHR^8$, or a 5- or 6-membered non aromatic heterocyclic ring.

In some embodiments, $R^1$ and $R^2$ are optionally substituted aryl or heteroaryl groups, which may be the same or different. In some embodiments, their substituents are selected from $C_{1-6}$ alkyl, halo, CN, $CF_3$, $C_1$-$C_6$ alkoxy, OH, $NH_2$, SH, $C_1$-$C_6$-alkylthio, or $C_{1-6}$ alkoxy carbonyl.

In the above formula (1), $R^3$ may be H, OH, cyano, $NR_2$, SR, SOR, $SO_2R$, $CO_2R$, $CONR_2$, or an optionally substituted alkyl or alkoxy, wherein R is independently H or $C_{1-6}$ alkyl; or $R^3$ may be a carbocyclic ring, a heterocyclic ring, an aryl, or a heteroaryl, each of which may be optionally substituted with halo, cyano, alkyl, alkoxy, cycloalkyl, heterocyclyl, aryl, heteroaryl, or N-oxide and/or fused with a carbocyclic, aryl, heterocyclic, or heteroaryl ring. In some examples, $R^3$ is cyclohexyl, tetrahydropyran, morpholine, phenyl optionally fused with a 5-6 membered heterocyclic ring, pyridinyl, thienyl, $C_{1-6}$ straight or branched alkyl, bicyclo[4.2.0]octa-1,3,5-triene, indolyl, benzodioxolyl, dihydrobenzofuranyl, dihydroisobenzofuranyl, benzofuranyl, dihydrobenzodioxinyl, pyrrolidin-2-one, tetrazole, imidazole, dioxolane, or isoxazole.

In other embodiments, $R^3$ is a cyclic or acyclic alkyl wherein one or more carbons may be substituted with at least one heteroatom; or a 5- or 6-membered non-aromatic ring, each of which is optionally substituted by one or more of cyclic alkyl acyclic alkyl, alkenyl, alkynyl, halogen, CN, OH, NH2, $NHR^5$, or $OR^5$; or phenyl, pyridine, or heteroaryl, each of which is optionally substituted by one or more of cyclic or acyclic alkyl, alkene, alkyne, halogen, CN, CHO, $CF_3$, $OCF_3$, $NO_2$, OH, NHC(O) $(C_{1-6}$ acyclic or $C_{3-6}$ cyclic alkyl), $NHC(O)CF_3$, $NHSO_2(C_{1-6}$ alkyl), $NHC(O)NH_2$, $NHC(O)(C_{1-6}$ alkyl), $C(O)NH_2$, C(O) $NHC_6H_5$, $C(O)C_6H_4C(O)OH$, $C(O)N(OC_{1-6}$ alkyl)$(C_{1-6}$ alkyl), $C(O)NHCH_2C(O)O(C_{1-6}$ alkyl), $C(O)(C_{1-6}$ alkyl), $C(O)O(C_{1-6}$ alkyl), C(O)(non-aromatic heterocylic ring), $OC(O)(C_{1-6}$ alkyl), $O(C_{1-6}$ alkyl), $O(C_{1-6}$ alkyl)$O(C_{1-6}$ alkyl), $O(C_{1-6}$ alkyl)C(O)OH, $OC_6H_4C(O)OH$, $OC_6H_4C(O)NH_2$, $O(C_{1-6}$ alkyl)$C(O)O(C_{1-6}$ alkyl), $O(C_{1-6}$ alkyl)$C(O)NH_2$, $O(C_{1-6}$ alkyl)$C(O)NHNH_2$, $OSO_2(C_{1-6}$ alkyl), $OC(O)O(C_{1-6}$ alkyl), $OC(O)N(C_{1-6}$ alkyl$)_2$, OC(O)(heteroaryl), COOH, $C(O)NH(C_{1-6}$ alkyl), $C(O)N(C_{1-6}$ alkyl$)_2$, $S(C_{1-6}$ alkyl), $CH=NOH$, $CH=NO(C_{1-6}$ alkyl), $CH=N(C_{1-6}$ alkyl), $(C_{1-6}$ alkyl)$C=NOH$, $(C_{1-6}$ alkyl)$C=NO(C_{1-6}$ alkyl), $(C_{1-6}$ alkyl) $C=N(C_{1-6}$ alkyl), $(C_{1-6}$ alkyl)$C_6H_4C(O)OH$, $(C_{1-6}$ alkyl) $NHC(O)(C_{1-6}$ alkyl), $CH=CHC(O)O(C_{1-6}$ alkyl), $CH=CHC(O)OH$, $SO_nR^6$ where n is 1 or 2; or phenyl, pyridine N-oxide, pyridine or heteroaryl each of which is optionally substituted by one or more of alkyl, alkene, alkyne, halogen, CN, $CF_3$, OH, $NH_2$, $OR^7$, $(C_{1-6}$ alkyl)$R^5$, $(C_{1-6}$ alkene)$R^5$, $(C_{1-6}$ alkyne)$R^5$, or a 5- or 6-membered non aromatic heterocyclic ring;

or $R^3$ can be phenyl, pyridinyl, thiazolyl, oxazolyl, pyrimidinyl, indolyl, indolinyl, isoindolinyl, 1,3-benzodioxolyl, 1,4-benzodioxanyl, benzofuranyl, 2,3-dihydroxybenzofuranyl or phthalanyl, each of which is optionally linked to one or more $C_{1-6}$ alkyl, trifluoromethyl, oxotrifluoromethyl, carboxylalkyl, cyano, halogen, sulfanyl, $SO_2R^9$, where $R^9$ is alkyl, amine or amino alkyl, $C(O)R^{10}$, where $R^{10}$ is alkyl, amine, morpholine, $NMe_2$, N(OMe)Me, NPh, piperidine, NHMe, piperazine, $NHCH_2C(O)OMe$ or $PhC(O)OH$, $OR^{11}$, where $R^{11}$ is H, alkyl, $(CH_2)_2OMe$, $CH_2C(O)NH_2$, $CH_2C(O)NHNH_2$, $CH_2C(O)OCMe_3$, $CH_2C(O)OMe$, $CH_2C(O)OH$, $PhC(O)OH$, $PhC(O)NH_2$, $SO_2Me$, C(O)Me, C(O)OMe, $C(O)NEt_2$, $C(O)NMe_2$ or

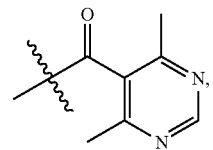

$NHR^{12}$, where $R^{12}$ is H, C(O)Me, $C(O)CF_3$, $SO_2Me$, $C(O)NH_2$, $C(O)NMe_2$ or

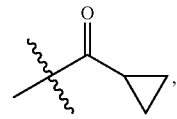

$NO_2$, $CH_2PhC(O)OH$, SOMe, $CH_2NHC(O)Me$, morpholine, $CH=CHC(O)OMe$, $CH=CHC(O)OH$,

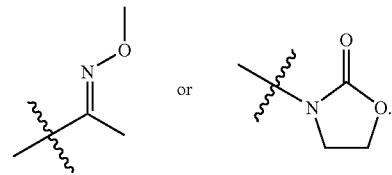

In the above formula (1), $R^4$ may be H or $C_{1-6}$ alkyl.

In the above formula (1), $R^5$ may be a $C_{1-6}$ alkyl, phenyl, pyridine, pyridine N-oxide or heteroaryl, each of which is optionally substituted by one or more of $C_{1-6}$ alkyl, OH, OMe, $NH_2$, $NH(C_{1-6}$ alkyl), $N(C_{1-6}$ alkyl$)_2$, halogen, CN, $CF_3$, $OCF_3$, $C(O)NH(C_{1-6}$ alkyl), $C(O)N(C_{1-6}$ alkyl$)_2$, $C(O)O(C_{1-6}$ alkyl), COOH, $SO_nNH(C_{1-6}$ alkyl), or $SO_n(C_{1-6}$ alkyl) where n is 1 or 2.

In the above formula (1), $R^6$ may be $C_{1-6}$ alkyl, $NH_2$, $NH(C_{1-6}$ alkyl), $N(C_{1-6}$ alkyl$)_2$, or benzyl.

In the above formula (1), $R^7$ may be a cyclic or acyclic alkyl, alkene, alkyne, phenyl, pyridine or heteroaryl, each of which is optionally substituted by one or more of $C_{1-6}$ alkyl, halogen, CN, $NH_2$, C(O)OH, $C(O)O(C_{1-6}$ alkyl), OH, SO$_n$NH$_2$ where n is 1 or 2, SO$_n$(C$_{1-6}$ alkyl) where n is 1 or 2, SO$_2$NH(C$_{1-6}$ alkyl), C(O)NH$_2$, C(O)NH(C$_{1-6}$ alkyl), or C(O)N(C$_{1-6}$ alkyl)$_2$; and R$^8$ may be a C$_{1-6}$ alkyl, alkene or alkyne, OH, or Ome.

In another aspect, the invention provides compounds having general formula 2:

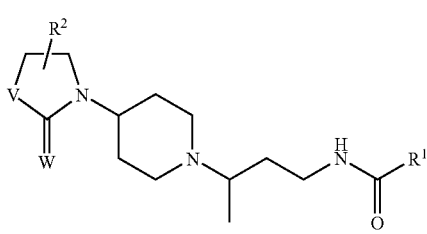

(2)

and pharmaceutically acceptable salts thereof;

wherein W is oxygen, sulfur, NR$^2$, NOR$^2$, NCN, NSO$_2$R$^2$, NAc, NNO$_2$, CRNO$_2$, NCOR$^2$, C(CN)$_2$ or CRCN;

V is O, S, N-L-R$^3$, or CR-L-R$^3$;

L is a bond or a (CR$_2$)$_m$ linker optionally having one carbon of (CR$_2$)$_m$ replaced by a group selected from O, S, and NR, and m is 1-3;

R$^1$ is an optionally substituted aryl or heteroaryl;

R$^2$ is H, an optionally substituted alkyl, a carbocyclic ring, a heterocyclic ring, an aryl, or a heteroaryl;

R$^3$ is H; an optionally substituted alkyl, alkenyl or alkynyl; hydroxy, alkoxy, cyano, amino, amido, COR$^2$, CO$_2$R$^2$, S=(O)$_p$R$^2$, CR=N—OR, O(CR$_2$)CN, NR—COR$^2$, SR$^2$; a carbocyclic ring, a heterocyclic ring, an aryl, or a heteroaryl; and R is H, C$_{1-6}$ alkyl, or C$_{3-6}$ cycloalkyl;

wherein in each said optionally substituted alkyl, alkenyl or alkynyl, a carbon may be optionally substituted with halo, N, O, or S, and/or replaced with N, O or S; and each carbocyclic ring, heterocyclic ring, aryl or heteroaryl may be optionally substituted and/or fused with a carbocyclic, aryl, heterocyclic, or heteroaryl ring.

In some embodiments of the compounds of formula (2), R$^1$ and R$^2$ are independently an optionally substituted aryl or heteroaryl; R$^3$ is H or an optionally substituted alkyl; or R$^3$ is a carbocyclic ring, a heterocyclic ring, an aryl, or a heteroaryl, each of which may be optionally substituted and/or fused with a carbocyclic, heterocyclic, aryl or heteroaryl ring; and each R is independently selected from H and C$_{1-6}$ alkyl.

In the above formula (2), R$^1$ may be phenyl, pyrimidinyl or pyridinyl, each optionally substituted with halo, cyano, alkyl, alkoxy, cycloalkyl, heterocyclyl, aryl, heteroaryl, or N-oxide.

In the above formula (2), R$^2$ may be phenyl, thienyl, or imidazolyl each optionally substituted with halo, cyano, alkoxy, heterocyclyl, aryl, heteroaryl, or N-oxide; or alkyl or cycloalkyl, each of which may be optionally substituted with halo, cyano, OR, SR, or N(R)$_m$, or in which one carbon may be optionally replaced with N, O, or S. In some examples, R$^2$ is attached to the C that is attached to the nitrogen to which the piperidine ring is linked. In other embodiments it is attached to the ring carbon to which V is attached.

In the above formula (2), R$^3$ may be a bond, H, C$_{1-10}$ straight or branched alkyl; or R$^3$ is a C$_{3-7}$ cycloalkyl, a 5-6 membered aryl, heteroaryl or heterocyclic ring, each optionally substituted with halo, cyano, alkyl, alkoxy, cycloalkyl, heterocyclyl, aryl, heteroaryl, or fused with a carbocyclic or heterocyclic ring. In some compounds of formula (2), R$^3$ is H, cyclopentyl, cyclohexyl, cycloheptyl, tetrahydropyran, morpholine, phenyl optionally fused to a 5-6 membered heterocyclic ring, pyridinyl, imidazole, furan, pyrimidine, thienyl, C$_{1-6}$ straight or branched alkyl, or bicyclo[4.2.0]octa-1,3,5-triene.

Examples of heteroaryl substituents in the above formula (1) or (2) include but are not limited to pyridine, quinoline, isoquinoline, imidazole, benzimidazole, benzotriazole, furan, morpholine, benzofuran, dihydrobenzofuran, thiazole, benzothiazole, benzodioxole, benzodioxane, oxazole, isoxazole, benzoxazole, pyrrole, indole, indoline, isoindoline, indazole, pyrrolidine, pyrrolidone, tetrahydroquinoline, tetrahydroisoquinoline, pyrazole, thiophene, isothiazole, triazole, tetrazole, oxadiazole, thiadiazole, benzopyran, pyridazine, pyrimidine, pyrazine, 1,3,5-triazine, cinnoline, tetrahydrocinnoline, quinazoline, tetrahydroquinazoline, quinoxaline, tetrahydroquinoxaline, phthalan or phthalazine.

Where an alkyl, aryl or heteroaryl group in a compound of formula (1) or (2) is described as optionally substituted, unless otherwise described, it may comprise one or more substituents selected from those set forth for R$^3$ above. Suitable substituents for alkyl groups include, in addition to those set forth above for R$^3$, =O, =NOH, and =NOR.

The present invention also relates to pharmaceutical compositions comprising compounds of formula (1) or (2), in combination with at least one pharmaceutically acceptable carrier. Furthermore, the present invention relates to methods for treating a CCR5 mediated disease in a system, comprising contacting a compound of formula (1) or (2) with a system (e.g., cell, tissue or organ), or administering a compound of formula (1) or (2) to a subject, which may be a human.

Examples of piperidine compounds having formula (1) include but are not limited to the following compounds:

Formula 1

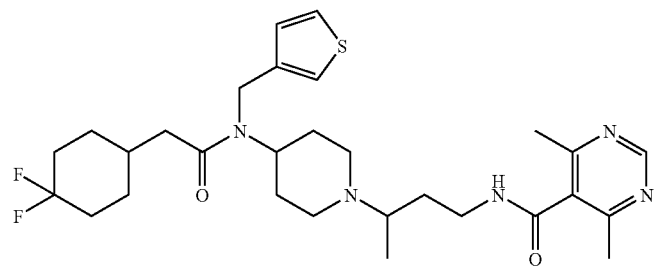

4,6-Dimethylpyrimidine-5-carboxylic acid [3-(4-{[2-(4,4-difluorocyclohexyl)-acetyl]-thiophen-3-ylmethylamino}-piperidin-1-yl)-butyl]-amide

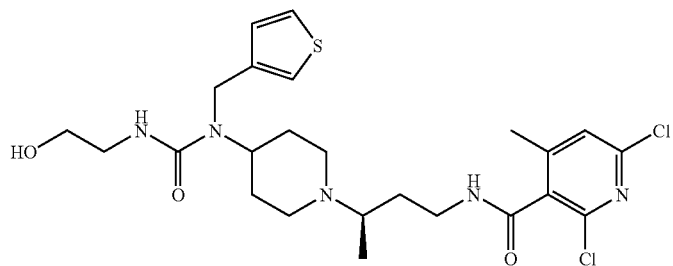

2,6-Dichloro-N-((R)-3-{4-[3-(2-hydroxy-ethyl)-1-thiophen-3-ylmethyl-ureido]-piperidin-1-yl}-butyl)-4-methyl-nicotinamide

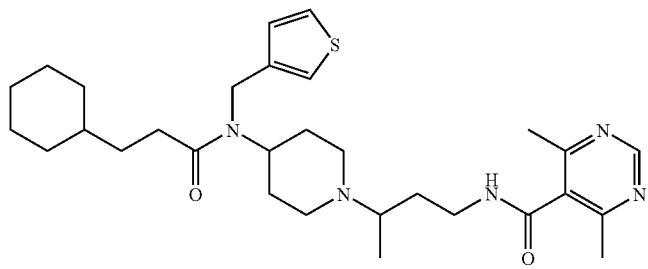

4,6-Dimethyl-pyrimidine-5-carboxylic acid (3-{4-[(3-cyclohexyl-propionyl)-thiophen-3-ylmethyl-amino]-piperidin-1-yl}-butyl)-amide

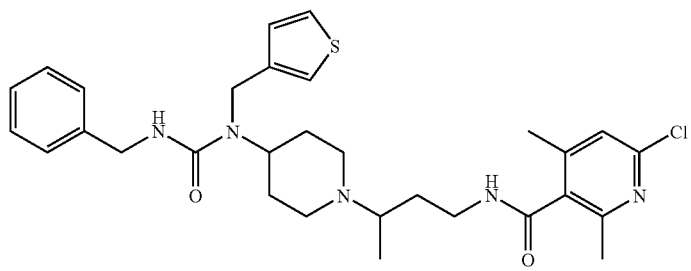

N-{3-[4-(3-Benzyl-1-thiophen-3-ylmethyl-ureido)-piperidin-1-yl]-butyl}-6-chloro-2,4-dimethyl-nicotinamide

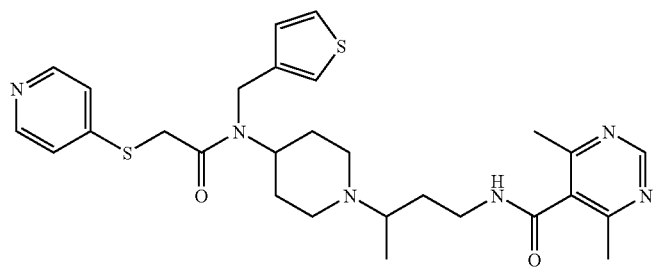

4,6-Dimethyl-pyrimidine-5-carboxylic acid (3-{4-{[2-(pyridin-4-ylsulfanyl)-acetyl]-thiophen-3-ylmethyl-amino}-piperidin-1-yl}-butyl]-amide

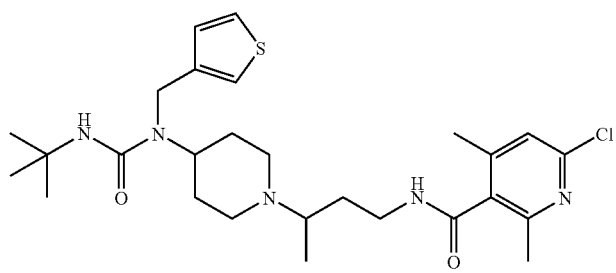

N-{3-[4-(3-tert-Butyl-1-thiophen-3-ylmethyl-ureido)-piperidin-1-yl]-butyl}-6-chloro-2,4-dimethyl-nicotinamide -continued

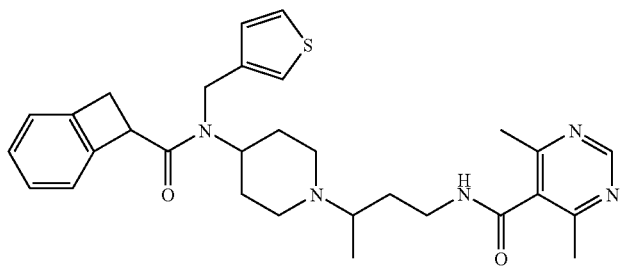

4,6-Dimethyl-pyrimidine-5-carboxylic acid (3-{4-[(bicyclo[4.2.0]octa-1(6), 2,4-triene-7-carbonyl)-thiophen-3-ylmethyl-amino]-piperidin-1-yl}-butyl)-amide

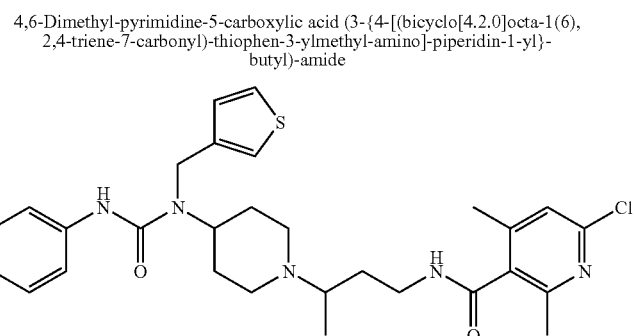

6-Chloro-2,4-dimethyl-N-{3-[4-(3-phenyl-1-thiophen-3-ylmethyl-ureido)-piperidin-1-yl]-butyl}-nicotinamide

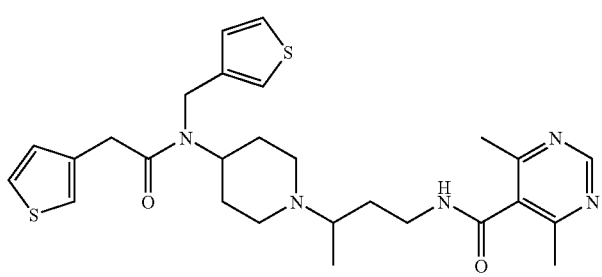

4,6-Dimethyl-pyrimidine-5-carboxylic acid (3-{4-[(2-thiophen-3-yl-acetyl)-thiophen-3-ylmethyl-amino]-piperidin-1-yl}-butyl)-amide

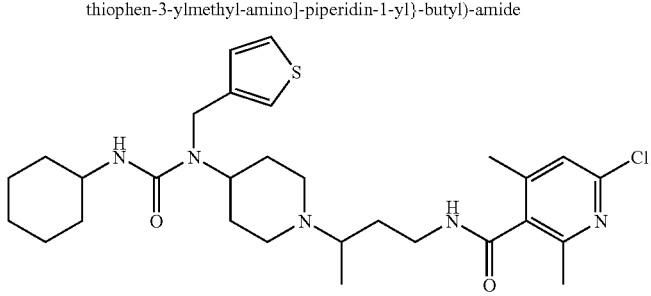

6-Chloro-N-{3-[4-(3-cyclohexyl-1-thiophen-3-ylmethyl-ureido)-piperidin-1-yl]-butyl}-2,4-dimethyl-nicotinamide

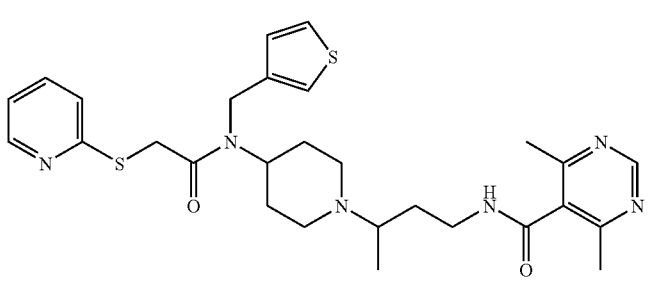

4,6-Dimethyl-pyrimidine-5-carboxylic acid [3-(4-{[2-(pyridin-2-ylsulfanyl)-acetyl]-thiophen-3-ylmethyl-amino}-piperidin-1-yl)-butyl]-amide

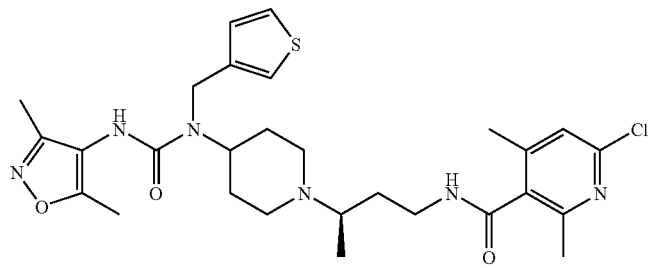

6-Chloro-N-((R)-3-{4-[3-(3,5-dimethyl-isoxazol-4-yl)-1-thiophen-3-ylmethyl-ureido]-piperidin-1-yl}-butyl)-2,4-dimethyl-nicotinamide

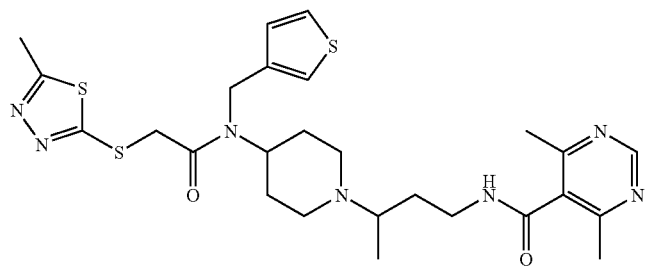

4,6-Dimethyl-pyrimidine-5-carboxylic acid [3-(4-{[2-(5-methyl-[1,3,4]thiadiazol-2-ylsulfanyl)-acetyl]-thiophen-3-ylmethyl-amino}-piperidin-1-yl)-butyl]-amide

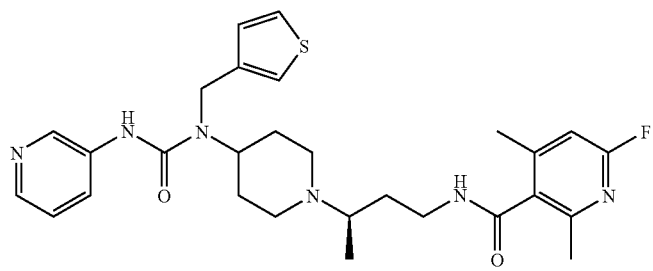

6-Fluoro-2,4-dimethyl-N-{(R)-3-[4-(3-pyridin-3-yl-1-thiophen-3-ylmethyl-ureido)-piperidin-1-yl]-butyl}-nicotinamide

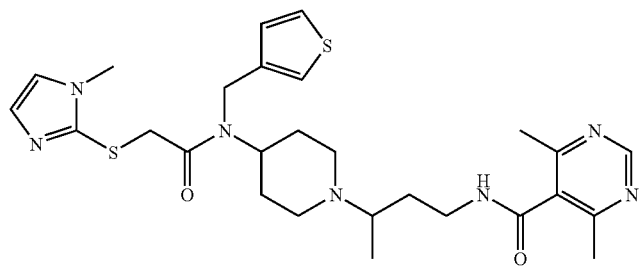

4,6-Dimethyl-pyrimidine-5-carboxylic acid [3-(4-{[2-(1-methyl-1H-imidazol-2-ylsulfanyl)-acetyl]-thiophen-3-ylmethyl-amino}-piperidin-1-yl)-butyl]-amide

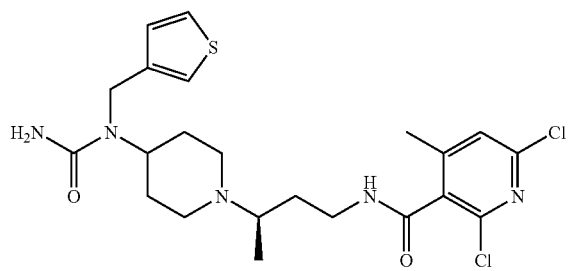

2,6-Dichloro-4-methyl-N-{(R)-3-[4-(1-thiophen-3-ylmethyl-ureido]-piperidin-1-yl]-butyl}-nicotinamide -continued

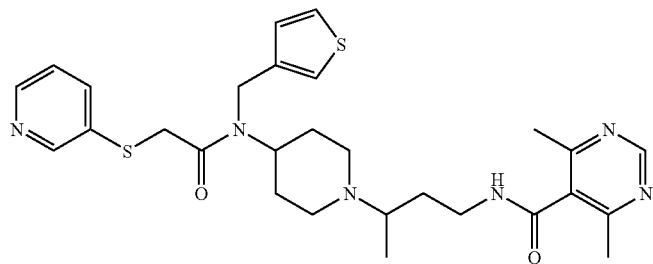

4,6-Dimethyl-pyrimidine-5-carboxylic acid [3-(4-{[2-(pyridin-3-ylsulfanyl)-acetyl]-thiophen-3-ylmethyl-amino}-piperidin-1-yl)-butyl]-amide

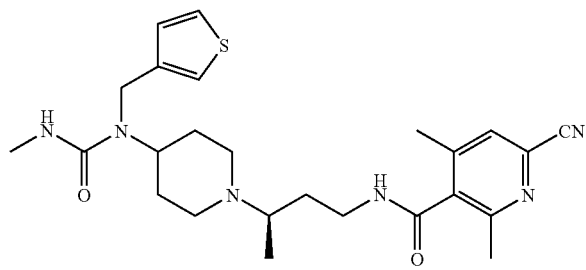

6-Cyano-2,4-dimethyl-N-{(R)-3-[4-(3-methyl-1-thiophen-3-ylmethyl-ureido)-piperidin-1-yl]-butyl}-nicotinamide

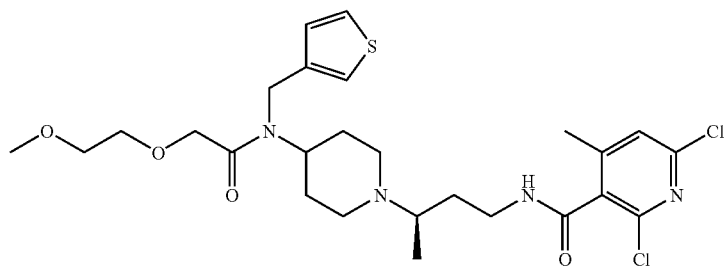

2,6-Dichloro-N-[(R)-3-(4-{[2-(2-methoxy-ethoxy)-acetyl]-thiophen-3-ylmethyl-amino}-piperidin-1-yl)-butyl]-4-methyl-nicotinamide

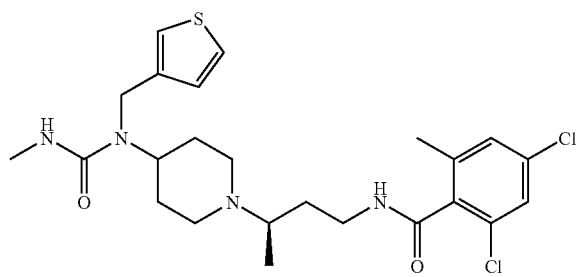

2,4-Dichloro-6-methyl-N-{(R)-3-[4-(3-methyl-1-thiophen-3-ylmethyl-ureido)-piperidin-1-yl]-butyl}-benzamide

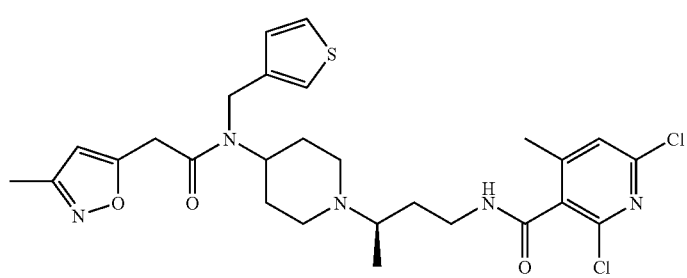

2,6-Dichloro-4-methyl-N-[(R)-3-(4-{[2-(3-methyl-isoxazol-5-yl)-acetyl]-thiophen-3-ylmethyl-amino)-piperidin-1-yl]-butyl]-nicotinamide -continued

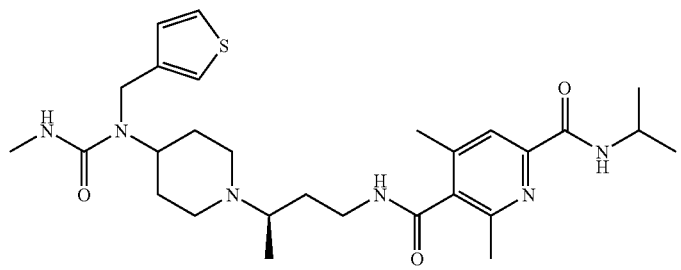

4,6-Dimethyl-pyridine-2,5-dicarboxylic acid 2-isopropylamide 5-({(R)-3-[4-(3-methyl-1-thiophen-3-ylmethyl-ureido)-piperidin-1-yl]-butyl}-amide)

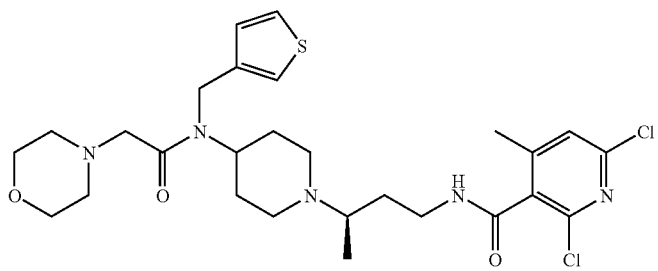

2,6-Dichloro-4-methyl-N-((R)-3-{4-[(2-morpholin-4-yl-acetyl)-thiophen-3-ylmethyl-amino]-piperidin-1-yl}-butyl)-nicotinamide

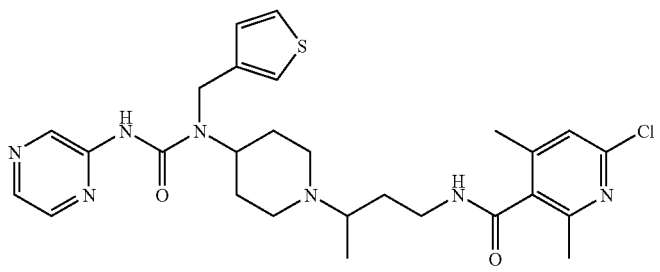

6-Chloro-2,4-dimethyl-N-{3-[4-(3-pyrazin-2-yl-1-thiophen-3-ylmethyl-ureido)-piperidin-1-yl]-butyl}-nicotinamide

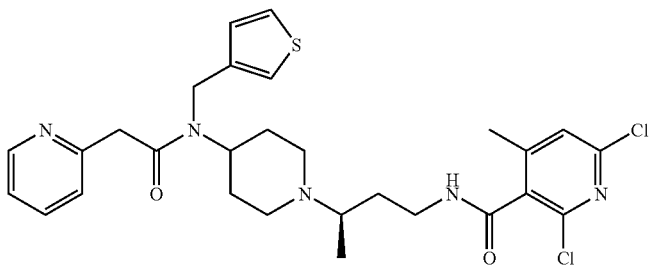

2,6-Dichloro-4-methyl-N-((R)-3-{4-[(2-pyridin-2-yl-acetyl)-thiophen-3-ylmethyl-amino]-piperidin-1-yl}-butyl)-nicotinamide

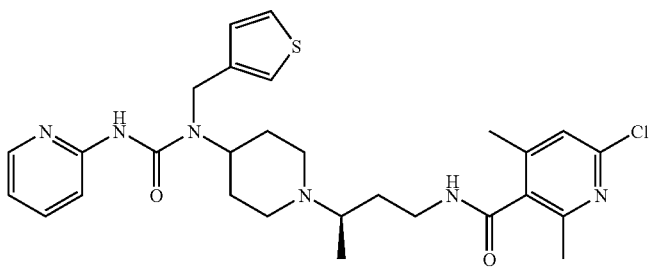

6-Chloro-2,4-dimethyl-N-{(R)-3-[4-(3-pyridin-2-yl-1-thiophen-3-ylmethyl-ureido)-piperidin-1-yl]-butyl}-nicotinamide

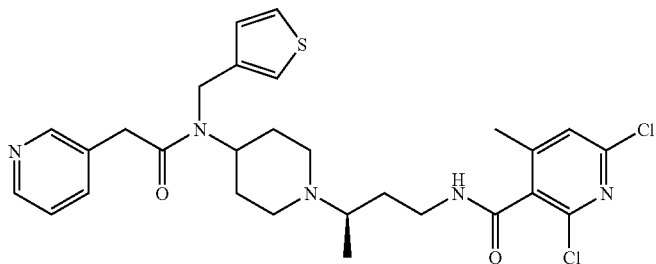

2,6-Dichloro-4-methyl-N-((R)-3-{4-[(2-pyridin-3-yl-acetyl)-thiophen-3-ylmethyl-amino]-piperidin-1-yl}-butyl)-nicotinamide

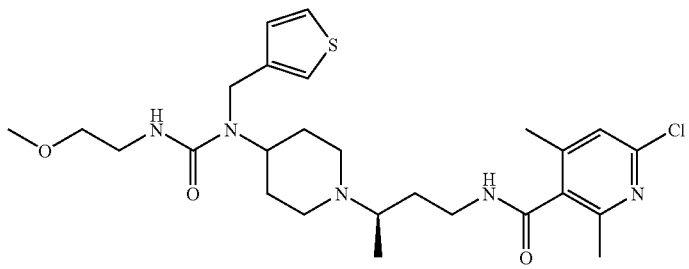

6-Chloro-N-((R)-3-{4-[3-(2-methoxy-ethyl)-1-thiophen-3-ylmethyl-ureido]-piperidin-1-yl}-butyl)-2,4-dimethyl-nicotinamide

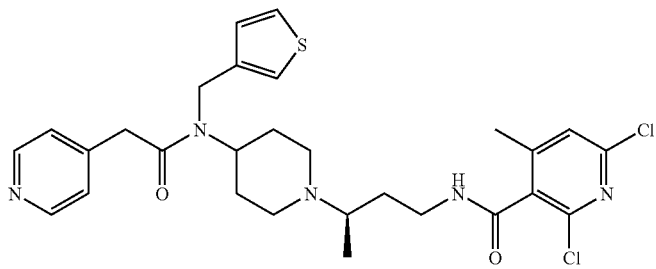

2,6-Dichloro-4-methyl-N-((R)-3-{4-[(2-pyridin-4-yl-acetyl)-thiophen-3-ylmethyl-amino]-piperidin-1-yl}-butyl)-nicotinamide

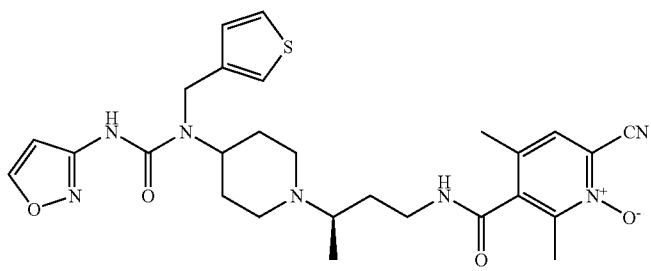

6-Cyano-N-{(R)-3-[4-(3-isoxazol-3-yl-1-thiophen-3-ylmethyl-ureido)-piperidin-1-yl]-butyl}-2,4-dimethyl-1-oxy-nicotinamide

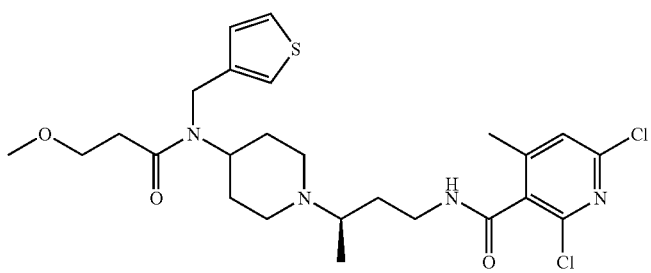

2,6-Dichloro-N-((R)-3-{4-[(3-methoxy-propionyl)-thiophen-3-ylmethyl-amino]-piperidin-1-yl}-butyl)-4-methyl-nicotinamide

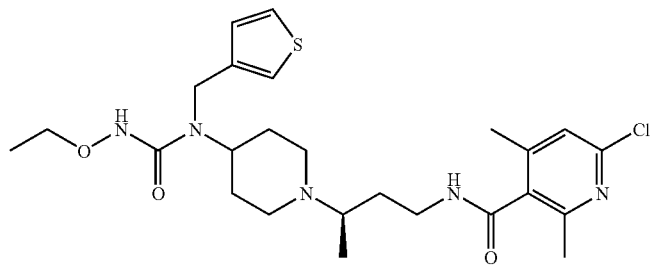

6-Chloro-2,4-dimethyl-N-{(R)-3-[4-(3-ethoxy-1-thiophen-3-ylmethyl-ureido)-piperidin-1-yl]-butyl}-nicotinamide

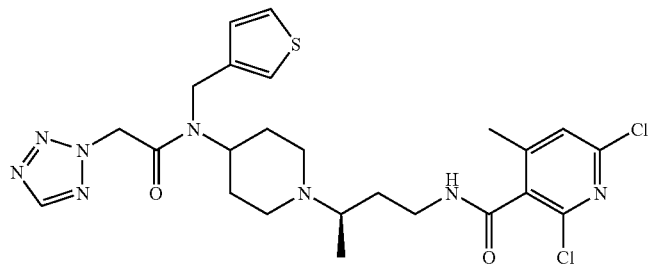

2,6-Dichloro-4-methyl-N-((R)-3-{4-[(2-tetrazol-2-yl-acetyl)-thiophen-3-ylmethyl-amino]-piperidin-1-yl}-butyl)-nicotinamide

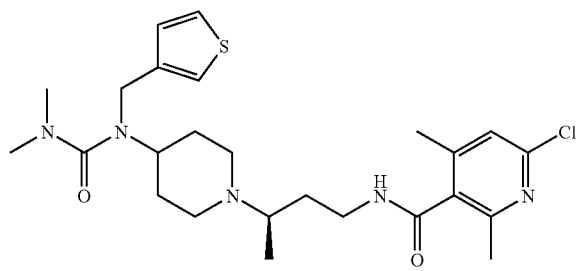

6-Chloro-N-{(R)-3-[4-(3,3-dimethyl-1-thiophen-3-ylmethyl-ureido)-piperidin-1-yl]-butyl}-2,4-dimethyl-nicotinamide

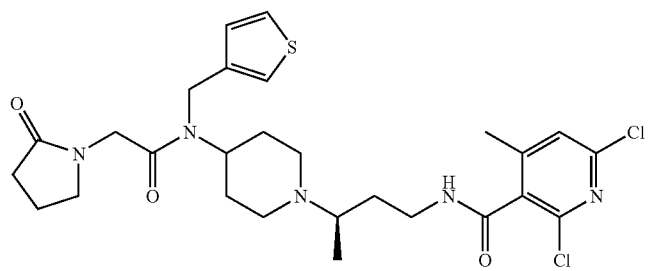

2,6-Dichloro-4-methyl-N-[(R)-3-(4-{[2-(2-oxo-pyrrolidin-1-yl)-acetyl]-thiophen-3-ylmethyl-amino}-piperidin-1-yl)-butyl]-nicotinamide

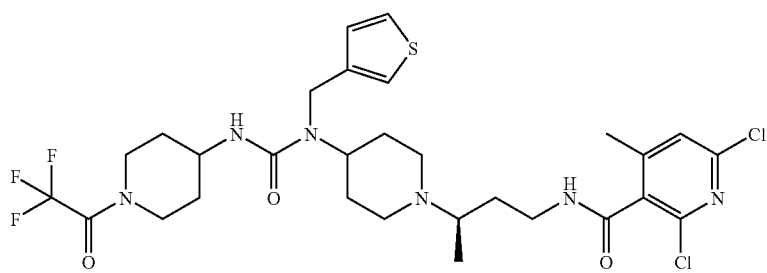

2,6-Dichloro-4-methyl-N-[(R)-3-(4-{1-thiophen-3-ylmethyl-3-[1-(2,2,2-trifluoro-acetyl)-piperidin-4-yl]-ureido}-piperidin-1-yl)-butyl]-nicotinamide -continued

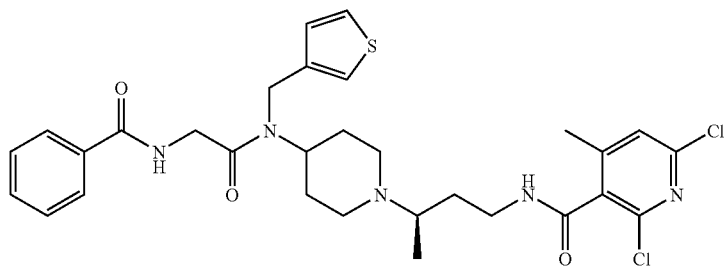

N-((R)-3-{4-[(2-Benzoylamino-acetyl)-thiophen-3-ylmethyl-amino]-piperidin-1-yl}-butyl)-2,6-dichloro-4-methyl-nicotinamide

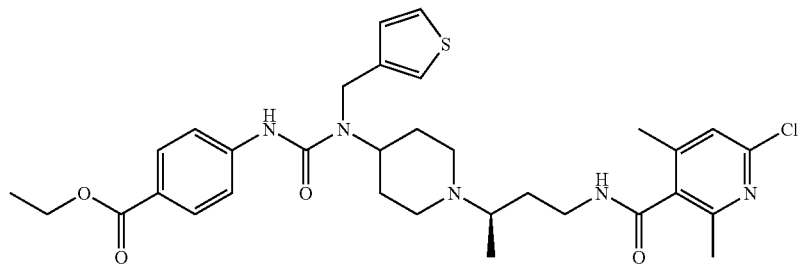

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid ethyl ester

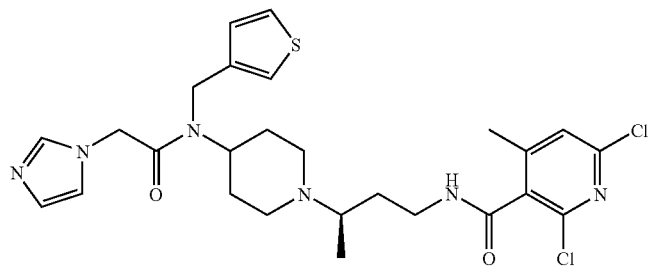

2,6-Dichloro-N-((R)-3-{4-[(2-imidazol-1-yl-acetyl)-thiophen-3-ylmethyl-amino]-piperidin-1-yl}-butyl)-4-methyl-nicotinamide

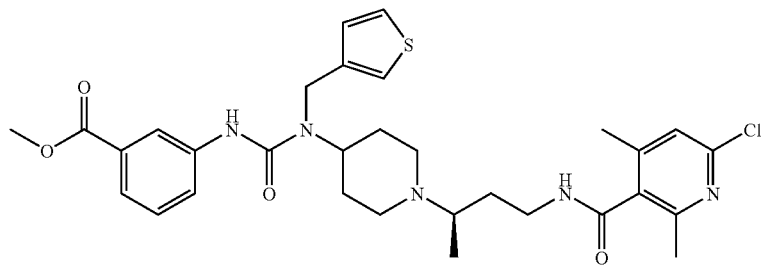

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid methyl ester

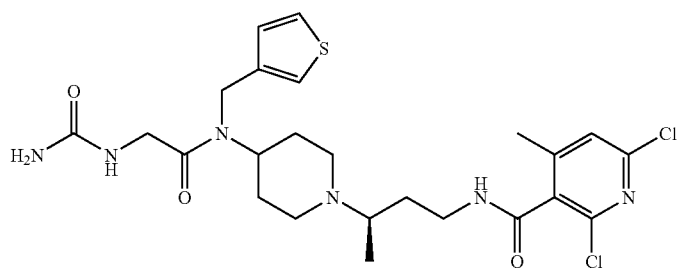

2,6-Dichloro-4-methyl-N-((R)-3-{4-[thiophen-3-ylmethyl-(2-ureido-acetyl)-amino]-piperidin-1-yl}-butyl)-nicotinamide -continued

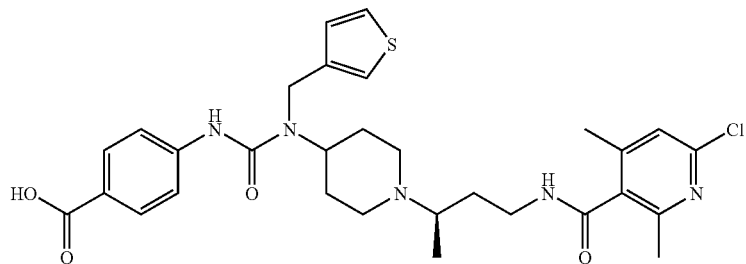

4-[3-(1-{(R)-3-[(6-chloro-2,4-dimethyl-pyridine-3-carbonyl)-amino]-1-methyl-propyl}-piperidin-4-yl)-3-thiophen-3-ylmethyl-ureido]-benzoic acid

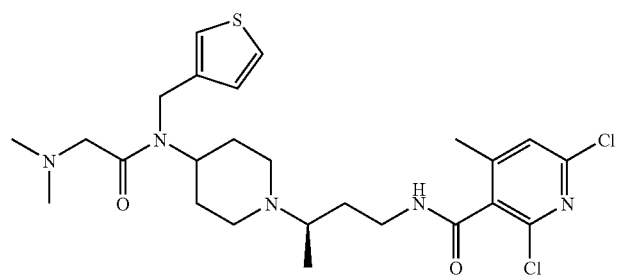

2,6-Dichloro-N-((R)-3-{4-[(2-dimethylamino-acetyl)-thiophen-3-ylmethyl-amino]-piperidin-1-yl}-butyl)-4-methyl-nicotinamide

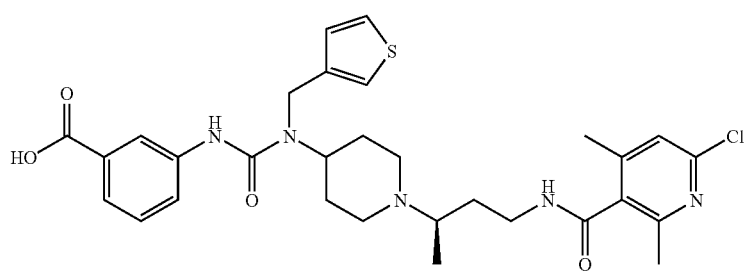

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid

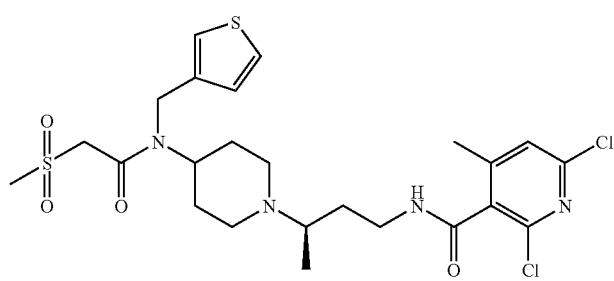

2,6-Dichloro-N-((R)-3-{4-[(2-methanesulfonyl-acetyl)-thiophen-3-ylmethyl-amino]-piperidin-1-yl}-butyl)-4-methyl-nicotinamide

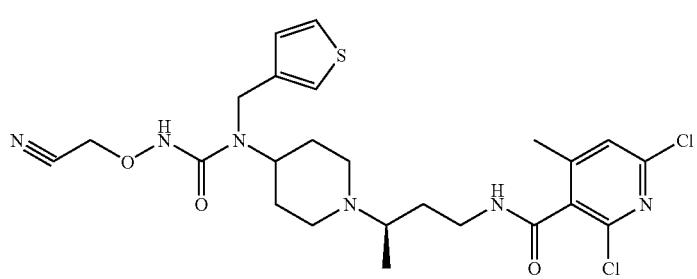

2,6-Dichloro-4-methyl-N-{(R)-3-[4-(3-(cyanomethoxy)-1-thiophen-3-ylmethyl-ureido)-piperidin-1-yl]-butyl}-nicotinamide

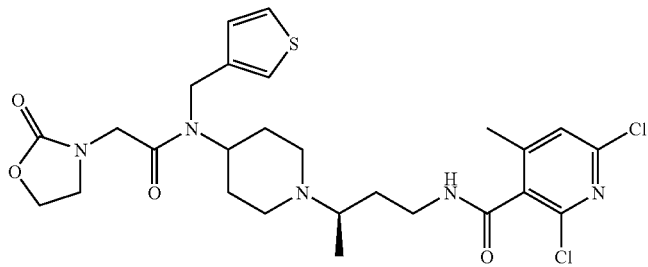

2,6-Dichloro-4-methyl-N-[(R)-3-(4-{[2-(2-oxo-oxazolidin-3-yl)-acetyl]-thiophen-3-ylmethyl-amino}-piperidin-1-yl)-butyl]-nicotinamide

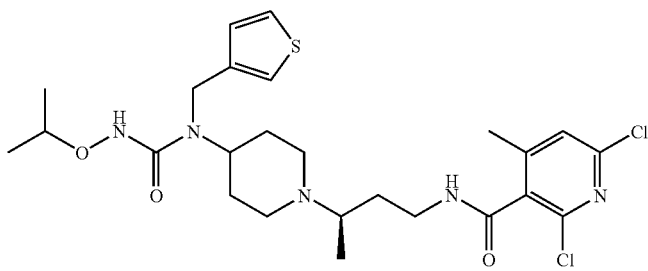

2,6-Dichloro-N-{(R)-3-[4-(3-isopropoxy-1-thiophen-3-ylmethyl-ureido)-piperidin-1-yl]-butyl}-4-methyl-nicotinamide

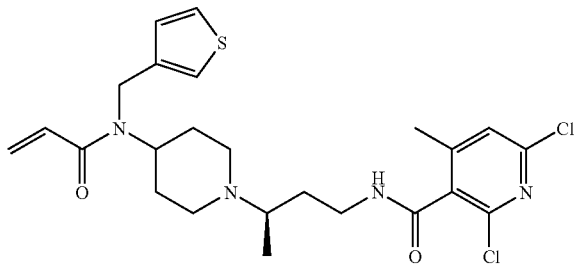

N-{(R)-3-[4-(Acryloyl-thiophen-3-ylmethyl-amino)-piperidin-1-yl]-butyl}-2,6-dichloro-4-methyl-nicotinamide

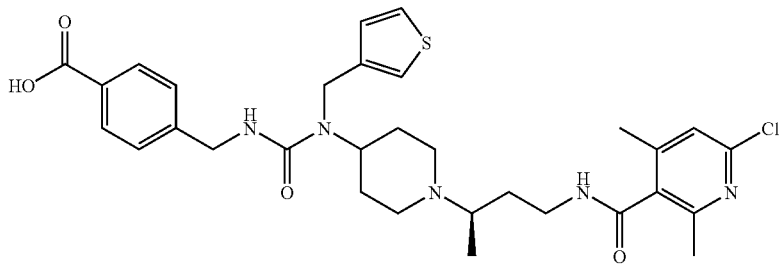

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid

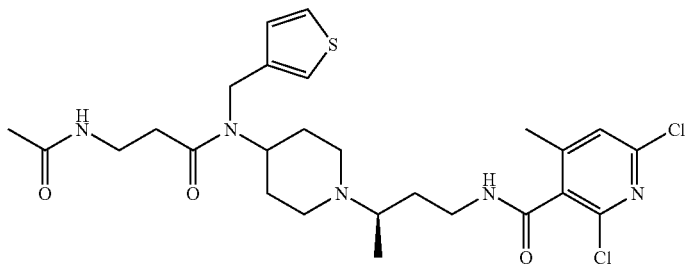

N-((R)-3-{4-[(3-Acetylamino-propionyl)-thiophen-3-ylmethyl-amino]-piperidin-1-yl}-butyl)-2,6-dichloro-4-methyl-nicotinamide -continued

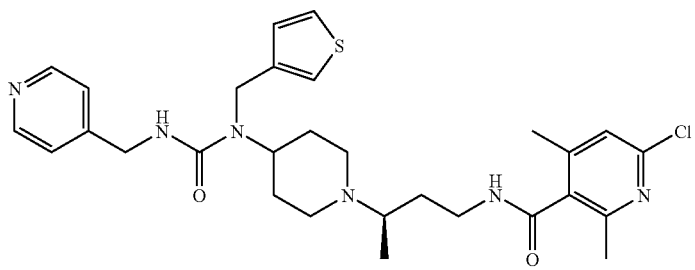

6-Chloro-2,4-dimethyl-N-{(R)-3-[4-(3-pyridin-4-ylmethyl-1-thiophen-3-ylmethyl-
ureido)-piperidin-1-yl]-butyl}-nicotinamide

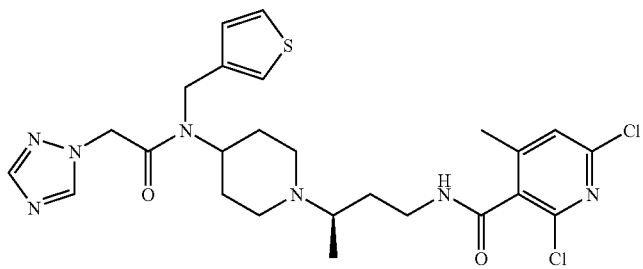

2,6-Dichloro-4-methyl-N-((R)-3-{4-[thiophen-3-ylmethyl-
(2-[1,2,4]triazol-1-yl-acetyl)-amino]-piperidin-1-yl}-butyl)-nicotinamide

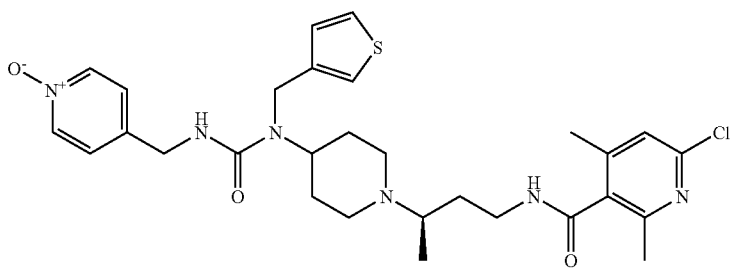

6-Chloro-2,4-dimethyl-N-((R)-3-{4-[3-(1-oxy-pyridin-4-ylmethyl)-1-thiophen-
3-ylmethyl-ureido]-piperidin-1-yl}-butyl)-nicotinamide

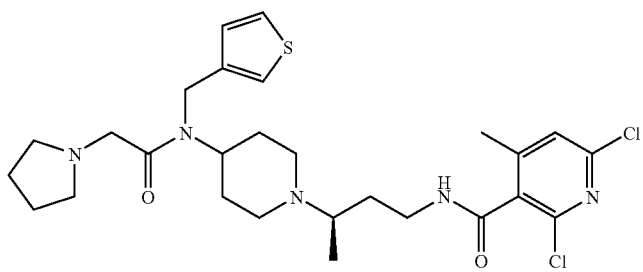

2,6-Dichloro-4-methyl-N-((R)-3-{4-[(2-pyrrolidin-1-yl-acetyl)-thiophen-
3-ylmethyl-amino]-piperidin-1-yl}-butyl)-nicotinamide

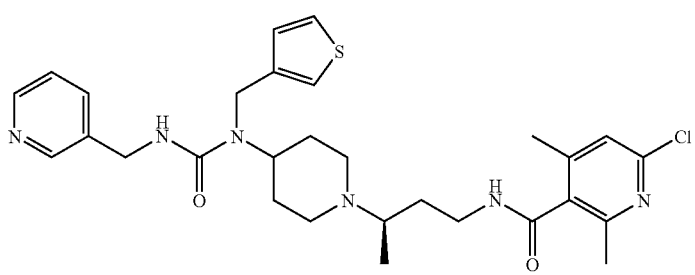

6-Chloro-2,4-dimethyl-N-{(R)-3-[4-(3-pyridin-3-ylmethyl-1-thiophen-3-ylmethyl-
ureido)-piperidin-1-yl]-butyl}-nicotinamide

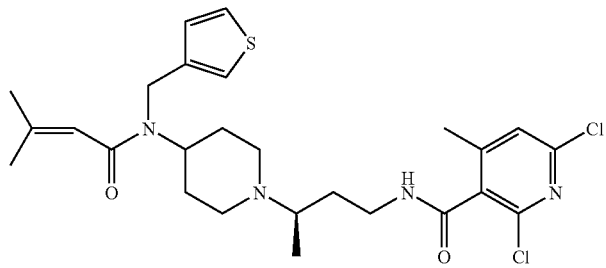

2,6-Dichloro-4-methyl-N-((R)-3-{4-[(3-methyl-but-2-enoyl)-thiophen-3-ylmethyl-amino]-piperidin-1-yl}-butyl)-nicotinamide

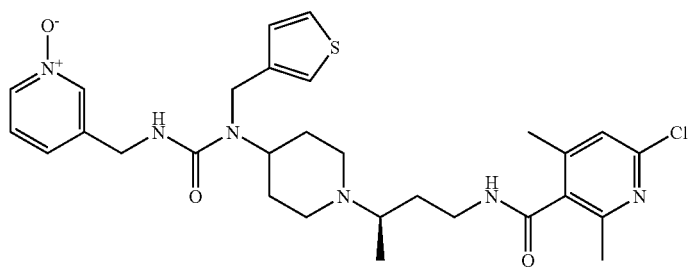

6-Chloro-2,4-dimethyl-N-((R)-3-{4-[3-(1-oxy-pyridin-3-ylmethyl)-1-thiophen-3-ylmethyl-ureido]-piperidin-1-yl}-butyl)-nicotinamide

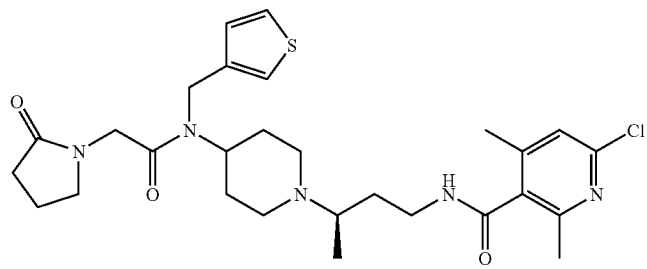

6-Chloro-2,4-dimethyl-N-[(R)-3-(4-{[2-(2-oxo-pyrrolidin-1-yl)-acetyl]-thiophen-3-ylmethyl-amino}-piperidin-1-yl)-butyl]-nicotinamide

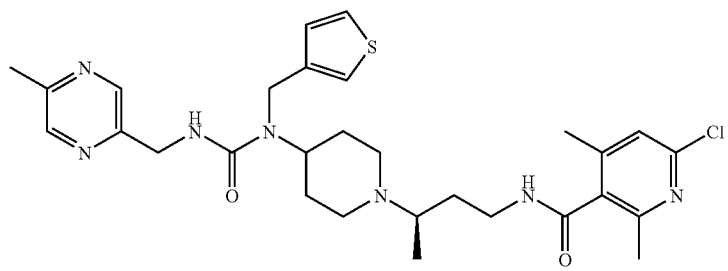

6-Chloro-2,4-dimethyl-N-((R)-3-{4-[3-(5-methyl-pyrazin-2-ylmethyl)-1-thiophen-3-ylmethyl-ureido]-piperidin-1-yl}-butyl)-nicotinamide

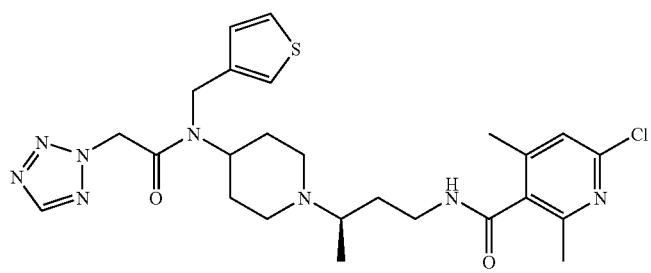

6-Chloro-2,4-dimethyl-N-((R)-3-{4-[(2-tetrazol-2-yl-acetyl)-thiophen-3-ylmethyl-amino]-piperidin-1-yl}-butyl)-nicotinamide

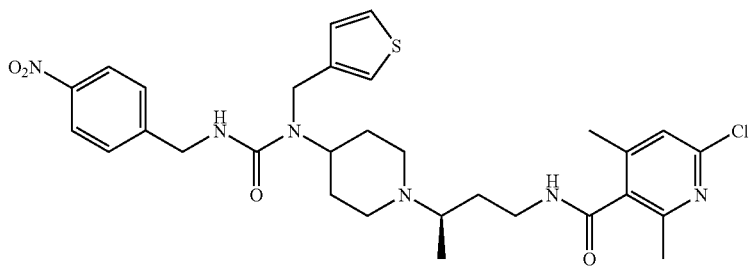

6-Chloro-2,4-dimethyl-N-((R)-3-{4-[3-(4-nitro-benzyl)-1-thiophen-3-ylmethyl-ureido]-piperidin-1-yl}-butyl)-nicotinamide

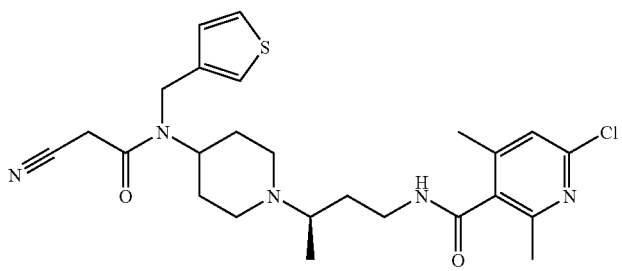

6-Chloro-N-((R)-3-{4-[(2-cyano-acetyl)-thiophen-3-ylmethyl-amino]-piperidin-1-yl}-butyl)-2,4-dimethyl-nicotinamide

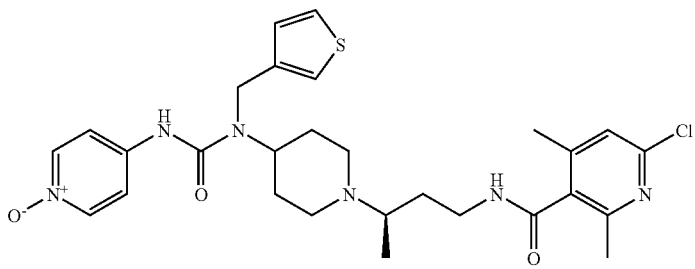

6-Chloro-2,4-dimethyl-N-((R)-3-{4-[3-(1-oxy-pyridin-4-yl)-1-thiophen-3-ylmethyl-ureido]-piperidin-1-yl}-butyl)-nicotinamide

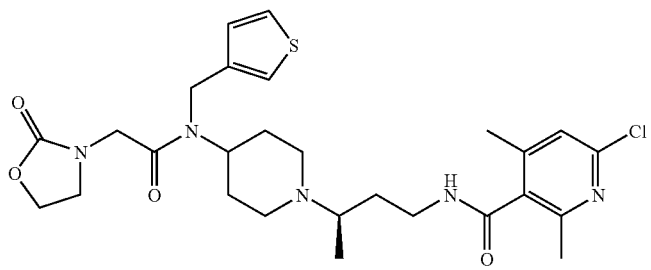

6-Chloro-2,4-dimethyl-N-[(R)-3-(4-{[2-(2-oxo-oxazolidin-3-yl)-acetyl]-thiophen-3-ylmethyl-amino}-piperidin-1-yl)-butyl]-nicotinamide

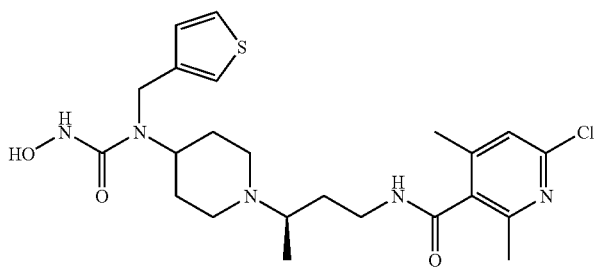

6-Chloro-N-{(R)-3-[4-(3-hydroxy-1-thiophen-3-ylmethyl-ureido)-piperidin-1-yl]-butyl}-2,4-dimethyl-nicotinamide

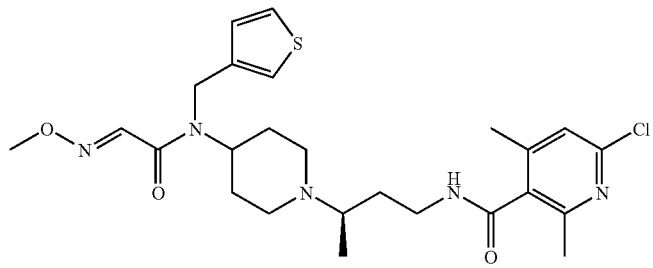

6-Chloro-N-((R)-3-{4-[(2-methoxyimino-acetyl)-thiophen-3-ylmethyl-amino]-piperidin-1-yl}-butyl)-2,4-dimethyl-nicotinamide

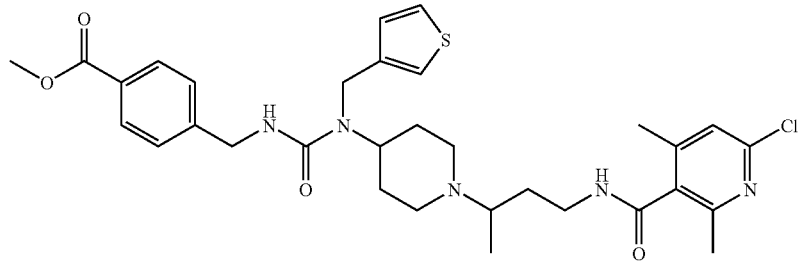

4-[3-(1-{3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid methyl ester

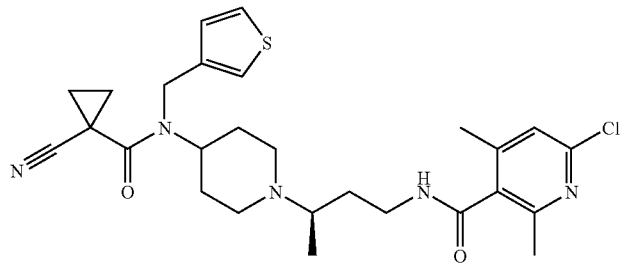

6-Chloro-N-((R)-3-{4-[(1-cyano-cyclopropanecarbonyl)-thiophen-3-ylmethyl-amino]-piperidin-1-yl}-butyl)-2,4-dimethyl-nicotinamide

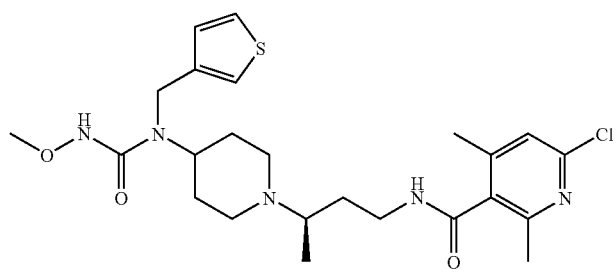

6-Chloro-N-{(R)-3-[4-(3-methoxy-1-thiophen-3-ylmethyl-ureido)-piperidin-1-yl]-butyl}-2,4-dimethyl-nicotinamide

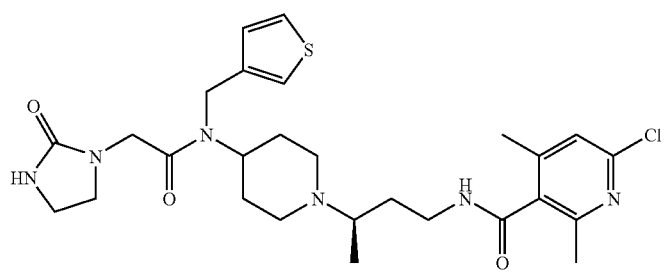

6-Chloro-2,4-dimethyl-N-[(R)-3-(4-{[2-(2-oxo-imidazolidin-1-yl)-acetyl]-thiophen-3-ylmethyl-amino}-piperidin-1-yl)-butyl]-nicotinamide -continued

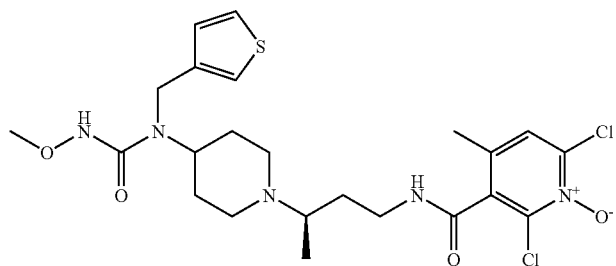

2,6-Dichloro-4-methyl-N-{(R)-3-[4-(3-methoxy-1-thiophen-3-ylmethyl-ureido)-piperidin-1-yl]-butyl}-nicotinamide-N-oxide

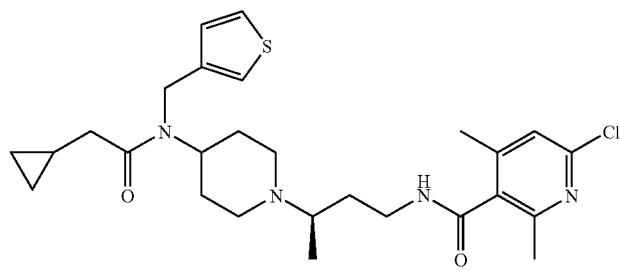

6-Chloro-N-((R)-3-{4-[(2-cyclopropyl-acetyl)-thiophen-3-ylmethyl-amino]-piperidin-1-yl}-butyl)-2,4-dimethyl-nicotinamide

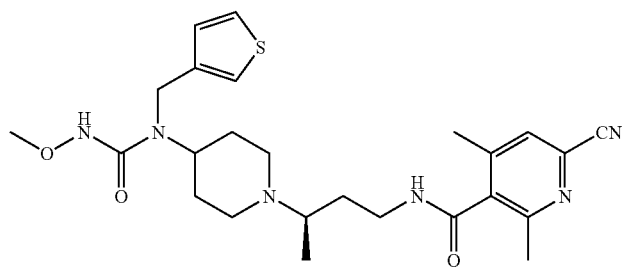

6-Cyano-2,4-dimethyl-N-{(R)-3-[4-(3-methoxy-1-thiophen-3-ylmethyl-ureido)-piperidin-1-yl]-butyl}-nicotinamide

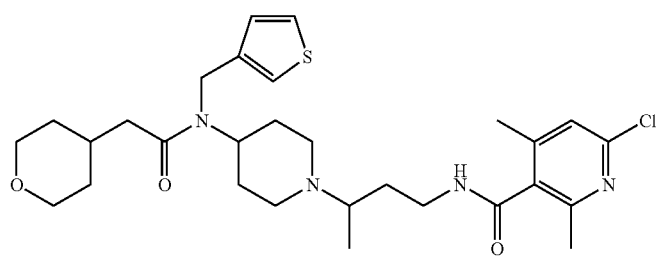

N-(3-{4-[(Thiophen-3-ylmethyl)-2-(tetrahydro-pyran-4-yl)-acetyl-amino]-piperidin-1-yl}-butyl)-6-chloro-2,4-dimethyl-nicotinamide

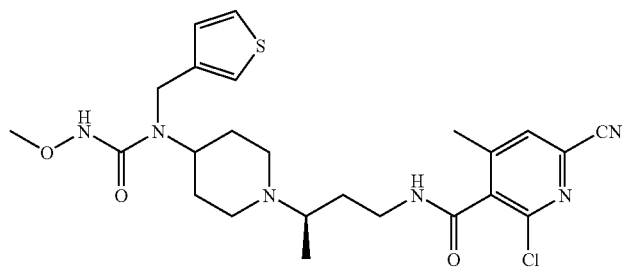

2-Chloro-6-cyano-4-methyl-N-{(R)-3-[4-(3-methoxy-1-thiophen-3-ylmethyl-ureido)-piperidin-1-yl]-butyl}-nicotinamide -continued

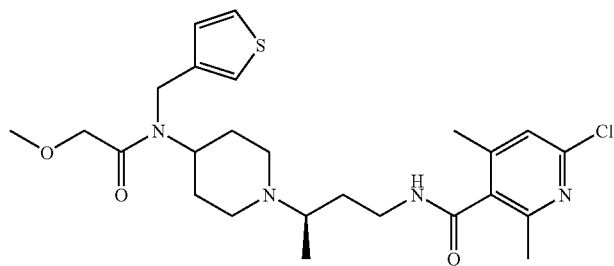

6-Chloro-N-((R)-3-{4-[2-methoxy-acetyl)-thiophen-3-ylmethyl-amino]-piperidin-1-yl}-butyl)-2,4-dimethyl-nicotinamide

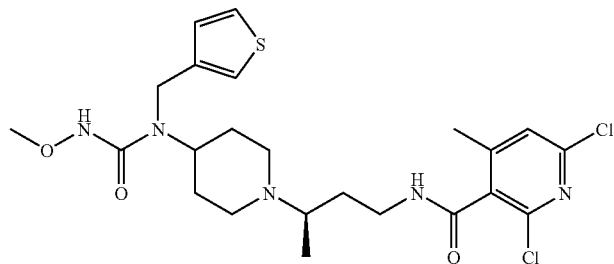

2,6-Dichloro-N-{(R)-3-[4-(3-methoxy-1-thiophen-3-ylmethyl-ureido)-piperidin-1-yl]-butyl}-4-methyl-nicotinamide

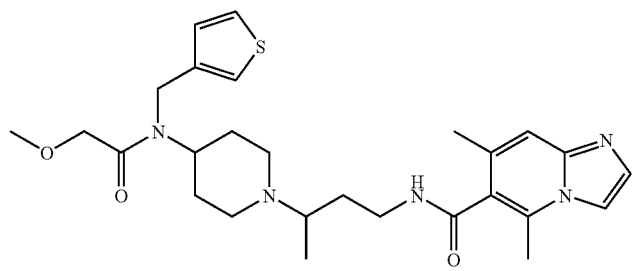

5,7-Dimethyl-imidazo[1,2-a]pyridine-6-carboxylic acid (3-{4-[(2-methoxy-acetyl)-thiophen-3-ylmethyl-amino]-piperidin-1-yl}-butyl)-amide

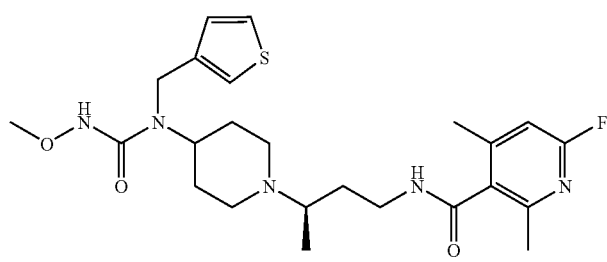

2,4-Dimethyl-6-fluoro-N-{(R)-3-[4-(3-methoxy-1-thiophen-3-ylmethyl-ureido)-piperidin-1-yl]-butyl}-nicotinamide

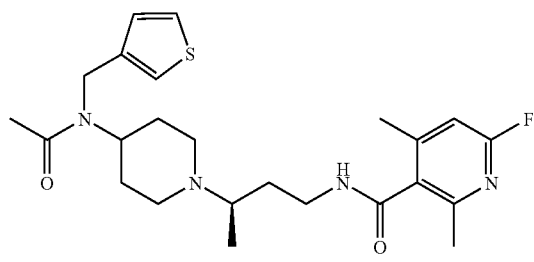

N-{(R)-3-[4-(Acetyl-thiophen-3-ylmethyl-amino)-piperidin-1-yl]-butyl}-6-fluoro-2,4-dimethyl-nicotinamide -continued

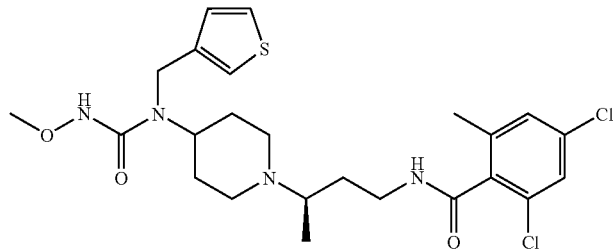

2,6-Dichloro-4-methyl-N-{(R)-3-[4-(3-methoxy-1-thiophen-3-ylmethyl-ureido)-piperidin-1-yl]-butyl}-benzamide

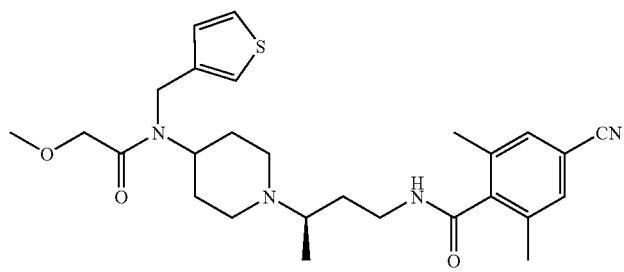

4-Cyano-N-((R)-3-{4-[(2-methoxy-acetyl)-thiophen-3-ylmethyl-amino]-piperidin-1-yl}-butyl)-2,6-dimethyl-benzamide

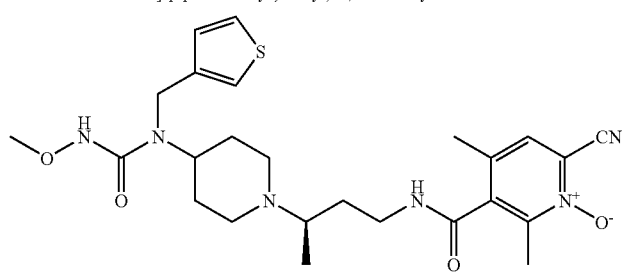

6-Cyano-2,4-dimethyl-N-{(R)-3-[4-(3-methoxy-1-thiophen-3-ylmethyl-ureido)-piperidin-1-yl]-butyl}-nicotinamide-N-oxide

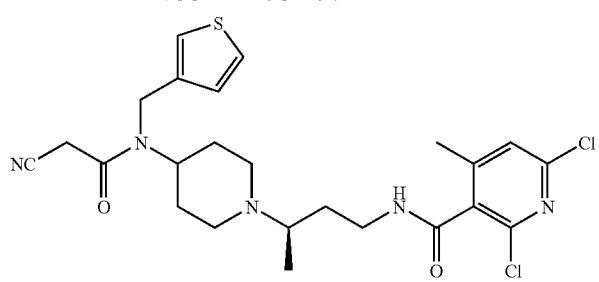

2,6-Dichloro-N-((R)-3-{4-[(2-cyano-acetyl)-thiophen-3-ylmethyl-amino]-piperidin-1-yl}-butyl)-4-methyl-nicotinamide

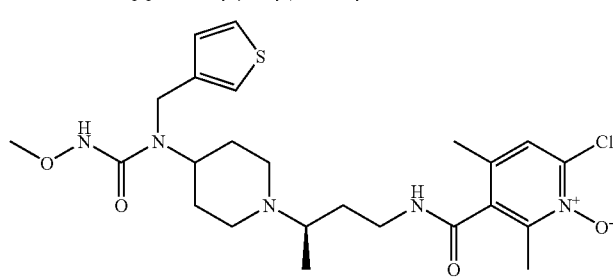

6-Chloro-2,4-dimethyl-N-{(R)-3-[4-(3-methoxy-1-thiophen-3-ylmethyl-ureido)-piperidin-1-yl]-butyl}-nicotinamide-N-oxide -continued

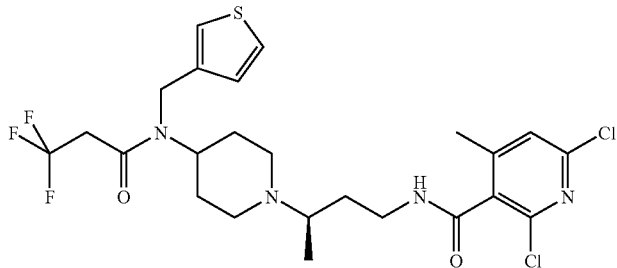

2,6-Dichloro-4-methyl-N-((R)-3-{4-[thiophen-3-ylmethyl-
(3,3,3-trifluoro-propionyl)-amino]-piperidin-1-yl}-butyl)-nicotinamide

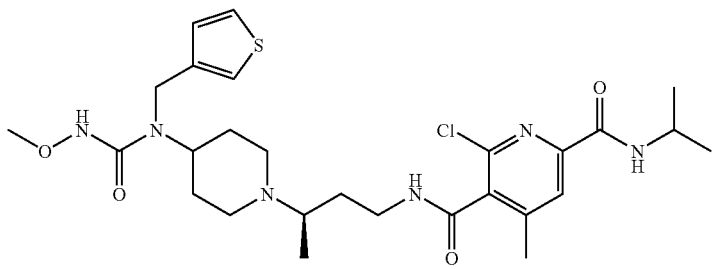

6-Chloro-4-methyl-pyridine-2,5-dicarboxylic acid 2-isopropylamide 5-
({(R)-3-[4-(3-methoxy-1-thiophen-3-ylmethyl-ureido)-piperidin-1-yl]-
butyl}-amide)

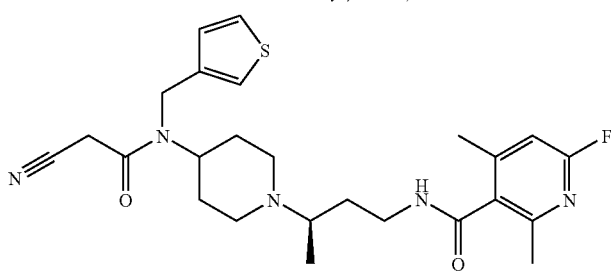

N-((R)-3-{4-[2-Cyano-acetyl)-thiophen-3-ylmethyl-amino]-
piperidin-1-yl}-butyl)-6-fluoro-2,4-dimethyl-nicotinamide

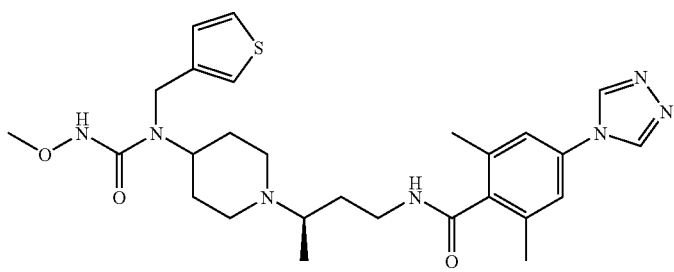

N-{(R)-3-[4-(3-methoxy-1-thiophen-3-ylmethyl-ureido)-
piperidin-1-yl]-butyl}-2,6-dimethyl-4-1,2,4-triazol-4-yl-benzamide

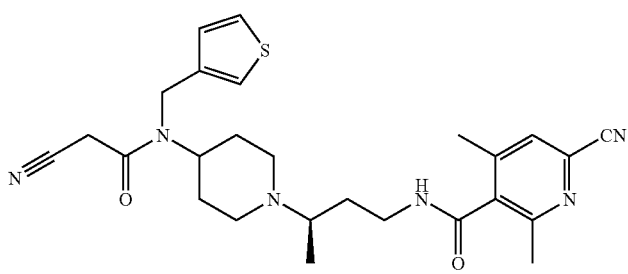

6-Cyano-N-((R)-3-{4-[(2-cyano-acetyl)-thiophen-3-ylmethyl-
amino]-piperidin-1-yl}-butyl)-2,4-dimethyl-nicotinamide -continued

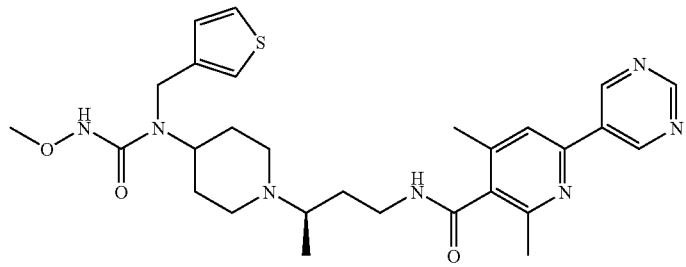

N-{(R)-3-[4-(3-methoxy-1-thiophen-3-ylmethyl-ureido)-piperidin-1-yl]-butyl}-2,4-dimethyl-6-pyrimidin-5-yl-nicotinamide

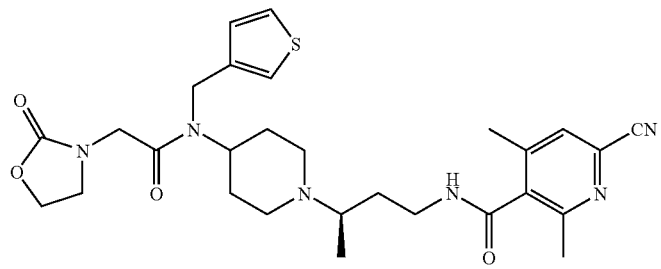

6-Cyano-2,4-dimethyl-N-[(R)-3-(4-{[2-(2-oxo-oxazolidin-3-yl)-acetyl]-thiophen-3-ylmethyl-amino}-piperidin-1-yl)-butyl]-nicotinamide

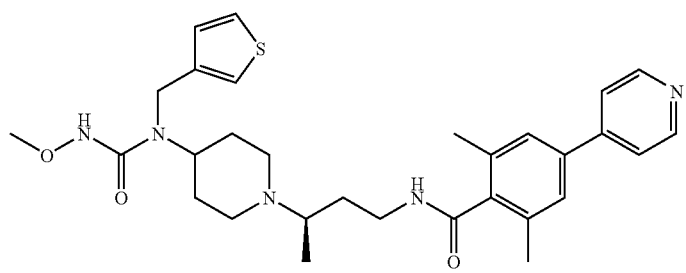

N-{(R)-3-[4-(3-methoxyl-1-thiophen-3-ylmethyl-ureido)-piperidin-1-yl]-butyl}-2,6-dimethyl-4-pyridin-4-yl-benzamide

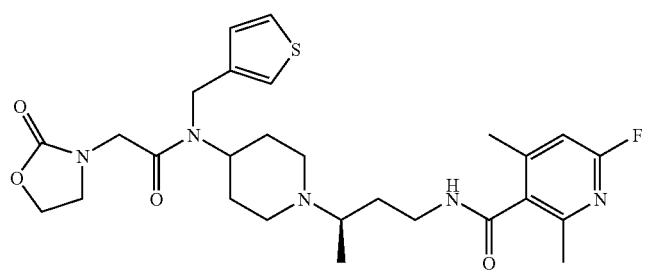

6-Fluoro-2,4-dimethyl-N-[(R)-3-(4-{[2-(2-oxo-oxazolidin-3-yl)-acetyl]-thiophen-3-ylmethyl-amino}-piperidin-1-yl)-butyl]-nicotinamide

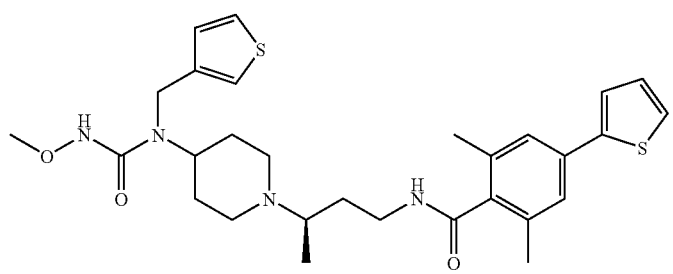

N-{(R)-3-[4-(3-methoxyl-1-thiophen-3-ylmethyl-ureido)-piperidin-1-yl]-butyl}-2,6-dimethyl-4-thiophen-2-yl-benzamide -continued

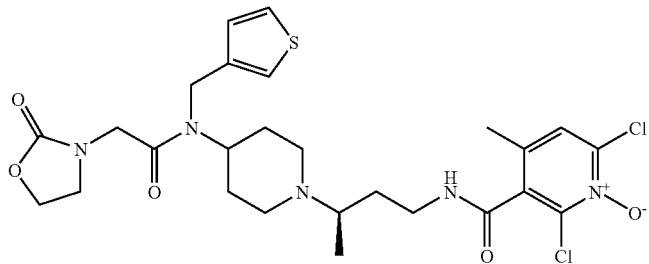

2,6-Dichloro-4-methyl-N-[(R)-3-(4-{[2-(2-oxo-oxazolidin-3-yl)-acetyl]-thiophen-3-ylmethyl-amino}-piperidin-1-yl)-butyl]-nicotinamide-N-oxide

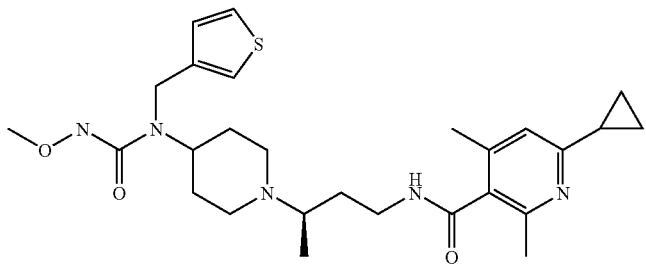

6-Cyclopropyl-N-{(R)-3-[4-(3-ethyl-1-thiophen-3-ylmethyl-ureido)-piperidin-1-yl]-butyl}-2,4-dimethyl-nicotinamide

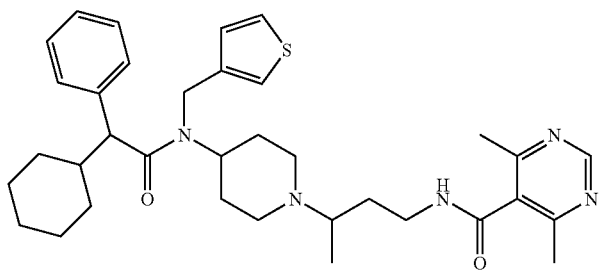

4,6-Dimethyl-pyrimidine-5-carboxylic acid (3-{4-[(2-cyclohexyl-2-phenyl-acetyl)-thiophen-3-ylmethyl-amino]-piperidin-1-yl}-butyl)-amide

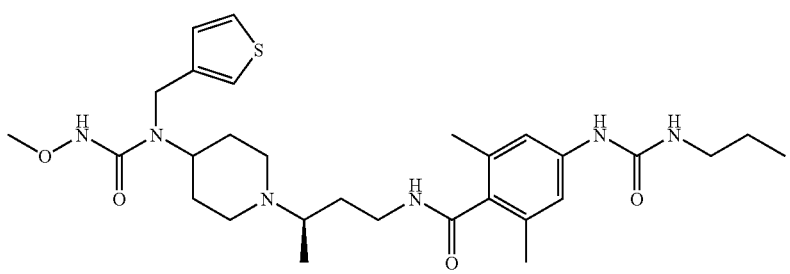

2,6-Dimethyl-N-{(R)-3-[4-(3-methoxy-1-thiophen-3-ylmethyl-ureido)-piperidin-1-yl]-butyl}-4-(3-propyl-ureido)-benzamide

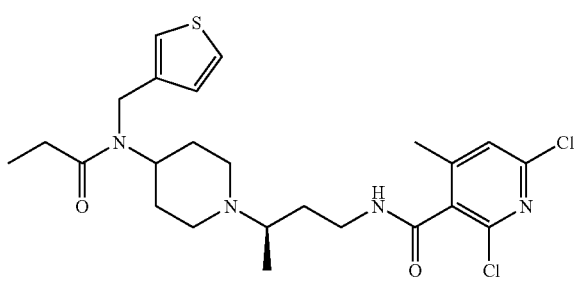

2,6-Dichloro-4-methyl-N-{(R)-3-[4-(propionyl-thiophen-3-ylmethyl-amino)-piperidin-1-yl]-butyl}-nicotinamide -continued

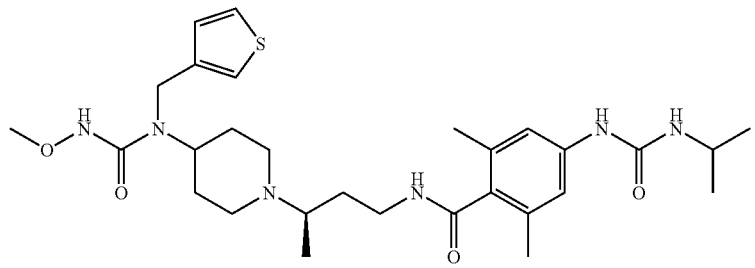

4-(3-Isopropyl-ureido)-2,6-dimethyl-N-{(R)-3-[4-(3-methoxy-1-thiophen-3-ylmethyl-ureido)-piperidin-1-yl]-butyl}-benzamide

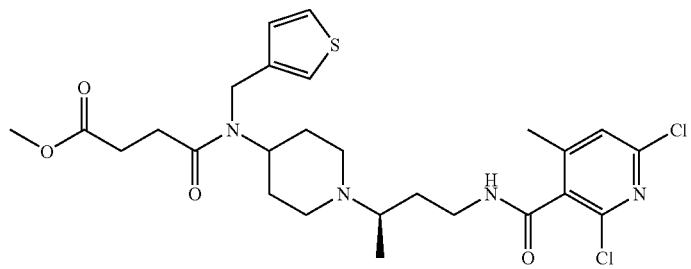

N-(1-{(R)-3-[(2,6-Dichloro-4-methyl-pyridine-3-carbonyl)-amino]-1-methyl-propyl}-piperidin-4-yl)-N-thiophen-3-ylmethyl-succinamic acid methyl ester

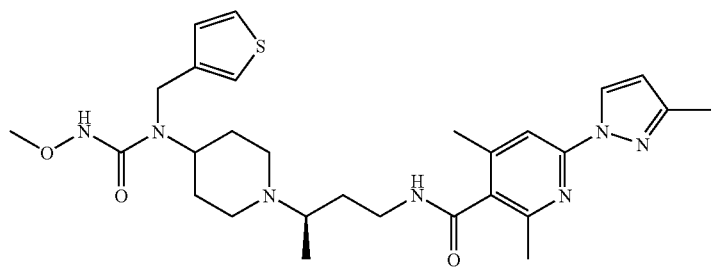

N-{(R)-3-[4-(3-methoxy-1-thiophen-3-ylmethyl-ureido)-piperidin-1-yl]-butyl}-2,4-dimethyl-6-(3-methyl-pyrazol-1-yl)-nicotinamide

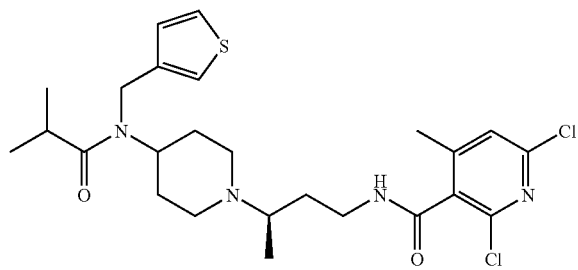

2,6-Dichloro-N-{(R)-3-[4-(isobutyryl-thiophen-3-ylmethyl-amino)-piperidin-1-yl]-butyl}-4-methyl-nicotinamide

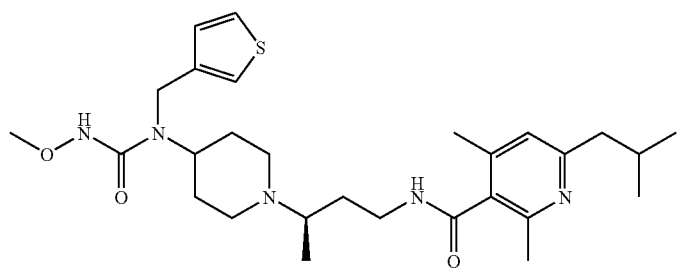

N-{(R)-3-[4-(3-methoxy-1-thiophen-3-ylmethyl-ureido)-piperidin-1-yl]-butyl}-6-isobutyl-2,4-dimethyl-nicotinamide -continued

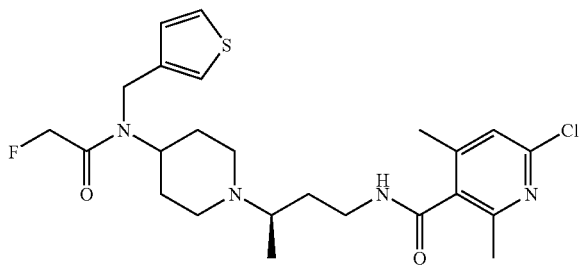

6-Chloro-N-((R)-3-{4-[(2-fluoro-acetyl)-thiophen-3-ylmethyl-amino]-piperidin-1-yl}-butyl)-2,4-dimethyl-nicotinamide

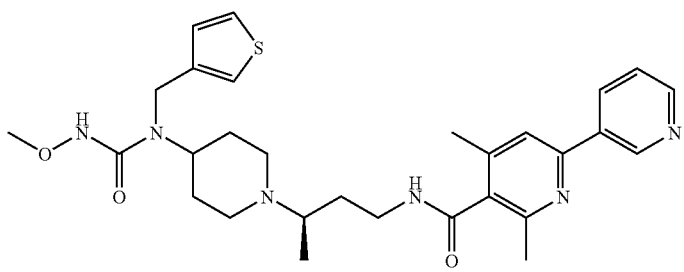

4,6-Dimethyl-[2,3']bipyridinyl-5-carboxylic acid {(R)-3-[4-(3-methoxyl-1-thiophen-3-ylmethyl-ureido)-piperidin-1-yl]-butyl}-amide

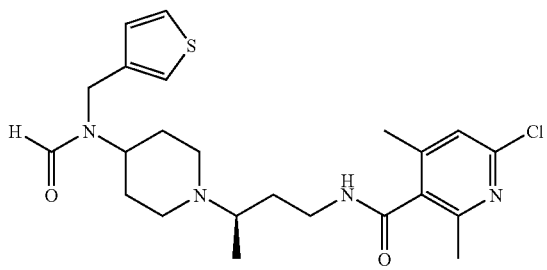

6-Chloro-N-{(R)-3-[4-(formyl-thiophen-3-ylmethyl-amino)-piperidin-1-yl]-butyl}-2,4-dimethyl-nicotinamide

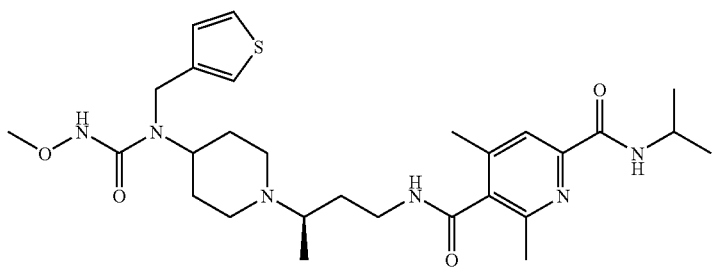

4,6-Dimethyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

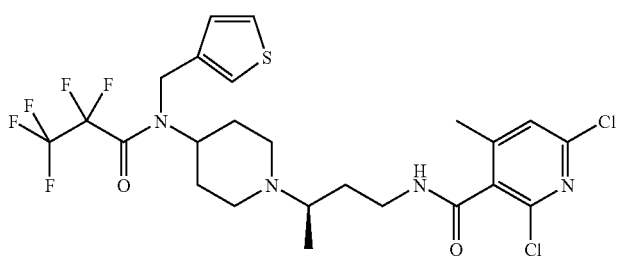

2,6-Dichloro-4-methyl-N-((R)-3-{4-[(2,2,3,3,3-pentafluoro-propionyl)-thiophen-3-ylmethyl-amino]-piperidin-1-yl}-butyl)-nicotinamide -continued

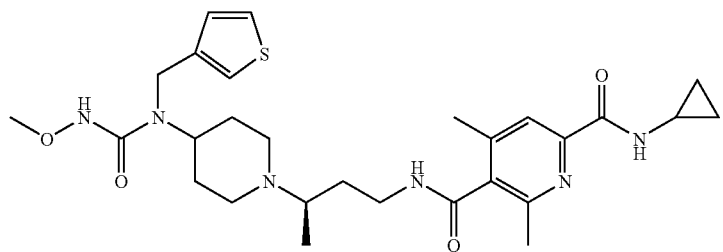

4,6-Dimethyl-pyridine-2,5-dicarboxylic acid 2-cyclopropylamide 5-
({(R)-3-[4-(3-methoxy-1-thiophen-3-ylmethyl-ureido)-piperidin-1-yl]-butyl}-amide)

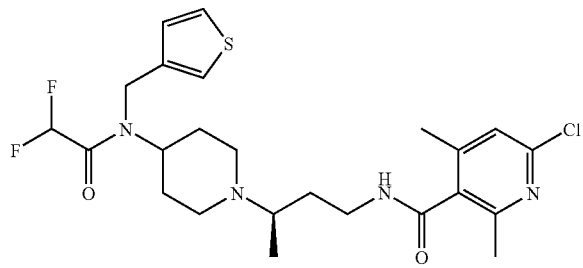

6-Chloro-N-((R)-3-{4-[(2,2,-difluoro-acetyl)-thiophen-
3-ylmethyl-amino]-piperidin-1-yl}-butyl)-2,4-dimethyl-nicotinamide

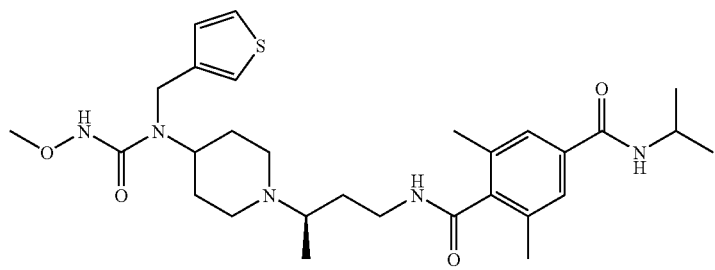

N-{(R)-3-[4-(3-methoxy-1-thiophen-3-ylmethyl-ureido)-piperidin-1-yl]-
butyl}-N'-isopropyl-2,6-dimethyl-terephthalamide

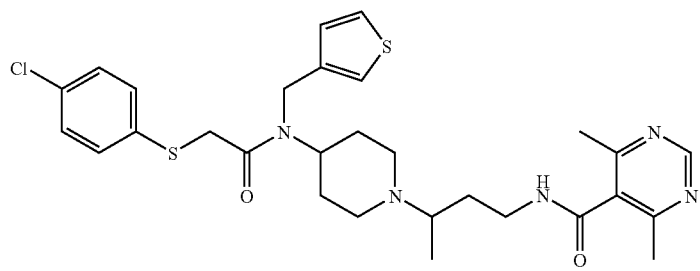

4,6-Dimethyl-pyrimidine-5-carboxylic acid [3-(4-{[2-(4-chloro-phenylsulfanyl)-
acetyl]-thiophen-3-ylmethyl-amino}-piperidin-1-yl)-butyl]-amide

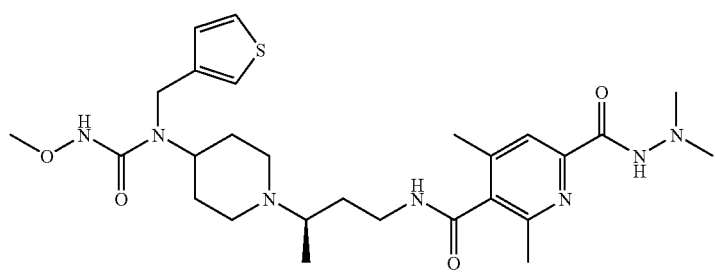

6-(N',N'-Dimethyl-hydrazinocarbonyl)-2,4-dimethyl-N-{(R)-3-[4-(3-methoxy-
1-thiophen-3-ylmethyl-ureido)-piperidin-1-yl]-butyl}-nicotinamide

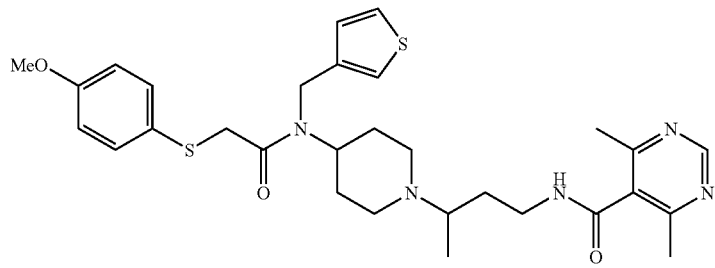

4,6-Dimethyl-pyrimidine-5-carboxylic acid [3-(4-{[2-(4-methoxy-phenylsulfanyl)-acetyl]-thiophen-3-ylmethyl-amino}-piperidin-1-yl)-butyl]-amide

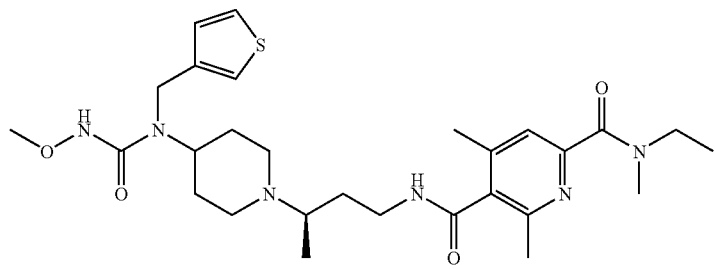

4,6-Dimethyl-pyridine-2,5-dicarboxylic acid 2-(ethyl-methyl-amide) 5-({(R)-3-[4-(3-methoxy-1-thiophen-3-ylmethyl-ureido)-piperidin-1-yl]-butyl}-amide)

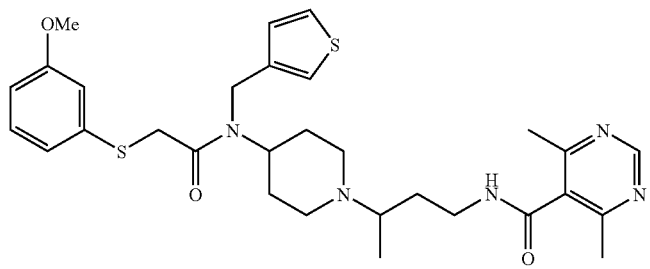

4,6-Dimethyl-pyrimidine-5-carboxylic acid [3-(4-{[2-(3-methoxy-phenylsulfanyl)-acetyl]-thiophen-3-ylmethyl-amino}-piperidin-1-yl)-butyl]-amide

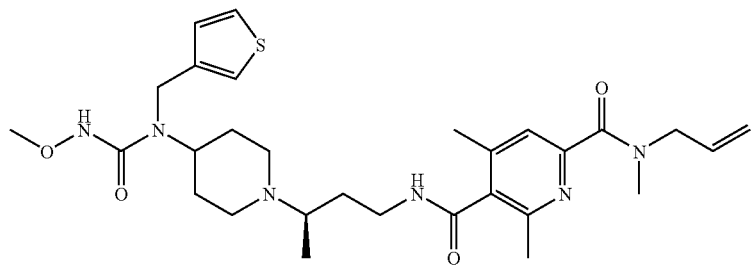

4,6-Dimethyl-pyridine-2,5-dicarboxylic acid 2-(allyl-methyl-amide) 5-({(R)-3-[4-(3-methoxy-1-thiophen-3-ylmethyl-ureido)-piperidin-1-yl]-butyl}-amide)

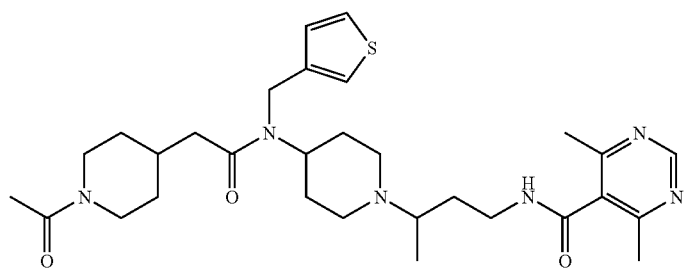

4,6-Dimethyl-pyrimidine-5-carboxylic acid [3-(4-{[2-(1-acetyl-piperidin-4-yl)-acetyl]-thiophen-3-ylmethyl-amino}-piperidin-1-yl)-butyl]-amide

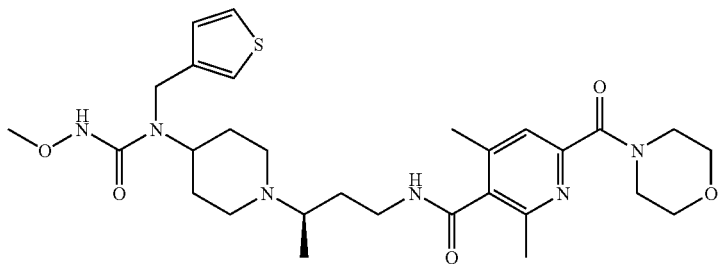

2,4-Dimethyl-6-(morpholine-4-carbonyl)-N-{(R)-3-[4-(3-methoxy-1-thiophen-3-ylmethyl-ureido)-piperidin-1-yl]-butyl}-nicotinamide

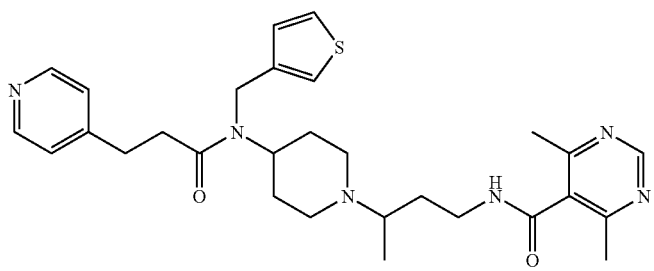

4,6-Dimethyl-pyrimidine-5-carboxylic acid (3-{4-[(3-pyridine-4-yl-propionyl)-thiophen-3-ylmethyl-amino]-piperidin-1-yl}-butyl)-amide

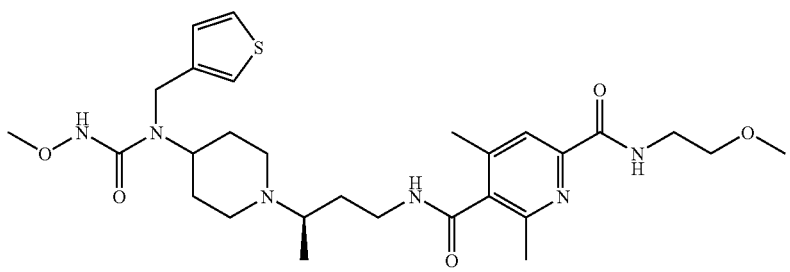

4,6-Dimethyl-pyridine-2,5-dicarboxylic acid 2-[(2-methoxy-ethyl)-amide] 5-({(R)-3-[4-(3-methoxy-1-thiophen-3-ylmethyl-ureido)-piperidin-1-yl]-butyl}-amide)

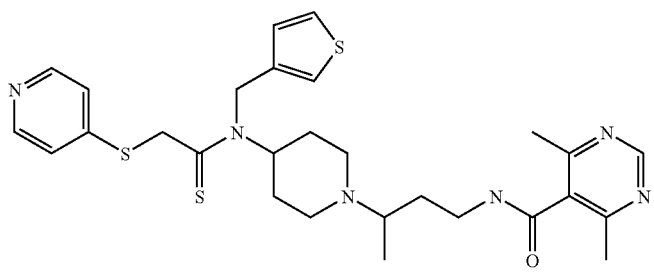

4,6-Dimethyl-pyrimidine-5-carboxylic acid [3-(4-{[2-(pyridin-4-ylsulfanyl)thioacetyl]-thiophen-3-ylmethyl-amino}-piperidin-1-yl)-butyl]-amide

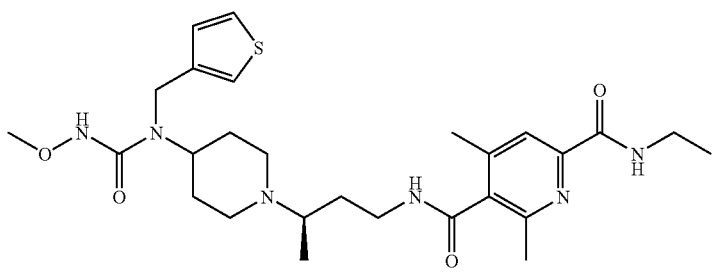

4,6-Dimethyl-pyridine-2,5-dicarboxylic acid 2-ethylamide 5-({(R)-3-[4-(3-methoxy-1-thiophen-3-ylmethyl-ureido)-piperidin-1-yl]-butyl}-amide)

-continued

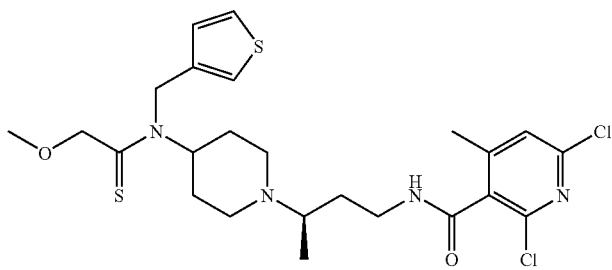

2,6-Dichloro-N-((R)-3-{4-[(2-methoxy-thioacetyl)-thiophen-3-ylmethyl-
amino]-piperidin-1-yl}-butyl)-4-methyl-nicotinamide

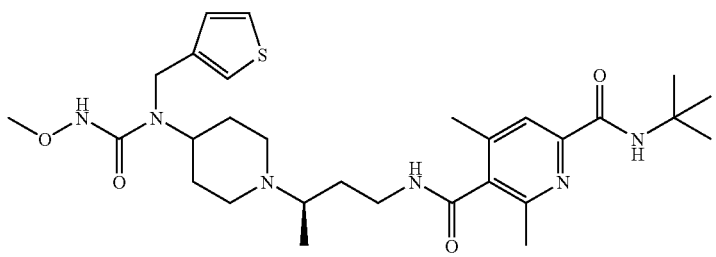

4,6-Dimethyl-pyridine-2,5-dicarboxylic acid 2-tert-butylamide 5-({(R)-3-[4-(3-
methoxy-1-thiophen-3-ylmethyl-ureido)-piperidin-1-yl]-butyl}-amide)

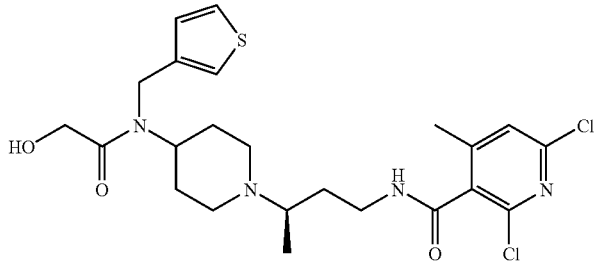

2,6-Dichloro-N-((R)-3-{4-[(2-hydroxy-acetyl)-thiophen-3-ylmethyl-amino]-
piperidin-1-yl}-butyl)-4-methyl-nicotinamide

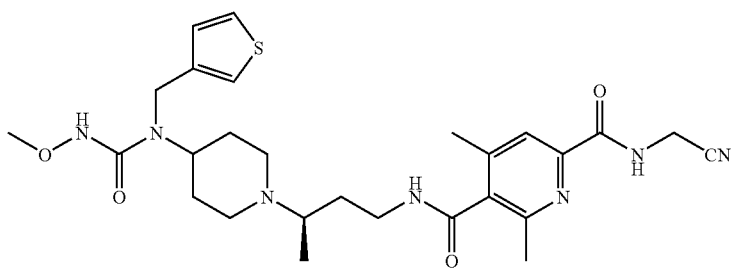

4,6-Dimethyl-pyridine-2,5-dicarboxylic acid 2-cyanomethyl 5-({(R)-3-[4-(3-
methoxy-1-thiophen-3-ylmethyl-ureido)-piperidin-1-yl]-butyl}-amide)

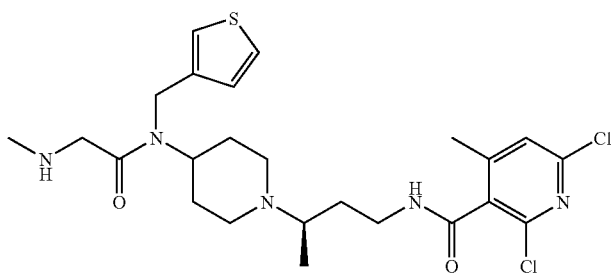

2,6-Dichloro-4-methyl-N-((R)-3-{4-[(2-methylamino-acetyl)-thiophen-3-
ylmethyl-amino]-piperidin-1-yl}-butyl)-nicotinamide -continued

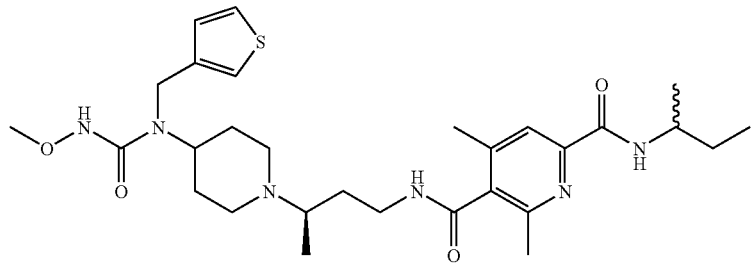

4,6-Dimethyl-pyridine-2,5-dicarboxylic acid 2-sec-butyl 5-({(R)-3-[4-(3-methoxy-1-thiophen-3-ylmethyl-ureido)-piperidin-1-yl]-butyl}-amide)

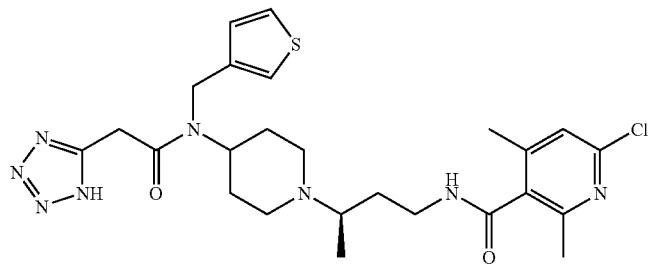

6-Chloro-2,4-dimethyl-N-((R)-3-{4-[(2-1H-tetrazol-5-yl-acetyl)-thiophen-3-ylmethyl-amino]-piperidin-1-yl}-butyl)-nicotinamide

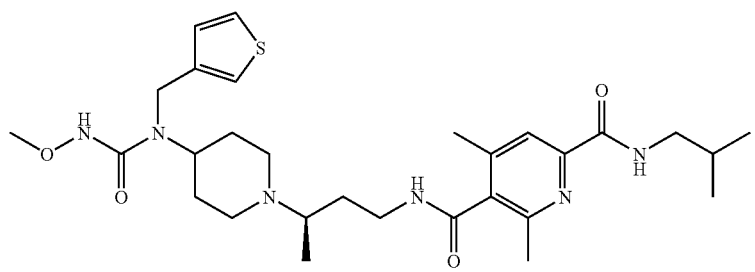

4,6-Dimethyl-pyridine-2,5-dicarboxylic acid 2-isobutyl 5-({(R)-3-[4-(3-methoxy-1-thiophen-3-ylmethyl-ureido)-piperidin-1-yl]-butyl}-amide)

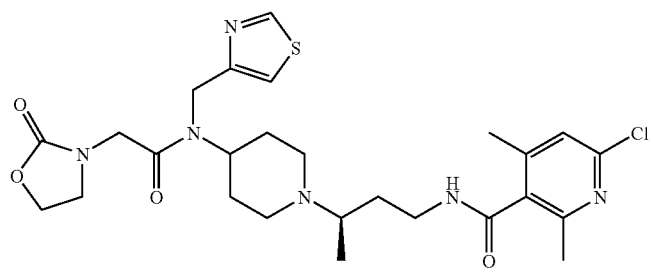

6-Chloro-2,4-dimethyl-N-[(R)-3-(4-{[2-(2-oxo-oxazolidin-3-yl)-acetyl]-thiazol-4-ylmethyl-amino}-piperidin-1-yl)-butyl]-nicotinamide

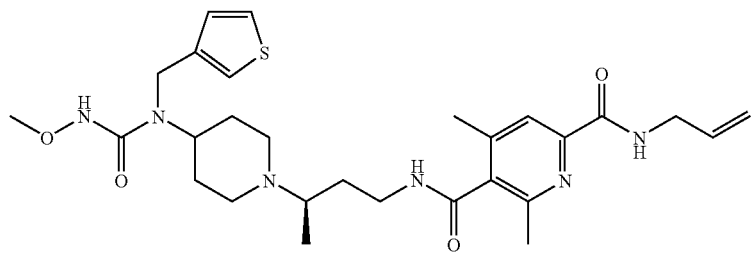

4,6-Dimethyl-pyridine-2,5-dicarboxylic acid 2-allyl 5-({(R)-3-[4-(3-methoxy-1-thiophen-3-ylmethyl-ureido)-piperidin-1-yl]-butyl}-amide)

-continued

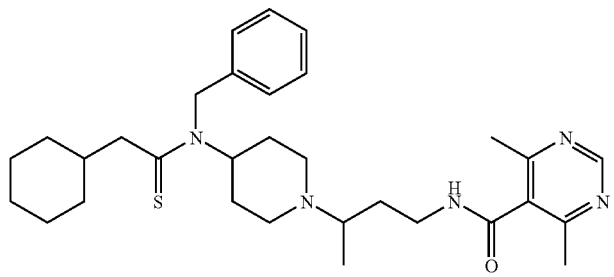

4,6-Dimethyl-pyrimidine-5-carboxylic acid (3-{4-[benzyl-(2-cyclohexyl-thioacetyl)-amino]-piperidin-1-yl}-butyl)-amide

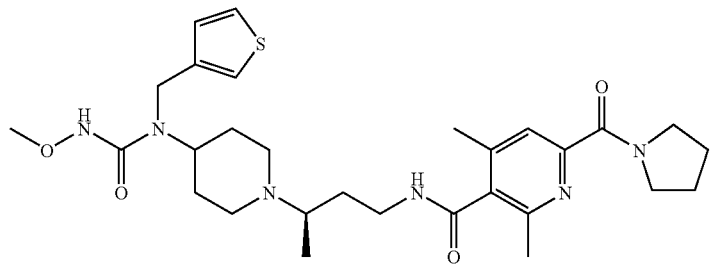

2,4-Dimethyl-N-{(R)-3-[4-(3-methyl-1-thiophen-3-ylmethyl-ureido)-piperidin-1-yl]-butyl}-6-(pyrrolidine-1-carbonyl)-nicotinamide

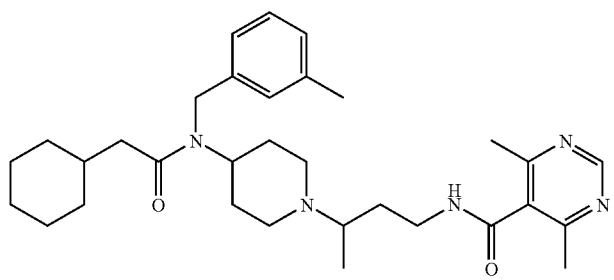

4,6-Dimethyl-pyrimidine-5-carboxylic acid (3-{4-[(2-cyclohexyl-acetyl)-(3-methyl-benzyl)-amino]-piperidin-1-yl}-butyl)-amide

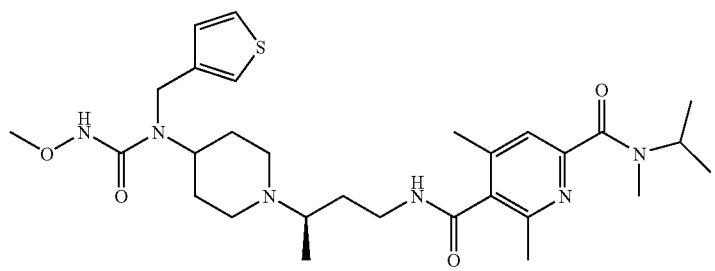

4,6-Dimethyl-pyridine-2,5-dicarboxylic acid 2-(isopropyl-methyl-amide) 5-({(R)-3-[4-(3-methoxy-1-thiophen-3-ylmethyl-ureido)-piperidin-1-yl]-butyl}-amide)

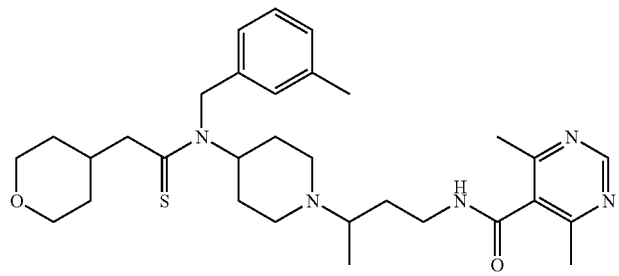

4,6-Dimethyl-pyrimidine-5-carboxylic acid (3-{4-[(3-methylbenzyl)-(2-tetrahydropyran-4-yl-thioacetyl)-amino]-piperidin-1-yl}-butyl)-amide

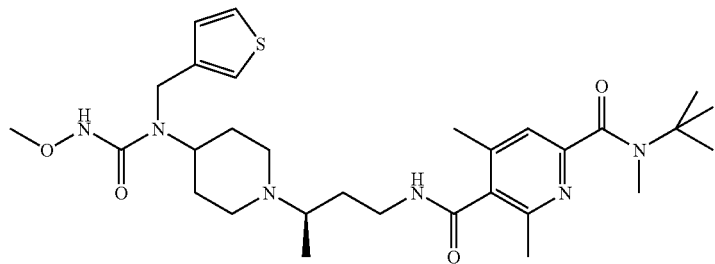

4,6-Dimethyl-pyridine-2,5-dicarboxylic acid 2-(methyl-tert-butyl-amide) 5-({(R)-3-[4-(3-methoxy-1-thiophen-3-ylmethyl-ureido)-piperidin-1-yl]-butyl}-amide)

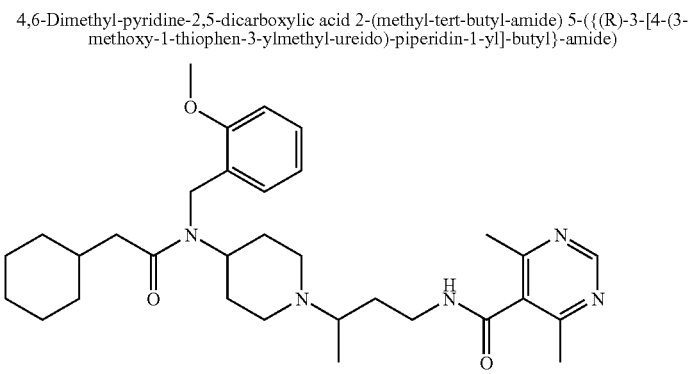

4,6-Dimethyl-pyrimidine-5-carboxylic acid (3-{4-[(2-cyclohexyl-acetyl)-(2-methoxy-benzyl)-amino]-piperidin-1-yl}-butyl)-amide

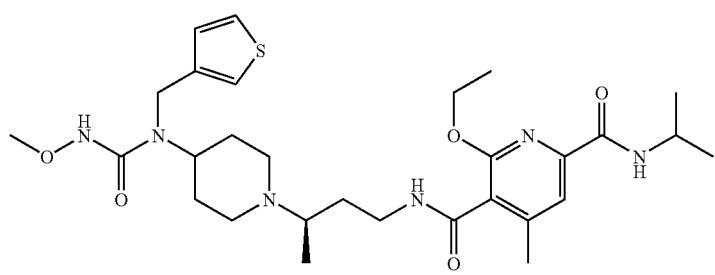

6-Ethoxy-4-methyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

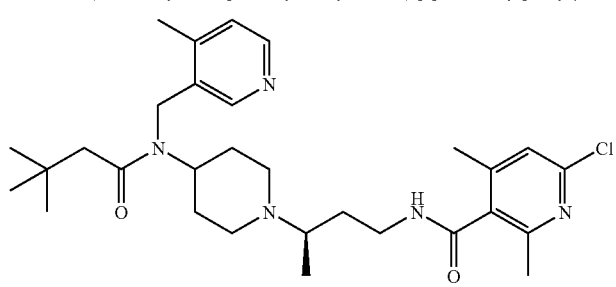

6-Chloro-N-((R)-3-{4-[(3,3-dimethyl-butyryl)-(4-methyl-pyridin-3-ylmethyl)-amino]-piperidin-1-yl}-butyl)-2,4-dimethyl-nicotinamide

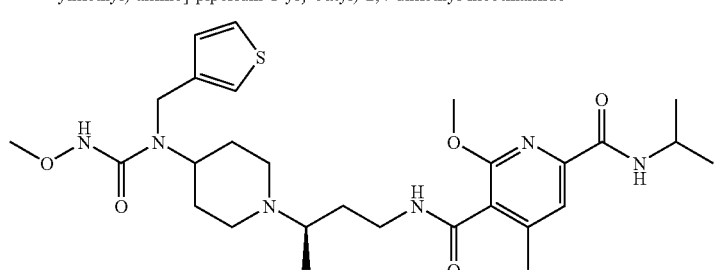

6-Methoxy-4-methyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

-continued

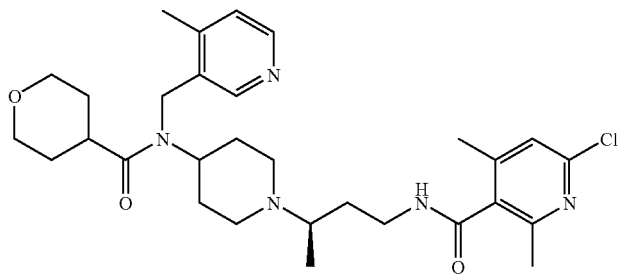

6-Chloro-2,4-dimethyl-N-((R)-3-{4-[(4-methyl-pyridin-3-ylmethyl)-
(tetrahydro-pyran-4-carbonyl)-amino]-piperidin-1-yl}-butyl)-nicotinamide

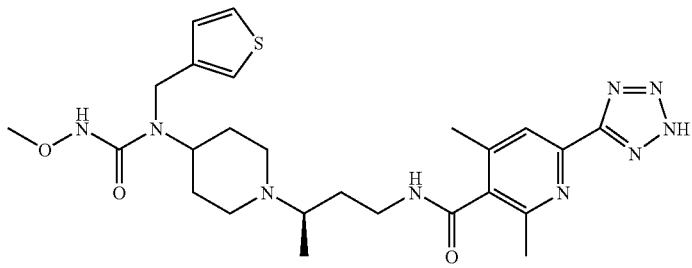

2,4-Dimethyl-N-{(R)-3-[4-(3-methoxy-1-thiophen-3-ylmethyl-ureido)-
piperidin-1-yl]-butyl}-6-(2H-tetrazol-5-yl)-nicotinamide

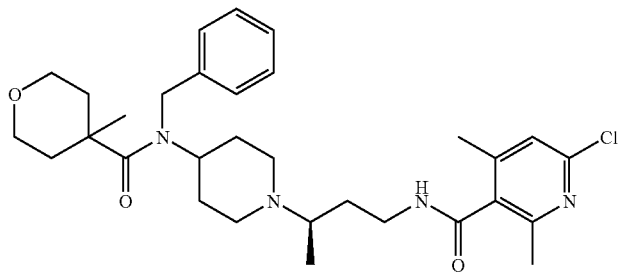

N-((R)-3-{4-[Benzyl-(4-methyl-tetrahydro-pyran-4-carbonyl)-amino]-
piperidin-1-yl}-butyl)-6-chloro-2,4-dimethyl-nicotinamide

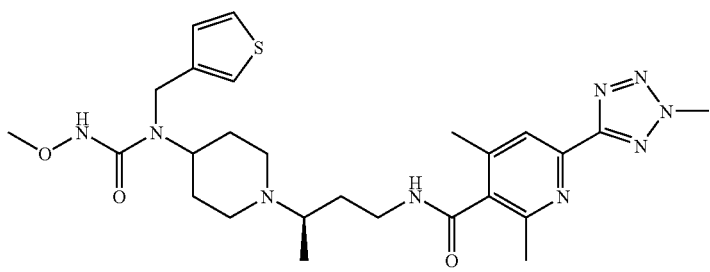

2,4-Dimethyl-6-(2-methyl-2H-tetrazol-5-yl)-N-{(R)-3-[4-(3-methoxy-1-
thiophen-3-ylmethyl-ureido)-piperidin-1-yl]-butyl}-nicotinamide

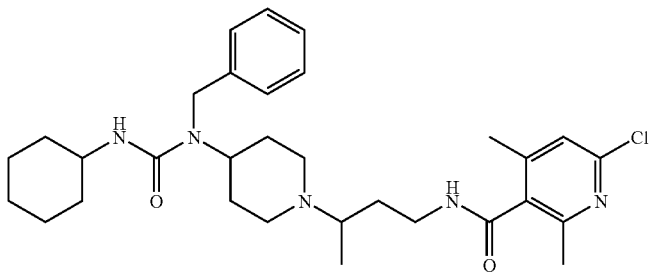

N-{3-[4-(1-Benzyl-3-cyclohexyl-ureido)-piperidin-1-yl]-butyl}-
6-chloro-2,4-dimethyl-nicotinamide -continued

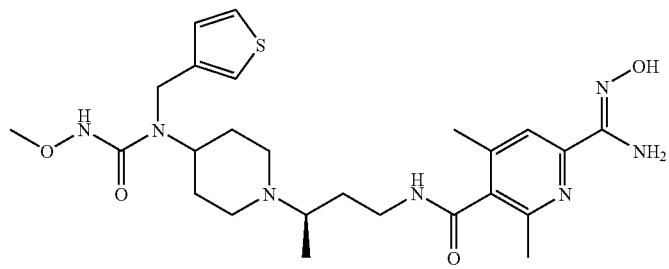

N-{(R)-3-[4-(3-methoxy-1-thiophen-3-ylmethyl-ureido)-piperidin-1-yl]-butyl}-6-
(N-hydroxycarbamimidoyl)-2,4-dimethyl-nicotinamide

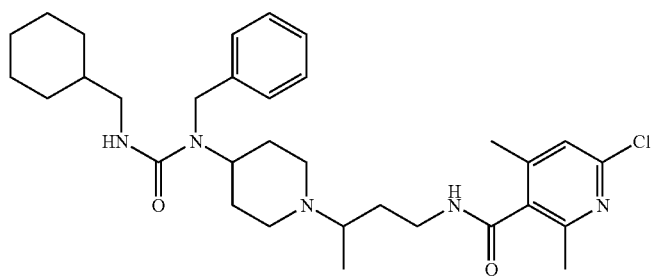

N-{3-[4-(1-Benzyl-3-cyclohexylmethyl-ureido)-piperidin-1-yl]-butyl}-
6-chloro-2,4-dimethyl-nicotinamide

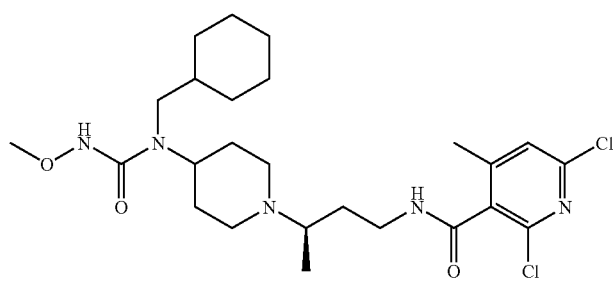

2,6-Dichloro-N-{(R)-3-[4-(1-cyclohexylmethyl-3-methoxy-ureido)-
piperidin-1-yl]-butyl}-4-methyl-nicotinamide

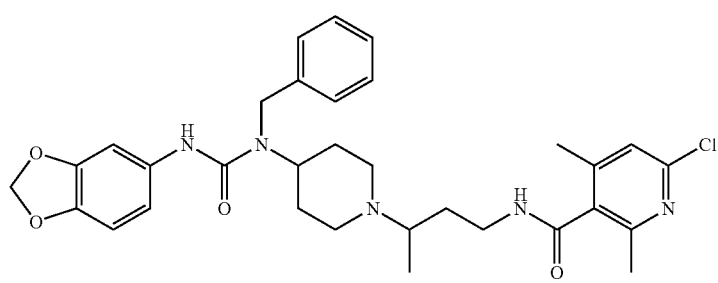

N-{3-[4-(3-Benzo[1,3]dioxol-5-yl-1-benzyl-ureido)-piperidin-1-yl]-butyl}-
6-chloro-2,4-dimethyl-nicotinamide

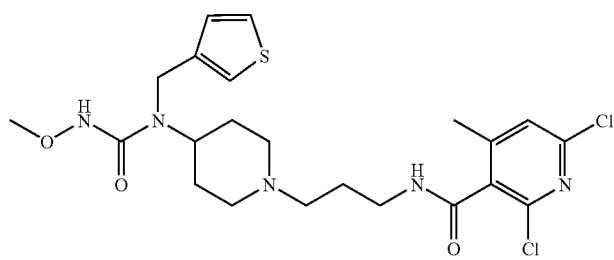

2,6-Dichloro-4-methyl-N-{3-[4-(3-methoxy-1-thiophen-3-ylmethyl-ureido)-
piperidin-1-yl]-propyl}-nicotinamide

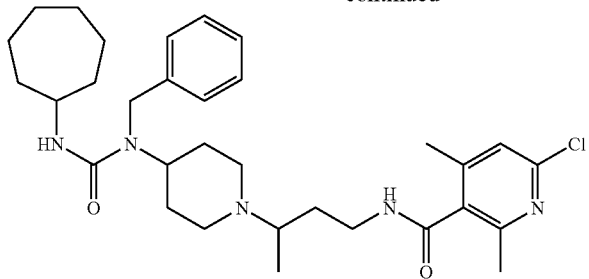

N-{3-[4-(1-Benzyl-3-cycloheptyl-ureido)-piperidin-1-yl]-
butyl}-6-chloro-2,4-dimethyl-nicotinamide

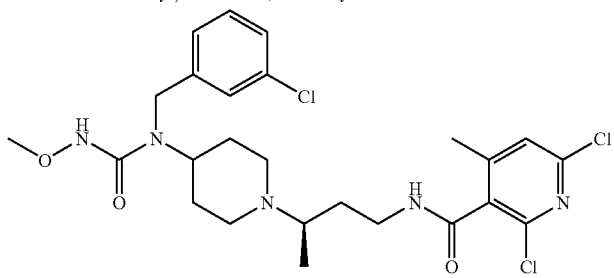

2,6-Dichloro-N-((R)-3-{4-[1-(3-chloro-benzyl)-3-methoxy-
ureido]-piperidin-1-yl}-butyl)-4-methyl-nicotinamide

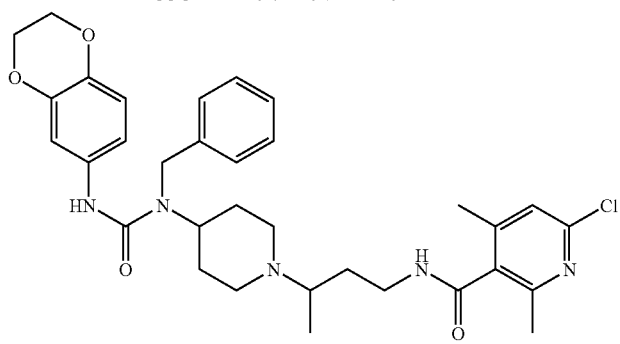

N-(3-{4-[1-Benzyl-3-(2,3-dihydro-benzo[1,4]dioxin-6-yl)-ureido]-piperidin-
1-yl}-butyl)-6-chloro-2,4-dimethyl-nicotinamide

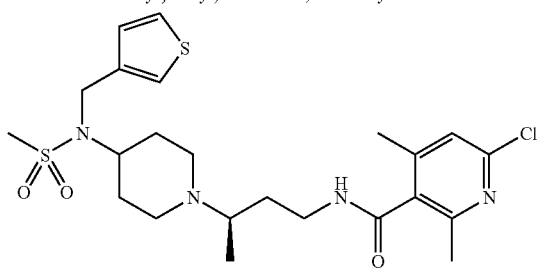

6-Chloro-N-{(R)-3-[4-(methanesulfonyl-thiophen-3-ylmethyl-amino)-
piperidin-1-yl]-butyl}-2,4-dimethyl-nicotinamide

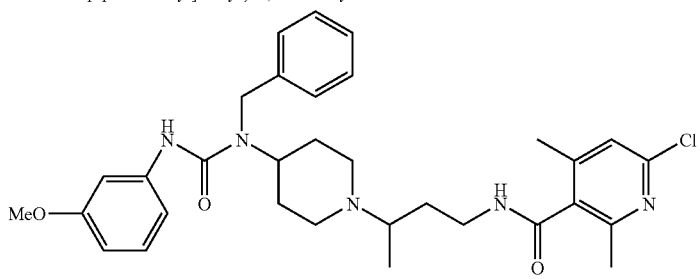

N-(3-{4-[1-Benzyl-3-(3-methoxy-phenyl)-ureido]-piperidin-1-yl}-
butyl)-6-chloro-2,4-dimethyl-nicotinamide -continued

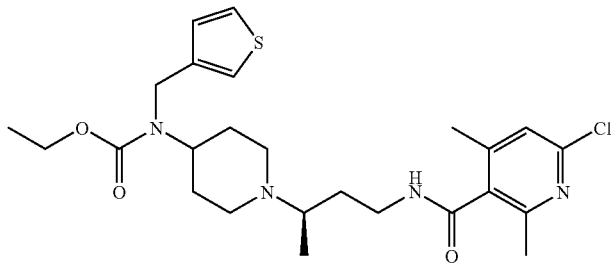

(1-(R)-{3-[(6-Chloro-2,4-dimethyl-pyridine-3-carbonyl)-amino]-1-methyl-propyl}-piperidin-4-yl)-thiophen-3-ylmethyl-carbamic acid ethyl ester

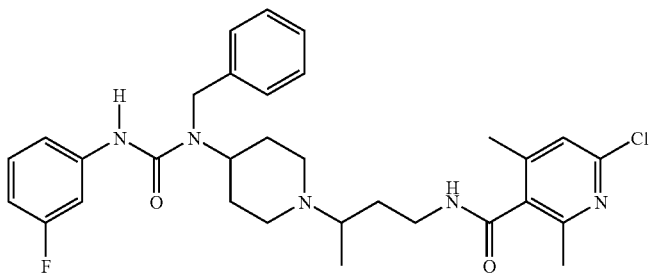

N-(3-{4-[1-Benzyl-3-(3-fluoro-phenyl)-ureido]-piperidin-1-yl}-butyl)-6-chloro-2,4-dimethyl-nicotinamide

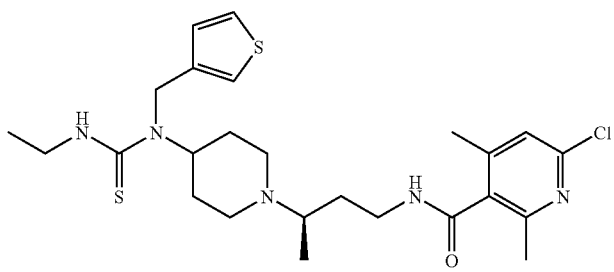

6-Chloro-N-{(R)-3-[4-(3-ethyl-1-thiophen-3-ylmethyl-thioureido)-piperidin-1-yl]-butyl}-2,4-dimethyl-nicotinamide

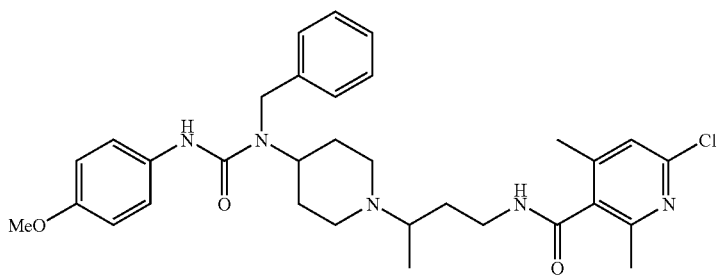

N-(3-{4-[1-Benzyl-3-(4-methoxy-phenyl)-ureido]-piperidin-1-yl}-butyl)-6-chloro-2,4-dimethyl-nicotinamide

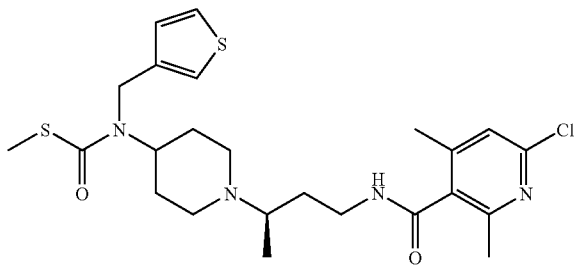

(1-{(R)-3-[(6-Chloro-2,4-dimethyl-pyridine-3-carbonyl)-amino]-1-methyl-propyl}-piperidin-4-yl)-thiophen-3-ylmethyl-thiocarbamic-acid S-methyl ester -continued

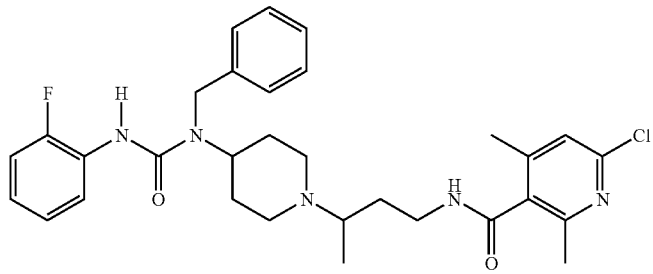

N-(3-{4-[1-Benzyl-3-(2-fluoro-phenyl)-ureido]-piperidin-1-yl}-butyl)-
6-chloro-2,4-dimethyl-nicotinamide

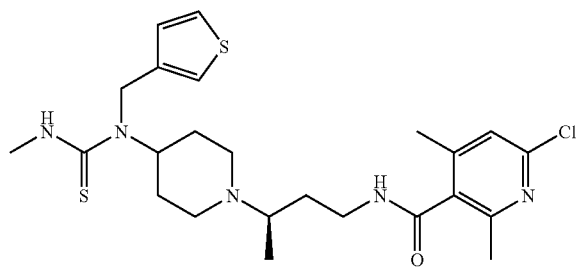

6-Chloro-2,4-dimethyl-N-{(R)-3-[4-(3-methyl-1-thiophen-3-ylmethyl-
thioureido)-piperidin-1-yl]-butyl}-nicotinamide

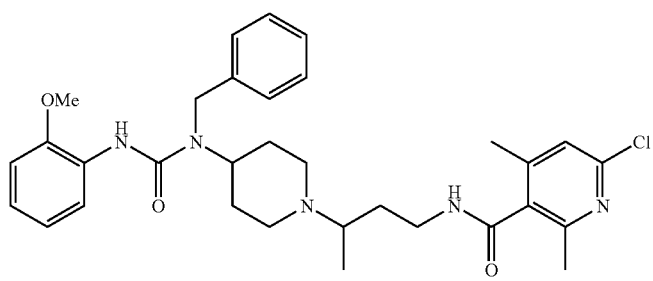

N-(3-{4-[1-Benzyl-3-(2-methoxy-phenyl)-ureido]-piperidin-1-yl}-butyl)-
6-chloro-2,4-dimethyl-nicotinamide

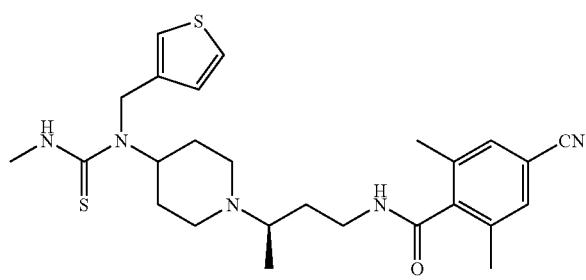

4-Cyano-2,6-dimethyl-N-{(R)-3-[4-(3-methyl-1-thiophen-3-ylmethyl-
thioureido)-piperidin-1-yl]-butyl}-benzamide

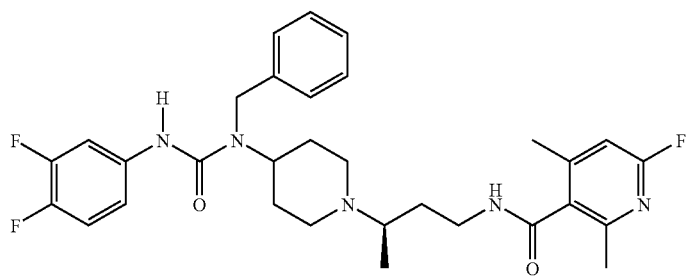

N-((R)-3-{4-[1-Benzyl-3-(3,4-difluoro-phenyl)-ureido]-piperidin-1-yl}-butyl)-
6-fluoro-2,4-dimethyl-nicotinamide

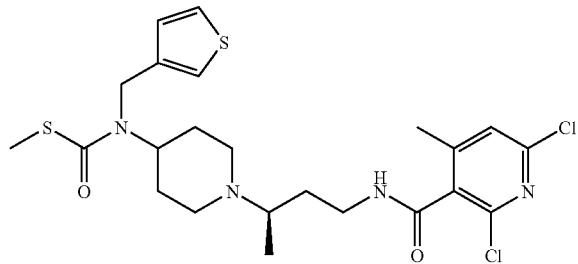

(1-{(R)-3-[(2,6-Dichloro-4-methyl-pyridine-3-carbonyl)-amino]-1-methyl-
propyl}-piperidin-4-yl)-thiophen-3-ylmethyl-thioarbamic
acid S-methyl ester

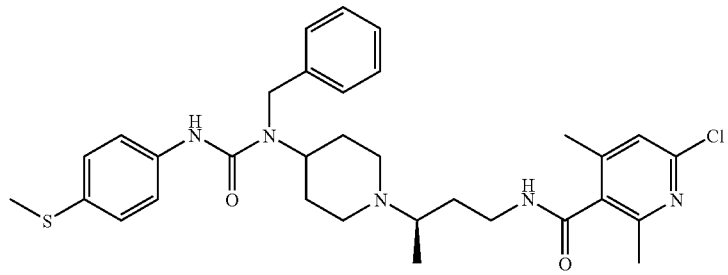

N-((R)-3-{4-[1-Benzyl-3-(4-methylsulfanyl-phenyl)-ureido]-piperidin-1-yl}-
butyl)-6-chloro-2,4-dimethyl-nicotinamide

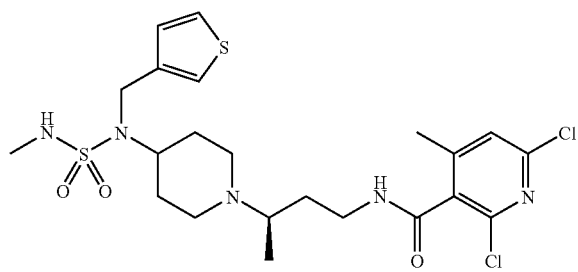

2,6-Dichloro-4-methyl-N-{(R)-3-[4-(3-methyl-1-thiophen-3-ylmethyl-
sulfonamido)-piperidin-1-yl]-butyl}-nicotinamide

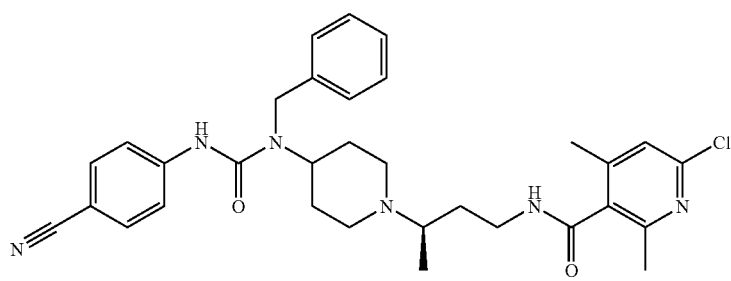

N-((R)-3-{4-[1-Benzyl-3-(4-cyano-phenyl)-ureido]-piperidin-1-yl}-butyl)-6-chloro-
2,4-dimethyl-nicotinamide

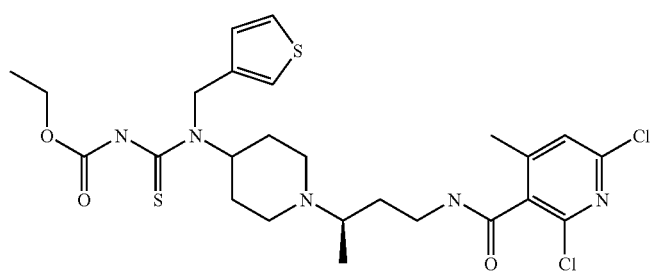

2,6-Dichloro-4-methyl-N-{(R)-3-[4-(3-formyl ethyl ester-1-thiophen-3-ylmethyl-
thioureido)-piperidin-1-yl]-butyl}-nicotinamide

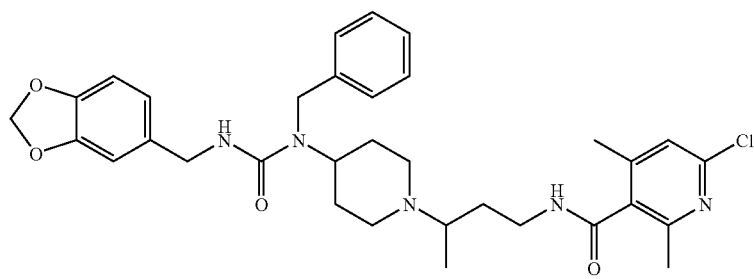

N-{3-[4-(3-1,3-Benzodioxol-5-ylmethyl-1-benzyl-ureido)-piperidin-1-yl]-butyl}-
6-chloro-2,4-dimethyl-nicotinamide

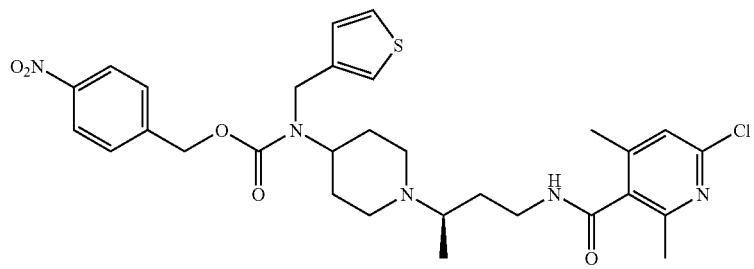

(1-{(R)-3-[(6-Chloro-2,4-dimethyl-pyridine-3-carbonyl)-amino]-1-methyl-propyl}-
piperidin-4-yl)-thiophen-3-ylmethyl-carbamic acid 4-nitro-benzyl ester

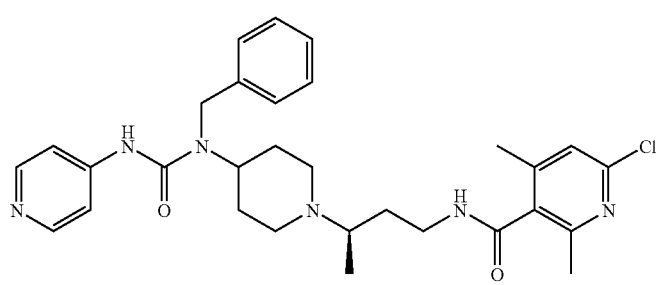

N-{(R)-3-[4-(1-Benzyl-3-pyridin-4-yl-ureido)-piperdin-1-yl]-butyl}-
6-chloro-2,4-dimethyl-nicotinamide

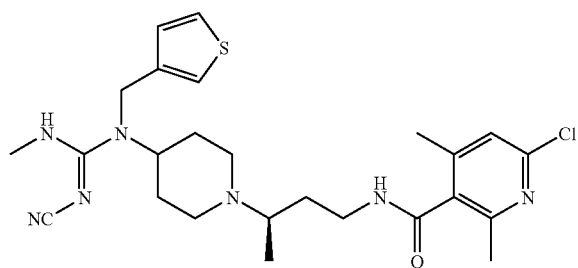

6-Chloro-2,4-dimethyl-N-{(R)-3-[4-(N'-methyl-N-thiophen-3-ylmethyl-
N''-cyanoguanidino)-piperidin-1-yl]-butyl}-nicotinamide

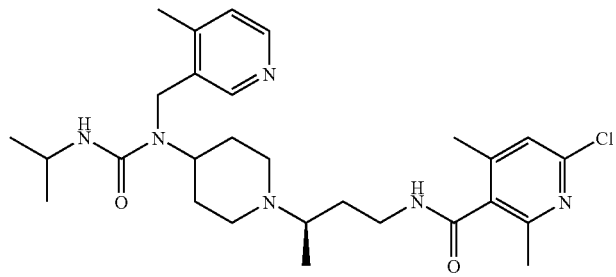

6-Chloro-N-((R)-3-{4-[3-isopropyl-1-(4-methyl-pyridin-3-ylmethyl)-
ureido]-piperidin-1-yl}-butyl)-2,4-dimethyl-nicotinamide -continued

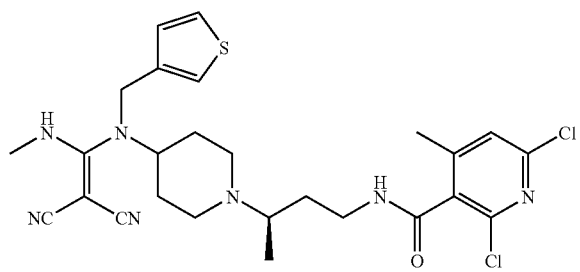

2,6-Dichloro-N-((R)-3-{4-[(2,2-dicyano-1-methylamino-vinyl)-thiophen-3-ylmethyl-amino]-piperidin-1-yl}-butyl)-4-methyl-nicotinamide

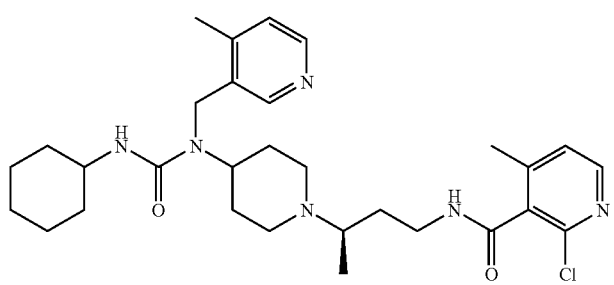

2-Chloro-N-((R)-3-{4-[3-cyclohexyl-1-(4-methyl-pyridin-3-ylmethyl)-ureido]-piperidin-1-yl}-butyl)-4-methyl-nicotinamide

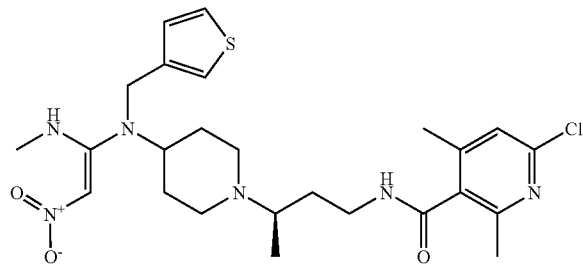

6-Chloro-2,4-dimethyl-N-((R)-3-{4-[(1-methylamino-2-nitro-vinyl)-thiophen-3-ylmethyl-amino]-piperidin-1-yl}-butyl)-nicotinamide

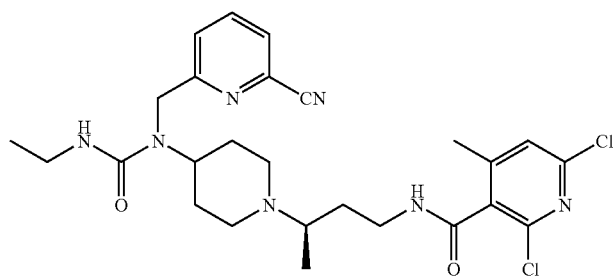

2,6-Dichloro-N-((R)-3-{4-[1-(6-cyano-pyridin-2-ylmethyl)-3-ethyl-ureido]-piperidin-1-yl}-butyl)-4-methyl-nicotinamide

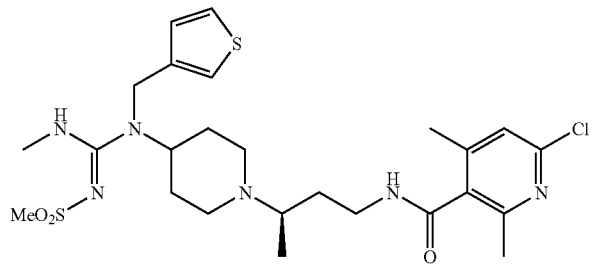

6-Chloro-2,4-dimethyl-N-{(R)-3-[4-(N'-methyl-N-thiophen-3-ylmethyl-N''-methanesulfonylguanidino)-piperidin-1-yl]-butyl}-nicotinamide -continued

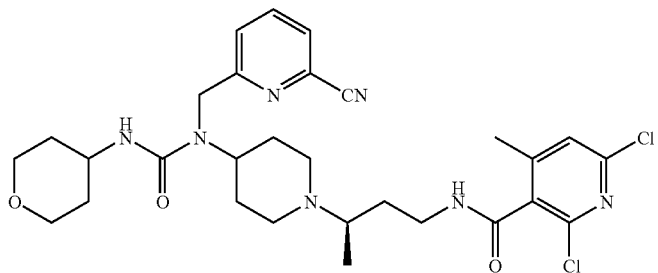

2,6-Dichloro-N-((R)-3-{4-[1-(6-cyano-pyridin-2-ylmethyl)-3-(tetrahydro-pyran-4-yl)-ureido]-piperidin-1-yl}-butyl)-4-methyl-nicotinamide

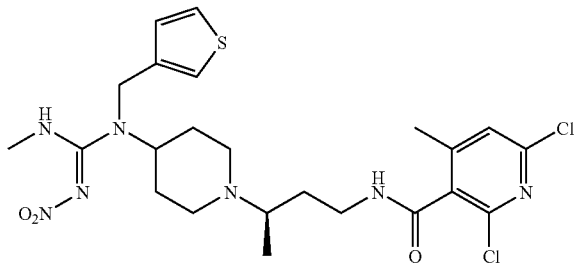

2,6-Dichloro-4-methyl-N-{(R)-3-[4-(N'-methyl-N-thiophen-3-ylmethyl-N''-nitroguanidino)-piperidin-1-yl]-butyl}-nicotinamide

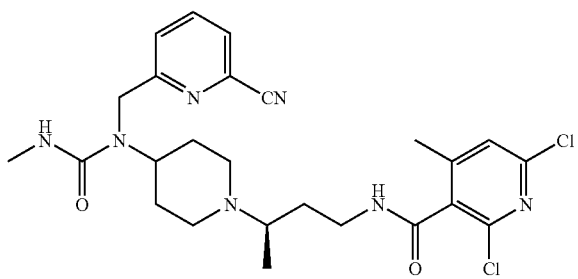

2,6-Dichloro-N-((R)-3-{4-[1-(6-cyano-pyridin-2-ylmethyl)-3-methyl-ureido]-piperidin-1-yl}-butyl)-4-methyl-nicotinamide

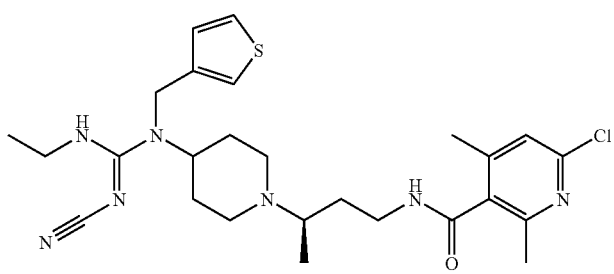

6-Chloro-N-{(R)-3-[4-(N'-ethyl-N-thiophen-3-ylmethyl-cyanoguanidino)-piperidin-1-yl]-butyl}-2,4-dimethyl-nicotinamide

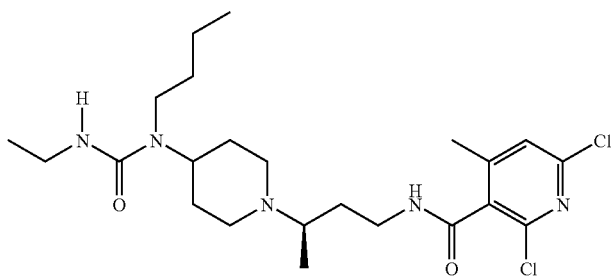

N-{(R)-3-[4-(1-Butyl-3-ethyl-ureido)-piperidin-1-yl]-butyl}-2,6-dichloro-4-methyl-nicotinamide -continued

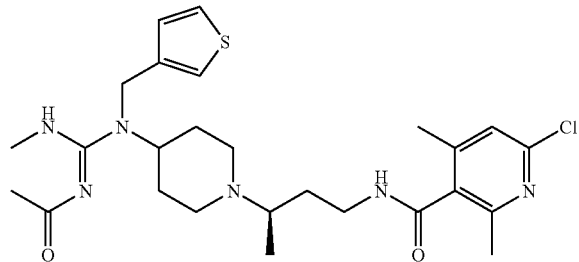

6-Chloro-2,4-dimethyl-N-{(R)-3-[4-(N'-methyl-N-thiophen-3-ylmethyl-N''-acetylguanidino)-piperidin-1-yl]-butyl}-nicotinamide

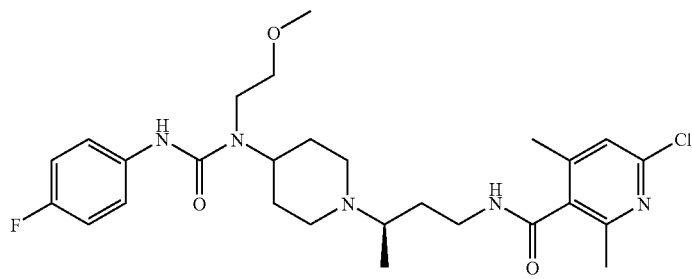

6-Chloro-N-((R)-3-{4-[3-(4-fluoro-phenyl)-1-(2-methoxy-ethyl)-ureido]-piperidin-1-yl}-butyl)-2,4-dimethyl-nicotinamide

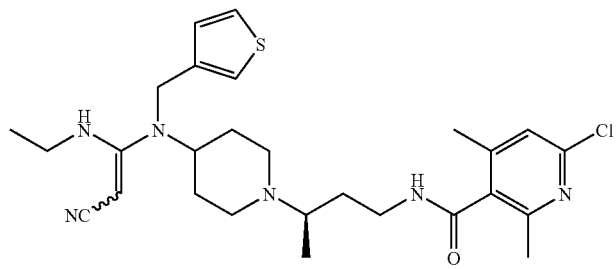

6-Chloro-N-((R)-3-{4-[(2-cyano-1-ethylamino-vinyl)-thiophen-3-ylmethyl-amino]-piperidin-1-yl}-butyl)-2,4-dimethyl-nicotinamide

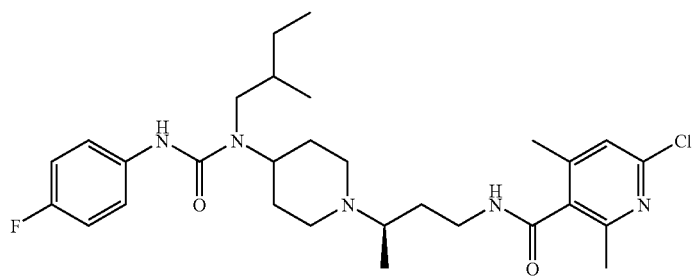

6-Chloro-N-((R)-3-{4-[3-(4-fluoro-phenyl)-1-(2-methyl-butyl)-ureido]-piperidin-1-yl}-butyl)-2,4-dimethyl-nicotinamide

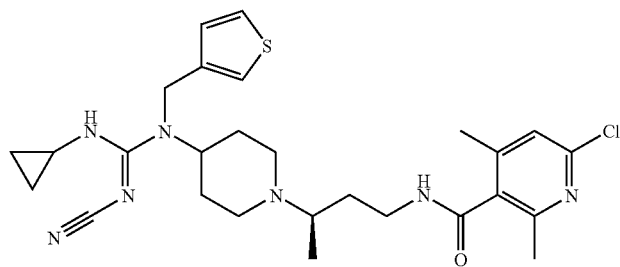

6-Chloro-N-{(R)-3-[4-(N'-cyclopropyl-N-thiophen-3-ylmethyl-cyanoguanidino)-piperidin-1-yl]-butyl}-2,4-dimethyl-nicotinamide

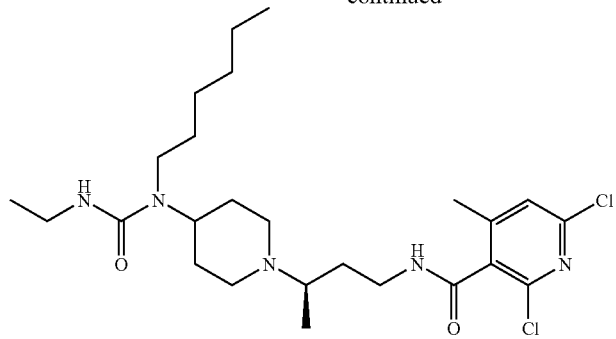

2,6-Dichloro-N-{(R)-3-[4-(3-ethyl-1-hexyl-ureido)-piperidin-1-yl]-butyl}-4-methyl-nicotinamide

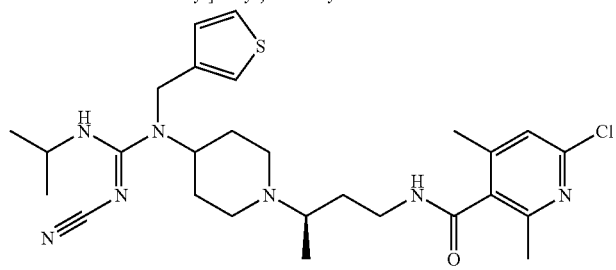

6-Chloro-N-{(R)-3-[4-(N'-isopropyl-N-thiophen-3-ylmethyl-cyanoguanidino)-piperidin-1-yl]-butyl}-2,4-dimethyl-nicotinamide

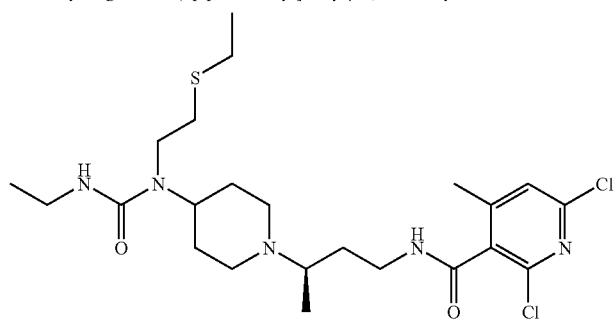

2,6-Dichloro-N-((R)-3-{4-[3-ethyl-1-(2-ethylsulfanyl-ethyl)-ureido]-piperidin-1-yl}-butyl)-4-methyl-nicotinamide

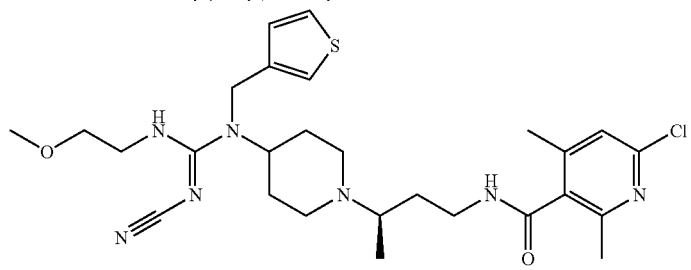

6-Chloro-N-((R)-3-{4-[N'-(2-methoxy-ethyl)-N-thiophen-3-ylmethyl-cyanoguanidino]-piperidin-1-yl}-butyl)-2,4-dimethyl-nicotinamide

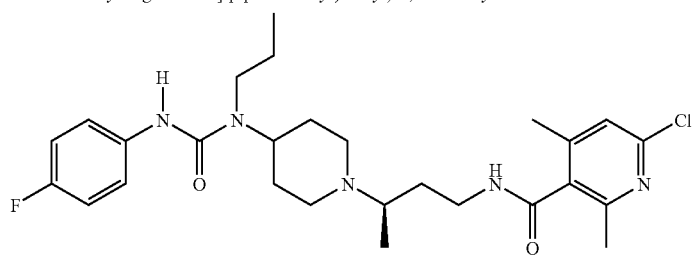

6-Chloro-N-((R)-3-{4-[3-(4-fluoro-phenyl)-1-propyl-ureido]-piperidin-1-yl}-butyl)-2,4-dimethyl-nicotinamide -continued

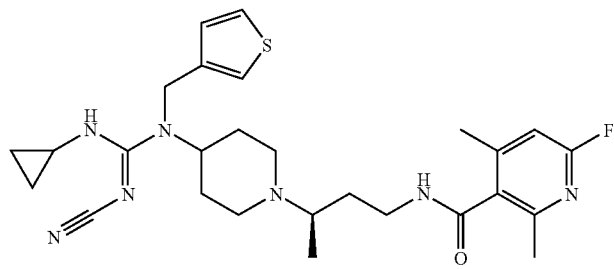

N-{(R)-3-[4-(N'-Cyclopropyl-N-thiophen-3-ylmethyl-cyanoguanidino)-piperidin-1-yl]-butyl}-6-fluoro-2,4-dimethyl-nicotinamide

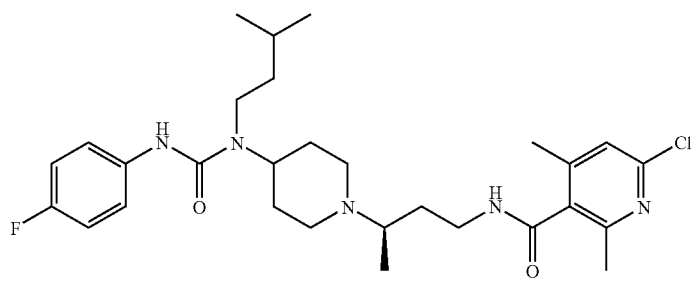

6-Chloro-N-((R)-3-{4-[3-(4-fluoro-phenyl)-1-(3-methyl-butyl)-ureido]-piperidin-1-yl}-butyl)-2,4-dimethyl-nicotinamide

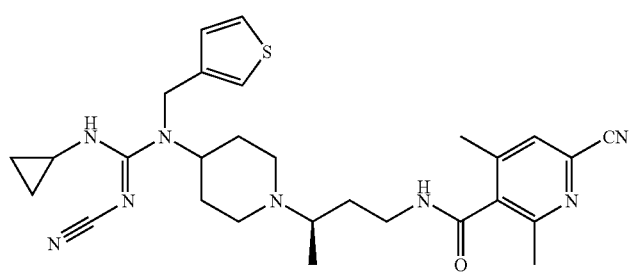

6-Cyano-N-{(R)-3-[4-(N'-cyclopropyl-N-thiophen-3-ylmethyl-cyanoguanidino)-piperidin-1-yl]-butyl}-2,4-dimethyl-nicotinamide

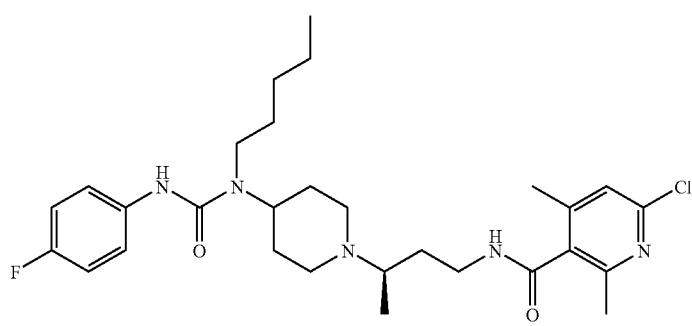

6-Chloro-N-((R)-3-{4-[3-(4-fluoro-phenyl)-1-pentyl-ureido]-piperidin-1-yl}-butyl)-2,4-dimethyl-nicotinamide

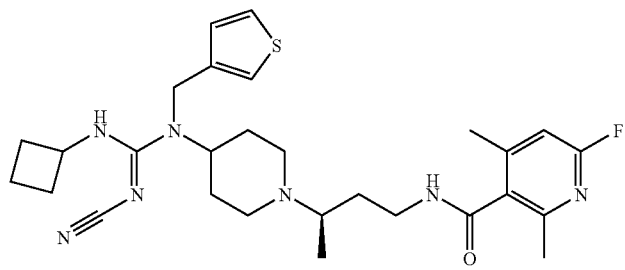

N-{(R)-3-[4-(N'-Cyclobutyl-N-thiophen-3-ylmethyl-cyanoguanidino)-piperidin-1-yl]-butyl}-6-fluoro-2,4-dimethyl-nicotinamide -continued

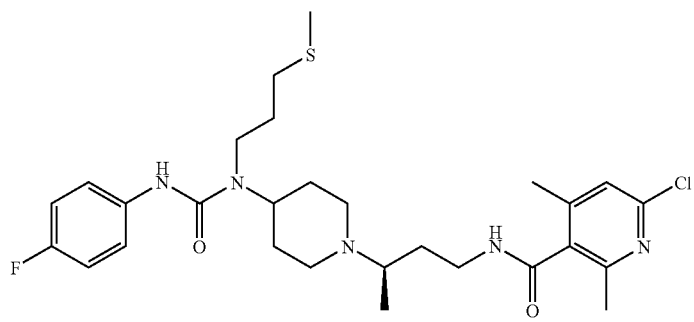

6-Chloro-N-((R)-3-{4-[3-(4-fluoro-phenyl)-1-(3methyl sulfanyl-propyl)-ureido]-piperidin-1-yl}-butyl)-2,4-dimethyl-nicotinamide

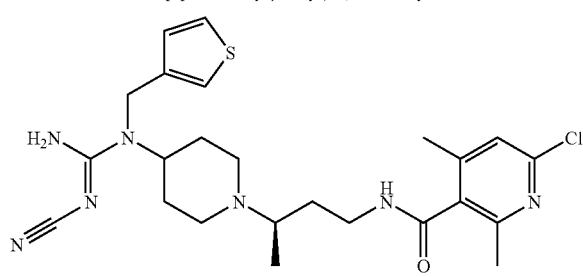

6-Chloro-2,4-dimethyl-N-{(R)-3-[4-(N-thiophen-3-ylmethyl-N″-cyanoguanidino)-piperidin-1-yl]-butyl}-nicotinamide

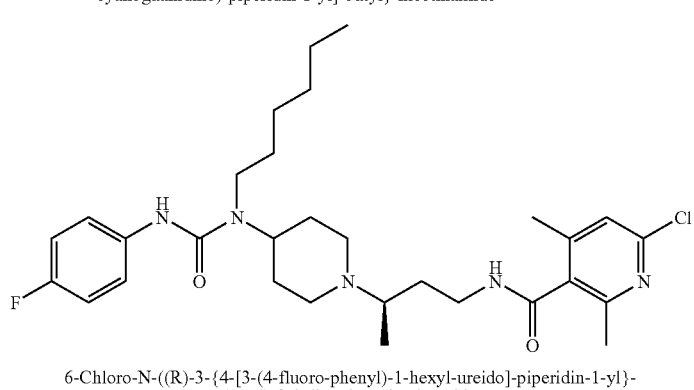

6-Chloro-N-((R)-3-{4-[3-(4-fluoro-phenyl)-1-hexyl-ureido]-piperidin-1-yl}-butyl)-2,4-dimethyl-nicotinamide

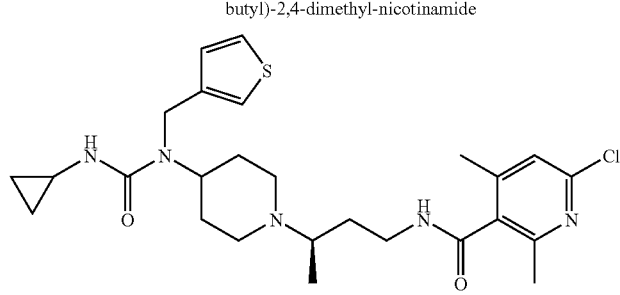

6-Chloro-N-{(R)-3-[4-(3-cyclopropyl-1-thiophen-3-ylmethyl-ureido)-piperidin-1-yl]-butyl}-2,4-dimethyl-nicotinamide -continued

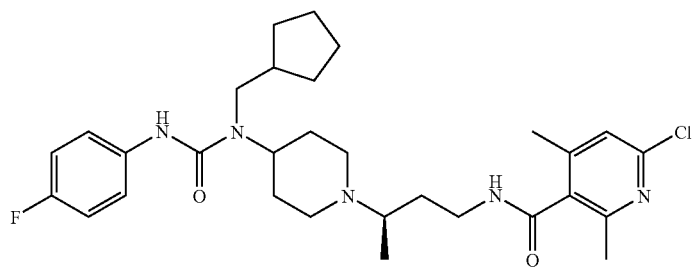

6-Chloro-N-((R)-3-{4-[1-cyclopentylmethyl-3-(4-fluoro-phenyl)-ureido]-piperidin-1-yl}-butyl)-2,4-dimethyl-nicotinamide

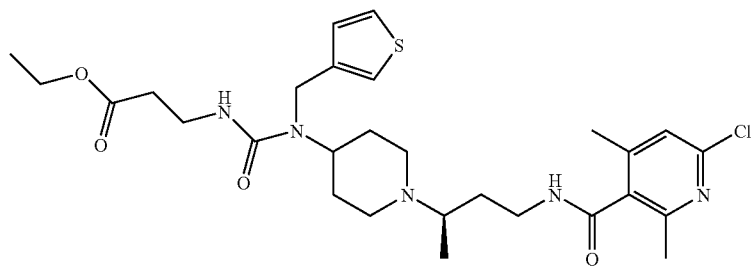

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-propionic acid ethyl ester

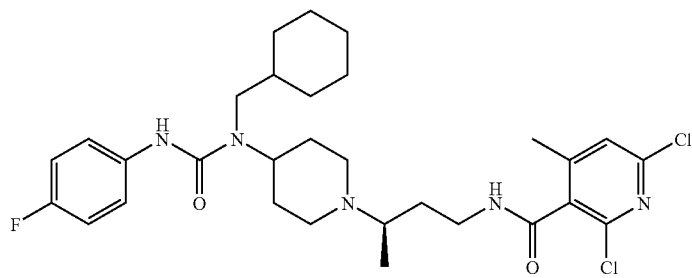

2,6-Dichloro-N-((R)-3-{4-[1-cyclohexylmethyl-3-(4-fluoro-phenyl)-ureido]-piperidin-1-yl}-butyl)-4-methyl-nicotinamide

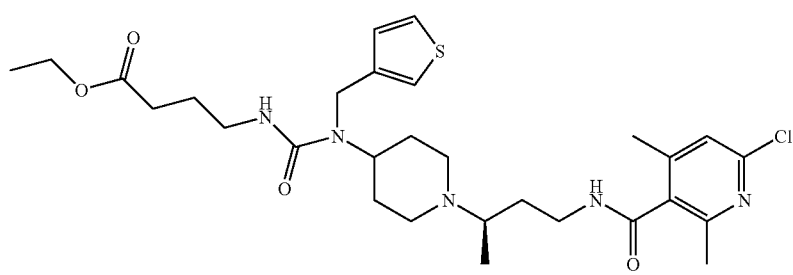

4-[3-(1-{(R)-3-[(6-Chloro-2,4-dimethyl-pyridine-3-carbonyl)-amino]-1-methyl-propyl}-piperdin-4-yl)-3-thiophen-3-ylmethyl-ureido]-butyric acid ethyl ester

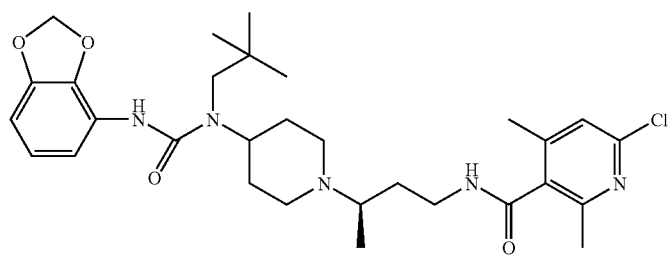

N-((R)-3-{4-[3-1,3-Benzodioxol-4-yl-1-(2,2-dimethyl-propyl)-ureido]-piperidin-1-yl}-butyl)-6-chloro-2,4-dimethyl-nicotinamide -continued

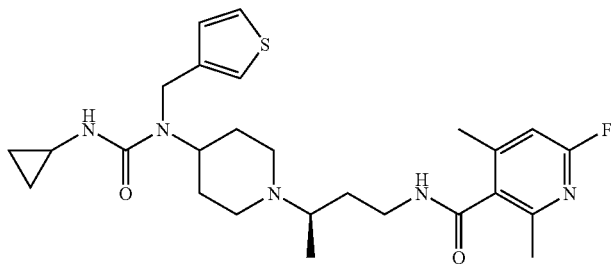

N-{(R)-3-[4-(3-Cyclopropyl-1-thiophen-3-ylmethyl-ureido)-piperidin-1-yl]-butyl}-6-fluoro-2,4-dimethyl-nicotinamide

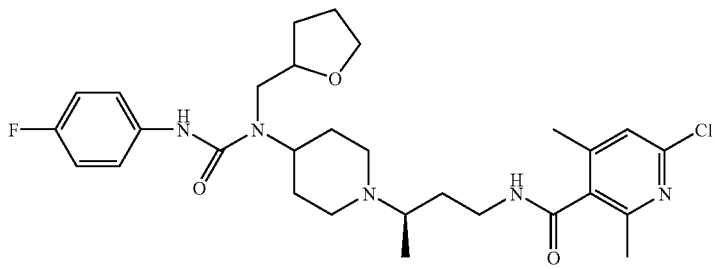

6-Chloro-N-((R)-3-{4-[3-(4-fluoro-phenyl)-1-(tetrahydro-furan-2-ylmethyl)-ureido]-piperidin-1-yl}-butyl)-2,4-dimethyl-nicotinamide

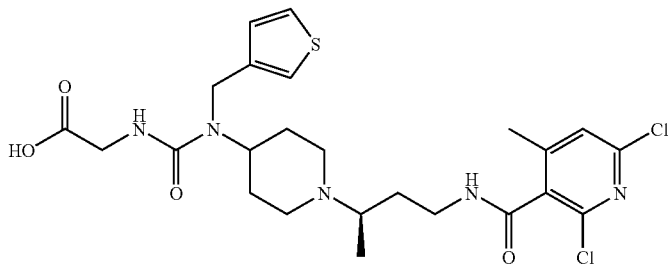

[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid

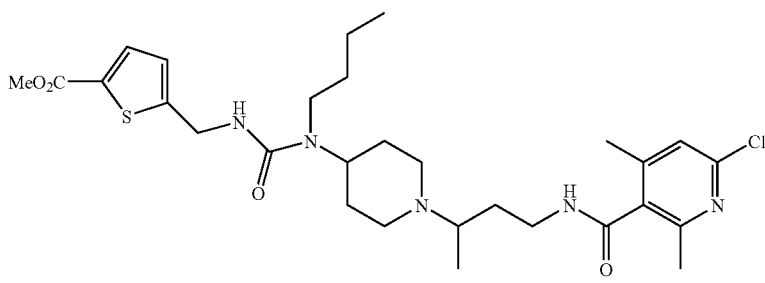

5-[3-Butyl-3-(1-{3-[(6-chloro-2,4-dimethyl-pyridine-3-carbonyl)-amino]-1-methyl-propyl}-piperidin-4-yl)-ureidomethyl]-thiophene-2-carboxylic acid methyl ester

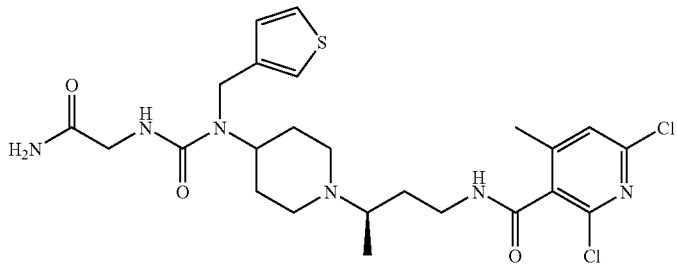

N-{(R)-3-[4-(3-Carbamoylmethyl-1-thiophen-3-ylmethyl-ureido)-piperidin-1-yl]-butyl}-2,6-dichloro-4-methyl-nicotinamide -continued

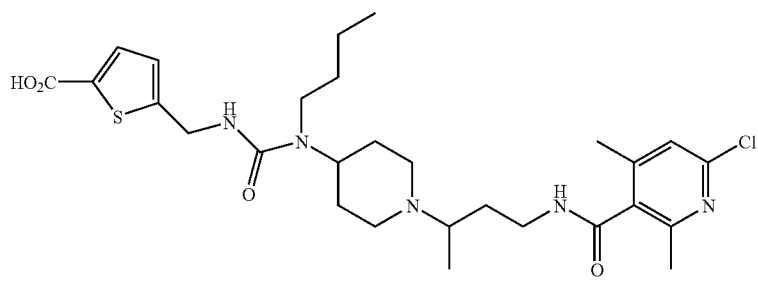

5-[3-Butyl-3-(1-{3-[(6-chloro-2,4-dimethyl-pyridine-3-carbonyl)-amino]-1-methyl-propyl}-piperidin-4-yl)-ureidomethyl]-thiophene-2-carboxylic acid

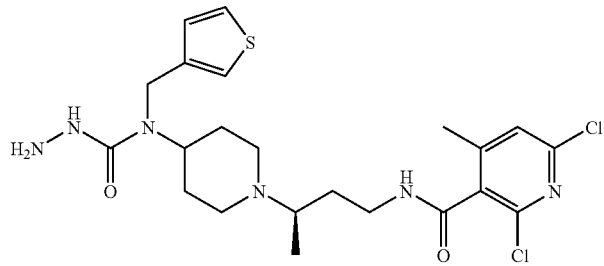

2,6-Dichloro-4-amino-N-{(R)-3-[4-(3-methyl-1-thiophen-3-ylmethylureido)-piperidin-1-yl]-butyl}-nicotinamide

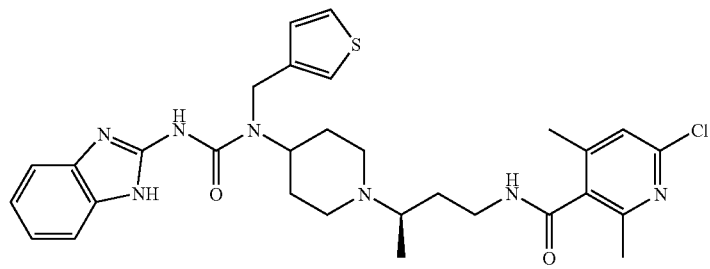

N-((R)-3-{4-[3-(1H-Benzoimidazol-2-yl)-1-thiophen-3-ylmethyl-ureido]-piperidin-1-yl}-butyl)-6-chloro-2,4-dimethyl-nicotinamide

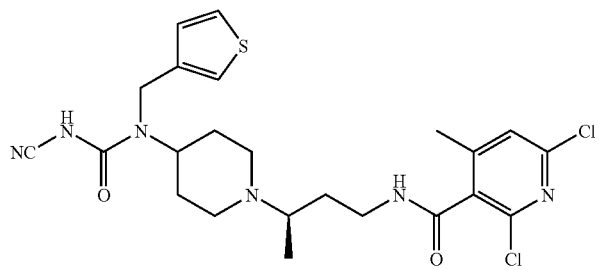

2,6-Dichloro-4-methyl-N-{(R)-3-[4-(3-cyano-1-thiophen-3-ylmethyl-ureido)-piperidin-1-yl]-butyl}-nicotinamide

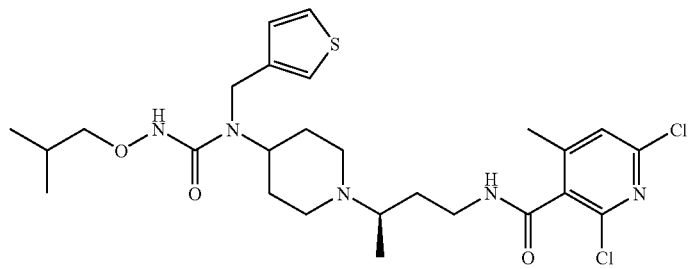

2,6-Dichloro-4-isobutoxy-N-{(R)-3-[4-(3-methyl-1-thiophen-3-ylmethyl-ureido)-piperidin-1-yl]-butyl}-nicotinamide -continued

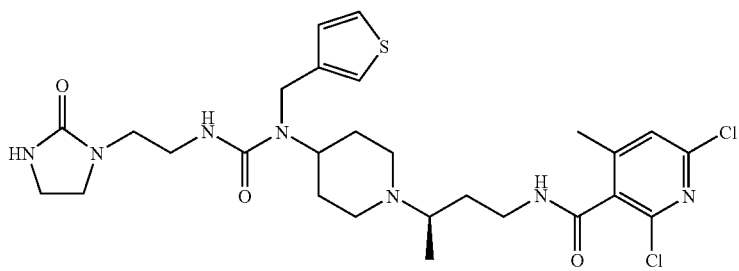

2,6-Dichloro-4-methyl-N-[(R)-3-(4-{3-[2-(2-oxo-imidazolidin-1-yl)-ethyl]-1-thiophen-3-ylmethyl-ureido}-piperidin-1-yl)-butyl]-nicotinamide

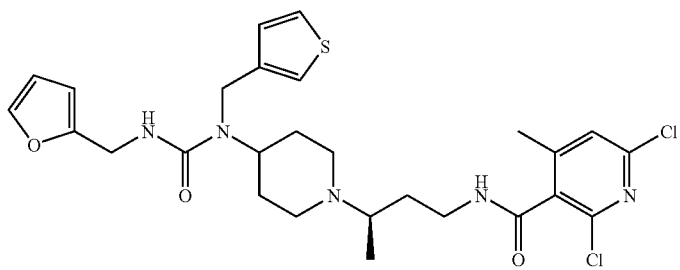

2,6-Dichloro-N-{(R)-3-[4-(3-furan-2-ylmethyl-1-thiophen-3-ylmethyl-ureido)-piperidin-1-yl]-butyl}-4-methyl-nicotinamide

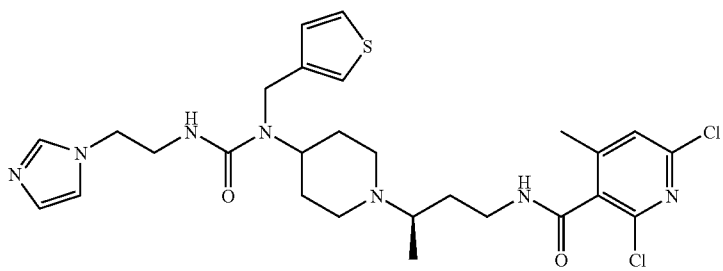

2,6-Dichloro-N-((R)-3-{4-[3-(2-imidazol-1-yl-ethyl)-1-thiophen-3-ylmethyl-ureido]-piperidin-1-yl}-butyl)-4-methyl-nicotinamide

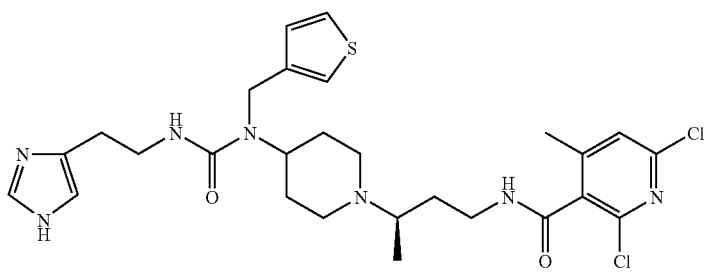

2,6-Dichloro-N-[(R)-3-(4-{3-[2-(1H-imidazol-4-yl)-ethyl]-1-thiophen-3-ylmethyl-ureido}-piperidin-1-yl)-butyl]-4-methyl-nicotinamide

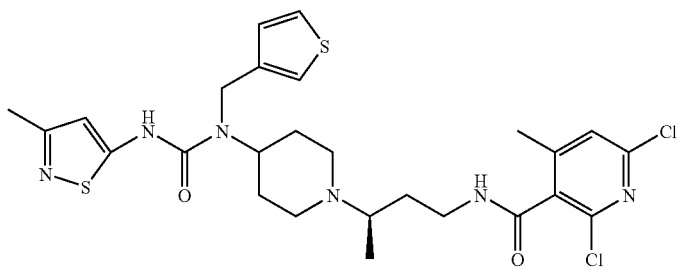

2,6-Dichloro-4-methyl-N-((R)-3-{4-[3-(3-methyl-isothiazol-5-yl)-1-thiophen-3-ylmethyl-ureido]-piperidin-1-yl}-butyl)-nicotinamide -continued

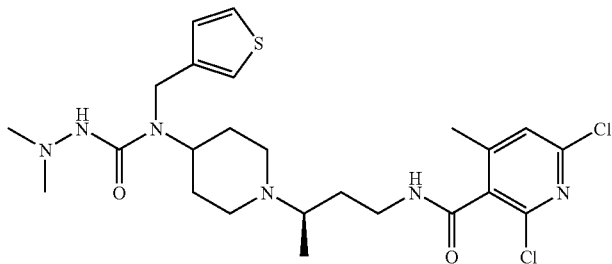

2,6-Dichloro-N-((R)-3-{4-[3-(2,2-dimethylhydrazin-1-ylcarbonylamino)-
1-thiophen-3-ylmethyl-ureido]-piperidin-1-yl}-butyl)-4-methyl-nicotinamide

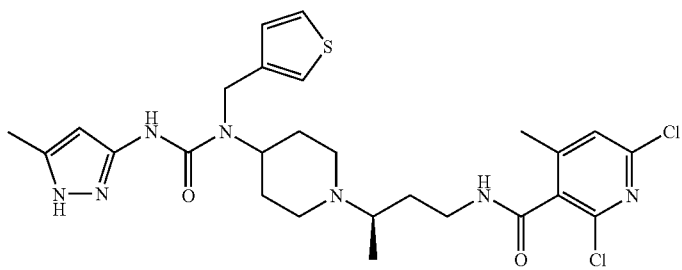

2,6-Dichloro-4-methyl-N-((R)-3-{4-[3-(5-methyl-1H-pyrazol-3-yl)-1-thiophen-3-
ylmethyl-ureido]-piperidin-1-yl}-butyl)-nicotinamide

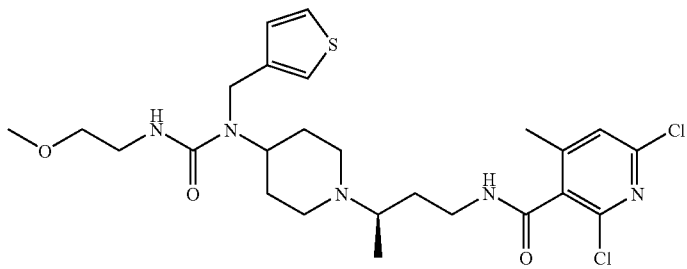

2,6-Dichloro-N-((R)-3-{4-[3-(2-methoxy-ethyl)-1-thiophen-3-ylmethyl-ureido]-
piperidin-1-yl}-butyl)-4-methyl-nicotinamide

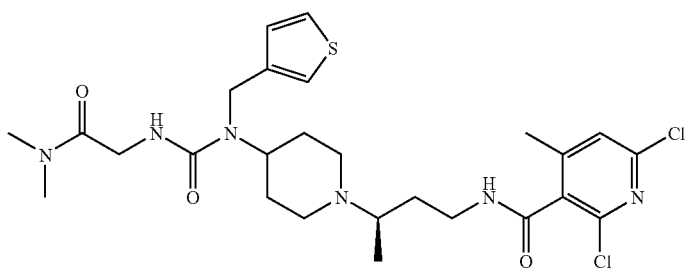

2,6-Dichloro-N-{(R)-3-[4-(3-dimethylcarbamoylmethyl-1-thiophen-3-ylmethyl-
ureido)-piperidin-1-yl]-butyl}-4-methyl-nicotinamide

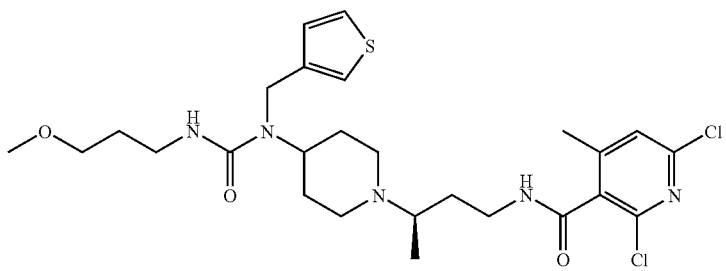

2,6-Dichloro-N-((R)-3-{4-[3-(3-methoxy-propyl)-1-thiophen-3-ylmethyl-
ureido]-piperidin-1-yl}-butyl)-4-methyl-nicotinamide -continued

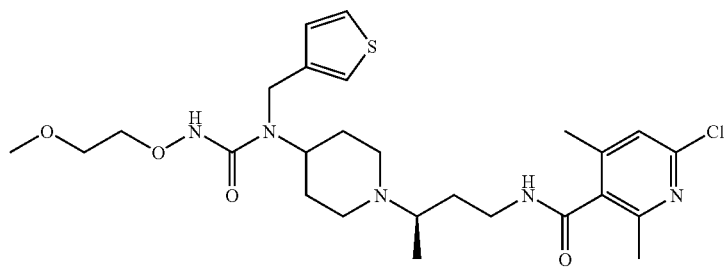

6-Chloro-N-((R)-3-{4-[3-(2-methoxyethoxy)-1-thiophen-3-ylmethyl-ureido]-piperidin-1-yl}-butyl)-2,4-dimethyl-nicotinamide

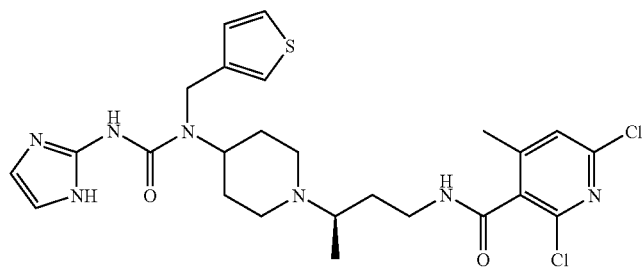

2,6-Dichloro-N-((R)-3-{4-[3-(1H-imidazol-2-yl)-1-thiophen-3-ylmethyl-ureido]-piperidin-1-yl}-butyl)-4-methyl-nicotinamide

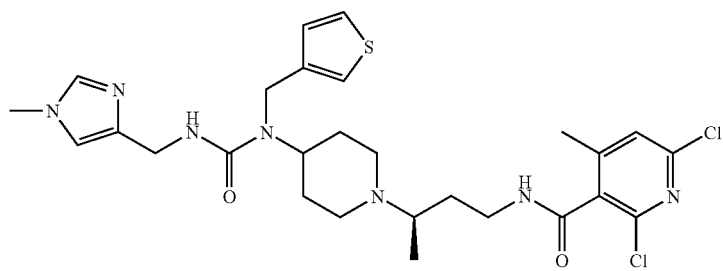

2,6-Dichloro-4-methyl-N-((R)-3-{4-[3-(1-methyl-1H-imidazol-4-ylmethyl)-1-thiophen-3-ylmethyl-ureido]-piperidin-1-yl}-butyl)-nicotinamide

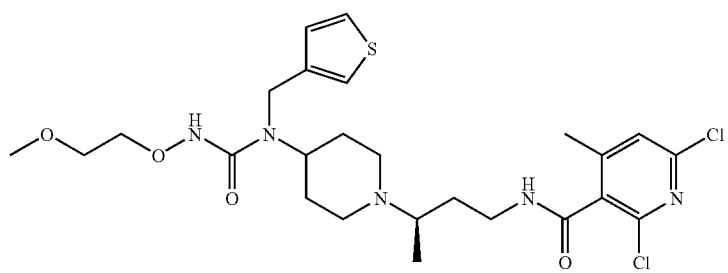

2,6-Dichloro-N-{(R)-3-[4-(3-(2-methoxyethoxy)-1-thiophen-3-ylmethyl-ureido)-piperidin-1-yl]-butyl}-4-methyl-nicotinamide

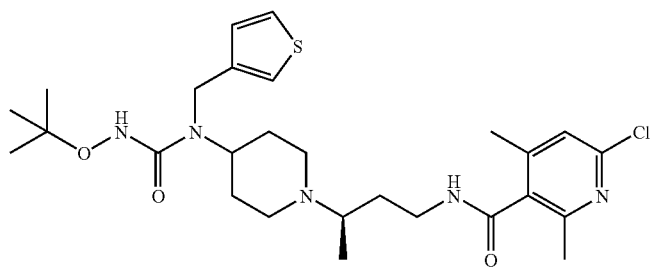

6-Chloro-N-{(R)-3-[4-(3-t-butoxy-1-thiophen-3-ylmethyl-ureido)-piperidin-1-yl]-butyl}-2,4-dimethyl-nicotinamide -continued

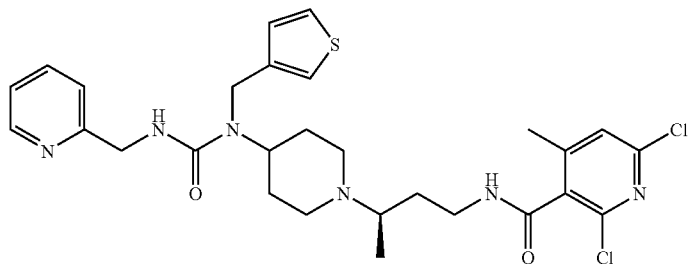

2,6-Dichloro-4-methyl-N-{(R)-3-[4-(3-pyridin-2-ylmethyl-1-thiophen-3-ylmethyl-ureido)-piperidin-1-yl]-butyl}-nicotinamide

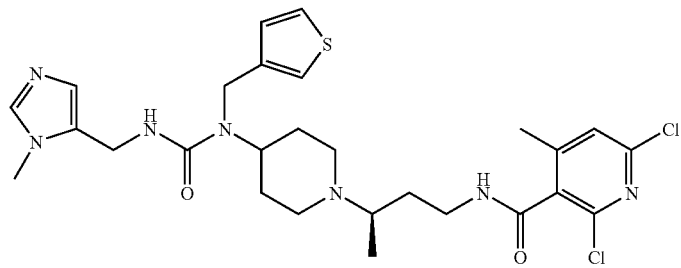

2,6-Dichloro-4-methyl-N-((R)-3-{4-[3-(3-methyl-3H-imidazol-4-ylmethyl)-1-thiophen-3-ylmethyl-ureido]-piperidin-1-yl}-butyl)-nicotinamide

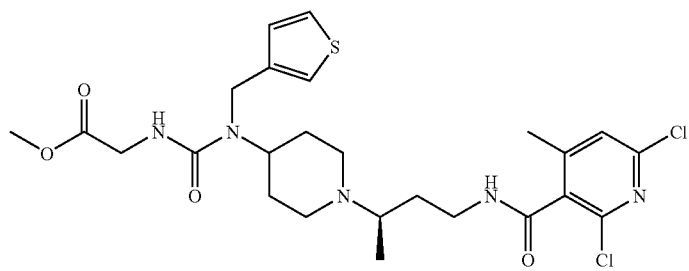

[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid methyl ester

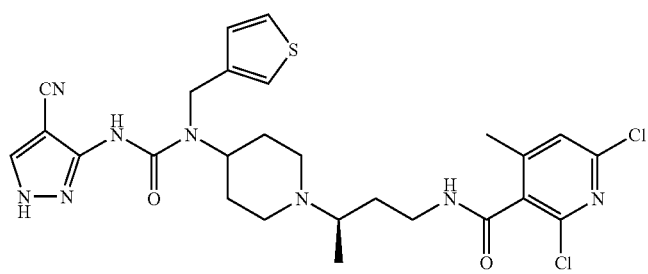

2,6-Dichloro-N-((R)-3-{4-[3-(4-cyano-1H-pyrazol-3-yl)-1-thiophen-3-ylmethyl-ureido]-piperidin-1-yl}-butyl)-4-methyl-nicotinamide

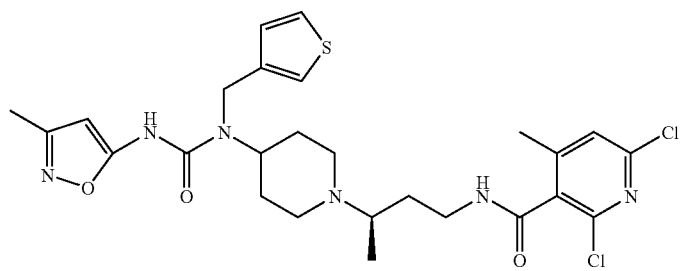

2,6-Dichloro-4-methyl-N-((R)-3-{4-[3-(3-methyl-isoxazol-5-yl)-1-thiophen-3-ylmethyl-ureido]-piperidin-1-yl}-butyl)-nicotinamide -continued

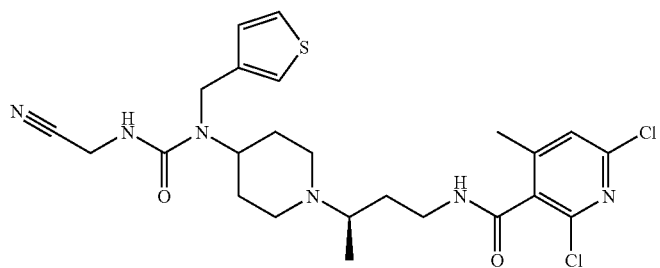

2,6-Dichloro-N-{(R)-3-[4-(3-cyanomethyl-1-thiophen-3-ylmethyl-ureido)-piperidin-1-yl]-butyl}-4-methyl-nicotinamide

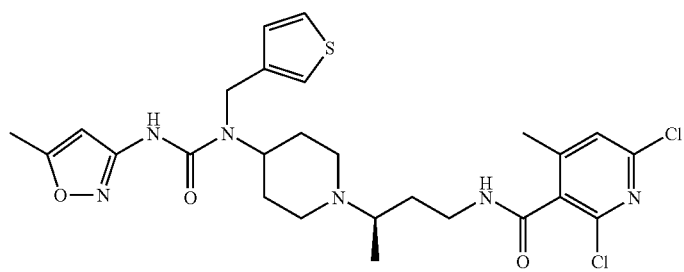

2,6-Dichloro-4-methyl-N-((R)-3-{4-[3-(5-methyl-isoxazol-3-yl)-1-thiophen-3-ylmethyl-ureido]-piperidin-1-yl}-butyl)-nicotinamide

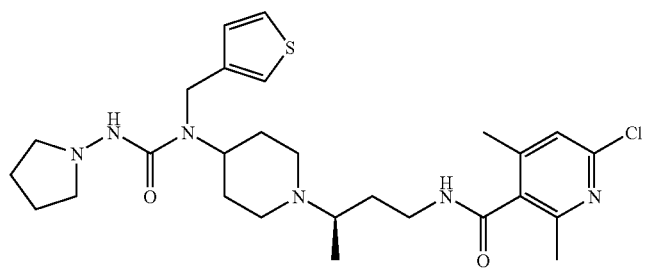

6-Chloro-2,4-dimethyl-N-{(R)-3-[4-(3-pyrrolidin-1-yl-1-thiophen-3-ylmethyl-ureido)-piperidin-1-yl]-butyl}-nicotinamide

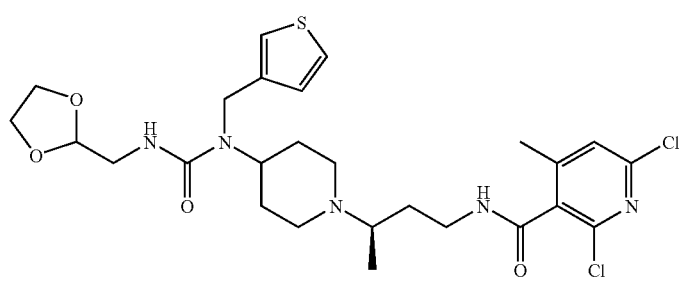

2,6-Dichloro-N-{(R)-3-[4-(3-1,3-dioxolan-2-ylmethyl-1-thiophen-3-ylmethyl-ureido)-piperidin-1-yl]-butyl}-4-methyl-nicotinamide

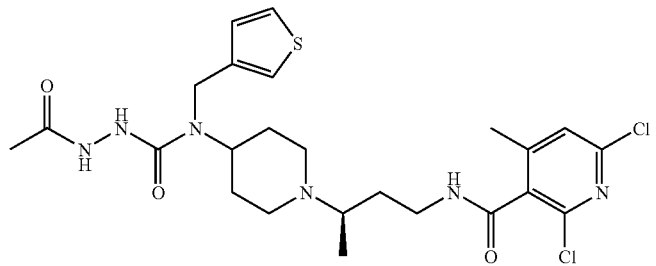

2,6-Dichloro-4-methyl-N-{(R)-3-[4-(3-acetamido-1-thiophen-3-ylmethyl-ureido)-piperidin-1-yl]-butyl}-nicotinamide

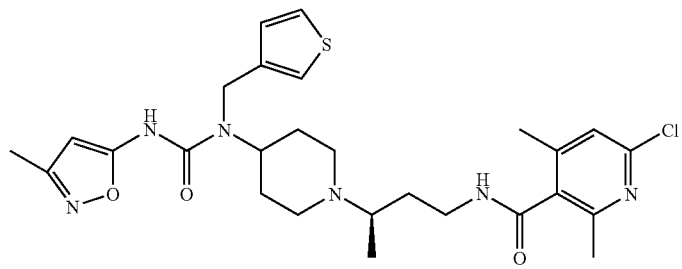

6-Chloro-2,4-dimethyl-N-((R)-3-{4-[3-(3-methyl-isoxazol-5-yl)-
1-thiophen-3-ylmethyl-ureido]-piperidin-1-yl}-butyl)-nicotinamide

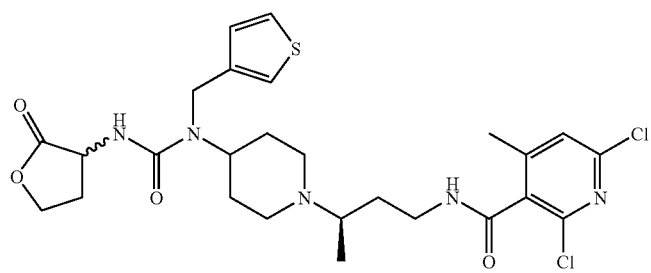

2,6-Dichloro-4-methyl-N-((R)-3-{4-[3-(2-oxo-tetrahydro-furan-3-yl)-
1-thiophen-3-ylmethyl-ureido]-piperidin-1-yl}-butyl)-nicotinamide

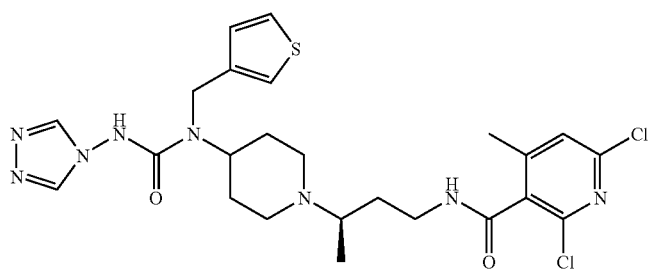

2,6-Dichloro-4-methyl-N-{(R)-3-[4-(1-thiophen-3-ylmethyl-3-[1,2,4]triazol-
4-yl-ureido)-piperidin-1-yl]-butyl}-nicotinamide

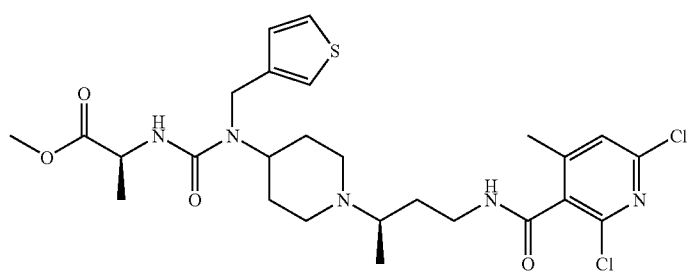

(S)-2-[3-(1-{(R)-3-[(2,6-Dichloro-4-methyl-pyridine-3-carbonyl)-amino]-
1-methyl-propyl}-piperidin-4-yl)-3-thiophen-3-ylmethyl-ureido]-propionic
acid methyl ester -continued

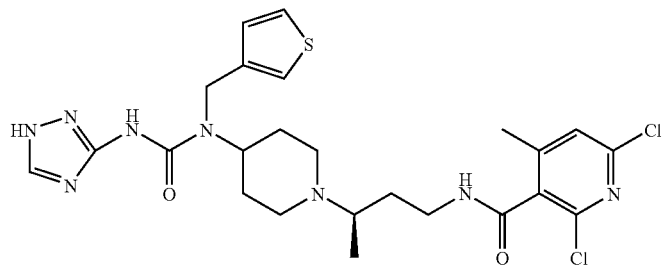

2,6-Dichloro-4-methyl-N-((R)-3-{4-[1-thiophen-3-ylmethyl-3-(1H-[1,2,4]triazol-3-yl)-ureido]-piperidin-1-yl}-butyl)-nicotinamide

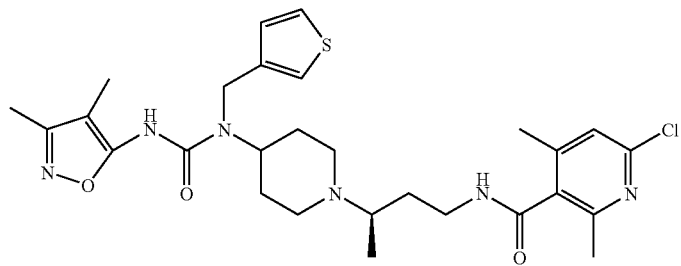

6-Chloro-N-((R)-3-{4-[3-(3,4-dimethyl-isoxazol-5-yl)-1-thiophen-3-ylmethyl-ureido]-piperidin-1-yl}-butyl)-2,4-dimethyl-nicotinamide

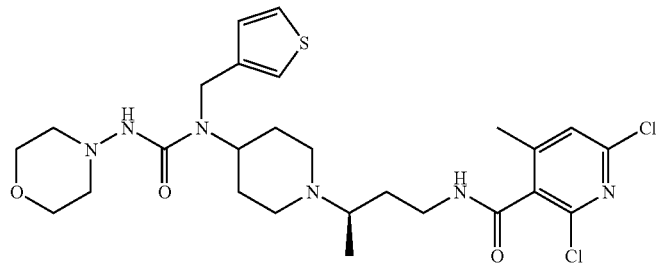

2,6-Dichloro-4-methyl-N-{(R)-3-[4-(3-morpholin-4-yl-1-thiophen-3-ylmethyl-ureido)-piperidin-1-yl]-butyl}-nicotinamide

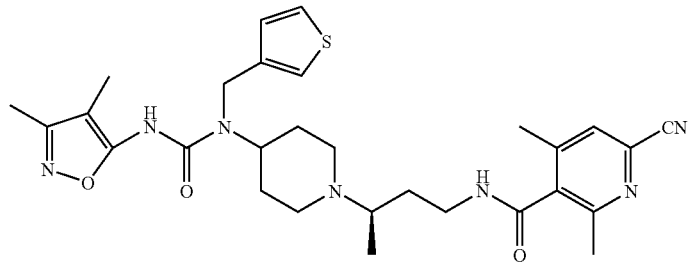

6-Cyano-N-((R)-3-{4-[3-(3,4-dimethyl-isoxazol-5-yl)-1-thiophen-3-ylmethyl-ureido]-piperidin-1-yl}-butyl)-2,4-dimethyl-nicotinamide; and

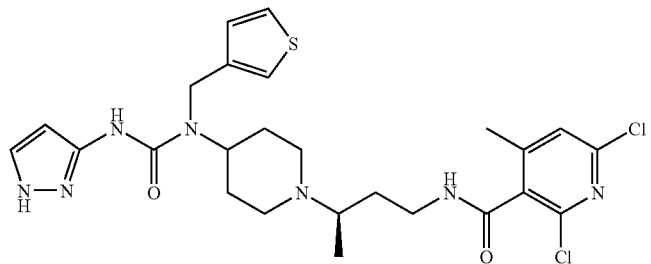

2,6-Dichloro-4-methyl-N-((R)-3-{4-[3-(1H-pyrazol-3-yl)-1-thiophen-3-ylmethyl-ureido]-piperidin-1-yl}-butyl)-nicotinamide.

Examples of compounds having formula (2) include but are not limited to the following compounds:

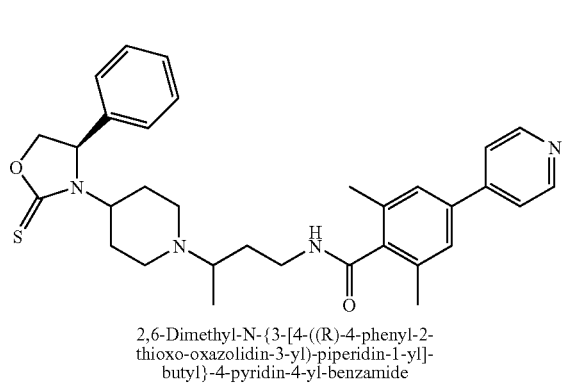

2,6-Dimethyl-N-{3-[4-((R)-4-phenyl-2-thioxo-oxazolidin-3-yl)-piperidin-1-yl]-butyl}-4-pyridin-4-yl-benzamide

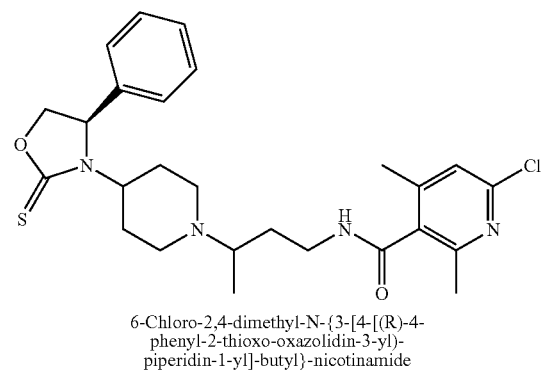

6-Chloro-2,4-dimethyl-N-{3-[4-[(R)-4-phenyl-2-thioxo-oxazolidin-3-yl)-piperidin-1-yl]-butyl}-nicotinamide

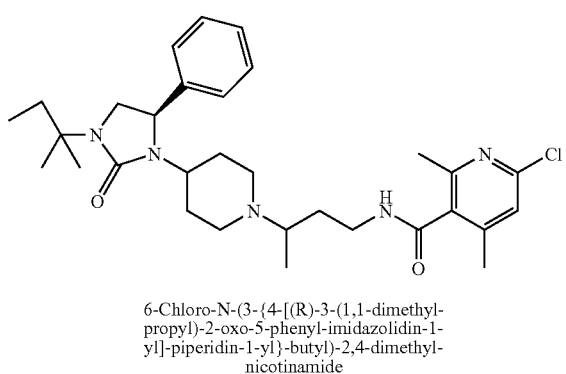

6-Chloro-N-(3-{4-[(R)-3-(1,1-dimethyl-propyl)-2-oxo-5-phenyl-imidazolidin-1-yl]-piperidin-1-yl}-butyl)-2,4-dimethyl-nicotinamide

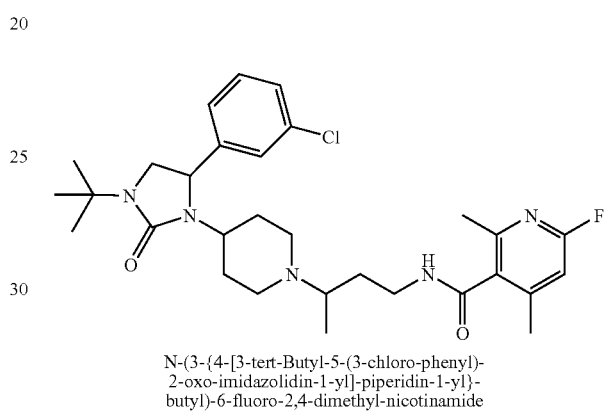

N-(3-{4-[3-tert-Butyl-5-(3-chloro-phenyl)-2-oxo-imidazolidin-1-yl]-piperidin-1-yl}-butyl)-6-fluoro-2,4-dimethyl-nicotinamide

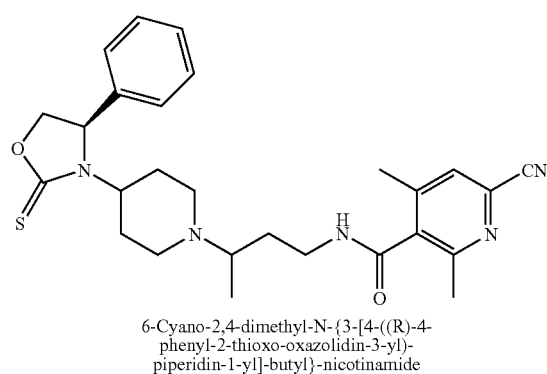

6-Cyano-2,4-dimethyl-N-{3-[4-((R)-4-phenyl-2-thioxo-oxazolidin-3-yl)-piperidin-1-yl]-butyl}-nicotinamide

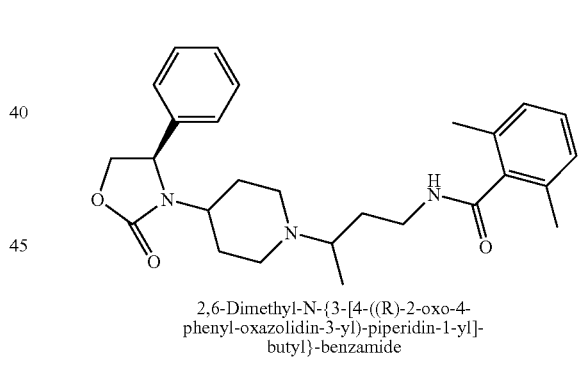

2,6-Dimethyl-N-{3-[4-((R)-2-oxo-4-phenyl-oxazolidin-3-yl)-piperidin-1-yl]-butyl}-benzamide

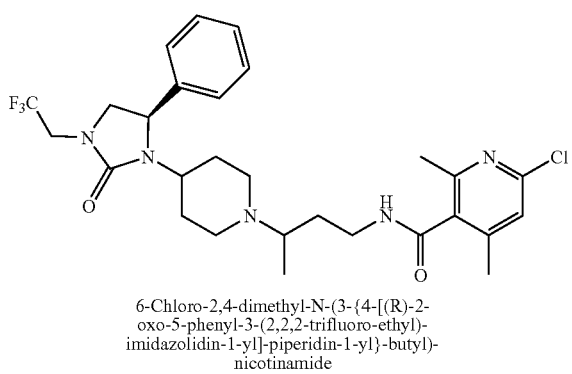

6-Chloro-2,4-dimethyl-N-(3-{4-[(R)-2-oxo-5-phenyl-3-(2,2,2-trifluoro-ethyl)-imidazolidin-1-yl]-piperidin-1-yl}-butyl)-nicotinamide

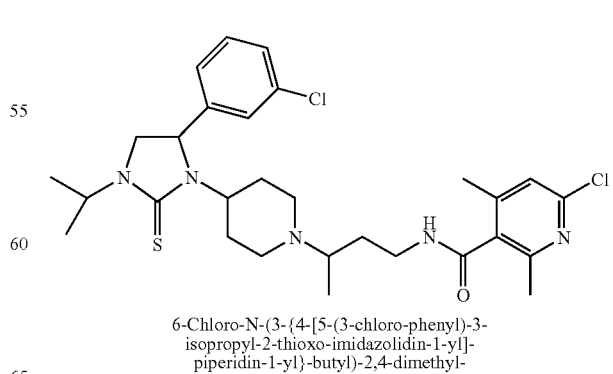

6-Chloro-N-(3-{4-[5-(3-chloro-phenyl)-3-isopropyl-2-thioxo-imidazolidin-1-yl]-piperidin-1-yl}-butyl)-2,4-dimethyl-nicotinamide

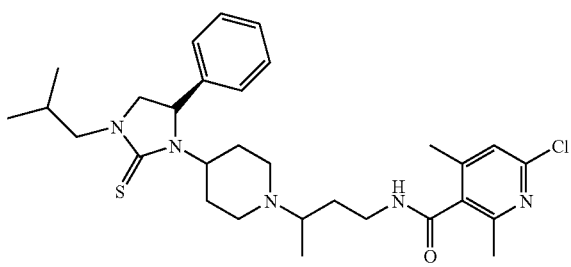

6-Chloro-2,4-dimethyl-N-{3-[4-((R)-2-oxo-5-phenyl-3-(2-methylpropyl)-imidazolidin-1-yl)-piperidin-1-yl]-butyl}-nicotinamide

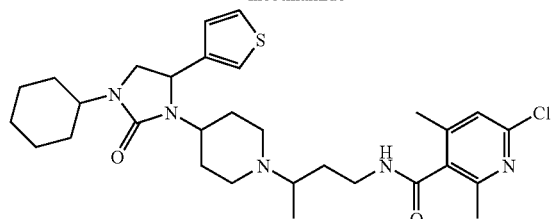

6-Chloro-N-{3-[4-(3-cyclohexyl-2-oxo-5-thiophen-3-yl-imidazolidin-1-yl)-piperidin-1-yl]-butyl}-2,4-dimethyl-nicotinamide

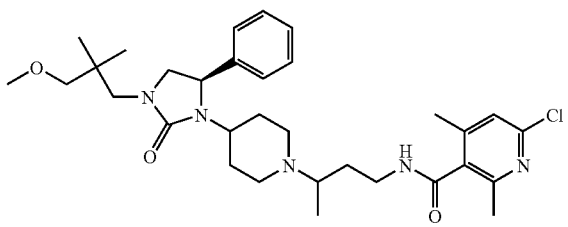

6-Chloro-N-(3-{4-[(R)-3-(3-methoxy-2,2-dimethyl-propyl)-2-oxo-5-phenyl-imidazolidin-1-yl]-piperidin-1-yl}-butyl)-2,4-dimethyl-nicotinamide

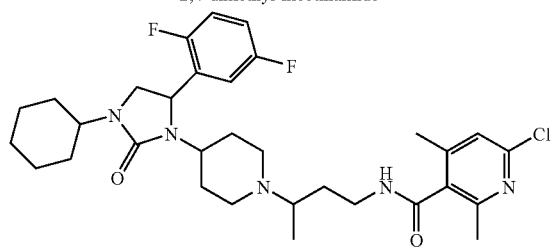

6-Chloro-2,4-dimethyl-N-{3-[4-(2-oxo-5-{2,5-difluoro-phenyl}-3-cyclohexyl-imidazolidin-1-yl)-piperidin-1-yl]-butyl}-nicotinamide

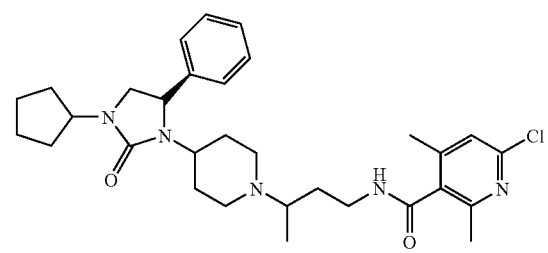

6-Chloro-2,4-dimethyl-N-{3-[4-((R)-2-oxo-5-phenyl-3-(2-cyclopentyl)-imidazolidin-1-yl)-piperidin-1-yl]-butyl}-nicotinamide

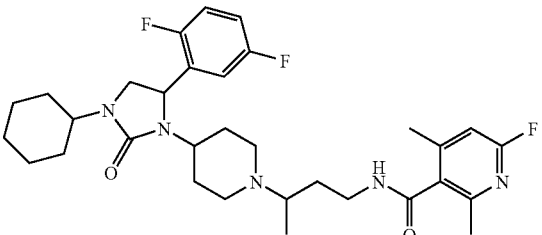

6-Fluoro-2,4-dimethyl-N-{3-[4-(2-oxo-5-{2,5-difluorophenyl}-3-cyclohexyl-imidazolidin-1-yl)-piperidin-1-yl]-butyl}-nicotinamide

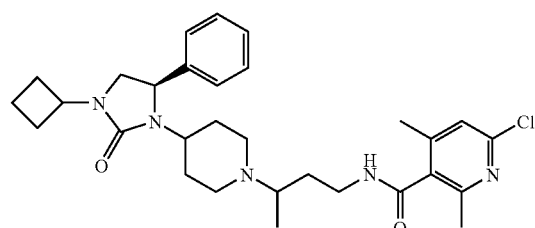

6-Chloro-N-{3-[4-((R)-cyclobutyl-2-oxo-5-phenyl-imidazolidin-1-yl)-piperidin-1-yl]-butyl}-2,4-dimethyl-nicotinamide

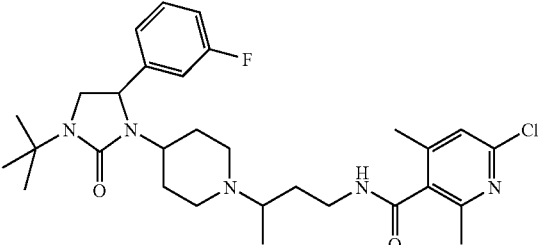

N-(3-{4-[3-tert-Butyl-5-(3-fluoro-phenyl)-2-oxo-imidazolidin-1-yl]-piperidin-1-yl}-butyl)-6-chloro-2,4-dimethyl-nicotinamide

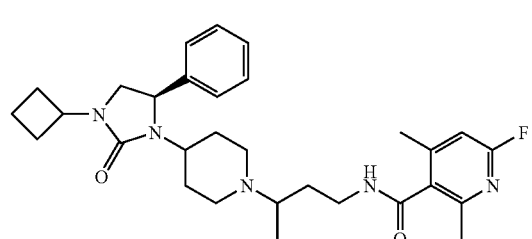

6-Fluoro-N-{3-[4-((R)-3-cyclobutyl-2-oxo-5-phenyl-imidazolidin-1-yl)-piperidin-1-yl]-butyl}-2,4-dimethyl-nicotinamide

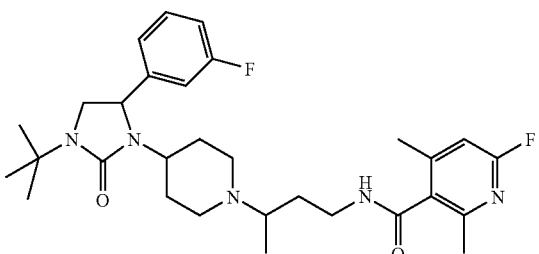

N-(3-{4-[3-tert-Butyl-5-(3-fluoro-phenyl)-2-oxo-imidazolidin-1-yl]-piperidin-1-yl}-butyl)-6-fluoro-2,4-dimethyl-nicotinamide -continued

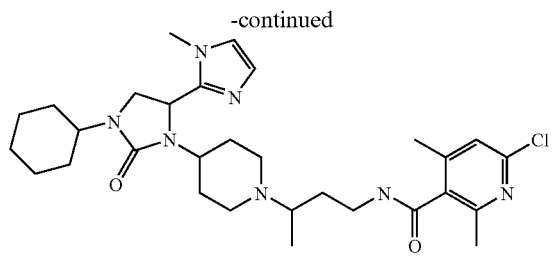

6-Chloro-N-{3-[4-(1′-cyclohexyl-1-methyl-2′-oxo-1′,2′,4′,5′-tetrahydro-1H-[2,4′]biimidazolyl-3′-yl)-piperidin-1-yl]-butyl}-2,4-dimethyl-nicotinamide

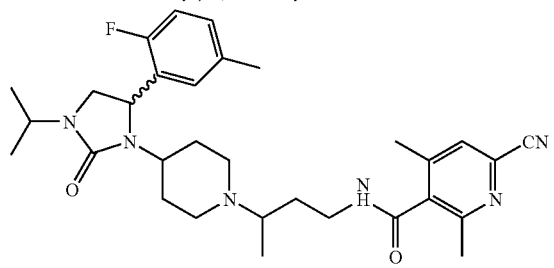

6-Cyano-N-(3-{4-[5-(2-fluoro-5-methyl-phenyl)-3-isopropyl-2-oxo-imidazolidin-1-yl]-piperidin-1-yl}-butyl)-2,4-dimethyl-nicotinamide

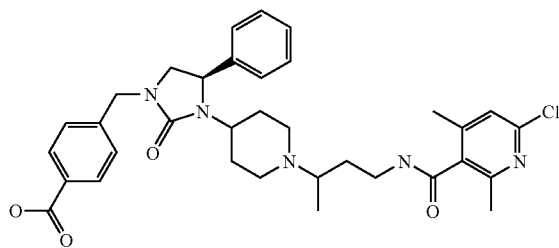

6-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-nicotinic acid

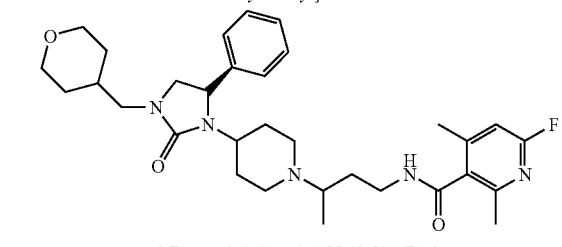

6-Fluoro-2,4-dimethyl-N-{3-[4-((R)-2-oxo-5-phenyl-3-(tetrahydro-pyran-4-ylmethyl)-imidazolidin-1-yl)-piperidin-1-yl]-butyl}-nicotinamide

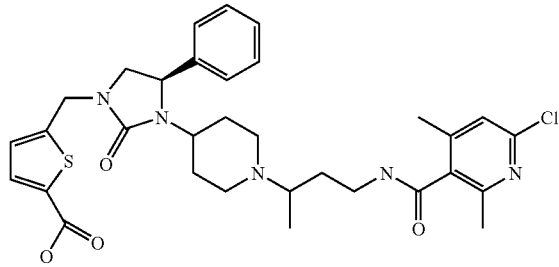

5-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-thiophene-2-carboxylic acid -continued

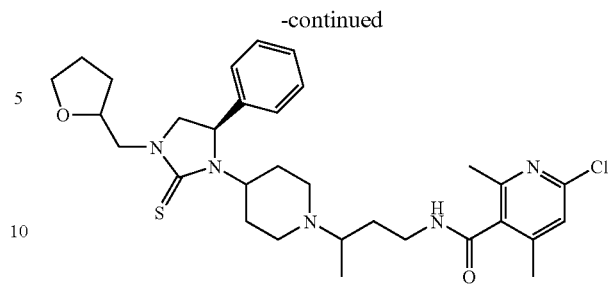

6-Chloro-2,4-dimethyl-N-(3-{4-[(R)-2-oxo-5-phenyl-3-(tetrahydro-furan-2-ylmethyl)-imidazolidin-1-yl]-piperidin-1-yl}-butyl)-nicotinamide

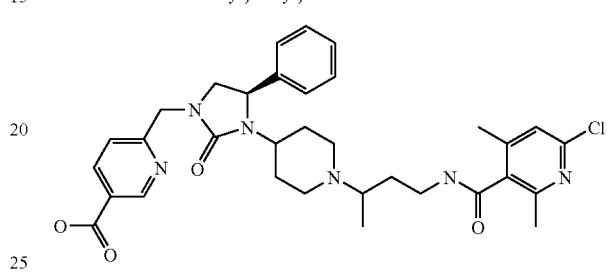

6-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-nicotinic acid

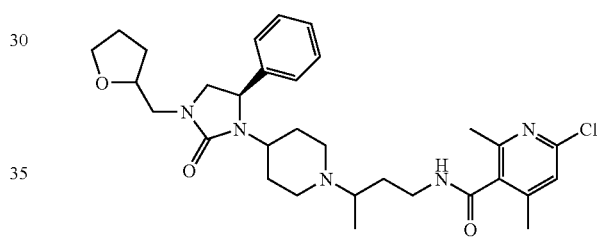

6-Chloro-2,4-dimethyl-N-(3-{4-[(R)-5-phenyl-3-(tetrahydro-furan-2-ylmethyl)-2-thioxo-imidazolidin-1-yl]-piperidin-1-yl}-butyl)-nicotinamide

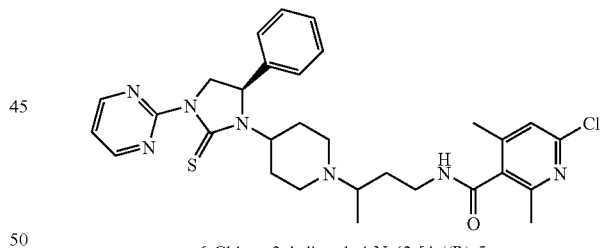

6-Chloro-2,4-dimethyl-N-{3-[4-((R)-5-phenyl-3-pyrimidin-2-yl-2-thioxo-imidazolidin-1-yl)-piperidin-1-yl]-butyl}-nicotinamide

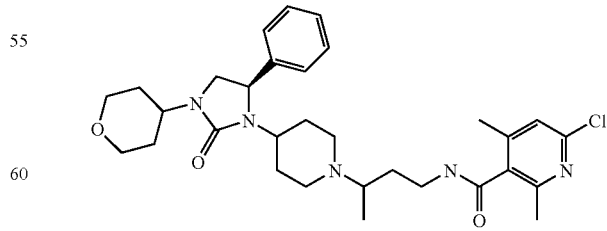

6-Chloro-2,4-dimethyl-N-(3-{4-[(R)-2-oxo-5-phenyl-3-(tetrahydro-pyran-4-yl)-imidazolidin-1-yl]-piperidin-1-yl}-butyl)-nicotinamide -continued

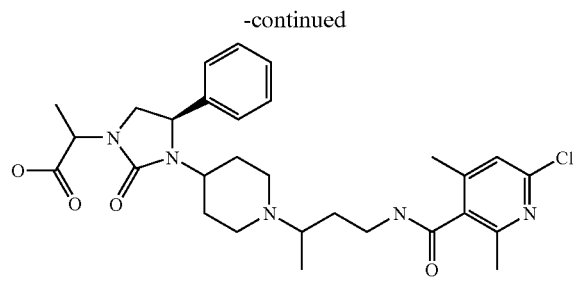

2-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-yl]-propionic acid

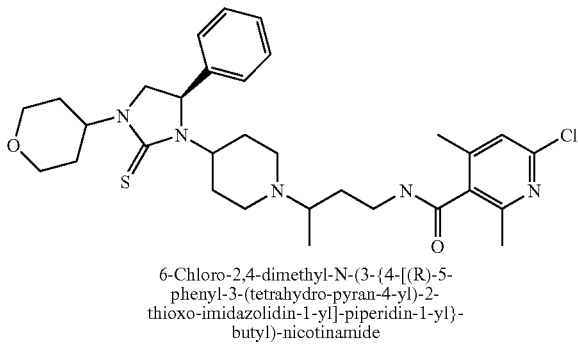

6-Chloro-2,4-dimethyl-N-(3-{4-[(R)-5-phenyl-3-(tetrahydro-pyran-4-yl)-2-thioxo-imidazolidin-1-yl]-piperidin-1-yl}-butyl)-nicotinamide

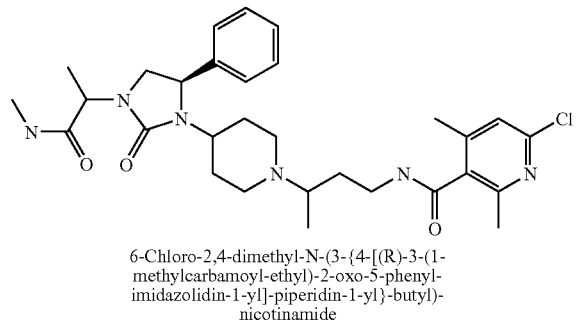

6-Chloro-2,4-dimethyl-N-(3-{4-[(R)-3-(1-methylcarbamoyl-ethyl)-2-oxo-5-phenyl-imidazolidin-1-yl]-piperidin-1-yl}-butyl)-nicotinamide

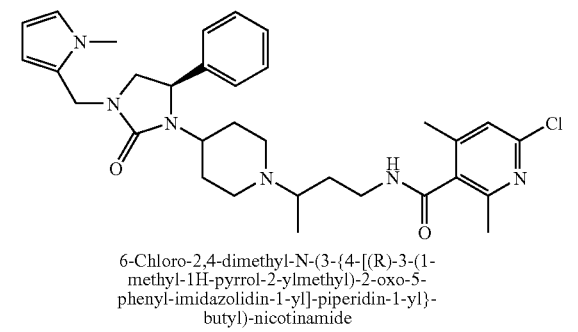

6-Chloro-2,4-dimethyl-N-(3-{4-[(R)-3-(1-methyl-1H-pyrrol-2-ylmethyl)-2-oxo-5-phenyl-imidazolidin-1-yl]-piperidin-1-yl}-butyl)-nicotinamide

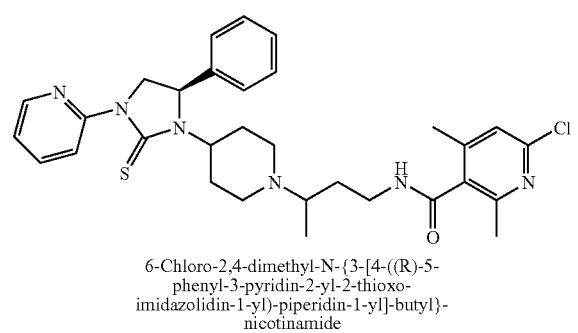

6-Chloro-2,4-dimethyl-N-{3-[4-((R)-5-phenyl-3-pyridin-2-yl-2-thioxo-imidazolidin-1-yl)-piperidin-1-yl]-butyl}-nicotinamide -continued

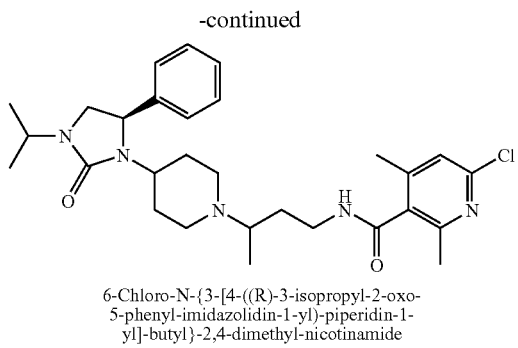

6-Chloro-N-{3-[4-((R)-3-isopropyl-2-oxo-5-phenyl-imidazolidin-1-yl)-piperidin-1-yl]-butyl}-2,4-dimethyl-nicotinamide

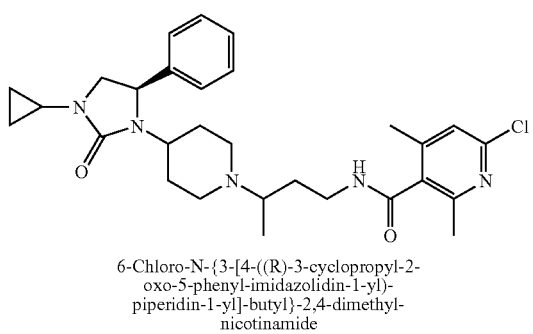

6-Chloro-N-{3-[4-((R)-3-cyclopropyl-2-oxo-5-phenyl-imidazolidin-1-yl)-piperidin-1-yl]-butyl}-2,4-dimethyl-nicotinamide

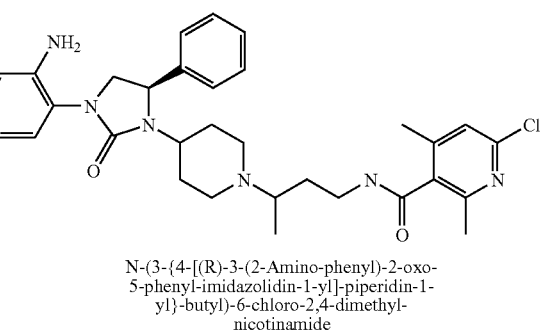

N-(3-{4-[(R)-3-(2-Amino-phenyl)-2-oxo-5-phenyl-imidazolidin-1-yl]-piperidin-1-yl}-butyl)-6-chloro-2,4-dimethyl-nicotinamide

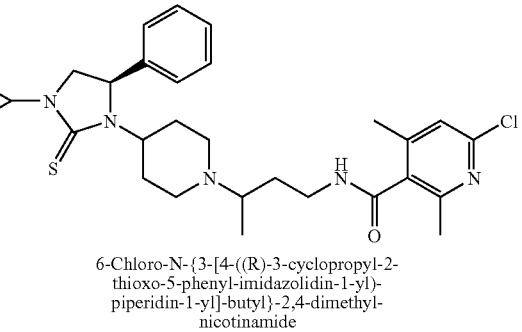

6-Chloro-N-{3-[4-((R)-3-cyclopropyl-2-thioxo-5-phenyl-imidazolidin-1-yl)-piperidin-1-yl]-butyl}-2,4-dimethyl-nicotinamide

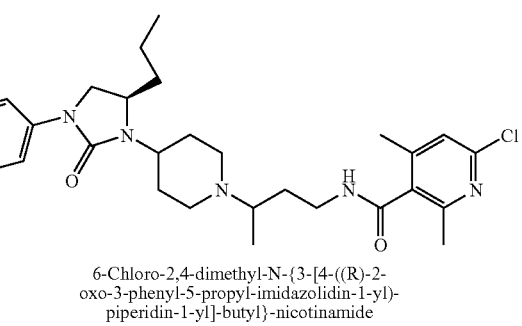

6-Chloro-2,4-dimethyl-N-{3-[4-((R)-2-oxo-3-phenyl-5-propyl-imidazolidin-1-yl)-piperidin-1-yl]-butyl}-nicotinamide

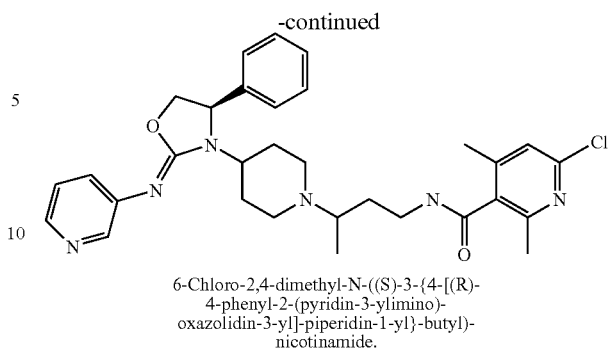

6-Chloro-2,4-dimethyl-N-((S)-3-{4-[(R)-4-phenyl-2-(pyridin-3-ylimino)-oxazolidin-3-yl]-piperidin-1-yl}-butyl)-nicotinamide.

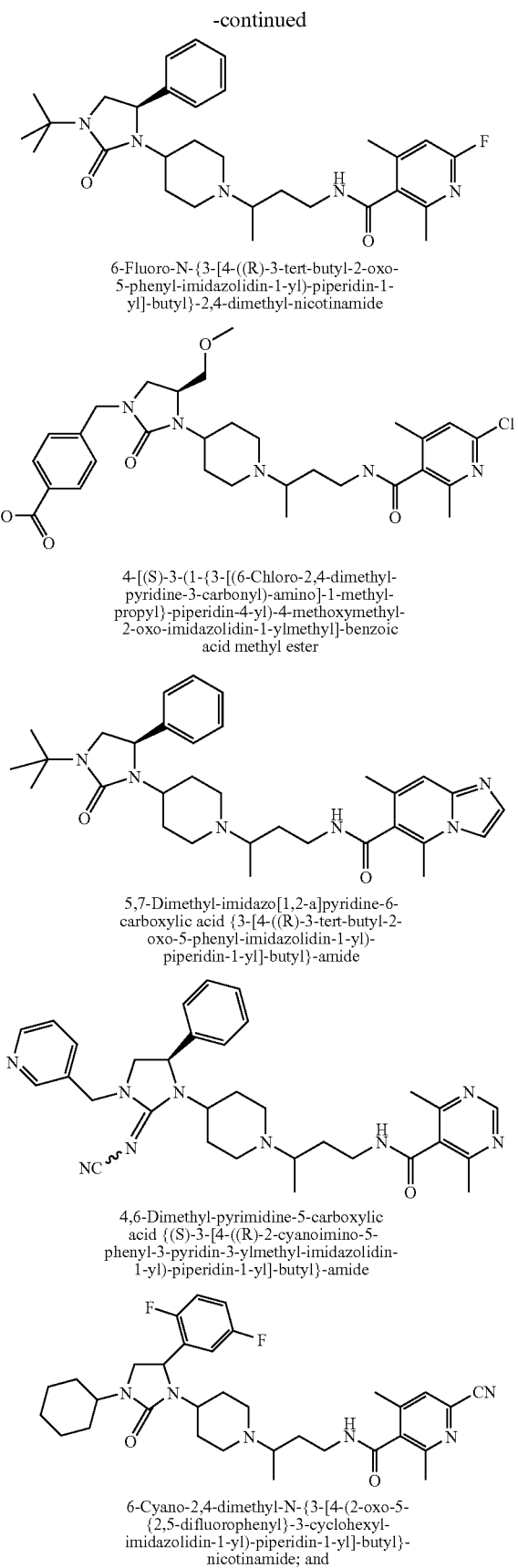

6-Fluoro-N-{3-[4-((R)-3-tert-butyl-2-oxo-5-phenyl-imidazolidin-1-yl)-piperidin-1-yl]-butyl}-2,4-dimethyl-nicotinamide 4-[(S)-3-(1-{3-[(6-Chloro-2,4-dimethyl-pyridine-3-carbonyl)-amino]-1-methyl-propyl}-piperidin-4-yl)-4-methoxymethyl-2-oxo-imidazolidin-1-ylmethyl]-benzoic acid methyl ester 5,7-Dimethyl-imidazo[1,2-a]pyridine-6-carboxylic acid {3-[4-((R)-3-tert-butyl-2-oxo-5-phenyl-imidazolidin-1-yl)-piperidin-1-yl]-butyl}-amide 4,6-Dimethyl-pyrimidine-5-carboxylic acid {(S)-3-[4-((R)-2-cyanoimino-5-phenyl-3-pyridin-3-ylmethyl-imidazolidin-1-yl)-piperidin-1-yl]-butyl}-amide 6-Cyano-2,4-dimethyl-N-{3-[4-(2-oxo-5-{2,5-difluorophenyl}-3-cyclohexyl-imidazolidin-1-yl)-piperidin-1-yl]-butyl}-nicotinamide; and The present invention also relates to pharmaceutical compositions comprising a piperidine derivative including but not limited to compounds 1-303, and a pharmaceutically acceptable carrier. Furthermore, the present invention relates to methods for treating a CCR5 mediated disease in a system, comprising contacting a piperidine derivative, including but not limited to compounds 1-303, with the system. In one embodiment, the system is a cell or tissue. The present invention also relates to methods for treating a CCR5 mediated disease in a subject, comprising administering a piperidine derivative, including but not limited to compounds 1-303, to the subject. The subject may be human or an animal.

Moreover, the compounds may be supplied as "pro-drugs" or protected forms, which release the compound after administration to a subject. The terms "administration" and or administering" as used herein should be understood to mean providing a compound of the invention to the subject in need of treatment. For example, the compound may carry a protective group which is split off by hydrolysis in body fluids, e.g., in the bloodstream, thus releasing the active compound or is oxidized or reduced in body fluids to release the compound. A discussion of pro-drugs may be found in "Smith and Williams' Introduction to the Principles of Drug Design," H.J. Smith, Wright, Second Edition, London (1988).

The compounds of the present invention may be administered in the form of pharmaceutically acceptable salts that are non-toxic. The term "pharmaceutically acceptable salt" as used herein means an active ingredient comprising compounds of Formula 1 or 2 used in the form of a salt thereof, particularly where the salt form confers on the active ingredient improved pharmacokinetic properties as compared to the free form of the active ingredient or other previously disclosed salt form. The term "pharmaceutically acceptable salt" encompasses all acceptable salts including but not limited to acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or pro-drug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

All of the compounds of the invention contain at least one chiral center. The invention includes mixtures of stereoisomers, individual stereoisomers, and enantiomeric mixtures, and mixtures of multiple stereoisomers. In short, the compound may be supplied in any desired degree of chiral purity.

Utility and Administration

In one aspect, the invention is directed to compounds of Formula 1 or 2 that may modulate chemokine receptor activity. Chemokine receptors include but are not limited to CCR1, CCR2, CCR3, CCR4, CCR5, CXCR3, and CXCR4.

In one embodiment, the invention provides compounds of Formula 1 or 2 that may demonstrate protective effects on target cells from HIV infection by binding specifically to the chemokine receptor, thus affecting the binding of a natural ligand to the CCR5 and/or CXCR4 of a target cell.

In another embodiment, the compounds of the present invention may be useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

As used herein, the terms "modulators and/or modulation" encompass antagonist/antagonism, agonist/agonism, partial antagonist/partial antagonism, and or partial agonist/partial agonism, i.e., inhibitors, and activators. The compounds of Formula 1 or 2 described herein may possess biological activity such that they are able to modulate CCR5 chemokine receptor activity and consequent or associated pathogenic processes subsequently mediated by the CCR5 receptor and its natural ligands.

In one embodiment, compounds of Formula 1 or 2 demonstrate a protective effect against HIV infection by inhibiting the binding of HIV to a chemokine receptor of a target cell such as CCR5 and/or CXCR4. Such modulation is obtained by a method which comprises contacting a target cell with an effective amount of the compound to inhibit the binding of the virus to the chemokine receptor. As used herein, the terms "modulation and/or modulation" encompass modulating activity in all types and subtypes of CCR5 receptors of a target cell, in any tissues of a particular patient where they are found, and in any cell components comprising those tissues that the target cell may be located.

Compounds that inhibit chemokine receptor activity and function may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinophilic myotis, eosinophilic fascitis; and cancers.

In addition, compounds that activate or promote chemokine receptor function are used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes. Compounds that activate or promote chemokine receptor function are also used for the treatment of infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

Compounds of the present invention may be used in combination with any other active agents or pharmaceutical compositions where such combined therapy is useful to modulate chemokine receptor activity and thereby prevent and treat inflammatory and immunoregulatory diseases.

Furthermore, the compounds may be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D (or SCH350634); TAK779; UK 427, 857 and TAK 449; or CXCR4-receptor inhibitors such as T22, T134, T140, 18 amino acid analogs of polyphemusin II, ALX40-4C, ALK40-4C, AMD3100 and AMD070;

(6) Integrase inhibitors such as L-870,810; GW-810781 (S-1360); and (7) Budding inhibitors such as PA-344; and PA-457.

Combinations of compounds of the present invention with HIV agents are not limited to the above examples, but include the combination with any agent useful for the treatment of HIV. Combinations the compounds of the invention and other HIV agents may be administered separately or in conjunction. The administration of one agent may be prior to, concurrent to, or subsequent to the administration of other agent(s).

The compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other species, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals.

The invention also relates to a pharmaceutical composition comprising a pharmaceutically acceptable carrier or diluent and an effective amount of compound of Formula 1 or 2. The compounds may be administered alone or as a mixture with a pharmaceutically acceptable carrier (e.g., solid formulations such as tablets, capsules, granules, powders, etc.; liquid formulations such as syrups, injections, etc.). The compounds may be administered orally or non-orally. Examples of non-oral formulations include injections, drops, suppositories, pessaries.

In the treatment or prevention of conditions which require chemokine receptor modulation, an appropriate dosage level will generally be about 0.01 to 500 mg per kg subject body weight per day, and can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In another aspect of the present invention, a compound of Formula 1 or 2 may be used in screening assays for compounds which modulate the activity of chemokine receptors, preferably CCR5 receptors. The ability of a test compound to inhibit gp120 and CD4/CCR5-dependent cell-cell fusion may be measured using a cell fusion assay known in the art.

The compounds of Formula 1 or 2 as disclosed herein may be useful for isolating receptor mutants, which can then be made into screening tools for the discovery of even more potent compounds, following procedures described herein and procedures known in the art. The compounds of Formula 1 or 2 may also be useful in establishing or characterizing the binding sites of other ligands, including compounds other than those of Formula 1 or 2 to chemokine receptors, e.g., by competitive inhibition. The compounds of the present invention may also be useful for the evaluation of putative specific modulators of various chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus, the compounds of this invention are commercial products to be sold for these purposes.

The invention is further described by means of examples, but not in any limitative sense.

EXPERIMENTAL

Compounds of the invention are often readily prepared by known methods; some methods for making compounds and intermediates of the invention are described in a co-pending application by Bridger, et al., which is International Patent Application No. PCT/US2004/041865.

General Procedures

General procedure A: Reductive Amination with $NaBH(OAc)_3$

To a stirred solution of the amine (1 equivalent) in $CH_2Cl_2$ (concentration ~0.2M) at room temperature were added the carbonyl compound (1-2 equivalents), glacial AcOH (0-2 equivalents) and sodium triacetoxyborohydride ($NaBH(OAc)_3$) (~1.5-3 equivalents) and the resultant solution was stirred at room temperature. In a standard workup, the reaction mixture was poured into either saturated aqueous $NaHCO_3$ or 1N NaOH. The phases were separated and the aqueous extracted with $CH_2Cl_2$. The combined organic extracts were dried ($Na_2SO_4$ or $mgSO_4$), filtered and concentrated under reduced pressure. The crude material was purified by flash column chromatography on silica gel or by recrystallization.

General Procedure B: Reductive Amination with $NaCNBH_3$

To a stirred solution of the amine (1 equivalent) in MeOH (concentration ~0.1M) at room temperature were added the carbonyl compound (1-3 equivalents), glacial AcOH (0-1 equivalents) and sodium cyanoborohydride ($NaCNBH_3$) (~1.5-3 equivalents) and the resultant solution was heated to reflux. In a standard workup, the reaction mixture was concentrated under reduced pressure and diluted with saturated aqueous $NaHCO_3$. The aqueous was extracted with $CH_2Cl_2$ and the combined organic extracts were dried ($Na_2SO_4$ or $mgSO_4$), filtered and concentrated under reduced pressure. The crude material was purified by flash column chromatography on silica gel or by recrystallization.

General Procedure C: BOC Deprotection with TFA

The BOC-protected amine was dissolved in $CH_2Cl_2$ (~4 ml/mmol) and trifluoroacetic acid (TFA) (~2 ml/mmol) was added. The mixture was stirred at room temperature for 0.5-5 hours. In a standard work-up, the mixture was neutralized with saturated aqueous $NaHCO_3$ or 1N NaOH and the aqueous extracted with $CH_2Cl_2$. The combined extracts were dried ($Na_2SO_4$ or $mgSO_4$), filtered and concentrated under reduced pressure. The crude material was used in the next reaction as is or was purified by flash column chromatography on silica gel.

General Procedure D: Phthalimide Deprotection

To a solution of the phthalimide-protected amine in EtOH (0.05-0.2M) was added hydrazine hydrate (~10 equivalents). The resulting mixture was stirred at room temperature overnight or heated at 40-50° C. for 2-16 hours. In a standard work-up, the mixture was concentrated under reduced pressure, diluted with CH$_2$Cl$_2$ and filtered. The filtrate was concentrated under reduced pressure and purified by flash column chromatography on silica gel.

General Procedure E: EDCI Coupling

To a stirred solution of a primary or secondary amine (1 equivalent), a carboxylic acid (1.1-2.0 equivalents), 1-hydroxy-benzotriazole hydrate (HOBT) (1.1-2.0 equivalents) and diisopropylethylamine (DIPEA) or N-methylmorpholine (NMM) (1.5-3 equivalents) in CH$_2$Cl$_2$ or DMF (concentration ~0.05-1.5M) was added 1-[3-(dimethylamino)propyl]-3-ethylcarbodiimide hydrochloride (EDCI) (1.1-2.0 equivalents). The solution was stirred at room temperature for 1-3 days and concentrated in vacuo. In a standard work-up, the mixture was diluted with CH$_2$Cl$_2$ or EtOAc and washed consecutively with saturated aqueous NaHCO$_3$ and brine. The organic layer was dried (Na$_2$SO$_4$ or mgSO$_4$), filtered and concentrated under reduced pressure. The crude material was purified by flash column chromatography or by radial chromatography on silica gel.

General Procedure F: Formation of Thioamide with Lawesson's Reagent

A solution of amide (concentration ~0.1 mmol, 1 eq.) and Lawesson's reagent (1 eq.) in toluene was refluxed for 2.5 h. The toluene was removed and the residual material was purified on silica gel column (5% ether in CH$_2$Cl$_2$) to afford the desired product.

General Procedure G: Coupling with Acid Chloride

To a solution of the amine (1 equiv) and DIPEA (2 equiv) in dry CH$_2$Cl$_2$ (concentration 0.05-0.2 M) was added the acid chloride (1.2-1.5 equiv), and the resulting mixture was stirred overnight. The crude mixture was diluted with saturated aqueous NaHCO$_3$ and the aqueous layer was extracted with CH$_2$Cl$_2$. The combined organic extracts were washed with brine, dried (Na$_2$SO$_4$ or mgSO$_4$) and purified by flash chromatography on silica gel.

General Procedure H: Formation of Ureas with Isocyanates

To a solution of the amine (1 equiv) in dry CH$_2$Cl$_2$ (concentration 0.05-0.2 M) was added the isocyanate (1.2-1.5 equiv), and the resulting mixture was stirred overnight. The crude mixture was diluted with saturated aqueous NaHCO$_3$ and the aqueous layer was extracted with CH$_2$Cl$_2$. The combined organic extracts were washed with brine, dried (Na$_2$SO$_4$ or mgSO$_4$) and purified by flash chromatography on silica gel.

General Procedure I: Formation of Ureas with CDI

To a solution of the primary amine (or the HCl salt of the primary amine) (4 equiv) and DIPEA (4 equiv) in dry acetonitrile or 1,2-dichloroethane (concentration 0.1-0.5 M) was added carbonyldiimidazole (CDI) (4 equiv) and the resulting mixture was stirred at 60° C. for 2 h. At this point, the secondary amine (1 equiv) was added, and stirring was continued at 60° C. overnight. The crude mixture was concentrated, and then the residue was diluted with saturated aqueous NaHCO$_3$ and extracted with CH$_2$Cl$_2$. The combined organic extracts were washed with brine, dried (Na$_2$SO$_4$ or mgSO$_4$) and purified by flash chromatography on silica gel.

General Procedure J: Coupling with Phenyl Carbamate

To a solution of the phenylcarbamate (or the p-nitrophenylcarbamate) (1.25-2.0 equiv) and DIPEA (1.5-2.0 equiv) in dry THF or 1,2-dichloroethane (concentration 0.05-0.2 M) was added the secondary amine (1 equiv). The resulting mixture was stirred at 60-70° C. overnight, at which time the reaction was diluted with saturated aqueous NaHCO$_3$ and extracted with CH$_2$Cl$_2$. The combined organic extracts were washed with brine, dried (Na$_2$SO$_4$ or mgSO$_4$) and purified by flash chromatography on silica gel.

Intermediates 2,6-Dimethyl-N-[3-(4-oxo-piperidin-1-yl)-butyl]-benzamide

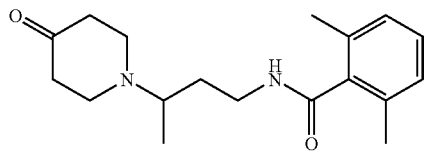

To a solution of 1,4-dioxa-8-azaspiro[4.5]decane (8.00 g, 55.9 mmol) in MeOH (70 ml) was added crotononitrile (18.74 g, 279 mol). The mixture was heated at 50° C. for 16 hours. MeOH and excess crotononitrile were removed by evaporation under reduced pressure to give 3-(1,4-dioxa-8-aza-spiro[4.5]dec-8-yl)-butyronitrile (11.75 g, 100%) as a pale yellow oil.

To a solution of 3-(1,4-dioxa-8-aza-spiro[4.5]dec-8-yl)-butyronitrile (2.80 g, 13.3 mmol), in MeOH (50 ml) was added Raney Ni (~5 ml). The mixture was hydrogenated at 50 psi at rt for 1.5 hours. The catalyst was removed by filtration through a layer of Celite® and the solvents were evaporated to give the crude product as a colorless oil (2.85 g, 100%).

Using general procedure E with 3-(1,4-dioxa-8-aza-spiro[4.5]dec-8-yl)-butylamine (2.30 g, 10.7 mmol) and 2,6-dimethylbenzoic acid (1.77 g, 11.8 mmol) followed by purification by column chromatography on silica gel (1-5% MeOH/CH$_2$Cl$_2$) gave N-[3-(1,4-dioxa-8-aza-spiro[4.5]dec-8-yl)-butyl]-2,6-dimethyl-benzamide (3.11 g, 83%).

A solution of N-[3-(1,4-dioxa-8-azaspiro[4.5]dec-8-yl)-butyl]-2,4-dimethyl-1-benzamide (3.11 mg, 8.95 mmol) in acetone (10 ml) and HCl 6N (aq, 8 ml) was refluxed for 18 h. The reaction mixture was quenched with NaOH (aq, 15%) to pH 7-8. The organic material was extracted with CH$_2$Cl$_2$ and the organic layer was dried over Na$_2$SO$_4$, filtered and concentrated. The residue was purified by column chromatography on silica gel (10% MeOH in CH$_2$Cl$_2$; 2.5% NH$_4$OH) to afford 2,4-dimethyl-N-[3-(4-oxo-piperidin-1-yl)butyl]-1-benzamide (543 mg, 22%). $^1$H NMR (CDCl$_3$) δ 1.00 (d, 3H, J=6.6 Hz), 1.57-1.67 (m, 1H), 1.73-1.83 (m, 1H), 2.12-2.28 (m, 4H), 2.31 (s, 6H), 2.60-2.68 (m, 2H), 2.84-2.97 (m, 3H), 3.42-3.50 (m, 1H), 3.69-3.79 (m, 1H), 6.98 (d, 2H, J=7.5 Hz), 7.11 (t, 1H, J=7.5 Hz), 7.20 (br s, 1H).

4,6-Dimethyl-pyrimidine-5-carboxylic acid [3-(4-oxo-piperidin-1-yl)-butyl]-amide

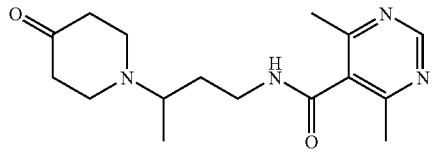

Using general procedure E with 3-(1,4-dioxa-8-aza-spiro[4.5]dec-8-yl)-butylamine (4.50 g, 21.0 mmol) and 4,6-dimethyl-pyrimidine-5-carboxylic acid (3.20 g, 21.0 mmol), followed by purification by column chromatography on silica gel (2-10% MeOH/CH$_2$Cl$_2$) gave 4,6-dimethyl-pyrimidine-5-carboxylic acid [3-(1,4-dioxa-8-aza-spiro[4.5]dec-8-yl)-butyl]-amide (5.10 g, 73%).

A solution of 4,6-dimethyl-pyrimidine-5-carboxylic acid [3-(1,4-dioxa-8-aza-spiro[4.5]dec-8-yl)-butyl]-amide (3.11 g, 8.95 mmol) in acetone (10 ml) and HCl 6N (aq, 8 ml) was refluxed for 18 h. The reaction mixture was quenched with NaOH (aq, 15%) to pH 7-8. The organic material was extracted with CH$_2$Cl$_2$ and the organic layer was dried over Na$_2$SO$_4$, filtered and concentrated. The residue was purified by column chromatography on silica gel (10% MeOH in CH$_2$Cl$_2$; 2.5% NH$_4$OH) to afford 4,6-dimethyl-pyrimidine-5-carboxylic acid [3-(4-oxo-piperidin-1-yl)-butyl]-amide (589 mg, 23%). $^1$H NMR (CDCl$_3$) δ 1.04 (d, 3H, J=6.6 Hz), 1.64-1.72 (m, 1H), 1.81-1.91 (m, 1H), 2.15-2.30 (m, 4H), 2.52 (s, 6H), 2.62-2.72 (m, 2H), 2.84-2.98 (m, 3H), 3.47-3.62 (m, 1H), 3.69-3.77 (m, 1H), 6.94 (br s, 1H), 8.93 (s, 1H).

2,4-Dimethyl-N-[3-(4-oxo-piperidin-1-yl)-butyl]-1-oxy-nicotinamide

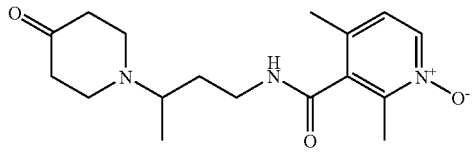

Using general procedure E with 3-(1,4-dioxa-8-aza-spiro[4.5]dec-8-yl)-butylamine (4.50 g, 21.0 mmol) and 2,4-dimethyl-1-oxy-nicotinic acid (3.20 g, 21.0 mmol), followed by purification by column chromatography on silica gel (2-10% MeOH/CH$_2$Cl$_2$) gave 4,6-dimethyl-N—O pyridine-5-carboxylic acid [3-(1,4-dioxa-8-aza-spiro[4.5]dec-8-yl)-butyl]-amide (5.3 g, 73%).

A solution 4,6-dimethyl-N—O pyridine-5-carboxylic acid [3-(1,4-dioxa-8-aza-spiro[4.5]dec-8-yl)-butyl]-amide (3.11 mg, 8.95 mmol) in acetone (10 ml) and HCl 6N (aq, 8 ml) was refluxed for 18 h. The reaction mixture was quenched with NaOH (aq, 15%) to pH 7-8. Organic material was extracted with CH$_2$Cl$_2$ and the organic layer was dried over Na$_2$SO$_4$, filtered and concentrated. The residue was purified by column chromatography on silica gel (10% MeOH in CH$_2$Cl$_2$; 2.5% NH$_4$OH) to afford 2,4-dimethyl-N-[3-(4-oxo-piperidin-1-yl)-butyl]-1-oxy-nicotinamide (533 mg, 24%). $^1$H NMR (CDCl$_3$) δ 0.96-1.05 (m, 2H), 1.04 (d, 3H, J=6.6 Hz), 1.50-1.97 (m, 3H), 2.31 (s, 3H), 2.33 (m, 3H), 2.32-2.50 (m, 2H), 2.63-2.75 (m, 2H), 2.85-3.05 (m, 2H), 3.58 (q, 2H, J=5.7 Hz), 6.89 (d, 1H, J=6.6 Hz), 7.85 (d, 1H, J=6.6 Hz), 8.51-8.53 (m, 1H).

(R)-3-[1-(3-Amino-1-methyl-propyl)-piperidin-4-yl]-4-phenyl-oxazolidine-2-thione

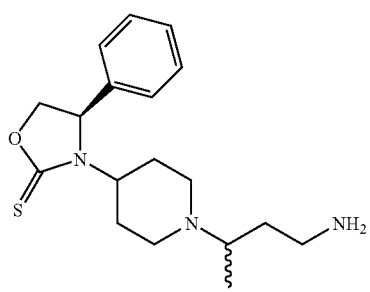

Using general procedure A, R-phenylglycinyl ((2.85 g, 0.02 mol) and (R,S)-[3-(4-oxo-piperidin-1-yl)-butyl]-carbamic acid tert-butyl ester (5.0 g, 0.0185 mol) gave the desired amine as a light yellow foam solid (7.6 g, 95%), which was used in the next step without purification.

To a solution of the above substrate (7.6 g, 0.019 mol) in DMF (50 ml) was added 1,1'-thiocarbonyldiimidazole (3.46 g, 0.0194 mol). The mixture stirred at rt for 16 hrs at which point only 35% conversion had occurred. 1,1'-Thiocarbonyldiimidazole (5.2 g, 0.029 mol) was added to the mixture and the reaction was complete by 5 hrs. The reaction was quenched with saturated aqueous NaHCO$_3$ and extracted with EtOAc. The organic layer was dried with mgSO$_4$ and the crude material was purified by a column chromatography to afforded (R,S)-3-[1-(3-amino-1-methyl-propyl)-piperidine-4-yl]-4-phenyl-oxazolidine-2-thione-1-carboxylic acid tert-butyl ester (5.45 g, 65%).

Using general procedure C the substrate (5.0 g, 0.012 mol) gave the desired amine. Due to the high water solubility of the compound, the mixture was neutralized with solid K$_2$CO$_3$ and the product was purified by column chromatography to afford (R,S)-3-[1-(3-amino-1-methyl-propyl)-piperidine-4-yl]-4-phenyl-oxazolidine-2-thione (1.6 g, 42%). $^1$H NMR (CDCl$_3$) δ 0.90 (d, 3H), 0.90-1.0 (m, 1H), 1.31-1.91 (m, 8H), 2.03-2.05 (m, 1H), 2.61-2.75 (m, 6H), 4.32-4.36 (m, 2H), 4.94-4.98 (m, 1H), 5.29 (d, 1H), 7.25-7.42 (m, 5H).

2,6-Dichloro-4-methyl-N—((R)-3-{4-[(thiophen-3-ylmethyl)-amino]-piperidin-1-yl}-butyl)-nicotinamide

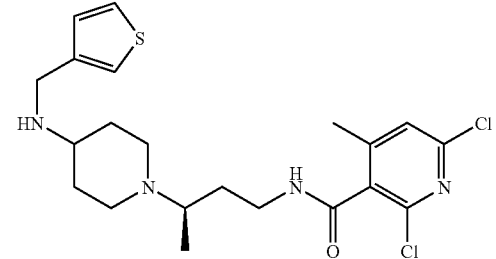

To a solution of ((R)-3-{4-[(thiophen-3-ylmethyl)-amino]-piperidin-1-yl}-butyl)-carbamic acid tert-butyl ester (3.01 g, 8.19 mmol) in THF (10 ml) was added 6 N HCl (10 ml) and the reaction stirred at 50° C. for 2 then at rt for 1 h. The mixture was concentrated, diluted with CH$_2$Cl$_2$ (50 ml) and 10 N NaOH (10 ml) and the aqueous layer extracted with CH$_2$Cl$_2$ (3×25 ml). The combined organic extracts were dried (Na$_2$SO$_4$) and concentrated to afford the deprotected material (1.88 g, 86%) as a yellow oil.

Following general procedure E: to a solution of the amine from above (1.88 g, 7.03 mmol) in CH$_2$Cl$_2$ (25 ml) was added 2,6-dichloro-4-methyl-nicotinic acid (1.5927 g, 7.73 mmol), HOBt (1.055 g, 7.81 mmol), DIPEA (1.3 ml, 7.48 mmol) and EDCI (1.5371 g, 8.02 mmol) and the reaction stirred overnight. Purification of the crude product by column chromatography through a plug of silica gel (CH$_2$Cl$_2$/MeOH/NH$_4$OH, 96:4:0 then 9:1:0 then 88:10:2) afforded the desired intermediate (2.42 g, 65% over 2 steps) as a yellow foam. $^1$H NMR (CDCl$_3$) δ 0.78-0.95 (m, 1H), 0.97-1.05 (m, 1H), 0.98 (d, 3H, J=6.6 Hz), 1.51-1.58 (m, 1H), 1.79-1.83 (m, 3H), 2.11-2.14 (m, 1H), 2.35 (s, 3H), 2.43-2.49 (m, 2H), 2.70-2.88 (m, 3H), 3.33-3.42 (m, 1H), 3.71 (s, 2H), 3.73-3.78 (m, 1H), 7.00 (d, 1H, J=4.8 Hz), 7.09 (d, 1H, J=3 Hz), 7.12 (s, 1H), 7.26 (dd, 1H, J=4.8, 3 Hz), 8.85 (br s, 1H).

Examples 1 to 37 were prepared following the scheme illustrated below. $R^1$ is as defined in the individual examples and $R^2COOH$ is as defined in the table.

TABLE 1

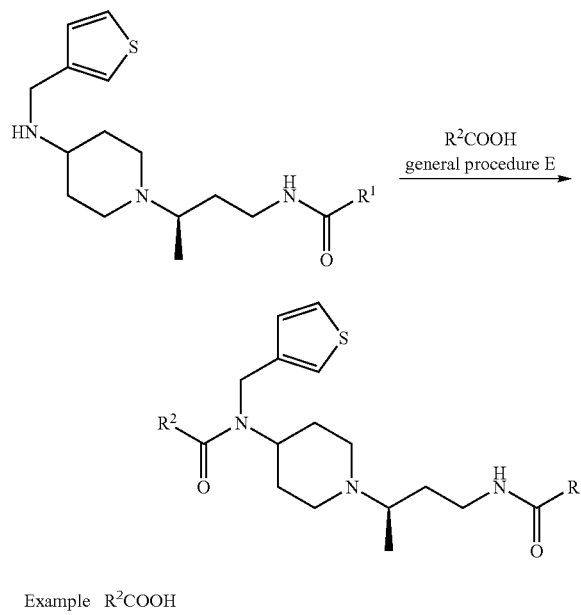

| Example | $R^2COOH$ |
|---|---|
| 1* | (4,4-difluorocyclohexyl)-acetic acid |
| 2* | 3-cyclohexyl-propionic acid |
| 3* | 4-pyridylthioacetic acid |
| 4* | 1-benzocyclobutenecarboxylic acid |
| 5* | 3-thiopheneacetic acid |
| 6* | (pyridin-2-ylsulfanyl)-acetic acid |
| 7* | (5-methyl-[1,3,4]thiadiazol-2-ylsulfanyl)-acetic acid |
| 8* | (1-methyl-1H-imidazol-2-ylsulfanyl)-acetic acid |
| 9* | (5-methyl-[1,3,4]thiadiazol-2-ylsulfanyl)-acetic acid |
| 10 | 2-(2-methoxyethoxy)acetic acid |
| 11 | 3-methyl-5-isoxazoleacetic acid |
| 12 | morpholin-4-yl-acetic acid |
| 13 | pyridin-2-yl-acetic acid hydrochloride |
| 14 | pyridin-3-yl-acetic acid hydrochloride |
| 15 | pyridin-4-yl-acetic acid hydrochloride |
| 16 | 3-methoxypropionic acid |
| 17 | tetrazol-1-ylacetic acid |
| 18 | (2-oxo-pyrrolidin-1-yl)-acetic acid |
| 19 | hippuric acid |
| 20 | imidazol-1-yl-acetic acid |
| 21 | hydantoic acid |
| 22 | N,N-dimethyl glycine |
| 23 | methane sulphonyl acetic acid |
| 24 | (2-oxo-oxazolidin-3-yl)-acetic acid |
| 25 | acrylic acid |
| 26 | N-acetyl-beta-alanine |
| 27 | 1,2,4-triazole-1-acetic acid |
| 28 | 1-pyrrolidineacetic acid |
| 29 | 3,3-dimethylacrylic acid |
| 30 | 2-oxo-1-pyrrolidineacetic acid |
| 31 | 1H-tetrazole-1-acetic acid |
| 32 | cyanoacetic acid |
| 33 | (2-oxo-oxazolidin-3-yl)-acetic acid (see COMPOUND 24) |
| 34 | methoxyiminoacetic acid (Graf, H. et al. Eur. Pat. Appl. (1983) EP 0088325) |
| 35 | 1-cyano-cyclopropanecarboxylic acid |
| 36 | (2-oxo-imidazolidin-1-yl)-acetic acid |
| 37 | cyclopropylacetic acid |

*= racemic

Example 1

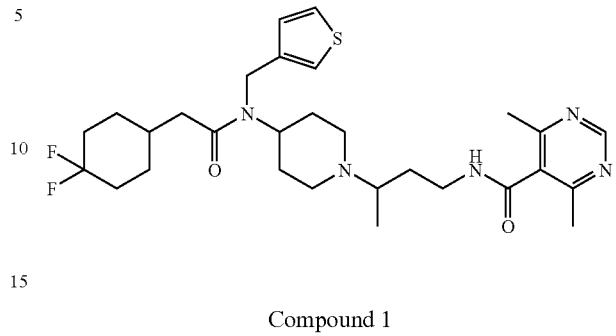

Compound 1

4,6-Dimethylpyrimidine-5-carboxylic acid [3-(4-{[2-(4,4-difluorocyclohexyl)-acetyl]-thiophen-3-ylmethylamino}-piperidin-1-yl)-butyl]-amide White solid. $^1H$ NMR (CDCl$_3$) mixture of rotomers: δ 0.77-1.48 (m, 9H), 1.49-2.45 (m, 13H), 2.48-2.59 (m, 6H), 2.63-2.93 (m, 3H), 3.24-3.46 (m, 1H), 3.73-4.09 (m, 3H), 4.39-4.56 (m, 1H), 6.96 (m, 2H), 7.31-7.38 (m, 1H), 7.86-7.94 and 8.59-8.75 (m, 1H), 8.89-8.95 (m, 1H); $^{13}C$ NMR (CDCl$_3$) δ 13.8, 22.4, 29.2, 29.3, 29.6, 30.1, 30.9, 31.7, 33.2, 33.5, 33.8, 34.1, 39.8, 40.8, 43.0, 43.8, 44.2, 51.6, 52.2, 56.1, 60.1, 60.8, 121.0, 121.6, 123.8, 125.9, 126.2, 127.3, 127.8, 140.0, 157.9, 158.2, 163.5, 172.6; ES-MS m/z 562 (M+H). Anal. Calcd. for $C_{29}H_{41}N_5F_2O_2S \cdot 0.5C_4H_{10} \cdot 0.1CH_2Cl_2$: C, 61.51; H, 7.67; N, 11.53. Found: C, 61.44; H, 7.58; N, 11.56.

Example 2

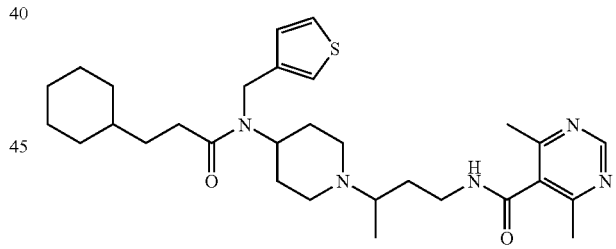

Compound 2

4,6-Dimethyl-pyrimidine-5-carboxylic acid (3-{4-[(3-cyclohexyl-propionyl)-thiophen-3-ylmethylamino]-piperidin-1-yl}-butyl)-amide White solid. $^1H$ NMR (CDCl$_3$) δ 0.70-1.30 (m, 12H), 1.31-2.80 (m, 12H), 2.05-2.80 (m, 13H), 3.20-4.55 (m, 5H), 6.86-7.30 (m, 3H), 7.95 (br s, 0.25H), 8.74 (s, 0.75H), 8.87 (s, 0.75H), 8.90 (s, 0.25H); $^{13}C$ NMR (CDCl$_3$) δ 13.81, 22.30, 26.60, 26.90, 30.89, 31.39, 31.57, 31.79, 32.22, 33.20, 37.70, 39.89, 40.51, 40.65, 43.01, 43.74, 44.34, 51.50, 52.16, 56.25, 59.87, 60.75, 120.85, 121.54, 125.64, 126.24, 127.00, 127.81, 131.07, 131.34, 140.40, 140.75, 157.87, 158.09, 163.49, 166.62, 166.86, 173.41, 174.51; ES-MS m/z 540

(M+H). Anal. Calcd. for C$_{30}$H$_{45}$N$_5$O$_2$S.1.3CH$_2$Cl$_2$: C, 65.15; H, 8.22; N, 12.58; S, 5.76. Found: C, 65.40; H, 8.26; N, 12.48, S, 5.71.

Example 3

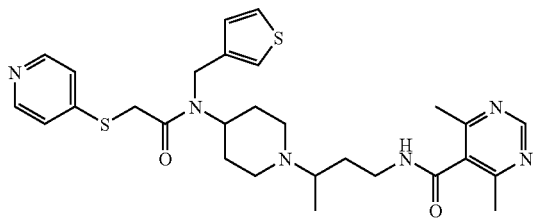

Compound 3

4,6-Dimethyl-pyrimidine-5-carboxylic acid (3-{4-{[2-(pyridin-4-ylsulfanyl)-acetyl]-thiophen-3-ylmethyl-amino}-piperidin-1-yl}-butyl]-amide $^1$H NMR (CDCl$_3$) δ 0.76-1.80 (m, 11H), 1.99-2.25 (m, 3H), 2.40-2.80 (m, 11H), 3.25-4.50 (m, 8H), 6.75-7.50 (m, 5H), 7.78 (br s, 2H), 7.25-7.49 (m, 2H), 8.52 (br s, 0.8H), 8.83 (s, 0.8H), 8.90 (br s, 0.2H); $^{13}$C NMR (CDCl$_3$) δ 13.84, 22.32, 29.87, 30.72, 31.13, 31.37, 32.11, 34.48, 34.84, 39.73, 40.33, 41.26, 43.48, 43.74, 44.30, 51.95, 52.68, 57.48, 59.63, 60.50, 121.37, 121.50, 121.85, 126.12, 127.50, 127.92, 131.28, 139.21, 148.08, 149.66, 149.84, 157.88, 158.08, 163.48, 166.66, 168.34; ES-MS m/z 553 (M+H). Anal. Calcd. for C$_{28}$H$_{36}$N$_6$O$_2$S$_2$.0.2CH$_2$Cl$_2$: C, 59.45; H, 6.44; N, 14.75. Found: C, 59.34; H, 6.57; N, 14.71.

Example 4

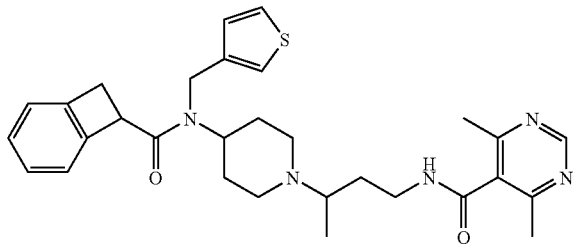

Compound 4

4,6-Dimethyl-pyrimidine-5-carboxylic acid (3-{-4-[(bicyclo[4.2.0]octa-1(6), 2,4-triene-7-carbonyl)-thiophen-3-ylmethyl-amino]-piperidin-1-yl}-butyl)-amide White solid. $^1$H NMR (CDCl$_3$) mixture of rotomers: δ 0.80-1.37 (m, 8H), 1.38-3.00 (m, 8H), 2.53 and 2.55 (s, 6H), 3.01-4.48 (m, 6H), 6.83-7.47 (m, 7H), 7.80 and 8.72 (s, 1H), 8.84-8.93 (s, 1H); $^{13}$C NMR (CDCl$_3$) δ 13.8, 22.4, 29.8, 30.9, 31.7, 31.9, 32.5, 34.1, 34.2, 34.5, 34.7, 40.0, 40.5, 41.0, 43.0, 43.8, 44.2, 45.8, 46.1, 52.2, 55.9, 60.0, 60.1, 60.8, 122.6, 123.8, 125.4, 126.4, 127.3, 127.5, 128.4, 128.6, 140.2, 143.9, 144.5, 158.0, 158.2, 163.6, 172.7; ES-MS m/z 532 (M+H). Anal. Calcd. for C$_{30}$H$_{37}$N$_5$O$_2$S.0.4CH$_2$Cl$_2$.0.5C$_4$H$_{10}$O: C, 64.56; H, 7.16; N, 11.62. Found: C, 64.94; H, 7.01; N, 11.58.

Example 5

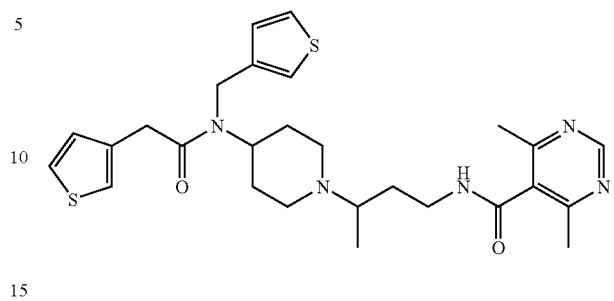

Compound 5

4,6-Dimethyl-pyrimidine-5-carboxylic acid (3-{4-[(2-thiophen-3-yl-acetyl)-thiophen-3-ylmethyl-amino]-piperidin-1-yl}-butyl)-amide White solid. $^1$H NMR (CDCl$_3$) δ 0.75-1.10 (m, 4H), 1.25-2.79 (m, 15H), 3.25-4.50 (m, 6H), 6.93-7.45 (m, 6H), 7.97 (br s, 0.25H), 8.59 (br s, 0.75H), 8.80 (s, 0.75H), 8.89 (s, 0.25H); $^{13}$C NMR (CDCl$_3$) δ 11.99, 20.50, 28.02, 28.91, 29.20, 29.39, 29.87, 30.23, 31.08, 34.49, 35.21, 36.70, 38.08, 38.58, 39.03, 41.50, 41.92, 42.47, 43.24, 50.14, 50.26, 55.08, 58.04, 58.78, 119.22, 119.91, 120.52, 123.94, 124.38, 124.62, 124.83, 125.48, 125.98, 126.56, 126.75, 129.44, 133.22, 133.50, 138.28, 138.43, 156.06, 156.27, 161.63, 164.85, 165.00, 168.89, 169.89; ES-MS m/z 526 (M+H). Anal. Calcd. for C$_{27}$H$_{35}$N$_5$S$_2$O$_2$.0.3CH$_4$O: C, 59.49; H, 6.51; N, 12.71. Found: C, 59.43; H, 6.49; N, 12.82.

Example 6

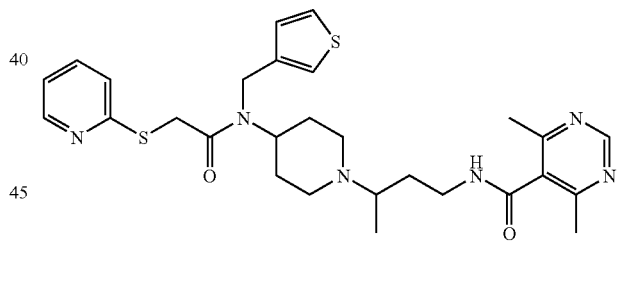

Compound 6

4,6-Dimethyl-pyrimidine-5-carboxylic acid [3-(4-{[2-(pyridin-2-ylsulfanyl)-acetyl]-thiophen-3-ylmethyl-amino}-piperidin-1-yl)-butyl]-amide A solution of 2-mercaptopyridine (484 mg, 4.35 mmol), methyl bromoacetate (0.45 ml, 4.8 mmol), and Et$_3$N (0.79 ml, 5.7 mmol) in CH$_3$CN (22 ml) was stirred at room temperature for 20 h to give (pyridin-2-ylsulfanyl)-acetic acid methyl ester as a colorless oil (752 mg, 94%) after aqueous work-up and purification.

A solution of the ester from above (751 mg, 4.10 mmol) in MeOH (50 ml) and 1N NaOH (10 ml) was stirred at room temperature for 45 minutes to give (pyridin-2-ylsulfanyl)-acetic acid (655 mg, 95%) after acidic work-up.

COMPOUND 6 was isolated as a yellow foam (2:1 mixture of rotamers). $^1$H NMR (CDCl$_3$) δ 0.87-1.93 (m, 19H), 2.09-2.29 (m, 2H), 2.51-2.79 (m, 19H), 3.30 (m, 2H), 3.69-4.22

(m, 11H), 4.44 (m, 1H), 6.92-7.12 (m, 6H), 7.17-7.28 (m, 3H), 7.34 (dd, 1H, J=4.8, 3.0 Hz), 7.43-7.53 (m, 2H), 8.05 (br s, 1H), 8.35 (d, 1H, J=4.5 Hz), 8.39 (d, 1H, J=4.5 Hz), 8.73 (m, 1H), 8.88 (s, 1H), 8.93 (s, 1H); $^{13}$C NMR (CDCl$_3$) δ 13.32, 13.44, 21.95, 29.34, 30.28, 30.52, 30.91, 31.21, 31.78, 32.00, 32.98, 39.65, 40.13, 40.78, 43.09, 43.29, 43.41, 51.52, 51.72, 52.05, 56.01, 59.65, 60.36, 119.68, 119.97, 120.86, 121.17, 121.96, 122.40, 125.34, 126.01, 126.73, 127.25, 130.71, 130.95, 136.00, 136.42, 139.60, 139.73, 149.07, 156.99, 157.55, 157.72, 163.12, 166.28, 166.43, 168.86, 169.63; ES-MS m/z 553 (M+H). Anal. Calcd. for C$_{28}$H$_{36}$N$_6$S$_2$O$_2$.0.5CH$_4$O: C, 60.18; H, 6.73; N, 14.78; S, 11.27. Found: C, 60.24; H, 6.44; N, 14.54; S, 11.10.

Example 7

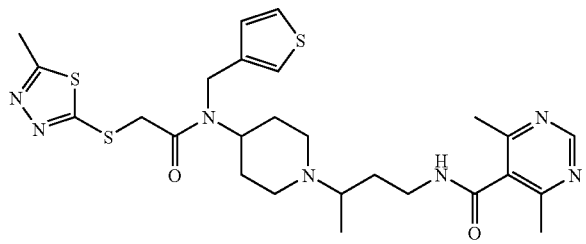

Compound 7

4,6-Dimethyl-pyrimidine-5-carboxylic acid [3-(4-{[2-(5-methyl-[1,3,4]thiadiazol-2-ylsulfanyl)-acetyl]-thiophen-3-ylmethyl-amino}-piperidin-1-yl)-butyl]-amide Colorless foam (2:1 mixture of rotamers). $^1$H NMR (CDCl$_3$) δ 0.90-1.80 (m, 18H), 2.14 (m, 2H), 2.53 (m, 14H), 2.67-2.82 (m, 12H), 3.34 (m, 2H), 3.64-3.85 (m, 3H), 4.02-4.26 (m, 6H), 4.39 (m, 3H), 6.94 (d, 1H, J=4.8 Hz), 7.02 (m, 2H), 7.11 (m, 1H), 7.21 (dd, 1H, J=5.0, 3.2 Hz), 7.36 (dd, 1H, J=4.8, 3.0 Hz), 7.89 (br s, 1H), 8.48 (br s, 1H), 8.87 (s, 1H), 8.93 (s, 1H); $^{13}$C NMR (CDCl$_3$) δ 13.83, 13.92, 15.96, 22.30, 29.84, 30.68, 31.23, 31.84, 32.08, 37.95, 39.75, 40.18, 41.32, 43.71, 43.83, 44.11, 51.62, 51.89, 53.05, 57.01, 59.63, 60.26, 121.45, 122.07, 125.96, 126.23, 127.56, 127.68, 131.07, 131.18, 139.17, 139.46, 157.90, 158.00, 163.41, 164.88, 165.14, 165.60, 165.71, 166.72, 166.84, 166.94, 167.85; ES-MS m/z 574 (M+H). Anal. Calcd. for C$_{26}$H$_{35}$N$_7$S$_3$O$_2$.0.2CH$_2$Cl$_2$: C, 53.27; H, 6.04; N, 16.60; S, 16.28. Found: C, 53.34; H, 6.15; N, 16.57; S, 16.17.

Example 8

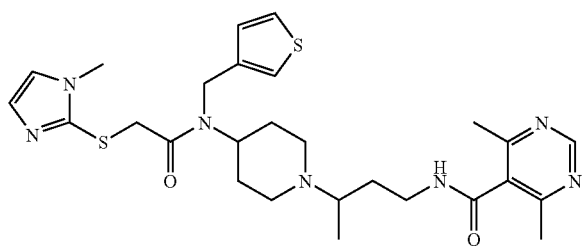

Compound 8

4,6-Dimethyl-pyrimidine-5-carboxylic acid [3-(4-{[2-(1-methyl-1H-imidazol-2-ylsulfanyl)-acetyl]-thiophen-3-ylmethyl-amino}-piperidin-1-yl)-butyl]-amide Colorless foam (2:1 mixture of rotamers). $^1$H NMR (CDCl$_3$) δ 0.81-1.35 (m, 10H), 1.48-1.80 (m, 8H), 2.11 (m, 2H), 2.47 (m, 14H), 2.64-2.79 (m, 6H), 3.31 (m, 2H), 3.56-3.83 (m, 11H), 3.94-4.19 (m, 6H), 4.35 (m, 1H), 6.90 (m, 3H), 6.99 (m, 5H), 7.19 (dd, 1H, J=5.1, 3.0 Hz), 7.32 (dd, 1H, J=5.0, 3.2 Hz), 8.02 (br s, 1H), 8.53 (m, 1H), 8.88 (s, 1H), 8.91 (s, 1H); $^{13}$C NMR (CDCl$_3$) δ 13.82, 13.90, 22.30, 29.74, 30.62, 31.11, 31.33, 31.66, 32.12, 33.73, 33.79, 37.54, 37.72, 39.89, 40.27, 41.15, 43.42, 43.76, 43.92, 51.62, 51.92, 52.52, 56.71, 59.84, 60.39, 121.13, 121.97, 122.99, 123.06, 125.76, 126.23, 127.30, 127.74, 129.61, 129.74, 131.11, 131.21, 139.64, 140.57, 140.91, 157.93, 158.01, 163.40, 166.70, 166.80, 168.22, 169.05; ES-MS m/z 556 (M+H). Anal. Calcd. for C$_{27}$H$_{37}$N$_7$S$_2$O$_2$.0.2CH$_2$Cl$_2$: C, 57.04; H, 6.58; N, 17.12; S, 11.20. Found: C, 56.77; H, 6.65; N, 16.97; S, 11.10.

Example 9

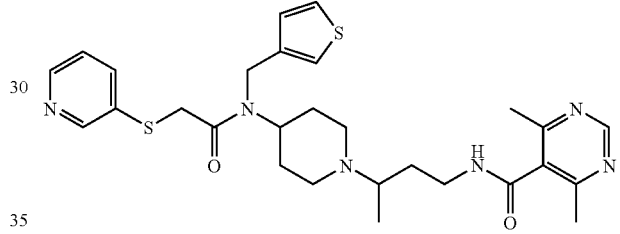

Compound 9

4,6-Dimethyl-pyrimidine-5-carboxylic acid [3-(4-{[2-(pyridin-3-ylsulfanyl)-acetyl]-thiophen-3-ylmethyl-amino}-piperidin-1-yl)-butyl]-amide White foam (mixture of rotamers). $^1$H NMR (CDCl$_3$) δ 0.85-1.80 (m, 9H), 2.10 (m, 1H), 2.30-2.80 (m, 9H), 3.25-4.45 (m, 8H), 3.34 (m, 2H), 6.94-8.95 (m, 9H); $^{13}$C NMR (CDCl$_3$) δ 13.81, 22.34, 29.82, 30.70, 31.01, 31.37, 31.83, 32.16, 37.27, 37.80, 39.88, 40.42, 41.08, 43.30, 43.65, 44.19, 51.98, 52.35, 57.33, 59.84, 60.62, 121.46, 121.99, 124.09, 124.30, 125.91, 126.08, 127.72, 131.28, 132.24, 138.47, 139.05, 139.39, 148.62, 151.15, 151.79, 157.92, 158.11, 163.49, 166.65, 168.82; ES-MS m/z 554.0 (M+2). Anal. Calcd. for C$_{28}$H$_{36}$N$_6$S$_2$O$_2$.0.6CH$_2$Cl$_2$: C, 56.90; H, 6.21; N, 13.92. Found: C, 57.00; H, 6.41; N, 13.88.

Example 10

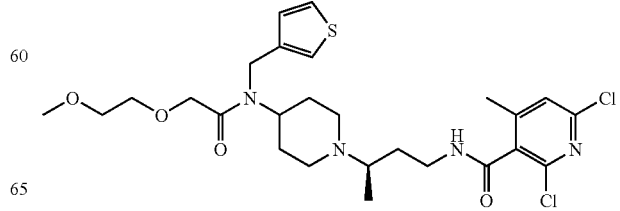

Compound 10

2,6-Dichloro-N—[(R)-3-(4-{[2-(2-methoxy-ethoxy)-acetyl]-thiophen-3-ylmethyl-amino}-piperidin-1-yl)-butyl]-4-methyl-nicotinamide $^1$H NMR (CDCl$_3$) (mixture of rotamers) δ 0.97 (d+m, 4H), 1.24 (m, 1H), 1.41-1.76 (m, 5H), 2.14 (m, 1H), 2.35 (s+m, 4H), 2.53 (br t, 1H), 2.74-2.84 (m, 3H), 3.35 (s+m, 4H), 3.53 (s, 2H), 3.65 (s, 3H), 3.76 (m, 1H), 4.03-4.08 (m, 3H), 4.23-4.35 (m, 1H), 6.97 (d, 1H, J=3.0 Hz), 7.02 (s, 1H), 7.11 (s, 1H), 7.20 (s) and 7.32 (s) (total 1H), 8.24 (br s) and 8.72 (br s) (total 1H); ES-MS m/z 571 (M+H).

Example 11

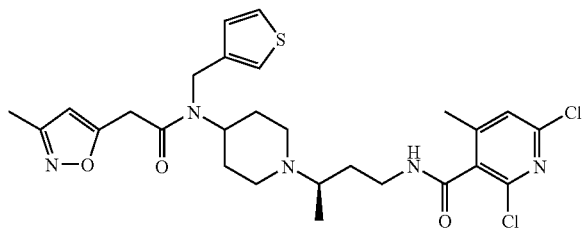

Compound 11

2,6-Dichloro-4-methyl-N—[(R)-3-(4-{[2-(3-methyl-isoxazol-5-yl)-acetyl]-thiophen-3-ylmethyl-amino}-piperidin-1-yl)-butyl]-nicotinamide $^1$H NMR (CDCl$_3$) (mixture of rotamers) δ 0.97 (d+m, 4H), 1.24 (m, 1H), 1.50-1.76 (m, 5H), 2.12 (br t, 1H), 2.28 (s, 3H), 2.36 (s, 3H), 2.49 (br t, 1H), 2.71-2.85 (m, 3H), 3.32 (m, 1H), 3.68 (s, 2H), 3.85 (m, 2H), 4.08 (m, 2H), 4.12 (m) and 4.39 (m) (total 1H), 6.01 (s) and 6.10 (s) (total 1H), 6.95 (m) and 7.01 (m) (total 1H), 7.02 (s) and 7.06 (s) (total 1H), 7.13 (s, 1H), 7.22 (m) and 7.37 (m) (total 1H), 8.07 (br s) and 8.55 (br s) (total 1H); ES-MS m/z 578 (M+H).

Example 12

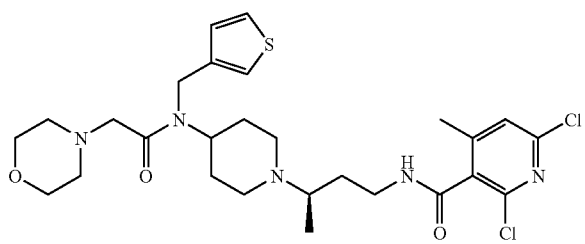

Compound 12

2,6-Dichloro-4-methyl-N—((R)-3-{4-[(2-morpholin-4-yl-acetyl)-thiophen-3-ylmethyl-amino]-piperidin-1-yl}-butyl)-nicotinamide A solution of methyl N-morpholinoacetate (0.85 g, 5.3 mmol) in 1:1 5N NaOH/THF (10 ml) was stirred at 50° C. for 1 h then neutralized to pH 3 with 6N HCl and concentrated. The yellowish solid was diluted with 1:1 MeOH/CH$_2$Cl$_2$ (25 ml), filtered to remove inorganic salts, and concentrated. The dilution, filtration and concentration were repeated to give morpholin-4-yl-acetic acid (695 mg, 90%) as a yellow solid.

COMPOUND 12 was isolated as a white solid (mixture of rotational isomers). $^1$H NMR (CDCl$_3$) δ 0.96-1.84 (m, 8H), 2.00-2.27 (m, 1H), 2.31-2.57 (m, 7H), 2.68-2.99 and 3.29-3.41 (m, 3H), 3.06 and 3.20 (s, 2H), 3.48 (s, 2H), 3.65-3.92 (m, 6H), 3.95-4.51 (m, 3H), 6.97-7.01 (m, 2H), 7.13 (s, 1H), 7.18-7.21 and 7.32-7.35 (m, 1H), 8.15 and 8.77 (br s, 1H); $^{13}$C NMR (CDCl$_3$) δ 13.67, 19.59, 29.25, 29.93, 30.95, 31.39, 31.99, 39.91, 40.62, 42.57, 44.01, 44.49, 52.00, 52.26, 53.84, 54.15, 55.96, 59.96, 60.47, 61.61, 62.46, 67.19, 120.85, 122.28, 124.79, 125.66, 126.23, 127.21, 128.02, 140.19, 147.01, 150.23, 151.31, 164.70, 169.26, 169.98; ES-MS m/z 582 (M+H).

Example 13

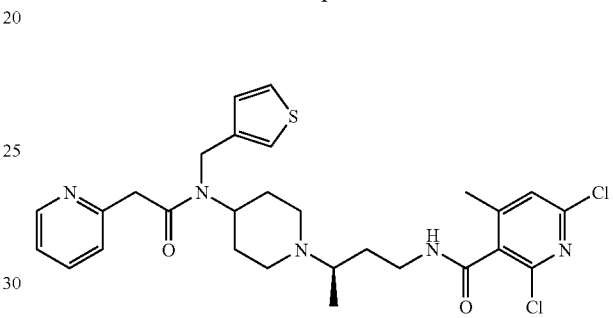

Compound 13

2,6-Dichloro-4-methyl-N—((R)-3-{4-[(2-pyridin-2-yl-acetyl)-thiophen-3-ylmethyl-amino]-piperidin-1-yl}-butyl)-nicotinamide Yellowish solid (mixture of rotational isomers). $^1$H NMR (CDCl$_3$) δ 0.91-1.85 (m, 9H), 2.35 and 2.37 (s, 3H), 2.39-3.02 (m, 4H), 3.23-3.46 (m, 1H), 3.68-3.81 (m, 3H), 3.97-4.53 (m, 4H), 6.97 and 7.01 (d, 1H, J=4.8 Hz), 7.07-7.25 (m, 4H), 7.28-7.39 (m, 1H), 7.59-7.69 (m, 1H), 8.51 (d, 1H, J=4.8 Hz), 8.24 and 8.67 (br s, 1H); $^{13}$C NMR (CDCl$_3$) δ 13.40, 13.51, 19.28, 29.07, 29.79, 30.70, 30.99, 31.39, 39.56, 40.48, 43.17, 43.81, 43.98, 44.73, 51.60, 51.71, 53.56, 55.97, 59.72, 60.08, 120.91, 121.69, 121.95, 122.19, 123.76, 124.49, 124.59, 125.30, 126.04, 126.85, 127.55, 132.52, 136.63, 136.92, 139.79, 149.32, 149.48, 150.00, 150.93, 155.83, 164.44, 169.87, 171.11; ES-MS m/z 574 (M+H).

Example 14

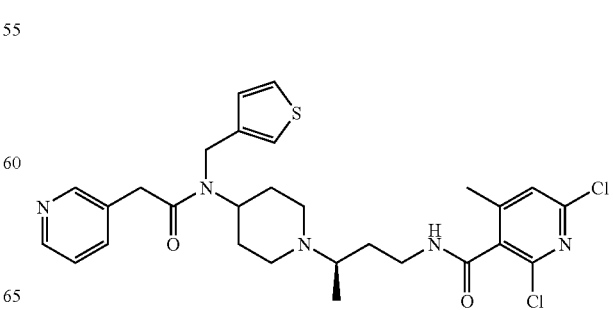

Compound 14

2,6-Dichloro-4-methyl-N—((R)-3-{4-[(2-pyridin-3-yl-acetyl)-thiophen-3-ylmethyl-amino]-piperidin-1-yl}-butyl)-nicotinamide White solid (mixture of rotational isomers). $^1$H NMR (CDCl$_3$) δ 0.91-1.90 (m, 9H), 1.98-2.24 (m, 1H), 2.34 and 2.37 (s, 3H), 2.48-2.62 (m, 1H), 2.64-2.82 (m, 3H), 3.22-3.43 (m, 1H), 3.56 (s, 2H), 3.72-3.91 (m, 1H), 3.95-4.19 (m, 2H), 4.32-4.51 (m, 1H), 6.93-7.13 (m, 3H), 7.21-7.26 (m, 1H), 7.38-7.40 (m, 1H), 7.52 and 7.65 (d, 1H, J=7.8 Hz), 8.02 and 8.29 (s, 1H), 8.48-8.52 (m, 1H), 8.73 (br s, 1H); $^{13}$C NMR (CDCl$_3$) δ 13.47, 19.25, 29.53, 30.29, 30.61, 31.18, 31.81, 38.03, 38.37, 29.61, 40.00, 40.53, 43.01, 43.51, 44.00, 51.72, 52.07, 56.65, 59.45, 60.22, 120.92, 121.90, 123.43, 123.67, 124.48, 125.50, 125.83, 127.29, 127.59, 130.86, 132.66, 136.64, 136.86, 139.56, 146.70, 148.30, 148.52, 149.95, 150.12, 151.08, 164.20, 170.75; ES-MS m/z 574 (M+H).

Example 15

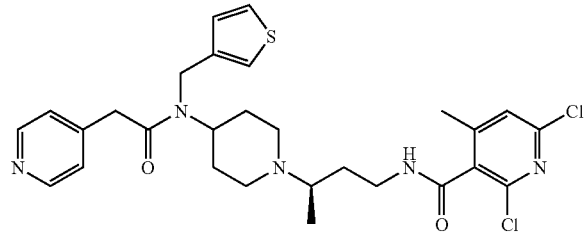

Compound 15

2,6-Dichloro-4-methyl-N—((R)-3-{4-[(2-pyridin-4-yl-acetyl)-thiophen-3-ylmethyl-amino]-piperidin-1-yl}-butyl)-nicotinamide Yellowish solid (mixture of rotational isomers). $^1$H NMR (CDCl$_3$) δ 0.93-1.78 (m, 9H), 2.07-2.26 (m, 1H), 2.34 and 2.38 (s, 3H), 2.50-2.69 (m, 1H), 2.70-2.96 (m, 3H), 3.24-3.54 (m, 1H), 3.56 (s, 2H), 3.71-3.92 (m, 1H), 3.97-4.18 (m, 2H), 4.33-4.52 (m, 1H), 6.95-7.21 (m, 6H), 7.37-7.39 (m, 1H), 8.50-8.56 (m, 1H), 7.95 and 8.70 (br s, 1H); $^{13}$C NMR (CDCl$_3$) δ 13.46, 19.31, 29.35, 30.09, 30.66, 31.22, 31.74, 39.91, 40.39, 40.85, 43.09, 43.57, 44.03, 51.78, 56.73, 59.53, 60.29, 120.98, 122.06, 124.18, 124.40, 124.50, 125.57, 125.84, 127.35, 127.65, 132.64, 139.47, 144.08, 146.72, 149.96, 150.21, 151.11, 164.28, 170.24; ES-MS m/z 574 (M+H).

Example 16

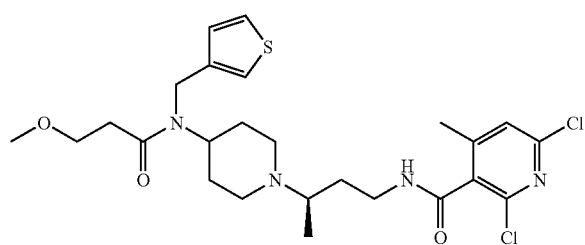

Compound 16

2,6-Dichloro-N—((R)-3-{4-[(3-methoxy-propionyl)-thiophen-3-ylmethyl-amino]-piperidin-1-yl}-butyl)-4-methyl-nicotinamide $^1$H NMR (CDCl$_3$) mixture of rotamers (~3:1) δ 0.90-0.96 (m, 4H), 1.08-2.12 (m, 7H), 2.03-2.19 (m, 1H), 2.34-2.82 (m, 8H), 3.28-3.35 (m, 4H), 3.61-3.85 (m, 3H), 4.02-4.48 (m, 2H), 6.93-7.01 (m, 2H), 7.12-7.18 (m, 1H), 7.30-7.32 (m, 1H), 8.25 (br s) and 8.80 (br s) (total 1H); ES-MS m/z 563 (M+Na).

Example 17

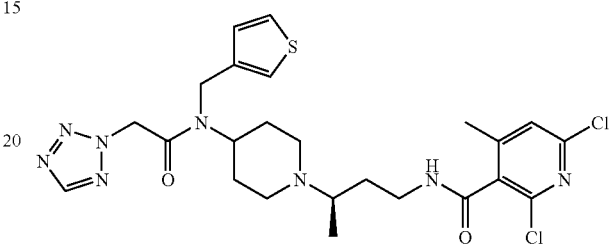

Compound 17

2,6-Dichloro-4-methyl-N—((R)-3-{4-[(2-tetrazol-2-yl-acetyl)-thiophen-3-ylmethyl-amino]-piperidin-1-yl}-butyl)-nicotinamide White foam (mixture of rotational isomers). $^1$H NMR (CDCl$_3$) δ 0.97-0.99 (m, 3H), 1.05-1.18 (m, 1H), 1.20-1.39 (m, 1H), 1.59 (s, 3H), 1.61-1.84 (br m, 4H), 2.14-2.21 (m, 1H), 2.36 (s, 3H), 2.51-2.67 (m 1H), 2.73-2.93 (m, 3H), 3.27-3.42 (m, 1H), 3.77-3.89 (m, 1H) 4.20 (s, 2H), 4.25-4.46 (m, 1H), 5.12 (s, 2H), 6.98-7.04 (m, 1H), 7.13 (br s, 2H), 7.45 (br s, 1H), 8.52 (br s, 1H), 8.78 (s, 1H); ES-MS m/z 565 (M+H).

Example 18

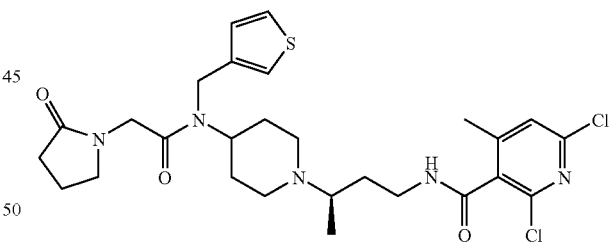

Compound 18

2,6-Dichloro-4-methyl-N—[(R)-3-(4-{[2-(2-oxo-pyrrolidin-1-yl)-acetyl]-thiophen-3-ylmethyl-amino}-piperidin-1-yl)-butyl]-nicotinamide N-Acetylglycine (0.031 ml, 0.22 mmol) was dissolved in 1:1 10N NaOH/THF (2 ml) and was stirred at 50° C. for 1 h. The mixture was neutralized to pH 4 with 6N HCl, then concentrated. The yellowish solid was diluted with 1:1 MeOH/CH$_2$Cl$_2$ (25 ml), filtered to remove inorganic salts, and concentrated. The solid obtained was diluted again with 1:1 MeOH/CH$_2$Cl$_2$ and concentrated to give (2-oxo-pyrrolidin-1-yl)-acetic acid as a white solid. The crude product was used in the next reaction without purification.

COMPOUND 18 was isolated as a white foam (mixture of rotamers). $^1$H NMR (CDCl$_3$) δ 0.97-0.99 (d, 3H, J=6 Hz), 1.05-1.19 (m, 1H), 1.20-1.32 (m, 3H), 1.48-1.72 (m, 3H), 1.73-1.87 (m, 1H), 1.93-2.23 (m, 4H), 2.34 (s, 3H), 2.47-2.54 (m, 1H), 2.69-2.93 (m, 3H), 3.24-3.58 (m, 3H), 3.68-3.83 (m, 1H), 3.97 (s, 2H), 3.99-4.20 (m, 2H), 4.29-4.43 (m, 1H), 7.01-7.02 (d, 1H, J=3 Hz), 7.10 (s, 1H), 7.19 (s, 1H), 7.34-7.35 (d, 1H, J=3 Hz), 8.21 (br s, 1H), 8.63 (br s, 1H); $^{13}$C NMR (CDCl$_3$) δ 13.38, 18.14, 19.30, 27.36, 29.27, 29.98, 30.49, 30.70, 30.91, 31.58, 39.84, 40.57, 42.28, 43.58, 43.81, 44.87, 48.18, 51.73, 52.22, 55.26, 59.68, 60.12, 120.10, 121.03, 122.04, 124.62, 125.63, 125.92, 126.63, 127.19, 127.58, 131.22, 132.62, 139.05, 146.73, 150.01, 151.09, 164.35, 168.21, 175.99; ES-MS m/z 580 (M+H).

Example 19

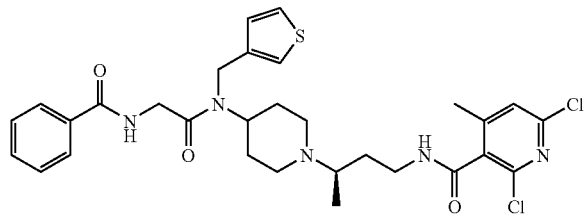

Compound 19

N—((R)-3-{4-[(2-Benzoylamino-acetyl)-thiophen-3-ylmethyl-amino]-piperidin-1-yl}-butyl)-2,6-dichloro-4-methyl-nicotinamide White solid (mixture of rotational isomers). $^1$H NMR (CDCl$_3$) δ 0.99-1.01 (m, 3H), 1.18-1.27 (m, 1H), 1.32-1.91 (m, 5H), 2.12-2.26 (m, 1H), 2.35 and 2.38 (s, 3H), 2.49-2.66 (m, 1H), 2.73-3.00 (m, 3H), 3.26-3.87 (m, 3H), 4.10-4.30 (m, 4H), 6.96-7.00 (m, 1H), 7.05-7.08 (m, 1H), 7.12 (d, 1H, J=4.5 Hz), 7.21-7.25 (m, 1H), 7.35-7.45 (m, 3H), 7.80-7.84 (m, 2H), 8.12-8.15 (m, 1H), 8.52-8.60 (m, 1H); $^{13}$C NMR (CDCl$_3$) δ 13.42, 19.32, 29.30, 29.83, 30.81, 31.10, 39.74, 40.86, 42.22, 42.41, 42.65, 43.65, 51.48, 51.80, 53.23, 54.86, 59.78, 60.19, 121.17, 122.08, 124.57, 124.67, 125.89, 126.38, 127.20, 127.36, 127.44, 128.69, 128.86, 131.77, 131.90, 132.81, 138.33, 139.14, 151.07, 164.41; ES-MS m/z 616 (M+H).

Example 20

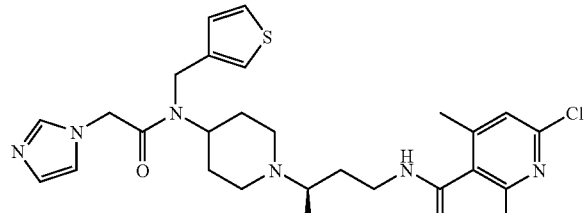

Compound 20

2,6-Dichloro-N—((R)-3-{4-[(2-imidazol-1-yl-acetyl)-thiophen-3-ylmethyl-amino]-piperidin-1-yl}-butyl)-4-methyl-nicotinamide Yellowish solid (mixture of rotational isomers). $^1$H NMR (CDCl$_3$) δ 0.98 (d, 3H, J=6 Hz), 1.01-1.15 and 1.23-1.34 (m, 1H), 1.44-1.82 (m, 5H), 2.07-2.23 (m, 1H), 2.35 (s, 3H), 2.48-2.59 (m, 1H), 2.68-2.93 (m, 3H), 3.26-3.40 (m, 1H), 3.72-3.88 (m, 1H), 3.82 (s, 2H), 4.27-4.46 (m, 1H), 4.58 (s, 2H), 6.83-6.84 (m, 1H), 7.02-7.11 (m, 4H), 7.31-7.43 (m, 2H), 8.66 (br s, 1H); $^{13}$C NMR (CDCl$_3$) δ 13.52, 19.31, 29.37, 30.04, 30.75, 39.82, 41.10, 42.55, 43.61, 48.35, 51.57, 52.65, 53.64, 60.13, 120.23, 121.13, 122.61, 124.58, 125.67, 127.94, 129.28, 132.69, 138.07, 146.64, 149.85, 151.20, 164.26, 167.03; ES-MS m/z 563 (M+H).

Example 21

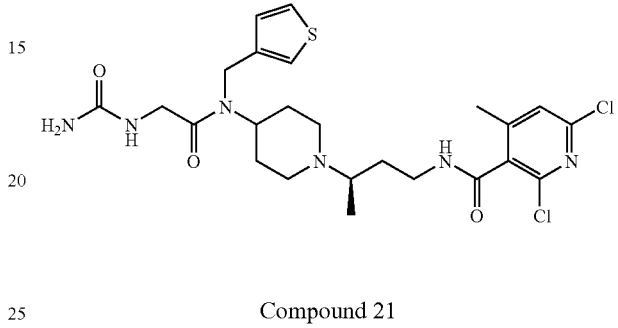

Compound 21

2,6-Dichloro-4-methyl-N—((R)-3-{4-[thiophen-3-ylmethyl-(2-ureido-acetyl)-amino]-piperidin-1-yl}-butyl)-nicotinamide $^1$H NMR (CDCl$_3$) (mixture of rotamers) δ 0.99 (m, 3H), 1.08-1.33 (m, 2H), 1.41-1.72 (m, 5H), 2.13 (m, 1H), 2.37 (s+s, 3H), 2.51 (br t, 1H), 2.74-2.83 (m, 3H), 3.32 (m, 1H), 3.48 (m) and 4.25 (m) (total 1H), 3.80 (m, 1H), 3.96 (m, 1H), 4.07-4.25 (m, 3H), 5.73 (br s) and 6.09 (br s) (total 1H), 6.93 (m, 1H), 6.99 (s) and 7.04 (s) (total 1H), 7.15 (s, 1H), 7.23 (m) and 7.33 (m) (total 1H), 8.17 (br s) and 8.56 (br s) (total 1H); ES-MS m/z 555 (M+H).

Example 22

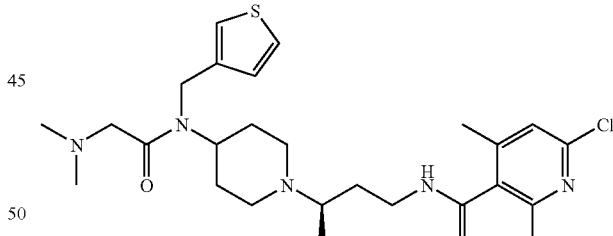

Compound 22

2,6-Dichloro-N—((R)-3-{4-[(2-dimethylamino-acetyl)-thiophen-3-ylmethyl-amino]-piperidin-1-yl}-butyl)-4-methyl-nicotinamide White foam. $^1$H NMR (CDCl$_3$) δ 0.96-0.98 (m, 4H), 1.15-1.22 (m, 2H), 1.48-1.49 (m, 1H), 1.70-1.75 (m, 1H), 2.11-2.27 (m, 8H), 2.35-2.39 (m, 4H), 2.53-2.57 (m, 1H), 2.68-2.82 (m, 3H), 2.98-3.11 (m, 2H), 3.29-3.34 (m, 1H), 3.80-3.86 (m, 1H), 4.13-4.37 (m, 2H), 6.91-7.03 (m, 2H), 7.12 (m, 1H), 7.32-7.34 (m, 1H), 8.72 (br S, 1H); ES-MS m/z 562 (M+Na).

Example 23

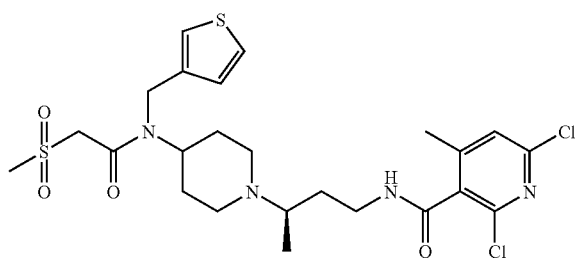

Compound 23

2,6-Dichloro-N—((R)-3-{4-[(2-methanesulfonyl-acetyl)-thiophen-3-ylmethyl-amino]-piperidin-1-yl}-butyl)-4-methyl-nicotinamide White foam. $^1$H NMR (CDCl$_3$) δ 0.96-0.99 (m, 3H), 1.01-1.45 (m, 2H), 1.60-1.77 (m, 5H), 2.14 (m, 1H), 2.35-2.37 (m, 3H), 2.52-2.53 (m, 1H), 2.72-2.85 (m, 3H), 3.11-3.14 (m, 3H), 3.30 (m, 1H), 3.76-3.81 (m, 1H), 3.90 (s, 1H), 4.12 (m, 1H), 4.22-4.31 (m, 2H), 7.00-7.04 (m, 2H), 7.05 (s, 1H), 7.38 (m, 1H), 8.38 (br s, 1H); ES-MS m/z 597 (M+Na).

Example 24

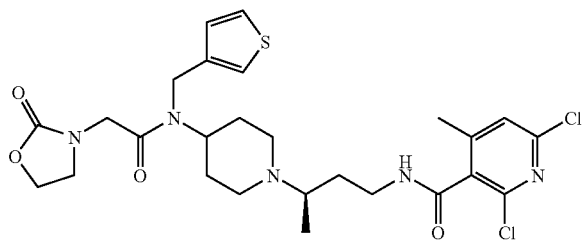

Compound 24

2,6-Dichloro-4-methyl-N—[(R)-3-(4-{[2-(2-oxo-oxazolidin-3-yl)-acetyl]-thiophen-3-ylmethyl-amino}-piperidin-1-yl)-butyl]-nicotinamide To a solution of 3-(2-hydroxy-ethyl)-oxazolidin-2-one (0.575 g, 4.38 mmol) in acetone (40 ml) was added 15% aqueous sodium bicarbonate (12 ml) to give a white slurry, which was then cooled to 0° C. (JOC 2003, 68, 4999-5001). Sodium bromide (0.090 g, 0.88 mmol) and TEMPO (0.014 g, 0.09 mmol) were added and the resulting mixture was stirred for 10 minutes followed by the addition of trichloroisocyanuric acid (2.03 g, 8.76 mmol) in four equal portions added every five minutes. The pale yellow slurry was warmed to 25° C. and stirred for an additional 12 hours to yield a yellow solution. Iso-propanol (3 ml) was added and the mixture was stirred for 45 minutes to give a white slurry, which was filtered through a Celite® cake. The filtrate was concentrated in vacuo, quenched with saturated aqueous sodium bicarbonate and extracted with ethyl acetate (30 ml). The aqueous phase was acidified with 4N HCl until pH ~2 and then put on for continuous extraction with methylene chloride (~100 ml) for 16 hours. The organic extract was dried over sodium sulfate, filtered and concentrated in vacuo to yield (2-oxo-oxazolidin-3-yl)-acetic acid (0.445 g, 70%) as a pale yellow solid.

COMPOUND 24 was isolated as a white foam. $^1$H NMR (CDCl$_3$) (mixture of rotamers) δ 0.97 (d+m, 4H), 1.22 (m, 1H), 1.51-1.75 (m, 4H), 2.10 (br t, 1H), 2.36 (s, 3H), 2.49 (br t, 1H), 2.72-2.82 (m, 3H), 3.32 (m, 1H), 3.64-3.84 (m, 3H), 3.94 (s, 2H), 4.05-4.11 (s+m, 3H), 4.35 (m, 3H), 6.95-7.09 (m, 2H), 7.15 (s, 1H), 7.21 (m) and 7.36 (m) (total 1H), 8.12 (br s) and 8.64 (br s) (total 1H); ES-MS m/z 582 (M+H).

Example 25

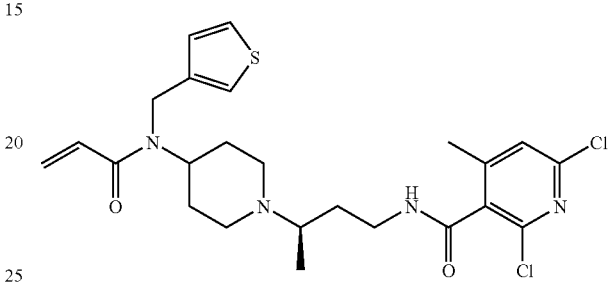

Compound 25

N—{(R)-3-[4-(Acryloyl-thiophen-3-ylmethyl-amino)-piperidin-1-yl]-butyl}-2,6-dichloro-4-methyl-nicotinamide $^1$H NMR (CDCl$_3$) (mixture of rotamers) δ 0.98 (d+m, 4H), 1.23 (m, 1H), 1.50-1.76 (m, 4H), 2.16 (br t, 1H), 2.37 (s, 3H), 2.54 (br t, 1H), 2.70-2.81 (m, 3H), 3.27 (m, 1H), 3.81 (m, 1H), 4.08 (m, 2H), 4.45 (m, 1H), 5.63 (m, 1H), 6.37 (m, 2H), 6.99 (s+d, 2H), 7.14 (s, 1H), 7.19 (m) and 7.33 (m) (total 1H), 8.09 (br s) and 8.81 (br s) (total 1H); ES-MS m/z 509 (M+H).

Example 26

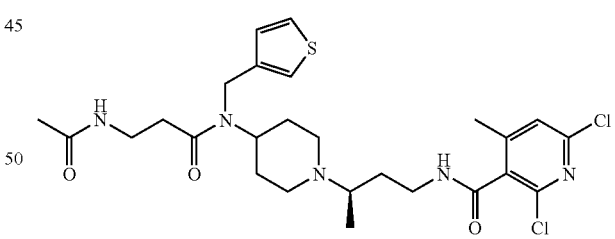

Compound 26

N—((R)-3-{4-[(3-Acetylamino-propionyl)-thiophen-3-ylmethyl-amino]-piperidin-1-yl}-butyl)-2,6-dichloro-4-methyl-nicotinamide Mixture of rotational isomers (~2:1). $^1$H NMR (CDCl$_3$) δ 0.81-1.37 (m, 5H), 1.47-1.85 (m, 4H), 1.94 (s, 3H), 2.01-2.20 (m, 1H), 2.35-2.58 (m, 5H), 2.71-2.84 (m, 3H), 3.25-3.31 (m, 1H), 3.42-3.50 (m, 4H), 3.74-3.84 (m, 1H), 4.01-4.39 (m, 2H), 6.37-6.41 (m, 1H), 6.93 (d, 1H, J=5.1 Hz), 6.96-6.99 (m, 1H), 7.11-7.16 (m, 1H), 7.23 (dd, J=4.8, 3 Hz) and 7.35 (dd, J=4.8, 3 Hz) (total 1H), 8.21 (br s) and 8.64 (br s) (total 1H); $^{13}$C NMR (CDCl$_3$) δ 13.77, 19.56, 23.77, 30.03, 30.89, 31.30, 32.01, 33.56, 33.89, 35.51, 40.13, 40.46, 40.66, 43.25, 43.85, 44.09, 51.99, 52.14, 52.59, 55.98, 60.04, 60.57, 121.05, 121.76, 124.80, 124.87, 125.92, 126.10, 127.33, 127.60, 132.75, 132.95, 139.49, 140.17, 147.01, 150.24, 150.57, 151.35, 164.48, 164.59, 170.27, 170.57, 171.76, 172.96; ES-MS m/z 590 (M+Na). Anal. Calcd. for C$_{26}$H$_{35}$N$_5$O$_3$SCl$_2$.0.8CH$_2$Cl$_2$.0.4H$_2$O: C, 50.01; H, 5.86; N, 10.88. Found: C, 49.79; H, 5.82; N, 10.88.

Example 27

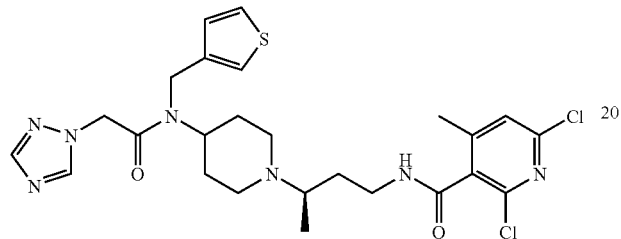

Compound 27

2,6-Dichloro-4-methyl-N—((R)-3-{4-[thiophen-3-ylmethyl-(2-[1,2,4]-triazol-1-yl-acetyl)-amino]-piperidin-1-yl}-butyl)-nicotinamide $^1$H NMR (CDCl$_3$) δ 0.96 (d, 3H, J=6 Hz), 0.96-1.02 (m, 1H), 1.04-1.13 (m, 1H), 1.59-1.86 (m, 3H), 2.07-2.18 (m, 1H), 2.36 (s, 3H), 2.37-2.42 (m, 1H), 2.48-2.57 (m, 1H), 2.71-2.86 (m, 4H), 3.26-3.41 (m, 1H), 3.74-3.84 (m, 1H), 4.16 (s, 2H), 4.27-4.35 (m, 1H), 4.86 (s, 2H), 7.04-7.08 (m, 1H), 7.13 (s, 1H), 7.42 (br s, 1H), 7.93 (s, 1H), 8.15 (s, 1H), 8.59 (br s, 1H); ES-MS m/z 586 (M+Na).

Example 28

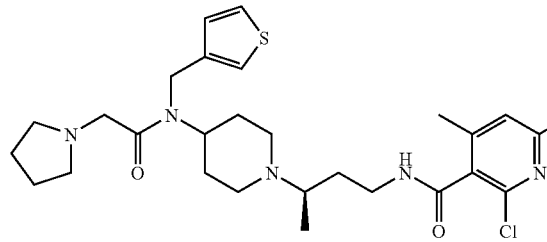

Compound 28

2,6-Dichloro-4-methyl-N—((R)-3-{4-[(2-pyrrolidin-1-yl-acetyl)-thiophen-3-ylmethyl-amino]-piperidin-1-yl}-butyl)-nicotinamide $^1$H NMR (CDCl$_3$) δ 0.87-1.02 (m, 4H), 1.08-1.13 (m, 1H), 1.59-1.67 (m, 2H), 1.76-1.84 (m, 4H), 2.11-2.18 (m, 1H), 2.35 (s, 3H), 2.49-2.58 (m, 4H), 2.76-2.89 (m, 2H), 3.18 (br s, 2H), 3.27-3.41 (m, 3H), 3.47-3.53 (m, 1H), 3.76-3.87 (m, 2H), 4.17 (d, 1H, J=12 Hz), 4.28-4.42 (m, 1H), 6.95-7.02 (m, 3H), 7.12 (s, 1H), 7.30-7.34 (m, 1H), 8.24 and 8.79 (br s, 1H); ES-MS m/z 566 (M+H).

Example 29

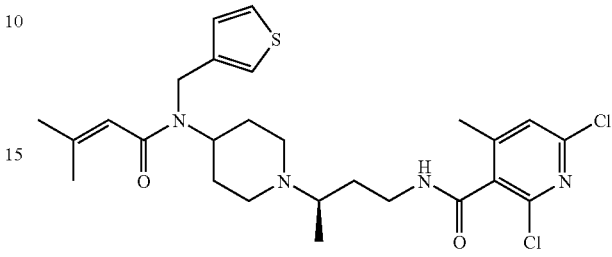

Compound 29

2,6-Dichloro-4-methyl-N—((R)-3-{4-[(3-methyl-but-2-enoyl)-thiophen-3-ylmethyl-amino]-piperidin-1-yl}-butyl)-nicotinamide $^1$H NMR (CDCl$_3$) (mixture of rotamers) δ 0.97 (d+m, 4H), 1.13 (m, 1H), 1.49-1.60 (m, 4H), 1.75 (s) and 1.86 (s) (total 3H), 1.91 (s) and 1.97 (s) (total 3H), 2.17 (br t, 1H), 2.37 (s, 3H), 2.56 (br t, 1H), 2.68-2.80 (m, 3H), 3.30 (m, 1H), 3.81 (m, 1H), 4.03 (m, 2H), 4.39 (m, 1H), 5.73 (s) and 5.79 (s) (total 1H), 6.98 (m, 2H), 7.15 (s, 1H), 7.20 (m) and 7.31 (m) (total 1H), 8.21 (br s) and 8.85 (br s) (total 1H); ES-MS m/z 537 (M+H).

Example 30

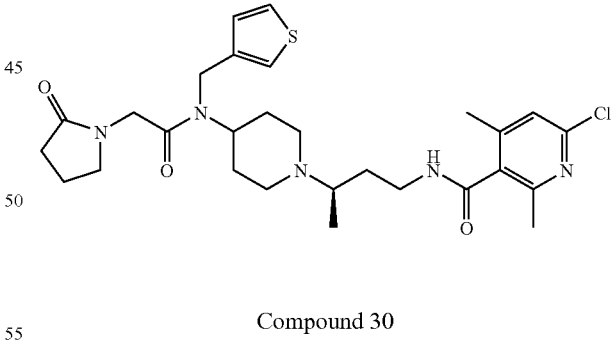

Compound 30

6-Chloro-2,4-dimethyl-N—[(R)-3-(4-{[2-(2-oxo-pyrrolidin-1-yl)-acetyl]-thiophen-3-ylmethyl-amino}-piperidin-1-yl)-butyl]-nicotinamide $^1$H NMR (CDCl$_3$) mixture of rotational isomers δ 0.79-086 (m, 1H), 0.95 (d, 3H, J=6 Hz), 0.98-1.09 (m, 1H), 1.48-1.68 (m, 2H), 1.72-1.78 (m, 1H), 1.98-2.16 (m, 4H), 2.29 (s, 3H), 2.33-2.41 (m, 2H), 2.47-2.54 (m, 4H), 2.67-2.86 (m, 3H), 3.22-3.29 (m, 1H), 3.42 (t, 2H, J=6 Hz), 3.47-3.53 (m, 1H), 3.73-3.83 (m, 1H), 3.89-3.99 (m, 2H), 4.12 (br s, 1H), 4.25-

4.41 (m, 1H), 7.00-7.11 (m, 2H), 7.11 (s, 1H), 7.32-7.37 (m, 1H), 7.98 and 8.65 (br s, 1H); ES-MS m/z 582 (M+Na).

Example 31

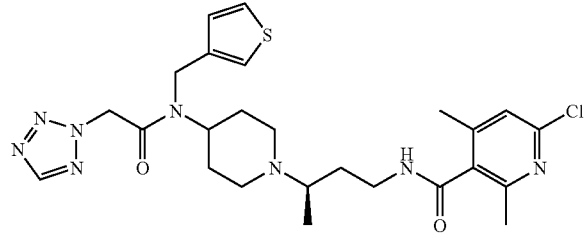

Compound 31

6-Chloro-2,4-dimethyl-N—((R)-3-{4-[(2-tetrazol-2-yl-acetyl)-thiophen-3-ylmethyl-amino]-piperidin-1-yl}-butyl)-nicotinamide ¹H NMR (CDCl₃) δ 0.90-0.95 (m, 1H), 0.97 (d, 3H, J=6 Hz), 1.06-1.16 (m, 1H), 1.51-1.57 (m, 1H), 1.63-1.81 (m, 3H), 2.05-2.16 (m, 1H), 2.30 (s, 3H), 2.50 (s, 3H), 2.50-2.57 (m, 1H), 2.69-2.84 (m, 3H), 3.23-3.27 (m, 1H), 3.78-3.91 (m, 1H), 4.07 (d, 2H, J=9 Hz), 4.29-4.42 (m, 1H), 5.12 (s, 2H), 7.02 (s, 1H), 7.09 (d, 1H, J=3 Hz), 7.16 (s, 1H), 7.42-7.47 (m, 1H), 8.55 (br s, 1H), 8.75 (s, 1H); ES-MS m/z 567 (M+Na).

Example 32

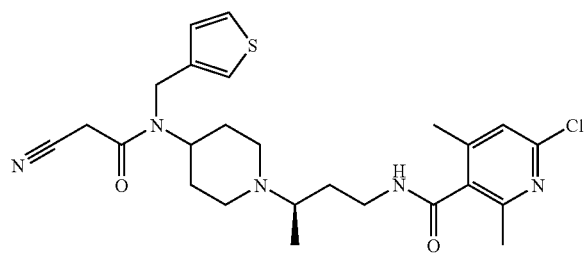

Compound 32

6-Chloro-N—((R)-3-{4-[(2-cyano-acetyl)-thiophen-3-ylmethyl-amino]-piperidin-1-yl}-butyl)-2,4-dimethyl-nicotinamide ¹H NMR (CDCl₃) mixture of rotamers (~4:1) δ 0.90-1.15 (m, 5H), 1.53-1.73 (m, 4H), 2.15 (t, 1H, J=12 Hz), 2.28-2.31 (m, 3H), 2.47-2.52 (m, 4H), 2.68-2.83 (m, 3H), 3.25-3.53 (m, 3H), 3.85-4.43 (m, 4H), 6.99-7.05 (m, 3H), 7.25 (br s) and 7.40 (dd, J=7, 4 Hz) (total 1H), 7.71 (br s) and 8.54 (br s) (total 1H); ¹³C NMR (CDCl₃) mixture of rotamers (~4:1) δ 13.5, 18.7, 22.1, 25.7, 29.4, 30.3, 30.6, 40.1, 42.8, 43.1, 51.6, 52.5, 60.6, 113.8, 121.1, 122.1, 122.6, 125.5, 127.9, 137.9, 147.7, 150.1, 155.4, 162.6, 166.9; ES-MS m/z 524 (M+Na). Anal Calcd. for C₂₅H₃₂N₅O₂SCl·0.2H₂O: C, 59.38; H, 6.46; N, 13.85. Found: C, 59.36; H, 6.39; N, 13.73.

Example 33

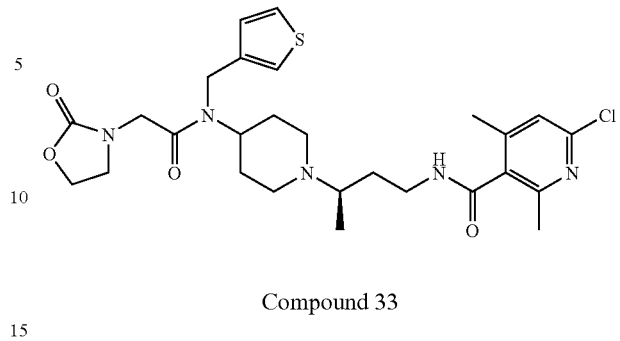

Compound 33

6-Chloro-2,4-dimethyl-N—[(R)-3-(4-{[2-(2-oxo-oxazolidin-3-yl)-acetyl]-thiophen-3-ylmethyl-amino}-piperidin-1-yl)-butyl]-nicotinamide ¹H NMR (CDCl₃) (mixture of rotamers) δ 0.98 (d+m, 5H), 1.51-1.75 (m, 4H), 2.12 (br t, 1H), 2.30 (s, 3H), 2.49 (s+br t, 4H), 2.70-2.79 (m, 3H), 3.29 (m, 1H), 3.66-3.83 (m, 3H), 3.93 (s+m, 4H), 4.36 (m, 3H), 6.95-7.10 (m, 3H), 7.36 (s, 1H), 7.93 (br s) and 8.64 (br s) (total 1H). ES-MS m/z 562 [M+H]⁺. Anal Calcd. for C₂₇H₃₆N₅O₄SCl: C, 55.80; H, 6.28; N, 11.92. Found: C, 55.64; H, 6.39; N, 11.83.

Example 34

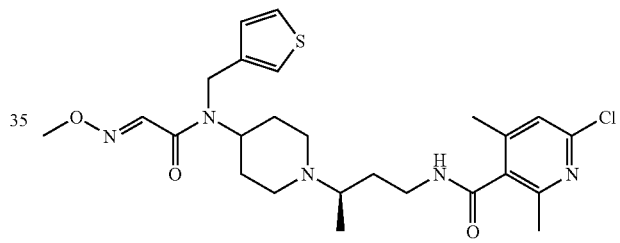

Compound 34

6-Chloro-N—((R)-3-{4-[(2-methoxyimino-acetyl)-thiophen-3-ylmethyl-amino]-piperidin-1-yl}-butyl)-2,4-dimethyl-nicotinamide ¹H NMR (CDCl₃) mixture of rotamers (~2:1) δ 0.91-1.76 (m, 9H), 2.02-2.23 (m, 1H), 2.30-2.33 (m, 3H), 2.41-2.56 (m, 4H), 2.66-2.84 (m, 3H), 3.25-3.41 (m, 1H), 3.78-4.48 (m, 7H), 7.01-7.05 (m, 3H), 7.24 (br s) and 7.33 (dd, J=6, 6 Hz) (total 1H), 7.60 (s) and 7.71 (s) (total 1H), 7.99 (br s) and 8.61 (br s) (total 1H); ES-MS m/z 542 (M+Na).

Example 35

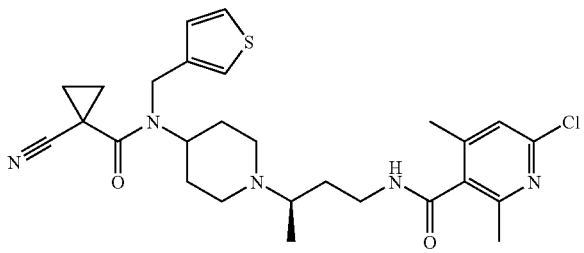

Compound 35

6-Chloro-N—((R)-3-{4-[(1-cyano-cyclopropanecarbonyl)-thiophen-3-ylmethyl-amino]-piperidin-1-yl}-butyl)-2,4-dimethyl-nicotinamide ¹H NMR (CDCl₃) δ 0.82-0.99 (m, 1H), 1.00 (d, 3H, J=7 Hz), 1.15-1.58 (m, 7H), 1.72-1.77 (m, 3H), 2.20 (t, 1H, J=12 Hz), 1.77 (s, 3H), 2.52-2.56 (m, 4H), 2.75-2.88 (m, 3H), 3.26-3.37 (m, 1H), 3.79-3.84 (m, 1H), 3.98-4.28 (m, 3H), 6.95 (d, 1H, J=6 Hz), 6.97 (s, 1H), 7.05 (br s, 1H), 8.06 (br s, 1H); ES-MS m/z 550 (M+Na).

Example 36

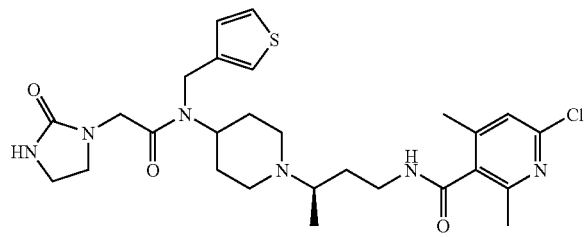

Compound 36

6-Chloro-2,4-dimethyl-N—[(R)-3-(4-{[2-(2-oxo-imidazolidin-1-yl)-acetyl]-thiophen-3-ylmethyl-amino}-piperidin-1-yl)-butyl]-nicotinamide To a solution of 1-(2-hydroxy-ethyl)-imidazolidin-2-one (1.00 g, 7.68 mmol) in acetone (70 ml) was added 15% aqueous sodium bicarbonate (21 ml) to give a white slurry, which was then cooled to 0° C. (JOC 2003, 68, 4999-5001). Sodium bromide (0.16 g, 1.54 mmol) and TEMPO (0.024 g, 0.15 mmol) were added and the resulting mixture was stirred for 10 minutes followed by the addition of trichloroisocyanuric acid (3.57 g, 15.4 mmol) in four equal portions added every five minutes. The pale yellow slurry was warmed to 25° C. and stirred for an additional 12 hours to yield a yellow solution. Iso-propanol (9 ml) was added and the mixture was stirred for 45 minutes to give a white slurry, which was filtered through a Celite® cake. The filtrate was concentrated in vacuo, quenched with saturated aqueous sodium bicarbonate and extracted with ethyl acetate (50 ml). The aqueous phase was acidified with 4N HCl until pH ~2 and then put on for continuous extraction with 5% methanol in methylene chloride (~120 ml) for 16 hours. The organic extract was dried over sodium sulfate, filtered and concentrated in vacuo to yield (2-oxo-imidazolidin-1-yl)-acetic acid (0.530 g, 48%) as a white solid.

COMPOUND 36 was isolated as a white foam. ¹H NMR (CDCl₃) (mixture of rotamers) δ 0.98 (d+m, 5H), 1.53-1.70 (m, 4H), 2.11 (br t, 1H), 2.30 (s+br t, 4H), 2.37 (s+m, 4H), 2.66 (m, 1H), 2.79 (m, 2H), 3.24 (m, 2H), 3.44-3.61 (m, 3H), 3.83-3.98 (m, 4H), 4.36 (m, 2H), 6.97-7.10 (m, 3H), 7.21 (m) and 7.35 (m) (total 1H), 8.04 (br s) and 8.69 (br s) (total 1H); ES-MS m/z 561 (M+H).

Example 37

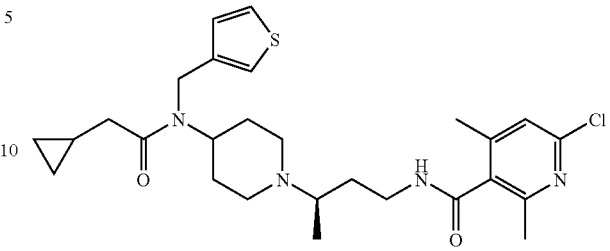

Compound 37

6-Chloro-N—((R)-3-{4-[(2-cyclopropyl-acetyl)-thiophen-3-ylmethyl-amino]-piperidin-1-yl}-butyl)-2,4-dimethyl-nicotinamide ¹H NMR (CDCl₃) mixture of rotational isomers: δ 0.08-0.12 (m, 2H), 0.49 (d, 2H, J=6 Hz), 0.54-0.63 (m, 1H), 0.69-0.81 (m, 1H), 0.99 (d, 3H, J=6 Hz), 0.99-1.05 (m, 1H), 1.52-1.64 (m, 3H), 1.74-1.82 (m, 2H), 2.16-2.22 (m, 3H), 2.29-2.32 (m, 3H), 2.50-2.53 (m, 3H), 2.59-2.82 (m, 3H), 3.21-3.28 (m, 1H), 3.76-3.99 (m, 3H), 4.43-4.55 (m, 1H), 6.94-7.02 (m, 3H), 7.29-7.35 (m, 1H), 8.80 (br s, 1H); ES-MS m/z 539 (M+Na).

Examples 38 to 49 were prepared following the scheme below wherein R¹COOH and R²COOH are defined in the table.

TABLE 2

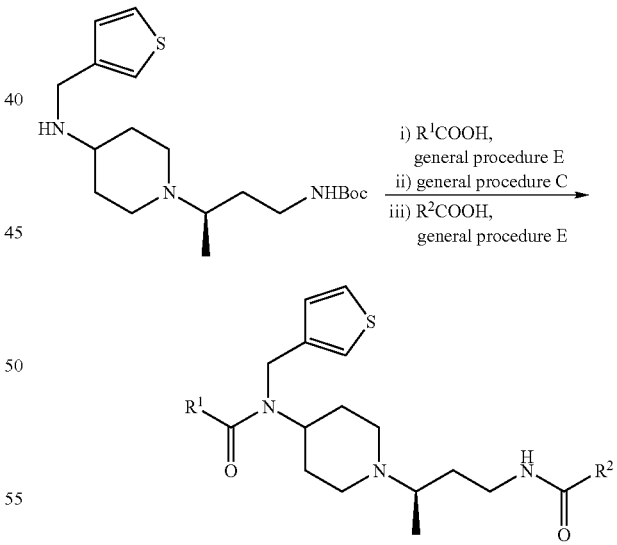

| Example | R¹COOH | R²COOH |
|---|---|---|
| 38* | (tetrahydro-pyran-4-yl)-acetic acid | 6-chloro-2,4-dimethyl-nicotinic acid |
| 39 | methoxyacetic acid | 6-chloro-2,4-dimethyl-nicotinic acid |
| 40* | methoxyacetic acid | 5,7-dimethyl-imidazo[1,2-a]pyridine-6-carboxylic acid (see EXAMPLE 280) |
| 41 | acetic acid | 6-fluoro-2,4-dimethyl-nicotinic acid hydrochloride |
| 42 | methoxyacetic acid | 4-cyano-2,6-dimethyl-benzoic acid |
| 43 | cyanoacetic acid | 2,6-chloro-4-methyl-nicotinic acid |

TABLE 2-continued

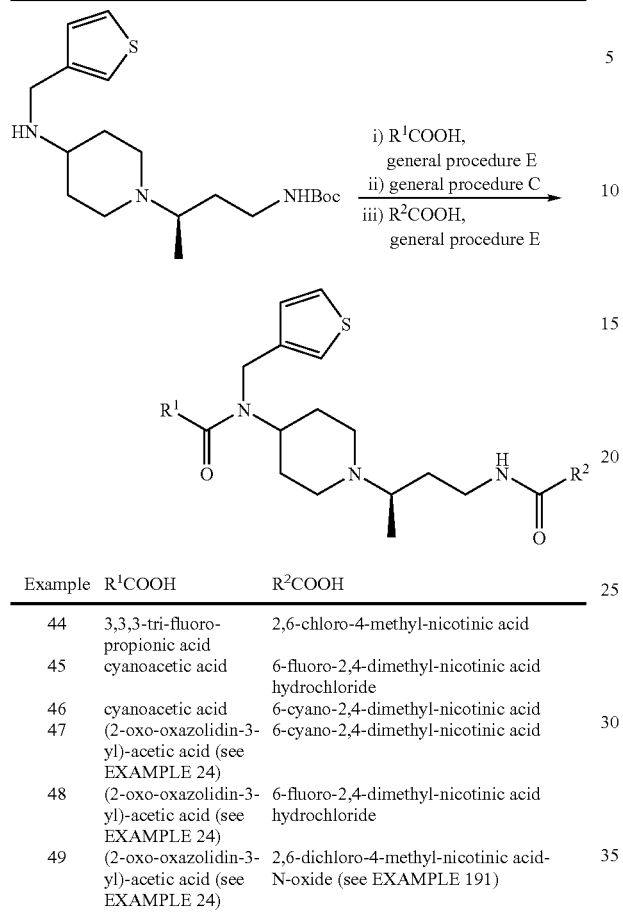

| Example | R¹COOH | R²COOH |
|---|---|---|
| 44 | 3,3,3-tri-fluoro-propionic acid | 2,6-chloro-4-methyl-nicotinic acid |
| 45 | cyanoacetic acid | 6-fluoro-2,4-dimethyl-nicotinic acid hydrochloride |
| 46 | cyanoacetic acid | 6-cyano-2,4-dimethyl-nicotinic acid |
| 47 | (2-oxo-oxazolidin-3-yl)-acetic acid (see EXAMPLE 24) | 6-cyano-2,4-dimethyl-nicotinic acid |
| 48 | (2-oxo-oxazolidin-3-yl)-acetic acid (see EXAMPLE 24) | 6-fluoro-2,4-dimethyl-nicotinic acid hydrochloride |
| 49 | (2-oxo-oxazolidin-3-yl)-acetic acid (see EXAMPLE 24) | 2,6-dichloro-4-methyl-nicotinic acid-N-oxide (see EXAMPLE 191) |

Example 38

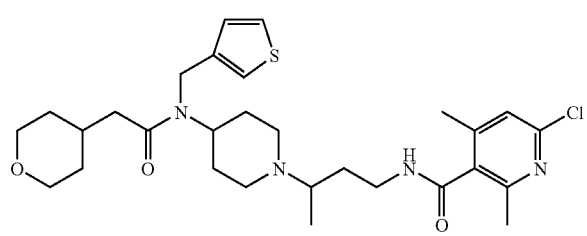

Compound 38

N-(3-{4-[(Thiophen-3-ylmethyl)-2-(tetrahydro-pyran-4-yl)-acetyl-amino]-piperidin-1-yl}-butyl)-6-chloro-2,4-dimethyl-nicotinamide White solid. $^1$H NMR (CDCl$_3$) δ 0.73-0.90 (m, 1H), 0.96 (d, 3H, J=6.0 Hz), 1.09-3.95 (m, 25H), 2.28 (s, 3H), 2.49 (s, 3H), 4.36-4.56 (m, 1H), 6.86-7.14 (m, 3H), 7.31-7.45 (m, 1H), 8.80 (br s, 1H); $^{13}$C NMR (CDCl$_3$) δ 13.79, 19.16, 22.45, 28.86, 29.89, 30.82, 31.36, 31.71, 32.24, 32.52, 33.26, 33.58, 39.97, 40.59, 40.82, 42.66, 43.63, 44.20, 51.60, 52.22, 53.82, 56.13, 60.12, 61.04, 68.25, 120.92, 121.65, 122.86, 123.01, 125.71, 126.19, 127.12, 127.81, 133.33, 140.31, 148.06, 150.44, 155.81, 167.35, 172.65; ES-MS m/z 561 (M+1).

Example 39

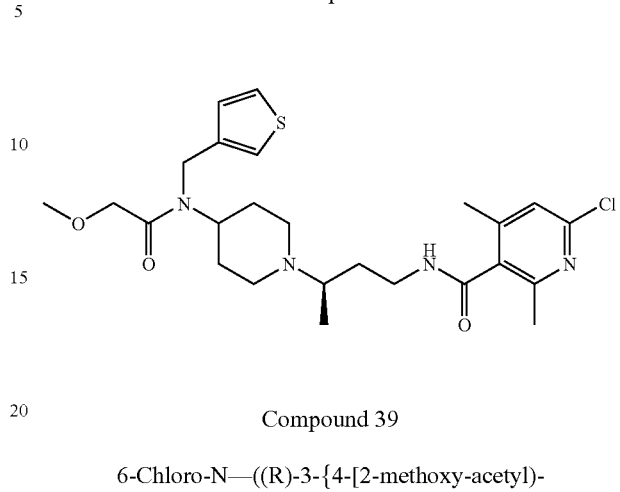

Compound 39

6-Chloro-N—((R)-3-{4-[2-methoxy-acetyl)-thiophen-3-ylmethyl-amino]-piperidin-1-yl}-butyl)-2,4-dimethyl-nicotinamide White solid. $^1$H NMR (CD$_3$OD) δ 1.03 (d, 3H, J=6.6 Hz), 1.55-1.87 (m, 6H), 2.06-2.29 (m, 4H), 2.43-2.49 (m, 4H), 2.74-2.87 (m, 3H), 3.06-3.63 (m, 7H), 4.07 (s, 1H), 4.26 (s, 1H), 4.33-4.49 (d, 2H, J=8.7 Hz), 7.00 (d, 1H, J=4.8 Hz), 7.16-7.21 (m, 2H), 7.29-7.43 (s, 1H); $^{13}$C NMR (CD$_3$OD) δ 13.84, 19.13, 22.42, 29.70, 30.63, 30.98, 40.36, 40.58, 41.80, 43.68, 51.94, 59.55, 60.70, 71.51, 120.94, 122.88, 126.17, 127.23, 133.24, 139.74, 148.03, 156.37, 155.69, 167.37, 171.71. Anal. Calcd. for C$_{25}$H$_{35}$N$_4$O$_3$S.0.12CH$_2$Cl$_2$: C, 58.33; H, 6.87; N, 10.83. Found: C, 57.97; H, 6.90; N, 10.83.

Example 40

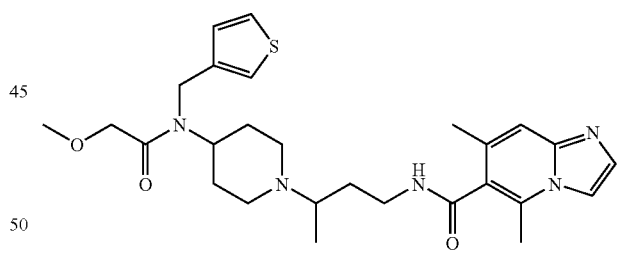

Compound 40

5,7-Dimethyl-imidazo[1,2-a]pyridine-6-carboxylic acid (3-{4-[(2-methoxy-acetyl)-thiophen-3-ylmethyl-amino]-piperidin-1-yl}-butyl)-amide $^1$H NMR (CDCl$_3$) mixture of rotational isomers: δ 0.89-1.21 (m, 1H), 0.99 (d, 3H, J=6 Hz), 1.49-1.92 (m, 4H), 2.06-2.22 (m, 1H), 2.37 (s, 3H), 2.58 (s, 3H), 2.68-2.86 (m, 4H), 3.31 (s, 2H), 3.34-3.51 (m, 6H), 3.79 (s, 2H), 3.82-3.96 (m, 1H), 4.01-4.13 (m, 1H), 4.31-4.52 (m, 1H), 6.72-6.85 (m, 2H), 7.32 (s, 1H), 7.69 (s, 1H), 8.52 (br s, 1H); ES-MS m/z 512 (M+H).

Example 41

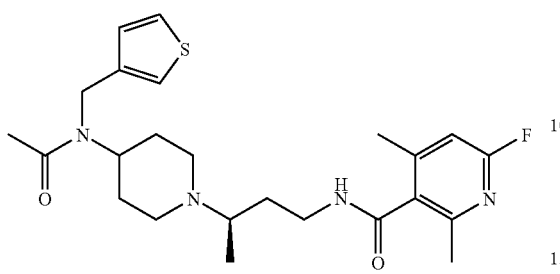

Compound 41

N—{(R)-3-[4-(Acetyl-thiophen-3-ylmethyl-amino)-piperidin-1-yl]-butyl}-6-fluoro-2,4-dimethyl-nicotinamide White foam. $^1$H NMR (CDCl$_3$) mixture of rotational isomers δ 0.86 (m, 1H), 0.98 (m+d, 4H), 1.52-1.61 (m, 4H), 1.73 (m, 1H), 1.97 (s, 3H), 2.12 (br t, 1H), 2.32 and 2.36 (s and s, total 3H), 2.46 and 2.49 (s and s, total 3H), 2.65 (m, 1H), 2.77-2.81 (m, 3H), 3.27 (m, 1H), 3.80 (m, 1H), 3.88 and 3.95 (d and d, total 2H), 4.45 (m, 1H), 6.53 and 6.57 (s and s, total 1H), 6.97 (m, 1H), 7.18 and 7.34 (m and m, total 1H), 7.76 and 8.68 (m and m, total 1H); ES-MS m/z 461 (M+H). Anal. Calcd. for C$_{24}$H$_{33}$N$_4$O$_2$SF.0.7H$_2$O: C, 60.92; H, 7.33; N, 11.84. Found: C, 60.89; H, 7.04; N, 11.60.

Example 42

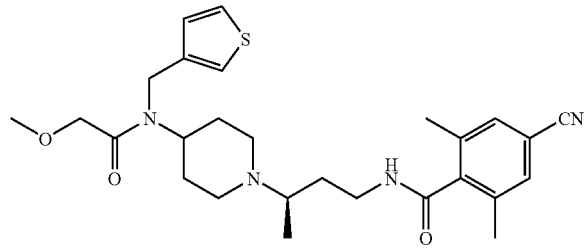

Compound 42

4-Cyano-N—((R)-3-{4-[(2-methoxy-acetyl)-thiophen-3-ylmethyl-amino]-piperidin-1-yl}-butyl)-2,6-dimethyl-benzamide White solid. $^1$H NMR (CDCl$_3$) δ 0.75-1.04 (m, 4H), 1.25-1.87 (m, 7H), 2.05-2.25 (m, 1H), 2.32, 2.36 (s, 3H), 2.50-2.58 (m, 1H), 2.64-2.92 (m, 4H), 3.34 (s, 2H), 3.34-3.41 (m, 1H), 3.49 (s, 3H), 3.87 (m, 2H), 4.04-4.16 (m, 1H), 4.32-4.53 (m, 1H), 6.92 (d, 1H, J=4.8 Hz), 6.98-7.00 (m, 1H), 7.24-7.26 (m, 2H), 7.35-7.39 (m, 1H), 8.45 (br s, 1H); ES-MS m/z 497 (M+H).

Example 43

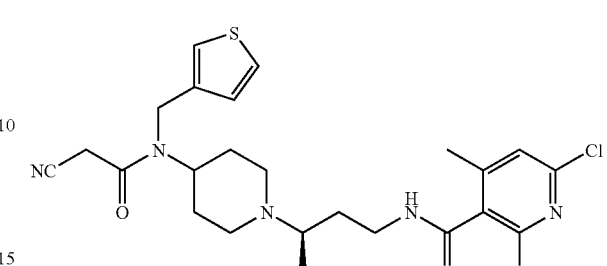

Compound 43

2,6-Dichloro-N—((R)-3-{4-[(2-cyano-acetyl)-thiophen-3-ylmethyl-amino]-piperidin-1-yl}-butyl)-4-methyl-nicotinamide White foam. $^1$H NMR (CDCl$_3$) δ 0.97-0.99 (d, 3H, J=6.6 Hz), 0.99-1.10 (m, 1H), 1.25-1.31 (m, 1H), 1.51 (m, 1H), 1.66-1.76 (m, 3H), 2.11-2.19 (t, 1H, J=12 Hz), 2.36 (s, 3H), 2.50-2.58 (t, 1H, J=12 Hz), 2.73-2.96 (m, 3H), 3.31-3.34 (m, 3H), 3.79-3.86 (m, 1H), 4.05 (s, 2H), 4.29-4.33 (m, 1H), 6.98-7.00 (d, 1H, J=5.1 Hz), 7.06 (s, 1H), 7.13-7.15 (m, 1H), 7.40-7.42 (m, 1H), 8.58 (br s, 1H); ES-MS m/z 544 (M+Na).

Example 44

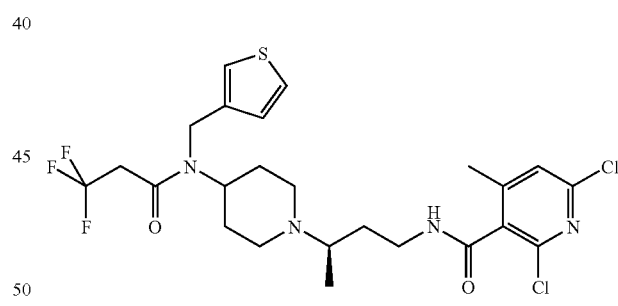

Compound 44

2,6-Dichloro-4-methyl-N—((R)-3-{4-[thiophen-3-ylmethyl-(3,3,3-trifluoro-propionyl)-amino]-piperidin-1-yl}-butyl)-nicotinamide Yellow foam. $^1$H NMR (CDCl$_3$) δ 0.96-1.00 (m, 4H), 1.21 (m, 1H), 1.50 (m, 1H), 1.62-1.76 (m, 3H), 2.10-2.14 (m, 1H), 2.36 (s, 3H), 2.53 (m, 1H), 2.71-2.84 (m, 3H), 3.03-3.13 (m, 2H), 3.26-3.29 (m, 1H), 3.79-3.86 (m, 1H), 4.04 (s, 2H), 4.38-4.46 (m, 1H), 7.00-7.04 (m, 2H), 7.14 (s, 1H), 7.38-7.39 (m, 1H), 8.66 (br s, 1H); ES-MS m/z 587 (M+Na).

Example 45

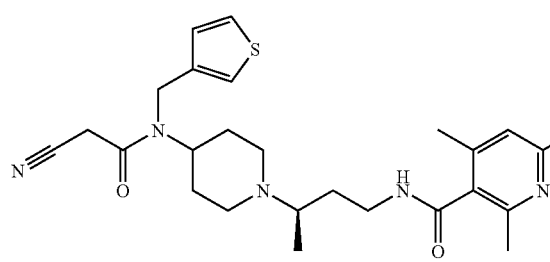

Compound 45

N—((R)-3-{4-[(2-Cyano-acetyl)-thiophen-3-ylmethyl-amino]-piperidin-1-yl}-butyl)-6-fluoro-2,4-dimethyl-nicotinamide $^1$H NMR (CDCl$_3$) (mixture of rotamers) δ 0.99 (d+m, 4H), 1.14 (m, 1H), 1.58 (m, 1H), 1.69 (m, 3H), 2.17 (br t, 1H), 2.32 (s) and 2.36 (s) (total 3H), 2.46 (s) and 2.50 (s) (total 3H), 2.54 (br t, 1H), 2.70-2.82 (m, 3H), 3.31 (s+m, 3H), 3.76 (m, 1H), 3.92 (s, 2H), 4.43 (m, 1H), 6.50 (s) and 6.58 (s) (total 1H), 6.96 (d, J=6.0 Hz, 1H), 7.03 (s, 1H), 7.41 (m, 1H), 8.46 (br s, 1H); ES-MS m/z 486 (M+H). Anal Calcd. for C$_{25}$H$_{32}$N$_5$O$_2$SF: C, 61.15; H, 6.59; N, 14.26; F, 3.87; S, 6.53. Found: C, 61.15; H, 6.59; N, 14.37; F, 3.95; S, 6.47.

Example 46

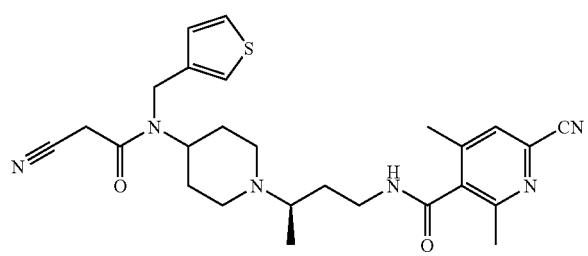

Compound 46

6-Cyano-N—((R)-3-{4-[(2-cyano-acetyl)-thiophen-3-ylmethyl-amino]-piperidin-1-yl}-butyl)-2,4-dimethyl-nicotinamide $^1$H NMR (CDCl$_3$) (mixture of rotamers) δ 0.99 (d+m, 4H), 1.22 (m, 1H), 1.56 (m, 1H), 1.67 (m, 3H), 2.16 (br t, 1H), 2.35 (s) and 2.37 (s) (total 3H), 2.55 (s+br t, 4H), 2.71-2.88 (m, 3H), 3.34 (s+m, 3H), 3.78 (m, 1H), 4.00 (s, 2H), 4.33 (m, 1H), 6.97 (d, 1H, J=6.0 Hz), 7.06 (s, 1H), 7.35 (s, 1H), 7.43 (m, 1H), 8.39 (br s, 1H); ES-MS m/z 493 (M+H).

Example 47

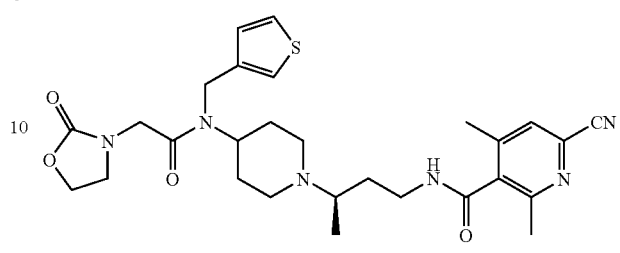

Compound 47

6-Cyano-2,4-dimethyl-N—[(R)-3-(4-{[2-(2-oxo-oxazolidin-3-yl)-acetyl]-thiophen-3-ylmethyl-amino}-piperidin-1-yl)-butyl]-nicotinamide $^1$H NMR (CDCl$_3$) (mixture of rotamers) δ 0.94 (d+m, 4H), 1.10 (m, 1H), 1.61-1.76 (m, 4H), 2.13 (br t, 1H), 2.36 (s, 3H), 2.49 (br t, 1H), 2.56 (s, 3H), 2.69 (m, 1H), 2.81 (m, 1H), 3.34 (m, 1H), 3.66-3.79 (m, 3H), 3.91-3.98 (s+s+m, 4H), 4.36 (m, 3H), 7.02 (m, 1H), 7.10 (m, 1H), 7.35 (s, 1H), 7.39 (m, 1H), 8.49 (br s, 1H); ES-MS m/z 553 (M+H).

Example 48

Compound 48

6-Fluoro-2,4-dimethyl-N—[(R)-3-(4-{[2-(2-oxo-oxazolidin-3-yl)-acetyl]-thiophen-3-ylmethyl-amino}-piperidin-1-yl)-butyl]-nicotinamide $^1$H NMR (CDCl$_3$) (mixture of rotamers) δ 0.98 (d+m, 4H), 1.12 (m, 1H), 1.55-1.77 (m, 4H), 2.14 (br t, 1H), 2.33 (s, 3H), 2.53 (s, 1H), 2.57 (br t, 3H), 2.72 (m, 1H), 2.81 (m, 1H), 3.30 (m, 1H), 3.63-3.79 (m, 3H), 3.90-3.98 (s+s+m, 4H), 4.35 (m, 3H), 6.56 (s, 1H), 6.96 (m, 1H), 7.06 (s, 1H), 7.22 (m) and 7.36 (m) (total 1H), 7.72 (br s) and 8.49 (br s) (total 1H); ES-MS m/z 546 (M+H).

Example 49

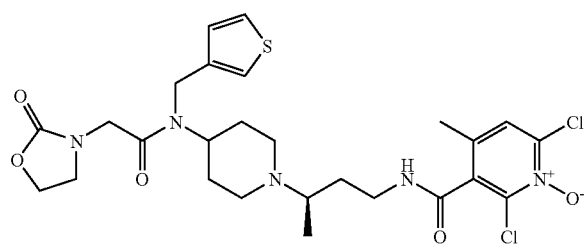

Compound 49

2,6-Dichloro-4-methyl-N—[(R)-3-(4-{[2-(2-oxo-oxazolidin-3-yl)-acetyl]-thiophen-3-ylmethyl-amino}-piperidin-1-yl)-butyl]-nicotinamide-N-oxide $^1$H NMR (CDCl$_3$) (mixture of rotamers) δ 0.97 (m, 1H), 1.08 (d+m, 4H), 1.66-1.75 (m, 4H), 1.95 (br t, 1H), 2.34 (s+br t, 4H), 2.60 (m, 1H), 2.85 (m, 1H), 2.97 (m, 2H), 3.46 (m, 1H), 3.66-3.73 (m, 3H), 3.97 (s, 2H), 4.11 (s, 1H), 4.35 (m, 3H), 6.98 (d, 1H, J=3.0 Hz), 7.10 (s, 1H), 7.26 (m) and 7.34 (m) (total 1H), 8.19 (br s) and 8.56 (br s) (total 1H); ES-MS m/Z 598 (M+H).

Example 50

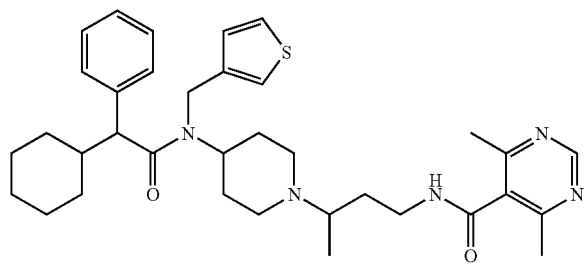

Compound 50

4,6-Dimethyl-pyrimidine-5-carboxylic acid (3-{4-[(2-cyclohexyl-2-phenyl-acetyl)-thiophen-3-ylm-ethyl-amino]-piperidin-1-yl}-butyl)-amide To a solution of 2-phenylcyclohexylacetic acid (200 mg, 0.92 mmol) in benzene (10 ml) at rt was added thionyl chloride (0.67 ml, 9 mmol) and the resultant mixture was heated at reflux for 2 h. The mixture was cooled down, concentrated to remove all volatiles and the residue was taken into benzene (5 ml). {4,6-Dimethyl-pyrimidine-5-carboxylic acid (3-{4-[(thiophen-3-ylmethyl-amino]-piperidin-1-yl}-butyl)-amide (49 mg, 0.122 mmol) and Na$_2$CO$_3$ (96 mg, 0.9 mmol) were added and the mixture was stirred at rt for 15 h. The solution was diluted with CH$_2$Cl$_2$ (15 ml) and washed with brine (15 ml), dried (Na$_2$SO$_4$), filtered and concentrated under reduced pressure. Purification of the residue by column chromatography on silica gel (1:9, MeOH/CH$_2$Cl$_2$) afforded COMPOUND 50 as a white solid (44 mg, 60%). $^1$H NMR (CDCl$_3$) δ 0.49-2.25 (m, 22H), 2.30-2.80 (m, 10H), 3.00-4.5 (m, 5H), 7.75-7.30 (m, 9H), 8.00-8.95 (m, 1H); $^{13}$C NMR (CDCl$_3$) δ 14.05, 22.62, 26.87, 27.09, 27.26, 30.35, 31.24, 31.32, 31.56, 31.92, 33.43, 40.46, 42.77, 42.84, 43.06, 44.11, 44.24, 52.17, 52.34, 52.50, 56.73, 56.78, 60.28, 60.87, 60.77, 121.37, 121.75, 121.79, 125.84, 126.71, 127.38, 127.62, 127.89, 129.11, 129.92, 129.31, 131.43, 139.14, 139.45, 140.87, 158.11, 158.40, 163.62, 163.66, 167.07, 167.16, 174.67; ES-MS m/z 602 (M+H). Anal. Calcd. for C$_{34}$H$_{37}$N$_5$S$_2$O$_2$·0.8CH$_2$Cl$_2$: C, 64.20; H, 7.31; N, 10.46. Found: C, 64.48; H, 7.24; N, 10.29.

Examples 51 to 54 were prepared following the scheme illustrated below. R$^1$(C=O)Cl is defined in the table.

TABLE 3

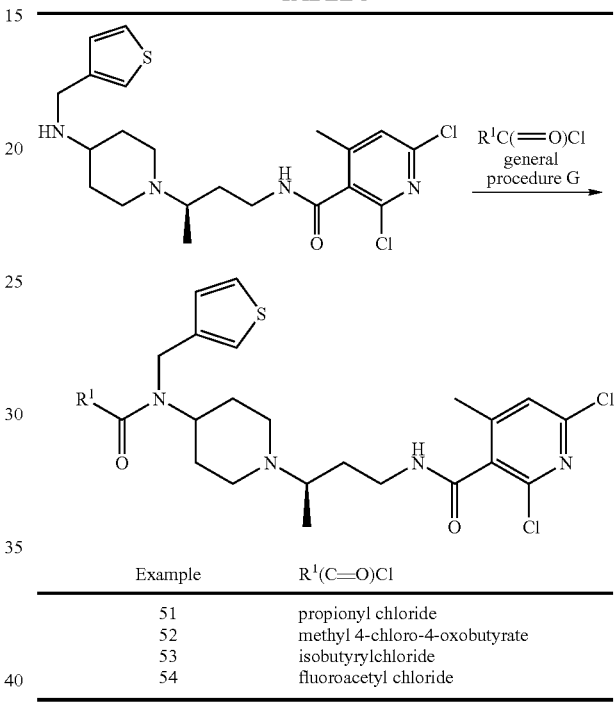

| Example | R$^1$(C=O)Cl |
|---|---|
| 51 | propionyl chloride |
| 52 | methyl 4-chloro-4-oxobutyrate |
| 53 | isobutyrylchloride |
| 54 | fluoroacetyl chloride |

Example 51

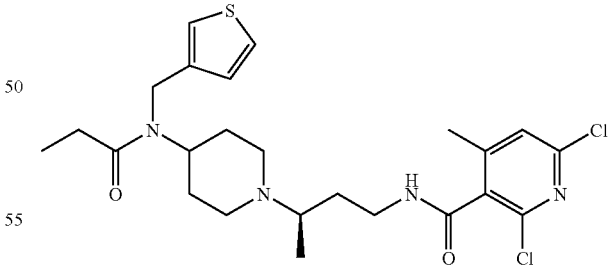

Compound 51

2,6-Dichloro-4-methyl-N—{(R)-3-[4-(propionyl-thiophen-3-ylmethyl-amino)-piperidin-1-yl]-butyl}-nicotinamide White foam. $^1$H NMR (CDCl$_3$) δ 0.91-1.25 (m, 10H), 1.43 (m, 1H), 1.59 (m, 1H), 2.14-2.27 (m, 3H), 2.35-2.39 (m, 3H), 2.53 (m, 1H), 2.69-2.80 (m, 3H), 3.25-3.32 (m, 1H), 3.80-3.84 (m, 1H), 3.99-4.00 (m, 2H), 4.38-4.42 (m, 1H), 6.91-6.98 (m, 2H), 7.12-7.21 (m, 1H), 7.27-7.34 (m, 1H), 8.83 (br s, 1H); ES-MS m/z 533 (M+Na).

Example 52

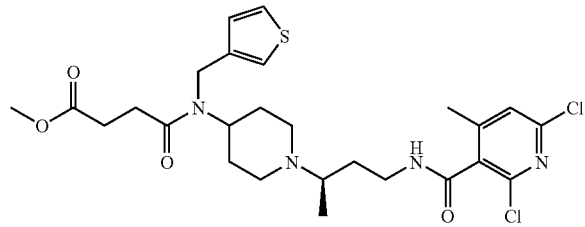

Compound 52

N-(1-{(R)-3-[(2,6-Dichloro-4-methyl-pyridine-3-carbonyl)-amino]-1-methyl-propyl}-piperidin-4-yl)-N-thiophen-3-ylmethyl-succinamic acid methyl ester Mixture of rotational isomers: $^1$H NMR (CDCl$_3$) δ 1.06 (d, 3H, J=6.6 Hz), 1.41-1.64 (m, 5H), 1.83-2.00 (m, 1H), 2.25-2.38 (m) and 2.45 (s) (total 5H), 2.60-2.70 (m, 4H), 2.84-3.04 (m, 3H), 3.31-3.43 (m, 1H), 3.66-3.73 (m, 4H), 4.20-4.28 (m, 2H), 4.45-4.56 (m, 1H), 6.92 (d, J=4.8 Hz) and 7.02 (d, J=4.8 Hz) (total 1H), 7.14 (br s, 2H), 7.18 (dd, J=4.8, 3 Hz) and 7.33 (dd, J=4.8, 3 Hz) (total 1H), 8.12 (br s) and 8.55 (br s) (total 1H); ES-MS m/z 569 (M+H).

Example 53

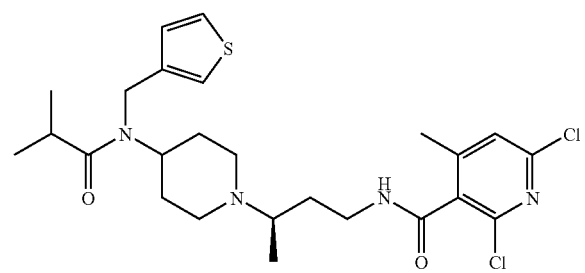

Compound 53

2,6-Dichloro-N—{(R)-3-[4-(isobutyryl-thiophen-3-ylmethyl-amino)-piperidin-1-yl]-butyl}-4-methyl-nicotinamide Colorless oil. $^1$H NMR (CDCl$_3$) (mixture of rotamers) δ 1.03 (m, 8H), 1.17 (m, 3H), 1.55-1.67 (m, 4H), 2.12 (br t, 1H), 2.36 (s) and 2.38 (s) (total 3H), 2.57 (m+br t, 2H), 2.67-2.80 (m, 4H), 3.30 (m, 1H), 3.83 (m, 1H), 4.02 (m, 2H), 3.56 (m) and 4.42 (m) (total 1H), 6.91-6.99 (m, 2H), 7.14 (s, 1H), 7.19 (m) and 7.34 (m) (total 1H), 8.19 (br s) and 8.84 (br s) (total 1H); ES-MS m/z 525 (M+H).

Example 54

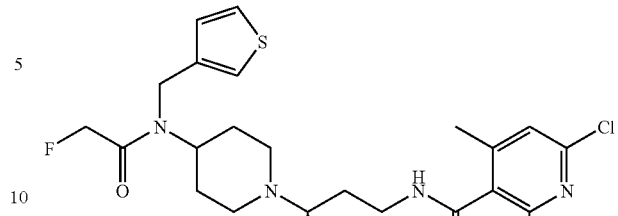

Compound 54

6-Chloro-N—((R)-3-{4-[(2-fluoro-acetyl)-thiophen-3-ylmethyl-amino]-piperidin-1-yl}-butyl)-2,4-dimethyl-nicotinamide $^1$H NMR (CDCl$_3$) mixture of rotamers (~3:1) 60.86-1.10 (m, 5H), 1.47-1.75 (m, 4H), 2.04-2.19 (m, 1H), 2.29 (s, 3H), 2.43-2.49 (m, 4H), 2.70-2.82 (m, 3H), 3.21-3.30 (m, 1H), 3.80-4.22 (m, 3H), 4.35-5.08 (m, 3H), 6.99 (br s, 2H), 7.04 (br s, 1H), 7.24 (br s) and 7.35 (br s) (total 1H), 7.82 (br s) and 8.68 (br s) (total 1H); ES-MS m/z 517 (M+Na).

Example 55

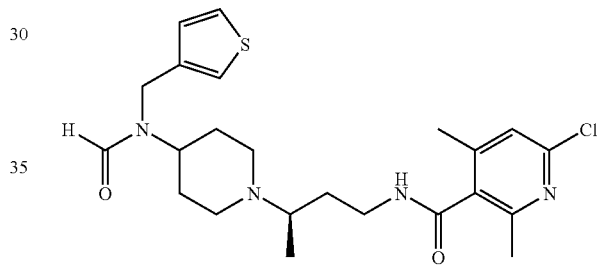

Compound 55

6-Chloro-N—{(R)-3-[(4-(formyl-thiophen-3-ylmethyl-amino)-piperidin-1-yl]-butyl}-2,4-dimethyl-nicotinamide Formic acetic anhydride was prepared following a literature procedure (J. Org. Chem., 1988, 53, 2365). The formic acetic anhydride (250 µL) was then added neat to a solution of ((R)-3-{4-[(thiophen-3-ylmethyl)-amino]-piperidin-1-yl}-butyl)-carbamic acid tert-butyl ester (372 mg, 1.01 mmol) in CH$_2$Cl$_2$ (6 ml) and the solution was allowed to stir at rt overnight. The reaction was diluted with CH$_2$Cl$_2$ (20 ml) and washed with 1N NaOH (15 ml), isolated and dried over Na$_2$SO$_4$, and concentrated. The resultant product was used crude in the next step.

Following general procedure C: the Boc-protected amine was taken up in CH$_2$Cl$_2$ (8 ml) and TFA (1.5 mL) was added. The reaction was allowed to stir for 2 h before solvent was removed. The crude was diluted with CH$_2$Cl$_2$ and washed with 1N NaOH before the organic layer was isolated and dried over Na$_2$SO$_4$. The crude residue (288 mg, 96% 2 steps) was used as is in the next step.

Following general procedure E: to a solution of the resultant crude product from above in DMF (3.5 ml) was added 6-chloro-2,4-dimethylnicotinic acid (120 mg, 0.54 mmol), HOBt (99 mg, 0.73 mmol), DIPEA (1 ml, 5.7 mmol) and EDCI (141 mg, 0.73 mmol) and the reaction stirred overnight.

Purification of the crude product by flash chromatography on silica gel (MeOH/CH$_2$Cl$_2$, 2%) afforded COMPOUND 55 (109 mg, 48%) as a white foam (mixture of rotational isomers). $^1$H NMR (CDCl$_3$) δ 0.95-0.98 (m, 3H), 1.01-1.47 (m, 3H), 1.52-1.81 (m, 4H), 2.03-2.17 (m, 1H), 2.08 (s, 3H), 2.12-2.24 (m, 1H), 2.32 (s, 3H), 2.67-2.81 (m, 3H), 3.16-3.42 (m, 1H), 3.68-4.55 (m, 6H), 6.94-6.99 (m, 1H), 7.06 (s, 1H), 7.21-7.24 and 7.31-7.34 (m, 1H), 7.76 and 8.48 (br s, 1H), 8.13 (m, 1H); ES-MS m/z 463 (M+H).

Example 56

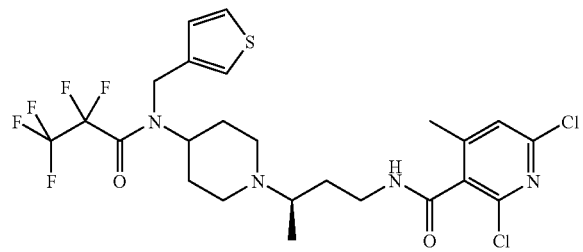

Compound 56

2,6-Dichloro-4-methyl-N—((R)-3-{4-[(2,2,3,3,3-pentafluoro-propionyl)-thiophen-3-ylmethyl-amino]-piperidin-1-yl}-butyl)-nicotinamide To a solution of 2,6-dichloro-4-methyl-N-(3-{4-[(thiophen-3-ylmethyl)-amino]-piperidin-1-yl}-butyl)-nicotinamide (0.085 g, 0.19 mmol) in methylene chloride (4 ml) was added pentafluoropropionic anhydride (74 μL, 0.38 mmol) and the resulting mixture was stirred at 25° C. for 6 hours. Standard basic workup gave the crude product as a tan oil. Purification by column chromatography on silica gel (Et$_2$O:MeOH:NH$_4$OH, 94:5:1, v/v/v) afforded COMPOUND 56 (0.045 g, 40%) as a white foam. $^1$H NMR (CDCl$_3$) (mixture of rotamers) δ 0.95 (d, J=6.0 Hz) and 0.99 (d, J=6.0 Hz) (total 3H), 1.39 (m, 1H), 1.55 (m, 3H), 1.69 (m, 3H), 2.13 (br t, 1H), 2.45 (s, 3H), 2.52 (br t, 1H), 2.82-2.91 (m, 3H), 3.36 (m, 1H), 3.73-3.84 (m, 2H), 4.11-4.42 (m, 3H), 6.95 (m, 1H), 7.08 (s, 1H), 7.14 (s) and 7.18 (s) (total 1H), 7.24 (m) and, 7.31 (m) (total 1H), 7.93 (br s) and 8.19 (br s) (total 1H); ES-MS m/z 601 (M+H).

Example 57 was prepared in a similar manner except that difluoroacetic anhydride was used in lieu of pentafluoropropionic anhydride.

Example 57

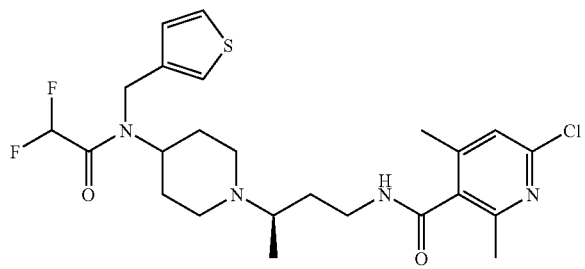

Compound 57

6-Chloro-N—((R)-3-{4-[(2,2-difluoro-acetyl)-thiophen-3-ylmethyl-amino]-piperidin-1-yl}-butyl)-2,4-dimethyl-nicotinamide $^1$H NMR (CDCl$_3$) mixture of rotamers (~1:1) δ 0.96 (d, J=7 Hz) and 0.99 (d, J=7 Hz) (total 3H), 1.12-1.77 (m, 6H), 2.08 (t, 1H, J=12 Hz), 2.30 (s) and 2.32 (s) (total 3H), 2.50-2.53 (m, 4H), 2.71-2.82 (m, 3H), 3.21-3.29 (m, 1H), 3.79-3.83 (m, 1H), 3.98-4.25 (m, 3H), 6.04 (q, J$_{F-H}$=60 Hz), 6.95-7.04 (m, 3H), 7.24 (dd, J=6, 3 Hz) and 7.35 (dd, J=6, 3 Hz) (total 1H), 7.95 (br s) and 8.28 (br s) (total 1H); ES-MS m/z 513 (M+H).

Example 58

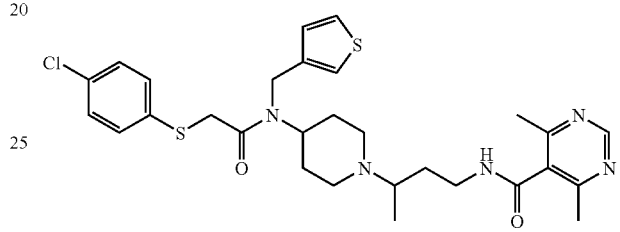

Compound 58

4,6-Dimethyl-pyrimidine-5-carboxylic acid [3-(4-{[2-(4-chloro-phenylsulfanyl)-acetyl]-thiophen-3-ylmethyl-amino}-piperidin-1-yl)-butyl]-amide To a solution of 4,6-dimethyl-pyrimidine-5-carboxylic acid (3-{4-[(thiophen-3-ylmethyl-amino]-piperidin-1-yl}-butyl)-amide (85 mg, 0.21 mmol) and NaHCO$_3$ (27 mg, 0.31 mmol) in CH$_2$Cl$_2$ (3 ml) was added chloroacetyl chloride (26.3 mg, 0.23 mmol) and the mixture was stirred at room temperature for 2 h. The mixture was diluted with CH$_2$Cl$_2$ (10 ml) and saturated aqueous NaHCO$_3$ (15 ml). The layers were separated and the aqueous was further extracted with CH$_2$Cl$_2$ (2×10 ml). The combined organic layers were dried (Na$_2$SO$_4$), filtered and concentrated under reduced pressure to give the product as a pure white foam.

To a solution of 4-chlorobenzenethiol (23 mg, 0.16 mmol) and NEt$_3$ (0.03 ml, 0.24 mmol) in CHCl$_3$ (2 ml) was added the above chloride (50 mg, 0.1 mmol). The mixture was stirred at 60° C. for 15 h. The mixture was diluted with CH$_2$Cl$_2$ (10 ml) and saturated aqueous NaHCO$_3$ (15 ml). The layers were separated and the aqueous was further extracted with CH$_2$Cl$_2$ (2×10 ml). The combined organic layers were dried (Na$_2$SO$_4$), filtered and concentrated under reduced pressure. The crude material was purified by flash column chromatography on silica gel (9:1, CH$_2$Cl$_2$/MeOH) to afford COMPOUND 58 as a white solid (36 mg, 60%). $^1$H NMR (CDCl$_3$) δ 0.75-1.04 (m, 5H), 1.05-1.45 (m, 1H), 2.25-2.80 (m, 12H), 3.25-3.45 (m, 1H), 3.58 (s, 2H), 3.76 (s, 6H), 3.80-4.70 (m, 3H), 6.70-7.33 (m, 7H), 7.85 (br s, 0.3H), 8.61 (br s, 0.7H), 8.88 (s, 0.7H), 8.92 (s, 0.3H); $^{13}$C NMR (CDCl$_3$) δ 13.80, 22.33, 29.78, 30.08, 30.66, 31.01, 31.32, 31.77, 32.12, 37.47, 38.00, 39.91, 40.40, 41.02, 43.28, 43.67, 44.14, 51.99, 52.26, 57.20, 59.87, 60.61, 121.14, 121.89, 125.80, 126.12, 127.61, 129.50, 129.66, 131.27, 132.00, 132.47, 133.57, 139.52, 157.92, 158.10, 163.49, 166.67, 166.84, 168.50, 169.10; ES-MS m/z 587 (M+H).

Example 59

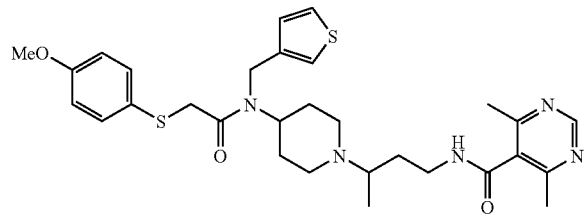

Compound 59

4,6-Dimethyl-pyrimidine-5-carboxylic acid [3-(4-{[2-(4-methoxy-phenylsulfanyl)-acetyl]-thiophen-3-ylmethyl-amino}-piperidin-1-yl)-butyl]-amide To a solution of 4-methoxybenzenethiol (33 mg, 0.23 mmol) and NEt$_3$ (0.03 ml, 0.24 mmol) in CHCl$_3$ (2 ml) was added 4,6-dimethyl-pyrimidine-5-carboxylic acid (3-{4-[(2-chloro-acetyl)-thiophen-3-ylmethyl-amino]-piperidin-1-yl}-butyl)-amide (see EXAMPLE 58) (55 mg, 0.11 mmol). The mixture was stirred at 61° C. for 15 h. The mixture was diluted with CH$_2$Cl$_2$ (10 ml) and saturated aqueous NaHCO$_3$ (15 ml). The layers were separated and the aqueous was further extracted with CH$_2$Cl$_2$ (2×10 ml). The combined organic layers were dried (Na$_2$SO$_4$), filtered and concentrated under reduced pressure. The crude material was purified by flash column chromatography on silica gel (9:1, CH$_2$Cl$_2$/MeOH) to afford COMPOUND 59 as a white solid (42 mg, 65%). $^1$H NMR (CDCl$_3$) δ 0.76-2.25 (m, 12H), 2.25-2.80 (m, 12H), 3.25-3.45 (m, 1H), 3.58 (s, 2H), 3.76 (s, 6H), 3.80-4.70 (m, 3H), 6.70-7.33 (m, 7H), 7.99 (br s, 0.3H), 8.56 (br s, 0.7H), 8.85 (s, 0.7H), 8.91 (s, 0.3H); $^{13}$C NMR (CDCl$_3$) δ 13.80, 22.32, 29.79, 30.66, 31.00, 31.29, 31.69, 32.10, 38.98, 39.49, 39.94, 40.37, 40.90, 43.14, 43.71, 44.13, 46.26, 51.98, 55.73, 57.03, 59.91, 60.56, 115.01, 115.16, 121.01, 121.96, 124.82, 125.63, 126.15, 127.37, 127.84, 131.07, 131.25, 134.38, 135.11, 139.78, 157.93, 158.09, 160.11, 163.45, 166.70, 166.84, 169.09, 169.69; ES-MS m/z 582.6 (M+H). Anal. Calcd. for C$_{30}$H$_{39}$N$_5$O$_3$S$_2$.0.3CH$_2$Cl$_2$: C, 59.93; H, 6.57; N, 11.53. Found: C, 60.10; H, 6.85; N, 11.30.

Example 60

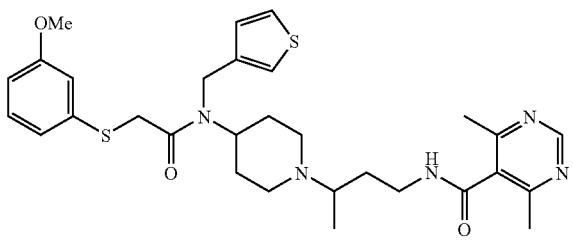

Compound 60

4,6-Dimethyl-pyrimidine-5-carboxylic acid [3-(4-{[2-(3-methoxy-phenylsulfanyl)-acetyl]-thiophen-3-ylmethyl-amino}-piperidin-1-yl)-butyl]-amide To a solution of 3-methoxybenzenethiol (33 mg, 0.23 mmol) and NEt$_3$ (0.03 ml, 0.24 mmol) in CHCl$_3$ (2 ml) was added 4,6-dimethyl-pyrimidine-5-carboxylic acid (3-{4-[(2-chloro-acetyl)-thiophen-3-ylmethyl-amino]-piperidin-1-yl}-butyl)-amide (see EXAMPLE 58) (55 mg, 0.11 mmol). The mixture was stirred at 61° C. for 15 h. The mixture was diluted with CH$_2$Cl$_2$ (10 ml) and saturated aqueous NaHCO$_3$ (15 ml). The layers were separated and the aqueous was further extracted with CH$_2$Cl$_2$ (2×10 ml). The combined organic layer was dried (Na$_2$SO$_4$), filtered and concentrated under reduced pressure. The crude material was purified by flash column chromatography on silica gel (9:1, CH$_2$Cl$_2$/MeOH) to afford COMPOUND 60 as a white solid (40 mg, 63%). $^1$H NMR (CDCl$_3$) δ 0.75-2.20 (m, 12H), 2.25-2.80 (m, 12H), 3.25-3.45 (m, 1H), 3.58 (s, 2H), 3.76 (s, 6H), 4.70-3.80 (m, 3H), 6.70-7.33 (m, 7H), 7.99 (br s, 0.3H), 8.56 (br s, 0.7H), 8.85 (s, 0.7H), 8.91 (s, 0.3H); $^{13}$C NMR (CDCl$_3$) δ 13.82, 22.33, 29.84, 30.73, 31.27, 31.66, 32.10, 36.46, 37.27, 37.86, 40.00, 40.45, 41.06, 43.22, 43.67, 44.04, 52.02, 52.20, 55.69, 57.09, 60.00, 60.65, 113.25, 115.53, 116.03, 121.11, 121.62, 122.35, 122.86, 125.77, 126.17, 127.49, 127.57, 130.18, 130.36, 131.27, 136.51, 139.64, 157.93, 158.11, 160.15, 163.46, 166.67, 168.78, 169.37; ES-MS m/z 582.4 (M+H). Anal. Calcd. for C$_{36}$H$_{39}$N$_5$O$_3$S$_2$.0.6CH$_2$Cl$_2$: C, 58.09; H, 6.40; N, 11.07. Found: C, 58.00; H, 6.50; N, 10.87.

Example 61

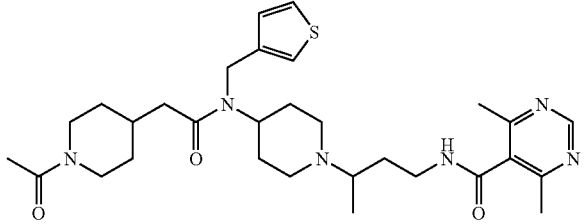

Compound 61

4,6-Dimethyl-pyrimidine-5-carboxylic acid [3-(4-{[2-(1-acetyl-piperidin-4-yl)-acetyl]-thiophen-3-ylmethyl-amino}-piperidin-1-yl)-butyl]-amide Following general procedure E: a solution of 4,6-dimethyl-pyrimidine-5-carboxylic acid (3-{4-[(thiophen-3-ylmethyl)-amino]-piperidin-1-yl}-butyl)-amide (41 mg, 0.1 mmol), 4-carboxymethyl-piperidine-1-carboxylic acid tert-butyl ester (50 mg, 0.22 mmol), EDCI (39 mg, 0.20 mmol), HOBT (27 mg, 0.20 mmol), and DIPEA (0.05 ml, 0.3 mmol) in CH$_2$Cl$_2$ (2 ml) was stirred overnight. Purification of the crude product by column chromatography on silica gel (CH$_2$Cl$_2$/MeOH, 9:1) afforded 4-{[(1-{3-[(4,6-dimethyl-pyrimidine-5-carbonyl)-amino]-1-methyl-propyl}-piperidin-4-yl)-thiophen-3-ylmethyl-carbamoyl]-methyl}-piperidine-1-carboxylic acid tert-butyl ester (50 mg, 80%).

Using general procedure C, the above obtained compound was treated with TFA (1 ml) in CH$_2$Cl$_2$ (1 ml). Following purification the material was immediately dissolved in CH₂Cl₂ (2 ml) at rt. NaHCO₃ (13 mg, 0.15 mmol) was added, followed by acetyl chloride (7.2 mg, 0.09 mmol). The mixture was stirred at rt for 5 h and was then washed with 1N NaOH (3×4 ml) to give COMPOUND 61 (45 mg, 100%) as a colorless foam (mixture of rotamers). ¹H NMR (CDCl₃) δ 0.75-4.60 (m, 39H), 6.91-6.95 (m, 2.8H), 7.18-7.33 (m, 1H), 7.91 (s, 0.1H), 8.68 (s, 0.3H), 8.88 (dd, 0.8H); ¹³C NMR (CDCl₃) δ 13.79, 21.83, 22.32, 29.87, 30.80, 30.98, 31.85, 32.08, 32.39, 32.92, 33.23, 33.41, 39.81, 40.03, 40.29, 40.83, 42.04, 43.01, 43.82, 44.28, 46.93, 51.67, 52.08, 56.13, 59.80, 60.92, 120.92, 121.67, 125.83, 126.14, 127.27, 127.76, 131.31, 140.03, 140.56, 157.86, 158.07, 163.51, 166.65, 169.10, 171.19, 172.34; ES-MS m/z 591 (M+Na).

Example 62

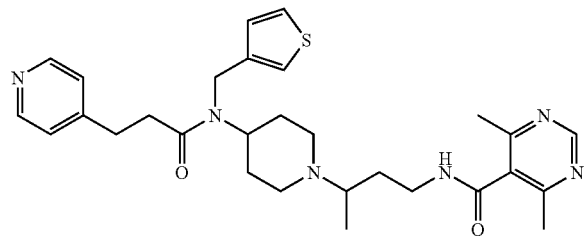

Compound 62

4,6-Dimethyl-pyrimidine-5-carboxylic acid (3-{4-[(3-pyridin-4-yl-propionyl)-thiophen-3-ylmethyl-amino]-piperidin-1-yl}-butyl)-amide Using general procedure A, 4-amino-1-Boc-piperidine (481 mg, 2.40 mmol) and 3-thiophenecarboxaldehyde (228 mg, 2.03 mmol) gave 4-[(thiophen-3-ylmethyl)-amino]-piperidine-1-carboxylic acid tert-butyl ester as a yellow oil (425 mg, 1.43 mmol, 71%). ¹H NMR (CDCl₃) δ 1.22-1.36 (m, 3H), 1.45 (s, 9H), 1.80-1.90 (m, 2H), 2.67 (tt, 1H, J=10.1, 3.9 Hz), 2.74-2.86 (m, 2H), 3.85 (s, 2H), 3.95-4.10 (m, 2H), 7.04 (dd, 1H, J=4.8, 1.5 Hz), 7.11-7.14 (m, 1H), 7.29 (dd, 1H, J=5.0, 2.9 Hz).

A solution of 4-pyridinecarboxaldehyde (333 mg, 3.11 mmol) and (carboethoxy-methylene)triphenylphosphorane (1.19 g, 3.42 mmol) in toluene (8.0 ml) was stirred at 90° C. under nitrogen for 3 hours. Once cooled, the solvent was removed under reduced pressure, the crude product was acidified with 1M HCl (25 ml) and the solution was washed with Et₂O (25 ml×2). The aqueous solution was made basic with 1M NaOH and extracted with CH₂Cl₂ (25 ml×2). The combined organic solution was dried (Na₂SO₄), filtered and concentrated under reduced pressure, giving (E)-3-pyridin-4-yl-acrylic acid ethyl ester as a white solid (238 mg, 1.34 mmol, 43%). ¹H NMR (CDCl₃) δ 1.35 (t, 3H, J=7.2 Hz), 4.29 (q, 2H, J=7.2 Hz), 6.59 (d, 1H, J=16.2 Hz), 7.37 (d, 2H, J=6.1 Hz), 7.60 (d, 1H, J=16.2 Hz), 8.66 (d, 2H, J=6.1 Hz).

A mixture of the unsaturated ester (235 mg, 1.33 mmol) and 10% Pd/C (50% wet with H₂O, 175 mg, 0.08 mmol) in EtOAc (10 ml) was stirred under H₂ (1 atm) for 1.5 hours. The mixture was filtered with suction through a pad of Celite®, washing with EtOAc. The filtrate was concentrated under reduced pressure and the residue was purified by flash column chromatography on silica (CH₂Cl₂/Et₂O, 4:1) giving 3-pyridin-4-yl-propionic acid ethyl ester as a yellow oil (179 mg, 1.00 mmol, 75%). ¹H NMR (CDCl₃) δ 1.23 (t, 3H, J=7.2 Hz), 2.64 (t, 2H, J=7.6 Hz), 2.95 (t, 2H, J=7.6 Hz), 4.13 (q, 2H, J=7.2 Hz), 7.13 (d, 2H, J=6.2 Hz), 8.50 (d, 2H, J=6.2 Hz).

A solution of the ethyl ester (179 mg, 1.00 mmol) and 10M NaOH (2.0 ml, 20 mmol) in MeOH (5.0 ml) was stirred at 50° C. for 17 hours. Once cooled, the pH was adjusted to 6 and the solvent was evaporated under reduced pressure. The solid residue was triturated with MeOH until no UV active material remained in the residue. The solution was concentrated, giving the crude carboxylic acid as a mixture with excess NaCl (390 mg).

Using general procedure E, the above acid and 4-[(thiophen-3-ylmethyl)-amino]-piperidine-1-carboxylic acid tert-butyl ester (212 mg, 0.72 mmol) gave the amide as a yellow oil (214 mg, 0.50 mmol, 70%).

Using general procedure C, the tert-butyl carbamate (214 mg, 0.50 mmol) gave N-piperidin-4-yl-3-pyridin-4-yl-N-thiophen-3-ylmethyl-propionamide as a yellow oil (62.3 mg, 0.19 mmol, 38%).

Using general procedure B, the piperidine (62.3 mg, 0.19 mmol) and 2-(3-oxo-butyl)-isoindole-1,3-dione (108 mg, 0.50 mmol) gave the desired tertiary amine as a white foam (47.5 mg, 0.090 mmol, 47%).

Using general procedure D, the phthalimide gave N-[1-(3-amino-1-methyl-propyl)-piperidin-4-yl]-3-pyridin-4-yl-N-thiophen-3-ylmethyl-propionamide as a cloudy, yellow oil (31.3 mg, 0.078 mmol, 87%).

A solution of the primary amine (31.3 mg, 0.078 mmol), 4,6-dimethylpyrimidine-5-carboxylic acid (15 mg, 0.099 mmol), EDCI (21 mg, 0.11 mmol), HOBT (19 mg, 0.14 mmol) and NMM (20 μL, 0.18 mmol) in DMF (0.50 ml) was stirred at room temperature for 17.5 hours. The reaction was diluted with saturated aqueous NaHCO₃ (20 ml) and extracted with CH₂Cl₂ (15 ml×3). The combined organic solution was dried (Na₂SO₄), filtered and concentrated under reduced pressure. Purification by flash column chromatography on silica (CH₂Cl₂/MeOH/NH₄OH, 19:1:0.13) gave COMPOUND 62 as a white foam (22.1 mg, 0.041 mmol, 53%). ¹H NMR (CDCl₃) δ 0.76-1.04 (m, 2H), 0.96 (d, 3H, J=6.6 Hz), 1.15-1.79 (m, 6H), 1.99-3.01 (m, 7H), 2.48 (s, 6H), 3.23-4.46 (m, 5H), 6.81-6.85 and 6.93-6.96 (m, 1H), 6.88 and 7.04 (d, 1H, J=5.3 Hz), 7.00 and 7.13 (d, 2H, J=5.7 Hz), 7.149 and 7.31 (dd, 1H, J=5.0, 3.2 Hz), 7.92 and 8.73 (br. s, 1H), 8.42 and 8.47 (d, 2H, J=5.7 Hz), 8.87 and 8.91 (s, 1H). ¹³C NMR (CDCl₃) δ 13.37, 21.88, 29.47, 30.35, 30.43, 30.44, 34.03, 40.11, 42.54, 43.19, 51.38, 51.67, 60.38, 120.45, 123.91, 125.65, 126.90, 130.93, 139.42, 149.68, 150.13, 157.45, 163.08, 166.15, 171.80. ESI-MS m/z 535 (MH)⁺. Anal. Calcd. for C₂₉H₃₈N₆O₂S.0.3CH₂Cl₂: C, 62.82; H, 6.94; N, 15.00. Found: C, 63.06; H, 7.24; N, 14.74.

Example 63

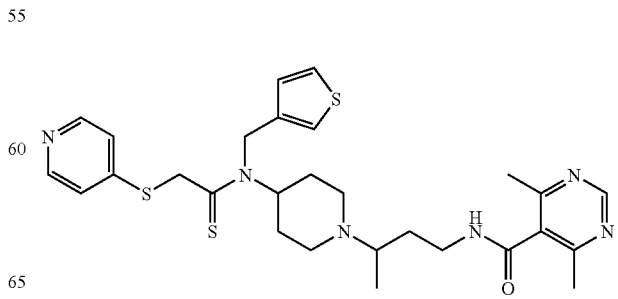

Compound 63

4,6-Dimethyl-pyrimidine-5-carboxylic acid [3-(4-{[2-(pyridin-4-ylsulfanyl)-thioacetyl]-thiophen-3-ylmethyl-amino}-piperidin-1-yl)-butyl]-amide Using general procedure E, 4-[(thiophen-3-ylmethyl)-amino]-piperidine-1-carboxylic acid tert-butyl ester (200 mg, 0.68 mmol) and 4-pyridylthioacetic acid (230 mg, 1.36 mmol) in $CH_2Cl_2$ (5 ml) afforded 4-{[2-(pyridin-4-ylsulfanyl)-acetyl]-thiophen-3-ylmethyl-amino}-piperidine-1-carboxylic acid tert-butyl ester as a white solid (290 mg, 95%).

Using general procedure F, 4-{[2-(pyridin-4-ylsulfanyl)-acetyl]-thiophen-3-ylmethyl-amino}-piperidine-1-carboxylic acid tert-butyl ester (290 mg, 0.65 mmol) in toluene (5 ml) and Lawsson's reagent (171 mg, 0.42 mmol) afforded 4-{[2-(pyridin-4-ylsulfanyl)-thioacetyl]-thiophen-3-ylmethyl-amino}-piperidine-1-carboxylic acid tert-butyl ester as a white solid (145 mg, 48%).

Using general procedure C, 4-{[2-(pyridin-4-ylsulfanyl)-thioacetyl]-thiophen-3-ylmethyl-amino}-piperidine-1-carboxylic acid tert-butyl ester (145 mg, 0.31 mmol) afforded the desired amine.

Using general procedure B followed by general procedure D, the crude material (140 mg, quantitative) afforded N-[1-(3-amino-1-methyl-propyl)-piperidin-4-yl]-2-(pyridin-4-ylsulfanyl)-N-thiophen-3-ylmethyl-thioacetamide as a colorless oil (60 mg, 45% over three steps).

Using general procedure E, N-[1-(3-amino-1-methyl-propyl)-piperidin-4-yl]-2-(pyridin-4-ylsulfanyl)-N-thiophen-3-ylmethyl-thioacetamide (60 mg, 0.138 mmol) and 4,6-dimethyl-pyrimidine-5-carboxylic acid (32 mg, 0.20 mmol) afforded COMPOUND 63 as a white solid (60 mg, 77%). $^1$H NMR ($CDCl_3$) mixture of rotamers: δ 0.75-1.24 (m, 5H), 1.25-2.85 (m, 20H), 3.25-5.50 (m, 6H), 6.80-7.40 (m, 5H), 7.65 (br s, 0.25H), 7.30-7.50 (m, 2H), 8.88 (br s, 0.7H), 8.95 (s, 0.3H); $^{13}$C NMR ($CDCl_3$) δ 13.93, 22.37, 28.97, 29.84, 31.13, 31.79, 31.94, 39.75, 40.37, 43.57, 43.68, 44.12, 46.93, 48.17, 51.76, 59.70, 60.00, 60.56, 62.02, 121.57, 122.05, 122.18, 125.86, 126.04, 127.07, 128.16, 131.29, 136.70, 137.25, 149.81; 150.00, 157.95, 158.16, 163.55, 166.62, 199.0; ES-MS m/z 569.5 (M+H). Anal. Calcd. for $C_{28}H_{36}N_6OS_3 \cdot 0.6CH_2Cl_2$: C, 55.43; H, 6.05; N, 13.56. Found: C, 55.25; H, 6.12; N, 13.46.

Example 64

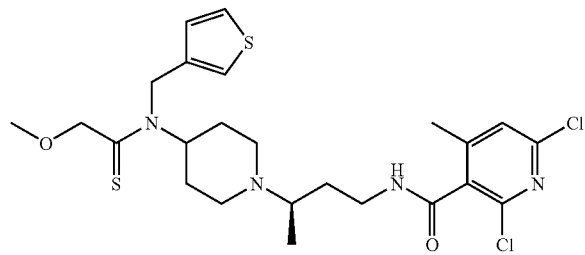

Compound 64

2,6-Dichloro-N—((R)-3-{4-[(2-methoxy-thioacetyl)-thiophen-3-ylmethyl-amino]-piperidin-1-yl}-butyl)-4-methyl-nicotinamide To a solution of 2,6-dichloro-N—((R)-3-{4-[(2-methoxy-acetyl)-thiophen-3-ylmethyl-amino]-piperidin-1-yl}-butyl)-4-methyl-nicotinamide (COMPOUND 39) (257 mg, 0.49 mmol) in toluene (5 ml) was added Lawesson's reagent (128 mg, 0.32 mmol). The mixture was refluxed at 125° C. for 2.5 h and concentrated in vacuo. The crude product was purified by preparative TLC (ether, 3% MeOH, 1% $NH_4OH$) and two products (the mono- and bis-thioamides) were isolated. The mono-thioamide COMPOUND 64 (84 mg, 32% yield) was a white solid and a mixture of rotational isomers. $^1$H NMR ($CDCl_3$) δ 0.97-0.99 (d, 3H, J=6 Hz), 1.17-1.45 (m, 1H), 1.50-1.65 (m, 2H), 1.65-1.81 (m, 2H), 2.10-2.25 (m, 1H), 2.36 and 2.38 (s, total 3H), 2.47-2.57 (m, 1H), 2.70-2.90 (m, 3H), 3.24-3.37 (m, 1H), 3.38 and 3.46 (s, total 3H), 3.73-3.86 (m, 1H), 4.30 and 4.44 (s, total 2H), 4.44 and 4.49 (s, total 2H), 4.68-4.98 (m, 1H), 5.31-5.48 (m, 1H), 6.96-7.00 (m, 1H), 7.15 (m, 1H), 7.15-7.16 (m, 1H), 7.33-7.36 (m, 1H), 7.97 and 8.56 (br s, total 1H); ES-MS m/z 543 (M+H).

Example 65

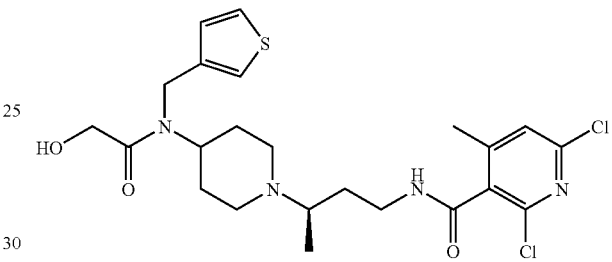

Compound 65

2,6-Dichloro-N—((R)-3-{4-[(2-hydroxy-acetyl)-thiophen-3-ylmethyl-amino]-piperidin-1-yl}-butyl)-4-methyl-nicotinamide To a solution of 2,6-dichloro-4-methyl-N—((R)-3-{4-[(thiophen-3-ylmethyl)-amino]-piperidin-1-yl}-butyl)-nicotinamide (177 mg, 0.39 mmol) in 1,2-dichloroethane (5 ml) was added DIPEA (0.35 ml, 2.01 mmol) followed by acetoxyacetyl chloride (0.1 ml, 0.93 mmol) and the reaction stirred at 65° C. for 3 h. The solution was cooled, treated with saturated aqueous $NaHCO_3$ (25 ml) and extracted with $CH_2Cl_2$ (3×15 ml). The combined organic extracts were dried ($Na_2SO_4$), filtered, and concentrated. Purification of the crude material by column chromatography on silica gel ($CH_2Cl_2$/MeOH/$NH_4OH$, 96:4:0 then 88:10:2) provided the desired amide (88 mg, 41%) as a brown oil. To a solution of the acetate from above (80 mg, 0.14 mmol) in MeOH (5 ml) was added $K_2CO_3$ (67 mg, 0.49 mmol) and the reaction stirred overnight. The mixture was concentrated then diluted with $CH_2Cl_2$ (25 ml) and saturated aqueous $NaHCO_3$ (20 ml). The aqueous layer was extracted with $CH_2Cl_2$ (2×10 ml) and the combined organic extracts were dried ($Na_2SO_4$), filtered, and concentrated. Purification of the crude material by column chromatography on silica gel ($CH_2Cl_2$/MeOH, 96:4 then 9:1) afforded COMPOUND 65 (48 mg, 59%) as a pale yellow foam and a mixture of two rotational isomers. $^1$H NMR ($CDCl_3$) δ 0.94-0.99 (m, 3H), 1.19-1.43 (m, 2H), 1.50-1.73 (m, 5H), 2.09-2.14 (m, 1H), 2.35 and 2.38 (s, total 3H), 2.51-2.57 (m, 1H), 2.70-2.85 (m, 3H), 3.19-3.40 (m, 1H), 3.75-3.82 (m, 1H), 3.98-4.28 (m, 5H), 6.93-6.95 (m, 1H), 7.02-7.05 (m, 1H), 7.12-7.15 (m, 1H), 7.23-7.35 (m, 1H), 7.86-7.88 and 8.57-8.60 (m, total 1H); ES-MS m/z 513

(M+H). Anal. Calcd. for $C_{23}H_{30}N_4O_3SCl_2 \cdot 0.3H_2O$: C, 53.24; H, 5.94; N, 10.80. Found: C, 53.27; H, 5.88; N, 10.54.

Example 66

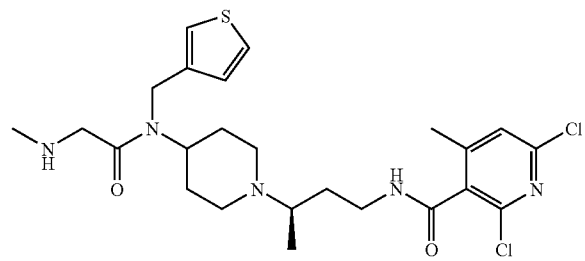

Compound 66

2,6-Dichloro-4-methyl-N—((R)-3-{4-[(2-methylamino-acetyl)-thiophen-3-ylmethyl-amino]-piperidin-1-yl}-butyl)-nicotinamide Following general procedure E: to a stirred solution of 2,6-dichloro-4-methyl-N—((R)-3-{4-[(thiophen-3-ylmethyl)-amino]-piperidin-1-yl}-butyl)-nicotinamide (62 mg, 0.137 mmol), (tert-butoxycarbonyl-methyl-amino)-acetic acid (28 mg, 0.159 mmol), HOBt (24 mg, 0.177 mmol) and DIPEA (59 µL, 0.34 mmol) in DMF (3 ml) was added EDCI (34 mg, 0.177 mmol). The reaction was stirred at rt overnight under $N_2$ pressure. The resultant crude product (88 mg) was used in the next step.

Following general procedure C: the Boc-protected amine from above (88 mg) provided COMPOUND 66 (49 mg, 68%). $^1$H NMR (CDCl$_3$) δ 0.97-0.99 (m, 4H), 1.92-1.25 (m, 2H), 1.49-1.54 (m, 2H), 1.64-1.76 (m, 2H), 2.15 (m, 1H), 2.35-2.39 (m, 6H), 2.45-2.54 (m, 1H), 2.71-2.84 (m, 3H), 3.25-3.41 (m, 3H), 3.81-3.81 (m, 1H), 3.99-4.00 (m, 2H), 4.37 (m, 1H), 6.97-7.03 (m, 2H), 7.13 (s, 1H), 7.33-7.35 (m, 1H), 8.78 (br s, 1H); ES-MS m/z 526 (M+H).

Example 67

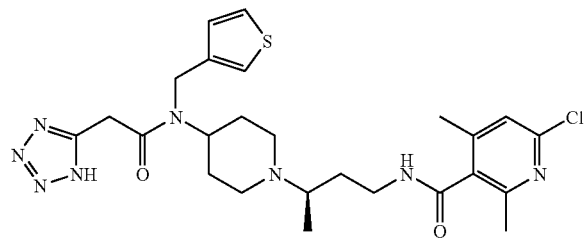

Compound 67

6-Chloro-2,4-dimethyl-N—((R)-3-{4-[(2-1H-tetrazol-5-yl-acetyl)-thiophen-3-ylmethyl-amino]-piperidin-1-yl}-butyl)-nicotinamide 6-Chloro-N-(3-{4-[(2-cyano-acetyl)-thiophen-3-ylmethyl-amino]-piperidin-1-yl}-butyl)-2,4-dimethyl-nicotinamide (0.080 g, 0.16 mmol) was dissolved in iso-propanol (3 ml) and diluted with water (6 ml) (Demke and Sharpless, JOC 2001, 66, 7945-50). To the milky solution were added ZnBr$_2$ (0.036 g, 0.16 mmol) and NaN$_3$ (0.011 g, 0.18 mmol) and the resulting mixture was refluxed for 16 h. The crude reaction mixture was dry-loaded onto silica gel and purified via column chromatography (MeCN/MeOH/NH$_4$OH, 7:2:1, v/v/v) to yield COMPOUND 67 (0.039 g, 45%) as a white solid. $^1$H NMR (CD$_3$OD) (mixture of rotamers) δ 1.22 (m, 3H), 1.46 (m, 1H), 1.70-1.94 (m, 5H), 2.36 (s, 3H), 2.50 (s, 3H), 2.54-2.75 (m, 2H), 2.98 (m, 2H), 3.05 (m, 1H), 3.50 (m, 2H), 4.00 (s) and 4.17 (s) (total 2H), 4.06 (m) and 4.41 (m) (total 1H), 4.55 (s) and 4.69 (s) (total 2H), 7.07 (m, 1H), 7.23 (s) and 7.34 (s) (total 1H), 7.28 (s, 1H), 7.33 (m) and 7.50 (m) (total 1H); ES-MS m/z 589 (M+2Na).

Example 68

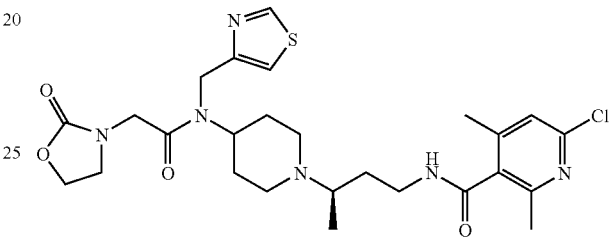

Compound 68

6-Chloro-2,4-dimethyl-N—[(R)-3-(4-{[2-(2-oxo-oxazolidin-3-yl)-acetyl]-thiazol-4-ylmethyl-amino}-piperidin-1-yl)-butyl]-nicotinamide Sodium azide (0.770 g, 11.9 mmol) was added to a solution of 4-bromomethyl-thiazole (1.22 g, 9.17 mmol) in N,N'-dimethylformamide (15 ml) and the resulting pale yellow solution was stirred at 50° C. for 16 hours. Standard basic workup gave the crude product as a white solid. The crude solid was dissolved in methanol (30 ml), treated with 10% Pd/C (0.40 g) and placed under 1 atm. H$_2$ for 12 hours. The mixture was filtered through Celite®, the cake was washed with MeOH and the combined filtrate was concentrated under reduced pressure to give a tan liquid. Purification by column chromatography on silica gel (CH$_2$C$_2$/MeOH/NH$_4$OH, 86:12:2, v/v/v) afforded 4-aminomethyl-thiazole (0.540 g, 52%) as a pale yellow liquid. $^1$H NMR (CDCl$_3$) δ 1.96 (s, 2H), 4.04 (s, 2H), 7.14 (s, 1H), 8.78 (s, 1H).

Using general procedure A, [3-(4-oxo-piperidin-1-yl)-butyl]-carbamic acid tert-butyl ester (0.780 g, 2.88 mmol), 4-aminomethyl-thiazole (0.328 g, 2.88 mmol), sodium triacetoxyborohydride (1.22 g, 5.76 mmol) and acetic acid (0.2 ml, cat.) in methylene chloride (50 ml) at 25° C. for 16 hours gave the crude product as a pale yellow oil.

Using general procedure C gave [1-(3-amino-1-methylpropyl)-piperidin-4-yl]-thiazol-4-ylmethyl-amine (0.54 g, 70%; 2-steps) as a pale yellow oil.

Following general procedure E: to a stirred solution of [1-(3-amino-1-methyl-propyl)-piperidin-4-yl]-thiazol-4-ylmethyl-amine (0.320 g, 1.19 mmol), EDCI (0.252 g, 1.31 mmol) and HOBt (0.177 g, 1.31 mmol) in DMF (5 ml) was added 6-chloro-2,4-dimethyl-nicotinic acid (0.243 g, 1.31 mmol) followed by DIPEA (343 µL, 1.78 mmol) and the resulting mixture was stirred at 25° C. for 16 hours. Standard workup and purification by column chromatography on silica gel (CH$_2$Cl$_2$/MeOH/NH$_4$OH, 93:5:2) afforded 6-chloro-2,4-dimethyl-N-(3-{4-[(thiazol-4-ylmethyl)-amino]-piperidin-1-yl}-butyl)-nicotinamide (0.42 g, 81%) as a colorless oil.

Following general procedure E: to a stirred solution of 6-chloro-2,4-dimethyl-N-(3-{4-[(thiazol-4-ylmethyl)-amino]-piperidin-1-yl}-butyl)-nicotinamide (0.094 g, 0.22 mmol), EDCI (0.045 g, 0.24 mmol) and HOBt (0.032 g, 0.24 mmol) in DMF (5 ml) was added (2-oxo-oxazolidin-3-yl)-acetic acid (see EXAMPLE 24) (0.034 g, 0.42 mmol) followed by DIPEA (62 μL, 0.32 mmol) and the resulting mixture was stirred at 25° C. for 16 hours. Standard workup and purification by column chromatography on silica gel (Et$_2$O/MeOH/NH$_4$OH, 83:15:2) afforded COMPOUND 68 (0.067 g, 55%) as a white foam. $^1$H NMR (CDCl$_3$) (mixture of rotamers) δ 0.94 (d+m, 4H), 1.08 (m, 1H), 1.51-1.75 (m, 4H), 2.11 (br t, 1H), 2.33 (s, 3H), 2.49 (br t, 1H), 2.52 (s, 3H), 2.65 (m, 1H), 2.78 (m, 2H), 3.27 (m, 1H), 3.71-3.83 (m, 3H), 4.08-4.19 (m, 4H), 4.37 (m, 3H), 6.92 (s) and 7.10 (s) (total 1H), 7.31 (s) and 7.38 (s) (total 1H), 8.03 (br s) and 8.50 (br s) (total 1H), 8.65 (s) and 8.75 (s) (total 1H); ES-MS m/z 563 (M+H).

Example 69

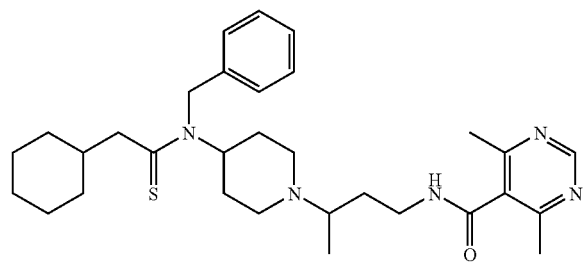

Compound 69

4,6-Dimethyl-pyrimidine-5-carboxylic acid (3-{4-[benzyl-(2-cyclohexyl-thioacetyl)-amino]-piperidin-1-yl}-butyl)-amide Using general procedure E, 4-benzylamino-piperidine-1-carboxylic acid tert-butyl ester (300 mg, 1.03 mmol) and cyclohexylacetic acid (161 mg, 1.13 mmol) afforded 4-[benzyl-(2-cyclohexyl-acetyl)-amino]-piperidine-1-carboxylic acid tert-butyl ester as a white solid (360 mg, 85%).

Using general procedure F, A solution of the above amide (142 mg, 0.34 mmol) and Lawesson's reagent (90 mg, 0.22 mmol) in toluene (3 ml) afforded 4-[benzyl-(2-cyclohexyl-thioacetyl)-amino]-piperidine-1-carboxylic acid tert-butyl ester (119 mg, 82%).

Using general procedure C with the above substrate (119 mg, 0.28 mmol), then general procedure B with the resulting amine and 2-(3-oxo-butyl)-isoindole-1,3-dione (120 mg, 0.55 mmol) and then using general procedure D afforded N-[1-(3-amino-1-methyl-propyl)-piperidin-4-yl]-N-benzyl-2-cyclohexyl-thioacetamide (45 mg, 41% over 3 steps).

Using general procedure E, the above amine (45 mg, 0.11 mmol) and 4,6-dimethylpyrimidine-5-carboxylic acid (19 mg, 0.12 mmol) afforded COMPOUND 69 as a white solid (50 mg, 85%). $^1$H NMR (CDCl$_3$) mixture of rotamers: δ 0.75-1.40 (m, 9H), 1.41-2.96 (m, 18H), 2.51 (s, 6H), 3.25-3.43 (m, 1H), 3.62-3.87 (m, 1H), 4.20-4.88 and 4.80-5.13 (m, 2H), 5.56-5.67 (m, 1H), 7.11 (d, 1H, J=7.2 Hz), 7.17-7.40 (m, 3H), 8.34-8.43 (m, 1H), 8.95 (s, 1H); $^{13}$C NMR (CDCl$_3$) δ 13.9, 22.4, 26.6, 29.2, 30.1, 31.1, 32.1, 33.3, 33.8, 39.7, 40.2, 40.4, 43.6, 44.3, 49.8, 51.2, 51.9, 52.0, 59.6, 60.6, 60.8, 126.0, 126.3, 126.7, 127.1, 128.0, 128.7, 129.3, 131.3, 136.8, 158.0, 158.2, 163.6, 166.7; ES-MS m/z 536 (M+H). Anal. Calcd. for C$_{31}$H$_{45}$N$_5$OS.0.2CH$_2$Cl$_2$: C, 67.79; H, 8.28; N, 12.67. Found: C, 67.74; H, 8.27; N, 12.52.

Example 70

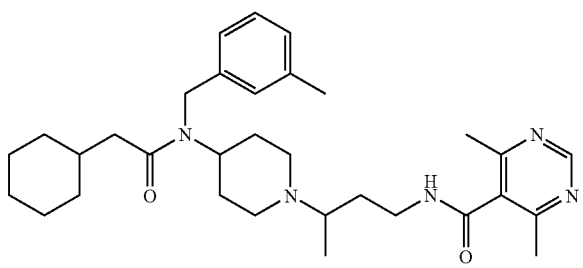

Compound 70

4,6-Dimethyl-pyrimidine-5-carboxylic acid (3-{4-[(2-cyclohexyl-acetyl)-(3-methyl-benzyl)-amino]-piperidin-1-yl}-butyl)-amide Using general procedure A, 3-methylbenzylamine (30 μL, 0.23 mmol) and 4,6-dimethylpyrimidine-5-carboxylic acid [3-(4-oxo-piperidin-1-yl)-butyl]-amide (66 mg, 0.22 mmol) afforded 4,6-dimethyl-pyrimidine-5-carboxylic acid {3-[4-(3-methyl-benzylamino)-piperidin-1-yl]-butyl}-amide (65 mg, 72%).

Using general procedure E, the above amine (65 mg, 0.16 mmol) and cyclohexylacetic acid (25 mg, 0.17 mmol) afforded COMPOUND 70 as a white solid (27 mg, 32%). $^1$H NMR (CDCl$_3$) mixture of rotamers: δ 0.74-1.40 (m, 9H), 1.47-1.96 (m, 1H), 2.00-2.95 (m, 7H), 2.35 (s, 3H), 2.50 (s, 6H), 3.24-3.42 (m, 1H), 3.60-4.12 (m, 3H), 4.36-4.52 (m, 1H), 6.80-6.98 (m, 2H), 7.06 (d, 1H, J=7.2 Hz), 7.22 (t, 1H, J=7.8 Hz), 8.53-8.68 (m, 1H), 8.94 (s, 1H); $^{13}$C NMR (CDCl$_3$) δ 13.8, 21.8, 22.3, 26.6, 26.7, 30.0, 31.0, 31.4, 31.8, 32.3, 33.6, 34.0, 35.5, 39.9, 40.4, 41.6, 43.8, 44.3, 44.8, 46.3, 51.8, 52.2, 56.3, 59.9, 60.7, 123.1, 123.9, 126.7, 127.6, 128.2, 128.5, 128.9, 138.7, 158.0, 163.5, 166.7, 173.8; ES-MS m/z 535 (M+H+1). Anal. Calcd. for C$_{32}$H$_{47}$N$_5$O$_2$.0.2CH$_2$Cl$_2$: C, 70.22; H, 8.67; N, 12.72. Found: C, 70.58; H, 8.90; N, 12.51.

Example 71

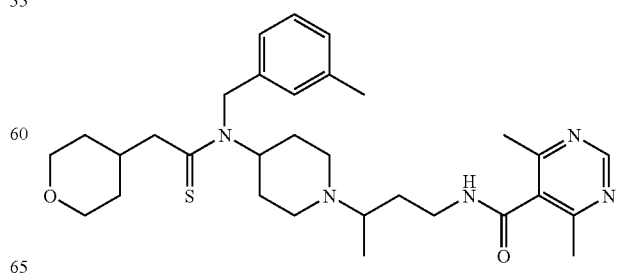

Compound 71

4,6-Dimethyl-pyrimidine-5-carboxylic acid (3-{4-[(3-methylbenzyl)-(2-tetrahydropyran-4-yl-thioacetyl)-amino]-piperidin-1-yl}-butyl)-amide Using general procedure A, 3-methylbenzylamine (198 µL, 1.58 mmol) and 1-Boc-4-piperidone (300 mg, 1.51 mmol) afforded 4-(3-methylbenzylamino)-piperidine-1-carboxylic acid tert-butyl ester as a white solid (375 mg, 82%).

Using general procedure E, 4-(3-methylbenzylamino)-piperidine-1-carboxylic acid tert-butyl ester (365 mg, 1.2 mmol) and (tetrahydropyran-4-yl)-acetic acid (173 mg, 1.2 mmol) afforded 4-[(3-methylbenzyl)-(2-tetrahydropyran-4-yl-acetyl)-amino]-piperidine-1-carboxylic acid tert-butyl ester as a white solid (217 mg, 42%).

Using general procedure F, the above amide (217 mg, 0.5 mmol) and Lawesson's reagent (132 mg, 0.32 mmol) in toluene (8 ml) afford 4-[(3-methylbenzyl)-(2-tetrahydropyran-4-yl-thioacetyl)-amino]-piperidine-1-carboxylic acid tert-butyl ester (164 mg, 74%).

Using general procedure C with the above substrate (164 mg, 0.37 mmol), then general procedure B with the resulting amine and 2-(3-oxo-butyl)-isoindole-1,3-dione (160 mg, 0.73 mmol) afforded and then using general procedure D afforded N-[1-(3-amino-1-methylpropyl)-piperidin-4-yl]-N-(3-methylbenzyl)-2-(tetrahydro-pyran-4-yl)-thioacetamide (121 mg, 79% over 3 steps).

Using general procedure E, N-[1-(3-amino-1-methylpropyl)-piperidin-4-yl]-N-(3-methylbenzyl)-2-(tetrahydro-pyran-4-yl)-thioacetamide (40 mg, 0.10 mmol) and 4,6-dimethyl-pyrimidine-5-carboxylic acid (16 mg, 0.11 mmol) afforded COMPOUND 71 as a white solid (40 mg, 75%). $^1$H NMR (CDCl$_3$) mixture of rotomers: δ 0.80-1.29 (m, 4H), 0.97 (d, 3H, J=6.6 Hz), 1.38-2.07 (m, 7H), 2.11-2.84 (m, 7H), 2.35 (s, 3H), 2.50 (s, 6H), 3.24-3.48 (m, 3H), 3.71-3.84 (m, 1H), 3.89 (d, 2H, J=11.4 Hz), 4.15-4.37 (m, 2H), 5.52-5.67 (m, 1H), 6.85-6.94 (m, 2H), 7.08 (d, 1H, J=7.5 Hz), 7.23 (t, 1H, J=8.5 Hz), 8.33-8.45 (m, 1H), 8.94 (s, 1H); $^{13}$C NMR (CDCl$_3$) δ 11.9, 19.9, 20.4, 27.1, 28.0, 29.2, 30.0, 30.2, 30.9, 31.4, 34.8, 37.6, 38.3, 41.7, 42.3, 47.8, 47.9, 49.8, 50.1, 57.5, 57.7, 58.1, 58.5, 58.8, 66.3, 120.9, 121.6, 124.5, 125.3, 125.9, 126.6, 126.8, 127.2, 129.3, 134.5, 134.7, 136.4, 137.2, 156.0, 156.2, 161.5, 164.7; ES-MS m/z 552 (M+H). Anal. Calcd. for C$_{31}$H$_{45}$N$_5$O$_2$S.0.2CH$_2$Cl$_2$: C, 65.89; H, 8.05; N, 12.31. Found: C, 65.56; H, 8.00; N, 12.19.

Example 72 was prepared in a similar manner as Example 70 except that 2-methoxybenzylamine was used in lieu of 3-methylbenzylamine.

Example 72

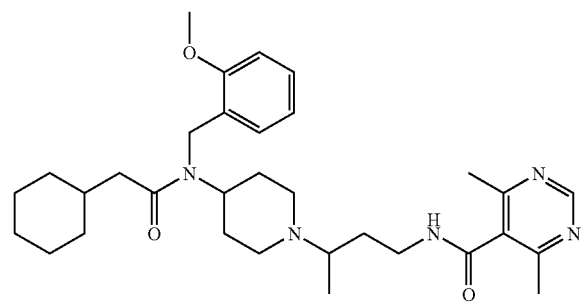

Compound 72

4,6-Dimethyl-pyrimidine-5-carboxylic acid (3-{4-[(2-cyclohexyl-acetyl)-(2-methoxy-benzyl)-amino]-piperidin-1-yl}-butyl)-amide Mixture of rotomers: $^1$H NMR (CDCl$_3$) δ 0.77-1.26 (m, 9H), 1.52-1.99 (m, 13H), 2.10-3.83 (m, 5H), 2.48 (s, 6H,), 3.26-3.44 (m, 1H), 3.74-3.93 (m, 1H), 3.94 (s, 3H), 4.13-4.18 (m, 2H), 4.36-4.52 (m, 1H), 6.80-7.00 (m, 3H), 7.19-7.22 (m, 1H), 7.75-7.77 (m, 1H), 8.85 (m, 1H); $^{13}$C NMR (CDCl$_3$) δ 13.8, 22.3, 26.6, 29.9, 30.5, 31.2, 31.9, 32.9, 33.6, 34.0, 35.5, 39.7, 40.1, 41.5, 42.1, 44.3, 44.6, 51.9, 52.1, 55.6, 56.4, 58.6, 59.7, 110.2, 120.6, 126.6, 126.8, 127.6, 128.4, 130.9, 156.6, 157.9, 163.3, 167.0, 174.1; ES-MS m/z 550 (M+H). Anal. Calcd. for C$_{32}$H$_{47}$N$_5$O$_3$.0.3CH$_2$Cl$_2$: C, 67.44; H, 8.34; N, 12.17. Found: C, 67.12; H, 8.54; N, 12.03.

Example 73

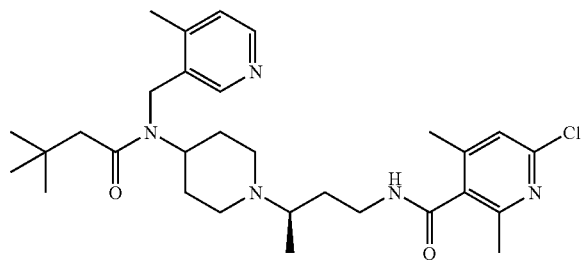

Compound 73

6-Chloro-N—((R)-3-{4-[(3,3-dimethyl-butyryl)-(4-methyl-pyridin-3-ylmethyl)-amino]-piperidin-1-yl}-butyl)-2,4-dimethyl-nicotinamide To a solution of tert-butylacetic acid (63 µL, 0.50 mmol) and DMF (3 drops) in methylene chloride (4 ml) was added oxalyl chloride (115 µL, 1.32 mmol) and the resulting orange solution was stirred at 25° C. for 3 hours. The solvent was removed in vacuo to give an orange residue. (3-{4-[(4-Methyl-pyridin-3-ylmethyl)-amino]-piperidin-1-yl}-butyl)-carbamic acid tert-butyl ester (0.125 g, 0.33 mmol) and triethylamine (115 µL, 0.83 mmol) dissolved in tetrahydrofuran (5 ml) were added to the flask containing the orange residue and the resulting mixture was stirred at 50° C. for 12 hours. Standard basic workup gave the crude product as an orange oil. Purification by column chromatography on silica gel (CH$_2$Cl$_2$/MeOH/NH$_4$OH, 93:5:2, v/v/v) afforded (3-{4-[(3,3-dimethyl-butyryl)-(4-methyl-pyridin-3-ylmethyl)-amino]-piperidin-1-yl}-butyl)-carbamic acid tert-butyl ester (0.095 g, 60%) as a tan oil.

Following general procedure C (3-{4-[(3,3-dimethyl-butyryl)-(4-methyl-pyridin-3-ylmethyl)-amino]-piperidin-1-yl}-butyl)-carbamic acid tert-butyl ester (0.095 g, 0.20 mmol) gave the crude amine. Following general procedure E: to a stirred solution of the amine, EDCI (0.042 g, 0.22 mmol) and HOBt (0.030 g, 0.22 mmol) in DMF (5 ml) was added 6-chloro-2,4-dimethyl-nicotinic acid (0.044 g, 0.22 mmol) followed by DIPEA (192 µL, 1.10 mmol) and the resulting mixture was stirred at 25° C. for 16 hours. Standard workup and purification by column chromatography on silica gel (Et$_2$O/MeOH/NH$_4$OH, 88:10:2) afforded COMPOUND 73

(0.082 g, 78%) as a white foam. $^1$H NMR (CDCl$_3$) (mixture of rotamers) δ 0.95-1.16 (m, 14H), 1.51-1.75 (m, 3H), 2.02 (m, 1H), 2.13 (m, 1H), 2.29 (s+m, 5H), 2.49 (s, 3H), 2.72-2.79 (m, 3H), 3.25-3.42 (m, 1H), 3.56-3.75 (m, 2H), 4.07-4.28 (m, 2H), 4.55 (m, 1H), 6.89-7.11 (m) and 7.76 (br s) (total 3H), 8.11-8.46 (m, 2H); ES-MS m/z 542 (M+H).

Example 74

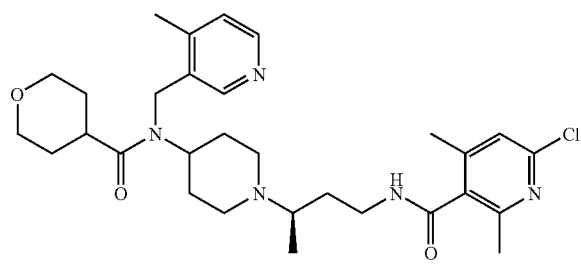

Compound 74

6-Chloro-2,4-dimethyl-N—((R)-3-{4-[(4-methyl-pyridin-3-ylmethyl)-(tetrahydro-pyran-4-carbonyl)-amino]-piperidin-1-yl}-butyl)-nicotinamide 4-Methylnicotinic acid (2.50 g, 14.4 mmol), EDCI (4.14 mg, 21.6 mmol) and HOBt (2.92 mg, 21.6 mmol) were combined in DMF (1 ml) and CH$_2$Cl$_2$ (75 ml) to give a pale yellow solution. To this solution was added ammonium chloride (2.31 g, 43.2 mmol) followed by DIPEA (12.5 ml, 72.0 mmol) and the resulting mixture was stirred at room temperature for 16 hours. The solvent was removed in vacuo and diluted with saturated aqueous NaHCO$_3$ (50 ml) and CH$_2$Cl$_2$ (50 ml). The solution was then basicified to pH ~14 with 10N NaOH. The phases were separated and the aqueous layer was extracted with CH$_2$Cl$_2$ (5×50 ml). The combined organic extracts were dried (Na$_2$SO$_4$), filtered and concentrated under reduced pressure. The crude material was purified by flash column chromatography on silica gel (94:5:1, CH$_2$Cl$_2$/MeOH/NH$_4$OH) to generate 4-methyl-nicotinamide as an off-white solid (0.95 g, 48%). $^1$H-NMR (CDCl$_3$) δ 2.53 (s, 3H), 7.20 (d, 1H, J=4 Hz), 8.53 (d, 1H, J=4 Hz), 8.69 (s, 1H).

To a solution of 4-methylnicotinamide (0.93 g, 6.84 mmol) in THF (100 ml) was added borane in THF (1M, 20.5 ml, 20.5 mmol) and the solution was heated at 60° C. for 72 hours. The reaction mixture was then cooled to room temperature followed by the addition of 9M HCl (67 ml). This solution was subsequently heated at 65° C. for 2.5 hours. The solution was cooled to room temperature and concentrated under reduced pressure followed by the addition of saturated aqueous NaHCO$_3$ (100 ml). The solution was basicified with 10N NaOH to pH ~13 and then extracted with CH$_2$Cl$_2$ (5×50 ml). The combined organic extracts were dried (Na$_2$SO$_4$), filtered and concentrated under reduced pressure. The crude material was purified by flash column chromatography on silica gel (44:5:1, CH$_2$Cl$_2$/MeOH/NH$_4$OH) to generate C-(4-methyl-pyridin-3-yl)-methylamine as a white solid (0.32 g, 38%). $^1$H-NMR (CDCl$_3$) δ 1.67 (s, 2H), 2.37, (s, 3H), 3.90 (s, 2H), 7.08 (d, 1H, J=3 Hz), 8.38 (d, 1H, J=3 Hz), 8.48 (s, 1H).

Following general procedure A: to a stirred solution of C-(4-methyl-pyridin-3-yl)-methylamine (0.78 g, 6.36 mmol) in CH$_2$Cl$_2$ (15 ml) were added (R)-[3-(4-oxo-piperidin-1-yl)-butyl]-carbamic acid tert-butyl ester (1.85 g, 7.00 mmol), glacial AcOH (0.36 ml, 6.36 mmol) and NaBH(OAc)$_3$ (1.89 g, 8.90 mmol) and the resultant solution was stirred at room temperature for 16 hours. Standard workup and purification by flash column chromatography on silica gel (94:5:1, Et$_2$O/MeOH/NH$_4$OH) generated (R)-(3-{4-[(4-methyl-pyridin-3-ylmethyl)-amino]-piperidin-1-yl}-butyl)-carbamic acid tert-butyl ester as an off-white solid (1.81 g, 76%). $^1$H-NMR (CDCl$_3$) δ 0.94 (d, 3H, J=6 Hz), 1.20 (d, 1H, J=6 Hz), 1.39 (s+m, 13H), 1.63 (m, 7H), 1.94 (d, 2H, J=9 Hz), 2.11 (t, 1H, J=11 Hz), 2.43 (s, 3H), 2.48 (m, 2H), 2.72 (m, 3H), 3.14 (m, 1H), 3.38 (m, 1H), 3.49 (s, 3H), 3.79 (s, 2H), 6.11 (br s, 1H), 7.07 (d, 1H, J=6 Hz), 8.36 (d, 2H, J=6 Hz), 8.43 (s, 1H).

To a stirred suspension of a tetrahydro-pyran-4-carboxylic acid (55.4 mg, 0.43 mmol) in CH$_2$Cl$_2$ (5 ml) were added DMF (2 drops) followed by oxalyl chloride (0.10 ml, 1.06 mmol) and the resultant mixture was stirred at room temperature for 1.5 hours. The mixture was concentrated under reduced pressure and the acid chloride was dried in vacuo for 45 minutes. To the acid chloride was added a solution of [3-(4-benzylamino-piperidin-1-yl)-butyl]-carbamic acid tert-butyl ester (0.10 g, 0.27 mmol) and triethylamine (0.10 ml, 0.66 mmol) in THF (5 ml) and the mixture was stirred at 50° C. for 16 hours. The mixture was concentrated under reduced pressure and then diluted with CH$_2$Cl$_2$ (30 ml) and 10 ml saturated aqueous NaHCO$_3$. The phases were separated and the aqueous layer was extracted with CH$_2$Cl$_2$ (5×30 ml). The organic layer was dried (Na$_2$SO$_4$), filtered and concentrated under reduced pressure. The crude material was purified by flash column chromatography on silica gel (96:3:1, CH$_2$Cl$_2$/MeOH/NH$_4$OH) to generate (R)-(3-{4-[(4-methyl-pyridin-3-ylmethyl)-(tetrahydro-pyran-4-carbonyl)-amino]-piperidin-1-yl}-butyl)-carbamic acid tert-butyl ester as a crude yellow oil (0.10 g).

Following general procedure C(R)-(3-{4-[(4-methyl-pyridin-3-ylmethyl)-(tetrahydro-pyran-4-carbonyl)-amino]-piperidin-1-yl}-butyl)-carbamic acid tert-butyl ester (0.10 g) gave the free amine. Following general procedure E: to a stirred solution of the amine, EDCI (56.2 mg, 0.29 mmol) and HOBt (39.6 mg, 0.29 mmol) in DMF (7 ml) was added 6-chloro-2,4-dimethylnicotinic acid hydrochloride salt (65.0 mg, 0.29 mmol) followed by DIPEA (255.0 µL, 1.46 mmol) and the resulting mixture was stirred at room temperature for 16 hours. Standard workup and purification by preparative TLC (91:8:1, CH$_2$C$_2$/MeOH/NH$_4$OH) afforded COMPOUND 74 as a white foam (29.8 mg, 20%). $^1$H NMR (CDCl$_3$) δ 0.98 (m, 3H), 1.61 (m, 5H), 2.02 (m, 2H), 2.32 (m, 6H), 2.48 (s, 3H), 2.84 (m, 2H), 3.22 (t, 1H, J=12 Hz), 3.46 (m, 2H), 3.66 (m, 1H), 3.94 (m, 1H), 4.28 (m, 1H), 6.98-7.14 (m, 2H), 7.71-8.42 (m, 2H); ES-MS m/z 556 (M+H), 578 (M+Na).

Example 75

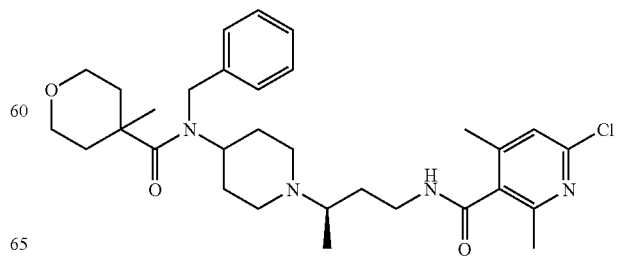

Compound 75

N—((R)-3-{4-[Benzyl-(4-methyl-tetrahydro-pyran-4-carbonyl)-amino]-piperidin-1-yl}-butyl)-6-chloro-2,4-dimethyl-nicotinamide Following general procedure A: to a stirred solution of benzylamine. (0.38 ml, 3.43 mmol) in $CH_2Cl_2$ (20 ml) were added (R)-[3-(4-oxo-piperidin-1-yl)-butyl]-carbamic acid tert-butyl ester (1.00 g, 3.77 mmol), glacial AcOH (0.20 ml, 3.43 mmol) and $NaBH(OAc)_3$ (1.02 g, 4.80 mmol) and the resultant solution was stirred at room temperature for 16 hours. Standard workup and purification by flash column chromatography on silica gel (94:5:1, $CH_2Cl_2$MeOH/$NH_4OH$) generated (R)-[3-(4-benzylamino-piperidin-1-yl)-butyl]-carbamic acid tert-butyl ester as an off-white solid (1.30 g, 100%). $^1$H-NMR ($CDCl_3$) δ 0.92 (d, 3H, J=8 Hz), 1.39 (m, 2H), 1.44 (s, 9H), 1.67 (m, 3H), 1.93 (d, 2H, J=13 Hz), 2.09 (t, 3H, J=11 Hz), 2.46 (m, 2H), 2.74 (m, 3H), 3.06 (m, 1H), 3.31 (m, 1H), 3.81 (s, 2H), 6.02 (br s, 1H), 7.24 (m, 1H), 7.31 (m, 4H).

To a stirred suspension of (4-methyl-tetrahydro-pyran-4-yl)-acetic acid (140.0 mg, 0.89 mmol) in $CH_2Cl_2$ (10 ml) were added DMF (4 drops) followed by oxalyl chloride (0.26 ml, 2.95 mmol) and the resultant mixture was stirred at room temperature for 1.5 hours. The mixture was concentrated under reduced pressure and the acid chloride was dried in vacuo for 45 minutes. To the acid chloride was added a solution of (R)-[3-(4-benzylamino-piperidin-1-yl)-butyl]-carbamic acid tert-butyl ester (262.8 mg, 0.74 mmol) and triethylamine (0.26 ml, 1.85 mmol) in THF (10 ml) and the mixture was stirred at 50° C. for 16 hours. The mixture was concentrated under reduced pressure and then diluted with $CH_2Cl_2$ (30 ml) and 10 ml saturated aqueous $NaHCO_3$. The phases were separated and the aqueous layer was extracted with $CH_2Cl_2$ (5×30 ml). The organic layer was dried ($Na_2SO_4$), filtered and concentrated under reduced pressure. The crude material was purified by flash column chromatography on silica gel (97:2:1, $CH_2Cl_2$MeOH/$NH_4OH$) to generate (R)-[3-(4-{benzyl-[2-(4-methyl-tetrahydro-pyran-4-yl)-acetyl]-amino}-piperidin-1-yl)-butyl]-carbamic acid tert-butyl ester as a crude yellow oil (315.0 mg).

Using general procedure C, (R)-[3-(4-{benzyl-[2-(4-methyl-tetrahydro-pyran-4-yl)-acetyl]-amino}-piperidin-1-yl)-butyl]-carbamic acid tert-butyl ester (315.0 mg) gave the free amine. Following general procedure E: to a stirred solution of the amine (85.0 mg), EDCI (94.7 mg, 0.23 mmol) and HOBt (31.5 mg, 0.23 mmol) in DMF (5 ml) was added 6-chloro-2,4-dimethylnicotinic acid hydrochloride salt (51.7 mg, 0.23 mmol) followed by DIPEA (185.0 μL, 1.06 mmol) and the resulting mixture was stirred at room temperature for 16 hours. Standard workup and purification by preparative TLC (91:8:1, $CH_2Cl_2$/MeOH/$NH_4OH$) afforded COMPOUND 75 as a white foam (70.6 mg, 59%). $^1$H NMR ($CDCl_3$) δ 0.77 (m, 1H), 0.96 (m, 3H), 1.10 (s, 3H), 1.47 (m, 2H), 1.68 (m, 2H), 2.15 (m, 2H), 2.30 (s, 3H), 2.52 (s, 3H), 2.62 (m, 1H), 2.78 (m, 2H), 3.25 (m, 1H), 3.62 (m, 4H), 3.72 (m, 1H), 3.84 (m, 1H), 4.02 (m, 2H), 4.48 (m, 1H), 7.02 (s, 1H), 7.20 (m, 2H), 7.35 (m, 3H), 8.75 (m, 1H); ES-MS m/z 569 (M+H), 591 (M+Na).

Examples 76 to 88 were prepared following the scheme below wherein $R^1$NCO is defined in the table and $R^2$ is as shown in the individual examples.

TABLE 4

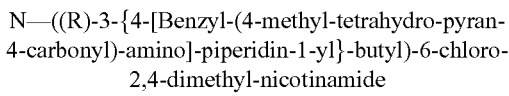

| Example | $R^1$NCO |
|---|---|
| 76* | cyclohexyl isocyanate |
| 77* | cyclohexane methyl isocyanate |
| 78* | 3,4-methylenedioxy phenyl isocyanate |
| 79* | Cycloheptyl isocyanate |
| 80* | 6-isocyanato-1,4-benzodioxane |
| 81* | 3-methoxyphenyl isocyanate |
| 82* | 3-fluoro-phenyl isocyanate |
| 83* | 4-methoxyl-phenyl isocyanate |
| 84* | 2-fluoro-phenyl isocyanate |
| 85* | 2-methoxyl-phenyl isocyanate |
| 86 | 3,4-difluoro-phenyl isocyanate |
| 87 | 4-methylsulfanyl-phenyl isocyanate |
| 88 | 4-cyanophenyl isocyanate |

*= racemic

Example 76

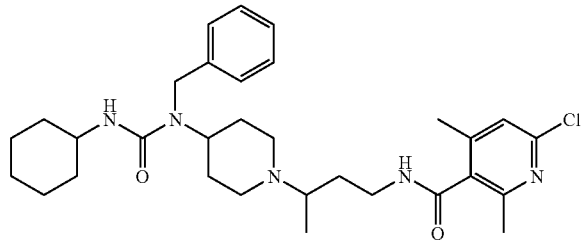

Compound 76

N-{3-[4-(1-Benzyl-3-cyclohexyl-ureido)-piperidin-1-yl]-butyl}-6-chloro-2,4-dimethyl-nicotinamide White foam. $^1$H NMR ($CDCl_3$) δ 0.80-0.87 (m, 3H), 0.98 (d, 3H, J=6.6 Hz), 1.03-1.07 (m, 1H), 1.18-1.30 (m, 2H), 1.44-1.54 (m, 4H), 1.67-1.76 (m, 6H), 2.13-2.20 (m, 2H), 2.26 (s, 3H), 2.49 (s, 3H), 2.57-2.60 (m, 1H), 2.67-2.70 (m, 1H), 2.79-2.83 (m, 2H), 3.20-3.30 (m, 1H), 3.49-3.55 (m, 1H), 3.75 (m, 2H), 3.82-3.87 (m, 1H), 4.00 (d, 1H, J=7.8 Hz), 4.30 (m, 1H), 6.93 (s, 1H), 7.28-7.29 (m, 3H), 7.34-7.39 (m, 2H), 8.00 (br s, 1H); ES-MS m/z 554 (M+H).

Example 77

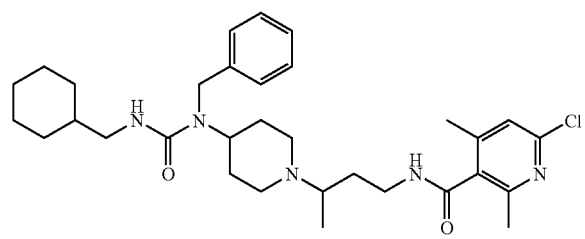

Compound 77

N-{3-[4-(1-Benzyl-3-cyclohexylmethyl-ureido)-piperidin-1-yl]-butyl}-6-chloro-2,4-dimethyl-nicotinamide White foam. $^1$H NMR (CDCl$_3$) δ 0.57-0.69 (m, 2H), 0.79-0.83 (m, 1H), 0.99 (d, 3H, J=6.6 Hz), 1.03-1.07 (m, 3H), 1.12-1.22 (m, 2H), 1.34-1.38 (m, 2H), 1.48-1.57 (m, 4H), 1.69-1.78 (m, 3H), 2.13-2.21 (m, 1H), 2.26 (s, 3H), 2.49 (s, 3H), 2.54-2.61 (m, 1H), 2.68-2.71 (m, 1H), 2.79-2.83 (m, 2H), 2.89-2.96 (m, 2H), 3.21-3.29 (m, 1H), 3.76 (s, 2H), 3.83-3.89 (m, 1H), 4.14-4.17 (m, 1H), 4.32 (m, 1H), 6.92 (s, 1H), 7.28-7.31 (m, 3H), 7.37-7.40 (m, 2H), 8.84 (br s, 1H); ES-MS m/z 568 (M+H).

Example 78

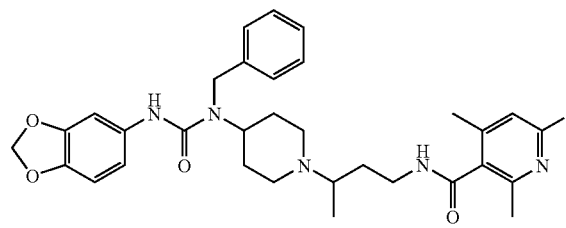

Compound 78

N-{3-[4-(3-Benzo[1,3]dioxol-5-yl-1-benzyl-ureido)-piperidin-1-yl]-butyl}-6-chloro-2,4-dimethyl-nicotinamide White foam. $^1$H NMR (CDCl$_3$) δ 0.88-0.93 (m, 1H), 0.99 (d, 3H, J=6.6 Hz), 1.05-1.10 (m, 1H), 1.50-1.56 (s, 2H), 1.75-1.78 (m, 3H), 2.16-2.24 (m, 1H), 2.28 (s, 3H), 2.50 (s, 3H), 2.60-2.64 (m, 1H), 2.71-2.74 (m, 1H), 2.83-2.85 (m, 2H), 2.84-2.91 (m, 3H), 3.27-3.31 (m, 1H), 3.84-3.91 (m, 3H), 5.88 (s, 2H), 5.97 (s, 1H), 6.28-6.31 (m, 1H), 6.59-6.62 (d, 1H, J=8.1 Hz), 6.84 (d, 1H, J=1.8 Hz), 6.95 (s, 1H), 7.34-7.45 (m, 5H), 8.75 (br s, 1H); ES-MS m/z 592 (M+H).

Example 79

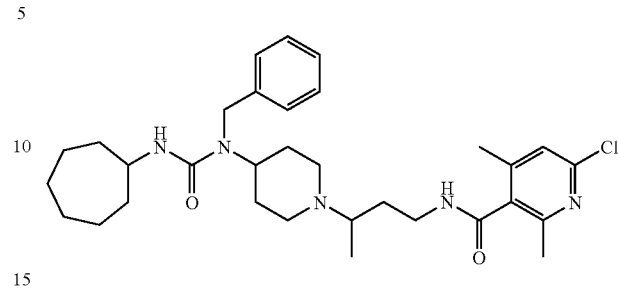

Compound 79

N-{3-[4-(1-Benzyl-3-cycloheptyl-ureido)-piperidin-1-yl]-butyl}-6-chloro-2,4-dimethyl-nicotinamide White foam. $^1$H NMR (CDCl$_3$) δ 0.78-0.83 (m, 1H), 0.97-1.03 (m, 1H), 0.99 (d, 3H, J=6.6 Hz), 1.16-1.22 (m, 2H), 1.33-1.34 (m, 6H), 1.44-1.54 (m, 3H), 1.57 (s, 1H), 1.64-1.78 (m, 5H), 2.13-2.20 (m, 1H), 2.26 (s, 3H), 2.49 (s, 3H), 2.53-2.60 (m, 1H), 2.67-2.71 (m, 1H), 2.79-2.82 (m, 2H), 3.22-3.29 (m, 1H), 3.72-3.77 (m, 3H), 3.84-3.88 (m, 1H), 4.04-4.06 (d, 1H, J=7.5 Hz), 4.30-4.34 (m, 1H), 6.93 (s, 1H), 7.28-7.29 (m, 2H), 7.37-7.39 (m, 2H), 8.84 (br s, 1H); ES-MS m/z 566 (M+H).

Example 80

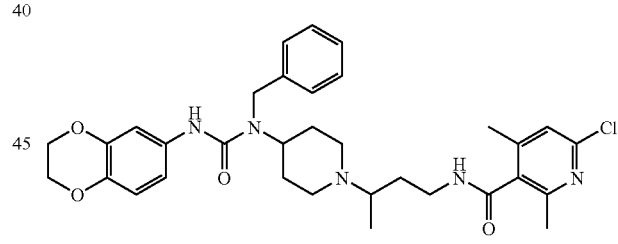

Compound 80

N-(3-{4-[1-Benzyl-3-(2,3-dihydro-benzo[1,4]dioxin-6-yl)-ureido]-piperidin-1-yl}-butyl)-6-chloro-2,4-dimethyl-nicotinamide White foam. $^1$H NMR (CDCl$_3$) δ 0.84-0.94 (m, 1H), 0.98 (d, 3H, J=6.6 Hz), 1.00-1.08 (m, 1H), 1.50 (m, 1H), 1.68-1.78 (m, 3H), 2.16-2.24 (m, 1H), 2.28 (s, 3H), 2.50 (s, 3H), 2.57-2.64 (m, 1H), 2.71-2.74 (m, 1H), 2.83-2.85 (m, 2H), 3.23-3.31 (m; 1H), 3.86-3.91 (m, 3H), 4.16-4.18 (m, 4H), 4.34 (m, 1H), 5.92 (s, 1H), 6.48-6.52 (m, 1H), 6.66-6.69 (m, 2H), 6.95 (s, 1H), 7.33-7.42 (m, 5H), 8.78 (br s, 1H); ES-MS m/z 628 (M+Na).

Example 81

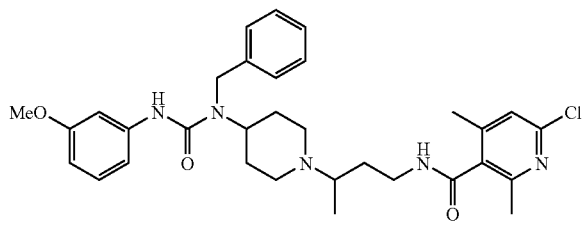

Compound 81

N-(3-{4-[1-Benzyl-3-(3-methoxy-phenyl)-ureido]-piperidin-1-yl}-butyl)-6-chloro-2,4-dimethyl-nicotinamide White foam. $^1$H NMR (CDCl$_3$) δ 0.93 (m, 1H), 0.99 (d, 3H, J=4.5 Hz), 1.11 (m, 1H), 1.50 (m, 1H), 1.77-1.79 (m, 3H), 2.22-2.25 (m, 1H), 2.29 (s, 3H), 2.50 (s, 3H), 2.62 (m, 1H), 2.71 (m, 1H), 2.83 (m, 2H), 3.29 (m, 1H), 3.74 (s, 3H), 3.87-3.93 (m, 3H), 4.36 (m, 1H), 6.14 (s, 1H), 6.48-6.54 (m, 2H), 6.94 (d, 2H, J=1.8 Hz), 7.03-7.09 (m, 1H), 7.34-7.43 (m, 5H), 8.74 (br s, 1H); ES-MS m/z 578 (M+H).

Example 82

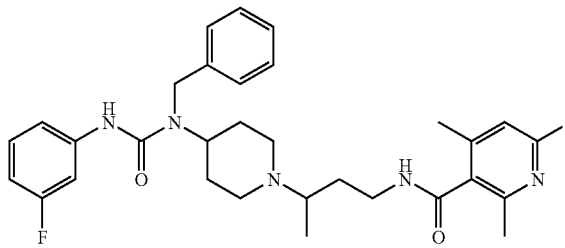

Compound 82

N-(3-{4-[1-Benzyl-3-(3-fluoro-phenyl)-ureido]-piperidin-1-yl}-butyl)-6-chloro-2,4-dimethyl-nicotinamide White foam. $^1$H NMR (CDCl$_3$) δ 0.91 (m, 1H), 0.96 (d, 3H, J=6.6 Hz), 1.01 (m, 1H), 1.50 (m, 1H), 1.77 (m, 3H), 2.28 (m, 1H), 2.29 (s, 3H), 2.50 (s, 3H), 2.63 (m, 1H), 2.75 (m, 1H), 2.86 (m, 2H), 3.30 (m, 1H), 3.85-3.95 (m, 3H), 4.35 (m, 1H), 6.19 (s, 1H), 6.62-6.68 (m, 2H), 6.95 (s, 2H), 7.06-7.13 (m, 2H), 7.35-7.47 (m, 6H); ES-MS m/z 566 (M+H).

Example 83

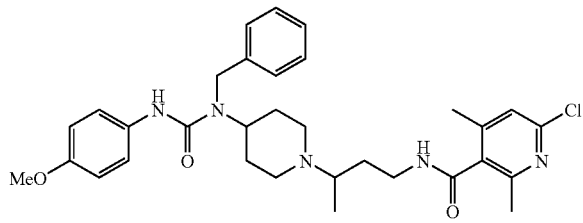

Compound 83

N-(3-{4-[1-Benzyl-3-(4-methoxy-phenyl)-ureido]-piperidin-1-yl}-butyl)-6-chloro-2,4-dimethyl-nicotinamide White foam. $^1$H NMR (CDCl$_3$) δ 0.87-0.92 (m, 1H), 0.98 (d, 3H, J=6.6 Hz), 1.05-1.23 (m, 1H), 1.49-1.55 (m, 1H), 1.68-1.78 (m, 3H), 2.16-2.23 (m, 1H), 2.28 (s, 3H), 2.50 (s, 3H), 2.56-2.63 (m, 1H), 2.70-2.74 (m, 1H), 2.83-2.85 (m, 2H), 3.23-3.31 (m, 1H), 3.73 (s, 3H), 3.85-3.99 (m, 3H), 4.35 (m, 1H), 5.97 (s, 1H), 6.72-6.77 (m, 2H), 6.95-7.02 (m, 3H), 7.31-7.45 (m, 5H), 8.77 (br s, 1H); ES-MS m/z 578 (M+H).

Example 84

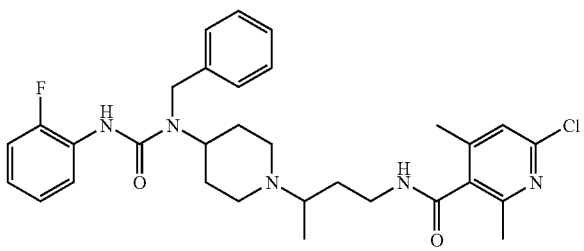

Compound 84

N-(3-{4-[1-Benzyl-3-(2-fluoro-phenyl)-ureido]-piperidin-1-yl}-butyl)-6-chloro-2,4-dimethyl-nicotinamide White foam. $^1$H NMR (CDCl$_3$) δ 0.93-1.15 (m, 5H), 1.55 (m, 1H), 1.78-1.82 (m, 3H), 2.23 (m, 1H), 2.28 (s, 3H), 2.50 (s, 3H), 2.62-2.66 (m, 1H), 2.74 (m, 1H), 2.85 (m, 2H), 3.27-3.30 (m, 1H), 3.85-4.00 (m, 3H), 4.35 (m, 1H), 6.42 (m, 1H), 6.88-6.93 (m, 3H), 7.01-7.06 (m, 1H), 7.31-7.44 (m, 5H), 7.98-8.04 (m, 1H), 8.65 (br s, 1H); ES-MS m/z 566 (M+H).

Example 85

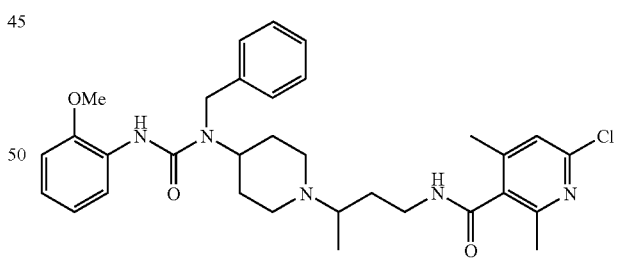

Compound 85

N-(3-{4-[1-Benzyl-3-(2-methoxy-phenyl)-ureido]-piperidin-1-yl}-butyl)-6-chloro-2,4-dimethyl-nicotinamide White foam. $^1$H NMR (CDCl$_3$) δ 0.91-0.95 (m, 1H), 0.99 (d, 3H, J=6.3 Hz), 1.09-1.12 (m, 1H), 1.57 (m, 1H), 1.78-1.82 (m, 3H), 2.23 (m, 1H), 2.27 (s, 3H), 2.50 (s, 3H), 2.63 (m, 1H), 2.67-2.72 (m, 1H), 2.84 (m, 2H), 3.29-3.32 (m, 1H), 3.47 (s, 3H), 3.84-3.86 (m, 1H), 3.89 (s, 2H), 4.38 (m, 1H), 6.67-6.71

(m, 1H), 6.85-6.93 (m, 4H), 7.28-7.43 (m, 5H), 8.04-8.07 (m, 1H), 8.73 (br s, 1H); ES-MS m/z 576 (M+H).

Example 86

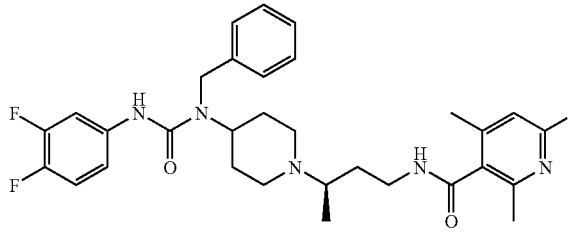

Compound 86

N—((R)-3-{4-[1-Benzyl-3-(3,4-difluoro-phenyl)-ureido]-piperidin-1-yl}-butyl)-6-fluoro-2,4-dimethyl-nicotinamide White foam. ¹H NMR (CDCl₃) δ 0.92-0.96 (m, 1H), 0.99 (d, 3H, J=6.6 Hz), 1.08-1.14 (m, 1H), 1.51 (m, 1H), 1.71-1.79 (m, 3H), 2.18-2.26 (m, 1H), 2.31 (s, 3H), 2.47 (s, 3H), 2.58-2.66 (m, 1H), 2.73-2.77 (m, 1H), 2.85-2.88 (m, 2H), 3.25-3.32 (m, 1H), 3.84-3.91 (m, 3H), 4.34 (m, 1H), 6.05 (s, 1H), 6.43 (s, 1H), 6.50-6.53 (m, 1H), 6.88-6.97 (m, 1H), 7.16-7.23 (m, 1H), 7.30-7.33 (d, 2H, J=7.2 Hz), 7.37-7.39 (d, 1H, J=6.9 Hz), 7.42-7.47 (m, 2H), 8:72 (br S, 1H); ES-MS m/z 568 (M+H).

Example 87

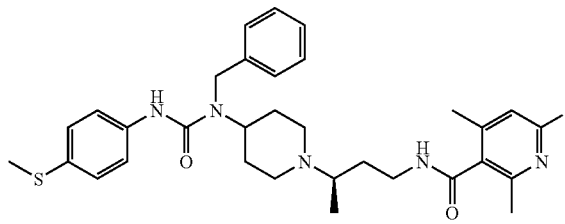

Compound 87

N—((R)-3-{4-[1-Benzyl-3-(4-methylsulfanyl-phenyl)-ureido]-piperidin-1-yl}-butyl)-6-chloro-2,4-dimethyl-nicotinamide ¹H NMR (CDCl₃) δ 1.38 (d, 3H, J=6.6 Hz), 1.94-2.05 (m, 4H), 2.19-2.32 (m, 4H), 2.23 (s, 3H), 2.41 (s, 3H), 2.44 (s, 3H), 2.87-2.95 (m, 1H), 3.04-3.12 (m, 1H), 3.30-3.40 (m, 1H), 3.46-3.56 (m, 2H), 4.50 (s, 2H), 4.69-4.80 (m, 1H), 6.30 (s, 1H), 6.93 (s, 1H), 7.05 (d, 2H, J=9 Hz), 7.15 (d, 2H, J=9 Hz), 7.26-7.41 (m, 5H), 7.74 (br s, 1H); ES-MS m/z 594 (M+H).

Example 88

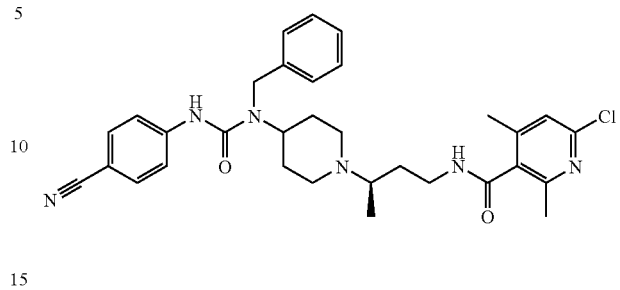

Compound 88

N—((R)-3-{4-[1-Benzyl-3-(4-cyano-phenyl)-ureido]-piperidin-1-yl}-butyl)-6-chloro-2,4-dimethyl-nicotinamide ¹H NMR (CDCl₃) δ 0.95-0.99 (m, 1H), 1.01 (d, 3H, J=6 Hz), 1.11-1.19 (m, 1H), 1.49-1.56 (m, 1H), 1.76-1.84 (m, 2H), 2.22-2.27 (m, 1H), 2.28 (s, 3H), 2.50 (s, 3H), 2.64-2.69 (m, 1H), 2.72-2.85 (m, 3H), 3.22-3.28 (m, 1H). 3.81-3.92 (m, 1H), 3.95 (s, 2H), 4.26-4.32 (m, 1H), 6.34 (s, 1H), 6.94 (s, 1H), 7.17 (d, 2H, J=9 Hz), 7.34-7.49 (m, 7H), 8.69 (br s, 1H); ES-MS m/z 573 (M+H).

Examples 89 and 90 were prepared following the scheme below wherein R¹NH₂ is defined in the table and R² is as shown in the individual examples.

TABLE 5

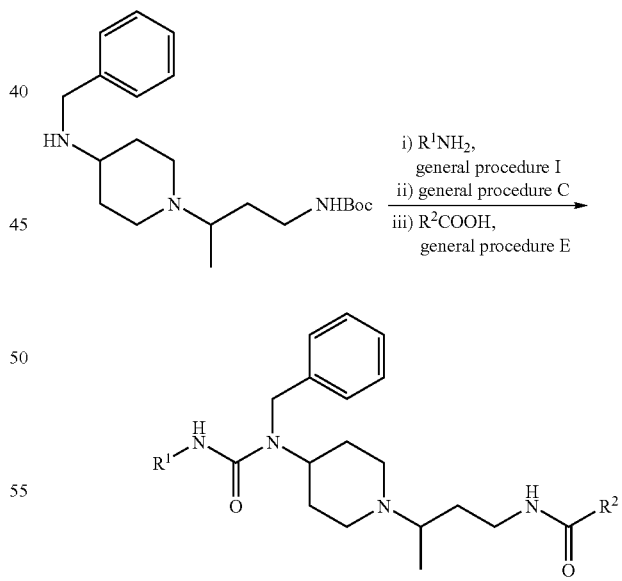

| Example | R¹NH₂ |
|---|---|
| 89* | piperonylamine |
| 90 | 4-aminopyridine |

*= racemic

Example 89

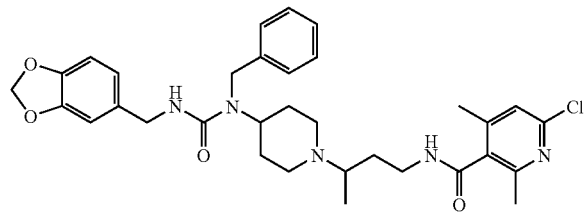

Compound 89

N-{3-[4-(3-1,3-Benzodioxol-5-ylmethyl-1-benzyl-ureido)-piperidin-1-yl]-butyl}-6-chloro-2,4-dimethyl-nicotinamide $^1$H NMR (CDCl$_3$) δ 0.77-1.09 (m, 2H), 0.97 (d, 3H, J=6.6 Hz), 1.47-1.56 (m, 1H), 1.66-1.78 (m, 3H), 2.17 (br t, 1H, J=11.4 Hz), 2.27 (s, 3H), 2.49 (s, 3H), 2.52-2.61 (m, 1H), 2.65-2.84 (m, 3H), 3.20-3.31 (m, 1H), 3.79-3.90 (m, 3H), 4.18 (d, 2H, J=5.4 Hz), 4.26-4.37 (m, 1H), 4.44 (t, 1H, J=5.7 Hz), 5.90 (s, 2H), 6.46-6.50 (m, 2H), 6.64 (d, 1H, J=7.8 Hz), 6.94 (s, 1H), 7.24-7.37 (m, 5H), 8.76 (d, 1H, J=6.0 Hz); ES-MS m/z 606 (M+H).

Example 90

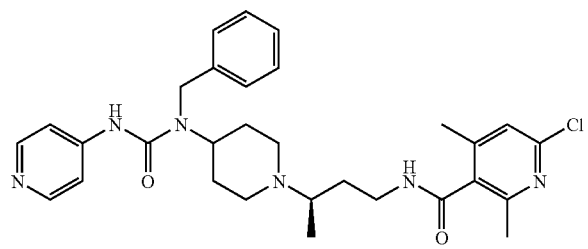

Compound 90

N—{(R)-3-[4-(1-Benzyl-3-pyridin-4-yl-ureido)-piperidin-1-yl]-butyl}-6-chloro-2,4-dimethyl-nicotinamide $^1$H NMR (CDCl$_3$) δ 0.96-0.98 (m, 1H), 1.01 (d, 3H, J=6 Hz), 1.12-1.21 (m, 1H), 1.48-1.53 (m, 1H), 1.74-1.81 (m, 3H), 2.21-2.25 (m, 1H), 2.28 (s, 3H), 2.50 (s, 3H), 2.64-2.71 (m, 1H), 2.75-2.92 (m, 3H), 3.22-3.30 (m, 1H), 3.87-3.93 (m, 1H), 3.96 (s, 2H), 4.27-4.35 (m, 1H), 6.30 (s, 1H), 6.94 (s, 1H), 7.01-7.05 (m, 2H), 7.34-7.49 (m, 5H), 8.30-8.34 (m, 2H), 8.63 (br s, 1H); ES-MS m/z 550 (M+H).

Examples 91 and 92 were prepared following the scheme below wherein R$^1$CNO is defined in the table and R$^2$ is as shown in the individual examples.

TABLE 6

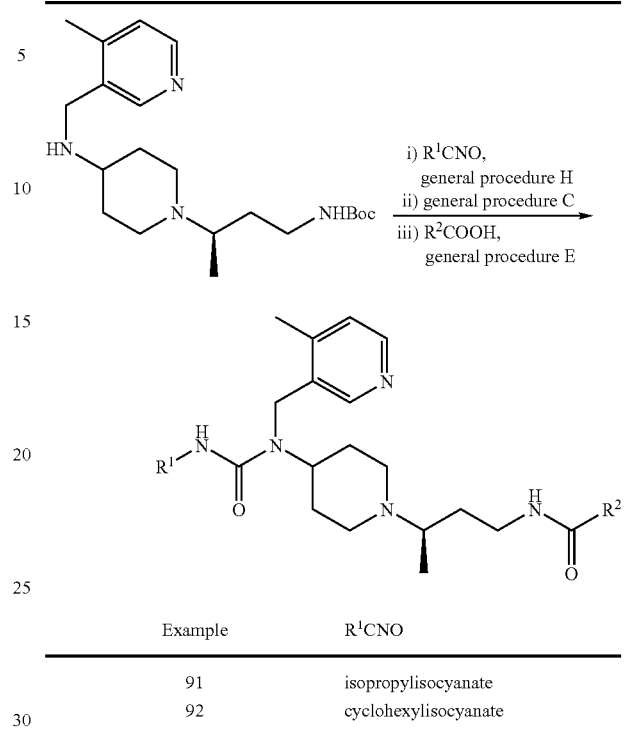

| Example | R$^1$CNO |
|---------|----------|
| 91 | isopropylisocyanate |
| 92 | cyclohexylisocyanate |

Example 91

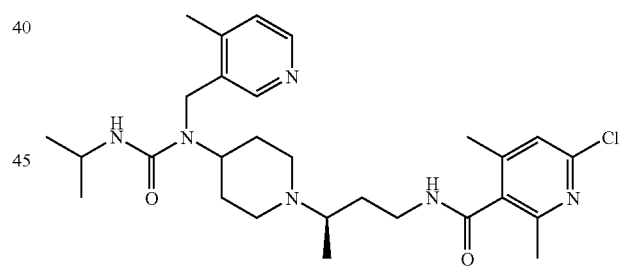

Compound 91

6-Chloro-N—((R)-3-{4-[3-isopropyl-1-(4-methyl-pyridin-3-ylmethyl)-ureido]-piperidin-1-yl}-butyl)-2,4-dimethyl-nicotinamide White foam. $^1$H NMR (CDCl$_3$) δ 0.95-1.03 (m, 10H), 1.09 (m, 1H), 1.59 (m, 1H), 1.75 (m, 4H), 2.20 (m, 1H), 2.29 (s, 3H), 2.36 (s, 3H), 2.49 (s, 3H), 2.51 (m, 1H), 2.63-2.78 (m, 3H), 3.34 (m, 1H), 3.68-3.94 (m, 3H), 4.02 (s, 2H), 4.17 (br t, 1H), 6.97 (s, 1H), 7.10 (d, 1H, J=4.5 Hz), 7.68 (br t, 1H), 8.33 (s, 1H), 8.39 (d, 1H, J=4.5 Hz); ES-MS m/z 529 (M+H).

Example 92

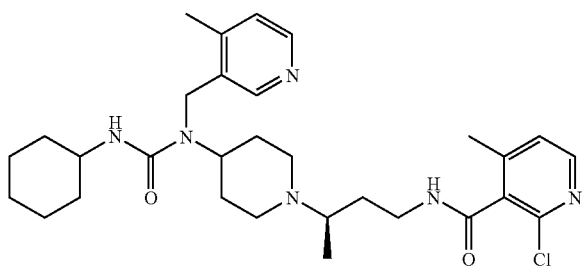

Compound 92

2-Chloro-N—((R)-3-{4-[3-cyclohexyl-1-(4-methyl-pyridin-3-ylmethyl)-ureido]-piperidin-1-yl}-butyl)-4-methyl-nicotinamide White foam. $^1$H NMR (CDCl$_3$) δ 0.85-0.95 (m, 2H), 0.96-1.07 (d+m, 5H), 1.29 (m, 3H), 1.50 (m, 3H), 1.72 (br m, 5H), 2.22 (br t, 1H), 2.34 (s, 3H), 2.39 (s, 3H), 2.58 (br t, 1H), 2.70-2.81 (m, 3H), 3.34 (m, 1H), 3.56 (m, 1H), 3.75-3.86 (m, 2H), 3.97 (s, 2H), 4.20 (br t, 1H), 6.91 (d, 1H, J=4.5 Hz), 7.12 (d, 1H, J=4.5 Hz), 7.87 (d, 1H, J=4.5 Hz), 8.20 (br s, 1H), 8.29 (s, 1H), 8.41 (d, 1H, J=4.5 Hz); ES-MS m/z 555 (M+H).

Example 93

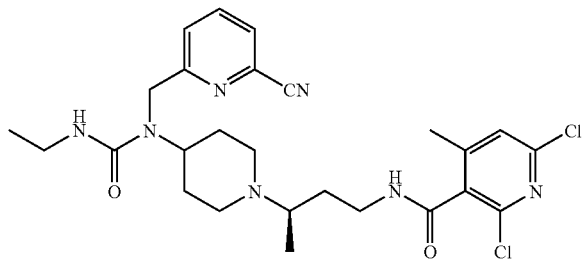

Compound 93

2,6-Dichloro-N—((R)-3-{4-[1-(6-cyano-pyridin-2-ylmethyl)-3-ethyl-ureido]-piperidin-1-yl}-butyl)-4-methyl-nicotinamide Sodium azide (0.280 g, 4.32 mmol) was added to a solution of 6-bromomethyl-pyridine-2-carbonitrile (0.610 g, 2.88 mmol) in DMF (12 ml) and the resulting pale yellow solution was stirred at rt for 16 h. Standard basic workup gave the crude product as a tan solid in quantitative yield (0.501 g). The crude solid was dissolved in MeOH (15 ml), treated with 10% Pd/C (0.050 g) and placed under 40 psi H$_2$ on a Parr shaker for 30 minutes (Note: it is imperative that this reduction is stopped at 30 minutes or reduction of the nitrile also occurs). The mixture was filtered through Celite®, the cake was washed with MeOH and the combined filtrate was concentrated under reduced pressure to give a yellow oil. Purification by column chromatography on silica gel (CH$_2$Cl$_2$/MeOH/NH$_4$OH, 83:15:2, v/v/v) afforded 6-aminomethyl-pyridine-2-carbonitrile (0.178 g, 46%) as a white crystalline solid. $^1$H NMR (CDCl$_3$) δ 1.96 (br s, 2H), 4.02 (s, 2H), 7.53 (d, 1H, J=9.0 Hz), 7.59 (d, 1H, J=9.0 Hz), 7.80 (t, 1H, J=9.0 Hz).

Using general procedure A, [3-(4-oxo-piperidin-1-yl)-butyl]-carbamic acid tert-butyl ester (0.361 g, 1.34 mmol), 6-aminomethyl-pyridine-2-carbonitrile (0.178 g, 1.34 mmol), sodium triacetoxyborohydride (0.425 g, 2.01 mmol) and acetic acid (0.2 ml, cat.) in CH$_2$Cl$_2$ (15 ml) at rt for 16 h gave the crude product as a pale yellow oil. Purification by column chromatography on silica gel (CH$_2$Cl$_2$/MeOH/NH$_4$OH, 86:12:2, v/v/v) afforded (3-{4-[(6-cyano-pyridin-2-ylmethyl)-amino]-piperidin-1-yl}-butyl)-carbamic acid tert-butyl ester (0.400 g, 77%) as a colorless oil. $^1$H NMR (CDCl$_3$) δ 0.93 (d, 3H, J=6.0 Hz), 1.40 (s+m, 13H), 1.65 (m, 1H), 1.92 (m, 2H), 2.13 (br t, 1H, J=9.0 Hz), 2.45 (m, 2H), 2.69-2.81 (m, 3H), 3.07 (m, 1H), 3.30 (m, 1H), 3.97 (s, 2H), 5.95 (br s, 1H), 7.56 (d, 1H, J=9.0 Hz), 7.59 (d, 1H, J=9.0 Hz), 7.77 (t, 1H, J=7.5 Hz).

(3-{4-[(6-Cyano-pyridin-2-ylmethyl)-amino]-piperidin-1-yl}-butyl)-carbamic acid tert-butyl ester (0.067 g, 0.17 mmol) and ethyl isocyanate (20 μL, 0.25 mmol) were combined in 1,2-dichloroethane (5 ml) and the resulting mixture was stirred at 55° C. for 16 h. The solvent was removed in vacuo and the crude residue was purified by column chromatography on silica gel (CH$_2$Cl$_2$:MeOH:NH$_4$OH, 93:6:1, v/v/v) to give (3-{4-[1-(6-cyano-pyridin-2-ylmethyl)-3-ethyl-ureido]-piperidin-1-yl}-butyl)-carbamic acid tert-butyl ester (0.075 g, 95%) as a white foam. $^1$H NMR (CDCl$_3$) δ 0.93 (d, 3H, J=6.0 Hz), 1.12 (t, 3H, J=7.5 Hz), 1.40 (s+m, 13H), 1.65 (m, 1H), 1.92 (m, 2H), 2.18 (br t, 1H, J=9.0 Hz), 2.52 (m, 2H), 2.69-2.85 (m, 3H), 3.09 (m, 1H), 3.21-3.33 (m, 3H), 4.12 (m, 1H), 4.44 (s, 2H), 5.33 (br s, 1H), 5.95 (br s, 1H), 7.57 (d, 1H, J=9.0 Hz), 7.61 (d, 1H, J=9.0 Hz), 7.83 (t, 1H, J=7.5 Hz).

(3-{4-[1-(6-cyano-pyridin-2-ylmethyl)-3-ethyl-ureido]-piperidin-1-yl}-butyl)-carbamic acid tert-butyl ester (0.075 g, 0.16 mmol) was dissolved in a 3:1 mixture of CH$_2$Cl$_2$ and TFA and the mixture was stirred at rt for 1 h. The solvent was removed in vacuo and the resulting brown oil pumped in vacuo (high vacuum system) for 2 h. The resulting amine, EDCI (0.035 g, 0.18 mmol) and HOBt (0.024 g, 0.18 mmol) were combined in DMF (5 ml) to give a pale yellow solution. To this solution was added 2,6-dichloro-4-methyl-nicotinic acid (synthesized according to reported patent procedure WO 03/027112) (0.037 g, 0.18 mmol) followed by DIPEA (188 μL, 1.08 mmol) and the resulting mixture was stirred at 25° C. for 16 h. Standard workup according to general procedure E gave the crude product as a tan oil. Purification by column chromatography on silica gel (Et$_2$O/MeOH/NH$_4$OH, 90:8:2, v/v/v) afforded COMPOUND 93 (0.048 g, 54%) as a white foam. $^1$H NMR (CDCl$_3$) δ 0.98 (m+d, 4H), 1.12 (t, 3H, J=7.5 Hz), 1.23 (m, 1H), 1.61 (m, 3H), 1.75 (m, 1H), 2.15 (br t, 1H), 2.42 (s, 3H), 2.54 (br t, 1H), 2.73 (m, 1H), 2.83-2.88 (m, 2H), 3.23 (m, 2H), 3.33 (m, 1H), 3.87 (m, 1H), 3.89 (dd, 2H, J=15.0, 4.5 Hz), 5.65 (br t, 1H), 7.20 (s, 1H), 7.59 (d, 1H, J=9.0 Hz), 7.62 (d, 1H, J=9.0 Hz), 7.88 (t, 1H, J=9.0 Hz), 8.96 (br d, 1H); ES-MS m/z 546 (M+H). Anal. Calcd. for C$_{26}$H$_{33}$N$_7$O$_2$Cl$_2$.0.3CH$_4$O.0.5H$_2$O: C, 55.90; H, 6.28; N, 17.35. Found: C, 55.83; H, 6.19; N, 17.27.

Examples 94 and 95 were prepared following the scheme below wherein R$^1$NH$_2$ is defined in the table and R$^2$ is as shown in the individual examples.

TABLE 7

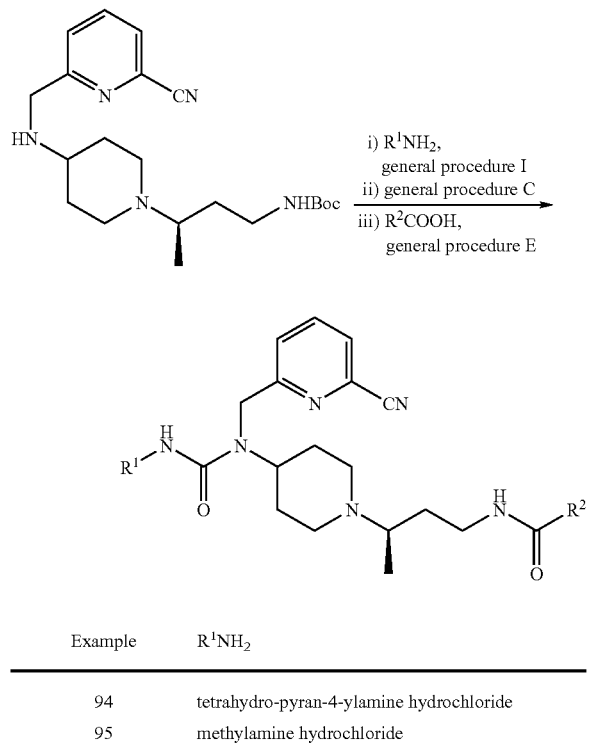

| Example | R¹NH₂ |
|---|---|
| 94 | tetrahydro-pyran-4-ylamine hydrochloride |
| 95 | methylamine hydrochloride |

Example 94

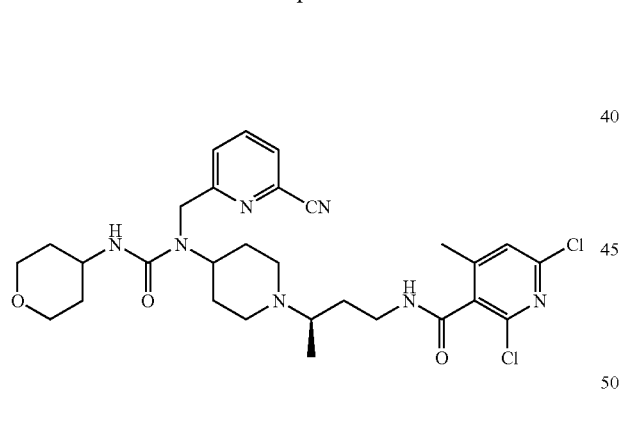

Compound 94

2,6-Dichloro-N—((R)-3-{4-[1-(6-cyano-pyridin-2-ylmethyl)-3-(tetrahydro-pyran-4-yl)-ureido]-piperidin-1-yl}-butyl)-4-methyl-nicotinamide White foam. $^1$H NMR (CDCl$_3$) δ 1.00 (d+m, 4H), 1.13 (m, 1H), 1.33-1.62 (m, 3H), 1.78 (m, 2H), 1.90 (m, 2H), 2.13 (br t, 1H), 2.43 (s, 3H), 2.53 (br t, 1H), 2.75-2.89 (m, 3H), 3.39-3.48 (m, 3H), 3.82-3.99 (m, 6H), 6.00 (br s, 1H), 7.20 (s, 1H), 7.63 (d+d, 2H, J=6.0 Hz), 7.90 (t, 1H, J=6.0 Hz), 8.99 (br s, 1H); ES-MS m/z 602 (M+H).

Example 95

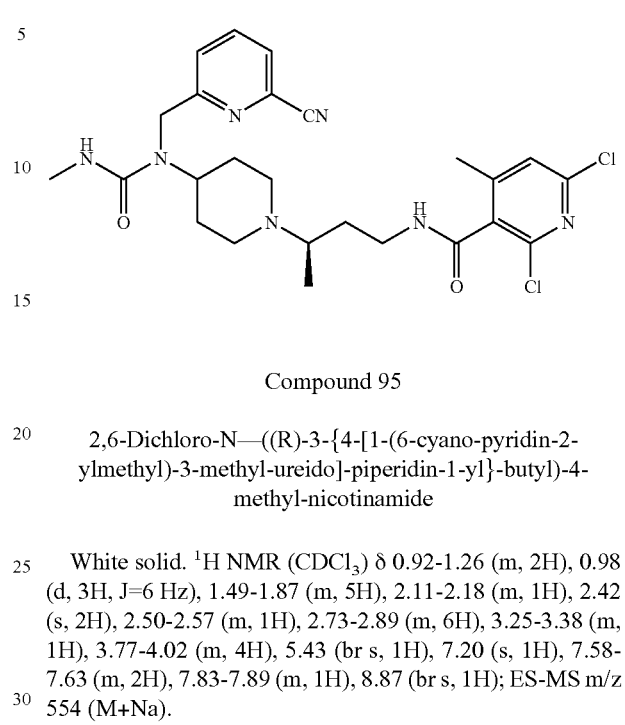

Compound 95

2,6-Dichloro-N—((R)-3-{4-[1-(6-cyano-pyridin-2-ylmethyl)-3-methyl-ureido]-piperidin-1-yl}-butyl)-4-methyl-nicotinamide White solid. $^1$H NMR (CDCl$_3$) δ 0.92-1.26 (m, 2H), 0.98 (d, 3H, J=6 Hz), 1.49-1.87 (m, 5H), 2.11-2.18 (m, 1H), 2.42 (s, 2H), 2.50-2.57 (m, 1H), 2.73-2.89 (m, 6H), 3.25-3.38 (m, 1H), 3.77-4.02 (m, 4H), 5.43 (br s, 1H), 7.20 (s, 1H), 7.58-7.63 (m, 2H), 7.83-7.89 (m, 1H), 8.87 (br s, 1H); ES-MS m/z 554 (M+Na).

Examples 96 to 107 were prepared following the scheme below wherein R¹NH₂ and R²CNO are as defined in the table and R³ is as shown in the individual examples.

TABLE 8

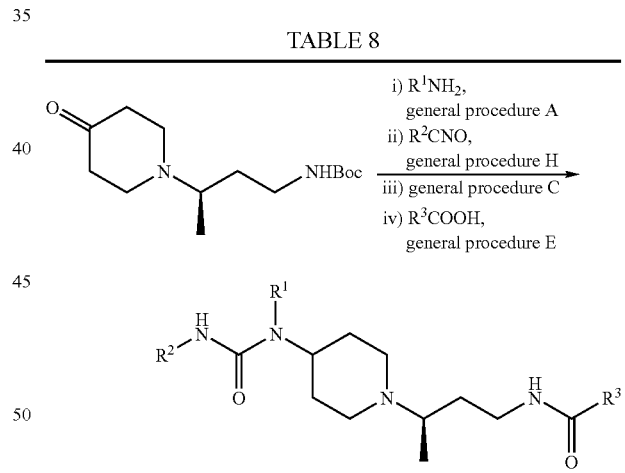

| Example | R¹NH₂ | R²CNO |
|---|---|---|
| 96 | n-butylamine | ethyl isocyanate |
| 97 | 2-methoxyethylamine | 4-fluoro-phenyl isocyanate |
| 98 | 2-methylbutylamine | 4-fluoro-phenyl isocyanate |
| 99 | n-hexylamine | ethyl isocyanate |
| 100 | 2-(ethylthio)ethylamine hydrochloride | ethyl isocyanate |
| 101 | n-propylamine | 4-fluoro-phenyl isocyanate |
| 102 | isoamylamine | 4-fluoro-phenyl isocyanate |
| 103 | amylamine | 4-fluoro-phenyl isocyanate |
| 104 | 3-(methylthio)-propylamine | 4-fluoro-phenyl isocyanate |
| 105 | n-hexylamine | 4-fluoro-phenyl isocyanate |
| 106 | cyclopentylmethylamine | 4-fluoro-phenyl isocyanate |
| 107 | cyclohexylmethylamine | 4-fluoro-phenyl isocyanate |

Example 96

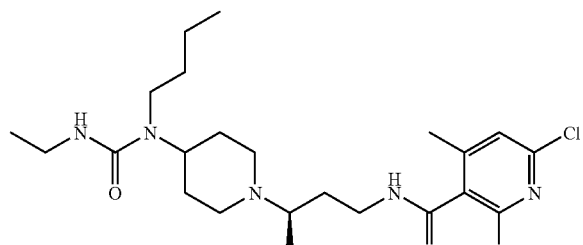

Compound 96

N—{(R)-3-[4-(1-Butyl-3-ethyl-ureido)-piperidin-1-yl]-butyl}-2,6-dichloro-4-methyl-nicotinamide White foam. ¹H NMR (CDCl$_3$) δ 0.93-0.99 (m, 7H), 1.10-1.15 (m, 4H), 1.17-1.40 (m, 5H), 1.60 (m, 2H), 1.73-1.75 (m, 1H), 2.14-2.17 (m, 1H), 2.39 (s, 3H), 2.50-2.61 (m, 3H), 2.73-2.86 (m, 3H), 3.21-3.31 (m, 3H), 3.84-3.86 (m, 1H), 4.03 (m, 1H), 4.18 (m, 1H), 7.15 (s, 1H), 8.74 (br s, 1H); ES-MS m/z 508 (M+Na).

Example 97

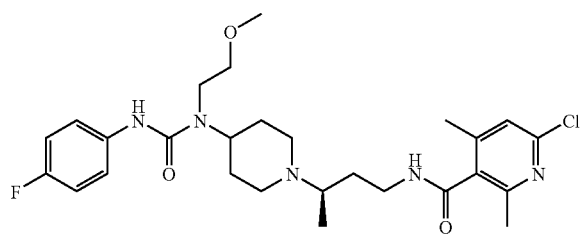

Compound 97

6-Chloro-N—((R)-3-{4-[3-(4-fluoro-phenyl)-1-(2-methoxy-ethyl)-ureido]-piperidin-1-yl}-butyl)-2,4-dimethyl-nicotinamide ¹H NMR (CDCl$_3$) δ 0.69-0.89 (m, 1H), 0.92-0.97 (m, 1H), 1.00 (d, 3H, J=6 Hz), 1.47-1.53 (m, 1H), 1.69-1.79 (m, 3H), 2.16-2.24 (m, 1H), 2.34 (s, 3H), 2.54 (s, 3H), 2.54-2.62 (m, 1H), 2.66-2.95 (m, 5H), 3.21-3.29 (m, 1H), 3.43 (br s, 2H), 3.49 (s, 3H), 3.82-3.91 (m, 1H), 3.99-4.13 (m, 1H), 6.90-697 (m, 2H), 7.06 (s, 1H), 7.21-7.25 (m, 2H), 8.55 (s, 1H), 9.10 (br s, 1H); ES-MS m/z 534 (M+H).

Example 98

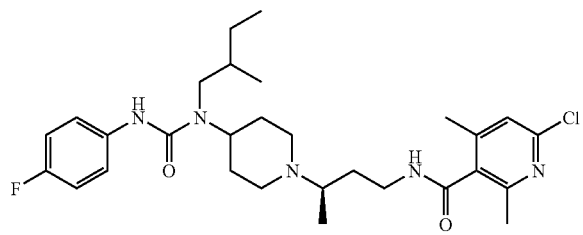

Compound 98

6-Chloro-N—((R)-3-{4-[3-(4-fluoro-phenyl)-1-(2-methyl-butyl)-ureido]-piperidin-1-yl}-butyl)-2,4-dimethyl-nicotinamide White foam. ¹H NMR (CDCl$_3$) δ 0.92-0.98 (m, 9H), 1.00-1.27 (m, 2H), 1.28 (m, 1H), 1.48-1.49 (m, 2H), 1.69-1.78 (m, 3H), 2.13-2.20 (m, 2H), 2.33 (s, 3H), 2.51 (m, 1H), 2.54 (s, 3H), 2.58-2.63 (m, 1H), 2.71-2.81 (m, 4H), 3.33 (m, 1H), 3.83-3.87 (m, 1H), 3.98 (m, 1H), 6.21 (s, 1H), 6.98-7.02 (m, 3H), 7.26-7.29 (m, 2H), 8.08 (br s, 1H); ES-MS m/z 548 (M+H).

Example 99

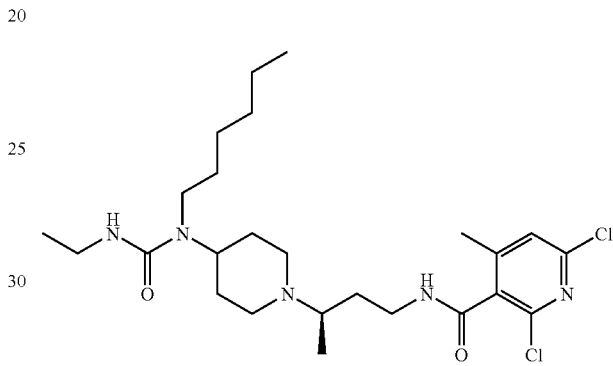

Compound 99

2,6-Dichloro-N—{(R)-3-[4-(3-ethyl-1-hexyl-ureido)-piperidin-1-yl]-butyl}-4-methyl-nicotinamide White foam. ¹H NMR (CDCl$_3$) δ 0.89-0.99 (m, 9H), 1.09-1.16 (m, 4H), 1.21-1.30 (m, 4H), 1.43 (s, 3H), 1.56-1.81 (m, 7H), 2.10 (t, 1H, J=12 Hz), 2.38 (s, 3H), 2.52-2.57 (m, 3H), 2.69-2.82 (m, 3H), 2.91-3.03 (m, 1H), 3.21-3.33 (m, 3H), 3.81-3.89 (m, 1H), 3.94-4.07 (m, 1H), 4.18-4.25 (m, 1H), 7.13 (s, 1H), 8.74 (s, 1H); ES-MS m/z 514 (M+H).

Example 100

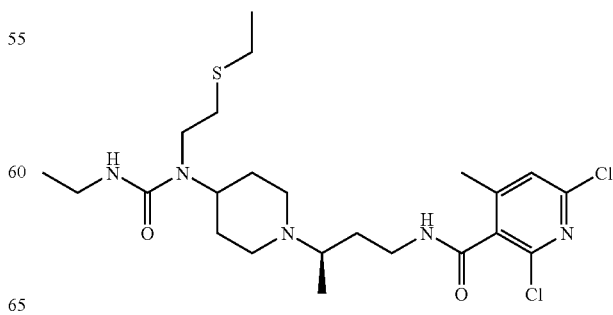

Compound 100

2,6-Dichloro-N—((R)-3-{4-[3-ethyl-1-(2-ethylsulfanyl-ethyl)-ureido]-piperidin-1-yl}-butyl)-4-methyl-nicotinamide ¹H NMR (CDCl₃) δ 0.99 (d, 3H, J=6 Hz), 1.06-1.15 (m, 3H), 1.21-1.29 (m, 3H), 1.51-1.84 (m, 6H), 2.09-2.19 (m, 1H), 2.39 (s, 3H), 2.49-2.68 (m, 5H), 2.71-2.84 (m, 5H), 3.22-3.37 (m, 3H), 3.77-3.91 (m, 2H), 5.10 (br s, 1H), 7.20 (s, 1H), 8.74 (br s, 1H); ES-MS m/z 540 (M+Na).

Example 101

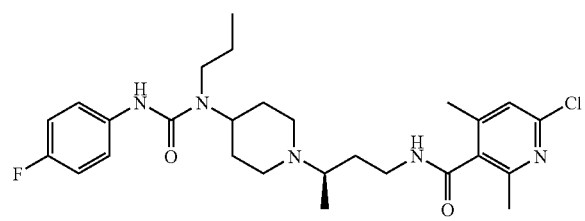

Compound 101

6-Chloro-N—((R)-3-{4-[3-(4-fluoro-phenyl)-1-propyl-ureido]-piperidin-1-yl}-butyl)-2,4-dimethyl-nicotinamide White foam. ¹H NMR (CDCl₃) δ 0.90-1.03 (m, 7H), 1.12-1.17 (m, 1H), 1.49-1.54 (m, 4H), 1.67-1.73 (m, 2H), 1.75-1.79 (m, 1H), 2.13-2.20 (m, 1H), 2.35 (s, 3H), 2.53 (br s, 1H), 2.55 (s, 3H), 2.60-2.86 (m, 5H), 3.27-3.34 (m, 1H), 3.86-3.91 (m, 1H), 4.10 (m, 1H), 6.15 (s, 1H), 6.95-7.01 (m, 2H), 7.05 (s, 1H), 7.29-7.32 (m, 1H), 8.57 (br d, 1H); ES-MS m/z 518 (M+H).

Example 102

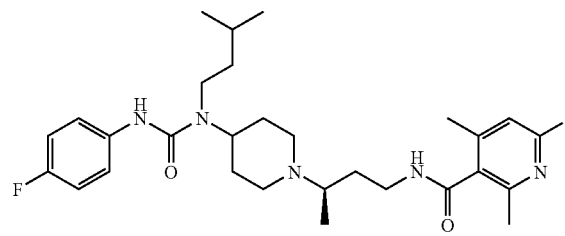

Compound 102

6-Chloro-N—((R)-3-{4-[3-(4-fluoro-phenyl)-1-(3-methyl-butyl)-ureido]-piperidin-1-yl}-butyl)-2,4-dimethyl-nicotinamide White foam. ¹H NMR (CDCl₃) δ 0.95-1.02 (m, 10H), 1.19-1.24 (m, 1H), 1.36-1.44 (m, 2H), 1.55 (m, 1H), 1.59-1.80 (m, 4H), 2.14-2.21 (m, 1H), 2.33 (s, 3H), 2.52-2.59 (m, 1H), 2.54 (s, 3H), 2.72-2.85 (m, 5H), 3.29-3.37 (m, 1H), 3.83-3.89 (m, 1H), 4.04-4.12 (m, 1H), 6.16 (s, 1H), 6.95-7.03 (m, 3H), 7.29-7.33 (m, 2H), 8.18 (br s, 1H); ES-MS m/z 546 (M+H).

Example 103

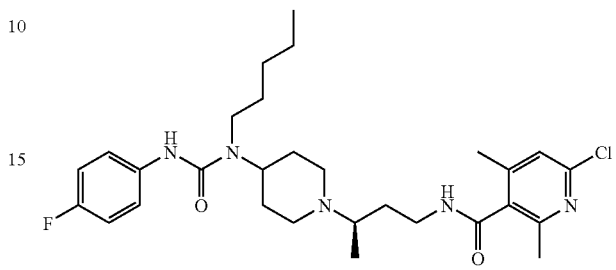

Compound 103

6-Chloro-N—((R)-3-{4-[3-(4-fluoro-phenyl)-1-pentyl-ureido]-piperidin-1-yl}-butyl)-2,4-dimethyl-nicotinamide ¹H NMR (CDCl₃) δ 0.95-1.08 (m, 7H), 1.12-1.23 (m, 1H), 1.28-1.42 (m, 4H), 1.49-1.58 (m, 3H), 1.65 (br s, 3H), 1.68-1.77 (m, 1H), 2.17-2.22 (m, 1H), 2.33 (s, 3H), 2.54 (s, 3H), 2.56-2.82 (m, 5H), 3.24-3.32 (m, 1H), 3.85-3.91 (m, 1H), 4.04-4.12 (m, 1H), 6.18 (s, 1H), 6.93-7.02 (m, 3H), 7.25-7.32 (m, 1H), 8.44 (br s, 1H); ES-MS m/z 546 (M+H).

Example 104

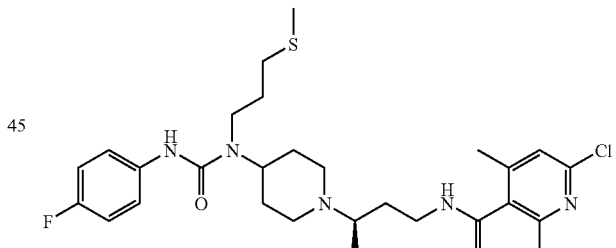

Compound 104

6-Chloro-N—((R)-3-{4-[3-(4-fluoro-phenyl)-1-(3-methyl sulfanyl-propyl)-ureido]-piperidin-1-yl}-butyl)-2,4-dimethyl nicotinamide White foam. ¹H NMR (CDCl₃) δ 0.88-0.93 (m, 1H), 0.99 (d, 3H, J=6.6 Hz), 1.08-1.14 (m, 1H), 1.55 (m, 1H), 1.69-1.79 (m, 5H), 2.13 (s, 3H), 2.17-2.21 (m, 1H), 2.34 (s, 3H), 2.55 (s, 3H), 2.55-2.66 (m, 3H), 2.73-2.87 (m, 5H), 3.29-3.33 (m, 1H), 3.87-3.91 (m, 1H), 4.17 (m, 1H), 6.93-6.99 (t, 2H, J=8.7 Hz), 7.05 (s, 1H), 7.39-7.46 (m, 3H), 8.79 (br s, 1H); ES-MS m/z 564 (M+H).

Example 105

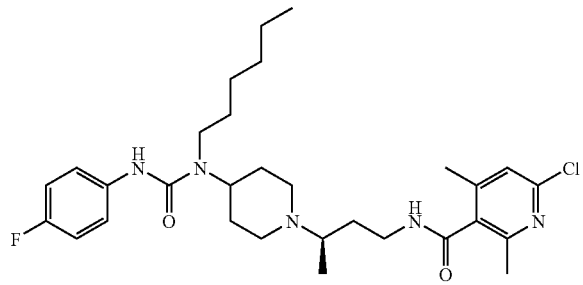

Compound 105

6-Chloro-N—((R)-3-{4-[3-(4-fluoro-phenyl)-1-hexyl-ureido]-piperidin-1-yl}-butyl)-2,4-dimethyl-nicotinamide White foam. $^1$H NMR (CDCl$_3$) δ 0.92-1.01 (m, 7H), 1.13-1.18 (m, 1H), 1.34 (br s, 6H), 1.45-1.52 (m, 2H), 1.66-1.78 (m, 4H), 2.13-2.20 (t, 1H, J=10.8 Hz), 2.34 (s, 3H), 2.54 (s, 3H), 2.59-2.85 (m, 6H), 3.31 (m, 1H), 3.84-3.91 (m, 1H), 4.09 (m, 1H), 6.16 (s, 1H), 6.95-7.03 (m, 2H), 7.03-7.30 (m, 2H), 8.45 (br s, 1H); ES-MS m/z 560 (M+H).

Example 106

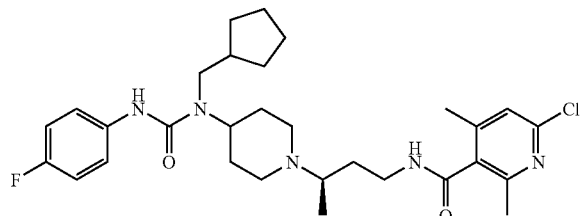

Compound 106

6-Chloro-N—((R)-3-{4-[1-cyclopentylmethyl-3-(4-fluoro-phenyl)-ureido]-piperidin-1-yl}-butyl)-2,4-dimethyl-nicotinamide White foam. $^1$H NMR (CDCl$_3$) δ 0.98 (d, 3H, J=12 Hz), 0.99-1.07 (m, 1H), 1.09-1.18 (m, 3H), 1.51-1.92 (m, 1H), 1.94-2.01 (m, 1H), 2.15 (t, 1H, J=12 Hz), 2.33 (s, 3H), 2.51-2.57 (m, 1H), 2.53 (s, 3H), 2.71-2.86 (m, 4H), 3.32 (t, 1H, J=12 Hz), 3.86-3.92 (m, 1H), 3.97-4.04 (m, 1H), 6.28 (s, 1H), 6.94-7.01 (m, 3H), 7.27-7.32 (m, 2H), 8.30 (br s, 1H); ES-MS m/z 558 (M+H).

Example 107

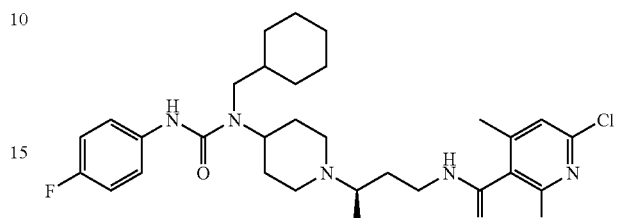

Compound 107

2,6-Dichloro-N—((R)-3-{4-[1-cyclohexylmethyl-3-(4-fluoro-phenyl)-ureido]-piperidin-1-yl}-butyl)-4-methyl-nicotinamide To a solution of cyclohexylmethanol (2.4 ml, 20 mmol) in CH$_2$Cl$_2$ (42 ml) was added Et$_3$N (3.0 ml, 22 mmol). The mixture was cooled to 0° C. when mesyl chloride (1.7 ml, 22 mmol) was added. It was then stirred at rt for 30 min, diluted with CH$_2$Cl$_2$ (20 ml), washed with 1N NaOH (3×60 ml), dried over Na$_2$SO$_4$ and concentrated. The crude methanesulfonic acid cyclohexylmethyl ester (3.50 g, 87%) was a yellow oil and was used in the next reaction without purification.

To a solution of the above mesylate (3.50 g, 18.2 mmol) in DMF (20 ml) was added NaN$_3$ (1.8 g, 27.3 mmol). The mixture was stirred at 65° C. overnight, cooled, diluted with H$_2$O (30 ml) and extracted with 1:1 hexanes/ether (2×50 ml). The combined organic layers were washed with saturated NaCl solution (3×25 ml) to remove residual DMF, dried with mgSO$_4$ and concentrated. The crude azidomethyl-cyclohexane (2.06 g, 90%) was a yellow oil and was used in the next reaction without purification.

To a solution of the above azide (2.06 g, 14.8 mmol) in MeOH (20 ml) was added Pd/C (0.515 g, 25 wt %). The mixture was placed on the hydrogenator for 2 h at 50 psi hydrogen, then filtered through Celite® and concentrated. $^1$H NMR and TLC (2:1 hexanes/ethyl acetate) showed two products. Hydrogenation for another 2 h showed the same result. The crude cyclohexylmethylamine (1.83 g) was used in the next reaction without purification.

COMPOUND 107 was isolated as a yellowish solid. $^1$H NMR (CDCl$_3$) δ 0.85-0.92 (m, 2H), 0.98-1.00 (d, 3H, J=6 Hz), 1.18-1.21 (m, 2H), 1.24-1.83 (m, 13H), 2.08-2.13 (m, 1H), 2.39 (s, 3H), 2.49-2.62 (m, 1H), 2.62-2.77 (m, 2H), 2.77-2.88 (m, 2H), 3.28-3.42 (m, 1H), 3.49 (s, 2H), 3.77-3.98 (m, 1H), 6.21 (s, 1H), 6.97-7.03 (m, 2H), 7.13 (s, 1H), 7.27-7.29 (m, 2H), 8.37 (br s, 1H); ES-MS m/z 592 (M+H).

Examples 108 and 109 were prepared following the scheme below wherein R$^1$CHO and R$^2$CNO are as defined in the table and R$^3$ is as shown in the individual examples.

TABLE 9

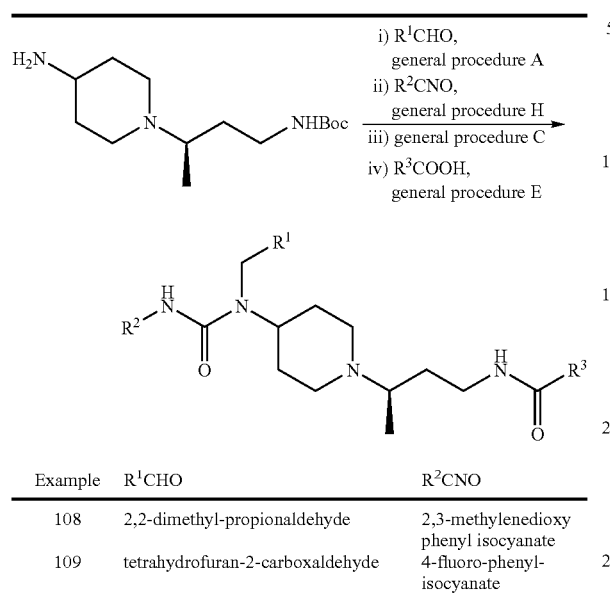

| Example | R¹CHO | R²CNO |
|---------|-------|-------|
| 108 | 2,2-dimethyl-propionaldehyde | 2,3-methylenedioxy phenyl isocyanate |
| 109 | tetrahydrofuran-2-carboxaldehyde | 4-fluoro-phenyl-isocyanate |

Example 108

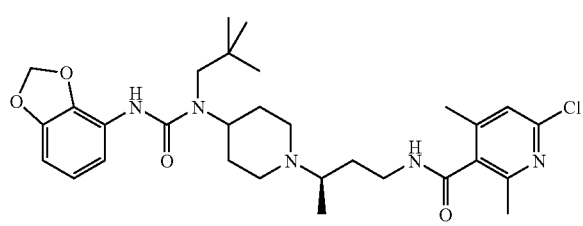

Compound 108

N—((R)-3-{4-[3-1,3-Benzodioxol-4-yl-1-(2,2-dimethyl-propyl)-ureido]-piperidin-1-yl}-butyl)-6-chloro-2,4-dimethyl-nicotinamide $^1$H NMR (CD$_3$OD) δ 0.9-1.1 (m, 13H), 1.70-2.20 (m, 7H), 2.30 (s, 3H), 2.50-2.55 (m, 4H), 2.80-3.00 (m, 5H), 3.20-3.40 (m, 2H), 3.70-3.85 (m, 1H), 5.92, (s, 2H), 6.28 (s, 1H), 6.57 (dd, 1H, J=9, 3 Hz), 6.70 (d, 1H, J=9 Hz), 6.98 (s, 1H), 7.04 (s, 1H), 7.70 (s, 1H); ES-MS m/z 572 (M+1).

Example 109

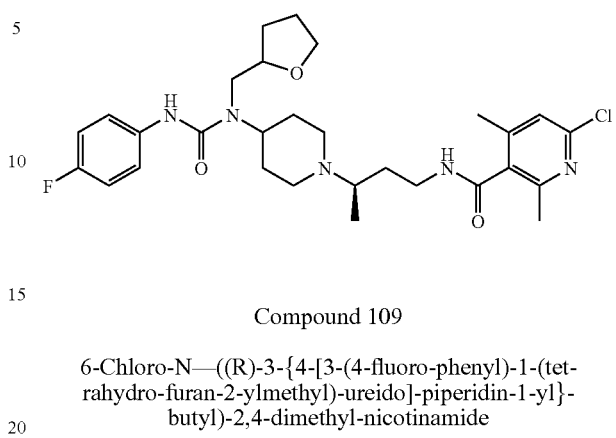

Compound 109

6-Chloro-N—((R)-3-{4-[3-(4-fluoro-phenyl)-1-(tetrahydro-furan-2-ylmethyl)-ureido]-piperidin-1-yl}-butyl)-2,4-dimethyl-nicotinamide $^1$H NMR (CDCl$_3$) δ 0.70-1.25 (m, 10H), 1.48-2.24 (m, 9H), 2.27 (s, 3H), 2.49-2.54 (m, 4H), 2.65-4.10 (m, 1H), 6.87-6.93 (m, 2H), 6.99 (s, 1H), 7.22-7.26 (m, 2H), 8.50 (s, 0.55H), 8.51 (s, 0.45H), 8.94 (s, 0.55H), 8.97 (s, 0.45H); ES-MS m/z 560 (M+H).

Example 110

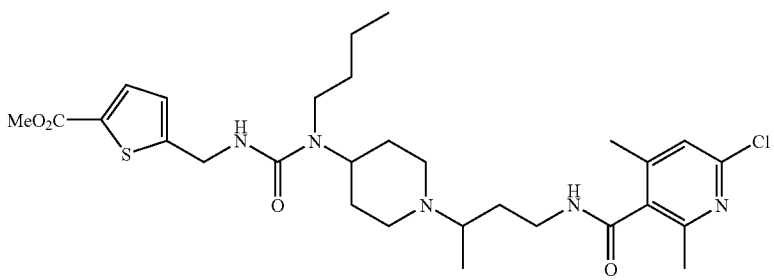

Compound 110

5-[3-Butyl-3-(1-{3-[(6-chloro-2,4-dimethyl-pyridine-3-carbonyl)-amino]-1-methyl-propyl}-piperidin-4-yl)-ureidomethyl]-thiophene-2-carboxylic acid methyl ester To a 0° C. solution of 5-aminomethyl-thiophene-2-carboxylic acid methyl ester (Rueckle, T. et al.; *J. Med. Chem.;* 47; 2004; 6921-6934) (65 mg, 0.38 mmol) and Et$_3$N (106 μL, 0.76 mmol) in CH$_2$Cl$_2$ was added dropwise phenyl chloroformate (52 μL, 0.42 mmol). The resulting mixture was stirred at 0° C. for 1 h. Standard aqueous workup and purification by column chromatography on silica gel (49:1, CH$_2$Cl$_2$/MeOH) afforded the phenyl carbamate intermediate.

Following general procedure J, the above phenyl carbamate and N-[3-(4-butylamino-piperidin-1-yl)-butyl]-6-chloro-2,4-dimethyl-nicotinamide (prepared following the Scheme outlined in Table 8) afforded COMPOUND 110 as a mixture of diastereoisomers. $^1$H NMR (CDCl$_3$) δ 0.83-2.12 (m, 15H), 2.32 (s, 3H), 2.52 (s, 3H), 2.55-3.55 (m, 9H), 3.63-3.66 (m, 1H), 3.85 (s, 3H), 4.03-3.19 (m, 1H), 4.55-4.58 (m, 2H), 4.81 (m, 1H), 6.91 (d, 1H, J=3.9 Hz), 7.02 (s, 1H), 7.63 (d, 1H, J=3.6 Hz), 8.26 (s, 1H); ES-MS m/z 614 (M+Na).

Example 111

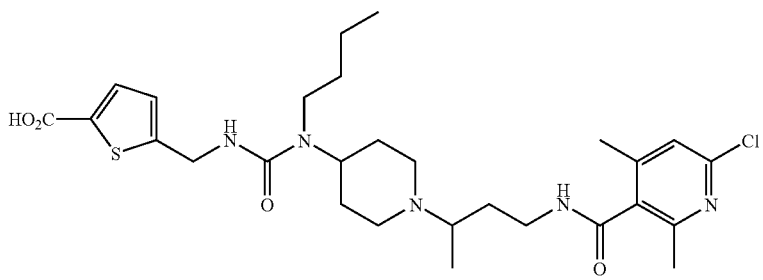

Compound 111

5-[3-Butyl-3-1-{3-[(6-chloro-2,4-dimethyl-pyridine-3-carbonyl)-amino]-1-methyl-propyl}-piperidin-4-yl)-ureidomethyl]-thiophene-2-carboxylic acid To a solution of 5-[3-butyl-3-(1-{3-[(6-chloro-2,4-dimethyl-pyridine-3-carbonyl)-amino]-1-methyl-propyl}-piperidin-4-yl)-ureidomethyl]-thiophene-2-carboxylic acid methyl ester (COMPOUND 110) (22 mg, 0.04 mmol) in MeOH (1 ml) was added an aqueous solution of NaOH [3.75 M] (60 µL, 0.22 mmol). The reaction mixture was stirred at 50° C. for 1 h and then diluted with water (3 ml). The solution was adjusted to pH 4-5 with aqueous HCl [6N]. The mixture was extracted with chloroform and the organic layer was dried over sodium sulfate and concentrated in vacuo. The crude acid (6.5 mg, 28%) was used without further purification. $^1$H NMR (CDCl$_3$) δ 0.80-0.97 (m, 3H), 1.12-1.52 (m, 6H), 1.70-1.92 (m, 3H), 2.17-2.43 (m, 3H), 2.26 (s, 3H), 2.44 (s, 3H), 2.71-2.74 (m, 1H), 2.77-3.17 (m, 5H), 3.46-3.68 (m, 5H), 4.30-4.34 (m, 1H), 4.46 (d, 1H, J=15.3 Hz), 4.55 (d, 1H, J=15.3 Hz), 4.72 (s, 1H), 6.85 (s, 1H), 6.95 (s, 1H), 7.05 (s, 1H), 8.56 (s, 1H); ES-MS m/z 578 (M+H).

Examples 112 to 151 were prepared following the scheme illustrated below. R$^1$ is as shown in the individual examples and R$^2$NH$_2$ is as defined in the table.

TABLE 10

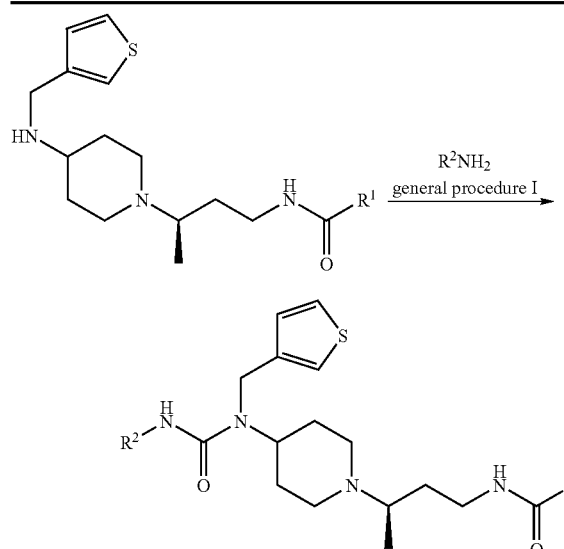

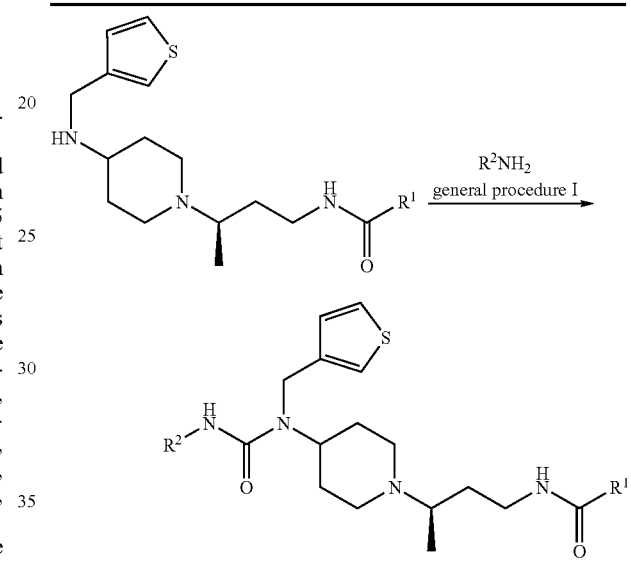

| Example | R$^2$NH$_2$ |
|---|---|
| 112 | 2-aminobenzimidazole |
| 113 | O-isobutylhydroxylamine hydrochloride |
| 114 | furfurylamine |
| 115 | 2-[1-(toluene-4-sulfonyl)-1H-imidazol-4-yl]-ethylamine (Bridger et al., U.S. 2004/209,921 A1) |
| 116 | 1,1-dimethylhyrazine |
| 117 | 1-methoxy-2-ethylamine |
| 118 | methoxylpropylamine |
| 119 | 2-aminoimidazole sulfate |
| 120 | O-(2-methoxy-ethyl)-hydroxylamine |
| 121 | 2-picolylamine |
| 122 | glycine methyl ester hydrochloride |
| 123 | 3-methyl-5-amino-isoxazole |
| 124 | 3-amino-5-methyl-isoxazole |
| 125 | 2-(aminomethyl-1,3-dioxolane) |
| 126 | 5-amino-3-methylisoxazole |
| 127 | 4-amino-1,2,4-triazole |
| 128 | 3-amino-1,2,4-triazole |
| 129 | 4-aminomorpholine |
| 130 | 3-amino-pyrazole |
| 131 | 1-(2-aminoethyl)-2-imidazolidone |
| 132 | 2-imidazol-1-yl-ethylamine (Bloomfield, G. C. et al., WO 2005/021519 A2) |
| 133 | 5-amino-3-methyl-isothiazole hydrochloride |
| 134 | 3-amino-5-methyl-pyrazole |
| 135 | 2-amino-N,N-dimethyl-acetamide |
| 136 | O-(2-Methoxy-ethyl)-hydroxylamine (Kim. D.-K. et al., J. Med. Chem., vol. 40(15), 1997, 2363-2373) |
| 137 | C-(1-methyl-1H-imidazol-4-yl)-methylamine |
| 138 | O-tert-butylhydroxylamine hydrochloride |
| 139 | C-(3-methyl-3H-imidazol-4-yl)-methylamine |
| 140 | 3-amino-4-pyrazolecarbonitrile |
| 141 | aminoacetonitrile hydrochloride |
| 142 | pyrrolidin-1-ylamine hydrochloride |

TABLE 10-continued

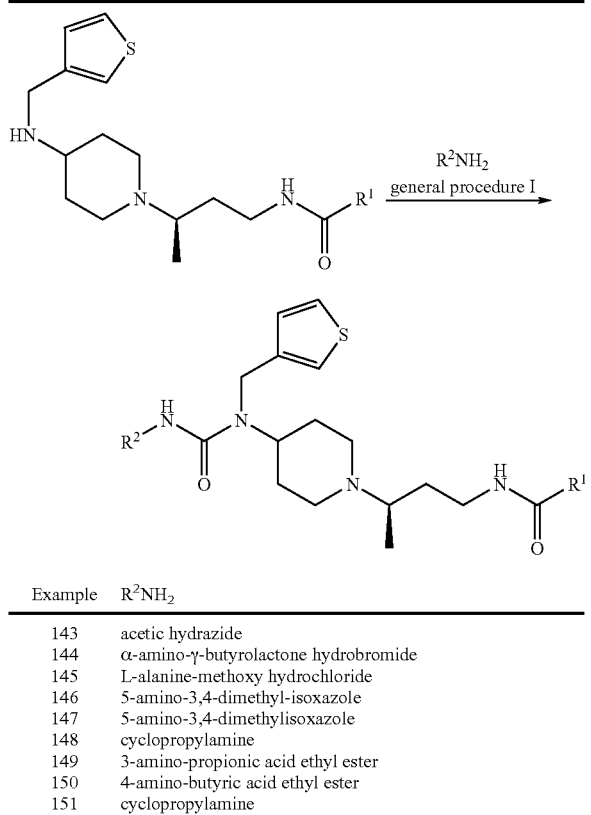

| Example | R²NH₂ |
|---|---|
| 143 | acetic hydrazide |
| 144 | α-amino-γ-butyrolactone hydrobromide |
| 145 | L-alanine-methoxy hydrochloride |
| 146 | 5-amino-3,4-dimethyl-isoxazole |
| 147 | 5-amino-3,4-dimethylisoxazole |
| 148 | cyclopropylamine |
| 149 | 3-amino-propionic acid ethyl ester |
| 150 | 4-amino-butyric acid ethyl ester |
| 151 | cyclopropylamine |

Example 112

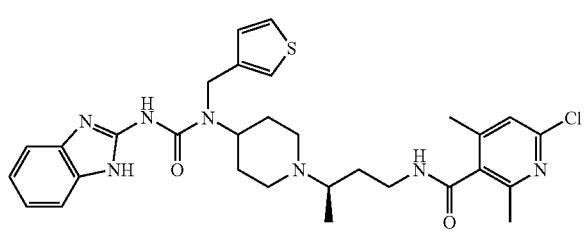

Compound 112

N—((R)-3-{4-[3-(1H-Benzoimidazol-2-yl)-1-thiophen-3-ylmethyl-ureido]-piperidin-1-yl}-butyl)-6-chloro-2,4-dimethyl-nicotinamide ¹H NMR (CDCl₃) δ 1.20-1.26 (m, 4H), 1.68-1.75 (m, 3H), 2.20-2.28 (m, 1H), 2.29 (s, 3H), 2.49 (s, 3H), 2.49-2.56 (m, 1H), 2.78-2.86 (m, 1H), 2.93-3.20 (m, 4H), 3.44-3.64 (m, 3H), 4.39-4.47 (m, 2H), 6.96 (s, 1H), 7.01 (d, 1H, J=6 Hz), 7.10-7.15 (m, 4H), 7.24-7.29 (m, 4H), 8.00 (br s, 1H); ¹³C NMR (CDCl₃) δ 13.24, 19.40, 22.66, 28.02, 29.07, 30.08, 31.89, 37.83, 42.30, 45.38, 52.11, 54.01, 59.89, 111.14, 111.69, 118.97, 122.11, 122.90, 122.99, 124.90, 125.88, 126.69, 127.56, 130.69, 132.38, 140.33, 147.83, 150.62, 155.67, 168.53; ES-MS m/z 594 (M+H). Anal. Calcd. for C₃₀H₃₆N₇O₂SCl·0.9CH₂Cl₂·1.2H₂O: C, 53.62; H, 5.85; N, 14.16. Found: C, 53.84; H, 5.88; N, 14.20.

Example 113

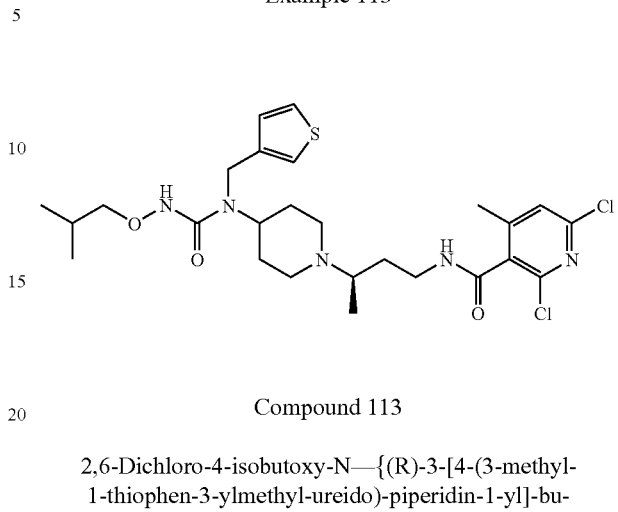

Compound 113

2,6-Dichloro-4-isobutoxy-N—{(R)-3-[4-(3-methyl-1-thiophen-3-ylmethyl-ureido)-piperidin-1-yl]-butyl}-nicotinamide ¹H NMR (CDCl₃) δ 0.88 (d, 6H, J=6 Hz), 0.92-0.97 (m, 1H), 0.98 (d, 3H, J=6 Hz), 1.14-1.26 (m, 1H), 1.47-1.53 (m, 1H), 1.70-1.74 (m, 3H), 1.79-1.86 (m, 1H), 2.09-2.24 (m, 1H), 2.33 (s, 3H), 2.52-2.62 (m, 1H), 2.72-2.84 (m, 3H), 3.25-3.36 (m, 1H), 3.53 (d, 2H, J=6 Hz), 3.76 (s, 2H), 3.77-3.86 (m, 1H), 4.14-4.26 (m, 1H), 6.95 (s, 1H), 7.00 (d, 1H, J=3 Hz), 7.04 (s, 1H), 7.11 (s, 1H), 7.35-7.41 (m, 1H), 8.83 (br s, 1H); ES-MS m/z 570 (M+H).

Example 114

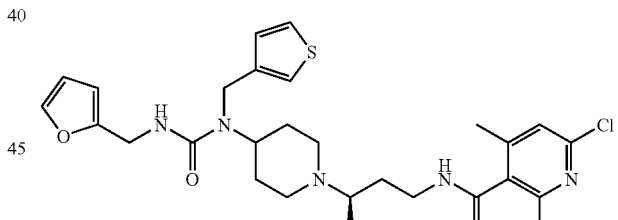

Compound 114

2,6-Dichloro-N—{(R)-3-[4-(3-furan-2-ylmethyl-1-thiophen-3-ylmethyl-ureido)-piperidin-1-yl]-butyl}-4-methyl-nicotinamide ¹H NMR (CDCl₃) δ 0.92-0.96 (m, 1H), 0.98 (d, 3H, J=6 Hz), 1.07-1.21 (m, 1H), 1.47-1.53 (m, 1H), 1.65-1.76 (m, 3H), 2.09-2.22 (m, 1H), 2.34 (s, 3H), 2.55-2.61 (m, 1H), 2.71-2.84 (m, 3H), 3.25-3.37 (m, 1H), 3.81 (s, 2H), 3.82-3.91 (m, 1H), 4.21-4.29 (m, 1H), 4.31 (d, 2H, J=6 Hz), 4.59-4.67 (m, 1H), 6.03 (br s, 1H), 6.26 (br s, 1H), 6.99 (d, 1H, J=3 Hz), 7.06 (s, 2H), 7.27 (s, 1H), 7.32-7.36 (m, 1H), 8.96 (br s, 1H); ES-MS m/z 579 (M+H).

Example 115

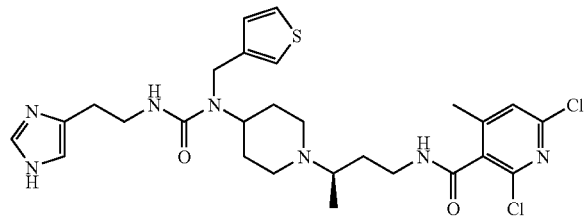

Compound 115

2,6-Dichloro-N—[(R)-3-(4-{3-[2-(1H-imidazol-4-yl)-ethyl]-1-thiophen-3-ylmethyl-ureido}-piperidin-1-yl)-butyl]-4-methyl-nicotinamide Pale yellow foam. $^1$H NMR (CDCl$_3$) δ 0.92-0.99 (m, 1H), 0.98 (d, 3H, J=6.6 Hz), 1.13-1.17 (m, 1H), 1.48-1.78 (m, 4H), 2.12-2.19 (m, 1H), 2.33 (s, 3H), 2.51-2.58 (m, 1H), 2.67-2.85 (m, 5H), 3.25-3.33 (m, 1H), 3.44 (q, 2H, J=6 Hz), 3.77-3.87 (m, 3H), 4.12-4.20 (m, 1H), 6.65 (s, 1H), 6.94 (d, 1H, J=5.1 Hz), 6.98 (br s, 1H), 7.06 (s, 1H), 7.27-7.30 (m, 1H), 7.44 (s, 1H), 8.94 (br d, 1H); $^{13}$C NMR (CDCl$_3$) δ 13.41, 19.10, 27.24, 30.16, 30.31, 30.99, 40.19, 41.61, 43.40, 51.78, 52.38, 60.25, 121.07, 124.32, 126.13, 126.70, 132.57, 134.61, 139.56, 146.61, 149.79, 150.85, 158.26, 164.07; ES-MS m/z 592 (M+H). Anal. Calcd. for C$_{27}$H$_{35}$N$_7$O$_2$SCl$_2$.1.0CH$_2$Cl$_2$.0.4H$_2$O: C, 49.12; H, 5.56; N, 14.32. Found: C, 49.34; H, 5.58; N, 14.39.

Example 116

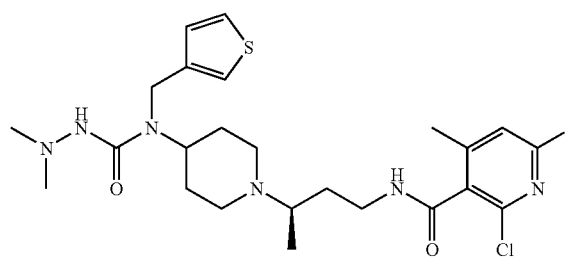

Compound 116

2,6-Dichloro-N—((R)-3-{4-[3-(2,2-dimethylhydrazine-1-ylcarbonylamino)-1-thiophen-3-ylmethyl-ureido]-piperidin-1-yl}-butyl)-4-methyl-nicotinamide White foam. $^1$H NMR (CDCl$_3$) δ 0.91-1.01 (m, 4H), 1.04-1.21 (m, 1H), 1.51-1.89 (m, 6H), 2.14-2.21 (m, 1H), 2.34 (s, 3H), 2.40 (s, 6H), 2.51-2.59 (m, 1H), 2.68-2.94 (m, 3H), 3.25-3.41 (m, 3H), 3.75-3.88 (m, 3H), 4.20-4.41 (m, 1H), 5.00 (s, 1H), 7.01 (d, 1H, J=3 Hz), 7.06 (s, 1H), 7.11 (s, 1H), 7.37 (m, 1H), 8.96 (br s, 1H); ES-MS m/z 541 (M+H).

Example 117

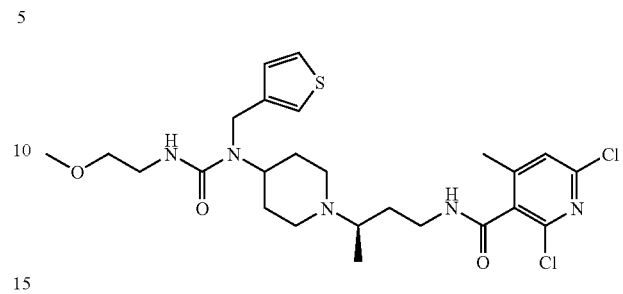

Compound 117

2,6-Dichloro-N—((R)-3-{4-[3-(2-methoxy-ethyl)-1-thiophen-3-ylmethyl-ureido]-piperidin-1-yl}-butyl)-4-methyl-nicotinamide White foam. $^1$H NMR (CDCl$_3$) δ 0.92-0.96 (m, 1H), 0.95 (d, 3H, J=12 Hz), 1.06-1.23 (m, 1H), 1.47-1.54 (m, 1H), 1.59-1.75 (m, 5H), 2.17 (t, 1H, J=12 Hz), 2.33 (s, 3H), 2.57 (t, 1H, J=12 Hz), 2.73-2.84 (m, 3H), 3.20 (s, 3H), 3.31 (s, 5H), 3.80-3.92 (m, 3H), 4.24 (m, 1H), 6.99 (d, 1H, J=3 Hz), 7.01 (s, 3H), 7.11 (s, 1H), 7.34 (m, 1H), 8.96 (br s, 1H); ES-MS m/z 556 (M+H).

Example 118

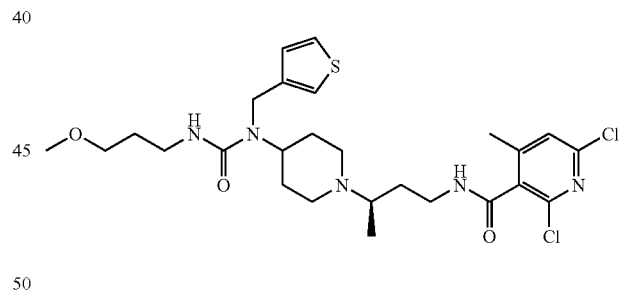

Compound 118

2,6-Dichloro-N—((R)-3-{4-[3-(3-methoxy-propyl)-1-thiophen-3-ylmethyl-ureido]-piperidin-1-yl}-butyl)-4-methyl-nicotinamide $^1$H NMR (CDCl$_3$) δ 0.82-0.94 (m, 1H), 0.98 (d, 3H, J=6 Hz), 1.04-1.18 (m, 1H), 1.49-1.56 (m, 1H), 1.61-1.89 (m, 4H), 2.08-2.19 (m, 1H), 2.34 (s, 3H), 2.52-2.61 (m, 1H), 2.72-2.86 (m, 3H), 3.12 (s, 3H), 3.21-3.32 (m, 5H), 3.46 (t, 1H, J=6 Hz), 3.79 (s, 2H), 3.80-3.87 (m, 1H), 4.21-4.27 (m, 1H), 4.88 (br s, 1H), 7.02 (d, 1H, J=6 Hz), 7.08 (s, 2H), 7.31-7.36 (m, 1H), 8.97 (br s, 1H); ES-MS m/z 592 (M+Na).

Example 119

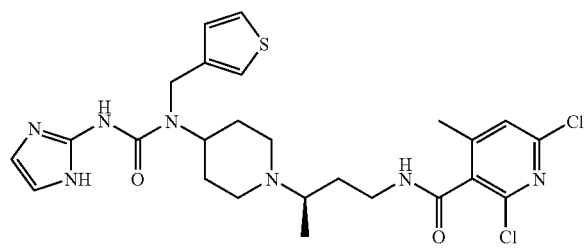

Compound 119

2,6-Dichloro-N—((R)-3-{4-[3-(1H-imidazol-2-yl)-1-thiophen-3-ylmethyl-ureido]-piperidin-1-yl}-butyl)-4-methyl-nicotinamide White foam. $^1$H NMR (CDCl$_3$) δ 0.98 (d, 3H, J=6.6 Hz), 1.08-1.12 (m, 1H), 1.26-1.31 (m, 1H), 1.51-1.56 (m, 1H), 1.68-1.78 (m, 4H), 2.09-2.16 (m, 1H), 2.36 (s, 3H), 2.54-2.61 (m, 1H), 2.73-2.86 (m, 3H), 3.28-3.35 (m, 1H), 3.78-3.83 (m, 1H), 4.02-4.09 (m, 3H), 6.66 (s, 2H), 6.97 (d, 1H, J=4.8 Hz), 7.10 (s, 2H), 7.33 (dd, 1H, J=4.8, 3 Hz), 8.62 (br d, 1H, J=6 Hz); $^{13}$C NMR (CDCl$_3$) δ 13.81, 19.58, 30.52, 30.89, 31.32, 40.53, 42.15, 43.71, 52.04, 53.75, 60.54, 119.37, 121.67, 124.80, 126.57, 127.21, 132.89, 139.29, 144.43, 147.06, 150.43, 151.31, 156.02, 164.53; ES-MS m/z 564 (M+H). Anal. Calcd. for C$_{25}$H$_{31}$N$_7$O$_2$SCl$_2$.0.9CH$_2$Cl$_2$.0.2H$_2$O: C, 48.26; H, 5.19; N, 15.21. Found: C, 48.28; H, 5.13; N, 15.02.

Example 120

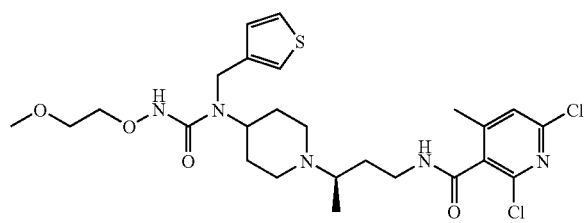

Compound 120

2,6-Dichloro-N—{(R)-3-[4-(3-(2-methoxyethoxy)-1-thiophen-3-ylmethyl-ureido)-piperidin-1-yl]-butyl}-4-methyl-nicotinamide To a solution of N-hydroxyphthalimide (4.60 g, 28.2 mmol) in DMF (15 ml) was added Et$_3$N (8.0 ml, 57.4 mmol) followed by 2-bromoethyl methyl ether (4.0 ml, 42.6 mmol) and the reaction stirred for 2.5 days. The mixture was diluted with EtOAc (50 ml) and brine (50 ml) and the aqueous layer was extracted with EtOAc (2×15 ml). The combined organic extracts were washed with brine (4×30 ml), dried (Na$_2$SO$_4$) and concentrated to afford the desired phthalimide as a beige solid (5.52 g, 88%). To a suspension of the phthalimide (2.13 g, 9.64 mmol) in MeOH (57 ml) was added hydrazine hydrate (0.4 ml, 12.86 mmol) and the mixture heated to reflux for 4 h then cooled to rt and stirred overnight. The reaction was filtered, concentrated and diluted with Et$_2$O (30 ml). The Et$_2$O layer was filtered and concentrated and re-diluted with Et$_2$O (30 ml). The Et$_2$O was filtered again and concentrated to afford O-(2-methoxy-ethyl)-hydroxylamine (775 mg, 88%) as a pale yellow oil. $^1$H NMR (CDCl$_3$) δ 3.38 (s, 3H), 3.55-3.58 (m, 2H), 3.81-3.84 (m, 2H), 4.25 (br s, 2H).

COMPOUND 120 was isolated as a yellow foam. $^1$H NMR (CDCl$_3$) δ 0.98 (d, 3H, J=6.6 Hz), 1.16-1.24 (m, 1H), 1.48-1.55 (m, 1H), 1.68-1.79 (m, 4H), 2.12-2.20 (m, 1H), 2.32 (s, 3H), 2.52-2.59 (m, 1H), 2.72-2.86 (m, 3H), 3.25-3.33 (m, 1H), 3.29 (s, 3H), 3.51-3.54 (m, 2H), 3.78-3.84 (m, 3H), 3.93-3.97 (m, 2H), 4.14-4.20 (m, 1H), 6.99 (d, 1H, J=4.8 Hz), 7.04 (s, 1H), 7.08-7.10 (m, 1H), 7.29 (s, 1H), 7.35 (dd, 1H, J=4.8, 3 Hz), 8.78 (br d, 1H, J=6 Hz); $^{13}$C NMR (CDCl$_3$) δ 13.33, 19.00, 29.77, 30.40, 30.51, 39.91, 41.00, 43.27, 51.46, 52.50, 58.80, 59.92, 70.74, 74.71, 121.21, 124.20, 125.88, 127.22, 132.44, 138.65, 146.48, 149.67, 150.76, 158.90, 163.98; ES-MS m/z 594 (M+Na). Anal. Calcd. for C$_{25}$H$_{35}$N$_5$O$_4$SCl$_2$.0.4H$_2$O: C, 51.79; H, 6.22; N, 12.08. Found: C, 51.89; H, 6.09; N, 12.46.

Example 121

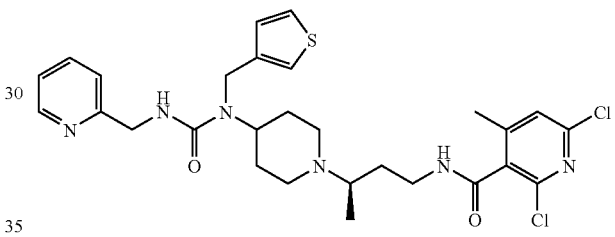

Compound 121

2,6-Dichloro-4-methyl-N—{(R)-3-[4-(3-pyridin-2-ylmethyl-1-thiophen-3-ylmethyl-ureido)-piperidin-1-yl]-butyl}-nicotinamide $^1$H NMR (CDCl$_3$) δ 0.91-0.95 (m, 1H), 0.98 (d, 3H, J=6 Hz), 1.07-1.20 (m, 1H), 1.49-1.56 (m, 1H), 1.69-1.78 (m, 3H), 2.09-2.22 (m, 1H), 2.34 (s, 3H), 2.53-2.60 (m, 1H), 2.71-2.83 (m, 3H), 3.24-3.35 (m, 1H), 3.80-3.89 (m, 1H), 3.89 (s, 2H), 4.21-4.27 (m, 1H), 4.44 (d, 2H, J=3 Hz), 5.57 (m, 1H), 7.01-7.05 (m, 2H), 7.09-7.18 (m, 3H), 7.30-7.36 (m, 1H), 7.56-7.61 (m, 1H), 8.41 (d, 1H, J=6 Hz), 8.96 (br s, 1H); ES-MS m/z 590 (M+H).

Example 122

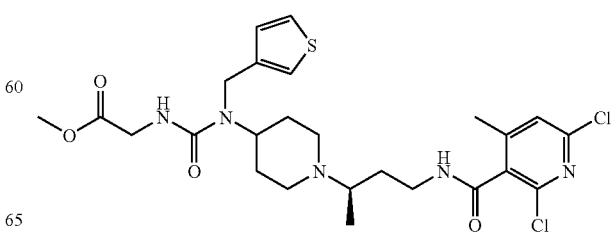

Compound 122

[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid methyl ester ¹H NMR (CDCl₃) δ 0.95-0.98 (m, 1H), 0.98 (d, 3H, J=6 Hz), 1.08-1.22 (m, 1H), 1.48-1.54 (m, 1H), 1.66-1.87 (m, 3H), 2.08-2.20 (m, 1H), 2.34 (s, 3H), 2.52-2.58 (m, 1H), 2.71-2.82 (m, 3H), 3.23-3.34 (m, 1H), 3.70 (s, 3H), 3.78-3.96 (m, 5H), 4.09-4.23 (m, 1H), 4.84-4.91 (m, 1H), 7.04-7.09 (m, 2H), 7.22 (s, 1H), 7.34-7.39 (m, 1H), 8.88 (br s, 1H); ES-MS m/z 570 (M+H).

Example 123

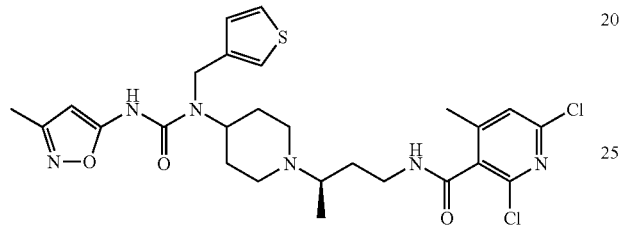

Compound 123

2,6-Dichloro-4-methyl-N—((R)-3-{4-[3-(3-methyl-isoxazol-5-yl)-1-thiophen-3-ylmethyl-ureido]-piperidin-1-yl}-butyl)-nicotinamide ¹H NMR (CDCl₃) δ 1.00 (d+m, 4H), 1.25 (m, 1H), 1.56 (m, 1H), 1.76 (m, 3H), 2.20 (s+br t, 4H), 2.35 (s, 3H), 2.61 (br t, 1H), 2.77-2.90 (m, 3H), 3.32 (m, 1H), 3.80 (m, 1H), 3.99 (s, 2H), 4.23 (m, 1H), 7.04 (d, 1H, J=6.0 Hz), 7.07 (s, 1H), 7.12 (s, 1H), 7.21 (s, 1H), 7.43 (m, 1H), 8.64 (br d, 1H); ES-MS m/z 579 (M+H).

Example 124

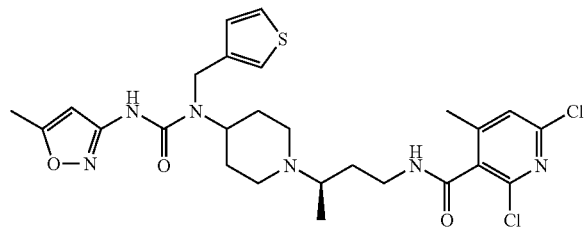

Compound 124

2,6-Dichloro-4-methyl-N—((R)-3-{4-[3-(5-methyl-isoxazol-3-yl)-1-thiophen-3-ylmethyl-ureido]-piperidin-1-yl}-butyl)-nicotinamide ¹H NMR (CDCl₃) δ 1.00 (d+m, 4H), 1.24 (m, 1H), 1.56 (m, 1H), 1.76 (m, 3H), 2.17 (br t, 1H), 2.35 (s, 6H), 2.60 (br t, 1H), 2.75-2.88 (m, 3H), 3.32 (m, 1H), 3.80 (m, 1H), 3.99 (s, 2H), 4.20 (m, 1H), 6.54 (s, 1H), 6.97 (s, 1H), 7.04 (d, 1H, J=6.0 Hz), 7.09 (s, 1H), 7.17 (s, 1H), 7.39 (m, 1H), 8.69 (br d, 1H); ES-MS m/z 579 (M+H).

Example 125

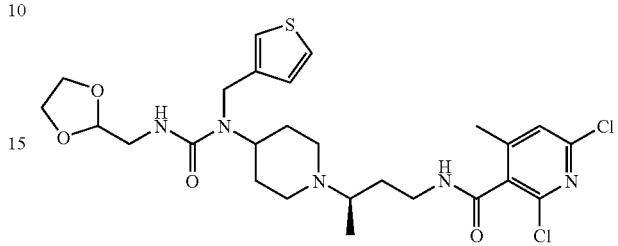

Compound 125

2,6-Dichloro-N—{(R)-3-[4-(3-1,3-dioxolan-2-ylmethyl-1-thiophen-3-ylmethyl-ureido)-piperidin-1-yl]-butyl}-4-methyl-nicotinamide ¹H NMR (CDCl₃) δ 0.95-0.99 (m, 4H), 1.05-1.25 (m, 1H), 1.54 (m, 1H), 1.68-1.73 (m, 3H), 2.15 (m, 1H), 2.34 (s, 3H), 2.56-2.56 (m, 1H), 2.82-2.86 (m, 3H), 3.38-3.42 (m, 3H), 3.74-3.88 (m, 7H), 4.26 (m, 1H), 4.56-4.59 (m, 1H), 4.83-5.29 (m, 1H), 7.01-7.05 (m, 2H), 7.13-7.13 (m, 1H), 7.33-7.35 (m, 1H), 8.98 (br s, 1H); ES-MS m/z 584(M+H).

Example 126

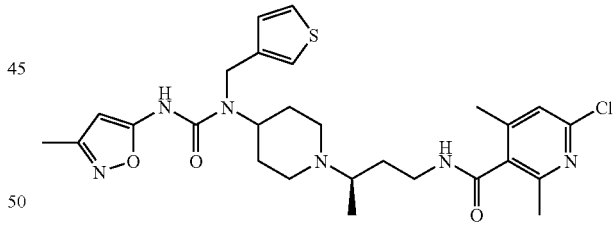

Compound 126

6-Chloro-2,4-dimethyl-N—((R)-3-{4-[3-(3-methyl-isoxazol-5-yl)-1-thiophen-3-ylmethyl-ureido]-piperidin-1-yl}-butyl)-nicotinamide White solid. ¹H NMR (CDCl₃) δ 0.88-1.21 (m, 4H), 1.52-1.74 (m, 5H), 2.21 (s, 3H), 2.29 (s, 3H), 2.50 (s, 3H), 2.52-2.70 (m, 1H), 2.71-2.96 (m, 3H), 3.22-3.31 (m, 2H), 3.76-3.83 (m, 3H), 4.11-4.24 (m, 1H), 5.97 (s, 1H), 6.96 (s, 1H), 7.07-7.10 (m, 1H), 7.21 (s, 1H), 7.42-7.43 (m, 1H), 8.57 (br s, 1H); ES-MS m/z 559 (M+H).

Example 127

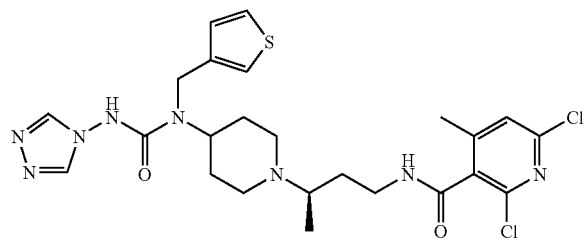

Compound 127

2,6-Dichloro-4-methyl-N—{(R)-3-[4-(1-thiophen-3-ylmethyl-3-[1,2,4]triazol-4-yl-ureido)-piperidin-1-yl]-butyl}-nicotinamide ¹H NMR (CDCl₃) δ 1.00 (br d, 3H), 1.25-1.47 (m, 2H), 1.55 (m, 1H), 1.78 (m, 3H), 2.19 (brt, 1H), 2.34 (s, 3H), 2.55 (brt, 1H), 3.33 (m, 1H), 3.73 (m, 1H), 4.13 (m, 3H), 7.02 (d, 1H, J=6.0 Hz), 7.08 (s, 1H), 7.18 (s, 1H), 7.36 (m, 1H), 7.96 (s, 2H), 8.51 (br s, 1H); ES-MS m/z 565 (M+H).

Example 128

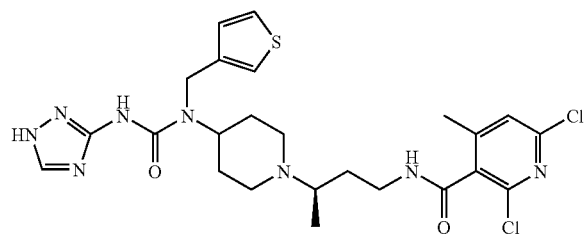

Compound 128

2,6-Dichloro-4-methyl-N—((R)-3-{4-[1-thiophen-3-ylmethyl-3-(1H-[1,2,4]triazol-3-yl)-ureido]-piperidin-1-yl}-butyl)-nicotinamide ¹H NMR (CDCl₃) δ 0.97 (d+m, 4H), 1.11 (m, 1H), 1.33 (m, 1H), 1.55 (m, 1H), 1.77 (m, 3H), 2.20 (br t, 1H), 2.36 (s, 3H), 2.60 (brt, 1H), 2.77-2.91 (m, 3H), 3.32 (m, 1H), 3.82 (m, 1H), 4.05 (s, 2H), 4.17 (m, 3H), 7.03 (d, 1H, J=6.0 Hz), 7.11 (s, 1H), 7.17 (s, 1H), 7.40 (m, 1H), 7.56 (s, 1H), 7.78 (br s, 1H), 8.57 (br s, 1H); ES-MS m/z 565 (M+H).

Example 129

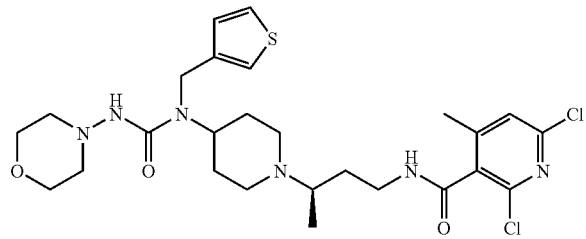

Compound 129

2,6-Dichloro-4-methyl-N—{(R)-3-[4-(3-morpholin-4-yl-1-thiophen-3-ylmethyl-ureido)-piperidin-1-yl]-butyl}-nicotinamide ¹H NMR (CDCl₃) δ 0.94 (d+m, 4H), 1.12 (m, 1H), 1.54 (m, 1H), 1.73 (m, 3H), 2.20 (br t, 1H), 2.34 (s, 3H), 2.59 (m, 5H), 2.76-2.86 (m, 3H), 3.32 (m, 1H), 3.47 (s, 1H), 3.69 (m, 4H), 3.83 (s+m, 3H), 4.24 (m, 1H), 7.00 (d, 1H, J=6.0 Hz), 7.05 (s, 1H), 7.11 (s, 1H), 7.38 (m, 1H), 8.84 (br s, 1H); ES-MS m/z 583 (M+H).

Example 130

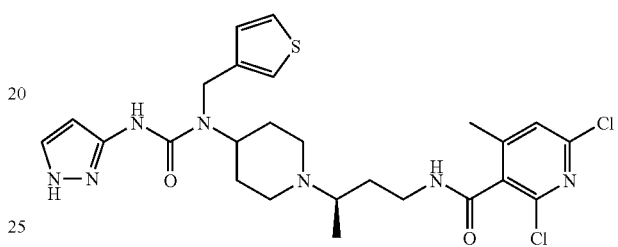

Compound 130

2,6-Dichloro-4-methyl-N—((R)-3-{4-[3-(1H-pyrazol-3-yl)-1-thiophen-3-ylmethyl-ureido]-piperidin-1-yl}-butyl)-nicotinamide ¹H NMR (CDCl₃) δ 0.97 (d+m, 4H), 1.22 (m, 1H), 1.54 (m, 1H), 1.75 (m, 3H), 2.20 (brt, 1H), 2.35 (s, 3H), 2.59 (m, 5H), 2.76-2.86 (m, 3H), 3.34 (m, 1H), 3.82 (m, 1H), 3.98 (s, 2H), 4.27 (m, 1H), 6.36 (br s, 1H), 6.91 (s, 1H), 7.06 (m, 1H), 7.09 (s, 1H), 7.21 (s, 1H), 7.39 (s+m, 1H), 8.79 (br s, 1H); ES-MS m/z 564 (M+H).

Example 131

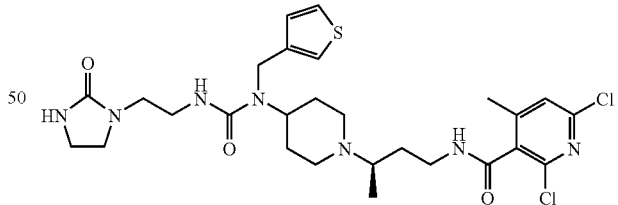

Compound 131

2,6-Dichloro-4-methyl-N—[(R)-3-(4-{3-[2-(2-oxo-imidazolidin-1-yl)-ethyl]-1-thiophen-3-ylmethyl-ureido}-piperidin-1-yl)-butyl]-nicotinamide ¹H NMR (CDCl₃) δ 0.98 (d+m, 4H), 1.16 (m, 1H), 1.24 (m, 2H), 1.55 (m, 1H), 1.66-1.76 (m, 3H), 2.08 (brt, 1H), 2.33 (s, 3H), 2.58 (m, 2H), 2.65 (m, 1H), 2.83 (m, 2H), 3.21 (m, 2H), 3.31 (m, 3H), 3.78 (m, 1H), 3.85 (s, 2H), 4.07 (m, 1H), 4.86

(br t, 1H), 6.98 (d, 1H, J=6.0 Hz), 7.05 (s, 1H), 7.08 (s, 1H), 7.11 (s, 1H), 7.31 (m, 1H), 7.66 (s, 1H), 8.82 (br s, 1H); ES-MS m/z 586 (M+H).

Example 132

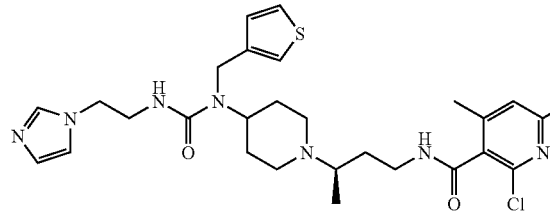

Compound 132

2,6-Dichloro-N—((R)-3-{4-[3-(2-imidazol-1-yl-ethyl)-1-thiophen-3-ylmethyl-ureido]-piperidin-1-yl}-butyl)-4-methyl-nicotinamide $^1$H NMR (CDCl$_3$) δ 0.92-0.99 (m, 1H), 0.98 (d, 3H, J=6.6 Hz), 1.13-1.26 (m, 1H), 1.48-1.78 (m, 5H), 2.13-2.20 (m, 1H), 2.33 (s, 3H), 2.52-2.60 (m, 10H), 2.73-2.87 (m, 3H), 3.26-3.33 (m, 1H), 3.39-3.46 (m, 2H), 3.75 (s, 2H), 3.77-3.86 (m, 1H), 4.00 (t, 1H, J=5.7 Hz), 4.10-4.22 (m, 1H), 4.38-4.46 (m, 1H), 6.72 (s, 1H), 6.92 (d, 1H, J=4.8 Hz), 6.97 (br s, 1H), 7.00 (s, 1H), 7.06 (s, 1H), 7.29 (s, 1H), 7.35 (dd, 1H, J=4.8, 3 Hz), 8.82 (br d, 1H); $^{13}$C NMR (CDCl$_3$) δ 13.79, 19.52, 30.52, 30.84, 31.32, 40.52, 42.07, 43.77, 47.06, 52.17, 52.80, 60.62, 119.04, 121.61, 124.71, 126.28, 127.84, 130.07, 132.99, 137.53, 139.47, 147.04, 150.19, 151.28, 158.24, 164.45; ES-MS m/z 614 (M+Na). Anal. Calcd. for C$_{27}$H$_{35}$N$_7$O$_2$SCl$_2$.0.6CH$_2$Cl$_2$.0.6H$_2$O: C, 50.66; H, 5.76; N, 14.98. Found: C, 50.70; H, 5.77; N, 15.01.

Example 133

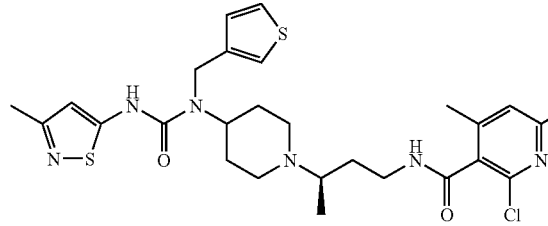

Compound 133

2,6-Dichloro-4-methyl-N—((R)-3-{4-[3-(3-methyl-isothiazol-5-yl)-1-thiophen-3-ylmethyl-ureido]-piperidin-1-yl}-butyl)-nicotinamide $^1$H NMR (CDCl$_3$) δ 1.00 (d+m, 4H), 1.25 (m, 1H), 1.53 (m, 1H), 1.76 (m, 3H), 2.20 (br t, 1H), 2.30 (s, 3H), 2.37 (s, 3H), 2.58 (br t, 1H), 2.81-2.87 (m, 3H), 3.32 (m, 1H), 3.76 (m, 1H), 4.02 (s, 2H), 4.32 (m, 1H), 7.05 (d, 1H, J=6.0 Hz), 7.07 (s, 1H), 7.23 (s, 1H), 7.43 (m, 1H), 7.48 (s, 1H), 8.71 (br s, 1H); ES-MS m/z 596 (M+H).

Example 134

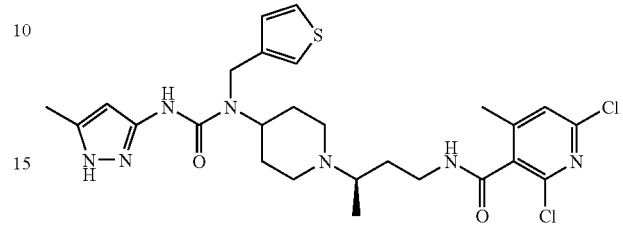

Compound 134

2,6-Dichloro-4-methyl-N—((R)-3-{4-[3-(5-methyl-1H-pyrazol-3-yl)-1-thiophen-3-ylmethyl-ureido]-piperidin-1-yl}-butyl)-nicotinamide $^1$H NMR (CDCl$_3$) δ 1.00 (d+m, 4H), 1.24 (m, 1H), 1.52 (m, 1H), 1.74 (m, 3H), 2.23 (s+brt, 4H), 2.35 (s, 3H), 2.58 (brt, 1H), 2.74-2.85 (m, 3H), 3.31 (m, 1H), 3.73 (m, 1H), 3.96 (s, 2H), 4.25 (m, 1H), 6.82 (s, 1H), 7.05 (d, 1H, J=6.0 Hz), 7.09 (s, 1H), 7.19 (s, 1H), 7.38 (m, 1H), 8.81 (br s, 1H); ES-MS m/z 578 (M+H).

Example 135

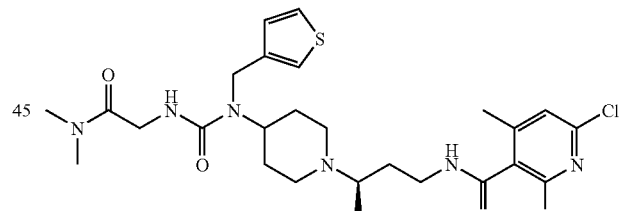

Compound 135

2,6-Dichloro-N—{(R)-3-[4-(3-dimethylcarbamoyl-methyl-1-thiophen-3-ylmethyl-ureido)-piperidin-1-yl]-butyl}-4-methyl-nicotinamide $^1$H NMR (CDCl$_3$) δ 0.98 (d, 3H, J=6 Hz), 0.98-1.07 (m, 1H), 1.09-1.22 (m, 1H), 1.47-1.51 (m, 1H), 1.70-1.79 (m, 3H), 2.07-2.20 (m, 1H), 2.34 (s, 3H), 2.54-2.62 (m, 1H), 2.73-2.88 (m, 3H), 2.94 (s, 6H), 3.26-3.35 (m, 1H), 3.75-3.80 (m, 1H), 3.81 (s, 2H), 3.96 (d, 2H, J=6 Hz), 4.01-4.16 (m, 1H), 5.44-5.49 (m, 1H), 7.01-7.06 (m, 2H), 7.20 (s, 1H), 7.28-7.35 (m, 1H), 8.86 (br s, 1H); ES-MS m/z 583 (M+H).

Example 136

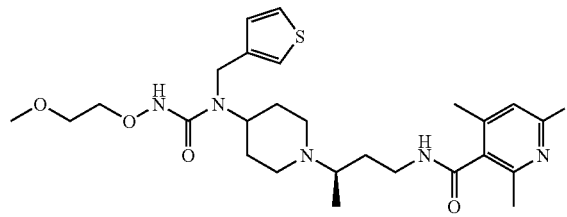

Compound 136

6-Chloro-N—((R)-3-{4-[3-(2-methoxyethoxy)-1-thiophen-3-ylmethyl-ureido]-piperidin-1-yl}-butyl)-2,4-dimethyl-nicotinamide $^1$H NMR (CDCl$_3$) δ 0.83-0.94 (m, 1H), 0.98 (d, 3H, J=6.6 Hz), 0.98-1.07 (m, 1H), 1.48-1.54 (m, 1H), 1.63-1.76 (m, 3H), 2.13-2.20 (m, 1H), 2.27 (s, 3H), 2.48 (s, 3H), 2.53-2.60 (m, 1H), 2.68-2.84 (m, 3H), 3.22-3.31 (m, 1H), 3.29 (s, 3H), 3.52-3.55 (m, 2H), 3.65-3.75 (m, 2H), 3.81-3.87 (m, 1H), 3.94-3.97 (m, 2H), 4.16-4.24 (m, 1H), 6.93 (s, 1H), 7.03 (d, 1H, J=4.8 Hz), 7.10 (br s, 1H), 7.28 (s, 1H), 7.37 (dd, 1H, J=4.8, 3 Hz), 8.76 (br d, 1H); $^{13}$C NMR (CDCl$_3$) δ 15.31, 20.57, 23.87, 31.52, 32.42, 41.89, 42.76, 45.12, 53.53, 54.14, 60.76, 62.25, 72.69, 76.68, 123.10, 124.26, 127.84, 129.17, 134.67, 140.61, 149.36, 151.85, 157.17, 160.83, 168.84; ES-MS m/z 574 (M+Na). Anal. Calcd. for C$_{26}$H$_{38}$N$_5$O$_4$SCl.0.3CH$_2$Cl$_2$.0.2H$_2$O: C, 54.35; H, 6.76; N, 12.05. Found: C, 54.35; H, 6.74; N, 12.07.

Example 137

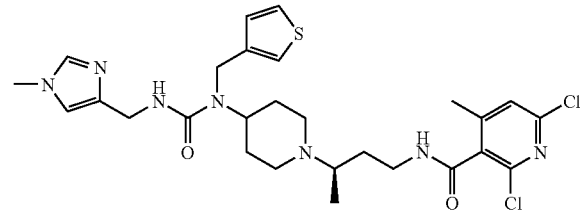

Compound 137

2,6-Dichloro-4-methyl-N—((R)-3-{4-[3-(1-methyl-1H-imidazol-4-ylmethyl)-1-thiophen-3-ylmethyl-ureido]-piperidin-1-yl}-butyl)-nicotinamide $^1$H NMR (CDCl$_3$) δ 0.93-0.96 (m, 1H), 0.98 (d, 3H, J=6 Hz), 1.04-1.19 (m, 1H), 1.46-1.53 (m, 1H), 1.66-1.78 (m, 4H), 2.07-2.20 (m, 1H), 2.34 (s, 3H), 2.54-2.60 (m, 1H), 2.71-2.83 (m, 3H), 3.24-3.38 (m, 1H), 3.60 (s, 3H), 3.83 (br s, 3H), 4.20-4.29 (m, 3H), 4.82-4.87 (m, 1H), 6.62 (s, 1H), 6.97-7.00 (m, 1H), 7.06-7.08 (m, 2H), 7.27-7.33 (m, 1H), 8.91 (br s, 1H); ES-MS m/z 592 (M+H).

Example 138

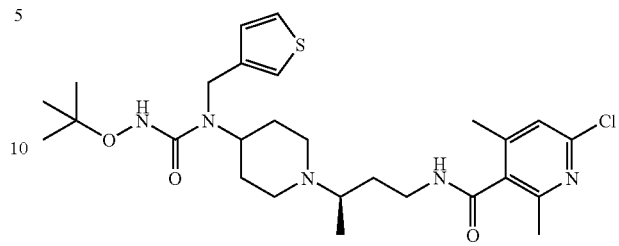

Compound 138

6-Chloro-N—{(R)-3-[4-(3-t-butoxy-1-thiophen-3-ylmethyl-ureido)-piperidin-1-yl]-butyl}-2,4-dimethyl-nicotinamide $^1$H NMR (CDCl$_3$) δ 0.78-0.93 (m, 1H), 0.98 (d, 3H, J=6 Hz), 098-1.02 (m, 1H), 1.14 (s, 9H), 1.48-1.55 (m, 1H), 1.63-1.77 (m, 3H), 2.15-2.22 (m, 1H), 2.27 (s, 3H), 2.49 (s, 3H), 2.52-2.59 (m, 1H), 2.68-2.86 (m, 3H), 3.21-3.30 (m, 1H), 3.71 (s, 2H), 3.77-3.91 (m, 1H), 4.19-4.28 (m, 1H), 6.57 (s, 1H), 6.90 (s, 1H), 7.01-7.05 (m, 1H), 7.13 (s, 1H), 7.35-7.40 (m, 1H), 8.82 (br s, 1H); ES-MS m/z 572 (M+Na).

Example 139

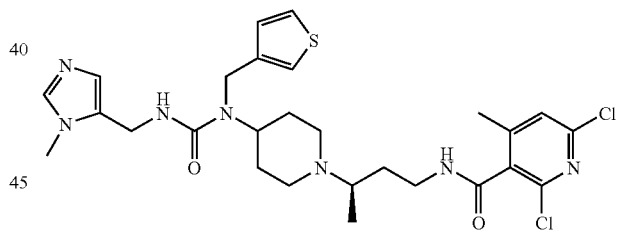

Compound 139

2,6-Dichloro-4-methyl-N—((R)-3-{4-[3-(3-methyl-3H-imidazol-4-ylmethyl)-1-thiophen-3-ylmethyl-ureido]-piperidin-1-yl}-butyl)-nicotinamide $^1$H NMR (CDCl$_3$) δ 0.93-0.98 (m, 1H), 0.98 (d, 3H, J=6 Hz), 1.09-1.19 (m, 1H), 1.48-1.54 (m, 1H), 1.68-1.79 (m, 3H), 2.08-2.20 (m, 1H), 2.33 (s, 3H), 2.56-2.62 (m, 1H), 2.70-2.84 (m, 3H), 3.23-3.38 (m, 1H), 3.45 (s, 3H), 3.83 (s, 2H), 3.83-3.91 (m, 1H), 4.19-4.26 (m, 1H), 4.28 (d, 2H, J=6 Hz), 4.40-4.47 (m, 1H), 6.73 (br s, 1H), 6.94-6.98 (m, 1H), 7.04 (s, 2H), 7.32-7.36 (m, 2H), 8.88 (br s, 1H); ES-MS m/z 592 (M+H).

Example 140

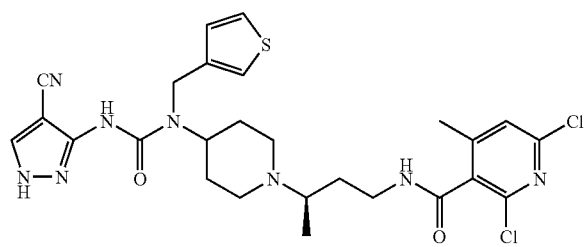

Compound 140

2,6-Dichloro-N—((R)-3-{4-[3-(4-cyano-1H-pyrazol-3-yl)-1-thiophen-3-ylmethyl-ureido]-piperidin-1-yl}-butyl)-4-methyl-nicotinamide $^1$H NMR (CDCl$_3$) δ 1.01 (d, 3H, J=6.0 Hz), 1.25 (m, 1H), 1.43 (s, 1H), 1.56 (m, 1H), 1.82 (m, 3H), 2.26 (br t, 1H), 2.35 (s, 3H), 2.67 (br t, 1H), 2.88-2.95 (m, 3H), 3.34 (m, 1H), 3.81 (m, 1H), 4.02 (s, 2H), 4.27 (m, 1H), 7.01 (s+d, 2H), 7.32 (s, 1H), 7.38 (s, 1H), 7.49 (m, 1H), 7.55 (s, 1H), 8.57 (br s, 1H); ES-MS m/z 589 (M+H).

Example 141

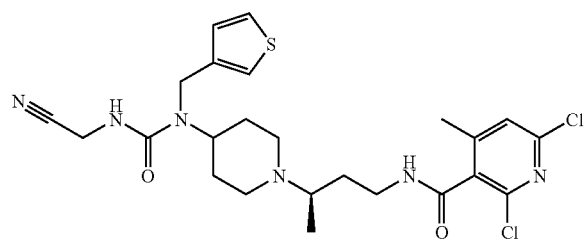

Compound 141

2,6-Dichloro-N—{(R)-3-[4-(3-cyanomethyl-1-thiophen-3-ylmethyl-ureido)-piperidin-1-yl]-butyl}-4-methyl-nicotinamide $^1$H NMR (CDCl$_3$) δ 0.99 (d+m, 4H), 1.23 (m, 1H), 1.50-1.77 (m, 4H), 2.14 (br t, 1H), 2.35 (s, 3H), 2.56 (br t, 1H), 2.73-2.84 (m, 3H), 3.29 (m, 1H), 3.84 (s+m, 3H), 4.03 (d, 2H, J=6.0 Hz), 4.21 (m, 1H), 4.62 (m, 1H), 7.02 (d, 2H, J=4.5 Hz), 7.13 (s+d, 2H), 7.41 (m, 1H), 8.80 (br s, 1H); ES-MS m/z 537 (M+H).

Example 142

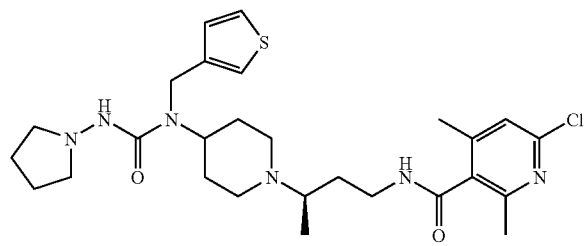

Compound 142

6-Chloro-2,4-dimethyl-N—{(R)-3-[4-(3-pyrrolidin-1-yl-1-thiophen-3-ylmethyl-ureido)-piperidin-1-yl]-butyl}-nicotinamide $^1$H NMR (CDCl$_3$) δ 0.72-0.84 (m, 1H), 0.97 (d, 3H, J=6 Hz), 098-1.03 (m, 1H), 1.46-1.52 (m, 1H), 1.62-1.78 (m, 7H), 2.14-2.21 (m, 1H), 2.27 (s, 3H), 2.48 (s, 3H), 2.50-2.55 (m, 1H), 2.57-2.69 (m, 5H), 2.77-2.86 (m, 2H), 3.21-3.27 (m, 1H), 3.68 (d, 2H, J=6 Hz), 3.78-3.92 (m, 1H), 4.21-4.29 (m, 1H), 5.01 (s, 1H), 6.93 (s, 1H), 7.02-7.06 (m, 1H), 7.11 (s, 1H), 7.33-7.38 (m, 1H), 8.91 (br s, 1H); ES-MS m/z 569 (M+Na).

Example 143

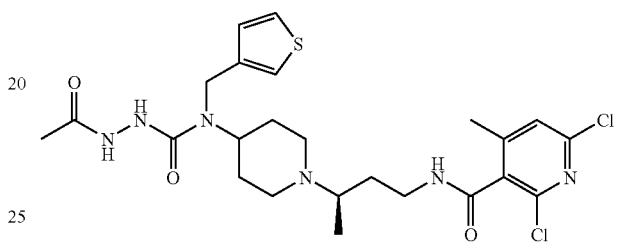

Compound 143

2,6-Dichloro-4-methyl-N—{(R)-3-[4-(3-acetamido-1-thiophen-3-ylmethyl-ureido)-piperidin-1-yl]-butyl}-nicotinamide $^1$H NMR (CDCl$_3$) δ 0.99 (d, 3H, J=6.0 Hz), 1.12 (m, 1H), 1.23 (m, 1H), 1.54 (m, 1H), 1.69-1.79 (m, 4H), 1.98 (s, 3H), 2.16 (br t, 1H), 2.34 (s, 3H), 2.57 (br t, 1H), 2.76 (m, 1H), 2.86 (m, 2H), 3.31 (m, 1H), 3.80 (m, 1H), 3.99 (s, 2H), 4.09 (m, 1H), 6.59 (br s, 1H), 7.06 (d, 1H, J=6.0 Hz), 7.11 (s, 1H), 7.28 (s, 1H), 7.37 (m, 1H), 7.75 (s, 1H), 8.65 (br s, 1H); ES-MS m/z 555 (M+H).

Example 144

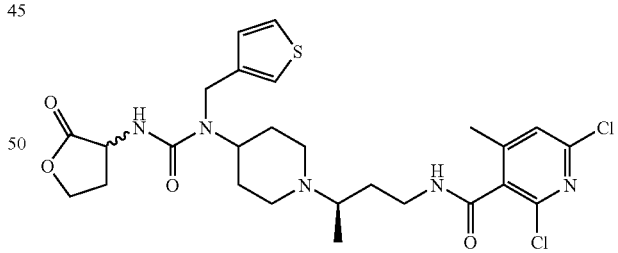

Compound 144

2,6-Dichloro-4-methyl-N—((R)-3-{4-[3-(2-oxo-tetrahydro-furan-3-yl)-1-thiophen-3-ylmethyl-ureido]-piperidin-1-yl}-butyl)-nicotinamide $^1$H NMR (CDCl$_3$) δ 0.98 (d+m, 4H), 1.25 (m, 1H), 1.57 (m, 1H), 1.69-1.77 (m, 4H), 2.08-2.17 (m, 2H), 2.35 (s, 3H), 2.56 (br t, 1H), 2.63-2.88 (m, 4H), 3.27 (m, 1H), 3.88 (s+m, 3H), 4.20 (m, 2H), 4.33 (m, 2H), 4.87 (m, 1H), 7.02 (d, 1H, J=6.0 Hz), 7.08 (s, 1H), 7.17 (s, 1H), 7.37 (m, 1H), 8.82 (br s, 1H); ES-MS m/z 582 (M+H).

Example 145

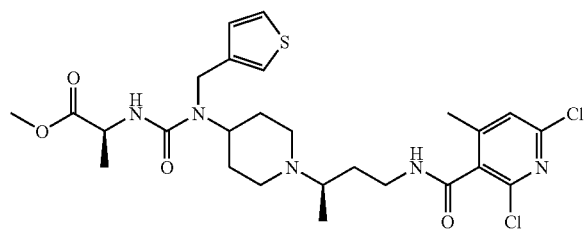

Compound 145

(S)-2-[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-propionic acid methyl ester $^1$H NMR (CDCl$_3$) δ 0.92 (d+m, 4H), 1.17 (m, 1H), 1.25 (d, 1H, J=6.0 Hz), 1.57 (m, 1H), 1.64-1.75 (m, 4H), 2.16 (br t, 1H), 2.35 (s, 3H), 2.53 (br t, 1H), 2.71 (m, 1H), 2.84 (m, 2H), 3.28 (m, 1H), 3.69 (s, 3H), 3.75-3.85 (m, 2H), 4.18 (m, 1H), 4.39 (m, 1H), 4.80 (d, 1H, J=6.0 Hz), 7.07 (m, 2H), 7.21 (s, 1H), 7.36 (m, 1H), 8.87 (br s, 1H); ES-MS m/z 584 (M+H).

Example 146

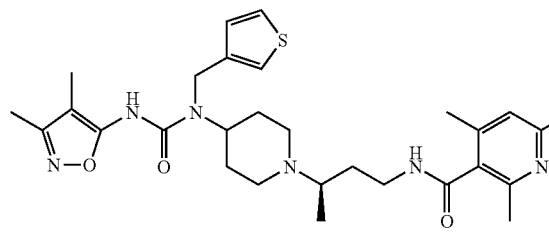

Compound 146

6-Chloro-N—((R)-3-{4-[3-(3,4-dimethyl-isoxazol-5-yl)-1-thiophen-3-ylmethyl-ureido]-piperidin-1-yl}-butyl)-2,4-dimethyl-nicotinamide $^1$H NMR (CDCl$_3$) δ 0.95 (d+m, 4H), 1.12 (m, 1H), 1.53 (m, 1H), 1.75 (s+m, 6H), 2.14 (s, 3H), 2.18 (br t, 1H), 2.29 (s, 3H), 2.50 (s, 3H), 2.60 (br t, 1H), 2.73 (m, 1H), 2.83 (m, 2H), 3.28 (br t, 1H), 3.83 (m, 1H), 3.90 (s, 2H), 4.25 (m, 1H), 6.33 (s, 1H), 6.97 (s, 1H), 7.10 (d, 1H, J=6.0 Hz), 7.23 (s, 1H), 7.43 (m, 1H), 8.73 (br s, 1H); ES-MS m/z 573 (M+H).

Example 147

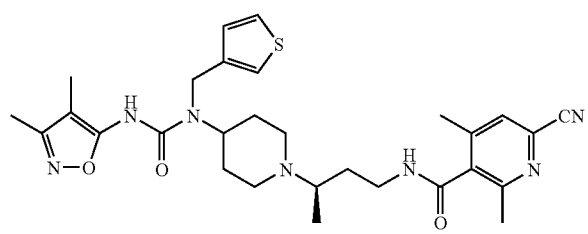

Compound 147

6-Cyano-N—((R)-3-{4-[3-(3,4-dimethyl-isoxazol-5-yl)-1-thiophen-3-ylmethyl-ureido]-piperidin-1-yl}-butyl)-2,4-dimethyl-nicotinamide $^1$H NMR (CDCl$_3$) δ 0.95 (d+m, 4H), 1.10 (m, 1H), 1.53 (m, 1H), 1.73 (s+m, 6H), 2.14 (s, 3H), 2.17 (br t, 1H), 2.35 (s, 3H), 2.56 (s, 3H), 2.59 (br t, 1H), 2.75 (m, 1H), 2.85 (m, 2H), 3.33 (br t, 1H), 3.82 (m, 1H), 3.91 (s, 2H), 4.26 (m, 1H), 6.32 (s, 1H), 7.06 (d, 1H, J=6.0 Hz), 7.26 (s, 2H), 7.47 (m, 1H), 8.65 (br s, 1H); ES-MS m/z 564 (M+H).

Example 148

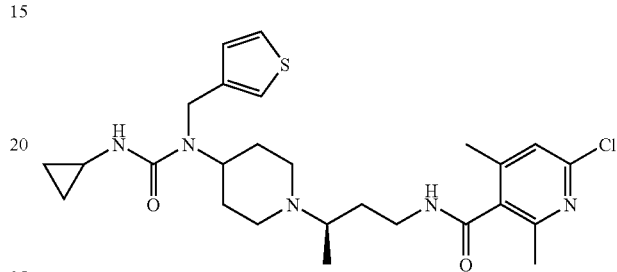

Compound 148

6-Chloro-N—{(R)-3-[4-(3-cyclopropyl-1-thiophen-3-ylmethyl-ureido)-piperidin-1-yl]-butyl}-2,4-dimethyl-nicotinamide $^1$H NMR (CDCl$_3$) δ 0.26-0.29 (m, 2H), 0.58-0.64 (m, 2H), 0.74-1.03 (m, 5H), 1.52-1.76 (m, 4H), 2.14 (t, 1H, J=12 Hz), 2.27 (s, 3H), 2.48-2.74 (m, 6H), 2.75-2.82 (m, 2H), 3.25 (br t, 1H, J=12 Hz), 3.58-3.70 (m, 2H), 3.78-3.91 (m, 1H), 4.23-4.28 (m, 1H), 4.48 (br s, 1H), 6.93 (s, 1H), 7.01 (d, 1H, J=6 Hz), 7.08 (br s, 1H), 7.34 (dd, 1H, J=6, 3 Hz), 8.92 (br s, 1H); ES-MS m/z 540 (M+Na).

Example 149

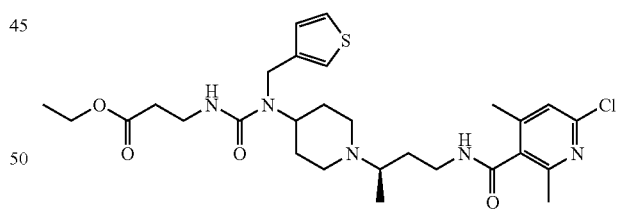

Compound 149

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-propionic acid ethyl ester $^1$H NMR (CDCl$_3$) δ 0.67-2.91 (m, 11H), 0.98 (d, 3H, J=6.6 Hz), 1.18 (t, 3H, J=7.2 Hz), 2.26 (s, 3H), 2.40 (t, 2H, J=6.0 Hz), 2.47 (s, 3H), 3.25-3.27 (m, 1H), 3.37 (q, 2H, J=6.0 Hz), 3.62-3.91 (m, 3H), 4.02 (q, 2H, J=7.2 Hz), 4.12-4.30 (m, 1H), 4.80-4.90 (m, 1H), 6.93 (s, 1H), 6.94-7.00 (m, 1H), 7.07 (s, 1H), 7.31-7.33 (m, 1H), 8.81 (s, 1H); ES-MS m/z 578 (M+H).

Example 150

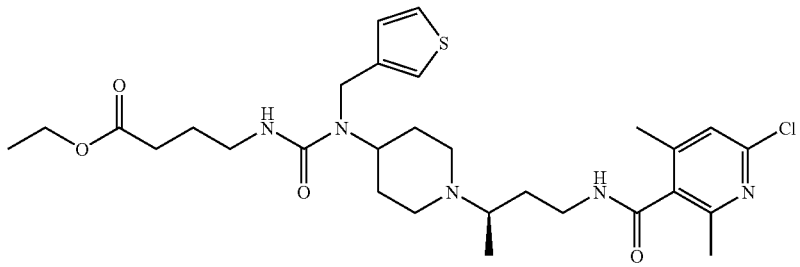

Compound 150

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-butyric acid ethyl ester $^1$H NMR (CDCl$_3$) δ 0.75-2.89 (m, 11H), 0.97 (d, 3H, J=6.6 Hz), 1.21 (t, 3H, J=6.9 Hz), 1.68 (t, 2H, J=7.2 Hz), 2.15 (t, 2H, J=7.2 Hz), 2.26 (s, 3H), 2.48 (s, 3H), 3.13 (q, 2H, J=6.3 Hz), 3.20-3.32 (m, 1H), 3.33-3.88 (m, 3H), 4.07 (q, 2H, J=7.2 Hz), 4.12-4.27 (m, 1H), 4.41-4.50 (m, 1H), 6.94 (s, 1H), 6.95-7.00 (m, 1H), 7.11 (s, 1H), 7.33-7.35 (m, 1H), 8.85 (s, 1H); ES-MS m/z 614 (M+Na).

Example 151

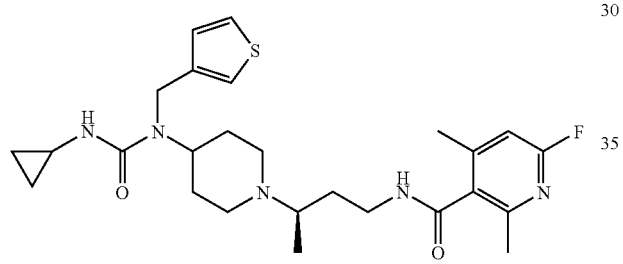

Compound 151

N—{(R)-3-[4-(3-Cyclopropyl-1-thiophen-3-ylmethyl-ureido)-piperidin-1-yl]-butyl}-6-fluoro-2,4-dimethyl-nicotinamide $^1$H NMR (CDCl$_3$) δ 0.25 (m, 2H), 0.59 (m, 2H), 0.8 (m, 1H), 1.0 (m, 9H), 1.52 (d, 1H, J=12 Hz), 1.65 (m, 5H), 2.15 (t, 1H, J=12 Hz), 2.30 (s, 3H), 2.45 (s, 3H), 2.5 (m, 3H), 2.8 (m, 1H), 2.85 (m, 2H), 3.25 (t, 1H, J=12 Hz), 3.61 (s, 2H), 3.85 (m, 1H), 4.26 (m, 1H), 4.44 (s, 1H), 6.43 (s, 1H), 6.95 (d, 1H, J=3 Hz), 7.05 (s, 1H), 7.35 (d, 1H, J=3 Hz), 8.85 (br d, 1H, J=6 Hz); ES-MS m/z 509 (M+H).

Example 152

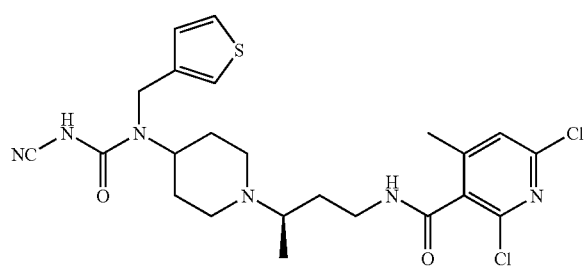

Compound 152

2,6-Dichloro-4-methyl-N—{(R)-3-[4-(3-cyano-1-thiophen-3-ylmethyl-ureido)-piperidin-1-yl]-butyl}-nicotinamide To a stirred solution of 2,6-dichloro-4-methyl-N—((R)-3-{4-[(thiophen-3-ylmethyl)-amino]-piperidin-1-yl}-butyl)-nicotinamide (128 mg, 0.28 mmol) and DIPEA (98 µL, 0.56 mmol) in CH$_2$Cl$_2$ (4 ml) was added solid triphosgene (25 mg, 0.084 mmol) in one portion. After 30 min, sodium hydrogencyanamide (22 mg, 0.34 mmol) was added and the resulting suspension was stirred overnight. A fine white precipitate was observed. The solvent was then removed under reduced pressure, and the crude material was purified by flash chromatography on silica gel (CH$_2$Cl$_2$/CH$_3$OH/NH$_4$OH, 10:2:0.5) to give COMPOUND 152 (114 mg, 77%) as a white solid. $^1$H NMR (CD$_3$OD) δ 1.37 (d, 3H, J=6.6 Hz), 1.80-1.86 (m, 3H), 2.07-2.13 (m, 3H), 2.36 (s, 3H), 3.03-3.10 (m, 2H), 3.31-3.53 (m, 4H), 4.21 (br s, 1H), 4.47 (br s, 2H), 4.60 (br s, 1H), 7.04 (d, 1H, J=4.5 Hz), 7.14 (br s, 1H), 7.31 (dd, 1H, J=5, 3 Hz), 7.41 (s, 1H); ES-MS m/z 523 (M+H).

Example 153

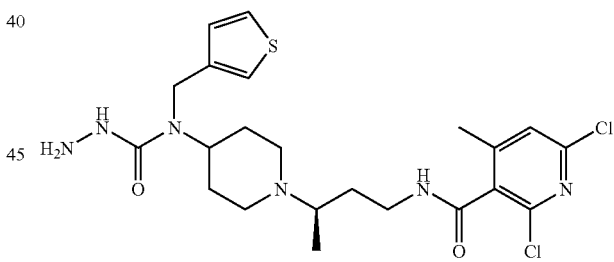

Compound 153

2,6-Dichloro-4-amino-N—{(R)-3-[4-(3-methyl-1-thiophen-3-ylmethylureido)-piperidin-1-yl]-butyl}-nicotinamide To a solution of N-aminophthalimide (285 mg, 1.76 mmol) in acetonitrile (4 mL) was added CDI (285 mg, 1.76 mmol) and diisopropylethylamine (310 µL, 1.76 mmol). The solution was stirred at 55° C. overnight and the reaction was subjected to aqueous work-up. The crude was immediately taken up in a solution of methanol (4 mL) and hydrazine (10 equiv, 78 µL) and allowed to stir at room temperature overnight. Solvent was removed in vacuo, followed by an aqueous work-up and purification by column chromatography (5% MeOH:DCM) to give COMPOUND 153 (73 mg, 56%) as a white solid. $^1$H NMR (CDCl$_3$) δ 0.98 (d, 3H, J=6 Hz), 0.98-1.01 (m, 1H), 1.10-1.22 (m, 1H), 1.47-1.76 (m, 3H), 2.06-2.18 (m, 1H), 2.33 (s, 3H), 2.51-2.63 (m, 1H), 2.72-2.83 (m, 3H), 3.22-3.31 (m, 1H), 3.67 (br s, 2H), 3.81 (br s, 2H), 3.81-3.90 (m, 1H), 4.04-4.18 (m, 1H), 5.50 (br s, 1H), 6.98 (d, 1H, J=3 Hz), 7.04-7.10 (m, 2H), 7.24 (s, 1H), 7.33-7.38 (m, 1H), 8.81 (br s, 1H); ES-MS m/z 513 (M+H).

Example 154

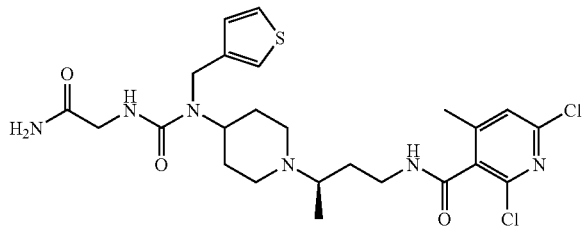

Compound 154

N—{(R)-3-[4-(3-Carbamoylmethyl-1-thiophen-3-ylmethyl-ureido)-piperidin-1-yl]-butyl}-2,6-dichloro-4-methyl-nicotinamide To a stirred solution of glycine methyl ester hydrochloride (109 mg, 0.87 mmol) and DIPEA (275 µL, 1.56 mmol) in CH$_2$Cl$_2$ (3 ml) was added CDI (155 mg, 0.96 mmol). The solution was stirred at 40° C. for 2 h before a solution of 2,6-dichloro-4-methyl-N—((R)-3-{4-[(thiophen-3-ylmethyl)-amino]-piperidin-1-yl}-butyl)-nicotinamide (130 mg, 0.29 mmol) in CH$_2$Cl$_2$ (3 ml) was added. Stirring was continued overnight at 40° C. Solvent was removed and the crude residue was purified by flash chromatography (MeOH/CH$_2$Cl$_2$, 3-4%) to give the ester (109 mg, 66%).

The above ester (30 mg, 0.05 mmol) was taken up in MeOH (4 ml) and the solution was saturated with gaseous ammonia. The saturated solution was allowed to stir at rt overnight. Solvent was removed and COMPOUND 154 (28 mg, 97%) was recovered as a white foam. $^1$H NMR (CDCl$_3$) δ 0.98 (d, 3H, J=12 Hz), 0.99-1.11 (m, 1H), 1.19-1.27 (m, 1H), 1.51-1.59 (m, 1H), 1.68-1.77 (m, 3H), 2.16 (t, 1H, J=12 Hz), 2.33 (s, 3H), 2.55 (t, 1H, J=12 Hz), 2.73-2.89 (m, 3H), 3.28-3.39 (m, 1H), 3.78 (d, 2H, J=3 Hz), 3.79-3.82 (m, 1H), 3.90 (s, 2H), 4.09-4.22 (m, 1H), 5.03-5.07 (m, 1H), 5.45 (br s, 1H), 6.18 (br s, 1H), 7.01 (d, 1H, J=3 Hz), 7.06 (s, 1H), 7.16 (br s, 1H), 7.34 (m, 1H), 8.81 (br s, 1H); ES-MS m/z 555 (M+H).

Example 155

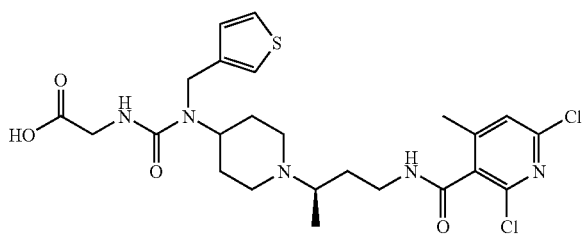

Compound 155

[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid To a solution of glycine t-butyl ester hydrochloride (74 mg, 0.44 mmol) in CH$_3$CN (5 ml) was added CDI (71 mg, 0.44 mmol), followed by DIPEA (0.077 mL, 0.44 mmol), and the mixture was stirred at 60° C. for 2 h. A solution of 2,6-dichloro-4-methyl-N—((R)-3-{4-[(thiophen-3-ylmethyl)-amino]-piperidin-1-yl}-butyl)-nicotinamide (50 mg, 0.11 mmol) in CH$_3$CN (5 ml) was then added to the previous mixture. After stirring at 60° C. overnight, the mixture was concentrated in vacuo and diluted with CH$_2$Cl$_2$ (15 ml) and saturated NaHCO$_3$ (20 ml). The aqueous layer was extracted with CH$_2$Cl$_2$ (3×10 ml), then the combined organic extracts were dried over Na$_2$SO$_4$ and concentrated. The crude product was purified by flash chromatography (CH$_2$Cl$_2$, 5% MeOH, 1% NH$_4$OH) to afford [3-(1-{(R)-3-[(2,6-dichloro-4-methyl-pyridine-3-carbonyl)-amino]-1-methyl-propyl}-piperidin-4-yl)-3-thiophen-3-ylmethyl-ureido]-acetic acid tert-butyl ester as a clear oil (95 mg). $^1$H NMR (CDCl$_3$) δ 0.96-0.98 (d, 3H, J=6 Hz), 1.11-1.38 (m, 2H), 1.42 (s, 9H), 1.48-1.57 (m, 1H), 1.61-1.79 (m, 3H), 2.10-2.23 (m, 1H), 2.34 (s, 3H), 2.50-2.58 (m, 1H), 2.73-2.93 (m, 3H), 3.24-3.38 (m, 1H), 3.81-3.85 (d, 2H, J=12 Hz), 3.89 (s, 2H), 4.11-4.23 (m, 1H), 4.76-4.82 (m, 1H), 7.04-7.06 (d, 1H, J=6 Hz), 7.09 (s, 1H), 7.20 (s, 1H), 7.33-7.35 (d, 1H, J=6 Hz), 7.66 (br s, 1H), 8.90 (br s, 1H).

To a solution of the above ester (0.11 mmol) in CH$_2$Cl$_2$ (3 ml), was added TFA (1 ml). The mixture was stirred at rt for 2 h, concentrated, then diluted with CH$_2$Cl$_2$ (20 ml) and H$_2$O (5 ml). The pH of the aqueous layer was adjusted to 5 with 1N NaOH and the product was extracted with CH$_2$Cl$_2$ (3×8 ml). The organic extracts were dried with Na$_2$SO$_4$ and concentrated. Due to low crude recovery, the aqueous layer and organic extracts were combined, concentrated in vacuo, and dry-loaded onto a column. The crude product was purified with 8:1:1 CH$_3$CN/MeOH/NH$_4$OH to give COMPOUND 155 (48 mg, 78% yield) as a white solid. $^1$H NMR (CDCl$_3$ with some CD$_3$OD): δ 1.11-1.13 (d, 3H, J=6 Hz), 1.50-1.91 (m, 4H), 2.22 (s, 3H), 2.50-2.63 (m, 1H), 2.72-2.81 (m, 1H), 2.96-3.17 (m, 3H), 3.22-3.48 (m, 2H), 3.60 (s, 2H), 3.67-3.77 (m, 3H), 4.02-4.12 (m, 1H), 4.16 (s, 2H), 6.84-6.86 (d, 1H, J=6 Hz), 7.03 (s, 1H), 7.06 (s, 1H), 7.17-7.18 (d, 1H, J=3 Hz). $^{13}$C NMR (CDCl$_3$ with some CD$_3$OD): δ 12.55, 18.89, 27.42, 27.76, 30.85, 36.83, 42.16, 44.35, 45.26, 48.06, 48.35, 48.63, 48.92, 49.20, 49.49, 49.77, 50.29, 50.99, 58.77, 121.39, 124.43, 126.23, 126.71, 131.88, 139.41, 146.41, 149.93, 150.81, 158.11, 165.48, 175.15. ES-MS m/z 556 (M+H).

Example 156

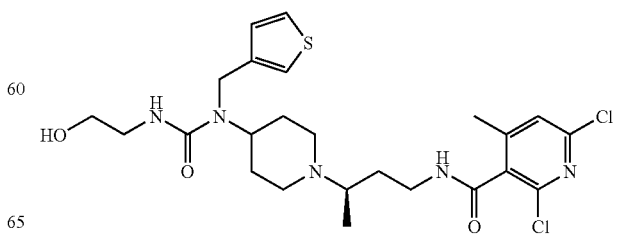

Compound 156

2,6-Dichloro-N-(3-{4-[3-(2-hydroxy-ethyl)-1-thiophen-3-ylmethyl-ureido]-piperidin-1-yl}-butyl)-4-methyl-nicotinamide To an ice cold solution of ethanolamine (9.27 ml, 154 mmol) in dichloromethane (15 ml) was added t-butyldiphenylsilyl chloride (4 ml, 15.4 mmol); the solution was allowed to stir at room temperature overnight. Following aqueous work up the crude 2-(tert-butyl-diphenyl-silanyloxy)-ethylamine was recovered as a colorless oil (4.53 g, 98%) and used as is in the next step. $^1$H NMR (CDCl$_3$) δ 1.06 (s, 9H), 1.61 (br s, 2H), 2.79 (t, 2H, J=6 Hz), 3.66 (t, 2H, J=6 Hz), 7.35-7.46 (m, 6H), 7.65-7.73 (m, 4H).

Using general procedure I, [2-(tert-butyl-diphenyl-silanyloxy)-ethylamine] and 2,6-dichloro-4-methyl-N—((R)-3-{4-[(thiophen-3-ylmethyl)-amino]-piperidin-1-yl}-butyl)-nicotinamide gave the desired urea. The resulting urea was taken up in methanol (25 ml) and concentrated HCl (0.5 ml). The resulting solution was allowed to stir at room temperature overnight. The solvent was removed and the residue was taken up in dichloromethane and washed with 1M NaOH, the organic layer was dried over Na$_2$SO$_4$. The crude was purified by column chromatography on silica gel (4% MeOH/DCM) to give COMPOUND 156 as a white solid (109 mg, 94%). $^1$H NMR (CDCl$_3$) δ 0.91-1.07 (m, 4H), 1.09-1.24 (m, 1H), 1.50-1.57 (m, 1H), 1.69-1.87 (m, 3H), 2.08-2.19 (m, 1H), 2.34 (s, 3H), 2.52-2.57 (m, 1H), 2.71-2.80 (m, 3H), 3.23-3.34 (m, 4H), 3.52-3.58 (m, 2H), 3.76-3.79 (m, 1H), 3.85 (s, 2H), 4.11-4.19 (m, 1H), 4.87-4.94 (m, 1H), 7.01 (d, 1H, J=3 Hz), 7.08 (s, 1H), 7.12 (s, 1H), 7.33-7.38 (m, 1H), 8.90 (br s, 1H); ES-MS m/z 542 (M+H).

Examples 157 to 165 were prepared following the scheme below wherein R$^1$NCO is defined in the table and R$^2$ is as shown in the individual examples.

TABLE 11

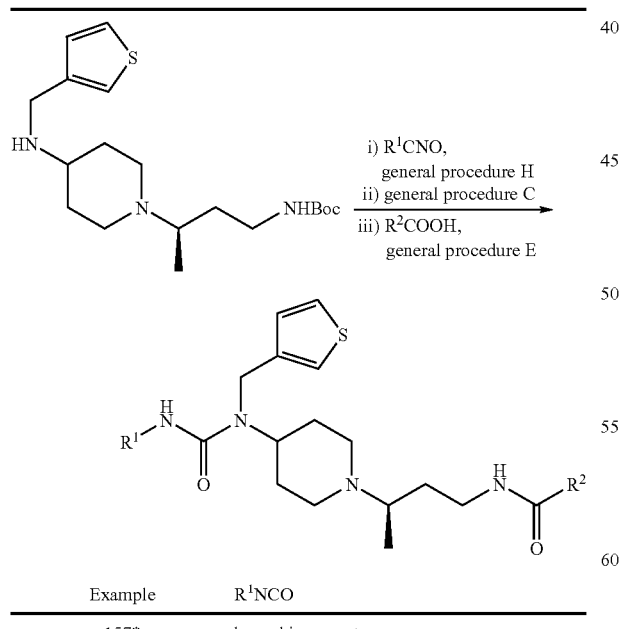

| Example | R$^1$NCO |
|---|---|
| 157* | benzyl isocyanate |
| 158* | tert-butyl isocyanate |
| 159* | phenyl isocyanate |
| 160* | Cyclohexyl isocyanate |
| 161 | 3,5-dimethylisoxazol-4-yl isocyanate |

TABLE 11-continued

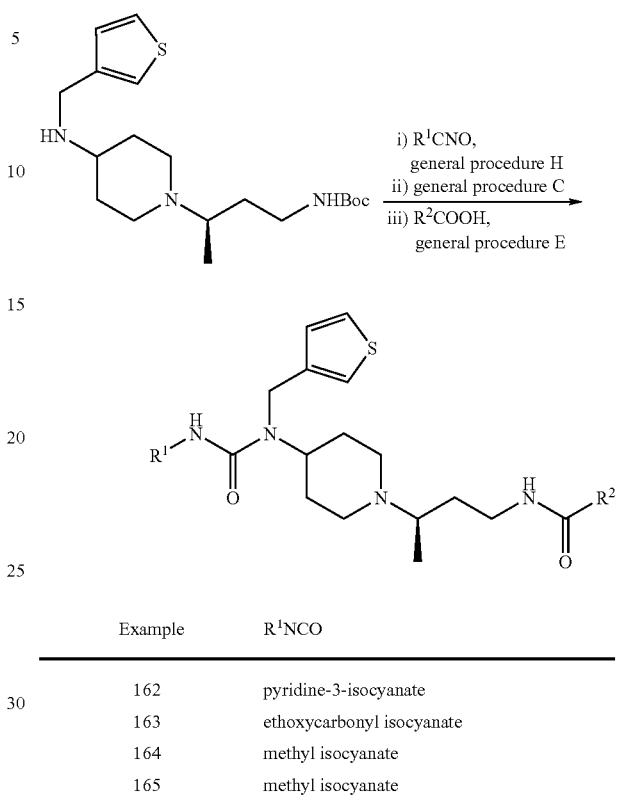

| Example | R$^1$NCO |
|---|---|
| 162 | pyridine-3-isocyanate |
| 163 | ethoxycarbonyl isocyanate |
| 164 | methyl isocyanate |
| 165 | methyl isocyanate |

*= racemic

Example 157

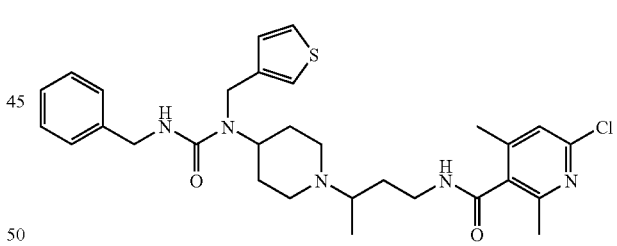

Compound 157

N-{3-[4-(3-Benzyl-1-thiophen-3-ylmethyl-ureido)-piperidin-1-yl]-butyl}-6-chloro-2,4-dimethyl-nicotinamide $^1$H NMR (CDCl$_3$) δ 0.81-0.99 (m, 1H), 0.99 (d, 3H, J=9 Hz), 0.99-1.07 (m, 1H), 1.69-1.78 (m, 3H), 2.20 (m, 1H), 2.28 (s, 3H), 2.49 (s, 3H), 2.52-2.60 (m, 1H), 2.71-2.89 (m, 3H), 3.26 (m, 1H), 3.74 (s, 2H), 3.76-3.88 (m, 1H), 4.25-4.36 (m, 1H), 4.30 (d, 2H, J=6 Hz), 4.63 (m, 1H), 6.93 (s, 1H), 7.02-7.11 (m, 4H), 7.19-7.27 (m, 4H), 7.32-7.37 (m, 1H), 8.96 (s, 1H); ES-MS m/z 569(M+H).

Example 158

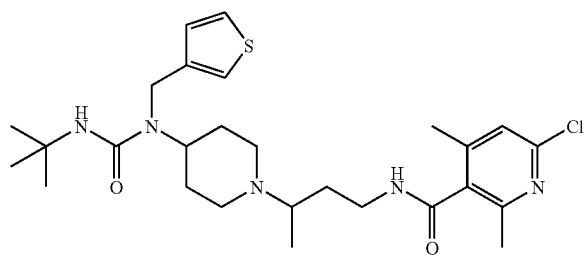

Compound 158

N-{3-[4-(3-tert-Butyl-1-thiophen-3-ylmethyl-ureido)-piperidin-1-yl]-butyl}-6-chloro-2,4-dimethyl-nicotinamide $^1$H NMR (CDCl$_3$) δ 0.77-0.93 (m, 1H), 0.98 (d, 3H, J=6 Hz), 098-1.02 (m, 1H), 1.16 (s, 9H), 1.51-1.58 (m, 1H), 1.62-1.79 (m, 3H), 2.15 (m, 1H), 2.27 (s, 3H), 2.49 (s, 3H), 2.52-2.58 (m, 1H), 2.67-2.87 (m, 3H), 3.26 (m, 1H), 3.64 (s, 2H), 3.92 (m, 1H), 4.17 (s, 1H), 4.26 (m, 1H), 6.91 (s, 1H), 7.00 (m, 1H), 7.13 (m, 1H), 7.36 (m, 1H), 8.99 (br s, 1H); ES-MS m/z 535 (M+H).

Example 159

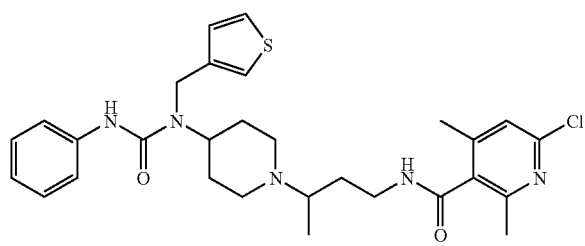

Compound 159

6-Chloro-2,4-dimethyl-N-{3-[4-(3-phenyl-1-thiophen-3-ylmethyl-ureido)-piperidin-1-yl]-butyl}-nicotinamide $^1$H NMR (CDCl$_3$) δ 0.81-1.17 (m, 5H), 1.50-1.57 (m, 1H), 1.72-1.78 (m, 3H), 2.22-2.27 (m, 1H), 2.30 (s, 3H), 2.51 (s, 3H), 2.52-2.57 (m, 1H), 2.63-2.89 (m, 4H), 3.26 (m, 1H), 3.81-3.87 (m, 3H), 4.28 (m, 1H), 6.30 (br s, 1H), 6.94-7.02 (m, 2H), 7.11-7.14 (m, 3H), 7.17-7.22 (m, 2H), 7.43-7.46 (m, 1H), 8.92 (br s, 1H); ES-MS m/z 554 (M+H).

Example 160

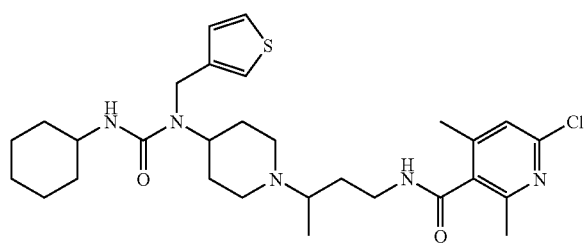

Compound 160

6-Chloro-N-{3-[4-(3-cyclohexyl-1-thiophen-3-ylmethyl-ureido)-piperidin-1-yl]-butyl}-2,4-dimethyl-nicotinamide $^1$H NMR (CDCl$_3$) δ 0.88-1.12 (m, 8H), 1.19-1.24 (m, 2H), 1.47-1.54 (m, 4H), 1.62-1.79 (m, 5H), 2.21-2.26 (m, 1H), 2.28 (s, 3H), 2.49 (s, 3H), 2.51-2.81 (m, 4H), 3.22-3.26 (m, 1H), 3.48-3.52 (m, 1H), 3.66 (s, 2H), 3.87-3.93 (m, 1H), 4.15 (d, 1H, J=6 Hz), 4.19-4.24 (m, 1H), 6.93 (s, 1H), 7.02 (d, 1H, J=3 Hz), 7.13 (s, 1H), 7.33-7.38 (m, 1H), 8.98 (br s, 1H); ES-MS m/z 560 (M+H).

Example 161

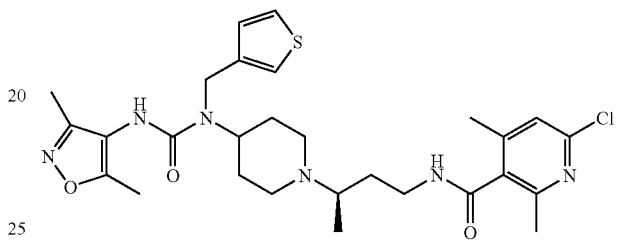

Compound 161

6-Chloro-N-(3-{4-[3-(3,5-dimethyl-isoxazol-4-yl)-1-thiophen-3-ylmethyl-ureido]-piperidin-1-yl}-butyl)-2,4-dimethyl-nicotinamide $^1$H NMR (CDCl$_3$) δ 0.87-0.91 (m, 1H), 0.99 (d, 3H, J=6 Hz), 1.01-1.09 (m, 1H), 1.49-1.61 (m, 1H), 1.72-1.81 (m, 3H), 1.97 (s, 3H), 2.13 (s, 3H), 2.19 (m, 1H), 2.29 (s, 3H), 2.51 (s, 3H), 2.61-2.66 (m, 1H), 2.72-2.80 (m, 3H), 3.21-3.28 (m, 1H), 3.85 (s, 2H), 3.86-3.89 (m, 1H), 4.25-4.34 (m, 1H), 5.37 (s, 1H), 6.93 (s, 1H), 7.11 (d, 1H, J=3 Hz), 7.25 (s, 1H), 7.43-7.45 (m, 1H), 8.87 (br s, 1H); ES-MS m/z 573 (M+H).

Example 162

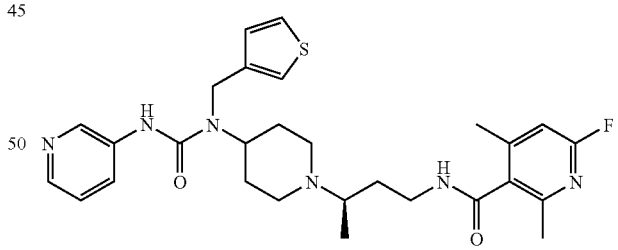

Compound 162

6-Fluoro-2,4-dimethyl-N—{(R)-3-[4-(3-pyridin-3-yl-1-thiophen-3-ylmethyl-ureido)-piperidin-1-yl]-butyl}-nicotinamide White foam. $^1$H NMR (CDCl$_3$) δ 0.92 (m, 1H), 0.94 (d, 3H, J=6 Hz), 1.04-1.19 (m, 1H), 1.49-1.56 (m, 1H), 1.66 (s, 3H), 1.75-1.78 (m, 3H), 2.21 (t, 1H, J=12 Hz), 2.33 (s, 3H), 2.47 (s, 3H), 2.62 (t, 1H, J=12 Hz), 2.74-2.95 (m, 3H), 3.31 (t, 1H, J=12 Hz), 3.85-3.91 (m, 3H), 4.33 (m, 1H), 6.32 (s, 1H), 6.44

(s, 1H), 7.05 (d, 1H, J=3 Hz), 7.19 (m, 1H), 7.24 (d, 1H, J=3 Hz), 7.45 (m, 1H), 7.74 (m, 1H), 8.10 (d, 1H, J=3 Hz), 8.20 (m, 1H), 8.81 (br s, 1H); ES-MS m/z 539 (M+H).

Example 163

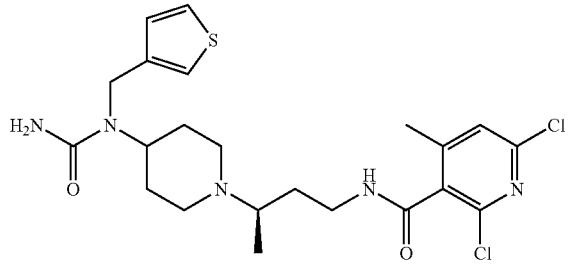

Compound 163

2,6-Dichloro-4-methyl-N—{(R)-3-[4-(1-thiophen-3-ylmethyl-ureido)-piperidin-1-yl]-butyl}-nicotinamide White foam. $^1$H NMR (CDCl$_3$) δ 0.97 (m+d, 4H), 1.24 (m, 1H), 1.53 (m, 1H), 1.67-1.76 (m, 4H), 2.15 (br t, 1H), 2.33 (s, 3H), 2.54 (br t, 1H), 2.75 (m, 1H), 2.83-2.86 (m, 2H), 3.29 (m, 1H), 3.78 (m, 1H), 3.85 (s, 2H), 4.19 (m, 1H), 4.43 (s, 2H), 7.00 (d, 1H, J=6.0 Hz), 7.05 (s, 1H), 7.12 (d, 1H, J=3.0 Hz), 7.34 (m, 1H), 8.85 (br d, 1H); ES-MS m/z 498 (M+H). Anal. Calcd. for C$_{22}$H$_{29}$N$_5$O$_2$Cl$_2$S.0.25CH$_4$O: C, 52.77; H, 5.97; N, 13.83. Found: C, 53.12; H, 6.19; N, 13.45.

Example 164

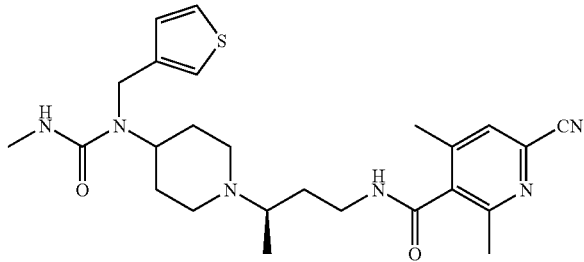

Compound 164

6-Cyano-2,4-dimethyl-N—{(R)-3-[4-(3-methyl-1-thiophen-3-ylmethyl-ureido)-piperidin-1-yl]-butyl}-nicotinamide White foam. $^1$H NMR (CDCl$_3$) δ 1.01 (br s, 3H), 1.44-1.74 (m, 5H), 2.10-2.24 (m, 1H), 2.32 (s, 3H), 2.54 (s, 3H), 2.57-2.85 (m, 9H), 3.26-3.31 (m, 1H), 3.67 (br s, 2H), 3.77-3.89 (m, 1H), 4.23 (br s, 2H), 7.01 (d, 1H, J=5 Hz), 7.12 (br s, 1H), 7.25 (s, 1H), 7.38 (dd, 1H, J=5, 3 Hz), 8.93 (br s, 1H); ES-MS m/z 483 (M+H).

Example 165

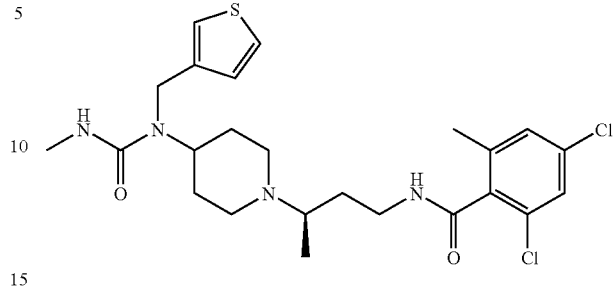

Compound 165

2,4-Dichloro-6-methyl-N—{(R)-3-[4-(3-methyl-1-thiophen-3-ylmethyl-ureido)-piperidin-1-yl]-butyl}-benzamide $^1$H NMR (CDCl$_3$) δ 0.90-1.13 (m, 5H), 1.48 (m, 1H), 1.65-1.78 (m, 3H), 2.12-2.20 (t, 1H, J=11.7 Hz), 2.30 (s, 3H), 2.53-2.60 (m, 1H), 2.66-2.67 (d, 3H, J=4.5 Hz), 2.72-2.75 (m, 1H), 2.81-2.88 (m, 2H), 3.27-3.30 (m, 1H), 3.68 (s, 2H), 3.88-3.90 (m, 1H), 4.17-4.18 (m, 1H), 4.26-4.29 (m, 1H), 6.94-6.95 (m, 1H), 7.04 (s, 1H), 7.07-7.08 (m, 1H), 7.15-7.15 (m, 1H), 7.35-7.36 (m, 1H), 8.86 (br s, 1H); ES-MS m/z 533 (M+Na).

Example 166

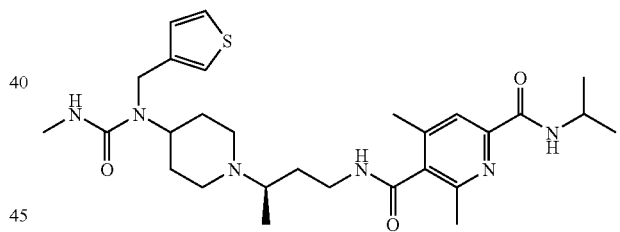

Compound 166

4,6-Dimethyl-pyridine-2,5-dicarboxylic acid 2-isopropylamide 5-({(R)-3-[4-(3-methyl-1-thiophen-3-ylmethyl-ureido)-piperidin-1-yl]-butyl}-amide)

Hydrolysis of COMPOUND 164 gave the acid and subsequent EDCI coupling with isopropylamine (similar procedure as used in EXAMPLE 210) afforded COMPOUND 166. $^1$H NMR (CDCl$_3$) δ 0.74 (m, 1H), 0.97 (d+m, 4H), 1.28 (d, 6H, J=6.0 Hz), 1.53 (m, 1H), 1.72 (m, 3H), 2.15 (br t, 1H), 2.33 (s, 3H), 2.55 (s+br t, 4H), 2.65 (s+m, 4H), 2.83 (m, 2H), 3.28 (m, 1H), 3.48-3.52 (m, 2H), 3.91 (m, 1H), 4.13 (m, 1H), 4.28 (m, 1H), 6.98 (d, 1H, J=6.0 Hz), 7.07 (s, 1H), 7.34 (m, 1H), 7.88 (s+m, 2H), 8.81 (br s, 1H); ES-MS m/z 543 (M+H).

Examples 167 to 171 were prepared following the scheme below wherein R$^1$NH$_2$ is defined in the table and R$^2$ is as shown in the individual examples.

TABLE 12

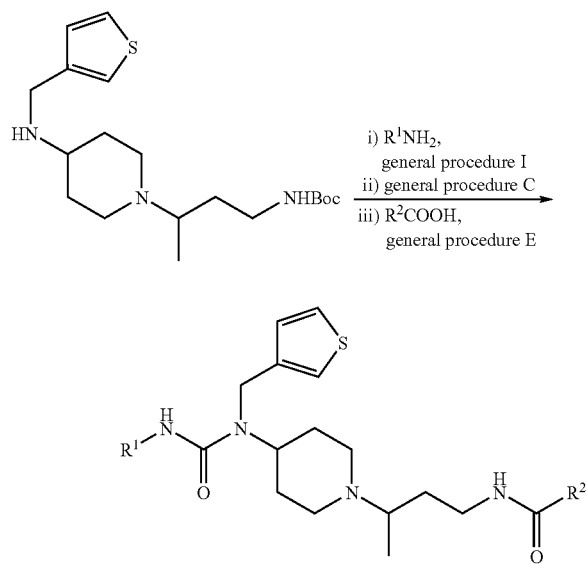

| Example | R¹NH₂ |
|---|---|
| 167* | aminopyrazine |
| 168 | 2-aminopyridine |
| 169 | 2-methoxyethylamine |
| 170 | 3-aminoisoxazole |
| 171 | O-ethylhydroxylamine hydrochloride |

*= racemic

Example 167

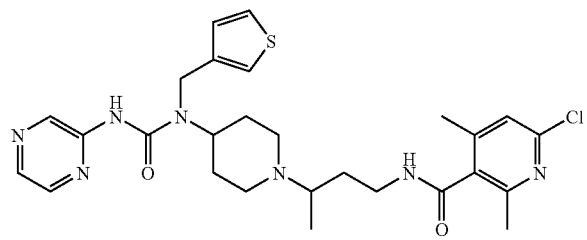

Compound 167

6-Chloro-2,4-dimethyl-N-{3-[4-(3-pyrazin-2-yl-1-thiophen-3-ylmethyl-ureido)-piperidin-1-yl]-butyl}-nicotinamide $^1$H NMR (CDCl$_3$) δ 0.92-0.96 (m, 1H), 0.99 (d, 3H, J=9 Hz), 1.12-1.19 (m, 1H), 1.51-1.56 (m, 1H), 1.69-1.81 (m, 3H), 2.19-2.24 (m, 1H), 2.30 (s, 3H), 2.51 (s, 3H), 2.56-2.63 (m, 1H), 2.69-2.79 (m, 3H), 3.23-3.29 (m, 1H), 3.78-3.84 (m, 1H), 3.94 (d, 2H, J=6 Hz), 4.22-4.31 (m, 1H), 6.97 (s, 1H), 7.02 (s, 1H), 7.09-7.15 (m, 1H), 7.24 (s, 1H), 7.38-7.45 (m, 1H), 8.05-8.08 (m, 1H), 8.19 (s, 1H), 8.69 (br s, 1H), 9.31 (s, 1H); ES-MS m/z 556 (M+H).

Example 168

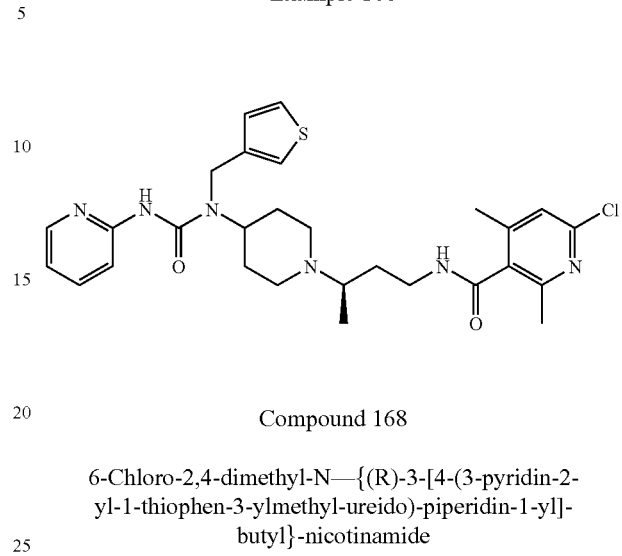

Compound 168

6-Chloro-2,4-dimethyl-N—{(R)-3-[4-(3-pyridin-2-yl-1-thiophen-3-ylmethyl-ureido)-piperidin-1-yl]-butyl}-nicotinamide $^1$H NMR (CDCl$_3$) δ 0.87-0.96 (m, 1H), 0.99 (d, 3H, J=6 Hz), 1.04-1.15 (m, 1H), 1.47-1.51 (m, 1H), 1.72-1.82 (m, 3H), 2.19-2.26 (m, 1H), 2.29 (s, 3H), 2.50 (s, 3H), 2.52-2.59 (m, 1H), 2.72-2.81 (m, 3H), 3.22-3.31 (m, 1H), 3.83-3.90 (m, 1H), 3.91 (d, 2H, J=12 Hz), 4.22-4.28 (m, 1H), 6.84-6.89 (m, 1H), 6.98 (s, 1H), 7.02-7.07 (m, 2H), 7.22 (s, 1H), 7.36-7.39 (m, 1H), 7.56-7.61 (m, 1H), 7.98 (d, 1H, J=6 Hz), 8.11-8.14 (m, 1H), 8.72 (br s, 1H); ES-MS m/z 577 (M+Na).

Example 169

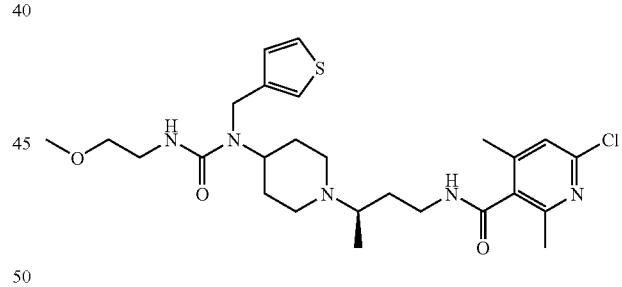

Compound 169

6-Chloro-N—((R)-3-{4-[3-(2-methoxy-ethyl)-1-thiophen-3-ylmethyl-ureido]-piperidin-1-yl}-butyl)-2,4-dimethyl-nicotinamide $^1$H NMR (CDCl$_3$) δ 0.91-0.95 (m, 1H), 0.98 (d, 3H, J=6 Hz), 0.98-1.06 (m, 1H), 1.47-1.51 (m, 1H), 1.55-1.73 (m, 3H), 2.07-2.17 (m, 1H), 2.28 (s, 3H), 2.49 (s, 3H), 2.50-2.55 (m, 1H), 2.69-2.79 (m, 3H), 3.20 (s, 3H), 3.33 (s, 4H), 3.33-3.39 (m, 1H), 3.70-3.74 (m, 2H), 3.87-3.96 (m, 1H), 4.19-4.27 (m, 1H), 4.68 (br s, 1H), 6.93 (s, 1H), 7.01-7.04 (m, 1H), 7.12 (br s, 1H), 7.32-7.36 (m, 1H), 8.84 (br s, 1H); ES-MS m/z 536 (M+H).

Example 170

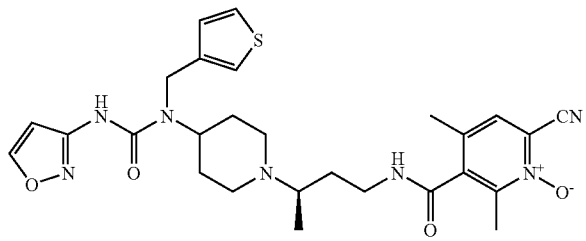

Compound 170

6-Cyano-N—{(R)-3-[4-(3-isoxazol-3-yl-1-thiophen-3-ylmethyl-ureido)-piperidin-1-yl]-butyl}-2,4-dimethyl-1-oxy-nicotinamide White solid. $^1$H NMR (CDCl$_3$) δ 1.00-1.02 (d, 3H, J=6 Hz), 1.28-1.70 (m, 4H), 1.74-1.91 (m, 3H), 2.17-2.32 (m, 1H), 2.34 (s, 3H), 2.41 (s, 3H), 2.50-2.63 (m, 1H), 2.71-2.92 (m, 3H), 3.60-3.75 (m, 1H), 4.12-4.25 (m, 1H), 4.29 (s, 2H), 6.91-6.92 (d, 1H, J=3 Hz), 6.99-7.01 (d, 1H, J=6 Hz), 7.18 (s, 1H), 7.23 (s, 1H), 7.37-7.38 (d, 1H, J=3 Hz), 7.39 (s, 1H), 8.14 (br s, 1H), 8.19-8.20 (d, 1H, J=3 Hz); $^{13}$C NMR (CDCl$_3$) δ 13.42, 15.05, 18.39, 30.21, 30.67, 32.05, 35.21, 38.53, 42.45, 44.12, 44.79, 50.92, 53.35, 53.66, 57.79, 76.53, 99.23, 111.51, 121.49, 123.95, 125.87, 127.49, 129.60, 133.83, 138.44, 139.53, 147.02, 153.91, 157.26, 158.72, 163.80; ES-MS m/z 574 (M+Na).

Example 171

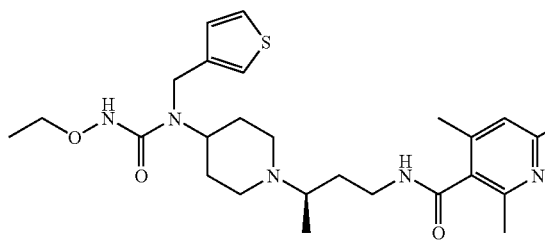

Compound 171

6-Chloro-2,4-dimethyl-N—{(R)-3-[4-(3-ethoxy-1-thiophen-3-ylmethyl-ureido)-piperidin-1-yl]-butyl}-nicotinamide $^1$H NMR (CDCl$_3$) δ 0.78-0.91 (m, 1H), 1.00 (d, 3H, J=6 Hz), 1.00-1.07 (m, 1H), 1.17 (t, 3H, J=3 Hz), 1.46-1.51 (m, 1H), 1.61-1.75 (m, 3H), 2.12-2.22 (m, 1H), 2.27 (s, 3H), 2.49 (s, 3H), 2.53-2.63 (m, 1H), 2.65-2.74 (m, 1H), 2.79-2.87 (m, 2H), 3.23-3.31 (m, 1H), 3.68-3.72 (m, 2H), 3.80 (q, 2H, J=6 Hz), 3.87-3.94 (m, 1H), 4.18-4.27 (m, 1H), 6.94 (d, 2H, J=6 Hz), 7.04 (d, 1H, J=3 Hz), 7.12 (br s, 1H), 7.35-7.41 (m, 1H), 8.78 (br s, 1H); ES-MS m/z 544 (M+Na).

Example 172

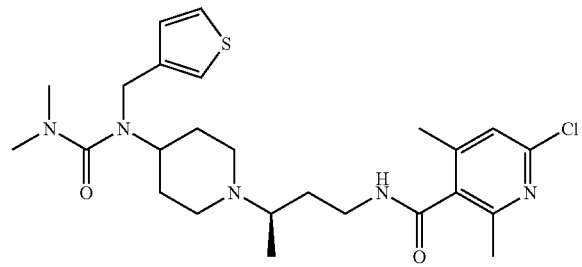

Compound 172

6-Chloro-N—{(R)-3-[4-(3,3-dimethyl-1-thiophen-3-ylmethyl-ureido)-piperidin-1-yl]-butyl}-2,4-dimethyl-nicotinamide To a solution of 6-chloro-2,4-dimethyl-N—((R)-3-{4-[(thiophen-3-ylmethyl)-amino]-piperidin-1-yl}-butyl)-nicotinamide (49 mg, 0.11 mmol) in 1,2-dichloroethane (5 ml) was added DIPEA (0.2 ml, 1.15 mmol) followed by dimethyl carbamylchloride (60 μL, 0.34 mmol) and the reaction stirred at 60° C. overnight. The solution was cooled, treated with saturated aqueous NaHCO$_3$ (25 ml) and extracted with CH$_2$Cl$_2$ (3×15 ml). The combined organic extracts were dried (Na$_2$SO$_4$), filtered, and concentrated. Purification of the crude material by column chromatography on silica gel (CH$_2$Cl$_2$/MeOH, 96:4 then 9:1) provided COMPOUND 172 (18 mg, 32%) as a pale yellow foam. $^1$H NMR (CDCl$_3$) δ 1.01-1.07 (m, 3H), 1.53-1.79 (m, 5H), 2.15-2.25 (m, 1H), 2.30 (s, 3H), 2.51 (s, 3H), 2.52-2.61 (m, 1H), 2.76 (s, 6H), 2.77-2.91 (m, 4H), 3.35-3.46 (m, 2H), 3.70-3.98 (m, 3H), 6.92 (dd, 1H, J=4.8, 0.9 Hz), 6.96 (s, 1H), 7.01-7.04 (m, 1H), 7.23 (dd, 1H, J=4.8, 3 Hz), 8.32 (br s, 1H); $^{13}$C NMR (CDCl$_3$) δ 13.60, 19.26, 22.54, 29.76, 30.54, 31.52, 38.73, 39.55, 43.50, 44.35, 52.28, 56.19, 60.34, 122.01, 122.86, 126.22, 128.02, 133.32, 137.56, 148.09, 150.38, 155.79, 167.34, 182.46; ES-MS m/z 506 (M+H). Anal. Calcd. for C$_{25}$H$_{36}$N$_5$O$_2$SCl.0.9CH$_3$OH.0.1CH$_2$Cl$_2$: C, 57.47; H, 7.38; N, 12.89. Found: C, 57.69; H, 7.02; N, 12.53.

Examples 173 to 175 were prepared following the scheme below wherein R$^1$NCO is defined in the table and R$^2$ is as shown in the individual examples.

TABLE 13

| Example | R$^1$NCO |
|---|---|
| 173 | N-(trifluoroacetyl)piperidine-4-isocyanate |
| 174 | ethyl 4-isocyanatobenzoate |
| 175 | methyl 3-isocyanatobenzoate |

Example 173

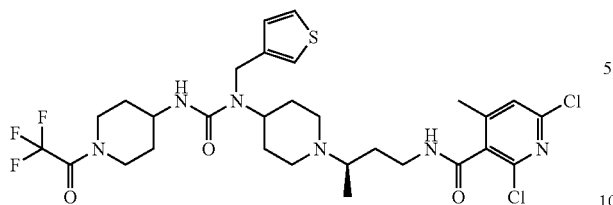

Compound 173

2,6-Dichloro-4-methyl-N—[(R)-3-(4-{1-thiophen-3-ylmethyl-3-[1-(2,2,2-trifluoro-acetyl)-piperidin-4-yl]-ureido}-piperidin-1-yl)-butyl]-nicotinamide $^1$H NMR (CDCl$_3$) δ 0.94-1.05 (m, 4H), 1.07-1.22 (m, 4H), 1.69-1.77 (m, 3H), 1.86-1.99 (m, 2H), 2.11-2.24 (m, 1H), 2.34 (s, 3H), 2.58-2.69 (m, 1H), 2.78-3.01 (m, 4H), 3.19-3.41 (m, 2H), 3.74-3.92 (m, 5H), 4.12-4.39 (m, 3H), 6.98 (d, 1H, J=3 Hz), 7.04 (s, 1H), 7.12 (s, 1H), 7.36-7.41 (m, 1H), 8.91 (br s, 1H); ES-MS m/z 677 (M+H).

Example 174

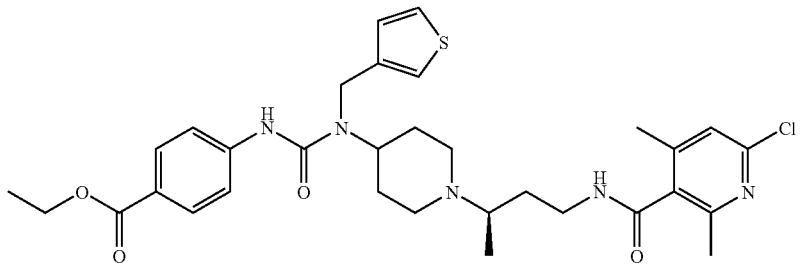

Compound 174

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid ethyl ester $^1$H NMR (CDCl$_3$) δ 0.83-1.17 (m, 5H), 1.36 (t, 3H, J=7.1 Hz), 1.48-1.85 (m, 4H), 2.15-2.28 (m, 1H), 2.30 (s, 3H), 2.50 (s, 3H), 2.56-2.67 (m, 1H), 2.71-2.93 (m, 3H), 3.23-3.36 (m, 1H), 3.79-3.96 (m, 3H), 4.26-4.39 (m, 1H), 4.32 (q, 2H, J=7.1 Hz), 6.51 (br s, 1H), 6.95 (s, 1H), 7.12 (d, 1H, J=3.9 Hz), 7.19 (d, 2H, J=8.8 Hz), 7.28 (dd, 1H, J=1.8, 0.9 Hz), 7.46 (dd, 1H, J=5.1, 2.8 Hz), 7.89 (d, 2H, J=8.8 Hz), 8.83 (br s, 1H); ES-MS m/z 626 (M+H), 628 (M+H+2).

Example 175

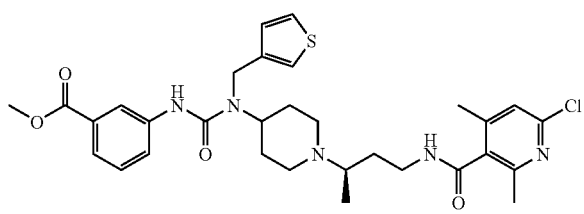

Compound 175

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid methyl ester To a 0° C. solution of methyl 3-aminobenzoate (188 mg, 1.24 mmol) and NEt$_3$ (0.26 ml, 1.9 mmol) in CH$_2$Cl$_2$ (4 ml) was added triphosgene (375 mg, 1.26 mmol). The resulting mixture was stirred at 0° C. for 15 minutes and at room temperature for an additional 2 hours. The solution was diluted with CH$_2$Cl$_2$ (30 ml) and was washed with H$_2$O (25 ml). The organic solution was dried (Na$_2$SO$_4$), filtered and concentrated under reduced pressure, giving the crude isocyanate as a light yellow solid (222 mg, quantitative). $^1$H NMR (CDCl$_3$) δ 3.90 (s, 3H), 7.24 (d, 1H, J=7.9 Hz), 7.37 (t, 1H, J=7.9 Hz), 7.72 (s, 1H), 7.83 (d, 1H, J=7.9 Hz).

$^1$H NMR (CDCl$_3$) δ 0.84-1.15 (m, 2H), 0.98 (d, 3H, J=7.0 Hz), 1.47-1.57 (m, 1H), 1.68-1.83 (m, 3H), 2.14-2.23 (m, 1H), 2.28 (s, 3H), 2.49 (s, 3H), 2.55-2.63 (m, 1H), 2.69-2.89 (m, 3H), 3.21-3.32 (m, 1H), 3.80-3.95 (m, 3H), 3.86 (s, 3H), 4.30 (tt, 1H, J=11.9, 3.5 Hz), 6.41 (s, 1H), 6.95 (s, 1H), 7.12 (d, 1H, J=4.7 Hz), 7.24-7.30 (m, 2H), 7.41-7.46 (m, 2H), 7.65 (d, 1H, J=7.7 Hz), 7.71 (s, 1H), 8.83 (br d, 1H, J=5.3 Hz); ES-MS m/z 612 (M+H), 614 (M+H+2).

Example 176

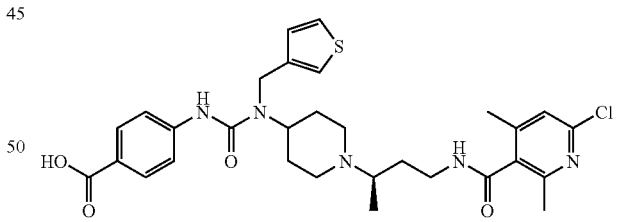

Compound 176

4-[3-(1-{(R)-3-[(6-chloro-2,4-dimethyl-pyridine-3-carbonyl)-amino]-1-methyl-propyl}-piperidin-4-yl)-3-thiophen-3-ylmethyl-ureido]-benzoic acid A solution of 4-[3-(1-{(R)-3-[(6-chloro-2,4-dimethyl-pyridine-3-carbonyl)-amino]-1-methyl-propyl}-piperidin-4-yl)-3-thiophen-3-ylmethyl-ureido]-benzoic acid ethyl ester (COMPOUND 174) (32 mg, 0.051 mmol) and 3.8M NaOH (0.07 ml, 0.27 mmol) in MeOH (0.45 ml) was stirred at 55° C. for 70 minutes. Once cooled, the reaction was diluted with $H_2O$ (10 ml), the pH was adjusted to 5 and the mixture was extracted with $CHCl_3$ (20 ml×4). The organic solution was dried ($Na_2SO_4$), filtered and concentrated under reduced pressure, giving COMPOUND 176 as a white solid (27.0 mg, 88%). $^1H$ NMR (MeOH-$d_4$) δ 1.26 (d, 3H, J=6.6 Hz), 1.69-1.81 (m, 1H), 1.85-2.10 (m, 4H), 2.35 (s, 3H), 2.49 (s, 3H), 2.68-2.78 (m, 1H), 2.82-2.93 (m, 1H), 3.05-3.22 (m, 3H), 3.36-3.61 (m, 3H), 4.25-4.36 (m, 1H), 4.62 (s, 2H), 7.10 (dd, 1H, J=5.0, 1.0 Hz), 7.26 (s, 1H), 7.28 (d, 1H, J=1.8 Hz), 7.42 (d, 2H, J=8.8 Hz), 7.44 (dd, 1H, J=5.0, 3.2 Hz), 7.92 (d, 2H, J=8.8 Hz); ES-MS m/z 598 (M+H), 600 (M+H+2).

Example 177

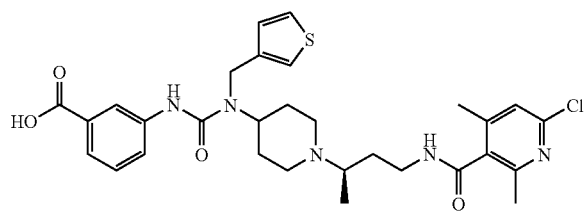

Compound 177

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid A solution of 3-[3-(1-{(R)-3-[(6-chloro-2,4-dimethyl-pyridine-3-carbonyl)-amino]-1-methyl-propyl}-piperidin-4-yl)-3-thiophen-3-ylmethyl-ureido]-benzoic acid methyl ester (COMPOUND 175) (47 mg, 0.077 mmol) and 3.8M NaOH (0.12 ml, 0.46 mmol) in MeOH (0.65 ml) was stirred at 55° C. for 80 minutes. Once cooled, the reaction was diluted with $H_2O$ (10 ml), the pH was adjusted to 5 and the mixture was extracted with $CHCl_3$ (20 ml×4). The organic solution was dried ($Na_2SO_4$), filtered and concentrated under reduced pressure, giving COMPOUND 177 as a white solid (27.3 mg, 59%). $^1H$ NMR (MeOH-$d_4$) δ 1.33 (d, 3H, J=6.0 Hz), 1.75-2.18 (m, 6H), 2.33 (s, 3H), 2.48 (s, 3H), 2.86-3.08 (m, 2H), 3.20-3.38 (m, 3H), 3.41-3.60 (m, 2H), 4.30-4.41 (m, 1H), 4.61 (s, 2H), 7.08 (d, 1H, J=4.7 Hz), 7.25 (s, 1H), 7.26 (br s, 1H), 7.32-7.43 (m, 4H), 7.54 (d, 1H, J=8.0 Hz), 7.68 (d, 1H, J=8.0 Hz), 7.92 (br s, 1H); ES-MS m/z 598 (M+H), 600 (M+H+2).

Example 178

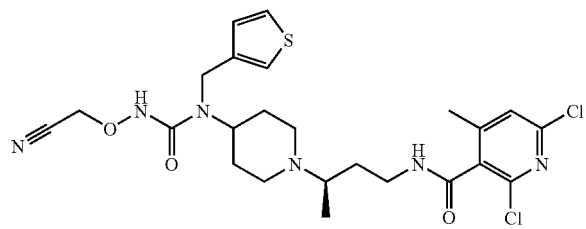

Compound 178

2,6-Dichloro-4-methyl-N—{(R)-3-[4-(3-(cyanomethoxy)-1-thiophen-3-ylmethyl-ureido)-piperidin-1-yl]-butyl}-nicotinamide To a solution of N-hydroxyphthalimide (5.20 g, 31.88 mmol) in DMF (20 ml) was added bromoacetonitrile (3.0 ml, 45.02 mmol) and $Et_3N$ (10.0 ml, 71.8 mmol) and the reaction stirred at room temperature for 2 d. The mixture was diluted with EtOAc (50 ml) and brine (40 ml) and the organic layer was washed with brine (4×20 ml) and 1 N NaOH (30 ml), dried ($Na_2SO_4$) and concentrated to afford (1,3-dioxo-1,3-dihydro-isoindol-2-yloxy)-acetonitrile (2.3 g, 36%) as a beige solid. $^1H$ NMR ($CDCl_3$) δ 4.96 (s, 2H), 7.80-7.84 (m, 2H), 7.89-7.92 (m, 2H).

To a suspension of the phthalimide from above (1.15 g, 5.69 mmol) in 1,2-dichloroethane (15 ml) was added hydrazine (0.20 ml, 6.43 mmol) and the reaction stirred at 50° C. for 1 h then room temperature overnight. Another portion of hydrazine was added (0.20 ml, 6.43 mmol) and the mixture heated to 60° C. for 3 additional h. The reaction was then cooled to 0° C. and filtered, washing with $CH_2Cl_2$. To the resultant filtrate was added 1,1'-carbonyldiimidazole (0.82 g, 5.06 mmol) and the solution heated to 60° C. for 2 h before adding 2,6-dichloro-4-methyl-N—((R)-3-{4-[(thiophen-3-ylmethyl)-amino]-piperidin-1-yl}-butyl)-nicotinamide (105 mg, 0.23 mmol) as a solid in one portion. The mixture was then stirred at 60° C. overnight, cooled and diluted with 1 N NaOH (25 ml). The layers were separated and the aqueous layer was extracted with $CH_2Cl_2$ (2×10 ml). The combined organic extracts were dried ($Na_2SO_4$), concentrated and purified by column chromatography on silica gel ($CH_2Cl_2$/MeOH/$NH_4OH$, 96:4:0 then 9:1:0 then 88:10:2) followed by radial chromatography on silica gel (1 mm plate, $CH_2Cl_2$/MeOH/$NH_4OH$, 100:1:1 then 50:1:1) to give COMPOUND 178 (45 mg, 35%) as a white foam. $^1H$ NMR ($CDCl_3$) δ 0.98-1.11 (m, 1H), 0.99 (d, 3H, J=6.6 Hz), 1.25-1.30 (m, 1H), 1.51-1.58 (m, 1H), 1.70-1.79 (m, 3H), 2.18 (dt, 1H, J=11.7, 1.8 Hz), 2.34 (s, 3H), 2.57 (dt, 1H, J=11.7, 1.8 Hz), 2.75-2.89 (m, 3H), 3.31-3.35 (m, 1H), 3.78-3.85 (m, 1H), 3.87 (s, 2H), 4.10-4.18 (m, 1H), 4.54 (s, 2H), 7.00 (dd, 1H, J=5.1, 1.2 Hz), 7.06 (br s, 1H), 7.14-7.16 (m, 1H), 7.35 (br s, 1H), 7.41 (dd, 1H, J=5.1, 3 Hz), 8.64 (br d, 1H); $^{13}C$ NMR ($CDCl_3$) δ 13.83, 19.54, 30.25, 30.95, 40.46, 41.49, 43.70, 51.98, 53.53, 60.49, 61.47, 115.86, 122.15, 124.79, 126.40, 128.30, 132.87, 138.41, 146.96, 150.33, 151.32, 158.66, 164.48; ES-MS m/z 553 (M+H). Anal. Calcd. for $C_{24}H_{30}N_6O_3SCl_2 \cdot 0.7CH_2Cl_2$: C, 48.40; H, 5.16; N, 13.71. Found: C, 48.31; H, 5.18; N, 13.42.

Examples 179 to 187 were prepared following the scheme below wherein $R^1NHCO_2Ph$ or $R^1NHCO_2PhNO_2$ is defined in the table and $R^2$ is as shown in the individual examples.

TABLE 14

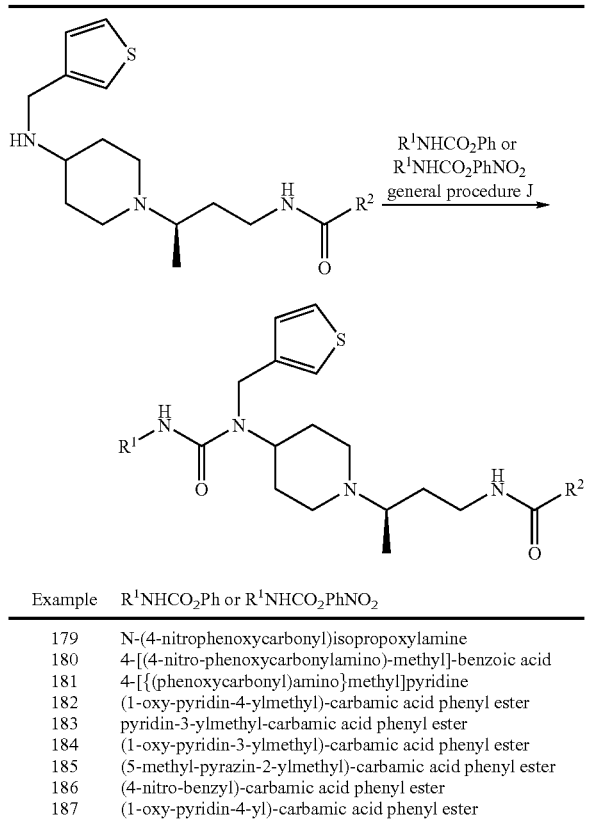

| Example | R¹NHCO₂Ph or R¹NHCO₂PhNO₂ |
|---|---|
| 179 | N-(4-nitrophenoxycarbonyl)isopropoxylamine |
| 180 | 4-[(4-nitro-phenoxycarbonylamino)-methyl]-benzoic acid |
| 181 | 4-[{(phenoxycarbonyl)amino}methyl]pyridine |
| 182 | (1-oxy-pyridin-4-ylmethyl)-carbamic acid phenyl ester |
| 183 | pyridin-3-ylmethyl-carbamic acid phenyl ester |
| 184 | (1-oxy-pyridin-3-ylmethyl)-carbamic acid phenyl ester |
| 185 | (5-methyl-pyrazin-2-ylmethyl)-carbamic acid phenyl ester |
| 186 | (4-nitro-benzyl)-carbamic acid phenyl ester |
| 187 | (1-oxy-pyridin-4-yl)-carbamic acid phenyl ester |

Example 179

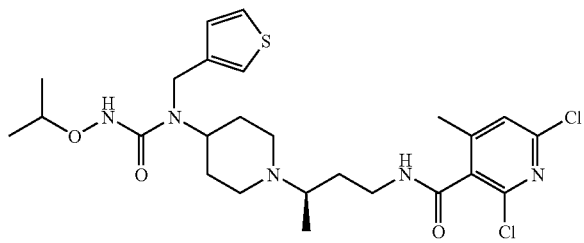

Compound 179

2,6-Dichloro-N—{(R)-3-[4-(3-isopropoxy-1-thiophen-3-ylmethyl-ureido)-piperidin-1-yl]-butyl}-4-methyl-nicotinamide To a suspension of N-hydroxyphthalimide (2.52 g, 15.45 mmol) in THF (60 ml) was added triphenylphosphine (4.10 g, 15.63 mmol), 2-propanol (1.2 ml, 15.67 mmol) and diethyl azodicarboxylate (2.68 ml, 17.0 mmol) and the reaction stirred overnight. The mixture was concentrated and purified by column chromatography on silica gel (Hexanes/EtOAc, 4:1) to afford 2-isopropoxy-isoindole-1,3-dione (2.59 g, 82%) as a white solid. $^1$H NMR (CDCl$_3$) δ 1.38 (d, 6H, J=6 Hz), 4.52-4.58 (m, 1H), 7.73-7.76 (m, 2H), 7.83-7.85 (m, 2H).

To a solution of the phthalimide from above (2.56 g, 12.5 mmol) in CH$_2$Cl$_2$ (12 ml) was added methylhydrazine (0.70 ml, 13.16 mmol) and the reaction stirred at room temperature overnight. The resultant suspension was then filtered, washing with Et$_2$O and the filtrate concentrated in vacuo (careful product is volatile) to provide O-isopropyl-hydroxylamine (200 mg) as a yellow oil.

To as solution of the crude O-isopropyl-hydroxylamine (200 mg) from above in CH$_2$Cl$_2$ (5 ml) was added Et$_3$N (0.30 ml, 2.16 mmol) and 4-nitrophenyl chloroformate (430 mg, 2.13 mmol) and the mixture stirred at room temperature for 30 min. before diluting with CH$_2$Cl$_2$ (20 ml) and brine (15 ml). The aqueous layer was extracted with CH$_2$Cl$_2$ (1×15 ml) and the combined organic extracts dried (Na$_2$SO$_4$), concentrated and purified by column chromatography on silica gel (Hexanes/EtOAc, 4:1) to afford N-(4-nitrophenoxycarbonyl)isopropoxylamine (290 mg) as a yellow oil.

COMPOUND 179 was isolated as a yellow foam. $^1$H NMR (CDCl$_3$) δ 0.91-1.03 (m, 1H), 0.98 (d, 3H, J=6.6 Hz), 1.12 (d, 6H, J=6 Hz), 1.15-1.25 (m, 1H), 1.48-1.55 (m, 1H), 1.68-1.78 (m, 3H), 2.16 (br t, 1H, J=11.1 Hz), 2.32 (s, 3H), 2.55 (br t, 1H, J=11.1 Hz), 2.72-2.86 (m, 3H), 3.26-3.31 (m, 1H), 3.79-3.83 (m, 1H), 3.80 (s, 2H), 3.93-3.98 (m, 1H), 4.13-4.25 (m, 1H), 6.86 (s, 1H), 6.99 (d, 1H, J=4.8 Hz), 7.03 (s, 1H), 7.11 (br s, 1H), 7.37 (dd, 1H, J=4.8, 3 Hz), 8.83 (br d, 1H); $^{13}$C NMR (CDCl$_3$) δ 13.82, 19.53, 20.84, 30.30, 30.75, 31.08, 40.62, 41.49, 43.67, 52.15, 52.86, 60.74, 77.01, 121.74, 124.71, 126.38, 127.93, 132.99, 139.31, 147.05, 150.22, 151.29, 159.59, 164.43; ES-MS m/z 556 (M+H). Anal. Calcd. for C$_{25}$H$_{35}$N$_5$O$_3$SCl$_2$.0.6CH$_2$Cl$_2$: C, 50.61; H, 6.01; N, 11.53. Found: C, 50.88; H, 5.99; N, 11.41.

Example 180

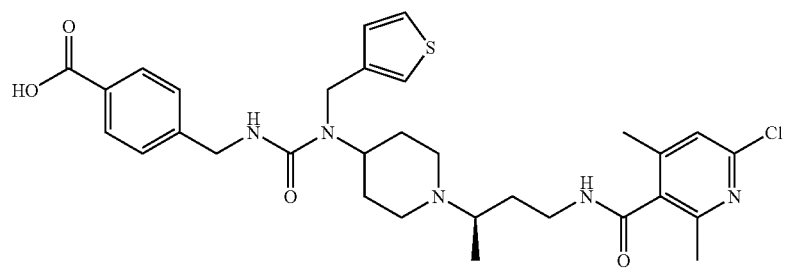

245

Compound 180

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid To a stirred slurry of 4-aminomethyl benzoic acid (1.51 g, 10 mmol) and NaHCO$_3$ (2.0 g, 24 mmol) in H$_2$O (30 ml) was added a solution of 4-nitrophenyl chloroformate (2.02 g, 10 mmol) in CH$_2$Cl$_2$ (25 ml) at room temperature. The mixture was stirred for 3 hours and then concentrated under reduced pressure. The mixture was diluted with H$_2$O (100 ml) and conc. HCl was added to pH~1. The mixture was filtered and the solid was dried in vacuo. Purification by column chromatography on silica gel (10:0 to 9:1, CH$_2$Cl$_2$/MeOH) afforded the desired nitrophenylcarbamate as a white solid (1.03 g, 29%).

$^1$H NMR (CD$_3$OD) δ 1.29 (d, 3H, J=6.6 Hz), 1.75-2.02 (m, 5H), 2.33 (s, 3H), 2.47 (s, 3H), 2.82 (t, 1H, J=11.0 Hz), 2.95 (t, 1H, J=11.0 Hz), 3.15-3.28 (m, 3H), 3.42-3.61 (m, 3H), 4.22-4.35 (m, 1H), 4.43 (s, 2H), 4.48 (s, 2H), 6.83 (br s, 1H), 7.01 (d, 1H, J=5.1 Hz), 7.16 (d, 1H, J=3.0 Hz), 7.23 (d, 2H, J=8.1 Hz), 7.25 (s, 1H), 7.39 (dd, 1H, J=3.0, 5.1 Hz), 7.89 (d, 2H, J=8.1 Hz); $^{13}$C NMR (CD$_3$OD) δ 12.81, 17.90, 20.91, 28.64, 28.84, 31.59, 37.05, 42.02, 44.13, 46.57, 49.99, 52.26, 59.12, 121.28, 122.98, 126.40, 126.72 (2C), 129.60 (2C), 144.15; ES-MS m/z 612 (M+H). Anal Calcd. for C$_{31}$H$_{38}$N$_5$SO$_4$Cl.0.5H$_2$O: C, 59.94; H, 6.33; N, 11.27. Found: C, 59.61; H, 6.38; N, 11.44.

Example 181

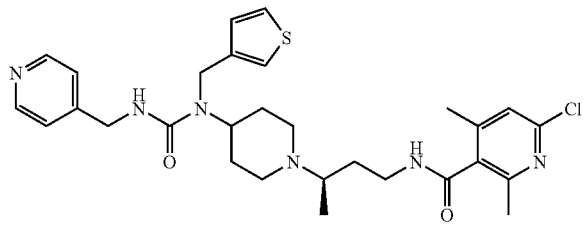

Compound 181

6-Chloro-2,4-dimethyl-N—{(R)-3-[4-(3-pyridin-4-ylmethyl-1-thiophen-3-ylmethyl-ureido)-piperidin-1-yl]-butyl}-nicotinamide To a 0° C. solution of 4-(aminomethyl)pyridine (0.50 ml, 5.0 mmol) and NEt$_3$ (1.0 ml, 7.2 mmol) in CH$_2$Cl$_2$ (25 ml) was added dropwise phenyl chloroformate (0.60 ml, 4.8 mmol) (Yoakim, C.; Ogilvie, W. W.; Cameron, D. R.; Chabot, C.; Guse, I.; Haché, B.; Naud, J.; O'Meara, J. A.; Plante, R.; Déziel, R. J. Med. Chem., 1998, 41, 2882-2891). The resulting yellow solution was stirred at 0° C. for 60 minutes and most of the solvent was removed under reduced pressure. The residue was taken up into EtOAc (75 ml) and washed with H$_2$O (50 ml) and brine (50 ml). The organic solution was dried (Na$_2$SO$_4$), filtered and concentrated under reduced pressure. Purification by flash column chromatography on silica (CH$_2$Cl$_2$/MeOH, 19:1) gave the carbamate as a yellow solid (704 mg, 64%). $^1$H NMR (CDCl$_3$) δ 4.44 (d, 2H, J=6.2 Hz), 5.90 (br s, 1H), 7.13-7.26 (m, 5H), 7.33-7.39 (m, 2H), 8.56 (d, 2H, J=5.6 Hz).

COMPOUND 181 was isolated as a white foam. $^1$H NMR (CDCl$_3$) δ 0.78-0.92 (m, 1H), 0.94-1.10 (m, 1H), 0.98 (d, 3H, J=6.6 Hz), 1.47-1.56 (m, 1H), 1.65-1.80 (m, 3H), 2.11-2.21 (m, 1H), 2.28 (s, 3H), 2.49 (s, 3H), 2.52-2.62 (m, 1H), 2.67-2.75 (m, 1H), 2.78-2.87 (m, 2H), 3.21-3.31 (m, 1H), 3.73 (d, 1H, J=17.7 Hz), 3.80 (d, 1H, J=17.7 Hz), 3.83-3.93 (m, 1H), 4.23-4.34 (m, 1H), 4.31 (d, 2H, J=5.6 Hz), 4.74 (br t, 1H, J=5.7 Hz), 6.93-6.97 (m, 3H), 7.06 (dd, 1H, J=4.8, 0.9 Hz), 7.14 (d, 1H, J=1.2 Hz), 7.39 (dd, 1H, J=4.8, 2.6 Hz), 8.46 (d, 2H, J=6.4 Hz), 8.91 (br d, 1H, J=6.0 Hz); $^{13}$C NMR (CDCl$_3$) δ 13.34, 18.65, 21.94, 29.92, 30.35, 30.91, 40.10, 41.30, 43.17, 43.42, 51.77, 51.97, 60.52, 121.22, 121.74, 122.31, 125.98, 127.34, 132.85, 139.26, 147.49, 148.57, 149.67, 149.87, 155.29, 157.68, 166.84; ES-MS m/z 569 (M+H), 571 (M+H+2).

Example 182

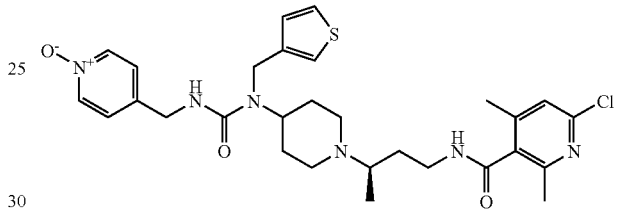

Compound 182

6-Chloro-2,4-dimethyl-N—((R)-3-{4-[3-(1-oxy-pyridin-4-ylmethyl)-1-thiophen-3-ylmethyl-ureido]-piperidin-1-yl}-butyl)-nicotinamide A solution of 4-[{(phenoxycarbonyl)amino}methyl]pyridine (230 mg, 1.01 mmol) and MMPP (80%, 623 mg, 1.01 mmol) in MeOH (3.5 ml) and CH$_2$Cl$_2$ (3.5 ml) was stirred at room temperature for 4 hours. After the first 1.5 hours, an additional portion (127 mg, 0.21 mmol) of MMPP was added. The reaction was diluted with saturated aqueous NaHCO$_3$ (30 ml) and was extracted with CH$_2$Cl$_2$ (25 ml×3). The combined organic solution was dried (Na$_2$SO$_4$), filtered and concentrated under reduced pressure, giving the crude N-oxide as a white solid (206 mg, 0.84 mmol, 84%). $^1$H NMR (CDCl$_3$) δ 4.43 (d, 2H, J=6.2 Hz), 5.84 (br s, 1H), 7.13 (d, 2H, J=7.9 Hz), 7.19-7.29 (m, 3H), 7.34-7.40 (m, 2H), 8.17 (d, 2H, J=7.1 Hz).

COMPOUND 182 was isolated as a white foam. $^1$H NMR (CDCl$_3$) δ 0.77-1.12 (m, 2H), 0.98 (d, 3H, J=6.6 Hz), 1.47-1.82 (m, 4H), 2.11-2.22 (m, 1H), 2.28 (s, 3H), 2.49 (s, 3H), 2.56-2.63 (m, 1H), 2.67-2.89 (m, 3H), 3.21-3.33 (m, 1H), 3.71-3.92 (m, 3H), 4.20-4.33 (m, 1H), 4.25 (d, 2H, J=6.3 Hz), 4.80 (br s, 1H), 6.93 (s, 1H), 6.95 (d, 2H, J=6.6 Hz), 7.04 (d, 1H, J=5.1 Hz), 7.13 (d, 1H, J=1.2 Hz), 7.39 (dd, 1H, J=5.0, 2.9 Hz), 8.05 (d, 2H, J=6.6 Hz), 8.87 (br s, 1H); $^{13}$C NMR (CDCl$_3$) δ 13.36, 18.66, 21.94, 29.88, 30.49, 30.81, 39.91, 41.32, 42.75, 43.30, 51.66, 52.10, 60.33, 121.16, 122.31, 124.46, 126.04, 127.33, 132.85, 138.66, 139.32, 139.45, 147.52, 149.82, 155.28, 157.57, 166.87; ES-MS m/z 585 (M+H), 587 (M+H+2).

Example 183

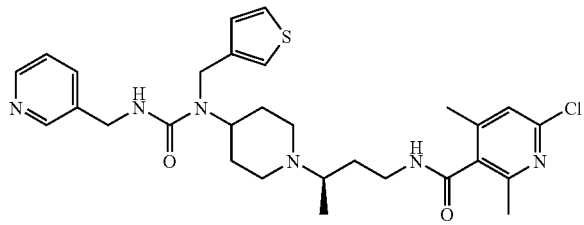

Compound 183

6-Chloro-2,4-dimethyl-N—{(R)-3-[4-(3-pyridin-3-ylmethyl-1-thiophen-3-ylmethyl-ureido)-piperidin-1-yl]-butyl}-nicotinamide To a 0° C. solution of 3-(aminomethyl)pyridine (0.50 ml, 4.9 mmol) and NEt$_3$ (1.0 ml, 7.2 mmol) in CH$_2$Cl$_2$ (25 ml) was added dropwise phenyl chloroformate (0.65 ml, 5.2 mmol). The resulting yellow solution was stirred at 0° C. for 60 minutes and most of the solvent was then removed under reduced pressure. The residue was taken up into EtOAc (75 ml) and washed with H$_2$O (50 ml) and brine (50 ml). The organic solution was dried (Na$_2$SO$_4$), filtered and concentrated under reduced pressure. Purification by flash column chromatography on silica (CH$_2$Cl$_2$/MeOH, 19:1) gave the carbamate as a white solid (923 mg, 83%). $^1$H NMR (CDCl$_3$) δ 4.43 (d, 2H, J=6.2 Hz), 5.84 (br s, 1H), 7.12 (d, 2H, J=7.9 Hz), 7.19 (t, 1H, J=7.4 Hz), 7.27 (dd, 1H, J=8.1, 4.6 Hz), 7.35 (d, 2H, J=7.6 Hz), 7.69 (d, 1H, J=8.0 Hz), 8.53 (d, 1H, J=4.9 Hz), 8.56 (s, 1H).

COMPOUND 183 was isolated as a white foam. $^1$H NMR (CDCl$_3$) δ 0.76-1.09 (m, 2H), 0.98 (d, 3H, J=6.6 Hz), 1.46-1.56 (m, 1H), 1.63-1.80 (m, 3H), 2.11-2.21 (m, 1H), 2.28 (s, 3H), 2.49 (s, 3H), 2.53-2.62 (m, 1H), 2.66-2.75 (m, 1H), 2.76-2.88 (m, 2H), 3.20-3.31 (m, 1H), 3.70 (d, 1H, J=18.0 Hz), 3.78 (d, 1H, J=18.0 Hz), 3.82-3.93 (m, 1H), 4.21-4.34 (m, 1H), 4.31 (d, 2H, J=5.6 Hz), 4.69 (t, 1H, J=5.9 Hz), 6.94 (s, 1H), 7.03 (d, 1H, J=4.8 Hz), 7.10 (d, 1H, J=0.9 Hz), 7.18 (dd, 1H, J=7.8, 5.1 Hz), 7.35 (dd, 1H, J=4.8, 3.0 Hz), 7.40 (d, 1H, J=8.0 Hz), 8.35 (s, 1H), 8.46 (d, 1H, J=4.5 Hz), 8.90 (br d, 1H, J=4.8 Hz); $^{13}$C NMR (CDCl$_3$) δ 13.38, 18.68, 21.98, 29.92, 30.32, 30.94, 40.20, 41.30, 42.19, 43.15, 51.85, 51.95, 60.66, 121.19, 122.36, 123.31, 125.98, 127.33, 132.87, 134.90, 134.98, 139.26, 147.52, 148.44, 148.79, 149.94, 155.33, 157.76, 166.89; ES-MS m/z 569 (M+H), 571 (M+H+2).

Example 184

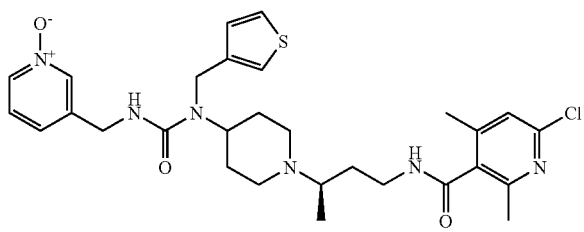

Compound 184

6-Chloro-2,4-dimethyl-N—((R)-3-{4-[3-(1-oxy-pyridin-3-ylmethyl)-1-thiophen-3-ylmethyl-ureido]-piperidin-1-yl}-butyl)-nicotinamide A solution of pyridin-3-ylmethyl-carbamic acid phenyl ester (240 mg, 1.05 mmol) and MMPP (80%, 782 mg, 1.26 mmol) in MeOH (3.5 ml) and CH$_2$Cl$_2$ (3.5 ml) was stirred at room temperature for 4 hours. The reaction was diluted with saturated aqueous NaHCO$_3$ (25 ml) and was extracted with CH$_2$Cl$_2$ (25 ml×3). The combined organic solution was washed with brine (30 ml), was dried (Na$_2$SO$_4$), filtered and concentrated under reduced pressure. Purification by flash column chromatography on silica (CH$_2$Cl$_2$/MeOH, 14:1) gave the N-oxide as a white solid (213 mg, 83%). $^1$H NMR (CDCl$_3$) δ 4.41 (d, 2H, J=6.2 Hz), 6.35 (br s, 1H), 7.11 (d, 2H, J=8.4 Hz), 7.18-7.39 (m, 5H), 8.14 (d, 1H, J=6.1 Hz), 8.23 (s, 1H).

COMPOUND 184 was isolated as a white foam. $^1$H NMR (CDCl$_3$) δ 0.78-1.10 (m, 2H), 0.97 (d, 3H, J=6.6 Hz), 1.46-1.56 (m, 1H), 1.62-1.84 (m, 3H), 2.09-2.20 (m, 1H), 2.28 (s, 3H), 2.47 (s, 3H), 2.50-2.60 (m, 1H), 2.66-2.75 (m, 1H), 2.76-2.87 (m, 2H), 3.20-3.32 (m, 1H), 3.74 (d, 1H, J=18.3 Hz), 3.78-3.90 (m, 1H), 3.81 (d, 1H, J=18.3 Hz), 4.17-4.29 (m, 1H), 4.24 (d, 2H, J=5.6 Hz), 4.89 (t, 1H, J=5.5 Hz), 6.96 (s, 1H), 6.99-7.06 (m, 2H), 7.10-7.16 (m, 2H), 7.37 (dd, 1H, J=4.9, 3.0 Hz), 7.95 (s, 1H), 8.01 (d, 1H, J=6.2 Hz), 8.85 (br d, 1H, J=5.3 Hz); ES-MS m/z 585 (M+H), 587 (M+H+2).

Example 185

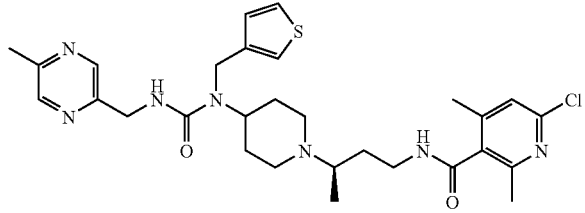

Compound 185

6-Chloro-2,4-dimethyl-N—((R)-3-{4-[3-(5-methyl-pyrazin-2-ylmethyl)-1-thiophen-3-ylmethyl-ureido]-piperidin-1-yl}-butyl)-nicotinamide To a 0° C. solution of 2-(aminomethyl)-5-methylpyrazine (137 mg, 1.11 mmol) and NEt$_3$ (0.22 ml, 1.6 mmol) in CH$_2$Cl$_2$ (5 ml) was added dropwise phenyl chloroformate (0.15 ml, 1.2 mmol). The reaction was stirred at 0° C. for 70 minutes and then was diluted with CH$_2$Cl$_2$ (50 ml) and washed with saturated aqueous NaHCO$_3$ (25 ml) and brine (25 ml). The organic solution was dried (Na$_2$SO$_4$), filtered and concentrated under reduced pressure. Purification by flash column chromatography on silica (CH$_2$Cl$_2$/MeOH, 29:1) gave the carbamate as a yellow solid (162 mg, 60%). $^1$H NMR (CDCl$_3$) δ 2.58 (s, 3H), 4.58 (d, 2H, J=5.8 Hz), 6.02 (br s, 1H), 7.13 (d, 2H, J=7.9 Hz), 7.20 (t, 1H, J=7.2 Hz), 7.36 (t, 2H, J=7.8 Hz), 8.42 (s, 1H), 8.52 (s, 1H).

COMPOUND 185 was isolated as a white foam. $^1$H NMR (CDCl$_3$) δ 0.77-1.09 (m, 2H), 0.97 (d, 3H, J=6.6 Hz), 1.46-1.56 (m, 1H), 1.62-1.80 (m, 3H), 2.10-2.20 (m, 1H), 2.28 (s, 3H), 2.49 (s, 3H), 2.50-2.61 (m, 1H), 2.52 (s, 3H), 2.65-2.74 (m, 1H), 2.76-2.87 (m, 2H), 3.19-3.31 (m, 1H), 3.74 (d, 1H, J=17.9 Hz), 3.81-3.92 (m, 1H), 3.82 (d, 1H, J=17.9 Hz), 4.24 (tt, 1H, J=12.0, 3.9 Hz), 4.42 (d, 2H, J=5.3 Hz), 5.25 (t, 1H, J=5.1 Hz), 6.94 (s, 1H), 7.06 (d, 1H, J=5.1 Hz), 7.15 (d, 1H, J=1.2 Hz), 7.34 (dd, 1H, J=4.8, 3.1 Hz), 8.27 (s, 1H), 8.33 (s, 1H), 8.88 (br d, 1H, J=5.8 Hz); $^{13}$C NMR (CDCl$_3$) δ 13.38, 18.70, 21.12, 22.00, 29.94, 30.33, 30.97, 40.24, 41.42, 43.18, 43.50, 51.92, 52.03, 60.70, 121.43, 122.40, 126.12, 126.94, 132.86, 139.27, 142.35, 143.28, 147.49, 150.02, 150.35, 151.98, 155.34, 157.96, 166.94; ES-MS m/z 584 (M+H), 586 (M+H+2).

Example 186

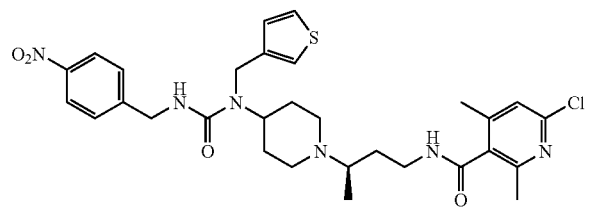

Compound 186

6-Chloro-2,4-dimethyl-N—((R)-3-{4-[3-(4-nitro-benzyl)-1-thiophen-3-ylmethyl-ureido]-piperidin-1-yl}-butyl)-nicotinamide To a 0° C. solution of 4-nitrobenzylamine hydrochloride (382 mg, 2.03 mmol) and NEt$_3$ (0.70 ml, 5.0 mmol) in CH$_2$Cl$_2$ (10 ml) was added dropwise phenyl chloroformate (0.27 ml, 2.2 mmol). The resulting suspension was stirred at 0° C. for 35 minutes. Following dilution with saturated aqueous NaHCO$_3$ (30 ml) the mixture was extracted with CH$_2$Cl$_2$ (25 ml×3). The combined organic solution was washed with brine (50 ml), was dried (Na$_2$SO$_4$), filtered and concentrated under reduced pressure. Purification by flash column chromatography on silica (CH$_2$Cl$_2$/Et$_2$O, 19:1) gave the carbamate as a white solid (370 mg, 67%). $^1$H NMR (CDCl$_3$) δ 4.56 (d, 2H, J=6.1 Hz), 5.50 (br s, 1H), 7.15 (d, 2H, J=7.9 Hz), 7.22 (t, 1H, J=7.4 Hz), 7.37 (t, 2H, J=7.9 Hz), 7.52 (d, 2H, J=8.6 Hz), 8.23 (d, 2H, J=8.6 Hz).

COMPOUND 186 was isolated as a white solid. $^1$H NMR (CDCl$_3$) δ 0.78-1.10 (m, 2H), 0.98 (d, 3H, J=7.0 Hz), 1.47-1.57 (m, 1H), 1.65-1.80 (m, 3H), 2.11-2.20 (m, 1H), 2.28 (s, 3H), 2.50 (s, 3H), 2.52-2.62 (m, 1H), 2.67-2.75 (m, 1H), 2.78-2.88 (m, 2H), 3.21-3.31 (m, 1H), 3.73 (d, 1H, J=18.6 Hz), 3.80 (d, 1H, J=18.6 Hz), 3.83-3.93 (m, 1H), 4.28 (tt, 1H, J=12.3, 4.0 Hz), 4.39 (d, 2H, J=5.7 Hz), 4.79 (t, 1H, J=5.9 Hz), 6.94 (s, 1H), 7.06 (dd, 1H, J=5.0, 0.8 Hz), 7.13 (dd, 1H, J=2.6, 1.1 Hz), 7.20 (d, 2H, J=8.7 Hz), 7.39 (dd, 1H, J=5.1, 2.9 Hz), 8.11 (d, 2H, J=8.7 Hz), 8.90 (br d, 1H, J=5.4 Hz); $^{13}$C NMR (CDCl$_3$) δ 13.38, 18.70, 22.00, 29.95, 30.34, 30.97, 40.23, 41.32, 43.14, 43.99, 51.85, 51.99, 60.69, 121.31, 122.35, 123.64, 126.02, 127.46, 127.62, 132.92, 139.24, 146.90, 147.23, 147.57, 149.92, 155.37, 157.67, 166.86; ESI-MS m/z 613 (M+H), 615 (M+H+2).

Example 187

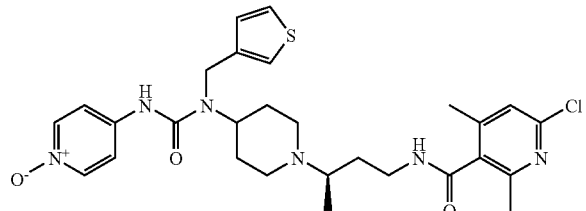

Compound 187

6-Chloro-2,4-dimethyl-N—((R)-3-{4-[3-(1-oxy-pyridin-4-yl)-1-thiophen-3-ylmethyl-ureido]-piperidin-1-yl}-butyl)-nicotinamide A solution of 4-aminopyridine (482 mg, 5.12 mmol), phenyl chloroformate (0.70 ml, 5.6 mmol) and NEt$_3$ (1.0 ml, 7.2 mmol) in CH$_2$Cl$_2$ (25 ml) was stirred at room temperature for 2.5 hours. The reaction was diluted with saturated aqueous NaHCO$_3$ (50 ml) and extracted with CH$_2$Cl$_2$ (30 ml×3). The combined organic solution was washed with brine (50 ml), was dried (Na$_2$SO$_4$), filtered and concentrated under reduced pressure, giving the crude carbamate as an off-white powder (994 mg, 91%). $^1$H NMR (CDCl$_3$) δ 7.19 (d, 2H, J=8.2 Hz), 7.25-7.30 (m, 1H), 7.33 (br s, 1H), 7.39-7.45 (m, 4H), 8.52 (d, 2H, J=6.4 Hz).

A solution of pyridin-4-yl-carbamic acid phenyl ester (262 mg, 1.22 mmol) and MMPP (80%, 895 mg, 1.45 mmol) in MeOH (4.0 ml) and CH$_2$Cl$_2$ (4.0 ml) was stirred at room temperature for 6 hours. The reaction was diluted with saturated aqueous NaHCO$_3$ (30 ml) and was extracted with CH$_2$Cl$_2$ (25 ml×3). The combined organic solution was washed with brine (50 ml), was dried (Na$_2$SO$_4$), filtered and concentrated under reduced pressure. Purification by flash column chromatography on silica (CH$_2$Cl$_2$/MeOH, 14:1, increased to 9:1) gave the N-oxide as a white solid (94.1 mg, 0.41 mmol, 34%). $^1$H NMR (MeOH-d$_4$) δ 7.24 (d, 2H, J=8.3 Hz), 7.31 (t, 1H, J=7.4 Hz), 7.46 (t, 2H, J=7.9 Hz), 7.75 (d, 2H, J=7.0 Hz), 8.29 (d, 2H, J=7.0 Hz).

COMPOUND 187 was isolated as a white solid. $^1$H NMR (CDCl$_3$) δ 0.87-1.19 (m, 2H), 1.00 (d, 3H, J=6.6 Hz), 1.49-1.58 (m, 1H), 1.67-1.83 (m, 3H), 2.15-2.25 (m, 1H), 2.29 (s, 3H), 2.49 (s, 3H), 2.55-2.65 (m, 1H), 2.71-2.91 (m, 3H), 3.23-3.34 (m, 1H), 3.81-3.93 (m, 1H), 3.89 (s, 2H), 4.27 (tt, 1H, J=12.1, 4.0 Hz), 6.79 (s, 1H), 6.94 (s, 1H), 7.09 (dd, 1H, J=5.0, 1.1 Hz), 7.15 (d, 2H, J=7.4 Hz), 7.24-7.28 (m, 1H), 7.45 (dd, 1H, J=4.7, 3.2 Hz), 7.95 (d, 2H, J=7.4 Hz), 8.76 (br d, 1H, J=4.8 Hz); $^{13}$C NMR (CDCl$_3$) δ 13.44, 18.68, 21.97, 29.92, 30.68, 30.81, 39.80, 41.52, 43.41, 51.51, 52.77, 60.07, 115.59, 121.49, 122.37, 126.09, 127.61, 132.81, 138.59, 138.92, 139.49, 147.53, 149.90, 154.43, 155.24, 166.94; ES-MS m/z 571 (M+H), 573 (M+H+2).

Example 188

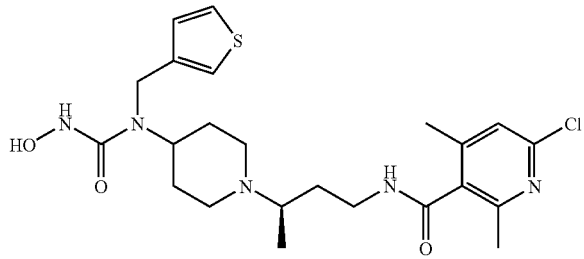

Compound 188

6-Chloro-N—{(R)-3-[4-(3-hydroxy-1-thiophen-3-ylmethyl-ureido)-piperidin-1-yl]-butyl}-2,4-dimethyl-nicotinamide To a solution of 6-chloro-2,4-dimethyl-N—((R)-3-{4-[(thiophen-3-ylmethyl)-amino]-piperidin-1-yl}-butyl)-nicotinamide (62 mg, 0.14 mmol) in THF (5 ml) was added N-(4-nitrophenoxycarbonyl)hydroxylamine (42 mg, 0.21 mmol) and the resultant mixture stirred at 70° C. for 5.5 h. The mixture was concentrated and purified by column chromatography on silica gel ($CH_2Cl_2$/MeOH/$NH_4OH$, 96:4:0 then 9:1:0 then 88:10:2) followed by radial chromatography on silica gel (1 mm plate, $CH_2Cl_2$/$CH_3OH$/$NH_4OH$, 100:1:1) to give COMPOUND 188 (63 mg, 91%) as a yellow foam. $^1$H NMR ($CDCl_3$) δ 0.99-1.01 (m, 1H), 0.99 (d, 3H, J=6.6 Hz), 1.13-1.17 (m, 1H), 1.50-1.76 (m, 5H), 2.13-2.21 (m, 1H), 2.28 (s, 3H), 2.48 (s, 3H), 2.52-2.61 (m, 1H), 2.71-2.86 (m, 3H), 3.25-3.34 (m, 1H), 3.78-3.85 (m, 3H), 4.09-4.17 (m, 1H), 6.60 (s, 1H), 6.92 (s, 1H), 7.01 (d, 1H, J=4.8 Hz), 7.12 (s, 1H), 7.37-7.39 (m, 1H), 8.58 (br d, 1H); $^{13}$C NMR ($CDCl_3$) δ 13.32, 18.76, 22.05, 29.65, 30.49, 30.90, 39.80, 41.00, 43.25, 51.60, 53.04, 60.04, 121.45, 122.43, 126.04, 127.60, 132.76, 138.36, 147.54, 150.07, 155.34, 161.29, 167.15; ES-MS m/z 494 (M+H). Anal. Calcd. for $C_{23}H_{32}N_5O_3SCl\cdot0.3CH_2Cl_2$: C, 53.87; H, 6.32; N, 13.48. Found: C, 54.25; H, 6.42; N, 13.12.

Example 189

Compound 189

4-[3-(1-{3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid methyl ester A solution of methyl 4-(bromomethyl)benzoate (1.04 g, 4.54 mmol) and $NaN_3$ (349 mg, 5.37 mmol) in DMF (12 ml) was stirred at 80° C. for 80 minutes. Once cooled, the reaction was diluted with brine (30 ml) and was extracted with 1:1 $Et_2O$/hexane (25 ml×3). The combined organic solution was washed with $H_2O$ (50 ml), was dried ($Na_2SO_4$), filtered and concentrated under reduced pressure, giving the crude azide as a colorless liquid (854 mg, 98%). $^1$H NMR ($CDCl_3$) δ 3.93 (s, 3H), 4.42 (s, 2H), 7.39 (d, 2H, J=8.2 Hz), 8.06 (d, 2H, J=8.2 Hz).

A solution of the crude azide (854 mg, 4.47 mmol), $PPh_3$ (1.26 g, 4.80 mmol) and $H_2O$ (3 ml) in THF (19 ml) was stirred at room temperature for 17 hours. The reaction was taken up in 1M HCl (30 ml) and this mixture was washed with $Et_2O$ (25 ml×3). The aqueous solution was made basic with 1.5M NaOH (30 ml) and was extracted with $CH_2Cl_2$ (25 ml×3). This organic solution was dried ($Na_2SO_4$), filtered and concentrated under reduced pressure. Purification by flash column chromatography on silica ($CH_2Cl_2$/MeOH, 19:1, increased to $CH_2Cl_2$/MeOH/$NH_4OH$, 19:1:0.2) gave the benzyl amine as a light yellow liquid (352 mg, 48%). $^1$H NMR ($CDCl_3$) δ 1.47 (s, 2H), 3.91 (s, 3H), 3.94 (s, 2H), 7.39 (d, 2H, J=8.1 Hz), 8.01 (d, 2H, J=8.1 Hz).

To a solution of the benzyl amine (179 mg, 1.08 mmol) and DIPEA (0.45 ml, 2.6 mmol) in $CH_2Cl_2$ (5 ml) was carefully added triphosgene (150 mg, 0.51 mmol) and the resulting solution was stirred at room temperature for 20 minutes (Majer, P.; Randad, R. S. *J. Org. Chem.*, 1994, 59, 1937-1938). A solution of 4-[(thiophen-3-ylmethyl)-amino]-piperidine-1-carboxylic acid tert-butyl ester (455 mg, 1.53 mmol) in $CH_2Cl_2$ (2 ml) was then added and the reaction was stirred at room temperature for an additional 18 hours. The mixture was diluted with saturated aqueous $NaHCO_3$ (25 ml) and was extracted with $CH_2Cl_2$ (20 ml×3). The combined organic solution was washed with brine (50 ml), was dried ($Na_2SO_4$), filtered and concentrated under reduced pressure. Purification by flash column chromatography on silica ($CH_2Cl_2$/$Et_2O$, 9:1, increased to 3:1) gave the urea as a light yellow foam (236 mg, 45%). $^1$H NMR ($CDCl_3$) δ 1.43 (s, 9H), 1.44-1.58 (m, 2H), 1.69-1.79 (m, 2H), 2.71-2.85 (m, 2H), 3.89 (s, 3H), 4.09-4.24 (m, 2H), 4.33 (s, 2H), 4.39 (d, 2H, J=5.8 Hz), 4.54 (tt, 1H, J=12.0, 3.7 Hz), 4.80 (t, 1H, J=5.7 Hz), 6.95 (d, 1H,

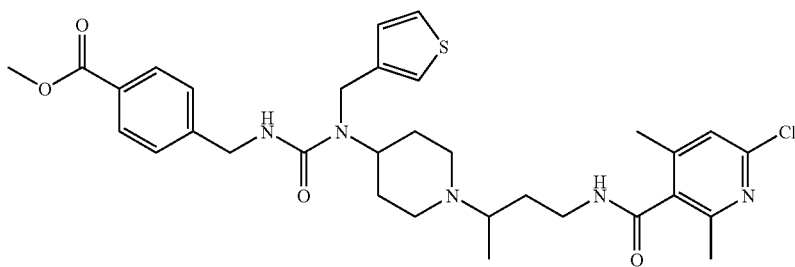

J=4.8 Hz), 7.07 (d, 1H, J=1.5 Hz), 7.13 (d, 2H, J=8.5 Hz), 7.34 (dd, 1H, J=5.0, 2.9 Hz), 7.91 (d, 2H, J=8.5 Hz).

A solution of the tert-butyl carbamate (236 mg, 0.48 mmol) and TFA (0.50 ml) in CH$_2$Cl$_2$ (2.5 ml) was stirred at room temperature for 60 minutes. The reaction was made basic with 0.5M NaOH (25 ml) and was extracted with CH$_2$Cl$_2$ (20 ml×3). The organic solution was dried (Na$_2$SO$_4$), filtered and concentrated under reduced pressure. Purification by flash column chromatography on silica (CH$_2$Cl$_2$/MeOH/NH$_4$OH, 14:1:0.15) gave the piperidine as a white foam (146 mg, 78%). $^1$H NMR (CDCl$_3$) δ 1.55 (qd, 2H, J=12.2, 4.1 Hz), 1.64 (s, 1H), 1.72-1.81 (m, 2H), 2.71 (td, 2H, J=12.1, 2.2 Hz), 3.07-3.16 (m, 2H), 3.90 (s, 3H), 4.39 (s, 2H), 4.40 (d, 2H, J=5.7 Hz), 4.45 (tt, 1H, J=12.2, 4.0 Hz), 4.76 (t, 1H, J=5.7 Hz), 6.97 (dd, 1H, J=5.0, 1.1 Hz), 7.07-7.10 (m, 1H), 7.15 (d, 2H, J=8.2 Hz), 7.33 (dd, 1H, J=5.0, 2.9 Hz), 7.92 (d, 2H, J=8.2 Hz).

A solution of 4-(3-piperidin-4-yl-3-thiophen-3-ylmethyl-ureidomethyl)-benzoic acid methyl ester (97 mg, 0.25 mmol), 2-(3-oxo-butyl)-isoindole-1,3-dione (109 mg, 0.50 mmol) and glacial AcOH (5 drops) in MeOH (1.2 ml) at 60° C. was added NaBH$_3$CN (50 mg, 0.80 mmol) and the reaction was stirred for 20.5 hours. The reaction was cooled, diluted with saturated aqueous NaHCO$_3$ (25 ml) and was extracted with CH$_2$Cl$_2$ (20 ml×3). The combined organic solution was dried (Na$_2$SO$_4$), filtered and concentrated under reduced pressure. Purification by flash column chromatography on silica (CH$_2$Cl$_2$/MeOH, 29:1) gave the tertiary piperidine as a white foam (86.3 mg, 59%). $^1$H NMR (CDCl$_3$) δ 0.95 (d, 3H, J=6.2 Hz), 1.18-1.71 (m, 5H), 1.84-1.97 (m, 1H), 2.09-2.20 (m, 1H), 2.40-2.50 (m, 1H), 2.63-2.83 (m, 3H), 2.64-2.88 (m, 2H), 3.89 (s, 3H), 4.11 (s, 2H), 4.19-4.31 (m, 1H), 4.36 (d, 2H, J=5.3 Hz), 4.69 (t, 1H, J=5.3 Hz), 6.92 (d, 1H, J=5.1 Hz), 7.04 (s, 1H), 7.09 (d, 2H, J=8.4 Hz), 7.33 (dd, 1H, J=5.1, 3.1 Hz), 7.57-7.63 (m, 2H), 7.75-7.81 (m, 2H), 7.90 (d, 2H, J=8.4 Hz).

A solution of the phthalimide (86.3 mg, 0.15 mmol) and hydrazine hydrate (0.10 ml, 1.8 mmol) in EtOH (1.5 ml) was stirred at room temperature for 16 hours. The resulting suspension was diluted with saturated aqueous NaHCO$_3$ (25 ml) and extracted with CH$_2$Cl$_2$ (20 ml×4). The organic solution was dried (Na$_2$SO$_4$), filtered and concentrated under reduced pressure, giving the crude primary amine as a white foam (60.0 mg, 89%). $^1$H NMR (CDCl$_3$) δ 0.94 (d, 3H, J=6.6 Hz), 1.32-1.68 (m, 6H), 1.71-1.79 (m, 2H), 2.18-2.27 (m, 1H), 2.42-2.52 (m, 1H), 2.63-2.84 (m, 5H), 3.89 (s, 3H), 4.32 (tt, 1H, J=11.9, 4.1 Hz), 4.37 (s, 2H), 4.40 (d, 2H, J=5.7 Hz), 4.75 (t, 1H, J=5.8 Hz), 6.96 (d, 1H, J=4.8 Hz), 7.07 (dd, 1H, J=2.4, 1.2 Hz), 7.14 (d, 2H, J=7.8 Hz), 7.32 (dd, 1H, J=4.8, 3.0 Hz), 7.92 (d, 2H, J=7.8 Hz).

A solution of the crude primary amine (60.0 mg, 0.13 mmol), 6-chloro-2,4-dimethylnicotinic acid hydrochloride (36 mg, 0.16 mmol), EDCI (37 mg, 0.19 mmol), HOBT (29 mg, 0.21 mmol) and NMM (45 μL, 0.41 mmol) in DMF (1.0 ml) was stirred at room temperature for 17.5 hours. The reaction was diluted with saturated aqueous NaHCO$_3$ (25 ml) and was extracted with CH$_2$Cl$_2$ (20 ml×3). The combined organic solution was dried (Na$_2$SO$_4$), filtered and concentrated under reduced pressure. Purification by flash column chromatography on silica (CH$_2$Cl$_2$/MeOH, 19:1, increased to 9:1) gave COMPOUND 189 as a light yellow foam (49.0 mg, 60%). $^1$H NMR (CDCl$_3$) δ 0.80-1.35 (m, 6H), 1.53-1.96 (m, 5H), 2.28 (s, 3H), 2.49 (s, 3H), 2.60-3.04 (m, 4H), 3.26-3.41 (m, 1H), 3.72-3.95 (m, 2H), 3.90 (s, 3H), 4.29-4.45 (m, 1H), 4.36 (d, 2H, J=5.3 Hz), 4.70-4.80 (m, 1H), 6.94 (s, 1H), 7.01 (d, 1H, J=4.8 Hz), 7.09 (s, 1H), 7.11 (d, 2H, J=8.4 Hz), 7.35 (dd, 1H, J=5.1, 2.8 Hz), 7.92 (d, 2H, J=8.4 Hz), 8.75 (br s, 1H); ES-MS m/z 626 (M+H), 628 (M+H+2).

Example 190

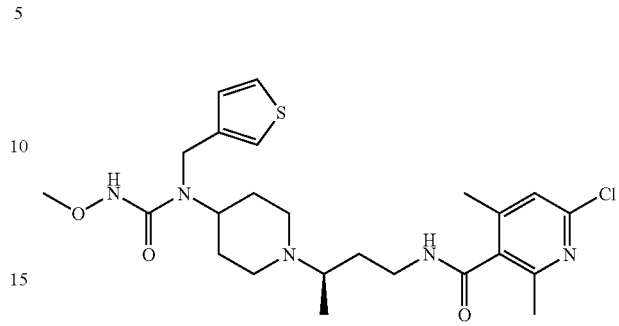

Compound 190

6-Chloro-N—{(R)-3-[4-(3-methoxy-1-thiophen-3-ylmethyl-ureido)-piperidin-1-yl]-butyl}-2,4-dimethyl-nicotinamide To a solution of ((R)-3-{4-[(thiophen-3-ylmethyl)-amino]-piperidin-1-yl}-butyl)-carbamic acid tert-butyl ester (104 mg, 0.28 mmol) in MeOH (5 ml) was added methyl trifluoroacetate (0.15 ml, 1.49 mmol) and the reaction stirred at rt overnight. The mixture was concentrated, diluted with CH$_2$Cl$_2$ (1.5 ml) and TFA (1.5 ml) and stirred for 1 h. The reaction was then concentrated and diluted with CH$_2$Cl$_2$ (10 ml) and 1 N NaOH (10 ml). The aqueous layer was extracted with CH$_2$Cl$_2$ (2×10 ml) and the combined organic extracts dried (Na$_2$SO$_4$) and concentrated.

Following general procedure E: to a solution of the above crude product in DMF (2 ml) was added 6-chloro-2,4-dimethyl-nicotinic acid (64 mg, 0.29 mmol), HOBt (47 mg, 0.35 mmol), DIPEA (0.25 ml, 1.44 mmol) and EDCI (68 mg, 0.35 mmol) and the reaction stirred overnight. Purification of the crude product by column chromatography on silica gel (CH$_2$Cl$_2$/MeOH/NH$_4$OH, 96:4:0 then 88:10:2) afforded the desired amide (72 mg, 48% over 3 steps) as a pale yellow oil. To a solution of the amide from above (72 mg, 0.14 mmol) in MeOH (5 ml) was added K$_2$CO$_3$ (77 mg, 0.56 mmol) and the reaction stirred at 60° C. for 2.5 h. The reaction was then cooled, concentrated and diluted with CH$_2$Cl$_2$ (25 ml) and saturated aqueous NaHCO$_3$ (20 ml). The aqueous layer was extracted with CH$_2$Cl$_2$ (2×10 ml) and the combined organic layers dried (Na$_2$SO$_4$) and concentrated to afford the crude product as a yellow oil.

To a suspension of methoxylamine hydrochloride (157 mg, 1.88 mmol) in CH$_3$CN (5 ml) was added DIPEA (0.55 ml, 3.16 mmol) followed by CDI (302 mg, 1.86 mmol) and the reaction stirred at rt for 1.5 h after which a solution of the amine from above (69 mg, 0.16 mmol) in CH$_3$CN (5 ml) was added and the reaction stirred at 60° C. overnight. The solution was cooled, treated with saturated aqueous NaHCO$_3$ (20 ml) and extracted with CH$_2$Cl$_2$ (3×15 ml). The combined organic extracts were dried (Na$_2$SO$_4$), filtered, and concentrated. Purification of the crude material by radial chromatography on silica gel (1 mm plate, CH$_2$Cl$_2$/MeOH/NH$_4$OH, 96:4:0 then 9:1:0 then 88:10:2) provided COMPOUND 190 (37 mg, 46%) as a white foam. $^1$H NMR (CDCl$_3$) δ 0.85-1.08 (m, 1H), 0.98 (d, 3H, J=6.6 Hz), 1.48-1.55 (m, 1H), 1.65-1.77 (m, 4H), 2.14-2.21 (m, 1H), 2.27 (s, 3H), 2.48 (s, 3H), 2.54-2.61 (m, 1H), 2.69-2.84 (m, 3H), 3.26-3.31 (m, 1H), 3.62 (s, 3H), 3.63-3.69 (m, 2H), 3.71-3.85 (m, 1H), 4.19-4.24 (m, 1H), 6.93 (s, 1H), 7.02-7.03 (m, 2H), 7.10-7.12 (m, 1H), 7.37 (dd, 1H, J=4.8, 3 Hz), 8.75 (br d, 1H); $^{13}$C NMR (CDCl$_3$) δ 13.83, 19.12, 22.42, 30.03, 30.91, 30.98, 40.50, 41.22, 43.61, 52.11, 52.57, 60.91, 64.66, 121.73, 122.82, 126.39, 127.95, 133.22, 139.09, 147.93, 150.44, 155.74, 159.43, 167.40; ES-MS m/z 508 (M+H). Anal. Calcd. for C$_{24}$H$_{34}$N$_5$O$_3$SCl.0.7CH$_2$Cl$_2$: C, 52.27; H, 6.29; N, 12.34. Found: C, 52.18; H, 6.27; N, 12.34.

Examples 191 to 208 were prepared following the scheme illustrated below. R$^1$COOH is as defined in the table.

TABLE 15

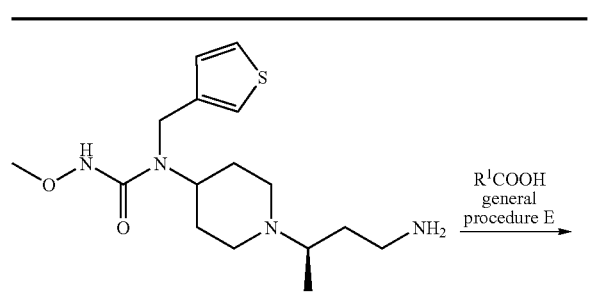

R$^1$COOH
general
procedure E

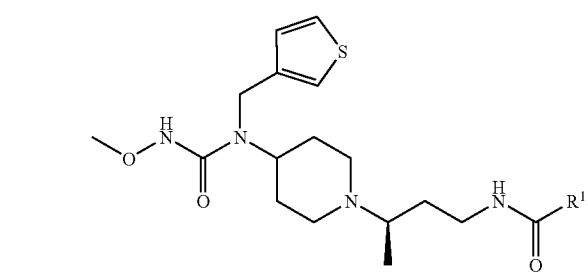

| Example | R$^1$COOH |
| --- | --- |
| 191 | 2,6-dichloro-4-methyl-nicotinic acid-N-oxide |
| 192 | 6-cyano-2,4-dimethyl-nicotinic acid |
| 193 | 2-chloro-6-cyano-4-methyl-nicotinic acid |
| 194 | 4-chloro-2,6-dimethyl-nicotinic acid |
| 195 | 6-fluoro-2,4-dimethyl-nicotinic acid |
| 196 | 2,4-dichloro-6-methyl-benzoic acid |
| 197 | 4-cyano-2,6-dimethyl-nicotinic acid-N-oxide |
| 198 | 4-chloro-2,6-dimethyl-nicotinic acid-N-oxide |
| 199 | 2-chloro-6-isopropylcarbamoyl-4-methyl-nicotinic acid |
| 200 | 2,6-dimethyl-4-[1,2,4]triazol-4-ylbenzoic acid (Schering patent PCT/US00/11632) |
| 201 | 2,4-dimethyl-6-pyrimidin-5-yl-nicotinic acid |
| 202 | 2,6-dimethyl-4-pyridin-4-yl-benzoic acid |
| 203 | 2,6-dimethyl-4-thiophen-2-yl-benzoic acid |
| 204 | 6-cyclopropyl-2,4-dimethyl-nicotinic acid |
| 205 | 4-(3-propyl-ureido)-benzoic acid |
| 206 | 2,6-dimethyl-4-(3-isopropyl-ureido)-benzoic acid |
| 207 | 2,4-dimethyl-6-(3-methyl-pyrazol-1-yl)-nicotinic acid |
| 208 | 6-isobutyl-2,4-dimethyl-nicotinic acid |

Example 191

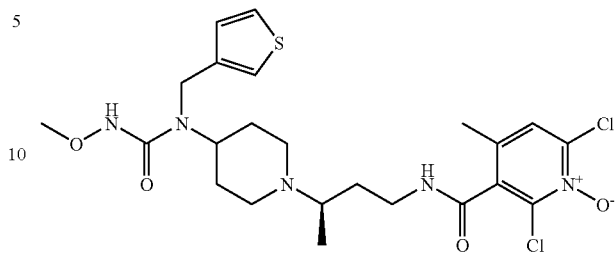

Compound 191

2,6-Dichloro-4-methyl-N—{(R)-3-[4-(3-methoxy-1-thiophen-3-ylmethyl-ureido)-piperidin-1-yl]-butyl}-nicotinamide-N-oxide 2,6-Dichloro-4-methyl-nicotinic acid (0.234 g, 1.14 mmol) and hydrogen peroxide-urea adduct (0.537 g, 5.70 mmol) were suspended in CH$_2$Cl$_2$ to give a white slurry. Trifluoroacetic anhydride (0.65 ml, 4.67 mmol) was added dropwise over 5 minutes and the resulting pale yellow solution was stirred overnight at rt. The reaction mixture was quenched with water (10 ml) and then dry loaded onto silica gel and purified using column chromatography (MeCN/MeOH/NH$_4$OH, 8:1:1, v/v/v) to give 2,6-dichloro-4-methyl-nicotinic acid-N-oxide as a pale yellow crystalline solid (0.103 g, 41%). $^1$H NMR (CD$_3$OD) δ 2.37 (s, 3H), 7.60 (s, 1H).

COMPOUND 191 was isolated as a white foam. $^1$H NMR (CDCl$_3$) δ 0.99 (d, 3H, J=9.0 Hz), 1.25 (m, 1H), 1.37 (m, 1H), 1.56 (m, 2H), 1.74 (m, 3H), 2.22 (br t, 1H), 2.31 (s, 3H), 2.57 (br t, 1H), 2.74-2.86 (m, 3H), 3.39 (m, 1H), 3.63 (m, 1H), 3.70 (m, 1H), 3.98 (s, 2H), 4.16 (m, 1H), 6.98 (d, 1H, J=6.0 Hz), 7.02 (s, 1H), 7.12 (s, 1H), 7.18 (s, 1H), 7.36 (m, 1H), 8.57 (br t, 1H); ES-MS m/z 499 (M+H). Anal. Calcd. for C$_{23}$H$_{31}$N$_5$O$_4$Cl$_2$S.0.5H$_2$O: C, 49.91; H, 5.83; N, 12.65. Found: C, 49.82; H, 5.68; N, 12.58.

Example 192

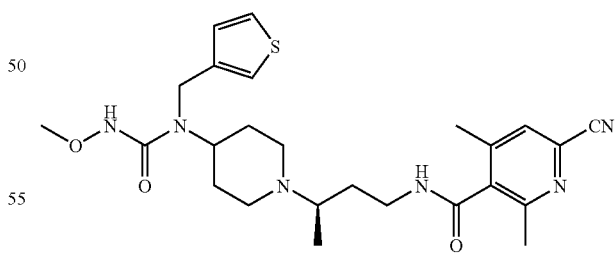

Compound 192

6-Cyano-2,4-dimethyl-N—{(R)-3-[4-(3-methoxy-1-thiophen-3-ylmethyl-ureido)-piperidin-1-yl]-butyl}-nicotinamide $^1$H NMR (CDCl$_3$) δ 0.95-1.06 (d+m, 5H), 1.51 (m, 1H), 1.66-1.77 (m, 4H), 2.20 (br t, 1H), 2.32 (s, 3H), 2.54 (s, 3H), 2.58 (br t, 1H), 2.70-2.85 (m, 3H), 3.31 (m, 1H), 3.62 (s, 3H), 3.68 (s, 2H), 3.86 (m, 1H), 4.21 (m, 1H), 7.00 (s, 2H), 7.14 (s, 1H), 7.21 (s, 1H), 7.41 (m, 1H), 8.75 (br s, 1H); ES-MS m/z 499 (M+H).

Example 193

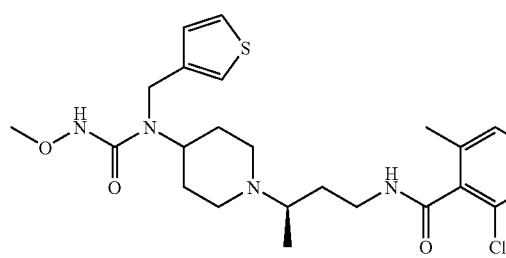

Compound 193

2-Chloro-6-cyano-4-methyl-N—{(R)-3-[4-(3-methoxy-1-thiophen-3-ylmethyl-ureido)-piperidin-1-yl]-butyl}-nicotinamide To a suspension of 2-chloro-4-methyl-nicotinic acid (4.38 g, 25.6 mmol) in 1,2-dichloroethane (110 ml) at room temperature was added hydrogen peroxide-urea adduct (ground to a powder with mortar and pestle, 11.85 g, 126.0 mmol) followed by trifluoroacetic anhydride (15.0 ml, 107.9 mmol) dropwise over 5 minutes and the resulting suspension was stirred at 65° C. overnight. The mixture was concentrated, diluted with 1 N HCl (20 ml) and extracted with $CH_2Cl_2$/MeOH (4:1, 10×100 ml). The organic extracts were dried ($Na_2SO_4$), concentrated and purified by column chromatography on silica gel (dry loaded, MeCN/MeOH/$NH_4OH$, 8:1:1) to give the desired N-oxide as a white solid (1.85 g, 39%). $^1$H NMR ($CD_3OD$) δ 2.39 (s, 3H), 7.32 (d, 1H, J=6.6 Hz), 8.27 (d, 1H, J=6.6 Hz).

To a suspension of 2-chloro-4-methyl-1-oxy-nicotinic acid (1.85 g, 9.84 mmol) in 1,2-dichloroethane/DMF (3:1, 40 ml) was added dimethylcarbamyl chloride (1.8 ml, 19.6 mmol) followed by trimethylsilyl cyanide (3.0 ml, 28.6 mmol) and the reaction stirred at 50° C. overnight. The mixture was concentrated, diluted with 1 N HCl (9 ml) and extracted with $CH_2Cl_2$/MeOH (9:1, 3×100 ml). The organic extracts were dried ($Na_2SO_4$), concentrated and purified by column chromatography (dry loaded, MeCN/MeOH/$NH_4OH$, 8:1:1) to afford 2-chloro-6-cyano-4-methyl-nicotinic acid (0.83 g, 43%) as a brown solid. $^1$H NMR ($CD_3OD$) δ 2.42 (s, 3H), 7.71 (s, 1H).

COMPOUND 193 was isolated as a white foam. $^1$H NMR ($CDCl_3$) δ 0.98-1.08 (m, 1H), 1.01 (d, 3H, J=6.6 Hz), 1.20-1.28 (m, 1H), 1.52-1.60 (m, 1H), 1.69-1.78 (m, 3H), 2.14-2.22 (m, 1H), 2.39 (s, 3H), 2.52-2.60 (m, 1H), 2.73-2.87 (m, 3H), 3.26-3.35 (m, 1H), 3.61 (s, 3H), 3.79-3.84 (m, 3H), 4.09-4.13 (m, 1H), 6.96 (d, 1H, J=4.8 Hz), 6.99 (s, 1H), 7.12 (br s, 1H), 7.33 (s, 1H), 7.41 (dd, 1H, J=4.8, 3 Hz), 8.83 (br d, 1H); $^{13}$C NMR ($CDCl_3$) δ 13.40, 19.09, 29.93, 30.51, 39.79, 41.44, 43.47, 51.38, 52.88, 59.67, 64.10, 115.62, 121.44, 125.85, 127.71, 128.97, 132.21, 136.94, 138.47, 148.62, 149.57, 158.85, 163.27; ES-MS m/z 541 (M+Na). Anal. Calcd. for $C_{24}H_{31}N_6O_3SCl.0.2H_2O.0.2CH_2Cl_2$: C, 53.86; H, 5.94; N, 15.57; Cl, 9.20; S, 5.94. Found: C, 53.79; H, 5.99; N, 15.69; Cl, 9.14; S, 5.89.

Example 194

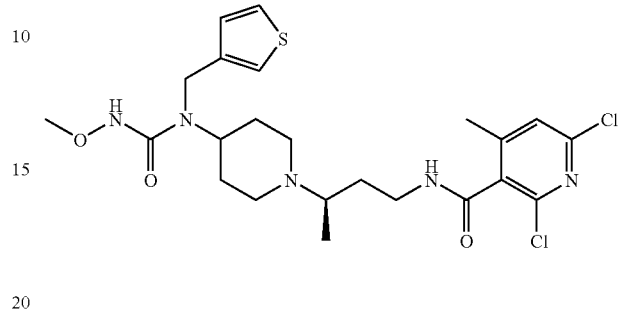

Compound 194

2,6-Dichloro-N—{(R)-3-[4-(3-methoxy-1-thiophen-3-ylmethyl-ureido)-piperidin-1-yl]-butyl}-4-methyl-nicotinamide $^1$H NMR ($CDCl_3$) δ 0.90-1.03 (m, 1H), 0.97 (d, 3H, J=6.6 Hz), 1.18-1.23 (m, 1H), 1.49-1.54 (m, 1H), 1.68-1.75 (m, 3H), 2.12-2.20 (m, 1H), 2.31 (s, 3H), 2.52-2.58 (m, 1H), 2.71-2.84 (m, 3H), 3.26-3.31 (m, 1H), 3.60 (s, 3H), 3.75-3.80 (m, 1H), 3.80 (s, 2H), 4.13-4.18 (m, 1H), 6.97 (d, 1H, J=4.8 Hz), 7.03-7.05 (m, 2H), 7.09 (s, 1H), 7.35 (dd, 1H, J=4.8, 3 Hz), 8.74 (br d, 1H); $^{13}$C NMR ($CDCl_3$) δ 13.35, 18.99, 29.76, 30.40, 30.48, 39.85, 40.88, 43.29, 51.39, 52.40, 59.86, 64.07, 121.25, 124.18, 125.92, 127.33, 132.43, 138.67, 146.45, 149.63, 150.75, 158.90, 163.97; ES-MS m/z 528 (M+H). Anal. Calcd. for $C_{23}H_{31}N_5O_3SCl_2.0.3CH_2Cl_2.0.4H_2O$: C, 49.87; H, 5.82; N, 12.48; Cl, 16.43; S, 5.71. Found: C, 49.84; H, 5.86; N, 12.16; Cl, 16.73; S, 5.62.

Example 195

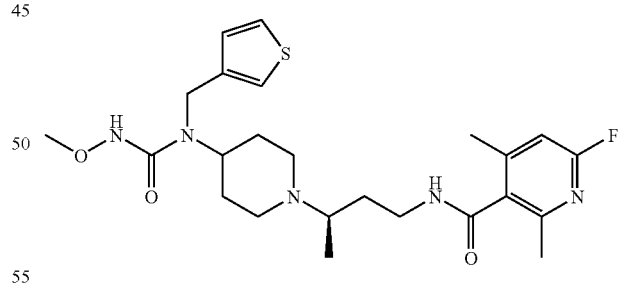

Compound 195

2,4-Dimethyl-6-fluoro-N—{(R)-3-[4-(3-methoxy-1-thiophen-3-ylmethyl-ureido)-piperidin-1-yl]-butyl}-nicotinamide $^1$H NMR ($CDCl_3$) δ 0.92 (m, 1H), 0.99 (d, 3H, J=6.0 Hz), 1.03 (m, 1H), 1.54 (m, 1H), 1.68-1.77 (m, 4H), 2.18 (br t, 1H), 2.30 (s, 3H), 2.45 (s, 3H), 2.60 (br t, 1H), 2.70 (m, 1H), 2.82 (m, 2H), 3.28 (m, 1H), 3.61 (s, 3H), 3.67 (s, 2H), 3.84 (m, 1H), 4.24 (m, 1H), 6.43 (s, 1H), 6.95-6.99 (s+m, 2H), 7.08 (s, 1H), 7.38 (m, 1H), 8.72 (br s, 1H); ES-MS m/z 492 (M+H).

Example 196

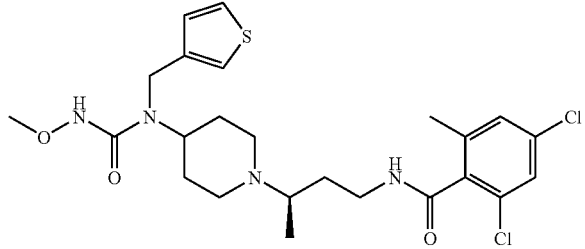

Compound 196

2,6-Dichloro-4-methyl-N—{(R)-3-[4-(3-methoxy-1-thiophen-3-ylmethyl-ureido)-piperidin-1-yl]-butyl}-benzamide ¹H NMR (CDCl₃) δ 0.98 (d+m, 4H), 1.13 (m, 1H), 1.50 (m, 1H), 1.68-1.75 (m, 4H), 2.20 (br t, 1H), 2.30 (s, 3H), 2.56 (br t, 1H), 2.75-2.92 (m, 3H), 3.28 (m, 1H), 3.61 (s, 3H), 3.69 (s, 2H), 3.82 (m, 1H), 4.24 (m, 1H), 6.93 (d, 1H, J=3.0 Hz), 6.94 (s, 1H), 6.98 (s, 1H), 7.10 (m, 2H), 7.38 (m, 1H), 8.72 (br s, 1H); ES-MS m/z 528 (M+H).

Example 197

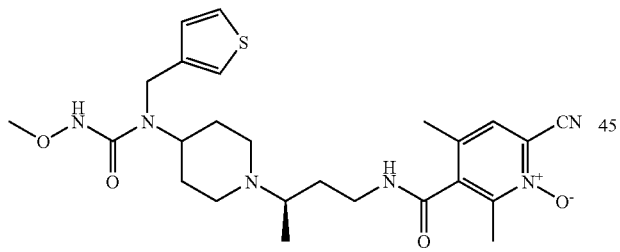

Compound 197

6-Cyano-2,4-dimethyl-N—{(R)-3-[4-(3-methoxy-1-thiophen-3-ylmethyl-ureido)-piperidin-1-yl]-butyl}-nicotinamide-N-oxide ¹H NMR (CDCl₃) δ 0.99 (d, 3H, J=9.0 Hz), 1.25 (m, 1H), 1.38 (m, 1H), 1.55 (m, 1H), 1.73-1.81 (m, 4H), 2.23 (br t, 1H), 2.31 (s, 3H), 2.43 (s, 3H), 2.59 (br t, 1H), 2.72-2.85 (m, 3H), 3.36 (m, 1H), 3.63 (s, 3H), 3.76 (m, 1H), 3.98 (s, 2H), 4.11 (m, 1H), 6.98 (d, 1H, J=3.0 Hz), 7.02 (s, 1H), 7.14 (s, 1H), 7.19 (s, 1H), 7.39 (m, 1H), 8.54 (br s, 1H); ES-MS m/z 515 (M+H).

Example 198

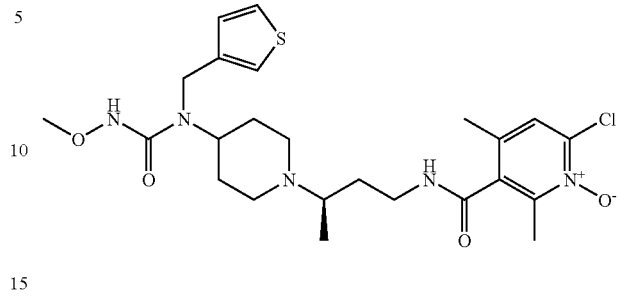

Compound 198

6-Chloro-2,4-dimethyl-N—{(R)-3-[4-(3-methoxy-1-thiophen-3-ylmethyl-ureido)-piperidin-1-yl]-butyl}-nicotinamide-N-oxide ¹H NMR (CDCl₃) δ 1.01 (d, 3H, J=7.5 Hz), 1.26 (m, 1H), 1.39 (m, 1H), 1.57 (m, 1H), 1.73-1.84 (m, 4H), 2.27 (s+m, 4H), 2.46 (s, 3H), 2.52 (br t, 1H), 2.74-2.84 (m, 3H), 3.36 (m, 1H), 3.63 (s, 3H), 3.68 (m, 1H), 3.97 (s, 2H), 4.21 (m, 1H), 6.99 (d, 1H, J=3.0 Hz), 7.05 (s, 1H), 7.09 (s, 1H), 7.12 (s, 1H), 7.37 (m, 1H), 8.55 (br s, 1H); ES-MS m/z 546 (M+H).

Example 199

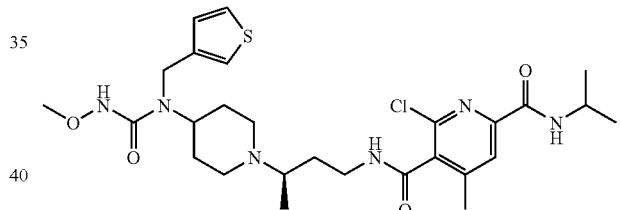

Compound 199

6-Chloro-4-methyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

2-Chloro-6-cyano-4-methyl-nicotinic acid (0.315 g, 1.61 mmol) in concentrated HCl (8 ml) was heated at 100° C. for 45 minutes and then all solvent was removed in vacuo to yield a pale yellow crystalline solid. The crude solid, EDCI (0.339 g, 1.77 mmol) and HOBt (0.239 g, 1.77 mmol) were combined in DMF (8 ml) to give a pale yellow solution. To this solution was added DIPEA (1.85 ml, 10.6 mmol) followed by isopropylamine (137 μL, 1.61 mmol) and the resulting mixture was stirred at 25° C. for 16 hours. The reaction mixture was quenched with water (3 ml) and then dry loaded onto silica gel and purified using column chromatography (MeCN/MeOH/NH₄OH, 8:1:1, v/v/v) to give 2-chloro-6-isopropyl-carbamoyl-4-methyl-nicotinic acid (0.195 g, 47%).

COMPOUND 199 was isolated as a white foam. ¹H NMR (CDCl₃) δ 1.00 (d+m, 4H), 1.12 (m, 1H), 1.28 (d, 6H, J=6.0 Hz), 1.56 (m, 1H), 1.69-1.78 (m, 3H), 2.19 (br t, 1H), 2.39 (s, 3H), 2.57 (br t, 1H), 2.74 (m, 1H), 2.87 (m, 2H), 3.34 (m, 1H), 3.66 (s+m, 5H), 3.83 (m, 1H), 4.19-4.27 (m, 2H), 6.94 (s+d, 2H), 7.09 (s, 1H), 7.36 (m, 1H), 7.57 (d, 1H, J=9.0 Hz), 7.95 (s, 1H), 8.70 (br d, 1H); ES-MS m/z 579 (M+H).

Example 200

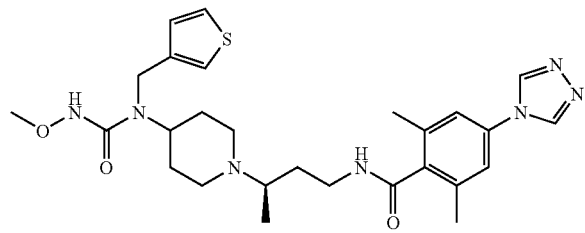

Compound 200

N—{(R)-3-[4-(3-methoxy-1-thiophen-3-ylmethyl-ureido)-piperidin-1-yl]-butyl}-2,6-dimethyl-4-1,2,4-triazol-4-yl-benzamide $^1$H NMR (CDCl$_3$) δ 1.02 (d, 3H, J=6.6 Hz), 1.18-1.23 (m, 1H), 1.54-1.73 (m, 5H) 2.18-2.25 (m, 1H), 2.37 (s, 6H), 2.54-2.63 (m, 1H), 2.75-2.90 (m, 3H), 3.28-3.39 (m, 1H), 3.58 (s, 3H), 3.65-3.81 (m, 3H), 4.12-4.20 (m, 1H), 6.69 (d, 1H, J=4.8 Hz), 6.85 (br s, 1H), 6.89 (s, 2H), 7.06 (s, 1H), 7.30 (dd, 1H, J=4.8, 3 Hz), 8.19 (br s, 1H), 8.35 (s, 2H); $^{13}$C NMR (CDCl$_3$) δ 13.89, 19.73, 30.33, 31.04, 31.55, 39.80, 41.43, 44.12, 51.91, 53.06, 60.19, 64.58, 120.59, 122.10, 126.29, 128.13, 133.70, 137.56, 139.04, 139.50, 141.30, 159.48, 168.64; ES-MS m/z 540 (M+H). Anal. Calcd. for C$_{27}$H$_{37}$N$_7$O$_3$S.1.3CH$_2$Cl$_2$.0.1H$_2$O: C, 52.14; H, 6.15; N, 15.04. Found: C, 52.14; H, 6.06; N, 14.76.

Example 201

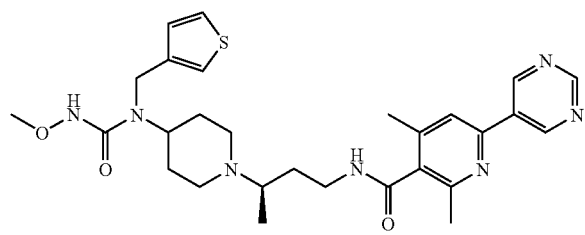

Compound 201

N—{(R)-3-[4-(3-methoxy-1-thiophen-3-ylmethyl-ureido)-piperidin-1-yl]-butyl}-2,4-dimethyl-6-pyrimidin-5-yl-nicotinamide To a solution of 6-chloro-2,4-dimethyl-nicotinic acid ethyl ester (0.30 g, 1.40 mmol) and 5-pyrimidine boronic acid (0.522 g, 4.21 mmol) in argon-degassed DME/2 M Na$_2$CO$_3$ (4:1, 12.5 ml) was added Pd(PPh$_3$)$_4$ (162 mg, 0.14 mmol) and the mixture heated to 90° C. overnight. The reaction was cooled, diluted with EtOAc (25 ml) and H$_2$O (15 ml). The aqueous layer was extracted with EtOAc (2×10 ml) and the combined organic extracts were dried (Na$_2$SO$_4$), concentrated and purified by column chromatography on silica gel (Hexanes/EtOAc, 3:2) to afford 2,4-dimethyl-6-pyrimidin-5-yl-nicotinic acid ethyl ester (306 mg, 85%). $^1$H NMR (CDCl$_3$) δ 1.43 (t, 3H, J=6 Hz), 2.44 (s, 3H), 2.64 (s, 3H), 4.47 (q, 2H, J=6 Hz), 7.44 (s, 1H), 9.26 (s, 1H), 9.32 (s, 2H).

A solution of the ester from above (306 mg, 1.19 mmol) in EtOH/2 N NaOH (1:2, mL) was heated to reflux for 3 d then cooled and acidified with concentrated HCl to pH 3. The mixture was concentrated to dryness, diluted with CH$_2$Cl$_2$/MeOH (4:1, 20 ml), filtered and concentrated to afford the acid as a white solid. $^1$H NMR (CD$_3$OD) δ 2.44 (s, 3H), 2.62 (s, 3H), 7.68 (s, 1H), 9.17 (s, 1H), 9.35 (s, 2H).

$^1$H NMR (CDCl$_3$) δ 0.95-1.01 (m, 1H), 1.01 (d, 3H, J=6.6 Hz), 1.21-1.26 (m, 1H), 1.54-1.80 (m, 4H), 2.20 (br t, 1H, J=11.4 Hz), 2.40 (s, 3H), 2.55-2.62 (m, 1H), 2.62 (s, 3H), 2.73-2.88 (m, 3H), 3.29-3.37 (m, 1H), 3.57 (s, 3H), 3.60 (s, 2H), 3.80-3.89 (m, 1H), 4.13-4.23 (m, 1H), 6.72 (dd, 1H, J=5.1, 0.9 Hz), 6.85 (br s, 1H), 6.88 (s, 1H), 7.26-7.28 (m, 1H), 7.31 (s, 1H), 8.44 (br s, 1H), 9.24 (s, 2H), 9.25 (s, 1H); $^{13}$C NMR (CDCl$_3$) δ 13.88, 19.49, 22.89, 30.28, 31.15, 31.35, 40.21, 41.14, 43.85, 52.03, 52.91, 60.47, 64.56, 119.39, 121.98, 126.27, 128.00, 132.04, 134.04, 138.99, 145.67, 151.12, 155.33, 155.71, 159.05, 159.46, 168.05; ES-MS m/z 552 (M+H). Anal. Calcd. for C$_{28}$H$_{37}$N$_7$O$_3$S.1.2H$_2$O: C, 58.66; H, 6.93; N, 17.10. Found: C, 58.75; H, 7.07; N, 16.99.

Example 202

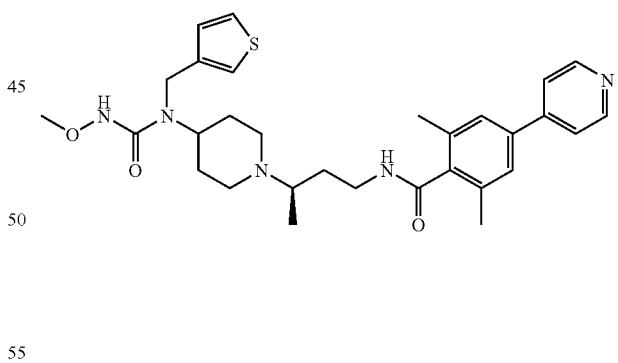

Compound 202

N—{(R)-3-[4-(3-methoxyl-1-thiophen-3-ylmethyl-ureido)-piperidin-1-yl]-butyl}-2,6-dimethyl-4-pyridin-4-yl-benzamide $^1$H NMR (CDCl$_3$) δ 0.97-1.05 (m, 4H), 1.54-1.70 (m, 5H), 2.18-2.25 (m, 1H), 2.38 (s, 6H), 2.54-2.63 (m, 1H), 2.75-2.95 (m, 3H), 3.26-3.37 (m, 1H), 3.47-3.58 (m, 2H), 3.57 (s, 3H), 3.76-3.85 (m, 1H), 4.11-4.25 (m, 1H), 6.56-6.75 (m, 2H), 6.86-6.94 (m, 1H), 7.20 (s, 2H), 7.22-7.27 (m, 1H), 7.41 (d, 2H, J=6 Hz), 8.45 (br s, 1H), 8.65 (d, 2H, J=6 Hz); ¹³C NMR (CDCl₃) δ 13.34, 19.25, 29.48, 30.33, 30.89, 39.36, 40.54, 43.50, 51.52, 52.11, 60.17, 64.07, 121.31, 121.53, 125.83, 127.28, 135.10, 137.75, 138.57, 147.39, 150.24, 159.03, 169.25; ES-MS m/z 550 (M+H). Anal. Calcd. for C₃₀H₃₉N₅O₃S.0.1CH₂Cl₂.1.3CH₃OH: C, 62.87; H, 7.46; N, 11.67. Found: C, 62.96; H, 7.19; N, 11.33.

Example 203

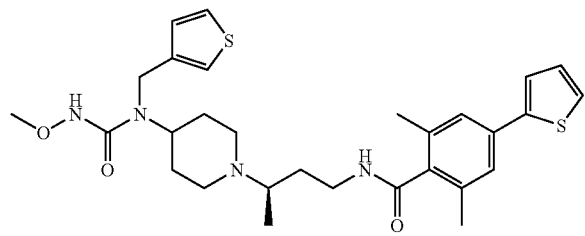

Compound 203

N—{(R)-3-[4-(3-methoxyl-1-thiophen-3-ylmethyl-ureido)-piperidin-1-yl]-butyl}-2,6-dimethyl-4-thiophen-2-yl-benzamide To a solution of 2,6-dimethyl-4-trifluoromethanesulfonyloxy-benzoic acid tert-butyl ester (prepared as described by patent Schering Corporation, WO 2000/66558 A1) (215 mg, 0.61 mmol) and 2-thiophene boronic acid (80 mg, 0.625 mmol) in argon-degassed THF/DME/2 M Na₂CO₃ (1:1:1, 4.5 ml) was added Pd(PPh₃)₄ (35 mg, 0.030 mmol) and the mixture heated to 90° C. overnight. The reaction was cooled, diluted with EtOAc (25 ml) and H₂O (15 ml). The aqueous layer was extracted with EtOAc (2×10 ml) and the combined organic extracts were dried (Na₂SO₄), concentrated and purified by column chromatography on silica gel (Hexanes/EtOAc, 92:8) to afford the desired coupled product (88 mg, 50%) as a clear oil. ¹H NMR (CDCl₃) δ 1.61 (s, 9H), 2.37 (s, 6H), 7.07 (dd, 1H, J=5.1, 3.6 Hz), 7.27-7.30 (m, 2H). ES-MS m/z 311 (M+Na).

A solution of the t-butyl ester from above (42 mg, 0.15 mmol) in CH₂Cl₂/TFA (1:6, 3.5 ml) was stirred overnight and concentrated to afford 2,6-dimethyl-4-thiophen-2-yl-benzoic acid as a white solid.

¹H NMR (CDCl₃) δ 0.91-0.99 (m, 1H), 0.98 (d, 3H, J=6.6 Hz), 1.08-1.14 (m, 1H), 1.43-1.78 (m, 4H), 2.17 (br t, 1H, J=11.4 Hz), 2.32 (s, 6H), 2.58 (dt, 1H, J=11.4, 1.8 Hz), 2.70-2.87 (m, 3H), 3.21-3.30 (m, 1H), 3.44-3.51 (m, 2H), 3.56 (s, 3H), 3.88-3.93 (m, 1H), 4.14-4.22 (m, 1H), 6.60 (dd, 1H, J=5.1, 1.2 Hz), 6.64-6.67 (m, 1H), 6.84 (s, 1H), 7.10 (dd, 1H, J=4.8, 3.6 Hz), 7.17 (s, 2H), 7.23-7.26 (m, 2H), 7.31 (dd, 1H, J=4.8, 1.2 Hz), 8.72 (br d, 1H); ES-MS m/z 555 (M+H).

Example 204

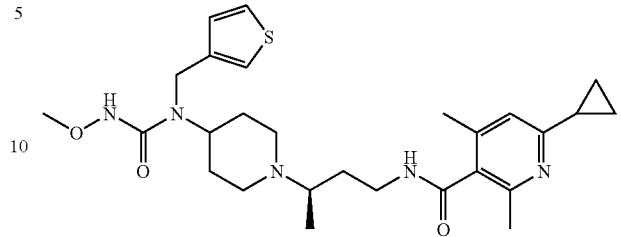

Compound 204

6-Cyclopropyl-N—{(R)-3-[4-(3-ethyl-1-thiophen-3-ylmethyl-ureido)-piperidin-1-yl]-butyl}-2,4-dimethyl-nicotinamide General Procedure for Preparation of 6-Substituted-2,4-dimethyl-nicotinic Acids:

To a solution of ethyl 2,4-dimethylpyridine-3-carboxylate (0.59 g, 3.29 mmol) and cyclopropane carboxylic acid (1.2 ml (15.1 mmol) in 10% aqueous H₂SO₄ (3 ml) was added AgNO₃ (154 mg, 0.91 mmol) followed by a solution of ammonium persulfate (1:541 g, 6.75 mmol) in water (6 ml) and the mixture stirred at room temperature overnight. The reaction was neutralized to pH 10 with saturated aqueous NH₄OH (5 ml) and extracted with EtOAc (3×20 ml). The combined organic extracts were dried (Na₂SO₄), concentrated and purified by column chromatography on silica gel (Hexanes/EtOAc, 96:4 then 1:1 then 0:100) to afford desired 6-cyclopropyl-2,4-dimethyl-nicotinic acid ethyl ester (133 mg, 18%) as a clear oil along with recovered starting ethyl 2,4-dimethylpyridine-3-carboxylate (0.31 g). ¹H NMR (CDCl₃) δ 0.93-0.97 (m, 4H), 1.38 (t, 3H, J=6 Hz), 1.92-2.02 (m, 1H), 2.28 (s, 3H), 2.47 (s, 3H), 4.39 (q, 2H, J=6 Hz), 6.73 (s, 1H).

A solution of the ester from above (133 mg, 0.61 mmol) in EtOH/10 N NaOH (1:1, 3 ml) was heated to reflux for 3 h then cooled and acidified with concentrated HCl (1.5 ml). The mixture was concentrated to dryness, diluted with CH₂C₂/MeOH (1:1, 30 ml), filtered and concentrated to afford 6-cyclopropyl-2,4-dimethyl-nicotinic acid (15 mg, 99%) as a white solid. ¹H NMR (CD₃OD) δ 1.26-1.31 (m, 2H), 1.46-1.52 (m, 2H), 2.39-2.44 (m, 1H), 2.63 (s, 3H), 2.82 (s, 3H), 7.39 (s, 1H).

¹H NMR (CDCl₃) δ 0.89-0.99 (m, 8H), 1.49-1.76 (m, 5H), 1.87-1.93 (m, 1H), 2.14-2.23 (m, 1H), 2.23 (s, 3H), 2.44 (s, 3H), 2.52-2.60 (m, 1H), 2.70-2.87 (m, 3H), 3.22-3.31 (m, 1H), 3.63 (s, 3H), 3.64-3.82 (m, 3H), 4.13-4.21 (m, 1H), 6.63 (s, 1H), 6.98 (d, 1H, J=4.8 Hz), 7.05 (s, 1H), 7.08 (br s, 1H), 7.35 (dd, 1H, J=4.8, 3 Hz), 8.32 (br s, 1H); ¹³C NMR (CDCl₃) δ 8.99, 9.03, 12.68, 16.38, 18.07, 21.68, 28.54, 29.49, 30.29, 38.81, 40.25, 42.83, 50.89, 51.44, 59.56, 63.56, 118.48, 120.66, 125.48, 126.66, 129.97, 138.37, 142.85, 152.84, 158.43, 161.39, 168.17; ES-MS m/z 514 (M+H). Anal. Calcd. for C₂₇H₃₉N₅O₃S.0.9CH₂Cl₂: C, 56.78; H, 6.97; N, 11.87. Found: C, 57.04; H, 7.01; N, 11.62.

Example 205

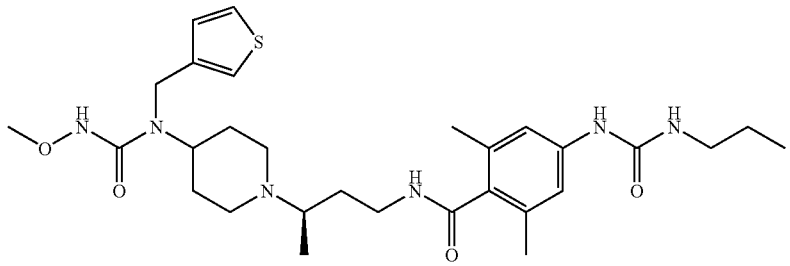

Compound 205

2,6-Dimethyl-N—{(R)-3-[4-(3-methoxy-1-thiophen-3-ylmethyl-ureido)-piperidin-1-yl]-butyl}-4-(3-propyl-ureido)-benzamide To a solution of 3,5-dimethylaniline (3.0 ml, 24 mmol) in ice cold dichloromethane (200 ml) was added trifluoroacetic anhydride (4.18 mL, 1.25 equivs). After 30 minutes, bromine (1.2 ml, 0.97 equivs) was slowly added over 5 minutes. After aqueous work-up and drying in vacuo the recovered crude (6.81 g, 96%) was taken up in dry THF (40 ml). The solution was cooled to −78° C. and methyl lithium lithium bromide complex (21 ml, 1.3 equivs) was added. After 5 minutes, s-butyllithium (20 ml, 1.3 equivs) was added followed by di-t-butyldicarbonate (8.02 g, 1.6 equivs). Following aqueous work up the crude amide was taken up in a 3:1 solution of methanol:water (100 ml) followed by sodium hydroxide (5 ml, 10M, 2 equivs). The reaction was stirred at 60° C. overnight. Solvent was removed and the crude was diluted with dichloromethane, washed with water, brine, and dried over sodium sulfate. The aniline was then taken up in dichloromethane (2 ml) and n-propylisocyanate (74 µL, 1.2 equivs). After two hours, solvent was removed and the crude residue was taken up in HCl/ethanol solution (1.2M, 15 ml) and stirred at 50° C. overnight. After solvent was removed, the crude 2,6-dimethyl-4-(3-propyl-ureido)-benzoic acid was isolated as a white solid (94 mg).

$^1$H NMR (CDCl$_3$) δ 0.83-0.99 (m, 7H), 1.02-1.11 (m, 1H), 1.46-1.77 (m, 8H), 2.11 (s, 6H), 2.48-2.57 (m, 1H), 1.66-1.82 (m, 3H), 3.12-3.22 (m, 3H), 3.52-3.20 (m, 4H), 3.75-3.82-3.90 (m, 1H), 4.11-4.25 (m, 1H), 5.67-5.75 (m, 1H), 6.61 (s, 2H), 6.89 (d, 1H, J=6 Hz), 7.03 (s, 1H), 7.22 (s, 1H), 7.27-7.32 (m, 1H), 7.48 (s, 1H), 8.87 (br s, 1H); ES-MS m/z 573 (M+H).

Example 206

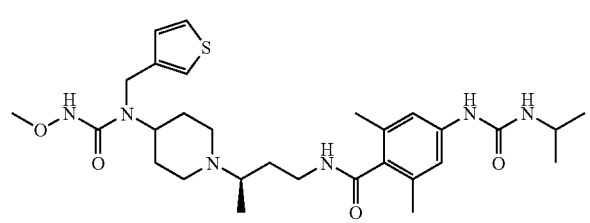

Compound 206

4-(3-Isopropyl-ureido)-2,6-dimethyl-N—{(R)-3-[4-(3-methoxy-1-thiophen-3-ylmethyl-ureido)-piperidin-1-yl]-butyl}-benzamide 2,6-Dimethyl-4-(3-isopropyl-ureido)-benzoic acid was prepared in the same manner as 2,6-dimethyl-4-(3-propyl-ureido)-benzoic acid (see EXAMPLE 205) except isopropyl isocyanate was used in lieu of n-propylisocyanate.

$^1$H NMR (CDCl$_3$) δ 0.82-0.89 (m, 1H), 0.97 (d, 3H, J=6 Hz), 1.07-1.21 (m, 1H), 1.18 (d, 6H, J=6 Hz), 1.47-1.55 (m, 1H), 1.57-1.63 (m, 4H), 1.65-1.76 (m, 2H), 2.14 (s, 6H), 2.55-2.61 (m, 1H), 2.67-2.81 (m, 3H), 3.18-3.26 (m, 1H), 3.53-3.62 (m, 3H), 3.81-3.87 (m, 1H), 3.87-3.98 (m, 1H), 4.22-4.24 (m, 1H), 5.30 (d, 1H, J=6 Hz), 6.62 (s, 2H), 6.89 (d, 1H, J=3 Hz), 7.05 (br s, 2H), 7.16 (s, 1H), 7.29-7.33 (m, 1H), 8.85 (br s, 1H); ES-MS m/z 595 (M+Na).

Example 207

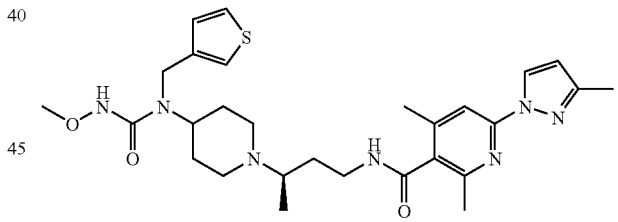

Compound 207

N—{(R)-3-[4-(3-methoxy-1-thiophen-3-ylmethyl-ureido)-piperidin-1-yl]-butyl}-2,4-dimethyl-6-(3-methyl-pyrazol-1-yl)-nicotinamide To a solution of 3-methylpyrazole (156 mg, 1.90 mmol) in DMF (2 ml) was added NaH (60% dispersion in oil, 76 mg, 1.9 mmol) and the reaction stirred at room temperature for 30 min. before adding 2-chloro-5-bromo-4,6-dimethylpyridine (227 mg, 1.03 mmol) as a solid in one portion. The mixture was heated to 85° C. for 2 d then cooled and diluted with EtOAc (35 ml) and brine (20 ml). The organic layer was washed with brine (2×15 ml) and water (1×10 ml), dried (Na$_2$SO$_4$), concentrated and purified by column chromatography on silica gel (Hexanes/Et$_2$O, 9:1) to afford 3-bromo-2,4-dimethyl-6-(3-methyl-pyrazol-1-yl)-pyridine (172 mg, 63%) as a white crystalline solid. $^1$H NMR (CDCl$_3$) δ 2.36 (s, 3H), 2.44 (s, 3H), 2.65 (s, 3H), 6.23 (d, 1H, J=3 Hz), 7.62 (s, 1H), 8.41 (d, 1H, J=3 Hz).

To a solution of 3-bromo-2,4-dimethyl-6-(3-methyl-pyrazol-1-yl)-pyridine (172 mg, 0.65 mmol) in anhydrous Et$_2$O (10 ml) at −78° C. was added a solution of t-BuLi (1.7 M in pentane, 0.76 ml, 1.29 mmol) and the reaction stirred at −78° C. for 20 min. Carbon dioxide (dry ice) was then bubbled into the resultant orange suspension at −78° C. for 15 min. and the reaction was warmed to room temperature and stirred for 30 min. The mixture was diluted with water (7 ml) and Et$_2$O (10 ml) and the layers separated. The aqueous layer was acidified with concentrated HCl to pH 2-3 and concentrated. The resultant solid was diluted with CH$_2$Cl$_2$/MeOH (5:1, 30 ml), filtered, concentrated and purified by column chromatography on silica gel (CH$_3$CN/MeOH/NH$_4$OH, 95:5:0 then 7:2:1) to afford 2,4-dimethyl-6-(3-methyl-pyrazol-1-yl)-nicotinic acid (100 mg, 67%) as a white solid. $^1$H NMR (CD$_3$OD) δ 2.39 (s, 3H), 2.49 (s, 3H), 2.58 (s, 3H), 6.37 (d, 1H, J=3 Hz), 7.61 (s, 1H), 8.51 (d, 1H, J=3 Hz).

$^1$H NMR (CDCl$_3$) δ 0.89-1.10 (m, 2H), 0.98 (d, 3H, J=6.6 Hz), 1.49-1.72 (m, 4H), 2.17 (br t, 1H, J=11.4 Hz), 2.34 (s, 3H), 2.39 (s, 3H), 2.50 (s, 3H), 2.57 (br t, 1H, J=11.4 Hz), 2.71-2.86 (m, 3H), 3.23-3.31 (m, 1H), 3.50 (br s, 2H), 3.57 (s, 3H), 3.82-3.89 (m, 1H), 4.14-4.24 (m, 1H), 6.26 (d, 1H, J=2.4 Hz), 6.77 (d, 1H, J=5.1 Hz), 6.86 (br s, 1H), 6.88 (s, 1H), 7.28 (dd, 1H, J=5.1, 3 Hz), 7.54 (s, 1H), 8.42 (d, 1H, J=2.4 Hz), 8.70 (br s, 1H); $^{13}$C NMR (CDCl$_3$) δ 13.82, 14.31, 19.52, 22.58, 29.94, 31.02, 40.50, 41.08, 43.60, 52.15, 52.57, 61.00, 64.59, 108.48, 110.39, 121.56, 126.24, 127.69, 128.31, 131.66, 139.05, 147.53, 150.63, 152.18, 153.92, 159.38, 168.30; ES-MS m/z 576 (M+Na). Anal. Calcd. for C$_{28}$H$_{39}$N$_7$O$_3$S.0.3CH$_2$Cl$_2$.0.2H$_2$O: C, 58.32; H, 6.92; N, 16.82. Found: C, 58.48; H, 6.97 N, 16.46.

Example 208

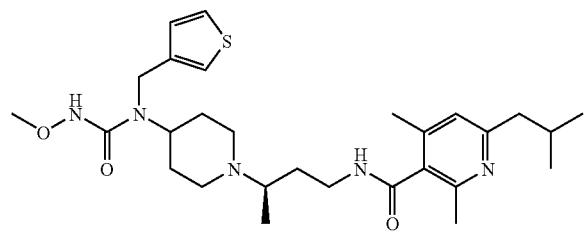

Compound 208

N—{(R)-3-[4-(3-methoxy-1-thiophen-3-ylmethyl-ureido)-piperidin-1-yl]-butyl}-6-isobutyl-2,4-dimethyl-nicotinamide 6-Isobutyl-2,4-dimethyl-nicotinic acid was prepared using General Procedure for Preparation of 6-Substituted-2,4-dimethyl-nicotinic Acids (see EXAMPLE 204).

$^1$H NMR (CDCl$_3$) δ 0.87-0.91 (m, 1H), 0.89 (d, 6H, J=6.6 Hz), 0.99 (d, 3H, J=6.6 Hz), 1.01-1.20 (m, 1H), 1.49-1.74 (m, 5H), 1.97-2.06 (m, 1H), 2.16-2.24 (m, 1H), 2.26 (s, 3H), 2.48 (d, 2H, J=7.5 Hz), 2.49 (s, 3H), 2.70-2.87 (m, 3H), 3.26-3.34 (m, 1H), 3.61 (s, 3H), 3.74-3.82 (m, 3H), 4.13-4.19 (m, 1H), 6.70 (s, 1H), 6.94 (dd, 1H, J=4.8, 0.9 Hz), 7.05-7.07 (m, 2H), 7.35 (dd, 1H, J=4.8, 3 Hz), 8.17 (br s, 1H); $^{13}$C NMR (CDCl$_3$) δ 13.30, 18.64, 22.18, 22.27, 28.97, 29.49, 30.41, 30.97, 39.46, 40.79, 43.36, 47.22, 51.44, 52.35, 59.81, 64.05, 121.22, 121.95, 126.01, 127.25, 131.00, 138.94, 143.61, 153.37, 158.95, 160.65, 168.61; ES-MS m/z 530 (M+H). Anal. Calcd. for C$_{28}$H$_{43}$N$_5$O$_3$S.0.2CH$_2$Cl$_2$.0.2H$_2$O: C, 61.55; H, 8.02; N, 12.73. Found: C, 61.45; H, 8.03; N, 12.69.

Example 209

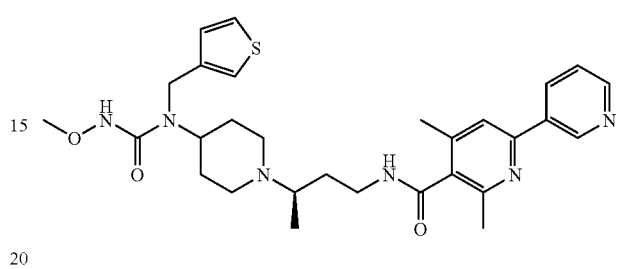

Compound 209

4,6-Dimethyl-[2,3']bipyridinyl-5-carboxylic acid {(R)-3-[4-(3-methoxyl-1-thiophen-3-ylmethyl-ureido)-piperidin-1-yl]-butyl}-amide To an argon-degassed solution of 6-chloro-2,4-dimethyl-N—((R)-3-{4-[(thiophen-3-ylmethyl)-amino]-piperidin-1-yl}-butyl)-nicotinamide (100 mg, 0.23 mmol) and 3-pyridine boronic acid (56 mg, 0.46 mmol) in DME/2 M Na$_2$CO$_3$ (5:2, 3.5 ml) was added Pd(PPh$_3$)$_4$ (15 mg, 0.013 mmol) and the reaction stirred at 90° C. overnight. The mixture was cooled, diluted with CH$_2$Cl$_2$ (25 ml) and saturated aqueous NaHCO$_3$ (25 ml). The aqueous layer was extracted with CH$_2$Cl$_2$ (2×10 ml) and the combined organic extracts were dried (Na$_2$SO$_4$), concentrated and purified by column chromatography on silica gel (CH$_2$Cl$_2$MeOH/NH$_4$OH, 96:4:0 then 88:10:2) to afford 4,6-dimethyl-[2,3']bipyridinyl-5-carboxylic acid ((R)-3-{4-[(thiophen-3-ylmethyl)-amino]-piperidin-1-yl}-butyl)-amide as a mixture of product and starting amine (~25%).

To a solution of the mixture from above (100 mg) in CH$_2$Cl$_2$ (5 ml) was added DIPEA (0.10 ml, 0.58 mmol) and N-(4-nitrophenoxycarbonyl)methoxylamine (58 mg, 0.27 mmol) and the reaction stirred at room temperature for 1.5 h. The mixture was diluted with CH$_2$Cl$_2$ (25 ml) and 1 N NaOH (20 ml) and the aqueous layer was extracted with CH$_2$Cl$_2$ (2×10 ml), dried (Na$_2$SO$_4$), concentrated and purified by column chromatography on silica gel (CH$_2$Cl$_2$/MeOH/NH$_4$OH, 96:4:0 then 9:1:0 then 88:10:2) followed by preparative thin layer chromatography on silica gel (1 mm plate, CH$_2$C$_2$/MeOH/NH$_4$OH, 9:1) to afford COMPOUND 209 (70 mg, 55% 2 steps) as a white solid. $^1$H NMR (CDCl$_3$) δ 1.01-1.09 (m, 4H), 1.44-1.72 (m, 5H), 2.28-2.37 (m, 1H), 2.37 (s, 3H), 2.60 (s, 3H), 2.60-2.94 (m, 4H), 3.39-3.46 (m, 1H), 3.57 (s, 3H), 3.61-3.76 (m, 3H), 4.20-4.30 (m, 1H), 6.73-6.77 (m, 1H), 6.82-6.87 (m, 1H), 7.01-7.05 (m, 1H), 7.26-7.28 (m, 1H), 7.32 (s, 1H), 7.39 (dd, 1H, J=7.8, 4.8 Hz), 8.27 (td, 1H, J=7.8, 2.1 Hz), 8.63 (d, 1H, J=4.8 Hz), 9.11 (br s, 1H); $^{13}$C NMR (CDCl$_3$) δ 13.28, 19.07, 22.50, 29.03, 29.96, 30.99, 39.00, 40.80, 43.81, 51.32, 51.86, 59.89, 64.10, 119.09, 121.33, 123.54, 125.90, 127.30, 132.70, 134.28, 138.61, 144.84, 148.01, 149.85, 153.48, 154.70, 159.00; ES-MS m/z 573 (M+Na). Anal. Calcd. for C$_{29}$H$_{38}$N$_6$O$_3$S.1.1CH$_2$Cl$_2$: C, 56.13; H. 6.29; N, 13.05. Found: C, 56.17; H, 6.39; N, 12.94.

Examples 210 to 226 were prepared following the scheme illustrated below. $R^1R^2NH$ is as defined in the table and X is CH or N as shown in the individual examples.

TABLE 16

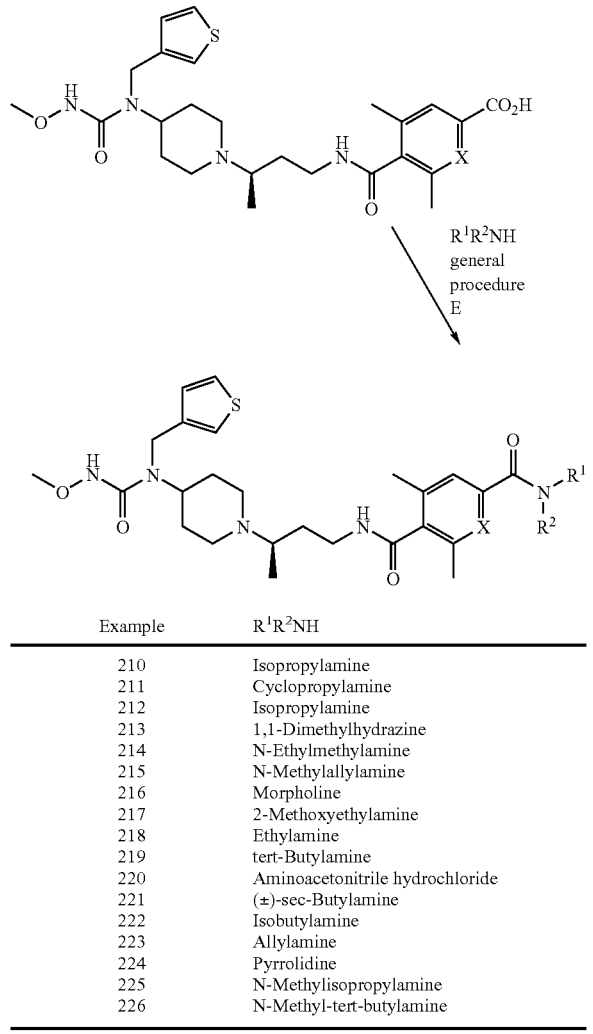

| Example | $R^1R^2NH$ |
|---|---|
| 210 | Isopropylamine |
| 211 | Cyclopropylamine |
| 212 | Isopropylamine |
| 213 | 1,1-Dimethylhydrazine |
| 214 | N-Ethylmethylamine |
| 215 | N-Methylallylamine |
| 216 | Morpholine |
| 217 | 2-Methoxyethylamine |
| 218 | Ethylamine |
| 219 | tert-Butylamine |
| 220 | Aminoacetonitrile hydrochloride |
| 221 | (±)-sec-Butylamine |
| 222 | Isobutylamine |
| 223 | Allylamine |
| 224 | Pyrrolidine |
| 225 | N-Methylisopropylamine |
| 226 | N-Methyl-tert-butylamine |

Example 210

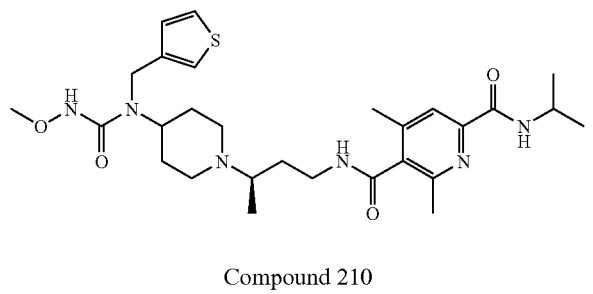

Compound 210

4,6-Dimethyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

1-[1-(3-Amino-1-methyl-propyl)-piperidin-4-yl]-3-methoxy-1-thiophen-3-ylmethyl-urea (0.150 g, 0.44 mmol), EDCI (0.093 g, 0.48 mmol) and HOBt (0.066 g, 0.48 mmol) were combined in DMF (8 ml) to give a pale yellow solution. To this solution was added 6-cyano-2,4-dimethyl-nicotinic acid (0.091 g, 0.48 mmol) followed by DIPEA (126 µL, 0.66 mmol) and the resulting mixture was stirred at 25° C. for 16 h. Standard workup according to general procedure E gave the crude product as a tan oil. Purification by column chromatography on silica gel (Et$_2$O:MeOH:NH$_4$OH, 90:8:2, v/v/v) afforded 6-cyano-2,4-dimethyl-N-{3-[4-(3-methyl-1-thiophen-3-ylmethyl-ureido)-piperidin-1-yl]-butyl}-nicotinamide (0.170 g, 77%) as a white foam. $^1$H NMR (CDCl$_3$) δ 0.95 (m, 1H), 1.03 (d+m, 4H), 1.48 (m, 1H), 1.56-1.73 (m, 5H), 2.22 (br t, 1H), 2.32 (s, 3H), 2.54 (s, 3H), 2.58 (br t, 1H), 2.71-2.85 (m, 3H), 3.31 (m, 1H), 3.62 (s, 1H), 3.66 (m, 1H), 3.75 (s, 2H), 3.86 (m, 1H), 4.21 (m, 1H), 7.00 (m, 2H), 7.14 (s, 1H), 7.21 (s, 1H), 7.41 (m, 1H), 8.75 (br d, 1H); ES-MS m/z 499 (M+H).

To a solution of 6-cyano-2,4-dimethyl-N-{3-[4-(3-methyl-1-thiophen-3-ylmethyl-ureido)-piperidin-1-yl]-butyl}-nicotinamide (0.150 g, 0.30 mmol) in ethanol (5 ml) was added 10 N NaOH (1 ml) and the resulting colorless solution was stirred for 16 h at 100° C. The reaction mixture was dry loaded onto silica gel and purified using column chromatography (MeCN:MeOH:NH$_4$OH, 6:3:1, v/v/v) to give 4,6-dimethyl-5-{3-[4-(3-methyl-1-thiophen-3-ylmethyl-ureido)-piperidin-1-yl]-butylcarbamoyl}-pyridine-2-carboxylic acid as a glassy white solid (0.117 g, 75%). $^1$H NMR (CD$_3$OD)) δ 1.31 (d, 3H, J=7.5 Hz), 1.86 (m, 4H), 2.03 (m, 3H), 2.31 (s, 3H), 2.43 (s, 3H), 2.86 (m, 1H), 3.06 (m, 2H), 3.23 (m, 1H), 3.52 (m, 2H), 3.64 (s, 3H), 4.09 (m, 1H), 4.38 (s, 2H), 6.98 (d, 1H, J=4.5 Hz), 7.17 (s, 1H), 7.32 (m, 1H), 7.61 (s, 1H).

COMPOUND 210 was isolated as a white foam. $^1$H NMR (CDCl$_3$) δ 0.84 (m, 1H), 0.97 (d+m, 4H), 1.29 (d, 6H, J=6.0 Hz), 1.53 (m, 1H), 1.72 (m, 3H), 2.17 (br t, 1H), 2.33 (s, 3H), 2.55 (s, 3H), 2.56 (br t, 1H), 2.68 (m, 1H), 2.82 (m, 2H), 3.29 (m, 1H), 3.48-3.52 (m, 2H), 3.60 (s, 3H), 3.86 (m, 1H), 4.22 (s, 2H), 4.29 (m, 1H), 6.95 (s, 1H), 6.97 (d, 1H, J=3.0 Hz), 7.09 (s, 1H), 7.36 (m, 1H), 7.85 (s, 1H), 7.86 (d, 1H, J=6.0 Hz), 8.64 (br d, 1H); ES-MS m/z 559 (M+H). Anal. Calcd. for C$_{28}$H$_{42}$N$_6$O$_4$S.0.9H$_2$O: C, 58.49; H, 7.68; N, 14.62. Found: C, 58.53; H, 7.44; N, 14.35.

Example 211

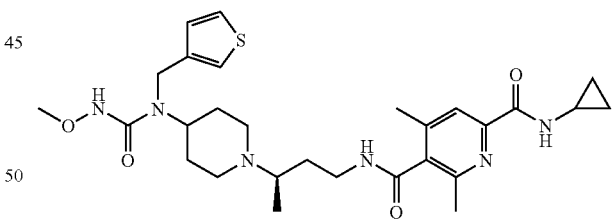

Compound 211

4,6-Dimethyl-pyridine-2,5-dicarboxylic acid 2-cyclopropylamide 5-({(R)-3-[4-(3-methoxy-1-thiophen-3-ylmethyl-ureido)-piperidin-1-yl]-butyl}-amide)

$^1$H NMR (CDCl$_3$) δ 0.66 (m, 2H), 0.86 (m, 3H), 0.98 (d+m, 4H), 1.55 (m, 1H), 1.65-1.72 (m, 4H), 2.17 (br t, 1H), 2.33 (s, 3H), 2.52 (s, 3H), 2.56 (br t, 1H), 2.69 (m, 1H), 2.82 (m, 2H), 2.93 (m, 1H), 3.29 (m, 1H), 3.49 (m, 2H), 3.60 (s, 3H), 3.88 (m, 1H), 4.19 (m, 1H), 6.97 (s+d, 2H), 7.10 (s, 1H), 7.36 (m, 1H), 7.83 (s, 1H), 8.01 (s, 1H), 8.71 (br s, 1H); ES-MS m/z 557 (M+H).

Example 212

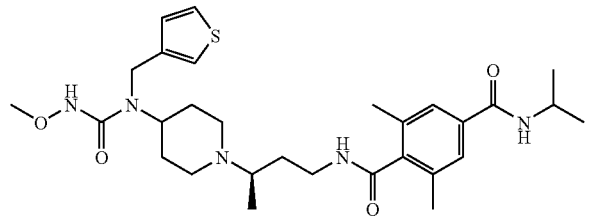

Compound 212

N—{(R)-3-[4-(3-methoxy-1-thiophen-3-ylmethyl-ureido)-piperidin-1-yl]-butyl}-N'-isopropyl-2,6-dimethyl-terephthalamide Following general procedure E: 1-[1-((R)-3-Amino-1-methyl-propyl)-piperidin-4-yl]-3-methoxy-1-thiophen-3-ylmethyl-urea (160 mg, 0.47 mmol), 4-cyano-2,6-dimethyl-benzoic acid (91 mg, 0.52 mmol), EDCI (99 mg, 0.52 mmol), HOBt (70 mg, 0.52 mmol), DIPEA (0.12 ml, 0.71 mmol), and DMF (5 ml) were combined and stirred at room temperature overnight. The crude product was purified by flash chromatography ($CH_2Cl_2$, 8% MeOH) to afford the product (175 mg, 75%) as a white solid.

To a solution of 4-cyano-N—{(R)-3-[4-(3-methoxy-1-thiophen-3-ylmethyl-ureido)-piperidin-1-yl]-butyl}-2,6-dimethyl-benzamide (175 mg, 0.35 mmol) in anhydrous alcohol (5 ml) was added 10N NaOH (1 ml). The mixture was stirred at 100° C. overnight, concentrated, then dry-loaded onto a column. The crude product was purified with 7:2:1 acetonitrile/methanol/$NH_4OH$ to afford the product (162 mg, 89%) as a white solid and possibly as a mixture of an amide and carboxylic acid.

COMPOUND 212 was isolated as a white solid. $^1$H NMR ($CDCl_3$) δ 0.58-1.12 (m, 2H), 0.98 (d, 3H, J=6.6 Hz), 1.28 (d, 6H, J=6.3 Hz), 1.44-1.58 (m, 1H), 1.63-1.87 (m, 3H), 2.11-2.48 (m, 1H), 2.31 (s, 6H), 2.52-2.64 (m, 1H), 2.72-2.76 (m, 1H), 2.77-2.93 (m, 1H), 3.26-3.32 (m, 1H), 3.49-3.50 (m, 2H), 3.59 (s, 3H), 3.81-3.97 (m, 1H), 4.13-4.38 (m, 2H), 5.87 (d, 1H, J=9 Hz), 6.96 (s, 1H), 6.98-6.99 (m, 1H), 7.11-7.12 (m, 1H), 7.30 (s, 2H), 7.31-7.37 (m, 1H), 8.77 (d, 1H, J=6 Hz); $^{13}$C NMR ($CDCl_3$) δ 13.46, 14.52, 19.19, 22.84, 29.17, 30.11, 31.08, 39.54, 40.61, 40.95, 42.06, 43.66, 51.59, 51.85, 53.54, 60.53, 61.31, 64.29, 121.60, 126.02, 126.28, 127.37, 134.61, 135.1, 138.94, 141.07, 159.14, 166.58, 169.22; ES-MS m/z 580 (M+Na).

Example 213

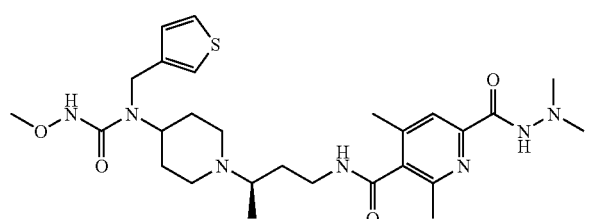

Compound 213

6-(N',N'-Dimethyl-hydrazinocarbonyl)-2,4-dimethyl-N—{(R)-3-[4-(3-methoxy-1-thiophen-3-ylmethyl-ureido)-piperidin-1-yl]-butyl}-nicotinamide $^1$H NMR ($CDCl_3$) δ 0.84 (m, 1H), 0.99 (d+m, 4H), 1.57 (m, 1H), 1.69 (m, 3H), 2.17 (br t, 1H), 2.32 (s, 3H), 2.55 (s+br t, 4H), 2.72 (s, 7H), 2.82 (m, 2H), 3.30 (m, 1H), 3.60 (s+m, 4H), 3.86 (m, 1H), 4.22 (m, 1H), 6.98 (m, 2H), 7.11 (s, 1H), 7.35 (m, 1H), 7.86 (s, 1H), 8.62 (br s, 2H); ES-MS m/z 560 (M+H).

Example 214

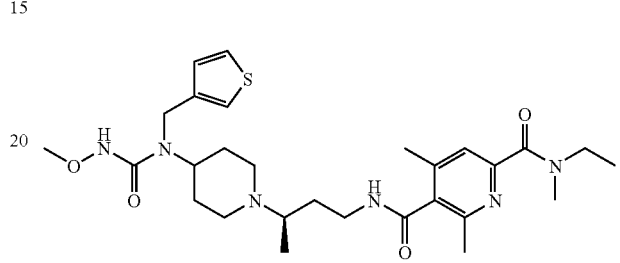

Compound 214

4,6-Dimethyl-pyridine-2,5-dicarboxylic acid 2-(ethyl-methyl-amide) 5-({(R)-3-[4-(3-methoxy-1-thiophen-3-ylmethyl-ureido)-piperidin-1-yl]-butyl}-amide)

$^1$H NMR ($CDCl_3$) (mixture of rotamers) δ 0.84 (m, 1H), 0.99 (d+m, 4H), 1.13 (t, J=6.0 Hz) and 1.25 (t, J=6.0 Hz) (total 3H), 1.56 (m, 1H), 1.69 (m, 3H), 2.17 (br t, 1H), 2.31 (s, 3H), 2.54 (s+br t, 4H), 2.72 (m, 1H), 2.82 (m, 2H), 2.96 (s) and 3.08 (s) (total 3H), 3.30 (m, 2H), 3.61 (s+m, 5H), 3.73 (m, 1H), 3.88 (m, 1H), 4.25 (m, 1H), 7.06 (d, J=3.0 Hz), 7.09 (s, 1H), 7.18 (m, 2H), 7.31 (m, 1H), 8.83 (br s, 1H); ES-MS m/z 559 (M+H).

Example 215

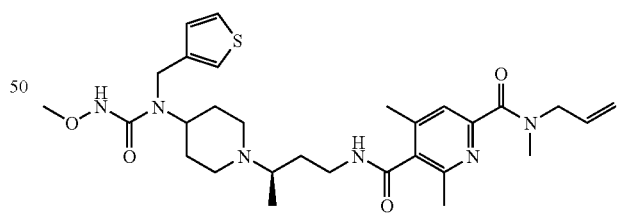

Compound 215

4,6-Dimethyl-pyridine-2,5-dicarboxylic acid 2-(allyl-methyl-amide) 5-({(R)-3-[4-(3-methoxy-1-thiophen-3-ylmethyl-ureido)-piperidin-1-yl]-butyl}-amide)

$^1$H NMR ($CDCl_3$) (mixture of rotamers) δ 0.85 (m, 1H), 0.98 (d+m, 4H), 1.55 (m, 1H), 1.65-1.76 (m, 3H), 2.17 (br t, 1H), 2.31 (s, 3H), 2.53 (s+br t, 4H), 2.68 (m, 1H), 2.82 (m, 2H), 2.95 (s) and 3.07 (s) (total 3H), 3.28 (m, 2H), 3.61 (s+m, 5H), 3.74 (m, 1H), 3.91 (m, 1H), 4.15-4.24 (m, 1H), 5.13-5.31 (m, 2H), 5.78 (m, 1H), 7.06 (d, 1H, J=3.0 Hz), 7.14 (m, 2H), 7.21 (s, 1H), 7.31 (m, 1H), 8.82 (br s, 1H); ES-MS m/z 571 (M+H).

Example 216

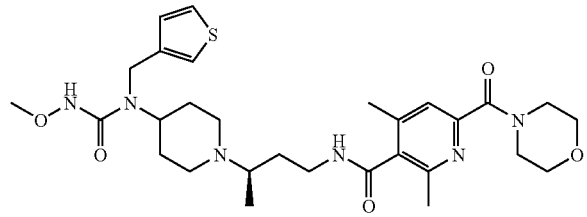

Compound 216

2,4-Dimethyl-6-(morpholine-4-carbonyl)-N—{(R)-3-[4-(3-methoxy-1-thiophen-3-ylmethyl-ureido)-piperidin-1-yl]-butyl}-nicotinamide $^1$H NMR (CDCl$_3$) δ 0.85 (m, 1H), 0.98 (d+m, 4H), 1.55 (m, 1H), 1.66-1.73 (m, 3H), 2.17 (br t, 1H), 2.32 (s, 3H), 2.53 (s, 3H), 2.57 (br t, 1H), 2.68 (m, 1H), 2.83 (m, 2H), 3.26 (m, 1H), 3.55 (m, 2H), 3.61 (s, 3H), 3.69 (m, 4H), 3.75 (s, 3H), 3.87 (m, 1H), 4.23 (m, 1H), 7.06 (d, 1H, J=3.0 Hz), 7.14 (m, 2H), 7.32 (m, 1H), 8.82 (br d, 1H); ES-MS m/z 587 (M+H).

Example 217

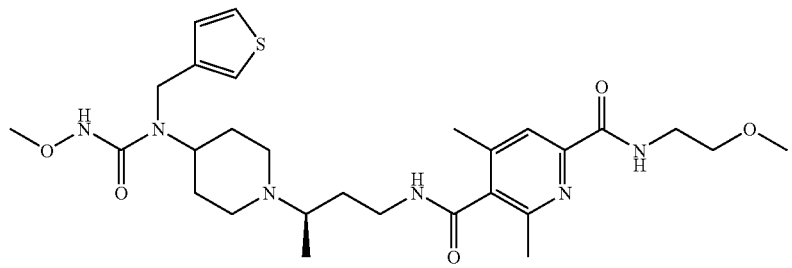

Compound 217

4,6-Dimethyl-pyridine-2,5-dicarboxylic acid 2-[(2-methoxy-ethyl)-amide]5-({(R)-3-[4-(3-methoxy-1-thiophen-3-ylmethyl-ureido)-piperidin-1-yl]-butyl}-amide)

$^1$H NMR (CDCl$_3$) δ 0.81 (m, 1H), 0.98 (d+m, 4H), 1.54 (m, 1H), 1.63-1.75 (m, 4H), 2.16 (br t, 1H), 2.34 (s, 3H), 2.52 (s+br t, 4H), 2.67 (m, 1H), 2.82 (m, 2H), 3.28 (m, 1H), 3.34 (s, 3H), 3.56 (m, 3H), 3.61 (s, 3H), 3.67 (m, 1H), 3.87 (m, 1H), 4.20 (m, 1H), 6.96 (d, 1H, J=6.0 Hz), 7.07 (s, 1H), 7.16 (s, 1H), 7.34 (m, 1H), 7.86 (s, 1H), 8.25 (br t, 1H), 8.75 (br d, 1H); ES-MS m/z 575 (M+H).

Example 218

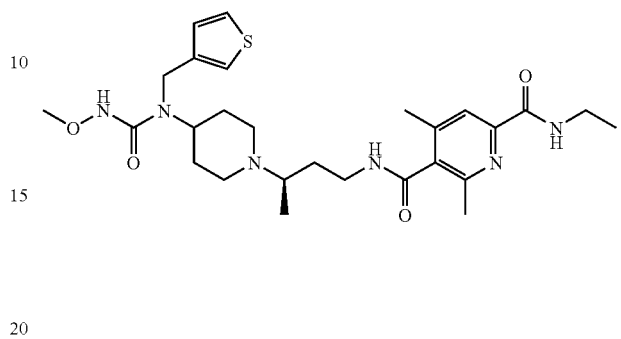

Compound 218

4,6-Dimethyl-pyridine-2,5-dicarboxylic acid 2-ethylamide 5-({(R)-3-[4-(3-methoxy-1-thiophen-3-ylmethyl-ureido)-piperidin-1-yl]-butyl}-amide)

$^1$H NMR (CDCl$_3$) δ 0.83 (m, 1H), 0.98 (d+m, 4H), 1.26 (t, 3H, J=6.0 Hz), 1.54 (m, 1H), 1.64-1.75 (m, 4H), 2.17 (br t, 1H), 2.32 (s, 3H), 2.52 (s, 3H), 2.54 (br t, 1H), 2.68 (m, 1H), 2.82 (m, 2H), 3.28 (m, 1H), 3.50 (m, 4H), 3.59 (s, 3H), 3.88 (m, 1H), 4.20 (m, 1H), 6.95 (s+d, 2H), 7.07 (s, 1H), 7.34 (m, 1H), 7.81 (s, 1H), 7.98 (br t, 1H), 8.65 (br d, 1H); ES-MS m/z 545 (M+H).

Example 219

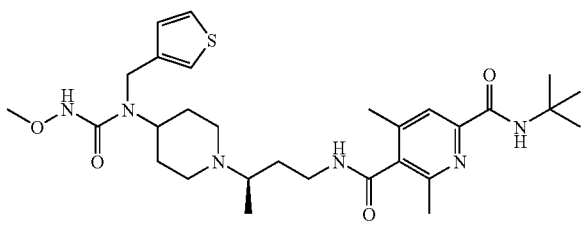

Compound 219

4,6-Dimethyl-pyridine-2,5-dicarboxylic acid 2-tert-butylamide 5-({(R)-3-[4-(3-methoxy-1-thiophen-3-ylmethyl-ureido)-piperidin-1-yl]-butyl}-amide)

$^1$H NMR (CDCl$_3$) δ 0.81 (m, 1H), 0.98 (d+m, 4H), 1.49 (s+m, 1H), 1.64-1.76 (m, 4H), 2.16 (br t, 1H), 2.32 (s, 3H), 2.54 (s+br t, 4H), 2.69 (m, 1H), 2.82 (m, 2H), 3.28 (m, 1H), 3.50 (m, 2H), 3.60 (s, 3H), 3.84 (m, 1H), 4.18 (m, 1H), 6.94 (s, 1H), 7.01 (d, 1H, J=6.0 Hz), 7.10 (s, 1H), 7.36 (m, 1H), 7.84 (s, 1H), 7.99 (s, 1H), 8.64 (br s, 1H); ES-MS m/z 573 (M+H).

Example 220

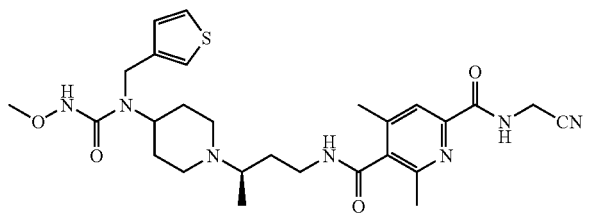

Compound 220

4,6-Dimethyl-pyridine-2,5-dicarboxylic acid 2-cyanomethyl 5-({(R)-3-[4-(3-methoxy-1-thiophen-3-ylmethyl-ureido)-piperidin-1-yl]-butyl}-amide)

$^1$H NMR (CDCl$_3$) δ 0.90 (m, 1H), 0.98 (d+m, 4H), 1.54 (m, 2H), 1.67-1.76 (m, 3H), 2.21 (br t, 1H), 2.36 (s, 3H), 2.55 (s+br t, 4H), 2.72 (m, 1H), 2.86 (m, 2H), 3.34 (m, 1H), 3.57 (s, 2H), 3.60 (s, 3H), 3.84 (m, 1H), 4.20 (m, 1H), 4.38 (d, 2H, J=6.0 Hz), 6.90 (d, 1H, J=3.0 Hz), 7.02 (s, 1H), 7.07 (s, 1H), 7.37 (m, 1H), 7.82 (s, 1H), 8.32 (br t, 1H), 8.64 (br s, 1H); ES-MS m/z 556 (M+H).

Example 221

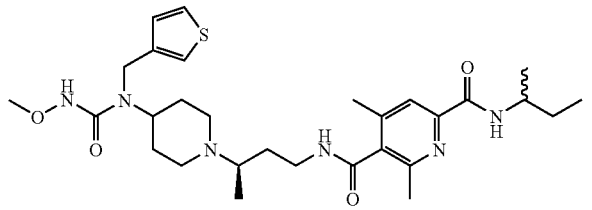

Compound 221

4,6-Dimethyl-pyridine-2,5-dicarboxylic acid 2-sec-butyl 5-({(R)-3-[4-(3-methoxy-1-thiophen-3-ylmethyl-ureido)-piperidin-1-yl]-butyl}-amide)

$^1$H NMR (CDCl$_3$) δ 0.85 (m, 1H), 0.98 (m, 7H), 1.26 (d, 3H, J=6.0 Hz), 1.51-1.75 (m, 7H), 2.17 (br t, 1H), 2.33 (s, 3H), 2.55 (s+br t, 4H), 2.68 (m, 1H), 2.82 (m, 2H), 3.29 (m, 1H), 3.52 (s, 2H), 3.60 (s, 3H), 3.88 (m, 1H), 4.10 (m, 1H), 4.17 (m, 1H), 6.93 (s, 1H), 6.98 (d, 1H, J=3.0 Hz), 7.09 (s, 1H), 7.37 (m, 1H), 7.85 (s+m, 2H), 8.65 (br s, 1H); ES-MS m/z 573 (M+H).

Example 222

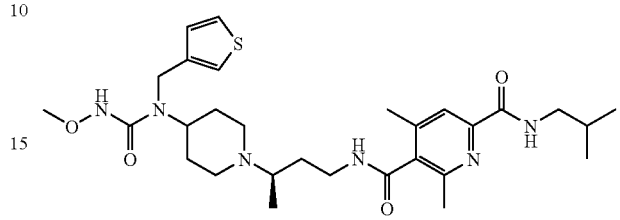

Compound 222

4,6-Dimethyl-pyridine-2,5-dicarboxylic acid 2-isobutyl 5-({(R)-3-[4-(3-methoxy-1-thiophen-3-ylmethyl-ureido)-piperidin-1-yl]-butyl}-amide)

$^1$H NMR (CDCl$_3$) δ 0.86 (m, 1H), 0.98 (d+d+m, 11H), 1.56 (m, 1H), 1.65-1.74 (m, 4H), 1.91 (m, 1H), 2.18 (br t, 1H), 2.33 (s, 3H), 2.54 (s, 3H), 2.57 (br t, 1H), 2.69 (m, 1H), 2.86 (m, 2H), 3.29 (m, 3H), 3.54 (s, 2H), 3.60 (s, 3H), 3.86 (m, 1H), 4.23 (m, 1H), 6.96 (s+d, 2H), 7.08 (s, 1H), 7.35 (m, 1H), 7.84 (s, 1H), 8.10 (br t, 1H), 8.66 (br s, 1H); ES-MS m/z 573 (M+H).

Example 223

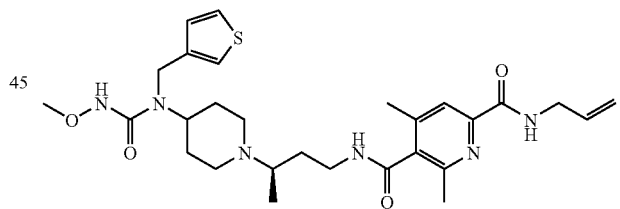

Compound 223

4,6-Dimethyl-pyridine-2,5-dicarboxylic acid 2-allyl 5-({(R)-3-[4-(3-methoxy-1-thiophen-3-ylmethyl-ureido)-piperidin-1-yl]-butyl}-amide)

$^1$H NMR (CDCl$_3$) δ 0.88 (m, 1H), 1.02 (d+m, 4H), 1.56 (m, 1H), 1.65-1.73 (m, 4H), 2.17 (br t, 1H), 2.33 (s, 3H), 2.53 (s, 3H), 2.56 (br t, 1H), 2.69 (m, 1H), 2.83 (m, 2H), 3.30 (m, 1H), 3.56 (s, 2H), 3.60 (s, 3H), 3.84 (m, 1H), 4.10 (t, 2H, J=6.0 Hz), 4.20 (m, 1H), 5.17 (m, 2H), 5.93 (m, 1H), 6.93 (s+d, 2H), 7.07 (s, 1H), 7.34 (m, 1H), 7.83 (s, 1H), 8.10 (br t, 1H), 8.65 (br s, 1H); ES-MS m/z 557 (M+H).

Example 224

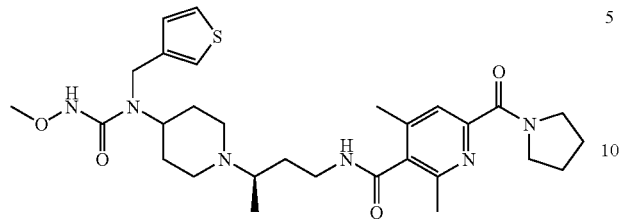

Compound 224

2,4-Dimethyl-N—{(R)-3-[4-(3-methyl-1-thiophen-3-ylmethyl-ureido)-piperidin-1-yl]-butyl}-6-(pyrrolidine-1-carbonyl)-nicotinamide ¹H NMR (CDCl₃) δ 0.83 (m, 1H), 0.99 (d+m, 4H), 1.56 (m, 1H), 1.65-1.77 (m, 4H), 1.94 (m, 4H), 2.17 (br t, 1H), 2.30 (s, 3H), 2.53 (s, 3H), 2.58 (br t, 1H), 2.69 (m, 1H), 2.84 (m, 2H), 3.29 (m, 1H), 3.60 (s, 3H), 3.62-3.69 (m, 6H), 3.88 (m, 1H), 4.23 (m, 1H), 7.06 (d, 1H, J=6.0 Hz), 7.11 (s, 1H), 7.18 (s, 1H), 7.31 (m, 1H), 7.40 (s, 1H), 8.86 (br s, 1H); ES-MS m/z 571 (M+H).

Example 225

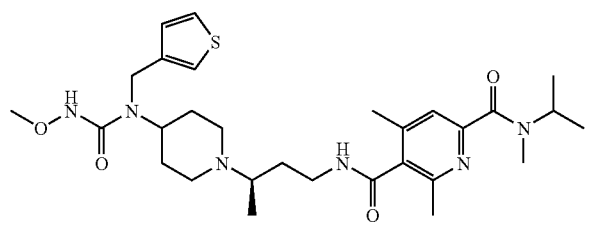

Compound 225

4,6-Dimethyl-pyridine-2,5-dicarboxylic acid 2-(isopropyl-methyl-amide) 5-({(R)-3-[4-(3-methoxy-1-thiophen-3-ylmethyl-ureido)-piperidin-1-yl]-butyl}-amide)

¹H NMR (CDCl₃) (mixture of rotamers) δ 0.84 (m, 1H), 0.98 (d+m, 4H), 1.15 (d, J=6.0 Hz) and 1.23 (d, J=6.0 Hz) (total 6H), 1.54 (m, 1H), 1.65-1.76 (m, 3H), 2.16 (br t, 1H), 2.30 (s, 3H), 2.52 (s, 3H), 2.56 (br t, 1H), 2.68 (m, 1H), 2.83 (m, 2H), 2.78 (s) and 2.95 (s) (total 3H), 3.28 (m, 2H), 3.60 (s, 3H), 3.70 (dd, 2H, J=18.0, 12.0 Hz), 3.88 (m) and 4.94 (m) (total 1H), 4.24 (m, 1H), 7.06 (d, 1H, J=3.0 Hz), 7.13 (m, 2H), 7.19 (s, 1H), 7.29 (m, 1H), 8.89 (br m, 1H); ES-MS m/z 573 (M+H).

Example 226

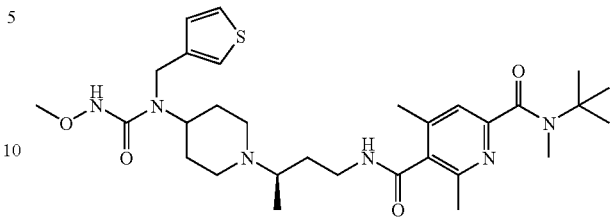

Compound 226

4,6-Dimethyl-pyridine-2,5-dicarboxylic acid 2-(methyl-tert-butyl-amide) 5-({(R)-3-[4-(3-methoxy-1-thiophen-3-ylmethyl-ureido)-piperidin-1-yl]-butyl}-amide)

¹H NMR (CDCl₃) δ 0.84 (m, 1H), 0.97 (d+m, 4H), 1.54 (s+m, 10H), 1.64-1.76 (m, 3H), 2.15 (brt, 1H), 2.30 (s, 3H), 2.52 (s, 3H), 2.56 (brt, 1H), 2.67 (m, 1H), 2.79 (m, 2H), 2.83 (s, 3H), 3.27 (m, 2H), 3.58 (s, 3H), 3.69 (dd, 2H, J=18.0, 12.0 Hz), 3.80 (m, 1H), 4.23 (m, 1H), 7.07 (s+d, 2H), 7.14 (s, 1H), 7.21 (s, 1H), 7.30 (m, 1H), 8.77 (br s, 1H); ES-MS m/z 587 (M+H).

Example 227 and

Example 228

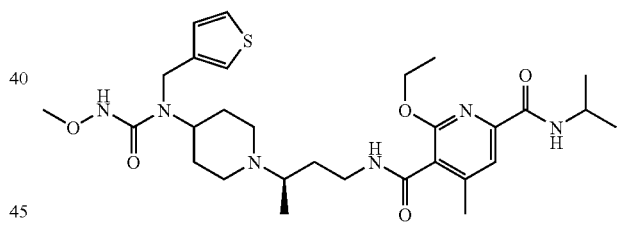

Compound 227

6-Ethoxy-4-methyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

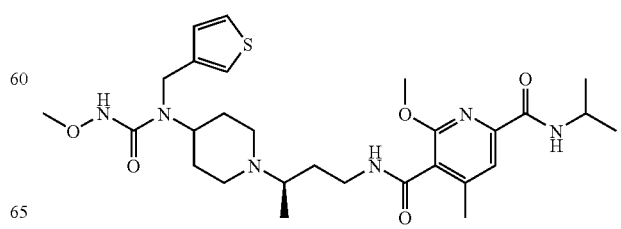

Compound 228

6-Methoxy-4-methyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

To a solution of 2-chloro-6-cyano-4-methyl-N-{3-[4-(3-methyl-1-thiophen-3-ylmethyl-ureido)-piperidin-1-yl]-butyl}-nicotinamide (0.150 g, 0.30 mmol) in reagent grade (75%) ethanol (5 ml) was added 10 N NaOH (1 ml) and the resulting colorless solution was stirred for 6 hours at 100° C. The reaction mixture was dry loaded onto silica gel and purified using column chromatography (MeCN/MeOH/NH$_4$OH, 6:3:1, v/v/v) to give a mixture of two products, 6-methoxy-4-methyl-5-{3-[4-(3-methyl-1-thiophen-3-ylmethyl-ureido)-piperidin-1-yl]-butylcarbamoyl}-pyridine-2-carboxylic acid and 6-ethoxy-4-methyl-5-{3-[4-(3-methyl-1-thiophen-3-ylmethyl-ureido)-piperidin-1-yl]-butylcarbamoyl}-pyridine-2-carboxylic acid, as a glassy white solid (0.291 g, 80%). $^1$H NMR and LC-MS of the mixture both confirmed that it was indeed a 1:1 mixture of the methoxy and ethoxy products.

The above acid mixture (0.070 g, 0.13 mmol), N-(3-dimethylaminopropyl)-N'-ethylcarbodiimide hydro-chloride (0.028 g, 0.14 mmol) and 1-hydroxybenzotriazole (0.020 g, 0.14 mmol) were combined in N,N-dimethylformamide (5 ml) to give a pale yellow solution. To this solution was added isopropylamine (12 µL, 0.14 mmol) followed by diisopropylethylamine (30 µL, 0.16 mmol) and the resulting mixture was stirred at 25° C. for 16 hours. Standard workup according to general procedure E gave the crude product as a tan oil. Purification by column chromatography on silica gel (Et$_2$O/MeOH/NH$_4$OH, 89:10:1, v/v/v) afforded both COMPOUND 227 (0.035 g, 46%) and COMPOUND 228.

COMPOUND 227: $^1$H NMR (CDCl$_3$) δ 0.98 (d+m, 4H), 1.21 (m, 1H), 1.29 (d, 6H, J=6.0 Hz), 1.37 (t, 3H, J=6.0 Hz), 1.53 (m, 1H), 1.72 (m, 3H), 2.18 (br t, 1H), 2.33 (s, 3H), 2.56 (br t, 1H), 2.71 (m, 1H), 2.85 (m, 2H), 3.30 (m, 1H), 3.60 (s, 3H), 3.64 (s, 2H), 3.79 (m, 1H), 4.24 (m, 2H), 4.35 (q, 2H, J=6.0 Hz), 6.92 (s+d, 2H), 7.07 (s, 1H), 7.34 (m, 1H), 7.49 (d, 1H, J=6.0 Hz), 7.63 (s, 1H), 8.26 (br d, 1H); ES-MS m/z 589 (M+H).

COMPOUND 228: $^1$H NMR (CDCl$_3$) δ 0.98 (d+m, 4H), 1.19 (m, 1H), 1.29 (d, 6H, J=6.0 Hz), 1.53 (m, 1H), 1.74 (m, 3H), 2.17 (br t, 1H), 2.34 (s, 3H), 2.58 (br t, 1H), 2.71 (m, 1H), 2.85 (m, 2H), 3.30 (m, 1H), 3.60 (s, 3H), 3.64 (s, 2H), 3.79 (m, 1H), 3.93 (s, 3H), 4.28 (m, 2H), 6.92 (s+d, 2H), 7.06 (s, 1H), 7.34 (m, 1H), 7.51 (d, 1H, J=6.0 Hz), 7.65 (s, 1H), 8.32 (br d, 1H); ES-MS m/z 575 (M+H).

Example 229

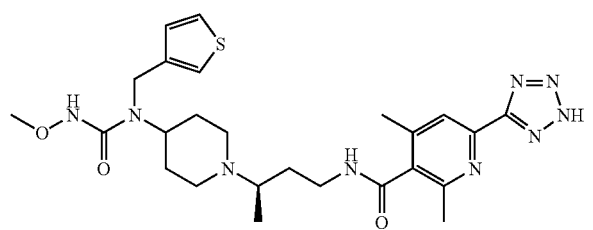

Compound 229

2,4-Dimethyl-N—{(R)-3-[4-(3-methoxy-1-thiophen-3-ylmethyl-ureido)-piperidin-1-yl]-butyl}-6-(2H-tetrazol-5-yl)-nicotinamide 6-Cyano-2,4-dimethyl-N-{3-[4-(3-methoxy-1-thiophen-3-ylmethyl-ureido)-piperidin-1-yl]-butyl}-nicotinamide (0.21 g, 0.42 mmol) was dissolved in iso-propanol (4 ml) and diluted with water (8 ml) (Demke and Sharpless, JOC 2001, 66, 7945-50). To the milky solution were added ZnBr$_2$ (0.094 g, 0.42 mmol) and NaN$_3$ (0.030 g, 0.46 mmol) and the resulting mixture was refluxed for 16 h. The crude reaction mixture was dry-loaded onto silica gel and purified via column chromatography (MeCN/MeOH/NH$_4$OH, 7:2:1, v/v/v) to yield COMPOUND 229 (0.13 g, 58%) as a white solid. $^1$H NMR (CD$_3$OD) δ 1.49 (d, 3H, J=6.0 Hz), 1.98 (m, 3H), 2.29 (m, 3H), 2.40 (s, 3H), 2.60 (s, 3H), 3.28 (m, 2H), 3.58 (m, 5H), 4.23 (m, 1H), 4.48 (s, 2H), 7.08 (d, 1H, J=6.0 Hz), 7.26 (s, 1H), 7.44 (m, 1H), 7.87 (s, 1H); ES-MS m/z 542 (M+H).

Example 230

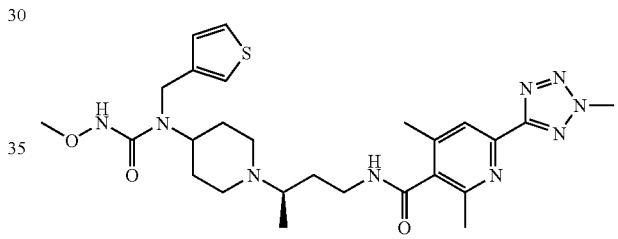

Compound 230

2,4-Dimethyl-6-(2-methyl-2H-tetrazol-5-yl)-N—{(R)-3-[4-(3-methoxy-1-thiophen-3-ylmethyl-ureido)-piperidin-1-yl]-butyl}-nicotinamide In a high-pressure sealed tube, methyl iodide (24 µL, 0.39 mmol) and K$_2$CO$_3$ (0.10 g, 0.78 mmol) were added to a solution of 2,4-dimethyl-N-{3-[4-(3-methoxy-1-thiophen-3-ylmethyl-ureido)-piperidin-1-yl]-butyl}-6-(2H-tetrazol-5-yl)-nicotinamide (0.070 g, 0.13 mmol) dissolved in DMF (4 ml). The resulting mixture was stirred at 80° C. for 16 h. Standard basic workup gave the crude product as a tan oil. Purification by column chromatography on silica gel (Et$_2$O/MeOH/NH$_4$OH, 87:11:2, v/v/v) afforded COMPOUND 230 (0.015 g, 21%) as a white foam. $^1$H NMR (CDCl$_3$) δ 0.91-1.11 (d+m, 5H), 1.54 (m, 1H), 1.69-1.81 (m, 3H), 2.21 (br t, 1H), 2.40 (s, 3H), 2.59 (s+br t, 4H), 2.63 (m, 1H), 2.75 (m, 2H), 3.35 (m, 1H), 3.50 (s, 2H), 3.55 (s, 3H), 3.88 (m, 1H), 4.21 (m, 1H), 4.34 (s, 3H), 6.73 (d, 1H J=3.0 Hz), 6.86 (s, 2H), 7.28 (m, 1H), 8.00 (s, 1H), 8.85 (br s, 1H). ES-MS m/z 556 (M+H).

Example 231

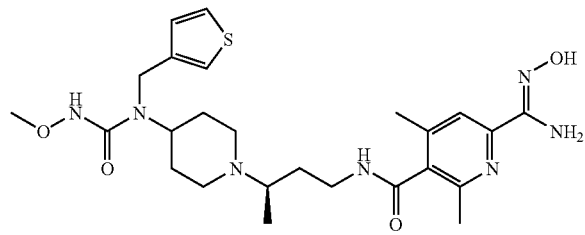

Compound 231

N—{(R)-3-[4-(3-methoxy-1-thiophen-3-ylmethyl-ureido)-piperidin 1-yl]-butyl}-6-(N-hydroxycarbamimidoyl)-2,4-dimethyl-nicotinamide To a solution of 6-cyano-2,4-dimethyl-N—((R)-3-{4-[(thiophen-3-ylmethyl)-amino]-piperidin-1-yl}-butyl)-nicotinamide (208 mg, 0.49 mmol) in EtOH (3 ml) was added hydroxylamine HCl (190 mg, 2.73 mmol) and NaHCO$_3$ (239 mg, 2.84 mmol) and the reaction heated to reflux overnight. The mixture was diluted with CH$_2$Cl$_2$ (25 ml) and water (10 ml) and saturated aqueous NaHCO$_3$ (20 ml). The aqueous layer was extracted with CH$_2$Cl$_2$ (2×5 ml) and the combined organic extracts were dried (Na$_2$SO$_4$) and concentrated to afford 6-(N-hydroxycarbamimidoyl)-2,4-dimethyl-N—((R)-3-{4-[(thiophen-3-ylmethyl)-amino]-piperidin-1-yl}-butyl)-nicotinamide (173 mg) as a beige foam.

To a solution of the amine from above (173 mg) in CH$_2$Cl$_2$ (5 ml) was added DIPEA (0.080 ml, 0.46 mmol) and N-(4-nitrophenoxycarbonyl)methoxyamine (89 mg, 0.42 mmol) and the reaction stirred at room temperature for 2 h. The mixture was diluted with CH$_2$Cl$_2$ (25 ml) and saturated aqueous NaHCO$_3$ (25 ml) and the aqueous layer was extracted with CH$_2$Cl$_2$ (2×10 ml), dried (Na$_2$SO$_4$), concentrated and purified by column chromatography on silica gel (CH$_2$Cl$_2$/MeOH/NH$_4$OH, 96:4:0 then 9:1:0 then 88:10:2) to afford COMPOUND 231 (123 mg, 47% 2 steps) as a yellow foam. $^1$H NMR (CDCl$_3$) δ 1.03 (d, 3H, J=6.6 Hz), 1.06-1.47 (m, 2H), 1.67-1.90 (m, 4H), 2.21-2.28 (m, 1H), 2.24 (s, 3H), 2.45 (s, 3H), 2.61 (br t, 1H, J=11.4 Hz), 2.75-2.94 (m, 3H), 3.47-3.53 (m, 1H), 3.61-3.65 (m, 1H), 3.63 (s, 3H), 3.90 (s, 2H), 4.21-4.28 (m, 1H), 5.54 (br s, 2H), 6.93 (dd, 1H, J=4.8, 1.2 Hz), 7.07 (br s, 1H), 7.09 (s, 1H), 7.19 (s, 1H), 7.31 (dd, 1H, J=4.8, 3 Hz), 8.22 (br m, 1H), 9.39 (br s, 1H); ES-MS m/z 554 (M+Na).

Example 232

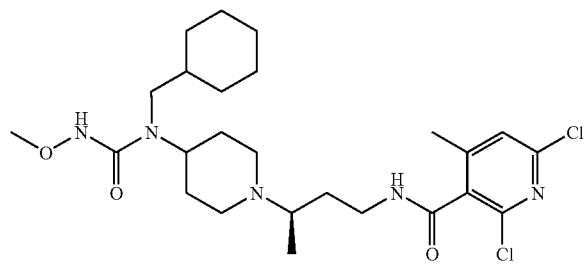

Compound 232

2,6-Dichloro-N—{(R)-3-[4-(1-cyclohexylmethyl-3-methoxy-ureido)-piperidin-1-yl]-butyl}-4-methyl-nicotinamide To a solution of {(R)-3-[4-(cyclohexylmethyl-amino)-piperidin-1-yl]-butyl}-carbamic acid tert-butyl ester (174 mg, 0.47 mmol) in THF (5 ml) was added methoxy-carbamic acid phenyl ester (94.7 mg, 0.56 mmol). The mixture was stirred at 60° C. for 3 d then concentrated in vacuo. The crude product was purified by flash chromatography (CH$_2$Cl$_2$, 7% MeOH, 1% NH$_4$OH) to afford {(R)-3-[4-(1-cyclohexylmethyl-3-methoxy-ureido)-piperidin-1-yl]-butyl}-carbamic acid tert-butyl ester (105 mg, 50%) as a yellow oil.

Following general procedure C: To a solution of the boc-protected amine (105 mg, 0.23 mmol) in CH$_2$Cl$_2$ (5 ml) was added TFA (1 ml). The reaction was stirred at room temperature for 2 h then concentrated to remove excess TFA. The crude product was used in the next reaction without purification. Following general procedure E: 1-[1-((R)-3-Amino-1-methyl-propyl)-piperidin-4-yl]-1-cyclohexylmethyl-3-ethyl-urea (77 mg, 0.23 mmol), 2,6-dichloro-4-methyl-nicotinic acid (51 mg, 0.25 mmol), EDCI (48 mg, 0.25 mmol), HOBt (34 mg, 0.25 mmol), DIPEA (0.059 ml, 0.35 mmol), and DMF (5 ml) were combined and stirred at room temperature overnight. The crude product was purified by preparative TLC (ether, 8% MeOH, 1% NH$_4$OH) to afford COMPOUND 232 (63 mg, 51%, 2 steps) as a white solid. $^1$H NMR (CDCl$_3$) δ 0.75-0.91 (m, 2H), 0.99 (d, 3H, J=6.0 Hz), 1.11-1.28 (m, 4H), 1.32-1.50 (m, 2H), 1.51-1.83 (m, 9H), 2.07-2.17 (m, 1H), 2.38 (s, 3H), 2.48-2.64 (m, 3H), 2.74-2.87 (m, 3H), 3.27-3.44 (m, 1H), 3.70 (s, 3H), 3.71-3.93 (m, 2H), 7.07 (s, 1H), 7.15 (s, 1H), 8.21 (br s, 1H); ES-MS m/z 528 (M+H).

Example 233

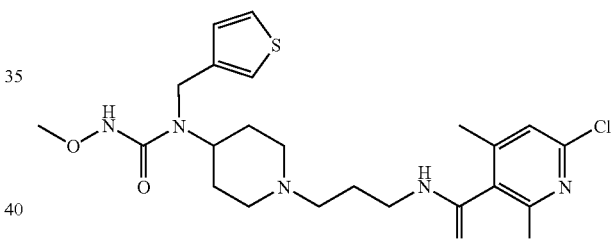

Compound 233

2,6-Dichloro-4-methyl-N-{3-[4-(3-methoxy-1-thiophen-3-ylmethyl-ureido)-piperidin-1-yl]-propyl}-nicotinamide Using general procedure A, 4-amino-piperidine-1-carboxylic acid tert-butyl ester (0.800 g, 4.30 mmol), thiophene-3-carbaldehyde (0.480 g, 4.30 mmol), acetic acid (20 drops, cat.) and sodium triacetoxyborohydride (1.27 g, 6.02 mmol) were combined in 1,2-dichloroethane (40 ml) and the resulting mixture was stirred at rt for 16 h. Standard basic workup gave the crude product as a tan oil. Purification by column chromatography on silica gel (CH$_2$Cl$_2$:MeOH:NH$_4$OH, 96:3:1, v/v/v) gave 4-[(thiophen-3-ylmethyl)-amino]-piperidine-1-carboxylic acid tert-butyl ester as a pale yellow oil (0.886 g, 73%). $^1$H-NMR (CDCl$_3$) δ 1.27 (m, 3H), 1.45 (s+m, 1H), 1.84 (d, 2H, J=12.0 Hz), 2.66 (m, 1H), 2.80 (t, 2H, J=12.0 Hz), 3.85 (s, 2H), 4.01 (br d, 2H), 7.03 (d, 1H, J=6.0 Hz), 7.12 (s, 1H), 7.29 (m, 1H).

To a suspension of methoxylamine hydrochloride (0.520 g, 6.25 mmol) in CH$_3$CN (15 ml) was added DIPEA (1.09 ml, 6.25 mmol) followed by CDI (1.02 g, 6.25 mmol) and the reaction stirred at rt for 1.5 h after which a solution of the amine from above (0.880 g, 3.12 mmol) in CH$_3$CN (10 ml) was added and the reaction stirred at 60° C. overnight. The solution was cooled, treated with saturated aqueous NaHCO$_3$ (20 ml) and extracted with CH$_2$Cl$_2$ (3×15 ml). The combined organic extracts were dried (Na$_2$SO$_4$), filtered, and concentrated. Purification by column chromatography on silica gel (CH$_2$Cl$_2$:MeOH:NH$_4$OH, 96:3:1, v/v/v) gave 4-(3-methoxy-1-thiophen-3-ylmethyl-ureido)-piperidine-1-carboxylic acid tert-butyl ester as a white foam (0.95 g, 86%). $^1$H-NMR (CDCl$_3$) δ 1.43 (s, 9H), 1.54 (m, 1H), 1.75 (d, 2H, J=9.0 Hz), 2.79 (br t, 1H), 3.65 (s, 3H), 4.17 (m, 2H), 4.27 (s, 2H), 6.96 (d, 1H, J=3.0 Hz), 7.08 (s, 1H), 7.11 (s, 1H), 7.36 (m, 1H).

4-(3-Methoxy-1-thiophen-3-ylmethyl-ureido)-piperidine-1-carboxylic acid tert-butyl ester (0.950 g, 2.69 mmol) was dissolved in a 3:1 mixture of CH$_2$Cl$_2$ and TFA and the mixture was stirred at rt for 1 h. The solvent was removed in vacuo and the resulting brown oil pumped in vacuo (high vacuum system) for 2 h. Using general procedure A, the crude amine, 3-(1,3-dioxo-1,3-dihydro-isoindol-2-yl)-propionaldehyde (0.561 g, 2.75 mmol), acetic acid (20 drops, cat.) and sodium triacetoxyborohydride (0.792 g, 3.75 mmol) were combined in CH$_2$Cl$_2$ (40 ml) and the resulting mixture was stirred at rt for 16 h. Standard basic workup gave the crude product as a tan oil. Purification by column chromatography on silica gel (CH$_2$Cl$_2$:MeOH:NH$_4$OH, 94:5:1, v/v/v) gave 1-{1-[3-(1,3-dioxo-1,3-dihydro-isoindol-2-yl)-propyl]-piperidin-4-yl}-3-methoxy-1-thiophen-3-ylmethyl-urea as a white foam (0.692 g, 62%). $^1$H NMR (CDCl$_3$) δ 1.36 (m, 2H), 1.59 (m, 2H), 1.85 (p, 2H, J=4.5 Hz), 1.91 (t, 2H, J=9.0 Hz), 2.39 (t, 2H, J=6.0 Hz), 2.88 (d, 2H, J=12.0 Hz), 3.62 (s, 3H), 3.75 (t, 2H, J=6.0 Hz), 4.04 (s, 2H), 4.23 (m, 1H), 6.90 (d, 1H, J=3.0 Hz), 6.99 (s, 1H), 7.06 (s, 1H), 7.36 (m, 1H), 7.62 (m, 2H), 7.81 (m, 2H).

To a solution of 1-{1-[3-(1,3-dioxo-1,3-dihydro-isoindol-2-yl)-propyl]-piperidin-4-yl}-3-methoxy-1-thiophen-3-ylmethyl-urea (0.69 g, 1.56 mmol) in EtOH (15 ml) was added hydrazine hydrate (0.49 ml, 15.6 mmol) and the reaction was stirred at rt for 16 h. The reaction mixture was diluted with Et$_2$O (40 ml) to give a white precipitate. The solid was removed via suction filtration and the filtrate was concentrated in vacuo to give a white foam. Purification by column chromatography on silica gel (CH$_2$Cl$_2$:MeOH:NH$_4$OH, 83:15:2, v/v/v) gave 1-[1-(3-amino-propyl)-piperidin-4-yl]-3-methoxy-1-thiophen-3-ylmethyl-urea as a white foam (0.280 g, 57%). $^1$H NMR (CDCl$_3$) δ 1.60-1.72 (m, 6H), 2.00 (t, 2H, J=9.0 Hz), 2.07 (br s, 3H), 2.39 (t, 2H, J=6.0 Hz), 2.75 (t, 2H, J=6.0 Hz), 2.98 (d, 2H, J=12.0 Hz), 3.65 (s, 3H), 4.25 (m, 1H), 4.29 (s, 2H), 6.95 (d, 1H, J=3.0 Hz), 7.10 (s, 2H), 7.34 (m, 1H).

The above amine (0.059 g, 0.19 mmol), EDCI (0.040 g, 0.21 mmol) and HOBt (0.028 g, 0.21 mmol) were combined in DMF (8 ml) to give a pale yellow solution. To this solution was added 2,6-dichloro-4-methyl-nicotinic acid (0.043 g, 0.21 mmol) followed by DIPEA (43 µL, 0.24 mmol) and the resulting mixture was stirred at 25° C. for 16 h. Standard workup according to general procedure E gave the crude product as a tan oil. Purification by column chromatography on silica gel (Et$_2$O:MeOH:NH$_4$OH, 86:12:2, v/v/v) afforded COMPOUND 233 (0.067 g, 69%) as a white foam. $^1$H NMR (CDCl$_3$) δ 1.26 (m, 2H), 1.70-1.79 (m, 4H), 2.06 (t, 2H, J=12.0 Hz), 2.35 (s, 3H), 2.54 (t, 2H, J=6.0 Hz), 2.97 (m, 2H), 3.57 (m, 2H), 3.63 (s, 3H), 3.95 (s, 2H), 4.27 (m, 1H), 6.98 (d, 1H, J=6.0 Hz), 7.06 (s, 1H), 7.10 (m, 2H), 7.36 (s, 1H), 8.36 (br t, 1H); ES-MS m/z 536 (M+Na). Anal. Calcd. for C$_{22}$H$_{29}$N$_5$O$_3$Cl$_2$S.1.1H$_2$O: C, 49.46; H, 5.89; N, 13.11. Found: C, 49.42; H, 5.63; N, 12.84.

Example 234

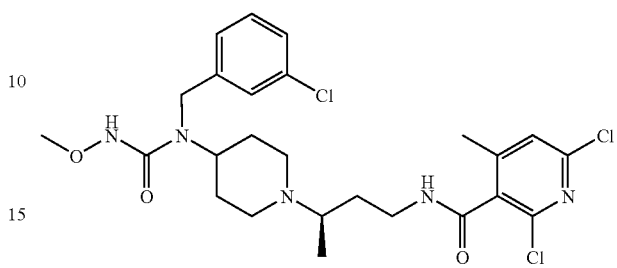

Compound 234

2,6-Dichloro-N—((R)-3-{4-[1-(3-chloro-benzyl)-3-methoxy-ureido]-piperidin-1-yl}-butyl)-4-methyl-nicotinamide Following general procedure A: to a solution of [(R)-3-(4-oxo-piperidin-1-yl)-butyl]-carbamic acid tert-butyl ester (0.25 g, 0.94 mmol) in CH$_2$Cl$_2$ (20 ml) was added 3-chloro-benzylamine (0.14 ml, 1.13 mmol) and the mixture was stirred for 5 min. NaBH(OAc)$_3$ (0.30 g, 1.41 mmol) and acetic acid (10 drops) were added and the mixture was stirred at rt under N$_2$ overnight. The crude product was purified by flash chromatography (CH$_2$Cl$_2$, 5% MeOH, 1% NH$_4$OH) to afford {(R)-3-[4-(3-chloro-benzylamino)-piperidin-1-yl]-butyl}-carbamic acid tert-butyl ester as a yellow oil (305 mg, 82%). $^1$H NMR (CDCl$_3$) δ 0.92-0.94 (d, 3H, J=6 Hz), 1.27-1.39 (m, 2H), 1.44 (s, 9H), 1.60-1.72 (m, 2H), 1.82-1.97 (m, 2H), 2.02-2.14 (m, 1H), 2.32-2.51 (m, 2H), 2.68-2.87 (m, 3H), 3.05-3.11 (m, 1H), 3.23-3.37 (m, 1H), 3.79 (s, 2H), 4.40 (s, 1H), 6.01 (br s, 1H), 7.16-7.25 (m, 3H), 7.33 (s, 1H).

To a solution of methoxyamine HCl (0.25 g, 3.04 mmol) in CH$_3$CN (5 ml) was added CDI (0.49 g, 3.04 mmol) and DIPEA (0.53 mL, 3.04 mmol). The mixture was stirred at 60° C. for 2 h, then a solution of {(R)-3-[4-(3-chloro-benzylamino)-piperidin-1-yl]-butyl}-carbamic acid tert-butyl ester (305 mg, 0.76 mmol) in CH$_3$CN (5 ml) was added to the previous mixture. After stirring at 60° C. overnight, the mixture was concentrated in vacuo and diluted with CH$_2$Cl$_2$ (15 ml) and saturated NaHCO$_3$ (20 ml). The aqueous layer was extracted with CH$_2$Cl$_2$ (3×10 ml), then the combined organic extracts were dried over Na$_2$SO$_4$ and concentrated. The crude product contained 2:1 product/starting material in the $^1$H NMR and was purified by flash chromatography (CH$_2$Cl$_2$, 7% MeOH, 1% NH$_4$OH) to afford ((R)-3-{4-[1-(3-chloro-benzyl)-3-methoxy-ureido]-piperidin-1-yl}-butyl)-carbamic acid tert-butyl ester as a yellow oil (215 mg, 60%). $^1$H NMR (CDCl$_3$) δ 0.92-0.95 (d, 3H, J=9 Hz), 1.37 (s, 9H), 1.47-1.82 (m, 6H), 2.13-2.25 (m, 1H), 2.48-2.57 (m, 1H), 2.63-2.89 (m, 3H), 2.99-3.09 (m, 1H), 3.23-3.38 (m, 1H), 3.65 (s, 3H), 4.14-4.26 (m, 1H), 4.31 (s, 2H), 5.90 (br s, 1H), 6.97 (s, 1H), 7.06-7.17 (m, 1H), 7.22 (s, 1H), 7.29 (s, 1H), 7.69 (s, 1H).

Following general procedure C: to a solution of the above Boc-protected amine (215 mg, 0.46 mmol) in CH$_2$Cl$_2$ (5 ml) was added TFA (1 ml). The reaction was stirred at rt for 1 h then concentrated. The crude 1-[1-((R)-3-amino-1-methyl-propyl)-piperidin-4-yl]-1-(3-chloro-benzyl)-3-methoxy-urea was used in the next reaction without purification.

285

Following general procedure E: 1-[1-((R)-3-amino-1-methyl-propyl)-piperidin-4-yl]-1-(3-chloro-benzyl)-3-ethyl-urea (77 mg, 0.21 mmol), 2,6-dichloro-4-methyl-nicotinic acid (48 mg, 0.23 mmol), EDCI (44 mg, 0.23 mmol), HOBt (31 mg, 0.23 mmol), DIPEA (0.055 ml, 0.32 mmol), and DMF (5 ml) were combined and stirred at rt overnight. The crude product was purified by preparative TLC (ether, 6% MeOH, 2% NH$_4$OH) to afford COMPOUND 234 as a white solid (81 mg, 62%, 2 steps). $^1$H NMR (CDCl$_3$) δ 0.99-1.01 (d, 3H, J=6 Hz), 1.12-1.26 (m, 1H), 1.49-1.57 (m, 1H), 1.62-1.86 (m, 4H), 2.13-2.26 (m, 1H), 2.34 (s, 3H), 2.51-2.64 (m, 1H), 2.72-2.93 (m, 3H), 3.25-3.44 (m, 1H), 3.63 (s, 3H), 3.72-3.82 (m, 1H), 3.89 (s, 2H), 4.06-4.24 (m, 1H), 6.90 (s, 1H), 7.10 (s, 1H), 7.14-7.16 (d, 1H, J=6 Hz), 7.21 (s, 1H), 7.28 (s, 1H), 7.31-7.34 (d, 1H, J=9 Hz), 8.59 (br s, 1H); $^{13}$C NMR (CDCl$_3$): δ 13.50, 19.21, 29.79, 30.50, 30.74, 39.78, 43.64, 44.53, 51.50, 53.02, 59.89, 64.30, 124.31, 124.46, 126.15, 127.93, 130.42, 132.52, 135.06, 139.86, 146.61, 149.90, 151.05, 159.18, 164.27; ES-MS m/z 556 (M+H).

Example 235

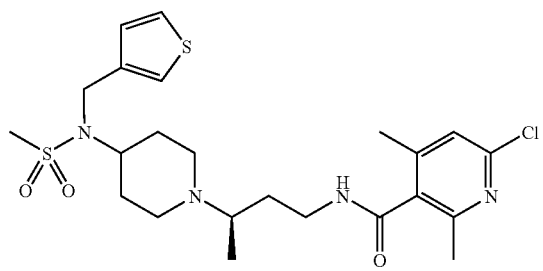

Compound 235

6-Chloro-N—{(R)-3-[4-(methanesulfonyl-thiophen-3-ylmethyl-amino)-piperidin-1-yl]-butyl}-2,4-dimethyl-nicotinamide To a solution of ((R)-3-{4-[(thiophen-3-ylmethyl)-amino]-piperidin-1-yl}-butyl)-carbamic acid tert-butyl ester (154 mg, 0.42 mmol) in CH$_2$Cl$_2$ (5 ml) at 0° C. was added DIPEA (0.20 ml, 1.15 mmol) and MsCl (0.08 ml, 1.03 mmol) and the reaction stirred from 0° C. to rt over 1.5 h. The mixture was diluted with saturated aqueous NaHCO$_3$ (20 ml) and extracted with CH$_2$Cl$_2$ (3×10 ml). The combined organic extracts were dried (Na$_2$SO$_4$), filtered, and concentrated. To a solution of the crude mesylate from above in CH$_2$Cl$_2$ (1.5 ml) was added TFA (1.5 ml) and the reaction stirred for 1 h then concentrated in vacuo.

Following general procedure E: to a solution of the resultant crude product from above in DMF (2 ml) was added 6-chloro-2,4-dimethyl-nicotinic acid (94 mg, 0.42 mmol), HOBt (75 mg, 0.56 mmol), DIPEA (0.4 ml, 2.30 mmol) and EDCI (104 mg, 0.54 mmol) and the reaction stirred overnight. Purification of the crude product by radial chromatography on silica gel (1 mm plate, CH$_2$Cl$_2$/MeOH, 96:4 then 92:8) afforded COMPOUND 235 (18 mg, 8% over 3 steps) as a white foam. $^1$H NMR (CDCl$_3$) δ 0.97 (d, 3H, J=6.6 Hz), 1.15-1.43 (m, 2H), 1.56-1.75 (m, 3H), 2.07-2.14 (m, 1H), 2.31 (s, 3H), 2.45-2.52 (m, 1H), 2.52 (s, 3H), 2.64 (s, 3H), 2.70-2.84 (m, 4H), 3.26-3.36 (m, 1H), 3.56-3.64 (m, 1H), 3.73-3.84 (m, 1H), 3.93 (d, 1H, J=15 Hz), 4.03 (d, 1H, J=15 Hz), 6.97 (s, 1H), 7.03 (d, 1H, J=4.8 Hz), 7.16-7.18 (m, 1H), 7.29 (dd, 1H, J=4.8, 3 Hz), 8.06 (br d, 1H); $^{13}$C NMR (CDCl$_3$) δ 15.14, 20.55, 23.86, 32.78, 32.96, 33.79, 41.48, 43.09, 43.86, 45.46, 53.63, 58.14, 61.70, 124.40, 125.10, 127.93, 129.19, 134.33, 140.47, 149.17, 152.10, 156.97, 168.98; ES-MS m/z 535 (M+Na). Anal. Calcd. for C$_{23}$H$_{33}$N$_4$O$_3$S$_2$Cl.1.3CH$_3$OH: C, 52.61; H, 6.94; N, 10.10. Found: C, 52.70; H, 6.57; N, 9.87.

Example 236

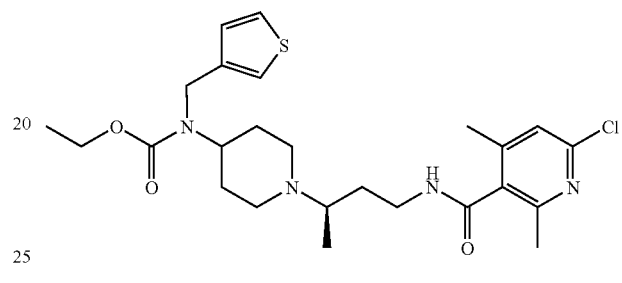

Compound 236

(1-(R)—{3-[(6-Chloro-2,4-dimethyl-pyridine-3-carbonyl)-amino]-1-methyl-propyl}-piperidin-4-yl)-thiophen-3-ylmethyl-carbamic acid ethyl ester To a solution of ((R)-3-{4-[(thiophen-3-ylmethyl)-amino]-piperidin-1-yl}-butyl)-carbamic acid tert-butyl ester (251 mg, 0.68 mmol) in CH$_2$Cl$_2$ (5 ml) was added ethyl chloroformate (143 μL, 1.50 mmol). The reaction was stirred for 3 h before being diluted with CH$_2$Cl$_2$ (40 ml) and washed with 1N NaOH (15 ml). The solution was dried over Na$_2$SO$_4$, concentrated, and purified by flash chromatography (MeOH/CH$_2$Cl$_2$, 5%) to give the desired product (269 mg, 90%).

Following general procedure C: the Boc-protected amine was taken up in CH$_2$Cl$_2$ (8 ml) and TFA (2 mL) was added. The reaction was allowed to stir for 2 h before solvent was removed. The crude was diluted with CH$_2$Cl$_2$ and washed with 1N NaOH before the organic layer was isolated and dried over Na$_2$SO$_4$. The crude residue was used as is in the next step.

Following general procedure E: to a solution of the resultant crude product from above in DMF (4 ml) was added 6-chloro-2,4-dimethylnicotinic acid (75 mg, 0.34 mmol), HOBt (57 mg, 0.42 mmol), DIPEA (1 ml, 5.7 mmol) and EDCI (82 mg, 0.43 mmol) and the reaction stirred overnight. Purification of the crude product by flash chromatography on silica gel (MeOH/CH$_2$Cl$_2$, 3%) afforded COMPOUND 236 (17 mg, 10% over 3 steps) as a white foam. $^1$H NMR (CDCl$_3$) δ 0.94 (d, 3H, J=6 Hz), 1.22 (m, 4H), 1.59 (m, 4H), 1.61-1.78 (m, 2H), 2.04 (m, 1H), 2.32 (s, 3H), 2.53 (s, 3H), 2.62-2.81 (m, 3H), 3.28 (t, 1H, J=12 Hz), 3.74-3.98 (m, 3H), 4.12 (m, 3H), 6.99 (m, 1H), 7.02 (s, 1H), 7.23 (m, 1H); ES-MS m/z 529 (M+Na).

Example 237

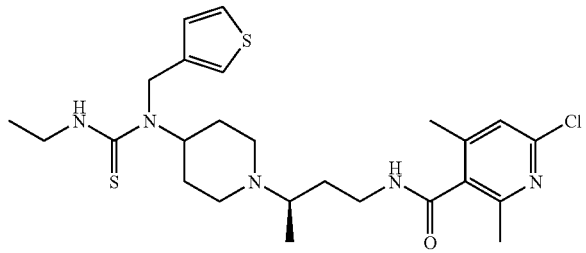

Compound 237

6-Chloro-N—{(R)-3-[4-(3-ethyl-1-thiophen-3-ylm-ethyl-thioureido)-piperidin-1-yl]-butyl}-2,4-dim-ethyl-nicotinamide To a solution of 6-chloro-2,4-dimethyl-N—((R)-3-{4-[(thiophen-3-ylmethyl)-amino]-piperidin-1-yl}-butyl)-nicotinamide (76 mg, 0.18 mmol) in CH$_2$Cl$_2$ (5 ml) was added ethyl isothiocyanate (30 μL, 0.34 mmol) and the reaction stirred at rt overnight. The mixture was concentrated and purified by column chromatography on silica gel (CH$_2$Cl$_2$/MeOH, 96:4) to provide COMPOUND 237 (34 mg, 36%) as a white foam. $^1$H NMR (CDCl$_3$) δ 0.85-0.95 (m, 1H), 098-1.03 (m, 7H), 1.48-1.82 (m, 5H), 2.23-2.31 (m, 1H), 2.28 (s, 3H), 2.48 (s, 3H), 2.63-2.87 (m, 4H), 3.21-3.28 (m, 1H), 3.53-3.59 (m, 2H), 3.84-3.91 (m, 3H), 5.38 (br s, 1H), 6.96 (s, 1H), 7.05 (d, 1H, J=4.8 Hz), 7.12-7.14 (m, 1H), 7.38 (dd, 1H, J=4.8, 3 Hz), 8.93 (br s, 1H); $^{13}$C NMR (CDCl$_3$) δ 13.86, 14.64, 19.14, 22.44, 29.57, 30.07, 30.80, 40.63, 41.23, 43.51, 44.06, 52.20, 57.74, 61.22, 122.01, 122.86, 126.22, 128.02, 133.32, 137.56, 148.09, 150.38, 155.79, 167.34, 182.46; ES-MS m/z 544 (M+Na). Anal. Calcd. for C$_{25}$H$_{36}$N$_5$OS$_2$Cl.0.2H$_2$O.0.2CH$_2$Cl$_2$: C, 55.77; H, 6.83; N, 12.90. Found: C, 55.94; H, 6.80; N, 12.55.

Example 238

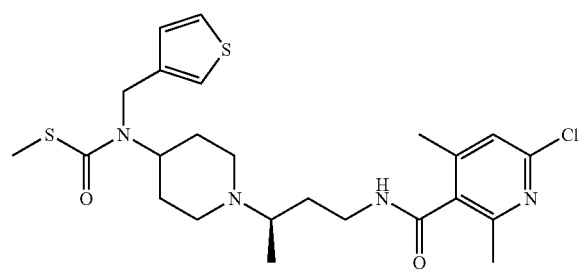

Compound 238

(1-{(R)-3-[(6-Chloro-2,4-dimethyl-pyridine-3-carbo-nyl)-amino]-1-methyl-propyl}-piperidin-4-yl)-thiophen-3-ylmethyl-thiocarbamic acid S-methyl ester To a solution of ((R)-3-{4-[(thiophen-3-ylmethyl)-amino]-piperidin-1-yl}-butyl)-carbamic acid tert-butyl ester (139 mg, 0.38 mmol) in CH$_2$Cl$_2$ (8 mL) was added thiomethyl-chloroformate (39 μL, 0.46 mmol) and DIPEA (160 μL, 0.91 mmol). The reaction was stirred overnight and then diluted with CH$_2$Cl$_2$ (25 ml) and washed with 1N NaOH (10 ml) and dried over Na$_2$SO$_4$. The crude residue was sufficiently pure to be used in the next step without further purification.

Following general procedure C: the Boc-protected amine was taken up in CH$_2$Cl$_2$ (8 ml) and TFA (2 ml) was added. The reaction was allowed to stir for 2 h before solvent was removed. The crude was diluted with CH$_2$Cl$_2$ and washed with 1N NaOH before the organic layer was isolated and dried over Na$_2$SO$_4$. The crude residue was purified by flash chromatography (MeOH/CH$_2$Cl$_2$/NH$_4$OH, 5:95:1) to give the desired amine (118 mg, 91% over 2 steps).

Following general procedure E: to a solution of the primary amine from above in DMF (4 ml) was added 6-chloro-2,4-dimethylnicotinic acid (85 mg, 0.38 mmol), HOBt (71 mg, 0.53 mmol), DIPEA (1 ml, 5.7 mmol) and EDCI (100 mg, 0.52 mmol) and the reaction stirred overnight. Purification of the crude product by flash chromatography on silica gel (MeOH/CH$_2$Cl$_2$, 2%) afforded COMPOUND 238 (107 mg, 61%) as a white foam. $^1$H NMR (CDCl$_3$) δ 0.96 (d, 3H, J=9 Hz), 1.01-1.26 (m, 4H), 1.49-1.83 (m, 5H), 2.09 (t, 1H, J=12 Hz), 2.31 (s, 3H), 2.32 (s, 3H), 2.46 (t, 1H, J=12 Hz), 2.51 (s, 3H), 2.68-2.81 (m, 3H), 3.24-3.29 (m, 1H), 3.75-3.84 (m, 1H), 3.96-4.21 (m, 1H), 6.99-7.08 (m, 3H), 7.26 (s, 1H); ES-MS m/z 510 (M+H).

Example 239

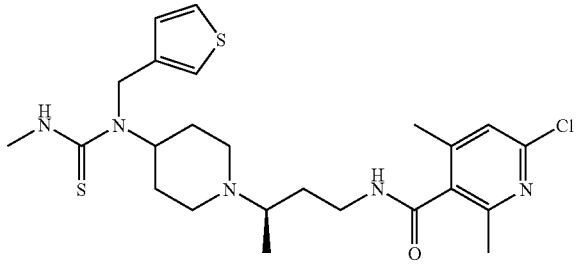

Compound 239

6-Chloro-2,4-dimethyl-N—{(R)-3-[4-(3-methyl-1-thiophen-3-ylmethyl-thioureido)-piperidin-1-yl]-butyl}-nicotinamide Following general procedure H, 6-chloro-2,4-dimethyl-N—((R)-3-{4-[(thiophen-3-ylmethyl)-amino]-piperidin-1-yl}-butyl)-nicotinamide and isothiocyanate afforded COMPOUND 239. $^1$H NMR (CDCl$_3$) δ 0.72-0.83 (m, 1H), 0.97-1.01 (m, 1H), 0.98 (d, 3H, J=6.6 Hz), 1.48-1.63 (m, 1H), 1.71-1.82 (m, 3H), 2.18-2.24 (m, 1H), 2.28 (s, 3H), 2.48 (s, 3H), 2.58-2.68 (m, 2H), 2.79-2.84 (m, 2H), 3.03 (d, 3H, J=3 Hz), 3.20-3.28 (m, 1H), 3.85-3.94 (m, 3H), 5.27-5.35 (m, 1H), 5.49 (br s, 1H), 6.99 (s, 1H), 7.09 (dd, 1H, J=5.1, 0.9 Hz), 7.10-7.11 (m, 1H), 7.39 (dd, 1H, J=5.1, 3 Hz), 8.98 (br d, 1H); $^{13}$C NMR (CDCl$_3$) δ 13.77, 19.17, 22.46, 29.17, 30.08, 30.93, 33.35, 40.35, 43.67, 44.24, 52.17, 57.78, 61.11, 121.88, 122.90, 126.22, 127.99, 129.25, 137.49, 148.09, 150.42, 155.78, 167.46, 183.82; ES-MS m/z 508 (M+H). Anal. Calcd.

for $C_{24}H_{34}N_5OS_2Cl \cdot 0.2CH_2Cl_2 \cdot 0.1H_2O$: C, 55.16; H, 6.62; N, 13.29. Found: C, 55.15; H, 6.72; N, 13.03.

Example 240

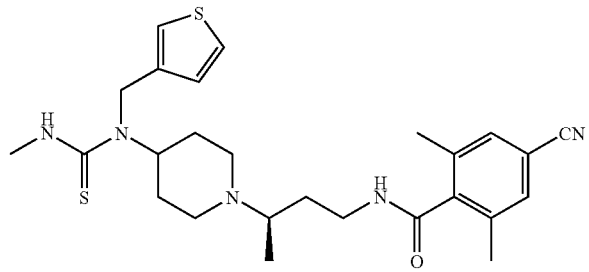

Compound 240

4-Cyano-2,6-dimethyl-N—{(R)-3-[4-(3-methyl-1-thiophen-3-ylmethyl-thioureido)-piperidin-1-yl]-butyl}-benzamide Following general procedure H: to ((R)-3-{4-[(Thiophen-3-ylmethyl)-amino]-piperidin-1-yl}-butyl)-carbamic acid tert-butyl ester (1.0 g, 2.72 mmol) in dry $CH_2Cl_2$ (20 ml) was added methylisothiocyanate (223 µl, 3.26 mmol). The reaction mixture was then allowed to stir at room temperature overnight under $N_2$ pressure to yield {(R)-3-[4-(3-methyl-1-thiophen-3-ylmethyl-thioureido)-piperidin-1-yl]-butyl}-carbamic acid tert-butyl ester as yellow oil.

The BOC-protected amine was dissolved in $CH_2Cl_2$ (~4 ml/mmol) and TFA (2 ml/mmol) was added. The mixture was stirred at room temperature for 20 min. In a standard work-up, the mixture was neutralized with saturated aqueous $NaHCO_3$ and the aqueous extracted with $CH_2Cl_2$. The combined extracts were dried with $Na_2SO_4$, filtered and concentrated under reduced pressure to afford the desired amine.

Following general procedure E: to a stirred solution of 1-[1-((R)-3-amino-1-methyl-propyl)-piperidin-4-yl]-3-methyl-1-thiophen-3-ylmethyl-thiourea (145 mg, 0.426 mmol), 4-cyano-2,6-dimethyl-benzoic acid (82 mg, 0.469 mmol), HOBt (75 mg, 0.554 mmol) and DIPEA (186 µl, 1.06 mmol) in $CH_2Cl_2$ (3 ml) was added EDCI (106 mg, 0.554 mmol). The solution was stirred at room temperature for overnight and concentrated in vacuo. In a standard work-up, the mixture was diluted with $CH_2Cl_2$ and washed consecutively with saturated aqueous $NaHCO_3$ and brine. The organic layer was dried with $Na_2SO_4$, filtered and concentrated under reduced pressure. The crude material was purified by tron (DCM, 2% MeOH, 2% $NH_4OH$) to yield COMPOUND 240 as a white foam (70 mg, 33% over 3 steps). $^1$H NMR (CDCl$_3$) δ 0.79-0.85 (m, 1H), 0.97-1.01 (m, 4H), 1.49-1.55 (m, 1H), 1.72-1.86 (m, 3H), 2.19-2.28 (m; 1H), 2.31 (s, 6H), 2.60-2.74 (m, 2H), 2.83-2.86 (m, 2H), 2.98-2.99 (d, 3H, J=4.2 Hz), 3.24-3.30 (m, 1H), 3.77 (s, 2H), 3.86-3.93 (m, 1H), 5.33-5.47 (m, 2H), 6.93-6.95 (m, 1H), 7.12-7.13 (d, 1H, J=3 Hz), 7.21 (s, 2H), 7.41-7.44 (m, 1H), 8.82-8.84 (br d, 1H); ES-MS m/z 498 (M+H).

Example 241

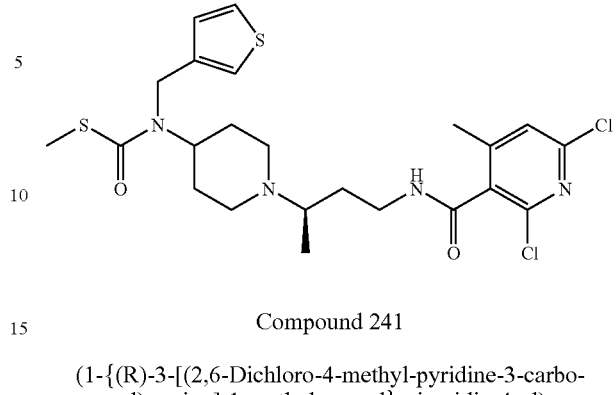

Compound 241

(1-{(R)-3-[(2,6-Dichloro-4-methyl-pyridine-3-carbonyl)-amino]-1-methyl-propyl}-piperidin-4-yl)-thiophen-3-ylmethyl-thiocarbamic acid S-methyl ester Following general procedure E the amine (see EXAMPLE 238) and 2,6-dichloro-4-methylnicotinic acid afforded COMPOUND 241. $^1$H NMR (CDCl$_3$) δ 0.99 (d, 3H, J=6 Hz), 1.08-1.42 (m, 4H), 1.43-1.81 (m, 4H), 2.07-2.14 (m, 1H), 2.32 (s, 2H), 2.37 (s, 3H), 2.43-2.51 (m, 1H), 2.73-2.81 (m, 3H), 3.25-3.41 (m, 1H), 3.76-3.84 (m, 1H), 4.04-4.27 (m, 2H), 7.01 (d, 1H, J=6 Hz), 7.08 (s, 1H), 7.15 (s, 1H), 7.22 (s, 1H), 8.47 (br s, 1H); ES-MS m/z 529 (M+H).

Example 242

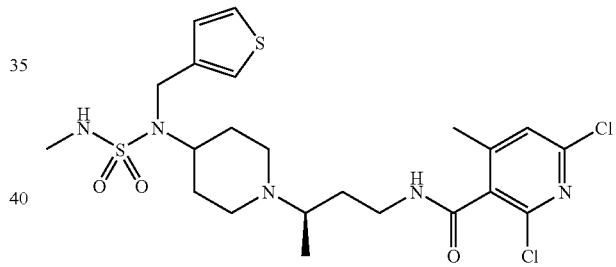

Compound 242

2,6-Dichloro-4-methyl-N—{(R)-3-[4-(3-methyl-1-thiophen-3-ylmethyl-sulfonamido)-piperidin-1-yl]-butyl}-nicotinamide To a suspension of methylsulfamic acid (55 mg, 0.49 mmol) in benzene (2 ml) was added PCl$_5$ (98 mg, 0.47 mmol) and the reaction stirred at reflux for 1.5 h. The mixture was then concentrated and diluted with 1,2-dichloroethane (3 ml). 2,6-Dichloro-4-methyl-N—((R)-3-{4-[(thiophen-3-ylmethyl)-amino]-piperidin-1-yl}-butyl)-nicotinamide (63 mg, 0.14 mmol) and DIPEA (0.20 ml, 1.15 mmol) were added and the reaction stirred at room temperature overnight. The mixture was diluted with $CH_2Cl_2$ (20 ml) and 1 N NaOH (20 ml) and the aqueous layer was extracted with $CH_2Cl_2$ (20 ml). The combined organic extracts were dried ($Na_2SO_4$) and the resultant crude purified by column chromatography on silica gel ($CH_2Cl_2$/MeOH, 96:4 then 9:1) to afford COMPOUND 242 (25 mg, 33%) as a white foam. $^1$H NMR (CDCl$_3$) δ 0.98 (d, 3H, J=6.6 Hz), 1.24-1.46 (m, 3H), 1.72-1.80 (m, 3H), 2.04-2.14 (m, 1H), 2.36 (s, 3H), 2.43-2.53 (m, 1H), 2.43 (d, 3H, J=5.4 Hz), 2.77-2.90 (m, 3H), 3.28-3.36 (m, 1H), 3.42-

3.51 (m, 1H), 3.77-3.86 (m, 2H), 3.98 (s, 2H), 7.02 (d, 1H, J=4.8 Hz), 7.08 (s, 1H), 7.17 (br s, 1H), 7.28 (dd, 1H, J=4.8, 3 Hz), 8.42 (br d, 1H); $^{13}$C NMR (CDCl$_3$) δ 13.71, 19.57, 29.51, 30.90, 31.14, 31.66, 40.29, 43.49, 44.15, 52.38, 57.46, 60.41, 123.56, 124.96, 126.54, 127.90, 132.73, 139.42, 146.85, 150.54, 151.18, 164.75; ES-MS m/z 548 (M+H). Anal. Calcd. for $C_{22}H_{31}N_5O_3S_2Cl_2$.0.3$C_6H_6$.0.9$H_2O$: C, 48.60; H, 5.93; N, 11.91. Found: C, 48.61; H, 6.00; N, 11.96.

Example 243

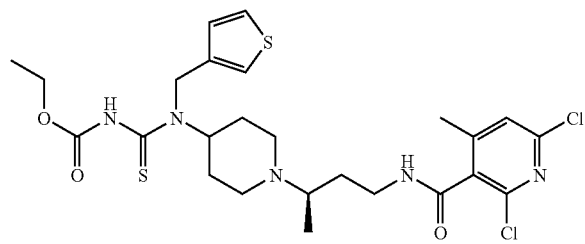

Compound 243

2,6-Dichloro-4-methyl-N—{(R)-3-[4-(3-formyl ethyl ester-1-thiophen-3-ylmethyl-thioureido)-piperidin-1-yl]-butyl}-nicotinamide To a solution of 2,6-dichloro-4-methyl-N-(3-{4-[(thiophen-3-ylmethyl)-amino]-piperidin-1-yl}-butyl)-nicotinamide (0.095 g, 0.21 mmol) in methylene chloride (4 ml) was added isothiocyanatoformate (38 μL, 0.33 mmol) and the resulting mixture was stirred at 25° C. for 16 hours. Standard basic workup gave the crude product as a tan oil. Purification by column chromatography on silica gel (CH$_2$Cl$_2$/MeOH/NH$_4$OH, 97:2:1) afforded COMPOUND 243 (0.059 g, 48%) as a white foam. $^1$H NMR (CDCl$_3$) δ 0.98 (d+m, 4H), 1.16 (m, 1H), 1.30 (t+m, 5H), 1.55 (m, 1H), 1.76 (m, 1H), 1.91 (m, 2H), 2.16 (brt, 1H), 2.36 (s, 3H), 2.54 (s, 3H), 2.75-2.89 (m, 3H), 3.35 (m, 1H), 3.78 (m, 1H), 4.17 (q, 2H, J=6.0 Hz), 7.01 (m, 1H), 7.11-7.15 (m, 3H), 7.32 (m, 1H); ES-MS m/z 586 (M+H).

Example 244

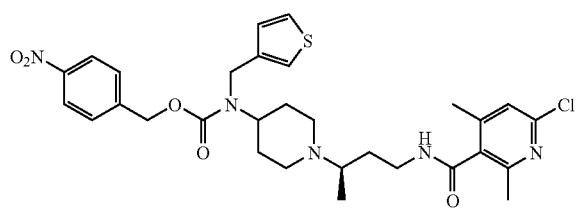

Compound 244

(1-{(R)-3-[(6-Chloro-2,4-dimethyl-pyridine-3-carbonyl)-amino]-1-methyl-propyl}-piperidin-4-yl)-thiophen-3-ylmethyl-carbamic acid 4-nitro-benzyl ester A solution of 6-chloro-2,4-dimethyl-N—((R)-3-{4-[(thiophen-3-ylmethyl)-amino]-piperidin-1-yl}-butyl)-nico- tinamide (52 mg, 0.12 mmol), 4-nitrobenzyl chloroformate (50 mg, 0.23 mmol) and DIPEA (50 μL, 0.29 mmol) in THF (0.90 ml) was stirred at 60° C. for 16 hours. Once cooled, the reaction was diluted with saturated aqueous NaHCO$_3$ (25 ml) and was extracted with CH$_2$Cl$_2$ (20 ml×3). The combined organic solution was dried (Na$_2$SO$_4$), filtered and concentrated under reduced pressure. Purification by flash column chromatography on silica (CH$_2$Cl$_2$/MeOH, 29:1) gave COMPOUND 244 as an off-white foam (47.2 mg, 64%). $^1$H NMR (CDCl$_3$) δ 0.85-1.30 (m, 2H), 0.97 (d, 3H, J=7.0 Hz), 1.48-1.81 (m, 4H), 2.05-2.17 (m, 1H), 2.31 (s, 3H), 2.43-2.57 (m, 1H), 2.52 (s, 3H), 2.66-2.87 (m, 3H), 3.22-3.35 (m, 1H), 3.77-4.06 (m, 4H), 5.17 (s, 2H), 6.93-7.05 (m, 3H), 7.20-7.32 (m, 3H), 8.13 (d, 2H, J=7.3 Hz), 8.60 (br s, 1H); ES-MS m/z 614 (M+H), 616 (M+H+2).

Examples 245 to 258 were prepared following the scheme illustrated below. R$^1$ is as shown in the individual examples and R$^2$—SMe is as defined in the table.

TABLE 17

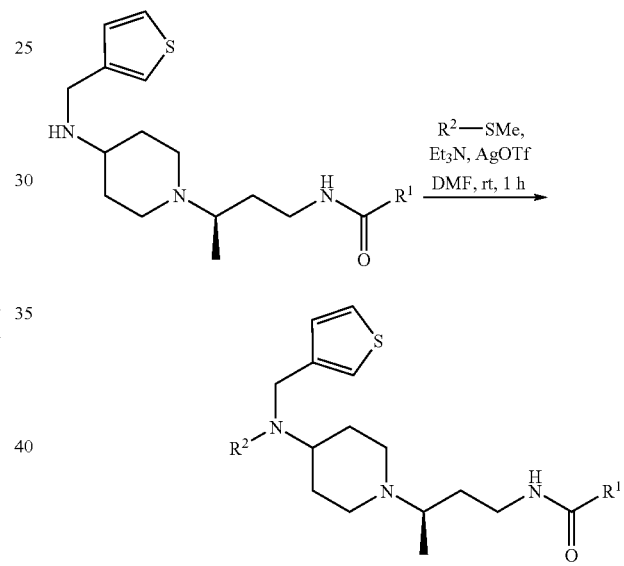

| Example | R$^2$—SMe |
|---|---|
| 245 | S-methyl N-cyano-N'-methylcarbamimidothioate |
| 246 | ((methylamino)methylthiomethylene)methane-1,1-dicarbonitrile |
| 247 | N-methyl-1-(methylthio)-2-nitroethanamine |
| 248 | S-methyl N-methanesulfonyl-N'-methylcarbamimidothioate |
| 249 | S-methyl N-nitro-N'-methylcarbamimidothioate |
| 250 | 1-ethyl-2-methyl-3-cyanoisothiourea |
| 251 | 1-acetyl-2,3-dimethyl-isothiourea |
| 252 | 3-ethylamino-3-methylsulfanyl-acrylonitrile |
| 253 | 1-cyclopropyl-2-methyl-3-cyanoisothiourea |
| 254 | 1-isopropyl-2-methyl-3-cyanoisothiourea |
| 255 | 1-methoxyethyl-2-methyl-3-cyanoisothiourea |
| 256 | 1-cyclopropyl-2-methyl-3-cyanoisothiourea (see EXAMPLE 253) |
| 257 | 1-cyclopropyl-2-methyl-3-cyanoisothiourea (see EXAMPLE 253) |
| 258 | 1-cyclobutyl-2-methyl-3-cyanoisothiourea |

Example 245

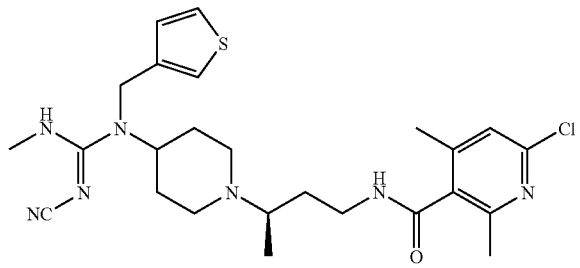

Compound 245

6-Chloro-2,4-dimethyl-N—{(R)-3-[4-(N'-methyl-N-thiophen-3-ylmethyl-N''-cyanoguanidino)-piperidin-1-yl]-butyl}-nicotinamide General Procedure for Formation of N-substituted Guanidines:

To a solution of 6-chloro-2,4-dimethyl-N—((R)-3-{4-[(thiophen-3-ylmethyl)-amino]-piperidin-1-yl}-butyl)-nicotinamide (82 mg, 0.14 mmol) in DMF (2 ml) was added S-methyl N-cyano-N'-methylcarbamimidothioate (31 mg, 0.24 mmol), Et$_3$N (0.10 ml, 0.72 mmol) and AgOTf (64 mg, 0.25 mmol) and the reaction stirred for 1 h. The mixture was diluted with CH$_2$Cl$_2$ (25 ml) and saturated aqueous NaHCO$_3$ (25 ml) and the aqueous layer extracted with CH$_2$Cl$_2$ (2×10 ml). The combined organic extracts were dried (Na$_2$SO$_4$), concentrated and purified by column chromatography on silica gel (CH$_2$Cl$_2$/MeOH/NH$_4$OH, 96:4:0 then 9:1:0 then 88:10:2) to afford COMPOUND 245 (45 mg, 45%) as a white foam. $^1$H NMR (CDCl$_3$) δ 0.84-0.95 (m, 1H), 0.97-1.04 (m, 1H), 1.01 (d, 3H, J=6.6 Hz), 1.50-1.77 (m, 4H), 2.13-2.21 (m, 1H), 2.29 (s, 3H), 2.48 (s, 3H), 2.52-2.61 (m, 1H), 2.69-2.84 (m, 3H), 3.06 (d, 3H, J=4.8 Hz), 3.21-3.30 (m, 1H), 3.71-3.91 (m, 3H), 4.26-4.35 (m, 1H), 4.72-4.77 (m, 1H), 6.99 (s, 1H), 7.07 (d, 1H, J=4.8 Hz), 7.11 (br s, 1H), 7.42 (dd, 1H, J=4.8, 3 Hz), 8.77 (br d, 1H); $^{13}$C NMR (CDCl$_3$) δ 13.92, 19.15, 22.44, 30.19, 30.90, 31.02, 31.27, 40.51, 43.51, 51.96, 55.53, 60.97, 117.54, 121.94, 122.87, 126.13, 128.28, 133.34, 137.93, 148.12, 150.37, 155.77, 159.80, 167.27; ES-MS m/z 516 (M+H). Anal. Calcd. for C$_{25}$H$_{34}$N$_7$OSCl.1.0CH$_2$Cl$_2$.0.4H$_2$O: C, 51.34; H, 6.10; N, 16.12. Found: C, 51.12; H, 5.95; N, 16.27.

Example 246

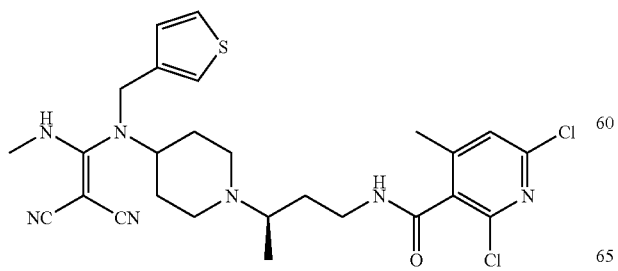

Compound 246

2,6-Dichloro-N—((R)-3-{4-[(2,2-dicyano-1-methylamino-vinyl)-thiophen-3-ylmethyl-amino]-piperidin-1-yl}-butyl)-4-methyl-nicotinamide $^1$H NMR (CDCl$_3$+drop of CD$_3$OD) δ 0.80-0.85 (m, 1H), 1.05-1.22 (m, 5H), 1.55-1.74 (m, 3H), 1.80-2.27 (m, 3H), 2.33 (s, 3H), 2.73 (br s, 3H), 2.85-2.96 (m, 3H), 3.34-3.40 (m, 1H), 3.62-3.66 (m, 1H), 3.85-3.93 (m, 1H), 4.05-4.16 (m, 1H), 6.81-6.84 (m, 1H), 7.08 (br s, 2H), 7.29-7.33 (m, 1H); ES-MS m/z 560 (M+H). Anal. Calcd. for C$_{26}$H$_{31}$N$_7$OSCl$_2$.0.8CH$_2$Cl$_2$.1.7CH$_3$OH: C, 50.12; H, 5.81; N, 14.36. Found: C, 50.30; H, 5.47; N, 14.04.

Example 247

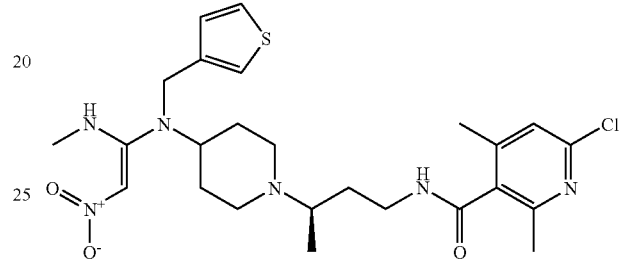

Compound 247

6-Chloro-2,4-dimethyl-N—((R)-3-{4-[(1-methylamino-2-nitro-vinyl)-thiophen-3-ylmethyl-amino]-piperidin-1-yl}-butyl)-nicotinamide $^1$H NMR (CDCl$_3$) δ 0.98 (d, 3H, J=7 Hz), 1.18-1.80 (m, 6H), 2.27 (t, 1H, J=12 Hz), 2.30 (s, 3H), 2.48-2.51 (m, 4H), 2.67-2.86 (m, 3H), 2.95 (d, 3H, J=6 Hz), 3.14-3.37 (m, 2H), 3.73-3.85 (m, 1H), 3.87 (s, 2H), 6.53 (s, 1H), 6.85 (dd, 1H, J=6, 3 Hz), 6.94 (s, 1H), 7.07 (br s, 1H), 7.28 (dd, 1H, J=6, 3 Hz), 8.01 (br s, 1H), 9.68 (br s, 1H); ES-MS m/z 557 (M+Na).

Example 248

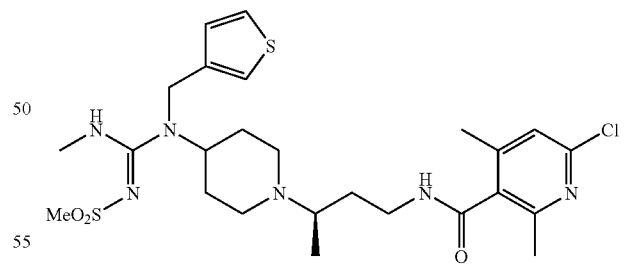

Compound 248

6-Chloro-2,4-dimethyl-N—{(R)-3-[4-(N'-methyl-N-thiophen-3-ylmethyl-N''-methanesulfonylguanidino)-piperidin-1-yl]-butyl}-nicotinamide To a solution of methanesulfonamide (2.11 g, 22.2 mmol) in DMF (22 ml) was added 10 N NaOH (2.8 ml) and the reaction cooled to 0° C. before adding carbon disulfide (0.80 ml, 13.3 mmol). The mixture was stirred for 15 min. before adding another portion of 10 N NaOH (1.3 ml) and carbon disulfide (0.40 ml, 6.7 mmol). The reaction was stirred at 0° C. for another 30 min. before warming to room temperature and stirring for 30 min. The reaction was cooled to 0° C., diluted with MeI (2.8 ml, 45.0 mmol), allowed to warm to room temperature and stirred for 1.5 h. The mixture was then diluted with water (30 ml) and extracted with EtOAc (4×25 ml). The combined organic extracts were dried ($Na_2SO_4$) and concentrated. The resultant crude product was washed with EtOAc/Hexanes to afford the desired N-methanesulfonylcarbonimidodithioic acid dimethyl ester (3.2 g, 77%) as a white solid. $^1$H NMR ($CDCl_3$) δ 2.55 (s, 6H), 3.13 (s, 3H).

To a solution of N-methanesulfonylcarbonimidodithioic acid dimethyl ester (1.5 g, 8.02 mmol) in MeOH (15 ml) was added a solution of methylamine in THF (2.0 M, 4.8 ml, 9.6 mmol) and the reaction heated to 50° C. for 2.5 h before another portion of methylamine was added (4.8 ml, 9.6 mmol) and the reaction heated to 50° C. for an additional 1 h. The mixture was concentrated and purified by column chromatography on silica gel (EtOAc/Hexanes, 1:1) to afford S-methyl N-methanesulfonyl-N'-methylcarbamimidothioate (0.95 g, 70%) as a clear oil. $^1$H NMR ($CDCl_3$) δ 2.40 (s, 3H), 2.96 (d, 3H, J=6 Hz), 3.01 (s, 3H), 7.95 (br s, 1H).

$^1$H NMR ($CDCl_3$) δ 0.99 (d, 3H, J=6.6 Hz), 1.05-1.34 (m, 2H), 1.51 1.82 (m, 4H), 2.07-2.15 (m, 1H), 2.29 (s, 3H), 2.49 (s, 3H), 2.49-2.55 (m, 1H), 2.66 (s, 3H), 2.75-2.87 (m, 3H), 2.90 (d, 3H, J=5.1 Hz), 3.27-3.34 (m, 1H), 3.61-3.95 (m, 4H), 6.30-6.34 (m, 1H), 6.95 (s, 1H), 6.98 (dd, 1H, J=4.8, 1.2 Hz), 7.09 (br s, 1H), 7.30 (dd, 1H, J=4.8, 3 Hz), 8.23 (br s, 1H); $^{13}$C NMR ($CDCl_3$) δ 13.84, 19.14, 22.45, 30.22, 31.05, 31.51, 32.50, 39.91, 42.64, 43.13, 44.11, 52.07, 57.82, 60.27, 121.93, 122.85, 126.86, 126.92, 132.97, 139.31, 147.81, 150.56, 155.63, 160.74, 167.57; ES-MS m/z 591 (M+Na). Anal. Calcd. for $C_{25}H_{37}N_6O_3S_2Cl \cdot 0.9CH_2Cl_2 \cdot 0.1H_2O$: C, 48.05; H, 6.07; N, 12.98. Found: C, 48.15; H, 6.08; N, 13.01.

was filtered, washed with water and dried to give 2-methyl-1-nitro-2-thiopseudourea (3.7 g). $^1$H NMR (DMSO-$d_6$) δ 2.38 (s, 3H), 9.11 (br s, 2H); ES-MS m/z 158 (M+Na).

To a solution of 2-methyl-1-nitro-2-thiopseudourea (430 mg, 3.19 mmol) in DMF (3 ml) was added $Cs_2CO_3$ (1.10 g, 3.38 mmol) and MeI (0.30 ml, 4.82 mmol) and the reaction stirred overnight. The mixture was then diluted with water (10 ml) and EtOAc (40 ml) and the organic layer washed with brine (3×15 ml), dried ($Na_2SO_4$) and concentrated. The resultant yellow oil was purified by column chromatography on silica gel (EtOAc/Hexanes, 1:1) to afford S-methyl N-nitro-N'-methylcarbamimidothioate (56 mg, 11%) as a white solid. $^1$H NMR ($CDCl_3$) δ 2.52 (s, 3H), 3.12 (d, 3H, J=6 Hz), 10.05 (br s, 1H).

$^1$H NMR ($CDCl_3$) δ 1.01 (d, 3H, J=6.6 Hz), 1.23-1.57 (m, 3H), 1.75-1.82 (m, 3H), 2.25-2.32 (m, 1H), 2.32 (s, 3H), 2.53-2.60 (m, 1H), 2.74-2.92 (m, 6H), 3.31-3.36 (m, 1H), 3.64-3.71 (m, 1H), 4.18-4.25 (m, 3H), 6.31 (br s, 1H), 7.02 (d, 1H, J=4.8 Hz), 7.11 (s, 1H), 7.22 (br s, 1H), 7.37 (dd, 1H, J=4.8, 3 Hz), 8.31 (br d, 1H); $^{13}$C NMR ($CDCl_3$) δ 14.00, 19.60, 29.93, 30.30, 30.56, 31.18, 39.67, 43.80, 44.05, 51.11, 57.18, 59.97, 122.66, 124.91, 126.28, 128.20, 132.79, 135.42, 146.83, 150.23, 151.55, 161.34, 164.66; ES-MS m/z 578 (M+Na). Anal. Calcd. for $C_{23}H_{31}N_7O_3SCl_2 \cdot 1.3CH_2Cl_2$: C, 43.76; H, 5.08; N, 14.70. Found: C, 43.67; H, 5.02; N, 14.75.

Example 250

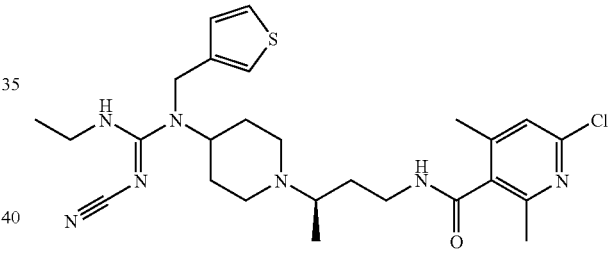

Compound 250

6-Chloro-N—{(R)-3-[4-(N'-ethyl-N-thiophen-3-ylmethyl-cyanoguanidino)-piperidin-1-yl]-butyl}-2,4-dimethyl-nicotinamide General Procedure for the Formation of 1-ethyl-2-methyl-3-cyanoisothiourea:

To a solution of dimethyl cyanodithioiminocarbonate (2.85 g, 17.6 mmol) in methanol (20 mL) was added ethylamine (2M soln, 9.7 mL, 19.4 mmol). The solution was allowed to stir at reflux overnight. The solution was cooled to room temperature and the desired product crystallized out of solution over 2 hours. The crystals were collected on a buchner funnel, washed with cold methanol several times, and dried in vacuo to give 1-ethyl-2-methyl-3-cyanoisothiourea as a white solid (1.08 g, 43%). $^1$H NMR ($CDCl_3$) δ 1.22 (t, 3H, J=6 Hz), 2.61 (s, 3H), 3.35 (s, 1H), 3.46 (q, 2H, J=6 Hz).

$^1$H NMR ($CDCl_3$) δ 0.77-0.91 (m, 1H), 0.98-1.09 (m, 6H), 1.46-1.52 (m, 2H), 1.64-1.78 (m, 3H), 2.13-2.24 (m, 1H), 2.28 (s, 3H), 2.48 (s, 3H), 2.51-2.61 (m, 1H), 2.65-2.72 (m, 1H), 2.78-2.85 (m, 2H), 3.22-3.29 (m, 1H), 3.48-3.55 (m, 2H), 3.77 (m, 2H), 3.87-3.94 (m, 1H), 4.27-4.32 (m, 1H),

Example 249

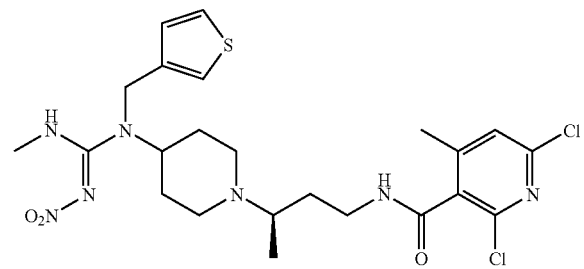

Compound 249

2,6-Dichloro-4-methyl-N—{(R)-3-[4-(N'-methyl-N-thiophen-3-ylmethyl-N''-nitroguanidino)-piperidin-1-yl]-butyl}-nicotinamide To a mixture of fuming nitric acid (10 ml) and concentrated sulfuric acid (20 ml) at −10° C. was added 2-methyl-2-thiopseudourea sulfate (2.5 g, 9.0 mmol) in portions over a period of 15 min. The reaction was warmed to 0° C. and another portion of 2-methyl-2-thiopseudourea sulfate (2.5 g, 9.0 mmol) was added. The mixture was stirred at 0° C. for 15 min. then poured onto ice (300 g). The resultant white solid 4.55-4.62 (m, 1H), 6.95 (s, 1H), 7.04 (d, 1H, J=6 Hz), 7.14 (s, 1H), 7.40-7.44 (m, 1H), 8.76 (br s, 1H); ES-MS m/z 530 (M+H).

Example 251

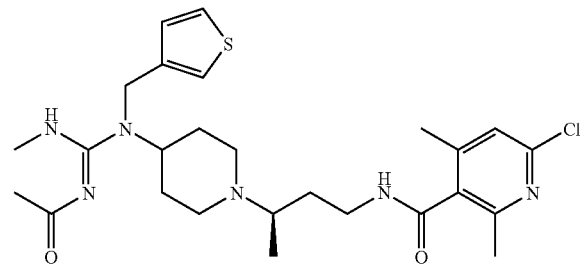

Compound 251

6-Chloro-2,4-dimethyl-N—{(R)-3-[4-(N'-methyl-N-thiophen-3-ylmethyl-N'-acetylguanidino)-piperidin-1-yl]-butyl}-nicotinamide To a suspension of 1-methyl-2-thiurea (2.12 g, 23.5 mmol) in MeOH (10 ml) was added MeI (1.60 ml, 25.7 mmol) and the reaction stirred for 1 h. The mixture was then concentrated to afford a white solid (5.55 g). To a solution of the solid from above (0.72 g) in THF (20 ml) was added Et$_3$N (2.0 ml, 14.3 mmol) and acetyl chloride (0.5 ml, 7.03 mmol) and the resulting suspension stirred at room temperature for 3.5 h. The mixture was diluted with CH$_2$Cl$_2$ (40 ml) and saturated aqueous NaHCO$_3$ (25 ml) and the organic extract washed with brine (1×25 ml), dried (Na$_2$SO$_4$), concentrated and purified by column chromatography on silica gel (EtOAc/Hexanes, 1:2 then 1:1) to afford 1,1-diacetyl-2,3-dimethyl-isothiourea (0.17 g, 29%) as a clear oil. $^1$H NMR (CDCl$_3$) δ 2.17 (s, 3H), 2.18 (s, 3H), 2.37 (s, 3H), 3.13 (s, 3H).

To a solution of 1,1-diacetyl-2,3-dimethyl-isothiourea (0.17 g, 0.90 mmol) in MeOH (10 ml) was added K$_2$CO$_3$ (250 mg, 1.81 mmol) and the reaction stirred at room temperature for 1.5 h. The mixture was concentrated, diluted with CH$_2$Cl$_2$ (25 ml) and water (20 ml) and the aqueous layer was extracted with CH$_2$Cl$_2$ (2×10 ml), dried (Na$_2$SO$_4$) and concentrated to afford 1-acetyl-2,3-dimethyl-isothiourea (112 mg, 85%) as a white solid. $^1$H NMR (CDCl$_3$) δ 2.10 (s, 3H), 2.43 (s, 3H), 2.93 (s, 3H).

$^1$H NMR (CDCl$_3$) δ 0.81-0.93 (m, 1H), 0.93-1.05 (m, 1H), 0.97 (d, 3H, J=6.6 Hz), 1.47-1.53 (m, 1H), 1.64-1.77 (m, 4H), 2.07 (s, 3H), 2.00-2.14 (m, 1H), 2.28 (s, 3H), 2.47 (s, 3H), 2.47-2.55 (m, 1H), 2.67-2.82 (m, 3H), 2.76 (d, 3H, J=4.2 Hz), 3.18-3.28 (m, 1H), 3.78-3.93 (m, 3H), 4.19-4.26 (m, 1H), 5.38-5.42 (m, 1H), 6.99 (s, 1H), 7.11 (dd, 1H, J=5.1, 1.2 Hz), 7.23 (br s, 1H), 7.37 (dd, 1H, J=5.1, 3 Hz), 8.74 (br d, 1H); $^{13}$C NMR (CDCl$_3$) δ 13.87, 19.09, 22.40, 26.42, 30.21, 30.43, 30.94, 31.24, 40.48, 42.68, 43.64, 52.14, 55.81, 60.92, 122.28, 122.91, 126.41, 127.71, 133.27, 137.09, 148.06, 150.42, 155.72, 163.87, 167.29, 175.23; ES-MS m/z 555 (M+Na). Anal. Calcd. for C$_{26}$H$_{37}$N$_6$O$_2$SCl.1.2CH$_2$Cl$_2$: C, 51.44; H, 6.25; N, 13.23. Found: C, 51.30; H, 6.14; N, 13.42.

Example 252

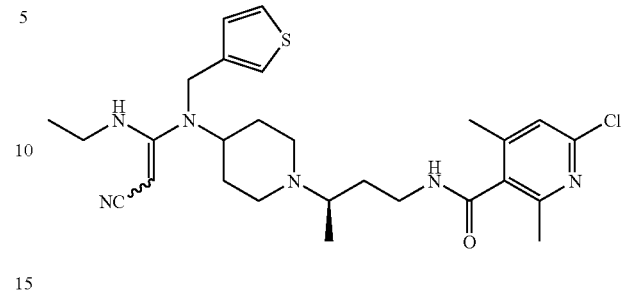

Compound 252

6-Chloro-N—((R)-3-{4-[(2-cyano-1-ethylamino-vinyl)-thiophen-3-ylmethyl-amino]-piperidin-1-yl}-butyl)-2,4-dimethyl-nicotinamide To a solution of distilled acetonitrile (1.0 ml, 19.1 mmol) in THF (20 ml) at −78° C. was added a solution of n-butyl lithium in hexanes (2.1 M, 9.0 ml, 18.9 mmol) and the mixture stirred at −78° C. for 30 min. before adding ethyl isothiocyanate (0.56 ml, 6.39 mmol). The mixture was stirred at −78° C. for 10 min. then at 0° C. (ice bath) for 30 min. before quenching with water (20 ml). The organic phase was washed with water (2×15 ml) and the combined aqueous layers washed with hexanes (1×25 ml). To the combined aqueous layers was added MeI (0.80 ml, 12.9 mmol) and the mixture stirred at room temperature for 2.5 h. The reaction was extracted with EtOAc (3×25 ml) and the organic extracts dried (Na$_2$SO$_4$), concentrated and purified by column chromatography (Hexanes/EtOAc, 9:1 then 3:1) to afford 3-ethylamino-3-methylsulfanyl-acrylonitrile (0.85 g, 94%) as a pale yellow oil and mixture of E/Z regioisomers (~2:1). $^1$H NMR (CDCl$_3$) δ 1.20-1.29 (m, total 3H), 2.33 (s, 1.1H), 2.50 (s, 1.9H), 3.03-3.12 (m, 1.3H), 3.36-3.41 (m, 0.7H), 3.65 (s, 0.3H), 4.11 (s, 0.7H), 4.38 (br s, 0.7H), 4.90 (br s, 0.3H).

1:1 Mixture of E/Z regioisomers: $^1$H NMR (CDCl$_3$) δ 0.91-1.15 (m, 8H), 1.48-1.55 (m, 1H), 1.66-1.76 (m, 2H), 1.86-1.93 (m, 1H), 2.04-2.20 (m, 1H), 2.28 (s) and 2.29 (s) (total 3H), 2.46-2.59 (m, 1H), 2.49 (s, 3H), 2.70-2.86 (m, 3H), 3.18-3.28 (m, 2H), 3.37-3.48 (m, 1H), 3.71-3.84 (m, 5H), 6.95-6.97 (m) and 7.00-7.05 (m) and 7.10 (br s) (total 3H), 7.29-7.32 (m, 1H), 8.39 (br d) and 8.87 (br d) (total 1H); ES-MS m/z 529 (M+H).

Example 253

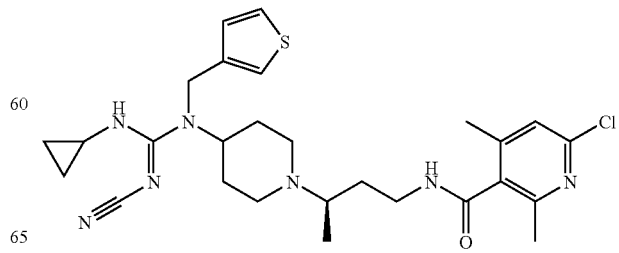

Compound 253

6-Chloro-N—{(R)-3-[4-(N'-cyclopropyl-N-thiophen-3-ylmethyl-cyanoguanidino)-piperidin-1-yl]-butyl}-2,4-dimethyl-nicotinamide 1-Cyclopropyl-2-methyl-3-cyanoisothiourea was prepared following the same procedure as for 1-ethyl-2-methyl-3-cyanoisothiourea (see EXAMPLE 250) except cyclopropylamine was used in lieu of ethylamine. $^1$H NMR (CDCl$_3$) δ 0.66-0.76 (m, 2H), 0.83-0.92 (m, 2H), 2.43 (s, 3H), 2.64 (br s, 1H), 6.78 (br s, 1H).

$^1$H NMR (CDCl$_3$) δ 0.34-0.39 (m, 2H), 0.80-0.89 (m, 3H), 0.98 (d, 3H, J=6 Hz), 0.98-1.09 (m, 1H), 1.47-1.53 (m, 1H), 1.64-1.75 (m, 3H), 2.13-2.24 (m, 1H), 2.27 (s, 3H), 2.47 (s, 3H), 2.52-2.62 (m, 1H), 2.64-2.74 (m, 1H), 2.78-2.86 (m, 2H), 2.88-2.94 (m, 1H), 3.20-3.28 (m, 1H), 3.71 (s, 2H), 3.78-3.84 (m, 1H), 4.25-4.32 (m, 1H), 5.02 (s, 1H), 6.92 (s, 1H), 6.96-7.00 (d, 1H, J=6 Hz), 7.09 (s, 1H), 7.39-7.43 (m, 1H), 8.72 (br s, 1H); ES-MS m/z 542 (M+H).

Example 254

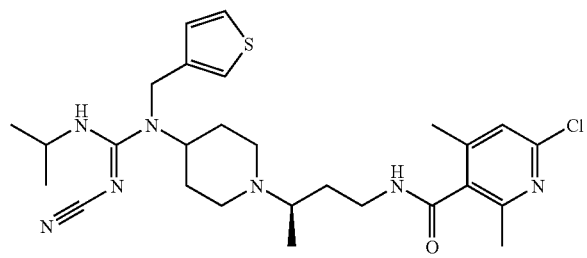

Compound 254

6-Chloro-N—{(R)-3-[4-(N'-isopropyl-N-thiophen-3-ylmethyl-cyanoguanidino)-piperidin-1-yl]-butyl}-2,4-dimethyl-nicotinamide 1-Isopropyl-2-methyl-3-cyanoisothiourea was prepared following the same procedure as for 1-ethyl-2-methyl-3-cyanoisothiourea (see EXAMPLE 250) except isopropylamine was used in lieu of ethylamine. $^1$H NMR (CDCl$_3$) δ 1.25 (d, 6H, J=6 Hz), 2.49 (br s, 3H), 3.84 (br s, 1H), 6.22 (br s, 1H).

$^1$H NMR (CDCl$_3$) δ 0.80-0.89 (m, 1H), 0.92-0.99 (m, 9H), 0.99-1.09 (m, 1H), 1.48-1.53 (m, 1H), 1.64-1.77 (m, 3H), 2.14-2.24 (m, 1H), 2.27 (s, 3H), 2.48 (s, 3H), 2.54-2.63 (m, 1H), 2.73-2.82 (m, 3H), 3.19-3.27 (m, 1H), 3.76 (s, 2H), 3.77-3.84 (m, 1H), 4.25-4.44 (m, 3H), 6.92 (s, 1H), 6.99-7.04 (d, 1H, J=6 Hz), 7.14 (s, 1H), 7.39-7.43 (m, 1H), 8.71 (br s, 1H); ES-MS m/z 544 (M+H).

Example 255

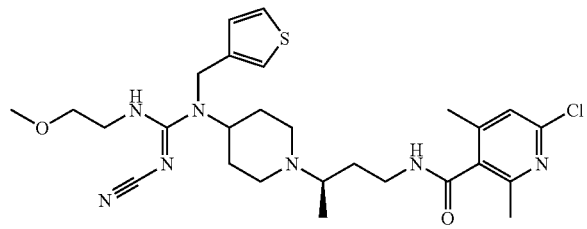

Compound 255

6-Chloro-N—((R)-3-{4-[N-(2-methoxy-ethyl)-N-thiophen-3-ylmethyl-cyanoguanidino]-piperidin-1-yl}-butyl)-2,4-dimethyl-nicotinamide 1-Methoxyethyl-2-methyl-3-cyanoisothiourea was prepared following the same procedure as for 1-ethyl-2-methyl-3-cyanoisothiourea (see EXAMPLE 250) except methoxyethylamine was used in lieu of ethylamine. $^1$H NMR (CDCl$_3$) δ 2.53 (br s, 3H), 3.37 (s, 3H), 3.52 (m, 4H), 6.29 (br s, 1H).

$^1$H NMR (CDCl$_3$) δ 0.79-0.91 (m, 1H), 0.99 (d, 3H, J=6 Hz), 1.00-1.09 (m, 1H), 1.47-1.52 (m, 1H), 1.62-1.74 (m, 3H), 2.13-2.23 (m, 1H), 2.28 (s, 3H), 2.48 (s, 3H), 2.53-2.63 (m, 1H), 2.64-2.74 (m, 1H), 2.78-2.86 (m, 2H), 3.20 (m, 3H), 3.21-3.27 (m, 1H), 3.34 (t, 2H, J=6 Hz), 3.61-3.67 (m, 2H), 3.78 (br s, 2H), 3.79-3.92 (m, 1H), 4.22-4.27 (m, 1H), 5.17-5.23 (m, 1H), 6.93 (s, 1H), 7.02 (d, 1H, J=6 Hz), 7.14 (s, 1H), 7.36-7.43 (m, 1H), 8.72 (br s, 1H); ES-MS m/z 582 (M+Na).

Example 256

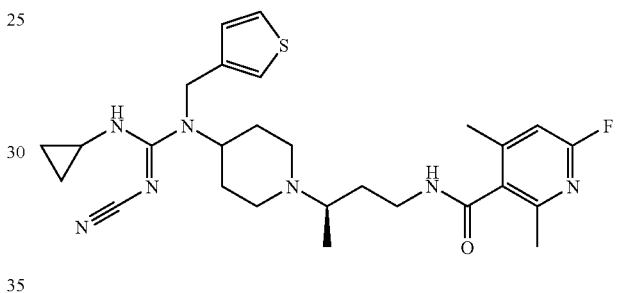

Compound 256

N—{(R)-3-[4-(N'-Cyclopropyl-N-thiophen-3-ylmethyl-cyanoguanidino)-piperidin-1-yl]-butyl}-6-fluoro-2,4-dimethyl-nicotinamide $^1$H NMR (CDCl$_3$) δ 0.30-0.35 (m, 2H), 0.75-0.89 (m, 3H), 1.00 (d, 3H, J=6 Hz), 1.00-1.09 (m, 1H), 1.49-1.57 (m, 1H), 1.72-1.84 (m, 3H), 2.14-2.23 (m, 1H), 2.29 (s, 3H), 2.44 (s, 3H), 2.53-2.61 (m, 1H), 2.69-2.92 (m, 4H), 3.21-3.28 (m, 1H), 3.70 (s, 2H), 3.78-3.85 (m, 1H), 4.27-4.38 (m, 1H), 5.05 (s, 1H), 6.41 (s, 1H), 6.89 (d, 1H, J=3 Hz), 7.04 (s, 1H), 7.38-7.43 (m, 1H), 8.65 (br s, 1H); ES-MS m/z 526 (M+H).

Example 257

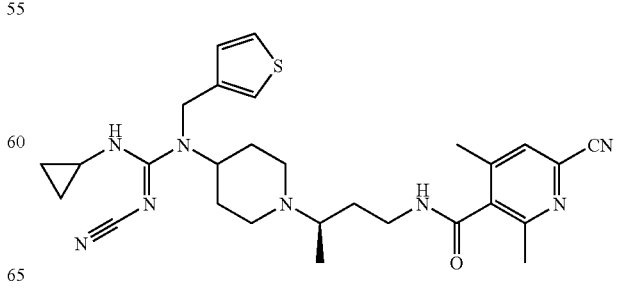

Compound 257

6-Cyano-N—{(R)-3-[4-(N'-cyclopropyl-N-thiophen-3-ylmethyl-cyanoguanidino)-piperidin-1-yl]-butyl}-2,4-dimethyl-nicotinamide $^1$H NMR (CDCl$_3$) δ 0.30-0.37 (m, 2H), 0.80-0.91 (m, 3H), 0.95-1.08 (m, 4H), 1.46-1.57 (m, 1H), 1.70-1.77 (m, 3H), 2.16-2.24 (m, 1H), 2.33 (s, 3H), 2.54 (s, 3H), 2.54-2.65 (m, 1H), 2.69-2.97 (m, 4H), 3.17-3.24 (m, 1H), 3.70 (s, 2H), 3.79-3.85 (m, 1H), 4.26-4.37 (m, 1H), 5.02 (s, 1H), 6.94 (d, 1H, J=6 Hz), 7.12 (br s, 1H), 7.22 (s, 1H), 7.42-7.47 (m, 1H), 8.70 (br s, 1H).

Example 258

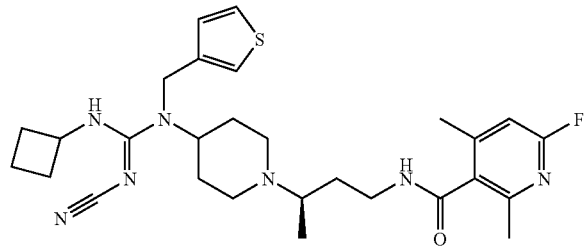

Compound 258

N—{(R)-3-[4-(N'-Cyclobutyl-N-thiophen-3-ylmethyl-cyanoguanidino)-piperidin-1-yl]-butyl}-6-fluoro-2,4-dimethyl-nicotinamide 1-Cyclobutyl-2-methyl-3-cyanoisothiourea was prepared following the same procedure as for 1-ethyl-2-methyl-3-cyanoisothiourea (see EXAMPLE 250) except that cyclobutylamine was used in lieu of ethylamine. $^1$H NMR (CDCl$_3$) δ 1.62-1.79 (m, 2H), 1.92-2.08 (m, 2H), 2.29-2.45 (m, 5H), 4.11 (br s, 1H), 6.74 (br s, 1H).

$^1$H NMR (CDCl$_3$) δ 0.78-0.90 (m, 1H), 0.99 (d, 3H, J=6 Hz), 0.99-1.09 (m, 1H), 1.47-1.62 (m, 5H), 1.63-1.81 (m, 3H), 2.14-2.22 (m, 1H), 2.31 (s, 3H), 2.31-2.40 (m, 2H), 2.45 (s, 3H), 2.54-2.63 (m, 1H), 2.72-2.86 (m, 3H), 3.21-3.29 (m, 1H), 3.74 (s, 2H), 3.81-3.90 (m, 1H), 4.24-4.32 (m, 1H), 4.44-4.52 (m, 1H), 4.80 (m, 1H), 6.42 (s, 1H), 6.94-6.98 (m, 1H), 7.12 (br s, 1H), 7.40-7.47 (m, 1H), 8.72 (br s, 1H); ES-MS m/z 562 (M+Na).

Example 259

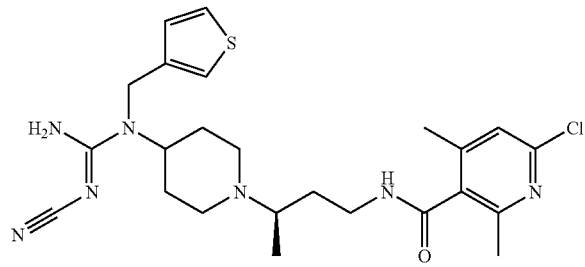

Compound 259

6-Chloro-2,4-dimethyl-N—{(R)-3-[4-(N-thiophen-3-ylmethyl-N''-cyanoguanidino)-piperidin-1-yl]-butyl}-nicotinamide To a stirred solution of 6-chloro-2,4-dimethyl-N—((R)-3-{4-[(thiophen-3-ylmethyl)-amino]-piperidin-1-yl}-butyl)-nicotinamide (100 mg, 0.23 mmol) in 1-butanol (5 ml) was added solid sodium dicyanamide (41 mg, 0.46 mmol) followed by a 4.0 M HCl/dioxane solution (0.12 ml, 0.46 mmol). The resulting solution was heated to reflux (120° C.) for 2 h, then cooled to rt. Saturated aqueous NaHCO$_3$ (10 ml) was added, and the mixture was extracted with CH$_2$Cl$_2$ (3×20 ml). The combined organic extracts were dried (MgSO$_4$) and concentrated, then purified by flash chromatography on silica gel (CH$_2$Cl$_2$/MeOH/NH$_4$OH, 20:2:1) to give COMPOUND 259 as a white foam (85 mg, 74%). $^1$H NMR (CDCl$_3$) δ 0.89-1.10 (m, 4H), 1.50-1.74 (m, 5H), 2.16 (t, 1H, J=12 Hz), 2.28 (s, 3H), 2.47 (s, 3H), 2.55 (t, 1H, J=9 Hz), 2.69-2.83 (m, 3H), 3.24-3.31 (m, 1H), 3.81-3.89 (m, 3H), 4.22-4.27 (m, 1H), 5.29 (br s, 2H), 6.97 (s, 1H), 7.04 (d, 1H, J=6 Hz), 7.13 (br s, 1H), 7.39 (dd, 1H, J=6, 3 Hz), 8.60 (br s, 1H); ES-MS m/z 524 (M+Na).

Example 260

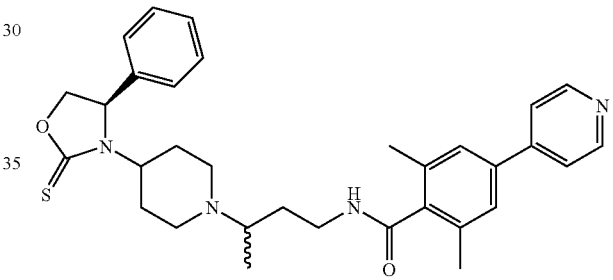

Compound 260

2,6-Dimethyl-N-{3-[4-((R)-4-phenyl-2-thioxo-oxazolidin-3-yl)-piperidin-1-yl]-butyl}-4-pyridin-4-yl-benzamide Using general procedure A, R-(−)-2-phenylglycinyl (91 mg, 0.66 mmol) and [3-(4-oxopiperidin-1-yl)butyl]-carbamic acid tert-butyl ester (225 mg, 0.834 mmol) provided {3-[4-(2-hydroxy-1-phenylethylamino)piperidin-1-yl]butyl}carbamic acid tert-butyl ester as a colorless foam (177 mg, 68%).

The above carbamate (159 mg, 0.407 mmol) was dissolved in CH$_2$Cl$_2$ (4 ml) and then cooled to 0° C. Trifluoroacetic acid (2.0 ml, 26 mmol) was added dropwise to the cooled solution and then the reaction was allowed to stir for 10 minutes at 0° C., and then 30 minutes at room temperature. The solution was concentrated and the residue dissolved in 9:1 CH$_2$Cl$_2$/MeOH (10 ml). mgSO$_4$ was added and the reaction mixture stirred for 30 minutes, then potassium carbonate (373 mg, 2.70 mmol) was added and the solution was concentrated to afford 2-[1-(3-amino-1-methylpropyl)piperidin-4-ylamino]-2-phenylethanol as a light yellow oil (106 mg, 89%) following purification.

Using general procedure E, the above amine (59 mg, 0.20 mmol) and 2,6-dimethyl-4-pyridin-4-ylbenzoic acid (60 mg, 0.27 mmol) gave N-{3-[4-(2-hydroxy-1-phenylethylamino) piperidin-1-yl]butyl}-2,6-dimethyl-4-pyridin-4-ylbenzamide as a light yellow foam (66 mg, 65%).

The above diamine (65 mg, 0.13 mmol) and thiocarbonyldiimidazole (26 mg, 0.15 mmol) in DMF (0.3 ml) were stirred at room temperature for 18 hours. The solution was concentrated under high vacuum and the residue was dissolved in EtOAc (35 ml) and distilled water (2.5 ml). Aqueous work-up and purification afforded COMPOUND 260 as a light yellow foam (33 mg, 46%). $^1$H NMR (CDCl$_3$) δ 0.77-0.97 (m, 9H), 1.10-2.91 (m, 32H), 3.24 (m, 1H), 3.41 (m, 1H), 3.59 (m, 1H), 3.87-4.48 (m, 10H), 7.07 (m, 4H), 7.26-7.49 (m, 14H), 8.64 (m, 4H); $^{13}$C NMR (CDCl$_3$) δ 13.24, 13.71, 19.41, 28.86, 29.62, 30.41, 31.22, 31.45, 32.28, 39.00, 43.48, 44.09, 51.00, 51.32, 53.46, 56.69, 58.80, 59.67, 60.54, 60.78, 28.86, 29.62, 30.41, 31.22, 31.45, 32.28, 39.00, 43.48, 44.09, 51.00, 51.32, 53.46, 56.69, 58.80, 59.67, 60.54, 60.78, 74.75, 121.17, 121.28, 126.03, 126.10, 129.12, 129.37, 135.47, 135.55, 137.98, 138.06, 139.14, 139.33, 140.08, 140.17, 147.15, 147.34, 150.41, 150.46, 168.97, 169.57, 187.17; ES-MS m/z 543 (M+H). Anal. Calcd. for C$_{32}$H$_{38}$N$_4$O$_2$S.0.75CH$_4$O.0.1CH$_2$Cl$_2$: C, 68.59; H, 7.22; N, 9.74; S, 5.57. Found: C, 68.95; H, 7.08; N, 9.68; S, 5.55.

Example 261

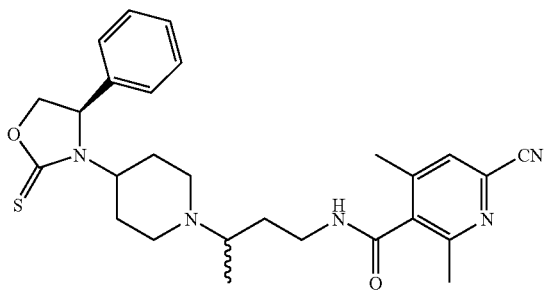

Compound 261

6-Cyano-2,4-dimethyl-N-{3-[4-((R)-4-phenyl-2-thioxo-oxazolidin-3-yl)-piperidin-1-yl]-butyl}-nicotinamide Using general procedure E, (R)-3-[1-(3-amino-1-methylpropyl)-piperidin-4-yl]-4-phenyl-oxazolidine-2-thione (31 mg, 0.093 mmol) and 6-cyano-2,4-dimethylnicotinic acid (21 mg, 0.12 mmol) gave COMPOUND 261 as a beige foam (42.6 mg, 93%). $^1$H NMR (CDCl$_3$) δ 0.73-1.10 (m, 2H), 0.94 and 0.95 (d, 3H, J=6.6 Hz), 1.16-1.78 (m, 4H), 1.87-1.96 (m, 1H), 2.18 and 2.18 (td, 1H, J=11.7, 2.2 Hz), 2.33-2.81 (m, 3H), 2.38 and 2.39 (s, 3H), 2.58 and 2.59 (s, 3H), 3.22-3.85 (m, 2H), 4.15-4.29 (m, 1H), 4.30 and 4.31 (d, 1H, J=8.8 Hz), 4.48 and 4.58 (dd, 1H, J=8.9, 3.4 Hz), 4.68 and 4.71 (dd, 1H, J=9.0, 5.4 Hz), 7.17-7.23 (m, 2H), 7.33-7.44 (m, 3H), 7.46 and 7.47 (s, 1H), 7.67 and 7.75 (br s, 1H). ES-MS m/z 492 (M+H).

Example 262

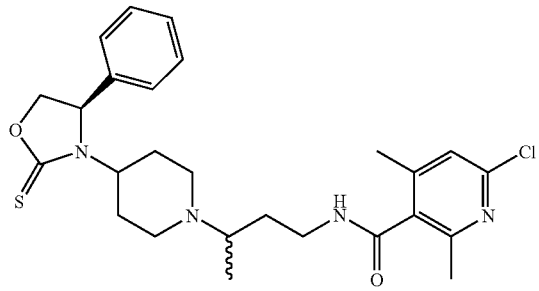

Compound 262

6-Chloro-2,4-dimethyl-N-{3-[4-((R)-4-phenyl-2-thioxo-oxazolidin-3-yl)-piperidin-1-yl]-butyl}-nicotinamide Using general procedure E, (R)-3-[1-(3-amino-1-methylpropyl)-piperidin-4-yl]-4-phenyl-oxazolidine-2-thione (31 mg, 0.093 mmol) and 6-chloro-2,4-dimethylnicotinic acid (24 mg, 0.13 mmol) gave COMPOUND 262 as a light yellow foam (37.1 mg, 80%). $^1$H NMR (CDCl$_3$) δ 0.63-1.09 (m, 2H), 0.93 and 0.95 (d, 3H, J=6.6 Hz), 1.21-2.04 (m, 5H), 2.18 and 2.37 (td, 1H, J=11.9, 2.2 Hz), 2.33 and 2.34 (s, 3H), 2.50-2.83 (m, 3H), 2.53 and 2.55 (s, 3H), 3.12-3.22 and 3.59-3.68 (m, 1H), 3.30-3.40 and 3.86-3.96 (m, 1H), 4.20-4.30 (m, 2H), 4.33 and 4.47 (dd, 1H, J=8.6, 3.1 Hz), 4.66 and 4.69 (dd, 1H, J=8.6, 4.0 Hz), 7.12 and 7.13 (s, 1H), 7.18-7.24 (m, 2H), 7.34-7.42 (m, 3H), 8.18 and 8.29 (br s, 1H). ES-MS m/z 501 (M+H).

Example 263

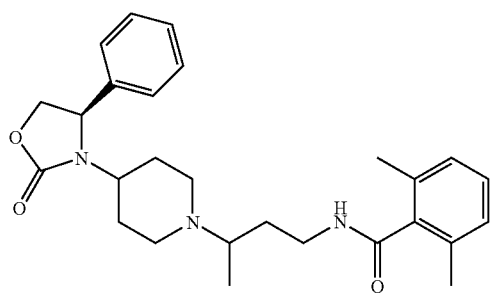

Compound 263

2,6-Dimethyl-N-{3-[4-((R)-2-oxo-4-phenyl-oxazolidin-3-yl)-piperidin-1-yl]-butyl}-benzamide Using general procedure A, R-(−)-2-phenylglycinyl (250 mg, 1.82 mmol) and N-Boc-piperidone (400 mg, 2.0 mmol) gave the desired secondary amine. The crude amine was treated with triphosgene (83 mg, 0.28 mmol) and pyridine (136 μL, 1.68 mmol) in CH$_2$Cl$_2$ to give the oxazolidinone. Using general procedure C, the crude oxazolidinone gave (R)-4-phenyl-3-piperidin-4-yl-oxazolidin-2-one (118 mg, 57% over 3 steps).

Using general procedure B with the above amine (101 mg, 0.41 mmol) and 2-(3-oxo-butyl)-isoindole-1,3-dione (179 mg, 0.82 mmol) followed by general procedure D gave (R)-3-[1-(3-amino-1-methyl-propyl)-piperidin-4-yl]-4-phenyl-oxazolidin-2-one (81 mg, 62% over 2 steps).

Using general procedure E with the above amine (48 mg, 0.16 mmol) and 2,6-dimethylbenzoic acid (26 mg, 0.18 mmol) gave COMPOUND 263 (57 mg, 81%). $^1$H NMR (CDCl$_3$) (mixture of diastereoisomer) δ 0.81-1.03 (m, 4H), 1.04-2.80 (m, 10H), 2.34 (s, 3H), 2.36 (s, 3H), 3.12-4.45 (m, 6H), 7.09-7.55 (m, 9H); $^{13}$C NMR (CDCl$_3$) δ 13.03, 13.60, 19.23, 29.10, 30.01, 30.58, 31.37, 31.56, 32.31, 39.05, 43.23, 44.06, 51.15, 51.66, 52.69, 57.08, 57.57, 58.94, 59.98, 70.68, 126.29, 127.51, 128.31, 128.70, 129.14, 134.35; ES-MS m/z 450 (M+H). Anal Calcd. for $C_{27}H_{35}N_3O_3 \cdot 0.1CH_2Cl_2$: C, 71.06; H, 7.74; N, 9.17. Found: C, 71.44; H, 7.80; N, 9.09.

Example 264

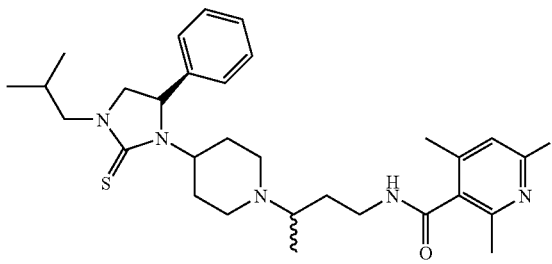

Compound 264

6-Chloro-2,4-dimethyl-N-{3-[4-((R)-2-oxo-5-phenyl-3-(2-methylpropyl)-imidazolidin-1-yl)-piperidin-1-yl]-butyl}-nicotinamide Using general procedure A, ((R)-2-amino-1-phenyl-ethyl)-carbamic acid tert-butyl ester (472 mg, 2.00 mmol) and 2-methylpropionaldehyde (181 μL, 2.00 mmol) afforded ((R)-2-(2-methylpropyl)amino-1-phenyl-ethyl)-carbamic acid tert-butyl ester (533 mg, 91%).

Using general procedure C, ((R)-2-(2-methylpropyl) amino-1-phenyl-ethyl)-carbamic acid tert-butyl ester (533 mg, 1.83 mmol) afforded (R)—N²-(2-methylpropyl)-1-phenyl-ethane-1,2-diamine (350 mg, 99%).

Using general procedure A, (R)—N²-(2-methylpropyl)-1-phenyl-ethane-1,2-diamine (350 mg, 1.82 mmol) and [3-(4-oxo-piperidin-1-yl)-butyl]-carbamic acid tert-butyl ester (493 mg, 1.83 mmol) afforded {3-[4-((R)-2-(2-methylpropyl)amino-1-phenyl-ethylamino)-piperidin-1-yl]-butyl}-carbamic acid tert-butyl ester (473 mg, 58%).

The diamine product was then dissolved in 4 ml of DCM. Pyridine (170 μL, 168 mg, 2.12 mmol) was added and the mixture was cooled to 0° C. Thiophosgene (85 μL, 128 mg, 1.11 mmol) was added slowly to the stirring solution. The reaction was allowed to warm up to room temperature with stirring for two hours. The reaction was then quenched by the addition of 50 ml of a saturated solution of NaHCO$_3$. Standard workup and purification by flash column chromatography gave {3-[4-((R)-3-(2-methylpropyl)-2-thioxo-5-phenyl-imidazolidin-1-yl)-piperidin-1-yl]-butyl}-carbamic acid tert-butyl ester (270 mg, 52%).

Using general procedure C with the above carbamate, and subsequently general procedure E with the resulting amine (44 mg, 0.113 mmol) and 6-chloro-2,4-dimethylnicotinic acid (25 mg, 0.113 mmol) afforded COMPOUND 264 as an off-white foam (40 mg, 64%). $^1$H NMR (CDCl$_3$) δ 0.67 (m, 1H), 0.87-0.95 (m, 9H), 1.31 (m, 1H), 1.52 (m, 1H), 1.61 (s, 3H), 1.68 (m, 1H), 1.87-1.98 (m, 3H), 2.23 (m, 1H), 2.34 (d, 3H, J=4.5 Hz), 2.55 (d, 3H, J=7.8 Hz), 2.64 (m, 1H), 2.73 (m, 1H), 3.10 (m, 2H), 3.33 (m, 2H), 3.62 (m, 1H), 3.73-3.85 (m, 2H), 4.03 (m, 1H), 4.48 (m, 1H), 7.13 (s, 1H), 7.19 (t, 2H, J=6.3 Hz), 7.29-7.37 (m, 4H), 8.56-8.82 (m, 1H); $^{13}$C NMR (CDCl$_3$) δ 13.10, 13.62, 18.82, 19.92, 20.11, 22.18, 27.02, 29.95, 31.24, 39.79, 43.03, 43.79, 51.51, 51.88, 54.67, 57.19, 57.62, 57.71, 59.94, 60.74, 122.55, 125.60, 128.19, 129.03, 133.02, 142.92, 147.80, 148.00, 150.03, 155.47, 155.52, 166.68, 167.41, 182.46; ES-MS m/z 556 (M+H), 578 (M+Na). Anal. Calcd. for $C_{30}H_{42}N_5OSCl \cdot 0.2(CH_2Cl_2)$: C, 63.28; H, 7.46; N, 12.22. Found: C, 63.18; H, 7.53; N, 12.18.

Examples 265 to 272 were prepared following similar chemistry.

Example 265

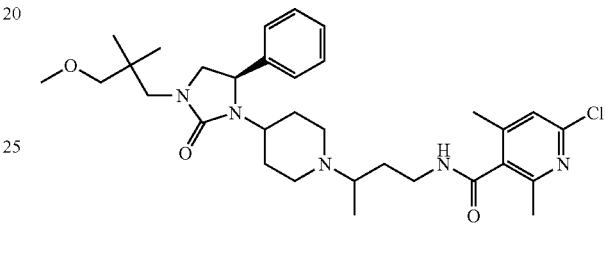

Compound 265

6-Chloro-N-(3-{4-[(R)-3-(3-methoxy-2,2-dimethyl-propyl)-2-oxo-5-phenyl-imidazolidin-1-yl]-piperidin-1-yl}-butyl)-2,4-dimethyl-nicotinamide 3-Methoxy-2,2-dimethyl-propionaldehyde (Effenberger, F. et al.; *Tetrahedron. Asymmetry;* 6; 1995; 271-282) was used in lieu of 2-methylpropionaldehyde. Mixture of diastereoisomers: $^1$H NMR (CDCl$_3$) δ 0.65-1.16 (m, 1H), 1.17-2.12 (m, 8H), 2.14-3.83 (m, 10H), 2.32 and 2.33 (s, 3H), 2.51 and 2.53 (s, 3H), 3.20 (s, 3H), 3.95-4.0 and 4.05-4.15 (m, 1H), 7.12 (s, 1H), 7.25-7.39 (m, 5H), 8.25 and 8.44 (s, 1H); ES-MS m/z 584 (M+H).

Example 266

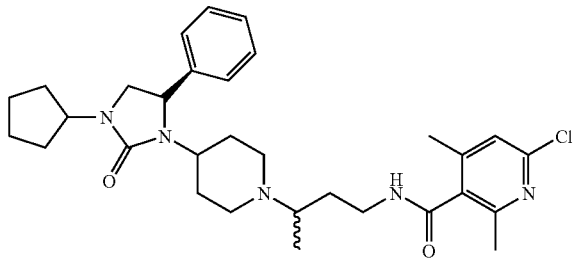

Compound 266

6-Chloro-2,4-dimethyl-N-{3-[4-((R)-2-oxo-5-phenyl-3-(2-cyclopentyl)-imidazolidin-1-yl)-piperidin-1-yl]-butyl}-nicotinamide Cyclopentanone was used in lieu of 2-methylpropionaldehyde. COMPOUND 266 was isolated as a white foam. $^1$H NMR (CDCl$_3$) δ 0.78-0.94 (m, 4H), 1.25-1.93 (m, 15H), 2.09

(m, 1H), 2.33 (d, 3H, J=4.2 Hz), 2.49 (m, 1H), 2.53 (d, 3H, J=7.2 Hz), 2.64-2.71 (m, 2H), 2.96 (m, 1H), 3.13-3.36 (m, 1H), 3.51-3.60 (m, 1H), 3.65 (t, 2H, J=9.0 Hz), 3.94-4.15 (m, 1H), 4.31 (m, 1H), 7.12 (d, 1H, J=2.7 Hz), 7.22-7.36 (m, 5H), 8.13-8.33 (m, 1H); $^{13}$C NMR (CDCl$_3$) δ 13.01, 13.53, 18.83, 22.15, 24.06, 24.16, 28.46, 28.55, 28.91, 29.98, 30.52, 31.66, 39.60, 39.80, 43.24, 44.00, 48.67, 51.67, 51.83, 52.13, 53.48, 55.05, 55.31, 59.66, 60.37, 122.62, 126.16, 127.90, 128.77, 132.70, 132.83, 143.47, 143.67, 147.61, 147.75, 150.10, 155.37, 160.27, 166.89, 167.49; ES-MS m/z 552 (M+H), 574 (M+Na). Anal. Calcd. for C$_{31}$H$_{42}$N$_5$O$_2$Cl 0.1CH$_2$Cl$_2$: C, 66.63; H, 7.59; N, 12.49. Found: C, 66.85; H, 7.70; N, 12.44.

Example 267

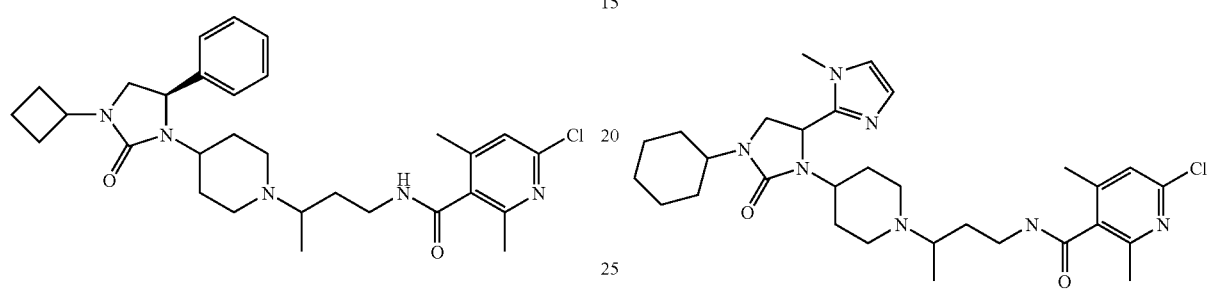

Compound 267

6-Chloro-N-{3-[4-((R)-3-cyclobutyl-2-oxo-5-phenyl-imidazolidin-1-yl)-piperidin-1-yl]-butyl}-2,4-dimethyl-nicotinamide Cyclobutanone was used in lieu of 2-methylpropionaldehyde. COMPOUND 267 was isolated as a white foam. $^1$H NMR (CDCl$_3$) δ 0.73-2.22 (m, 19H), 2.34 (s, 3H), 2.50 (double s, 3H), 2.61-4.57 (m, 8H), 7.09 (s, 1H), 7.18-7.45 (m, 5H), 7.95-8.31 (m, 1H); $^{13}$C NMR (CDCl$_3$) δ 11.36, 11.67, 13.18, 17.24, 17.30, 20.56, 25.52, 25.57, 26.85, 28.06, 29.22, 30.00, 37.46, 41.89, 42.60, 45.79, 47.40, 49.67, 49.96, 50.34, 53.43, 53.64, 57.84, 58.49, 121.00, 124.73, 126.45, 127.20, 131.00, 141.66, 146.04, 148.48, 153.71, 157.89, 165.51, 166.09; ES-MS m/z 539 (M+2). Anal. Calcd. for C$_{30}$H$_{40}$N$_5$ClO$_2$.0.7CH$_2$Cl$_2$: C, 61.70; H, 6.98; N, 11.72. Found: C, 61.89; H, 7.02; N, 11.51.

Example 268

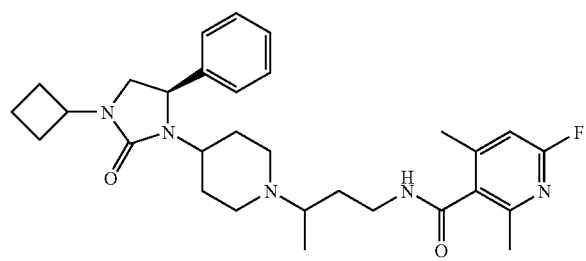

Compound 268

6-Fluoro-N-{3-[4-((R)-3-cyclobutyl-2-oxo-5-phenyl-imidazolidin-1-yl)-piperidin-1-yl]-butyl}-2,4-dimethyl-nicotinamide Cyclobutanone was used in lieu of 2-methylpropionaldehyde. COMPOUND 268 was isolated as a white foam. $^1$H NMR (CDCl$_3$) δ 0.70-2.18 (m, 19H), 2.32 (s, 3H), 2.51 (double s, 3H), 2.59-4.55 (m, 8H), 7.09 (s, 1H), 7.18-7.36 (m, 5H), 7.93-8.31 (m, 1H); $^{13}$C NMR (CDCl$_3$) δ 11.36, 11.67, 13.18, 17.24, 17.30, 20.56, 25.52, 25.57, 26.85, 28.06, 29.22, 30.00, 37.46, 41.89, 42.60, 45.79, 47.40, 49.67, 49.96, 50.34, 53.43, 53.64, 57.84, 58.49, 121.00, 124.73, 126.45, 127.20, 131.00, 141.66, 146.04, 148.48, 153.71, 157.89, 165.51, 166.09; ES-MS m/z 522 (M+H).

Example 269

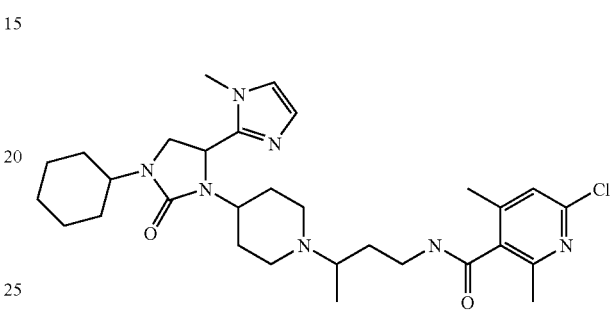

Compound 269

6-Chloro-N-{3-[4-(1'-cyclohexyl-1-methyl-2'-oxo-1', 2',4',5'-tetrahydro-1H-[2,4']biimidazolyl-3'-yl)-piperidin-1-yl]-butyl}-2,4-dimethyl-nicotinamide To a solution of NH$_4$Cl (1.07 g, 20.0 mmol) and NaCN (0.980 g, 20.0 mmol) in ammonium hydroxide (10 ml) was added a solution of 1-methyl-1H-imidazole-2-carbaldehyde (1.10 g, 10.0 mmol) in methanol (5 ml). The mixture was stirred at room temperature for 4 h. The mixture was diluted with water (20 ml), extracted with CH$_2$Cl$_2$-i-PrOH (4:1, v/v, 4×40 ml). The combined organic extracts were dried (Na$_2$SO$_4$) and concentrated to give a yellow oil. This was taken into CH$_2$Cl$_2$ (10 ml), Boc$_2$O (1.90 g) and triethylamine (1.5 ml) were added. The mixture was stirred at room temperature for 4 h. Solvents were evaporated under reduced pressure. The residue was dissolved in methanol (20 ml), saturated with ammonia, Raney nickel (ca. 1 g) was added and the mixture was hydrogenated at 45 psi for 5 h. The catalyst was removed by filtration through a layer of Celite®. Solvents were evaporated under reduced pressure to give the crude product. This was purified by column chromatography on silica gel, eluted with CH$_2$Cl$_2$-MeOH—NH$_4$OH (94:4:2) to give 2-amino-1-(1-methyl-1H-imidazol-2-yl)-ethyl]-carbamic acid tert-butyl ester (192 mg, 8%).

Cyclohexanone was used in lieu of 2-methylpropionaldehyde. COMPOUND 269 was isolated as a white foam. $^1$H NMR (CDCl$_3$) δ 0.98-1.41 (m, 12H), 1.63-2.00 (m, 12H), 2.32, and 2.33 (double s, 3H), 2.50 (s, 3H), 2.64-2.74 (m, 2H), 2.91 (br s, 2H), 3.31-3.78 (m, 7H), 4.69-4.82 (m, 1H), 6.80 (s, 1H), 6.86-6.92 (m, 1H), 7.07 (d, 1H, J=4.8 Hz), 7.47 (br s, 1H); ES-MS m/z 571 (M+H).

Example 270

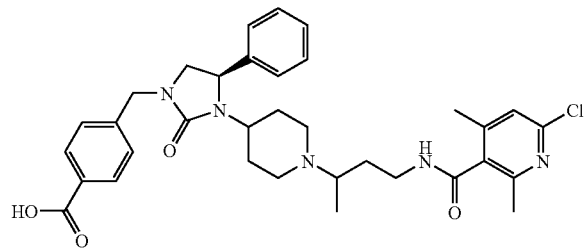

Compound 270

6-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-nicotinic acid Methyl 4-formylbenzoate was used in lieu of 2-methylpropionaldehyde. Hydrolysis of the methyl ester using standard conditions afforded COMPOUND 270. $^1$H NMR (CD$_3$OD) δ 1.26-1.25 (m, 4H), 1.95-2.20 (m, 6H), 2.28-2.80 (m, 4H), 2.29 (s, 3H), 2.30-2.50 (m, 4H), 3.00-3.10 (m, 3H), 3.20-3.75 (m, 16H, CH$_3$OH signal), 4.41 (d, 1H, J=15.3 Hz)), 4.52 (d, 1H, J=15.3 Hz), 7.21-7.35 (m, 8H), 7.93 (d, 2H, J=7.2 Hz); ES-MS m/z 618 (M+1).

Example 271

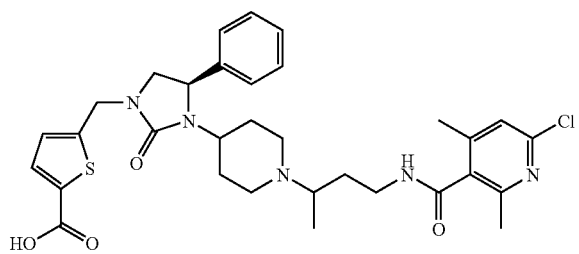

Compound 271

5-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-thiophene-2-carboxylic acid 5-Formyl-thiophene-2-carboxylic acid methyl ester was used in lieu of 2-methylpropionaldehyde. Hydrolysis of the methyl ester using standard conditions afforded COMPOUND 271. $^1$H NMR (CD$_3$OD) δ 1.05-4.05 (m, 28H, containing CH$_3$OH signal), 4.20-4.80 (m, 2H), 6.70-7.40 (m, 7H), 7.93-8.20 (m, 1H); ES-MS m/z 625 (M+1).

Example 272

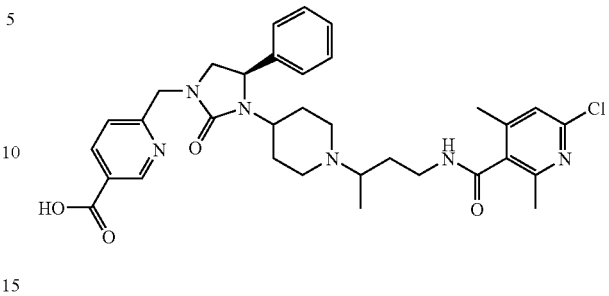

Compound 272

6-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-ylmethyl]-nicotinic acid 6-Formyl-nicotinic acid methyl ester was used in lieu of 2-propionaldehyde. Hydrolysis of the methyl ester using standard conditions afforded COMPOUND 272. $^1$H NMR (CD$_3$OD) δ 1.10-1.40 (m, 4H), 1.60-2.10 (m, 5H), 2.32 (s, 3H), 2.45 (s, 3H), 2.80-3.90 (m, 12H, CH$_3$OH signal), 4.61 (s, 2H), 4.75-4.85 (m, 1H, CH$_3$OH signal), 7.15-7.55 (m, 7H), 8.20-8.40 (m, 1H), 9.10 (s, 1H); ES-MS m/z 620 (M+1).

Examples 273 and 274 were prepared following similar chemistry except the first step involved N-alkylation of ((R)-2-amino-1-phenyl-ethyl)-carbamic acid tert-butyl ester with a commercially available bromide.

Example 273

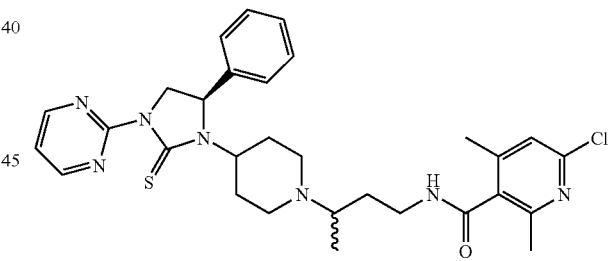

Compound 273

6-Chloro-2,4-dimethyl-N-{3-[4-((R)-5-phenyl-3-pyrimidin-2-yl-2-thioxo-imidazolidin-1-yl)-piperidin-1-yl]-butyl}-nicotinamide COMPOUND 273 was isolated as a yellow foam (1:1 mixture of diastereomers). $^1$H NMR (CDCl$_3$) δ 0.69-0.97 (m, 10H), 1.35-1.80 (m, 6H), 2.04 (m, 3H), 2.24 (m, 1H), 2.34 (s, 3H), 2.35 (s, 3H), 2.42-2.81 (m, 14H), 3.17 (m, 1H), 3.36 (m, 1H), 3.66 (m, 1H), 3.96 (m, 3H), 4.19 (m, 1H), 4.32 (m, 1H), 4.54 (m, 2H), 4.73 (m, 2H), 7.00 (m, 2H), 7.15 (m, 2H), 7.31 (m, 10H), 8.54 (d, 1H, J=6.6 Hz), 8.66 (m, 5H); $^{13}$C NMR (CDCl$_3$) δ 13.22, 13.74, 18.81, 22.21, 29.00, 29.90, 30.00, 30.50, 31.08, 31.43, 39.97, 40.22, 42.95, 43.50, 51.45, 51.68, 54.42, 54.51, 56.81, 57.24, 57.32, 60.07, 60.76, 116.50, 122.56, 125.56, 128.33, 129.13, 133.08, 141.57, 147.83, 148.03, 150.22, 155.50, 155.59, 157.66, 158.43, 166.67, 167.27, 178.71; ES-MS m/z 600 (M+Na). Anal. Calcd. for $C_{30}H_{36}N_7ClSO\cdot 0.2CH_2Cl_2\cdot 0.6CH_4O$: C, 60.21; H, 6.37; N, 15.96; Cl, 8.08; S, 5.22. Found: C, 60.09; H, 6.23; N, 15.74; Cl, 8.26; S, 5.19.

Example 274

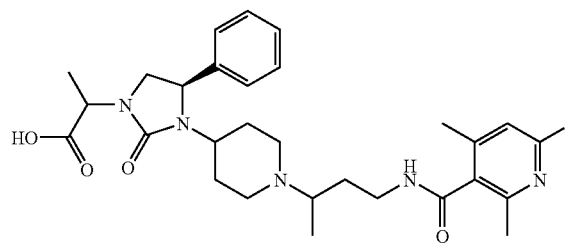

Compound 274

2-[(R)-3-(1-{3-[(6-Chloro-2,4-dimethyl-pyridine-3-carbonyl)-amino]-1-methyl-propyl}-piperidin-4-yl)-2-oxo-4-phenyl-imidazolidin-1-yl]-propionic acid Hydrolysis of the methyl ester using standard conditions afforded COMPOUND 274. $^1$H NMR (CDCl$_3$) mixture of diastereoisomers δ 1.20-4.95 (m, 30H), 6.77-8.35 (m, 7H); $^{13}$C NMR (CDCl$_3$) δ 11.83, 12.34, 12.62, 12.75, 14.89, 15.26, 19.10, 22.32, 26.32, 27.26, 31.06, 31.44, 36.45, 45.20, 49.58, 49.81, 50.03, 50.89, 51.72, 51.85, 54.63, 55.28, 57.82, 58.81, 122.51, 122.58, 126.35, 127.46, 127.65, 128.09, 128.25, 128.72, 129.07, 132.04, 141.22, 147.61, 147.74, 149.86, 155.33, 160.72, 161.16, 168.37, 168.49, 175.90, 128.77, 132.66, 132.80, 143.44, 143.64, 147.59, 147.73, 150.12, 155.37, 159.93, 166.93, 167.53; ES-MS m/z 557 (M+1).

Example 275

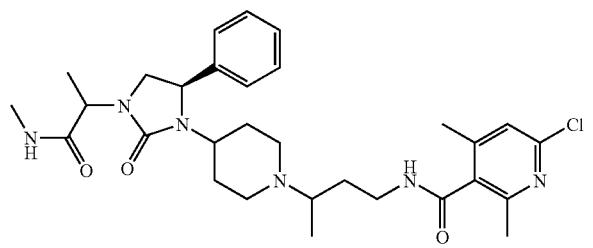

Compound 275

6-Chloro-2,4-dimethyl-N-(3-{4-[(R)-3-(1-methylcarbamoyl-ethyl)-2-oxo-5-phenyl-imidazolidin-1-yl]piperidin-1-yl}-butyl)-nicotinamide Following general procedure E, 2-[(R)-3-(1-{3-[(6-chloro-2,4-dimethyl-pyridine-3-carbonyl)-amino]-1-methyl-propyl}-piperidin-4-yl)-2-oxo-4-phenyl-imidazolidin-1-yl]-propionic acid (COMPOUND 274) and methylamine hydrochloride afforded the COMPOUND 275. $^1$H NMR (CDCl$_3$) mixture of diastereoisomers δ 1.00-4.50 (m, 33H), 6.60 (s, 0.5H), 6.46 (s, 0.5H), 7.03 (s, 1H), 7.16-7.33 (m, 5H), 7.67-8.15 (m, 1H); $^{13}$C NMR (CDCl$_3$) δ 12.95, 13.10, 13.62, 13.77, 18.88, 22.16, 26.10, 26.18, 28.88, 31.16, 31.63, 38.56, 44.31, 49.08, 49.16, 49.40, 51.17, 51.34, 55.85, 59.39, 59.72, 59.90, 122.62, 124.12, 124.85, 126.20, 126.28, 126.38, 128.41, 129.01, 141.87, 147.47, 160.25, 171.70; ES-MS m/z 570 (M+1).

Example 276

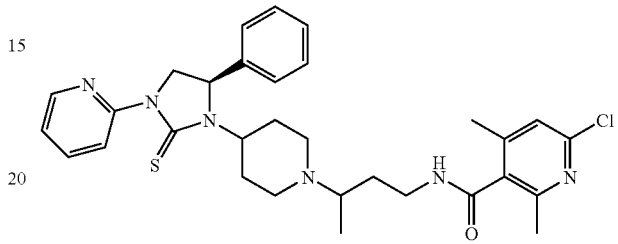

Compound 276

6-Chloro-2,4-dimethyl-N-{3-[4-((R)-5-phenyl-3-pyridin-2-yl-2-thioxo-imidazolidin-1-yl)-piperidin-1-yl]-butyl}-nicotinamide To a solution of (R)-(−)-2-phenylglycine (3.83 g, 25.3 mmol) in 1M NaOH (35 ml) was added a solution of Boc$_2$O (6.14 g, 28.1 mmol) in t-BuOH (20 ml). The resulting suspension was stirred at room temperature for 1 hour. The volatile solvent was removed under reduced pressure and the remaining solution was adjusted to pH 3 with 4M HCl. The resulting suspension was diluted with CHCl$_3$ (50 ml), the layers were separated and the aqueous solution was extracted with CHCl$_3$ (25 ml×2). The combined organic solution was dried (Na$_2$SO$_4$), filtered and concentrated under reduced pressure, to give crude (R)-tert-butoxycarbonylamino-phenyl-acetic acid as a colorless oil (6.92 g, quantitative).

To a solution of (R)-tert-butoxycarbonylamino-phenyl-acetic acid (510 mg, 2.03 mmol) in THF (10 ml) at 0° C. was added NMM (205 mg, 2.03 mmol) in THF (1 ml) and the mixture was stirred at 0° C. for minutes. Isobutyl chloroformate (0.26 ml, 2.0 mmol) was added, the mixture stirred for an additional 5 minutes at 0° C. then 2-aminopyridine (382 mg, 4.06 mmol) in THF (2 ml) was added dropwise over 10 minutes. The resulting solution was stirred at room temperature for 5.5 hours. Standard work-up and purification gave the crude amide (450 mg). Using general procedure C, the carbamate gave the amine, which was subsequently reduced with BH$_3$-THF (1.0M in THF, 4.1 ml, 4.1 mmol) in THF (10 ml) at reflux and treated with MeOH (10 ml) then 6N HCl (11 ml) at reflux to afford (R)-1-phenyl-N$^2$-pyridin-2-yl-ethane-1,2-diamine (109 mg, 25% over 3 steps) after basic work up and purification.

Using general procedure A, the above amine (109 mg, 0.511 mmol) and [3-(4-oxo-piperidin-1-yl)-butyl]-carbamic acid tert-butyl ester (180 mg, 0.666 mmol) afforded (3-{4-[(R)-1-phenyl-2-(pyridin-2-ylamino)-ethylamino]-piperidin-1-yl}-butyl)-carbamic acid tert-butyl ester (182 mg, 76%).

To the above substrate (182 mg, 0.389 mmol) and Et$_3$N (0.11 ml, 0.79 mmol) in CH$_2$Cl$_2$ (7.8 ml) cooled to 0° C. was

313 added thiophosgene (0.033 ml, 0.43 mmol) in CH₂Cl₂ (1 ml) dropwise and the mixture was stirred at 0° C. for 10 minutes and at room temperature for 1 hour. Standard work-up and purification gave 3,3-dimethyl-N-{3-[4-((R)-5-phenyl-3-pyridin-2-yl-2-thioxo-imidazolidin-1-yl)-piperidin-1-yl]-butyl}-butyramide (84 mg, 42%) as a yellow oil.

Using general procedure C with the above carbamate (84 mg, 0.16 mmol) then general procedure E with the resulting amine and 6-chloro-2,4-dimethylnicotinic acid hydrochloride (23 mg, 0.10 mmol) gave COMPOUND 276 as a yellow foam (17 mg, 44%). $^1$H NMR (CDCl$_3$) δ 0.71-1.06 (m, 10H), 1.25-1.79 (m, 6H), 1.92-2.07 (m, 3H), 2.22 (td, 1H, J=11.7, 1.8 Hz), 2.31-2.82 (m, 20H), 3.14-3.22 (m, 1H), 3.33-3.40 (m, 1H), 3.64-3.72 (m, 1H), 3.89-4.02 (m, 3H), 4.19-4.23 (m, 1H), 4.32-4.35 (m, 1H), 4.55-4.70 (m, 4H), 6.98-7.02 (m, 2H), 7.15 (s, 1H), 7.16 (s, 1H), 7.22-7.36 (m, 10H), 7.64-7.70 (m, 2H), 8.29-8.30 (m, 2H), 8.46 (br d, 1H, J=7.5 Hz), 8.60 (br s, 1H), 8.73 (s, 1H), 8.76 (s, 1H); $^{13}$C NMR (CDCl$_3$) δ 13.21, 13.70, 18.80, 22.19, 29.27, 29.70, 30.02, 30.25, 30.58, 31.11, 31.52, 39.92, 40.15, 43.05, 43.62, 51.49, 51.76, 54.59, 56.49, 57.07, 57.18, 60.01, 60.65, 117.59, 119.50, 122.58, 125.56, 128.25, 129.10, 132.98, 136.42, 142.05, 147.45, 147.75, 147.93, 150.28, 152.70, 155.45, 155.54, 166.76, 167.31, 179.15; ES-MS m/z 577 (M+H).

Examples 277 to 280 were prepared using similar chemistry.

Example 277

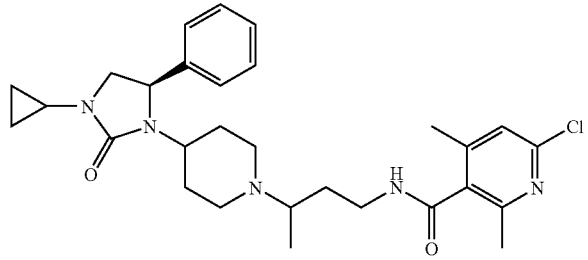

Compound 277

6-Chloro-N-{3-[4-((R)-3-cyclopropyl-2-oxo-5-phenyl-imidazolidin-1-yl)-piperidin-1-yl]-butyl}-2,4-dimethyl-nicotinamide Cyclopropylamine and triphosgene were used in lieu of 2-aminopyridine and thiophosgene, respectively. $^1$H NMR (CDCl$_3$) δ 0.39-2.77 (m, 25H), 2.82-3.05 (m, 1H), 3.09-4.18 (m, 5H), 7.11 (s, 1H), 7.20-7.39 (m, 5H), 8.13-8.29 (br d, 1H); $^{13}$C NMR (CDCl$_3$) δ 5.54, 5.78, 13.41, 13.89, 19.23, 22.53, 26.37, 29.58, 30.60, 30.90, 31.97, 40.00, 43.56, 44.28, 51.89, 52.07, 52.47, 54.34, 55.28, 55.56, 60.09, 60.78, 123.00, 126.47, 128.29, 129.15, 143.44, 143.65, 148.01, 148.14, 150.49, 155.79, 161.59, 167.25. Anal. Calcd. for C₂₉H₃₈N₅ClO₂.0.2CH₂Cl₂: C, 64.82; H, 7.15; N, 12.94. Found: C, 64.51; H, 7.14; N, 12.62; ES-MS m/z 524 (M+H).

314

Example 278

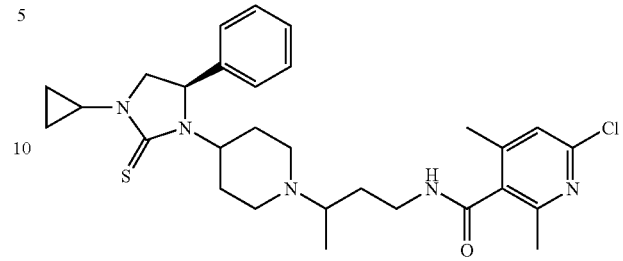

Compound 278

6-Chloro-N-{3-[4-((R)-3-cyclopropyl-2-thioxo-5-phenyl-imidazolidin-1-yl)-piperidin-1-yl]-butyl}-2,4-dimethyl-nicotinamide Cyclopropylamine was used in lieu of 2-aminopyridine. $^1$H NMR (CDCl$_3$) δ 0.41-3.0 (m, 25H), 3.04-4.55 (m, 6H), 7.00-7.36 (m, 6H), 8.36-8.79 (br d, 1H); $^{13}$C NMR (CDCl$_3$) δ 6.05, 7.73, 13.46, 14.05, 19.20, 22.55, 29.72, 30.09, 31.63, 32.20, 40.33, 43.31, 44.01, 51.90, 52.24, 54.75, 57.73, 58.18, 58.32, 60.42, 61.22, 122.95, 125.92, 128.60, 129.43, 142.92, 150.46, 184.11; Anal. Calcd. for C₂₉H₃₈N₅ClOS.0.4.CH₂Cl₂.0.2C₆H₁₄: C, 62.15; H, 7.09; N, 11.84. Found: C, 62.23; H, 7.18; N, 11.84; ES-MS m/z 540 (M+H).

Example 279

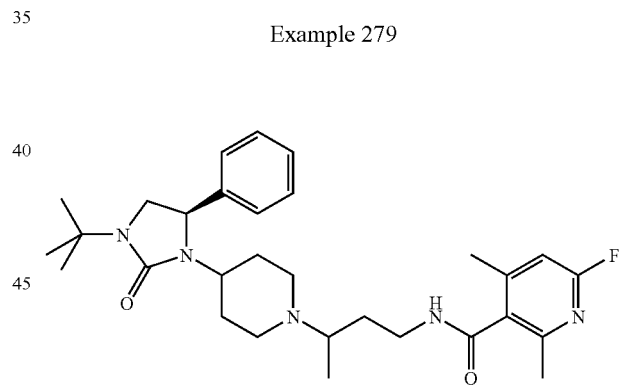

Compound 279

6-Fluoro-N-{3-[4-((R)-3-tert-butyl-2-oxo-5-phenyl-imidazolidin-1-yl)-piperidin-1-yl]-butyl}-2,4-dimethyl-nicotinamide tert-Butyl amine and triphosgene were used in lieu of 2-aminopyridine and thiophosgene, respectively. $^1$H NMR (CDCl$_3$) δ 0.73-1.00 (m, 4H), 1.27 (s, 9H), 1.41-2.16 (m, 7H), 2.32 (double s, 3H), 2.50 (double s, 3H), 2.55-4.20 (m, 9H), 6.68 (s, 1H), 7.14-7.41 (m, 5H), 7.77-8.18 (double broad, 1H); $^{13}$C NMR (CDCl$_3$) δ 12.99, 13.51, 19.20, 21.95, 27.42, 28.90, 29.92, 30.54, 30.78, 31.50, 31.83, 39.49, 43.41, 44.19, 50.77, 51.77, 52.17, 53.09, 53.44, 54.66, 54.84, 59.41, 60.13, 107.19, 107.67, 126.31, 127.90, 128.70, 131.88, 143.20, 143.33, 150.52, 153.61, 153.81, 160.78, 163.98, 167.19, 167.71; ES-MS m/z 524 (M+H).

Example 280

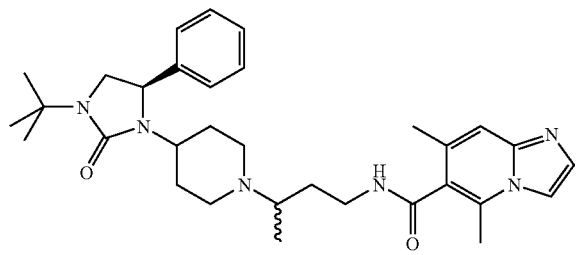

Compound 280

5,7-Dimethyl-imidazo[1,2-a]pyridine-6-carboxylic acid {3-[4-((R)-3-tert-butyl-2-oxo-5-phenyl-imidazolidin-1-yl)-piperidin-1-yl]-butyl}-amide 5-Bromo-4,6-dimethyl-pyridin-2-ylamine (1.51 g, 7.5 mmol) and chloroacetaldehyde (0.95 ml, 50% in water, 7.5 mmol) were mixed with toluene (12 ml). The mixture was heated to reflux for 3 h, upon which time a dark solid residue appeared at the bottom of the reaction flask. After cooling down to rt, NaHCO$_3$ (20 ml, sat. aq.) and CH$_2$Cl$_2$ (20 ml) were added. Layers were separated and the aqueous layer was further extracted with CH$_2$Cl$_2$ (20 ml×2). The combined CH$_2$Cl$_2$ was dried (Na$_2$SO$_4$), filtered and concentrated. The residue was purified by column chromatography on silica gel (CH$_2$Cl$_2$/CH$_3$OH, 18:1) to give the 6-bromo-5,7-dimethyl-imidazo[1,2-a]pyridine as a yellow oil (985 mg, 58%, contaminated with some starting material).

6-Bromo-5,7-dimethyl-imidazo[1,2-a]pyridine (985 mg, 4.26 mmol) was dissolved in DMF (15 ml). To this solution was added Zn(CN)$_2$ (512 mg, 4.36 mmol), Pd$_2$(dba)$_3$ (40 mg, 0.044 mmol) and DPPF (49 mg, 0.088 mmol). The mixture was heated at 120° C. for 48 h. The mixture was then concentrated under vacuum and the residue was taken into CH$_2$Cl$_2$ (40 ml) and washed with H$_2$O (30 ml×2) and brine (20 ml). The organic layer was concentrated and the residue was purified by column chromatography on silica gel (CH$_2$Cl$_2$/CH$_3$OH, 18:1) to give 5,7-dimethyl-imidazo[1,2-a]pyridine-6-carbonitrile (747 mg, 99%).

The above-prepared nitrile (500 mg, 2.9 mmol) was dissolved in a mixture of H$_2$SO$_4$ (conc. 4 ml) and H$_2$O (1 ml). The mixture was heated at 120° C. for 16 h. It was then cooled to 90° C. and NaNO$_2$ (1.4 g, 20 mmol) was added in small portions over 10 min. The reaction was heated at 90° C. for and additional 1 h and then cooled to rt and poured into an ice-water mixture (~20 ml). The chilled mixture was basified to PH=12 using 10N NaOH. The aqueous mixture was then washed with CH$_2$Cl$_2$ (15 ml×2) to remove impurities. It was then acidified to PH=2. After being concentrated under high vacuum to dryness, the residue was extracted with CH$_2$Cl$_2$/CH$_3$OH (4/1, 30 ml×3). The combined extracts were concentrated to give 5,7-dimethyl-imidazo[1,2-a]pyridine-6-carboxylic acid (500 mg, 90% containing impurities) as a beige solid. $^1$H NMR (CDCl$_3$) δ 2.56 (s, 3H), 2.83 (s, 3H), 7.74 (s, 1H), 8.08 (d, 1H, J=1.8 Hz), 8.22 (d, 1H, J=1.8 Hz).

$^1$H NMR (CDCl$_3$) rotameric mixtures δ 0.75-4.00 (m, 35H), 6.97-7.05 (m, 2H), 7.22-7.47 (m, 5H), 7.66 (s, 1H), 7.96-7.99 (m, 1H); ES-MS m/z 545 (M+H).

Example 281

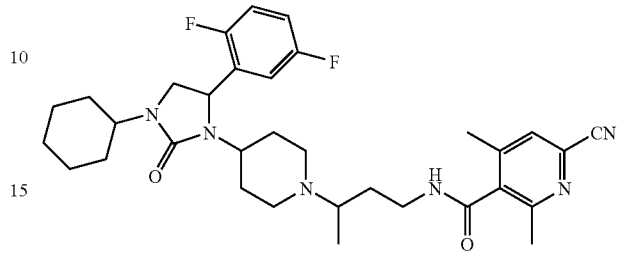

Compound 281

6-Cyano-2,4-dimethyl-N-{3-[4-(2-oxo-5-{2,5-difluorophenyl}-3-cyclohexyl-imidazolidin-1-yl)-piperidin-1-yl]-butyl}-nicotinamide Sodium cyanide (1.38 g, 28.2 mmol) and ammonium chloride (0.75 g, 14.1 mmol) were dissolved in ammonium hydroxide (14 ml). A methanol (7 mL) solution of 2,5-difluorobenzaldehyde (2.00 g, 14.1 mmol) was added to the stirring ammonium hydroxide solution. The reaction was left to stir at room temperature for three hours. After the reaction was complete, the solvent mixture was removed in vacuo, and the solid residue dissolved in 6M HCl (14 ml). This acid solution was refluxed for two hours. Again, after the reaction was complete, the volatiles were removed under vacuum. The solid residue was dissolved in dioxane (14 ml). Boc$_2$O (3.07 g, 14.1 mmol) and NaOH (2.8 ml of 10M solution, 28 ml of 1M solution) were added in succession. The reaction was allowed to stir at room temperature overnight. The basic solution was diluted with H$_2$O (~100 ml) such that the pH reached ~9. Impurities were removed by extracting this basic aqueous phase with DCM (3×100 ml). The basic solution was then acidified to pH ~3 with dilute aqueous HCl. The product was extracted from this aqueous phase with DCM (3×100 ml), and dried over Na$_2$SO$_4$. The solvent was removed by rotary evaporation to yield tert-butoxycarbonylamino-(2,5-difluorophenyl)-acetic acid (1.84 g, 46%).

Using general procedure E, tert-butoxycarbonylamino-(2,5-difluorophenyl)-acetic acid (1.84 g, 6.40 mmol) and cyclohexylamine (730 μL, 634 mg, 6.40 mmol) afforded [cyclohexylcarbamoyl-(2,5-difluorophenyl)-methyl]-carbamic acid tert-butyl ester (2.12 g, 90%).

Using general procedure C, the above carbamate (2.12 g, 5.74 mmol) gave the crude amine, which was subsequently reduced with BH$_3$-THF (1.0M in THF, 17.2 ml, 17.2 mmol) in THF (20 ml) at reflux for 3 hours. After the reaction was complete, it was treated with MeOH (22 ml) and refluxed for 15 minutes. Removal of all volatiles gave a crude solid, which was then dissolved in ethylenediamine (22 ml) and heated to 60° C. for 20 minutes. The reaction was quenched with a saturated solution of NaHCO$_3$, and the product extracted with DCM (3×100 ml). The organic solution was dried over Na$_2$SO$_4$ and the solvent removed to afford crude N$^2$-cyclohexyl-1-(2,5-difluorophenyl)-ethane-1,2-diamine which was purified by column chromatography (750 mg, 52%).

Using general procedure A, N$^2$-cyclohexyl-1-(2,5-difluorophenyl)-ethane-1,2-diamine (750 mg, 2.95 mmol) and [3-

(4-oxo-piperidin-1-yl)-butyl]-carbamic acid tert-butyl ester (797 mg, 2.95 mmol) afforded {3-[4-(2-cyclohexylamino-1-{2,5-difluorophenyl}-ethylamino)-piperidin-1-yl]-butyl}-carbamic acid tert-butyl ester (1.34 g, 89%).

The diamine product (499 mg, 0.983 mmol) was then dissolved in 4 ml of DCM. Pyridine (160 µL, 156 mg, 2.37 mmol) was added and the mixture was cooled to 0° C. Triphosgene (117 mg, 0.393 mmol) was added slowly to the stirring solution. The reaction was allowed to warm up to room temperature with stirring for two hours. The reaction was then quenched by the addition of 50 ml of a saturated solution of NaHCO$_3$. Standard workup and purification by flash chromatography gave {3-[4-(3-cyclohexyl-5-{2,5-difluorophenyl}-2-oxo-imidazolidin-1-yl)-piperidin-1-yl]-butyl}-carbamic acid tert-butyl ester (470 mg, 90%).

Using general procedure C with the above carbamate, and subsequently general procedure E with the resulting amine (56 mg, 0.130 mmol) and 6-cyano-2,4-dimethylnicotinic acid (27 mg, 0.156 mmol) afforded COMPOUND 281 as an off-white foam (53 mg, 69%). $^1$H NMR (CDCl$_3$) δ 0.93-1.00 (m, 3H), 1.04-1.26 (m, 3H), 1.36-1.48 (m, 4H), 1.51-1.78 (m, 10H), 1.87-2.11 (m, 1H), 2.38-2.46 (m, 4H), 2.58 (d, 3H, J=3.3 Hz), 2.61-2.74 (m, 3H), 2.99 (m, 1H), 3.23-3.38 (m, 2H), 3.68-3.72 (m, 3H), 3.91 (m, 1H), 4.45-4.56 (m, 1H), 7.02 (m, 2H), 7.45 (s, 1H), 8.02-8.11 (m, 1H); $^{13}$C NMR (CDCl$_3$) δ 13.15, 13.50, 18.80, 22.23, 25.42, 25.51, 29.45, 29.68, 30.12, 30.40, 30.64, 31.05, 31.70, 39.43, 39.51, 43.51, 44.04, 47.17, 47.25, 51.27, 51.62, 51.84, 52.08, 52.34, 59.34, 59.88, 113.91, 114.23, 115.77, 115.88, 116.09, 116.20, 116.63, 117.07, 117.21, 127.73, 132.51, 136.56, 136.63, 145.44, 145.49, 156.56, 156.62, 157.37, 159.52, 160.60, 166.40, 166.75; ES-MS m/z 593 (M+H), 615 (M+Na). Anal. Calcd. for C$_{33}$H$_{42}$N$_6$O$_2$F$_2$0.1(CH$_2$Cl$_2$): C, 66.13; H, 7.07; N, 13.98. Found: C, 65.73; H, 7.16; N, 13.94.

Examples 282 to 291 were prepared following similar chemistry.

Example 282

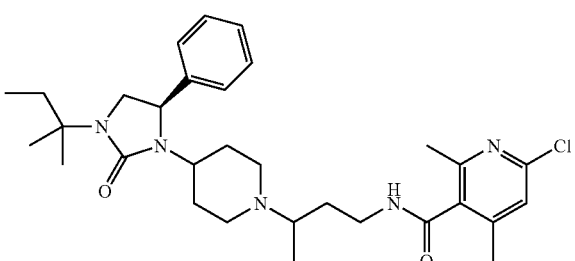

Compound 282

6-Chloro-N-(3-{4-[(R)-3-(1,1-dimethyl-propyl)-2-oxo-5-phenyl-imidazolidin-1-yl]-piperidin-1-yl}-butyl)-2,4-dimethyl-nicotinamide tert-Amylamine was used in lieu of cyclohexylamine. Mixture of diastereoisomers: $^1$H NMR (CDCl$_3$) δ 0.63-1.00 (m, 8H), 1.21-1.38 (m, 7H), 1.41-2.14 (m, 8H), 2.24-2.81 (m, 9H), 2.97-3.44 (m, 2H), 3.47-3.76 (m, 2H), 3.86-4.11 (m, 1H), 7.12 (s, 1H), 7.19-7.40 (m, 5H), 8.08 and 8.32 (br s, 1H); $^{13}$C NMR (CDCl$_3$) δ 9.1, 13.3, 14.0, 19.2, 22.5, 25.6, 28.2, 29.2, 30.4, 30.7, 31.3, 32.1, 32.2, 32.9, 40.0, 40.4, 43.6, 44.5, 51.6, 52.1, 52.7, 54.8, 54.9, 56.2, 60.1, 60.9, 123.0, 126.6, 127.0, 128.2, 129.1, 144.1, 148.0, 155.8, 161.0; ES-MS m/z 554 (M+H). Anal. Calcd. for C$_{31}$H$_{44}$ClN$_5$O$_2$: C, 67.19; H, 8.00; N, 12.64. Found: C, 67.15; H, 8.10; N, 12.45.

Example 283

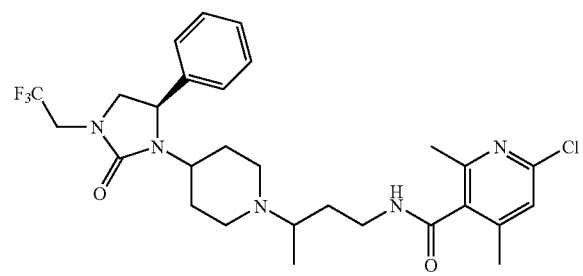

Compound 283

6-Chloro-2,4-dimethyl-N-(3-{4-[(R)-2-oxo-5-phenyl-3-(2,2,2-trifluoro-ethyl)-imidazolidin-1-yl]-piperidin-1-yl}-butyl)-nicotinamide 2,2,2-Trifluoroethylamine was used in lieu of cyclohexylamine. Mixture of diastereoisomers: $^1$H NMR (CDCl$_3$) δ 0.75-1.15 (m, 4H), 1.21-1.75 (m, 7H), 1.82-2.12 (m, 1H), 2.33 and 2.34 (s, 3H), 2.52 and 2.54 (s, 3H), 2.57-2.79 (m, 2H), 3.07-3.57 (m, 3H), 3.58-3.99 (m, 4H), 4.07-4.30 (m, 1H), 7.11 and 7.12 (s, 1H), 7.18-7.41 (m, 5H), 8.08 and 8.21 (br s, 1H); $^{13}$C NMR (CDCl$_3$) δ 13.4, 13.9, 19.2, 22.5, 29.7, 30.5, 31.0, 31.7, 32.0, 40.1, 40.2, 43.6, 44.2, 46.0, 46.4, 52.1, 52.4, 52.6, 54.0, 55.6, 57.0, 60.2, 60.8, 123.0, 123.1, 126.5, 126.6, 128.7, 128.8, 129.4, 142.8, 148.1, 155.7; ES-MS m/z 566 (M+H). Anal. Calcd. for C$_{28}$H$_{35}$ClF$_3$N$_5$O$_2$.0.31H$_2$O: C, 59.41; H, 6.23; N, 12.37. Found: C, 58.88; H, 6.39; N, 12.04.

Example 284

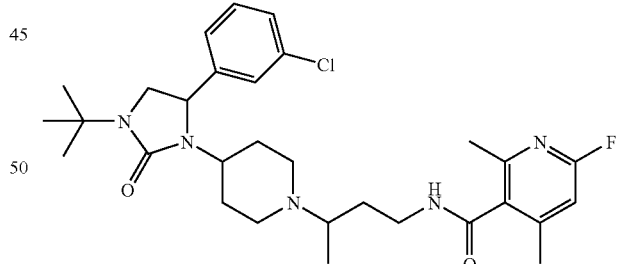

Compound 284

N-(3-{4-[3-tert-Butyl-5-(3-chloro-phenyl)-2-oxo-imidazolidin-1-1]-piperidin-1-yl}-butyl)-6-fluoro-2,4-dimethyl-nicotinamide To a 0° C. mixture of NH$_4$Cl (1.34 g, 25.1 mmol) and NaCN (1.35 g, 27.5 mmol) in NH$_4$OH—H$_2$O (15.6 ml) was added 3-chloro-benzaldehyde (2.85 ml, 25 mmol) in MeOH (25 ml) dropwise and then the resulting mixture was stirred at room temperature for 4 hours. The solvent was partially removed and a standard aqueous work-up gave a yellow solid, which was subsequently treated with 6N HCl (40 ml) and heated at 115° C. overnight. The mixture was concentrated in vacuo and diluted with aqueous NaOH (2.0 g in 30 ml) to adjust pH~14. 1,4-Dioxane (30 ml) and Boc$_2$O (9.82 g, 45 mmol) was added and the mixture stirred at room temperature overnight. The mixture was concentrated and acidified with saturated aqueous KHSO$_4$ to pH~4. The aqueous was extracted with CH$_2$Cl$_2$, dried (Na$_2$SO$_4$) and concentrated under reduced pressure to give tert-butoxycarbonylamino-(3-chloro-phenyl)-acetic acid (4.73 g, 66% over 3 steps).

tert-Butylamine was used in lieu of cyclohexylamine. $^1$H NMR (CDCl$_3$) mixture of diastereoisomers: δ 0.66-0.98 (m, 1H), 1.05-1.41 (m, 1H), 1.43-1.76 (m, 5H), 1.84 and 2.11 (m, 1H), 2.36 and 2.38 (s, 3H), 2.49 and 2.51 (s, 3H), 2.22-2.81 (m, 4H), 2.93-3.71 (m, 5H), 3.86-4.09 (m, 2H), 6.69 (s, 1H), 7.10-7.19 (m, 1H), 7.21-7.35 (m, 3H), 7.96 and 8.12 (br s, 1H); $^{13}$C NMR (CDCl$_3$) δ 13.4, 14.0, 19.6, 22.3, 27.8, 29.2, 30.4, 31.0, 31.2, 32.2, 40.0, 40.2, 43.6, 44.5, 50.9, 52.0, 52.2, 52.5, 54.3, 54.4, 59.9, 60.7, 107.6, 108.1, 124.7, 124.8, 126.7, 128.5, 130.5, 135.0, 146.0, 146.2, 150.9, 160.9; ES-MS m/z 558 (M+1). Anal. Calcd. for C$_{30}$H$_{41}$ClFN$_5$O$_2$.0.24H$_2$O: C, 64.05; H, 7.43; N, 12.45. Found: C, 64.07; H, 7.38; N, 12.35.

Example 285

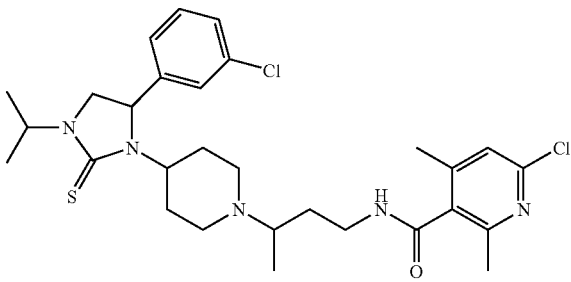

Compound 285

6-Chloro-N-(3-{4-[5-(3-chloro-phenyl)-3-isopropyl-2-thioxo-imidazolidin-1-yl]-piperidin-1-yl}-butyl)-2,4-dimethyl-nicotinamide Isopropylamine and thiophosgene was used in lieu of cyclohexylamine and triphosgene, respectively. 1:1 Ratio of diastereomers. $^1$H NMR (CDCl$_3$) δ 0.59-0.65 (m, 1H), 0.90-0.94 (m, 3H), 1.04-1.12 (m, 3H), 1.14-1.15 (m, 3H), 1.24-1.29 (m, 1H), 1.42-1.51 (m, 1H), 1.63-1.71 (m, 1H), 1.75-1.85 (m, 1H), 1.88-2.16 (m, 1H), 2.33-2.49 (m, 4H), 2.56-2.75 (m, 7H), 3.07-3.37 (m, 2H), 3.60-4.14 (m, 3H), 4.44-4.57 (m, 1H), 4.89-5.29 (m, 1H), 7.02-7.06 (m, 1H), 7.13 (s, 1H), 7.18 (d, 1H, J=6.9 Hz), 7.29 (s, 2H), 8.82 and 8.50 (s and d, 1H, J=6.6 Hz); $^{13}$C NMR (CDCl$_3$) δ 13.15, 13.74, 18.57, 18.64, 18.81, 19.79, 19.85, 22.14, 29.17, 29.62, 30.35, 31.22, 32.27, 39.96, 40.40, 42.90, 43.54, 46.95, 47.02, 50.99, 51.05, 51.48, 51.91, 53.45, 54.31, 56.87, 60.17, 60.92, 122.62, 123.65, 125.69, 128.38, 130.45, 133.08, 133.17, 134.89, 145.28, 145.35, 148.02, 148.16, 149.97, 155.50, 155.58, 166.51, 157.23, 180.79; ES-MS m/z 578 (M+H).

Example 286

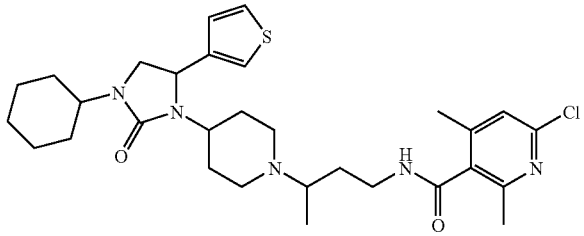

Compound 286

6-Chloro-N-{3-[4-(3-cyclohexyl-2-oxo-5-thiophen-3-yl-imidazolidin-1-yl)-piperidin-1-yl]-butyl}-2,4-dimethyl-nicotinamide To a solution of NH$_4$Cl (1.07 g, 20.0 mmol) and NaCN (0.980 g, 20.0 mmol) in ammonium hydroxide was added a solution of thiophene-3-carbaldehyde (1.12 g, 10.0 mmol) in methanol (5 ml). The mixture was stirred at room temperature for 4 h. 6 N HCl (10 ml) was added to the flask and the mixture was heated at refluxing temperature for 2 h. Solvents were evaporated under reduced pressure. The dried pale yellow solid was dissolved in methanol (10 ml) and 1N NaOH (20 ml). Boc$_2$O (2.06 g) was added to the reaction and the mixture was stirred at room temperature for 2 h. The mixture was acidified with 1 N HCl to pH=4-5, extracted with CHCl$_3$ (4×30 ml). The combined organic extracts were dried (MgSO$_4$) and concentrated to give a brown oil. This was purified by column chromatography on silica gel, eluted with CH$_2$Cl$_2$/MeOH (90:10) to give tert-butoxycarbonylamino-thiophen-3-yl-acetic acid (1.34 g, 52%).

$^1$H NMR (CDCl$_3$) δ 0.91-1.04 (m, 4H), 1.20-1.37 (m, 5H), 1.50-1.75 (m, 8H), 1.85-2.13 (m, 1H), 2.32, and 2.33 (double s, 3H), 2.51, and 2.53 (double s, 3H), 2.64-2.74 (m, 2H), 2.97-3.03 (m, 1H), 3.10-3.40 (m, 1H), 3.56 (t, 2H, J=6.0 Hz), 3.61-4.30 (m, 2H), 6.99-7.01 (m, 1H), 7.07-7.10 (m, 2H), 7.24-7.27 (m, 1H), 8.19-8.37 (m, 1H); $^{13}$C NMR (CDCl$_3$) δ 14.44, 14.92, 20.22, 20.25, 23.53, 26.86, 26.92, 26.96, 30.29, 31.55, 31.87, 32.72, 32.93, 41.02, 44.67, 45.45, 49.03, 49.08, 52.19, 52.39, 52.63, 52.83, 53.13, 53.60, 61.16, 61.86, 122.70, 122.84, 127.06, 128.06, 134.12, 134.26, 145.90, 146.08, 149.07, 149.23, 151.40, 151.46, 156.76, 160.87, 168.23, 168.83; ES-MS m/z 572 (M+H). Anal Calcd. for C$_{30}$H$_{42}$N$_5$ClO$_2$S.0.6CH$_2$Cl$_2$: C, 58.98; H, 6.99; N, 11.24; Br, 37.11. Found: C, 59.12; H, 6.94; N, 11.17.

Example 287

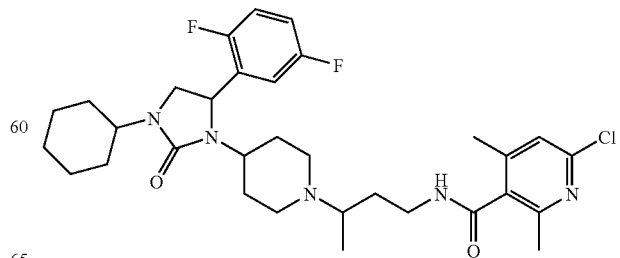

Compound 287

6-Chloro-2,4-dimethyl-N-{3-[4-(2-oxo-5-{2,5-difluoro-phenyl}-3-cyclohexyl-imidazolidin-1-yl)-piperidin-1-yl]-butyl}-nicotinamide COMPOUND 287 was isolated as an off-white foam. $^1$H NMR (CDCl$_3$) δ 0.94-1.05 (m, 6H), 1.19-1.43 (m, 7H), 1.56-1.78 (m, 14H), 1.99-2.15 (m, 1H), 2.32 (m, 3H), 2.53 (m, 3H), 2.68-2.76 (m, 2H), 2.99 (m, 1H), 3.19 (m, 1H), 3.47-3.57 (m, 1H), 3.71 (m, 2H), 3.91 (m, 1H), 4.43-4.54 (m, 1H), 6.91-7.08 (m, 3H), 7.76-7.86 (m, 1H); $^{13}$C NMR (CDCl$_3$) δ 13.03, 13.48, 18.83, 22.08, 25.50, 29.08, 30.05, 30.32, 31.09, 32.04, 39.23, 43.36, 44.11, 47.39, 47.70, 51.30, 51.51, 51.88, 59.17, 59.98, 113.97, 114.33, 115.71, 116.15, 116.62, 122.62, 132.58, 147.45, 150.05, 155.33, 159.53, 167.18, 167.69; ES-MS m/z 602 (M+H), 624 (M+Na). Anal. Calcd. for C$_{32}$H$_{42}$N$_5$O$_2$F$_2$Cl 0.1CH$_2$Cl$_2$: C, 63.14; H, 6.97; N, 11.47. Found: C, 62.75; H, 7.05; N, 11.24.

Example 288

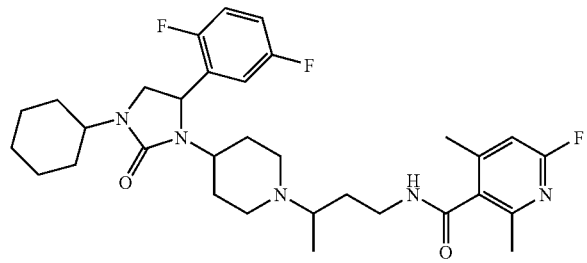

Compound 288

6-Fluoro-2,4-dimethyl-N-{3-[4-(2-oxo-5-{2,5-difluorophenyl}-3-cyclohexyl-imidazolidin-1-yl)-piperidin-1-yl]-butyl}-nicotinamide COMPOUND 288 was isolated as an off-white foam. $^1$H NMR (CDCl$_3$) δ 0.92-1.09 (m, 7H), 1.17-1.39 (m, 7H), 1.51-1.81 (m, 10H), 1.98-2.10 (m, 1H), 2.36 (d, 3H, J=3.6 Hz), 2.40-2.49 (m, 1H), 2.48 (d, 3H, J=4.8 Hz), 2.50-2.54 (m, 1H), 2.66-2.76 (m, 3H), 2.97 (m, 1H), 3.19 (m, 1H), 3.38-3.55 (m, 2H), 3.62-3.74 (m, 3H), 3.86 (m, 1H), 4.45-4.63 (m, 1H), 6.64 (s, 1H), 6.93-7.05 (m, 3H), 7.70-7.75 (m, 1H); $^{13}$C NMR (CDCl$_3$) δ 13.10, 13.53, 19.15, 21.86, 25.50, 29.25, 29.94, 30.01, 30.33, 31.11, 31.26, 32.06, 39.38, 43.36, 44.09, 47.29, 47.64, 48.22, 51.29, 51.49, 51.74, 51.85, 52.08, 59.18, 59.92, 107.16, 107.71, 113.92, 114.26, 115.77, 115.98, 116.09, 116.66, 116.92, 131.73, 150.29, 153.79, 157.36, 159.58, 160.57, 160.82, 163.98, 167.35, 167.80; ES-MS m/z 586 (M+H), 608 (M+Na). Anal. Calcd. for C$_{32}$H$_{42}$N$_5$O$_2$F$_3$ 0.1CH$_2$Cl$_2$: C, 64.89; H, 7.16; N, 11.79. Found: C, 64.83; H, 7.11; N, 11.83.

Example 289

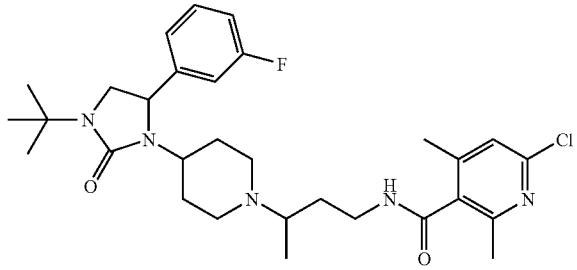

Compound 289

N-(3-{4-[3-tert-Butyl-5-(3-fluoro-phenyl)-2-oxo-imidazolidin-1-yl]-piperidin-1-yl}-butyl)-6-chloro-2,4-dimethyl-nicotinamide To a 0° C. mixture of NH$_4$Cl (535 mg, 10 mmol) and NaCN (539 mg, 11 mmol) in NH$_4$OH.H$_2$O (6.3 ml) was added 3-fluoro-benzaldehyde (1.06 ml, 10 mmol) in MeOH (10 ml) dropwise and then the resulting mixture was stirred at room temperature for 4 hours. The solvent was partially removed and a standard aqueous work-up gave a yellow oil, which was subsequently treated with 6N HCl (16 ml) and heated at 115° C. overnight. The mixture was concentrated in vacuo and diluted with aqueous NaOH (460 mg in 25 ml) to adjust pH~14. 1,4-Dioxane (25 ml) and Boc$_2$O (2.41 g, 11 mmol) was added and the mixture stirred at room temperature overnight. The mixture was concentrated and acidified with saturated aqueous KHSO$_4$ to pH~4. The aqueous was extracted with CH$_2$Cl$_2$, dried (Na$_2$SO$_4$) and concentrated under reduced pressure to give crude tert-butoxycarbonylamino-(3-fluoro-phenyl)-acetic acid.

tert-Butylamine was used in lieu of cyclohexylamine. 1:1 Ratio of diastereomers. $^1$H NMR (CDCl$_3$) δ 0.88-0.92 (m, 4H), 1.22-1.24 (m, 1H), 1.31-1.35 (m, 1H), 1.63-2.03 (m, 3H), 2.04-2.10 (m, 1H), 2.3 and 2.32 (two s, 3H), 2.38-2.42 (m, 1H), 2.50 and 2.52 (two s, 3H), 2.64-2.73 (m, 2H), 2.96-3.01 (m, 1H), 3.11 and 3.38 (two m, 1H), 3.56-3.60 (m, 2H), 3.89-3.91 (m, 1H), 4.02-4.11 (m, 1H), 6.93-7.06 (m, 3H), 7.10 (d, 1H, J=2.7 Hz), 7.28-7.33 (m, 1H), 8.2 and 8.01 (s, d, 1H, J=6 Hz); $^{13}$C NMR (CDCl$_3$) δ 13.36, 13.99, 19.18, 22.49, 27.81, 29.23, 30.35, 30.65, 31.23, 32.06, 32.22, 40.01, 40.34, 43.59, 44.40, 51.06, 52.00, 52.07, 52.56, 53.52, 54.21, 54.29, 60.05, 60.82, 113.35, 113.65, 115.06, 115.34, 122.19, 123.00, 130.67, 130.77, 133.17, 146.78, 148.12, 148.25, 150.44, 155.78, 160.90, 161.75, 165.02, 167.16, 167.79; ES-MS m/z 559 (M+H). Anal. Calcd. for C$_{30}$H$_{41}$N$_5$ClO$_2$F.0.54H$_2$O: C, 63.45; H, 7.47; N, 12.33. Found: C, 63.48; H, 7.46; N, 12.18.

Example 290

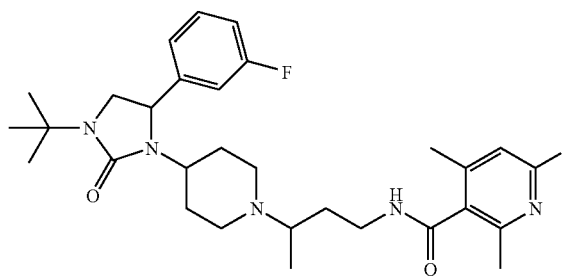

Compound 290

N-(3-{4-[3-tert-Butyl-5-(3-fluoro-phenyl)-2-oxo-imidazolidin-1-yl]-piperidin-1-yl}-butyl)-6-fluoro-2,4-dimethyl-nicotinamide tert-Butylamine was used in lieu of cyclohexylamine. 1:1 Ratio of diastereomers. $^1$H NMR (CDCl$_3$) δ 0.88-0.92 (m, 4H), 1.22-1.24 (m, 1H), 1.31-1.35 (m, 1H), 1.63-2.03 (m, 3H), 2.04-2.10 (m, 1H), 2.3 and 2.32 (two s, 3H), 2.38-2.42 (m, 1H), 2.50 and 2.52 (two s, 3H), 2.64-2.73 (m, 2H), 2.96-3.01 (m, 1H), 3.16 and 3.38 (two m, 1H), 3.40-4.07 (m, 4H), 6.66 (s, 1H), 6.93-7.02 (m, 3H), 7.25-7.33 (m, 1H), 7.95 and 8.01 (two s, 1H); $^{13}$C NMR (CDCl$_3$) δ 13.36, 13.99, 19.18, 22.49, 27.81, 29.23, 30.35, 30.65, 31.23, 32.06, 32.22, 40.01, 40.34, 43.59, 44.40, 51.06, 52.00, 52.07, 52.56, 53.52, 54.21, 54.29, 60.05, 60.82, 107.57, 108.06, 113.39, 113.68, 115.10, 115.38, 122.23, 130.67, 130.78, 132.12, 146.55, 151.02, 153.97, 154.17, 160.93, 161.17, 161.73, 164.33, 165.00, 168.04; ES-MS m/z 542 (M+H). Anal. Calcd. for C$_{30}$H$_{41}$N$_5$O$_2$F$_2$.1.0H$_2$O: C, 64.38; H, 7.74; N, 12.51. Found: C, 64.38; H, 7.48; N, 12.44.

Example 291

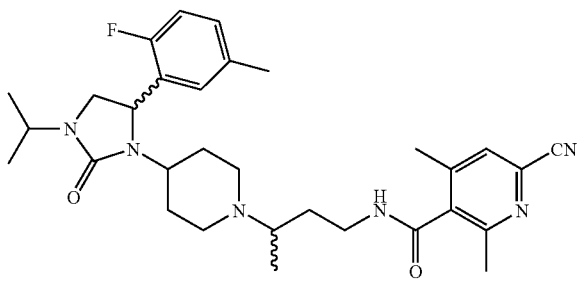

Compound 291

6-Cyano-N-(3-{4-[5-(2-fluoro-5-methyl-phenyl)-3-isopropyl-2-oxo-imidazolidin-1-yl]-piperidin-1-yl}-butyl)-2,4-dimethyl-nicotinamide To a 0° C. mixture of NH$_4$Cl (234 mg, 4.37 mmol) and NaCN (238 mg, 4.86 mmol) in NH$_4$OH.H$_2$O (3.0 ml) was added 2-fluoro-5-methyl-benzaldehyde (610 mg, 4.42 mmol) in MeOH (4.5 ml) dropwise and then the resulting mixture was stirred at room temperature for 2 hours. The solvent was partially removed and a standard aqueous work-up gave a yellow oil, which was subsequently treated with 6N HCl (15 ml) and heated at reflux overnight. The mixture was concentrated in vacuo and diluted with 10N NaOH to adjust pH 13. MeOH (5 ml) and Boc$_2$O (1.0 g, 4.6 mmol) was added and the mixture stirred at room temperature for 4 hours. Standard work-up gave tert-butoxycarbonylamino-(2-fluoro-5-methyl)-acetic acid (155 mg, 12% over 3 steps).

Isopropylamine was used in lieu of cyclohexylamine. COMPOUND 291 was isolated as a beige foam. $^1$H NMR (CDCl$_3$) δ 0.87-0.96 (m, 4H), 1.04-1.07 (m, 6H), 1.12-1.14 (m, 1H), 1.25-1.75 (m, 5H), 1.85-2.10 (m, 1H), 2.28 (s, 3H), 2.36-2.39 (m, 3H), 2.45-2.57 (m, 4H), 2.73-2.76 (m, 2H), 2.97-2.99 (m, 1H), 3.20-3.50 (m, 2H), 3.62-3.66 (m, 1H), 3.70-3.75 and 3.80-3.85 (m, 1H), 4.15-4.19 (m, 1H), 4.40-4.45 and 4.55-4.60 (m, 1H), 6.87-6.95 (m, 1H), 7.02-7.12 (m, 2H), 7.44 (s, 1H), 8.00-8.05 and 8.10-8.15 (m, 1H); $^{13}$C NMR (CDCl$_3$) δ 11.71, 17.49, 18.23, 19.48, 20.91, 27.93, 28.93, 29.66, 30.34, 38.07, 42.19, 42.67, 44.98, 46.96, 50.60, 58.21, 58.71, 113.77, 114.06, 115.93, 126.48, 127.70, 128.62, 131.23, 132.89, 135.24, 144.10, 155.24, 158.39, 165.19, 165.55; ES-MS m/z 549 (M+H). Anal. Calcd. for C$_{31}$H$_{41}$N$_6$O$_2$F.0.1C$_6$H$_{14}$.0.3CH$_2$Cl$_2$: C, 65.74; H, 7.44; N, 14.42. Found: C, 65.44; H, 7.30; N, 14.29.

Example 292

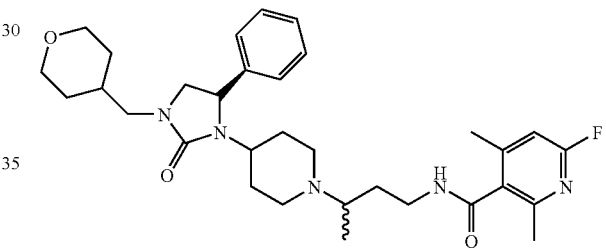

Compound 292

6-Fluoro-2,4-dimethyl-N-{3-[4-((R)-2-oxo-5-phenyl-3-(tetrahydro-pyran-4-ylmethyl)-imidazolidin-1-yl]-piperidin-1-yl]-butyl}-nicotinamide Methyl tetrahydro-2-H-pyran-4-carboxylate (400 μL, 3.00 mmol) was dissolved in a 5:1 mixture of 10M NaOH and MeOH (4.0 ml: 0.8 ml). The mixture was heated to 60° C. for 3 hours. After the reaction was complete, all volatiles were removed under high vacuum to leave a residual solid. The residue was dissolved in H$_2$O and subsequently acidified to pH~1 using aqueous HCl. The acidic aqueous phase was extracted with DCM and dried over Na$_2$SO$_4$. The solvent was removed to give tetrahydro-pyran-4-carboxylic acid (339 mg, 87%), which was used in the next step without further purification.

Using general procedure E, ((R)-2-amino-1-phenyl-ethyl)-carbamic acid tert-butyl ester (616 mg, 2.61 mmol) and tetrahydro-pyran-4-carboxylic acid (339 mg, 2.61 mmol) afforded ((R)-1-phenyl-2-[(tetrahydro-pyran-4-carbonyl)-amino]ethyl)-carbamic acid tert-butyl ester (908 mg, 99%).

Using general procedure C, ((R)-1-phenyl-2-[(tetrahydro-pyran-4-carbonyl)-amino]-ethyl)-carbamic acid tert-butyl ester (908 mg, 2.61 mmol) afforded (R)-tetrahydro-pyran-4-carboxylic acid (2-amino-2-phenyl-ethyl)-amide (450 mg, 70%).

(R)-tetrahydro-pyran-4-carboxylic acid (2-amino-2-phenyl-ethyl)-amide (450 mg, 1.82 mmol) was dissolved in dry THF; and 5.45 ml of borane-THF complex (1M in THF, 5.45 mmol) was added. The solution was refluxed for 3 hours. The reaction was then cooled to room temperature. Methanol (7 ml) was added slowly through the condenser, and the reaction brought to reflux for a further 15 minutes. The reaction was again cooled to room temperature; and the volatiles were removed under high vacuum. More methanol was added and subsequently evaporated (3×15 ml). The resulting residue was dissolved in ethylenediamine (7 ml) and the solution was heated to 60° C. for 20 minutes. The reaction was then quenched with the addition of a saturated aqueous solution of NaHCO$_3$. This aqueous phase was extracted with DCM; and the organic extracts dried over Na$_2$SO$_4$. The solvent was removed in vacuo to give the crude product. Purification by flash chromatography over silica gel afforded (R)-1-Phenyl-N$^2$-(tetrahydro-pyran-4-ylmethyl)-ethane-1,2-diamine (304 mg, 72%).

Using general procedure A, (R)-1-Phenyl-N$^2$-(tetrahydro-pyran-4-ylmethyl)-ethane-1,2-diamine (300 mg, 1.28 mmol) and [3-(4-oxo-piperidin-1-yl)-butyl]-carbamic acid tert-butyl ester (346 mg, 1.28 mmol) afforded [3-(4-{(R)-1-phenyl-2-[tetrahydro-pyran-4-ylmethyl]-amino-ethylamine}-piperidin-1-yl)-butyl]-carbamic acid tert-butyl ester (626 mg, 99%).

The diamine product (500 mg, 1.03 mmol) was then dissolved in 4 ml of DCM. Pyridine (175 µL, 164 mg, 2.05 mmol) was added and the mixture was cooled to 0° C. Triphosgene (121 mg, 0.410 mmol) was added slowly to the stirring solution. The reaction was allowed to warm up to room temperature with stirring for two hours. The reaction was then quenched by the addition of 50 ml of a saturated solution of NaHCO$_3$. Standard workup and purification by flash chromatography gave {3-[4-((R)-2-oxo-5-phenyl-3-{tetrahydro-pyran-4-ylmethyl}-imidazolidin-1-yl)-piperidin-1-yl]-butyl}-carbamic acid tert-butyl ester (377 mg, 72%).

Using general procedure C with the above carbamate, and subsequently general procedure E with the resulting amine (68 mg, 0.165 mmol) and 6-fluoro-2,4-dimethylnicotinic acid (38 mg, 0.198 mmol) gave COMPOUND 292 as an off-white foam (68 mg, 73%). $^1$H NMR (CDCl$_3$) δ 0.84-0.92 (m, 4H), 1.25-1.39 (m, 4H), 1.51-1.55 (m, 3H), 1.63-1.74 (m, 6H), 1.92-2.09 (m, 1H), 2.27-2.33 (m, 1H), 2.37 (d, 3H, J=4.2 Hz), 2.42-2.46 (m, 1H), 2.50 (d, 3H, J=6.6 Hz), 2.62-2.72 (m, 3H), 2.94-3.05 (m, 2H), 3.12-3.18 (m, 2H), 3.33-3.39 (m, 2H), 3.93-3.98 (m, 2H), 4.12-4.23 (m, 1H), 6.67 (s, 1H), 7.21-7.36 (m, 5H), 7.98-8.13 (m, 1H); $^{13}$C NMR (CDCl$_3$) δ 12.04, 12.48, 18.19, 20.92, 28.01, 28.97, 29.38, 29.62, 29.68, 29.87, 30.47, 30.74, 32.92, 38.43, 38.51, 42.36, 43.09, 48.81, 50.50, 50.83, 50.92, 52.76, 54.07, 54.41, 58.32, 59.00, 66.56, 106.16, 106.65, 125.07, 125.14, 127.02, 127.83, 130.73, 130.89, 141.96, 142.19, 149.41, 149.57, 149.68, 152.56, 152.76, 159.78, 159.93, 162.94, 166.17, 166.70; ES-MS m/z 566 (M+H), 588 (M+Na). Anal. Calcd. for C$_{32}$H$_{44}$N$_5$O$_3$F 0.1CH$_2$Cl$_2$: C, 67.14; H, 7.76; N, 12.20. Found: C, 66.85; H, 7.70; N, 12.02.

Examples 293 and 294 were prepared following similar chemistry.

Example 293

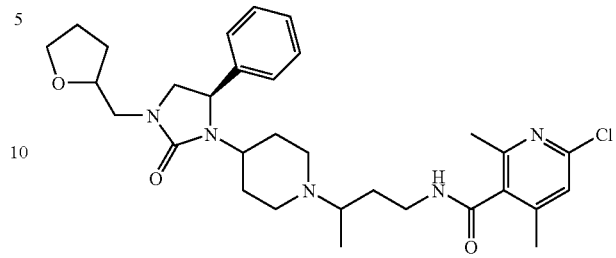

Compound 293

6-Chloro-2,4-dimethyl-N-(3-{4-[(R)-2-oxo-5-phenyl-3-(tetrahydro-furan-2-ylmethyl)-imidazolidin-1-yl]-piperidin-1-yl}-butyl)-nicotinamide Tetrahydro-2-furoic acid was used in lieu of tetrahydro-pyran-4-carboxylic acid. Mixture of diastereoisomers: $^1$H NMR (CDCl$_3$) δ 0.86-1.18 (m, 5H), 1.22-2.16 (m, 9H), 2.31 and 2.32 (s, 3H), 2.34-2.81 (m, 4H), 2.50 and 2.52 (s, 3H), 3.05-4.21 (m, 1H), 7.10 and 7.11 (s, 1H), 7.14-7.38 (m, 5H), 7.80 and 8.21 (br s, 1H); $^{13}$C NMR (CDCl$_3$) δ 12.0, 12.5, 17.8, 21.1, 24.6, 24.7, 27.7, 28.0, 29.5, 30.6, 38.6, 38.8, 42.9, 46.9, 47.0, 50.7, 50.9, 51.1, 53.1, 53.6, 54.6, 58.7, 59.3, 67.0, 67.1, 121.6, 125.2, 125.6, 126.8, 127.7, 131.7, 131.8, 142.2, 142.4, 146.5, 146.6, 149.1, 149.2, 154.3, 159.8, 159.9, 165.9, 166.4; ES-MS m/z 568 (M+H). Anal. Calcd. for C$_{31}$H$_{42}$ClN$_5$O$_3$.0.43H$_2$O: C, 65.53; H, 7.45; N, 12.33. Found: C, 64.73; H, 7.50; N, 11.79.

Example 294

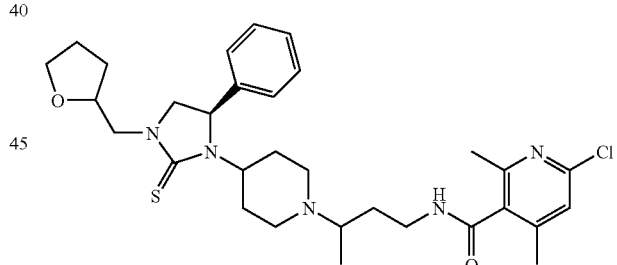

Compound 294

6-Chloro-2,4-dimethyl-N-(3-{4-[(R)-5-phenyl-3-(tetrahydro-furan-2-ylmethyl)-2-thioxo-imidazolidin-1-yl]-piperidin-1-yl}-butyl)-nicotinamide Tetrahydro-2-furoic acid and thiophosgene were used in lieu of tetrahydro-pyran-4-carboxylic acid and triphosgene, respectively. Mixture of diastereoisomers: $^1$H NMR (CDCl$_3$) δ 0.88-0.56 (m, 1H), 1.02-0.87 (m, 3H), 1.12 (m, 1H), 1.21-1.40 (m, 1H), 1.41-2.06 (m, 7H), 2.11-2.80 (m, 7H), 2.32 and 2.34 (s, 3H), 3.06-3.42 (m, 2H), 3.43-3.54 (m, 1H), 3.56-4.27 (m, 8H), 3.37-4.57 (m, 1H), 7.08-7.37 (m, 6H), 8.38 and 8.56 (m, 1H); $^{13}$C NMR (CDCl$_3$) δ 14.1, 19.2, 22.5, 25.8, 26.1, 28.8, 29.5, 30.3, 32.3, 40.3, 40.6, 43.4, 44.1, 51.1, 51.6, 52.0, 52.3, 55.5, 58.0, 58.2, 58.3, 58.9, 60.3, 61.1, 68.3, 68.4, 123.0, 126.1, 126.2, 128.5, 128.6, 129.3, 129.3, 129.4, 143.4, 167.4; ES-MS m/z 584 (M+H). Anal. Calcd. for C$_{31}$H$_{42}$ClN$_5$O$_2$S.0.3H$_2$O: C, 63.73; H, 7.25; N, 11.99; S, 5.49. Found: C, 63.20; H, 7.25; N, 11.68; S, 5.18.

Example 295

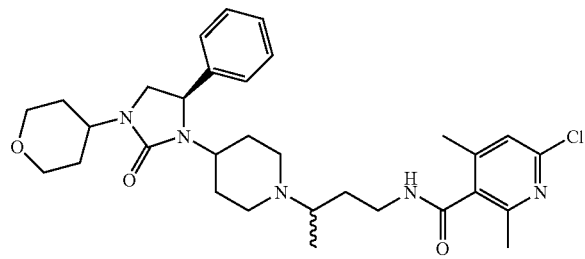

Compound 295

6-Chloro-2,4-dimethyl-N-(3-{4-[(R)-2-oxo-5-phenyl-3-(tetrahydro-pyran-4-yl)-imidazolidin-1-yl]-piperidin-1-yl}-butyl)-nicotinamide Following general procedure A: ((R)-2-amino-1-phenyl-ethyl)-carbamic acid tert-butyl ester (269 mg, 1.14 mmol), tetrahydro-4H-pyran-4-one (0.12 ml, 1.3 mmol) and NaBH(OAc)$_3$ (340 mg, 1.60 mmol) in CH$_2$Cl$_2$ (8.0 ml) was stirred at room temperature for 18 hours. Standard work-up and purification by flash column chromatography on silica (CH$_2$Cl$_2$/MeOH, 19:1) gave [(R)-1-phenyl-2-(tetrahydro-pyran-4-ylamino)-ethyl]-carbamic acid tert-butyl ester as a colorless oil (333 mg, 91%). $^1$H NMR (CDCl$_3$) δ 0.80-1.36 (m, 3H), 1.41 (s, 9H), 1.68-1.82 (m, 2H), 2.61 (tt, 1H, J=10.3, 4.1 Hz), 2.93 (d, 2H, J=5.1 Hz), 3.35 (tdd, 2H, J=11.6, 5.6, 2.2 Hz), 3.88-3.96 (m, 2H), 4.74 (br s, 1H), 5.45 (br d, 1H, J=5.7 Hz), 7.22-7.35 (m, 5H).

A solution of the tert-butyl carbamate (333 mg, 1.04 mmol) and TFA (1.0 ml) in CH$_2$Cl$_2$ (6.0 ml) was stirred at room temperature for 50 minutes. The excess solvent was removed under reduced pressure, giving the crude (R)-1-phenyl-N$^2$-(tetrahydro-pyran-4-yl)-ethane-1,2-diamine TFA salt as a pale yellow oil (849 mg).

Following general procedure A: crude (R)-1-phenyl-N$^2$-(tetrahydro-pyran-4-yl)-ethane-1,2-diamine TFA salt (1.12 mmol), 1-Boc-4-piperidone (246 mg, 1.23 mmol) and NaBH(OAc)$_3$ (338 mg, 1.59 mmol) in CH$_2$Cl$_2$ (7.5 ml) was stirred at room temperature for 17 hours. Standard workup gave crude (3-{4-[(R)-1-phenyl-2-(tetrahydro-pyran-4-ylamino)-ethylamino]-piperidin-1-yl}-butyl)-carbamic acid tert-butyl ester as a pale yellow oil (516 mg, quantitative).

To a 0° C. solution of the crude diamine (0.56 mmol) and pyridine (0.10 ml, 1.2 mmol) in CH$_2$Cl$_2$ (5.5 ml) was added triphosgene (85 mg, 0.29 mmol) and the reaction was stirred at 0° C. for 40 minutes. The reaction was diluted with saturated aqueous NaHCO$_3$ (25 ml) and extracted with CH$_2$Cl$_2$ (20 ml×3). The organic solution was dried (Na$_2$SO$_4$), filtered and concentrated under reduced pressure. Purification by flash column chromatography on silica (CH$_2$Cl$_2$/MeOH, 32:1) gave 4-[(R)-2-oxo-5-phenyl-3-(tetrahydro-pyran-4-yl)-imidazolidin-1-yl]-piperidine-1-carboxylic acid tert-butyl ester as a white foam (194 mg, 81%). $^1$H NMR (CDCl$_3$) δ 1.34-1.48 (m, 2H), 1.38 (s, 9H), 1.58-1.85 (m, 6H), 2.50-2.70 (m, 2H, 3.08 (dd, 1H, J=8.4, 6.9 Hz), 3.43-3.53 (m, 2H), 3.64 (t, 1H, J=9.0 Hz), 3.66-3.78 (m, 1H), 3.85-4.16 (m, 5H), 4.56 (dd, 1H, J=9.2, 7.0 Hz), 7.24-7.38 (m, 5H).

Following general procedure C, the tert-butyl carbamate (194 mg, 0.45 mmol) gave (R)-4-phenyl-3-piperidin-4-yl-1-(tetrahydro-pyran-4-yl)-imidazolidin-2-one as a white foam (128 mg, 86%). $^1$H NMR (CDCl$_3$) δ 1.07 (qd, 1H, J=12.4, 4.3 Hz), 1.41-1.50 (m, 2H), 1.56-1.84 (m, 6H), 2.47 (td, 1H, J=12.3, 2.5 Hz), 2.58 (td, 1H, J=12.0, 3.1 Hz), 2.84-2.92 (m, 1H), 3.02-3.09 (m, 1H), 3.06 (dd, 1H, J=8.4, 6.9 Hz), 3.43-3.52 (m, 2H), 3.64 (t, 1H, J=8.9 Hz), 3.69 (tt, 1H, J=11.9, 3.9 Hz), 3.94-4.10 (m, 3H), 4.60 (dd, 1H, J=9.5, 6.7 Hz), 7.28-7.37 (m, 5H).

Following general procedure B: a solution of the piperidine (128 mg, 9.39 mmol), 2-(3-oxo-butyl)-isoindole-1,3-dione (173 mg, 0.80 mmol) and glacial AcOH (6 drops) in MeOH (2.0 ml) at 55° C. under nitrogen was added NaBH$_3$CN (80 mg, 1.27 mmol) and the reaction was stirred for 22 hours. Standard workup and purification by flash column chromatography on silica (CH$_2$Cl$_2$/MeOH, 29:1) gave the phthalimide as a white foam (126 mg, 61%).

Following general procedure D, the phthalimide (126 mg, 0.24 mmol) gave (R)-3-[1-(3-amino-1-methyl-propyl)-piperidin-4-yl]-4-phenyl-1-(tetrahydro-pyran-4-yl)-imidazolidin-2-one as a colorless oil (90.3 mg, 95%). $^1$H NMR (CDCl$_3$) δ 0.86 (d, 3H, J=6.6 Hz), 1.00-1.92 (m, 12H), 1.99 and 2.12 (td, 1H, J=11.6, 2.2 Hz), 2.24 and 2.37 (td, 1H, J=11.4, 2.2 Hz), 2.49-2.79 (m, 5H), 3.05 (t, 1H, J=7.2 Hz), 3.43-3.52 (m, 2H), 3.54-3.64 and 4.00-4.10 (m, 1H), 3.63 (t, 2H, J=9.0 Hz), 3.94-4.03 (m, 2H), 4.59 (dd, 1H, J=9.2, 6.6 Hz), 7.28-7.37 (m, 5H).

Following general procedure E: a solution of (R)-3-[1-(3-amino-1-methyl-propyl)-piperidin-4-yl]-4-phenyl-1-(tetrahydro-pyran-4-yl)-imidazolidin-2-one (30.1 mg, 0.075 mmol), 6-chloro-2,4-dimethyl-nicotinic acid hydrochloride (22 mg, 0.099 mmol), EDCI (21 mg, 0.11 mmol), HOBT (17 mg, 0.13 mmol) and NMM (22 μL, 0.20 mmol) in DMF (0.50 ml) was stirred at room temperature for 18.5 hours. Standard workup and purification by flash column chromatography on silica (CH$_2$Cl$_2$/MeOH/NH$_4$OH, 32:1:0.17) gave COMPOUND 295 as a light yellow foam (32.9 mg, 77%). $^1$H NMR (CDCl$_3$) δ 0.70-1.03 (m, 1H), 0.90 and 0.92 (d, 3H, J=6.6 Hz), 1.19-1.37 (m, 2H), 1.45-1.76 (m, 7H), 1.86-2.12 (m, 1H), 2.33 and 2.34 (s, 3H), 2.35-3.00 (m, 4H), 2.52 and 2.54 (s, 3H), 3.08-3.69 (m, 6H), 3.91-4.20 (m, 5H), 7.11 and 7.12 (s, 1H), 7.20-7.37 (m, 5H), 8.11 and 8.31 (br s, 1H); ES-MS m/z 568 (M+H), 570 (M+H+2).

Example 296

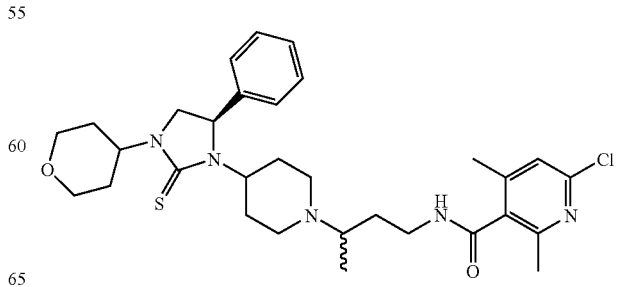

Compound 296

6-Chloro-2,4-dimethyl-N-(3-{4-[(R)-5-phenyl-3-(tetrahydro-pyran-4-yl)-2-thioxo-imidazolidin-1-yl]-piperidin-1-yl}-butyl)-nicotinamide COMPOUND 296 was prepared from 4-[(R)-1-phenyl-2-(tetrahydro-pyran-4-ylamino)-ethylamino]-piperidine-1-carboxylic acid tert-butyl ester following similar chemistry as for COMPOUND 295 except that thiophosgene was used in lieu of triphosgene. COMPOUND 296 was isolated as a pale yellow foam. $^1$H NMR (CDCl$_3$) δ 0.58-0.98 (m, 2H), 0.92 and 0.94 (d, 3H, J=6.6 Hz), 1.23-2.23 (m, 9H), 2.30-2.79 (m, 4H), 2.33 and 2.35 (s, 3H), 2.54 and 2.56 (s, 3H), 3.07-3.40 (m, 1H), 3.25 (dd, 1H, J=9.6, 3.1 Hz), 3.45-3.69 (m, 3H), 3.86 (td, 1H, J=9.9, 2.5 Hz), 3.91-4.05 (m, 2H), 4.09 and 4.22 (dd, 1H, J=9.9, 3.1 Hz), 4.42-4.58 (m, 1H), 4.80 (tt, 1H, J=11.9, 4.4 Hz), 7.11-7.17 (m, 3H), 7.29-7.37 (m, 3H), 8.42 and 8.68 (br s, 1H); ES-MS m/z 586 (M+H+2).

Example 297

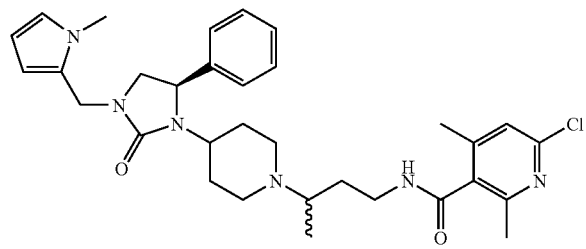

Compound 297

6-Chloro-2,4-dimethyl-N-(3-{4-[(R)-3-(1-methyl-1H-pyrrol-2-ylmethyl)-2-oxo-5-phenyl-imidazolidin-1-yl]-piperidin-1-yl}-butyl)-nicotinamide Following general procedure A: to a stirred solution of [(+/−)-3-(4-oxo-piperidin-1-yl)-butyl]-carbamic acid tert-butyl ester (942 mg, 3.49 mmol) in CH$_2$Cl$_2$ (15 ml) at rt was added 2-((R)-2-amino-2-phenyl-ethyl)-isoindole-1,3-dione (930 mg, 3.49 mmol) and NaBH(OAc)$_3$ (935 mg, 4.19 mmol) and the resultant solution was stirred at rt overnight. The resultant crude product (294 mg, yellow oil) was used directly in the next step.

Following general procedure C: to a stirred solution of the product from last step in CH$_2$Cl$_2$ (3 ml) at rt was added TFA (3 ml). The mixture was stirred at rt for 2 h to give crude amine 2-{(R)-2-[1-(3-amino-1-methyl-propyl)-piperidin-4-ylamino]-2-phenyl-ethyl}-isoindole-1,3-dione (1.68 g, 100%).

Following general procedure E: a solution of crude amine 2-{(R)-2-[1-(3-amino-1-methyl-propyl)-piperidin-4-ylamino]-2-phenyl-ethyl}-isoindole-1,3-dione (450 mg, 1.07 mmol), 6-chloro-2,4-dimethyl-nicotinic acid (238 mg, 1.07 mmol), EDCI (247 mg, 1.28 mmol), HOBT (174 mg, 1.28 mmol), and DIPEA (0.65 ml, 3.75 mmol) in CH$_2$Cl$_2$ (10 ml) was stirred overnight. Purification of the crude product by chromatography on silica gel (CH$_2$C$_2$/MeOH, 9:1) afforded 6-chloro-N-(3-{4-[(R)-2-(1,3-dioxo-1,3-dihydro-isoindol-2-yl)-1-phenyl-ethylamino]-piperidin-1-yl}-butyl)-2,4-dimethyl-nicotinamide (346 mg, 55%).

Following general procedure D: a solution of 6-chloro-N-(3-{4-[(R)-2-(1,3-dioxo-1,3-dihydro-isoindol-2-yl)-1-phenyl-ethylamino]-piperidin-1-yl}-butyl)-2,4-dimethyl-nicotinamide (194 mg, 0.33 mmol), hydrazine hydrate (0.05 ml ml, 0.1 mmol) in EtOH (2 ml) was stirred at rt overnight. Purification of the crude product by chromatography on silica gel (CH$_2$Cl$_2$/MeOH/NH$_4$OH, 100:10:2) afforded N-{3-[4-((R)-2-Amino-1-phenyl-ethylamino)-piperidin-1-yl]-butyl}-6-chloro-2,4-dimethyl-nicotinamide (102 mg, 67%).

A solution of N-{3-[4-((R)-2-Amino-1-phenyl-ethylamino)-piperidin-1-yl]-butyl}-6-chloro-2,4-dimethyl-nicotinamide (60 mg, 0.13 mmol) and 1-Methyl-1H-pyrrole-2-carbaldehyde (15 mg, 0.13 mmol) in CH$_3$OH (2 ml) was stirred at rt for 2 h. The mixture was then cooled to 0° C. NaBH$_4$ (8 mg, 0.2 mmol) was added. The mixture was stirred at this temperature for 20 min. NH$_4$Cl (aq. Sat. 1 ml) was then added and the mixture was extracted with CH$_2$Cl$_2$ (3×10 ml). The organic layer was dried and concentrated. Purification of the residue by chromatography on silica gel (CH$_2$Cl$_2$/MeOH, 9:1) afforded 6-chloro-2,4-dimethyl-N-[3-(4-{(R)-2-[(1-methyl-1H-pyrrol-2-ylmethyl)-amino]-1-phenyl-ethylamino}-piperidin-1-yl)-butyl]-nicotinamide (57 mg, 79%).

To a 0° C. solution of the crude diamine (57 mg, 0.1 mmol) and pyridine (0.02 ml, 0.25 mmol) in CH$_2$Cl$_2$ (2 ml) was added triphosgene (16 mg, 0.05 mmol) and the resulting solution was stirred at 0° C. for 30 minutes followed by 1 h at rt. Standard work-up and purification gave COMPOUND 297 (20 mg, 35%) as a yellow solid. $^1$H NMR (CDCl$_3$) mixture of diastereoisomers δ 0.77-2.20 (m, 10H), 2.26-2.80 (m, 10H), 3.10-4.00 (m, 7H), 4.01-4.25 (m, 1H), 4.35 (s, 2H), 5.97 (s, 2H), 6.57 (s, 1H), 7.16 (s, 1H), 7.18-7.33 (m, 5H), 7.95-8.13 (m, 1H); $^{13}$C NMR (CDCl$_3$) δ 13.41, 13.90, 19.21, 22.52, 29.52, 30.54, 30.81, 31.04, 31.88, 32.06, 33.16, 34.20, 39.95, 40.22, 40.57, 43.68, 44.36, 52.04, 52.45, 52.59, 55.58, 55.83, 59.94, 60.60, 106.98, 109.91, 117.16, 122.98, 123.41, 124.88, 126.54, 127.13, 127.66, 128.35, 129.15, 130.04, 133.01, 133.12, 143.20, 143.36, 147.91, 148.02, 150.56, 155.73, 160.54, 167.35, 167.84; ES-MS m/z 577 (M+1).

Example 298

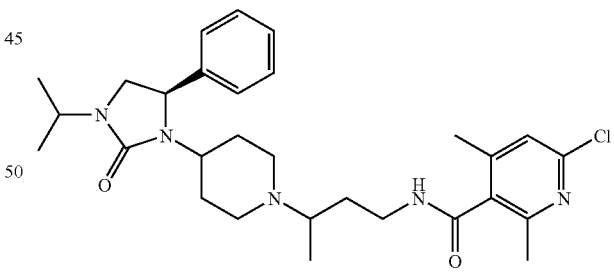

Compound 298

6-Chloro-N-{3-[4-((R)-3-isopropyl-2-oxo-5-phenyl-imidazolidin-1-yl)-piperidin-1-yl]-butyl}-2,4-dimethyl-nicotinamide Following general procedure A, N-{3-[4-((R)-2-amino-1-phenyl-ethylamino)-piperidin-1-yl]-butyl}-6-chloro-2,4-dimethyl-nicotinamide (see EXAMPLE 297) and acetone gave the desired amine. To a 0° C. solution of the crude diamine and pyridine in CH$_2$Cl$_2$ (2 ml) was added triphosgene and the resulting solution was stirred at 0° C. for 30 minutes followed by 1 h at rt. Standard work-up and purification gave COMPOUND 298 as a yellow solid. $^1$H NMR (CDCl$_3$) (mixture of diastereoisomers δ 0.77-2.20 (m, 10H), 2.26-2.80 (m, 10H), 3.10-4.00 (m, 7H), 4.01-4.25 (m, 1H), 4.35 (s, 2H), 5.97 (s, 2H), 6.57 (s, 1H), 7.16 (s, 1H), 7.18-7.33 (m, 5H), 7.95-8.13 (m, 1H); $^{13}$C NMR (CDCl$_3$) δ 13.41, 13.90, 19.21, 22.52, 29.52, 30.54, 30.81, 31.04, 31.88, 32.06, 33.16, 34.20, 39.95, 40.22, 40.57, 43.68, 44.36, 52.04, 52.45, 52.59, 55.58, 55.83, 59.94, 60.60, 106.98, 109.91, 117.16, 122.98, 123.41, 124.88, 126.54, 127.13, 127.66, 128.35, 129.15, 130.04, 133.01, 133.12, 143.20, 143.36, 147.91, 148.02, 150.56, 155.73, 160.54, 167.35, 167.84; ES-MS m/z 577 (M+H).

Example 299

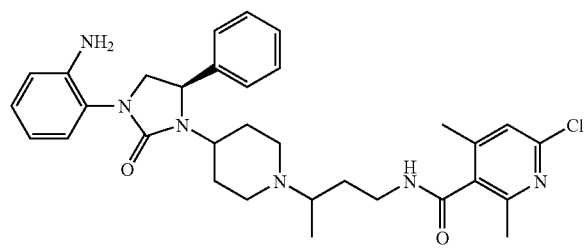

Compound 299

N-(3-{4-[(R)-3-(2-Amino-phenyl)-2-oxo-5-phenyl-imidazolidin-1-yl]-piperidin-1-yl}-butyl)-6-chloro-2,4-dimethyl-nicotinamide To a degassed solution of ((R)-2-amino-1-phenyl-ethyl)-carbamic acid tert-butyl ester (400 mg, 1.69 mmol) in toluene (10 ml), was added 2-nitroiodobenzene (423 mg, 1.69 mmol), Pd$_2$(dba)$_3$ (31 mg, 0.34 mmol), 4,5-bis(diphenylphosphino)-9,9-dimethyxanthene (39 mg, 0.68 mmol) and Cs$_2$CO$_3$ (551 mg, 1.69 mmol). The mixture was heated at 110° C. for 24 h. It was then concentrated and the residue was purified using column chromatography (4:1, Hexanes/EtOAc) to give [(R)-2-(2-nitro-phenylamino)-1-phenyl-ethyl]-carbamic acid tert-butyl ester (390 mg, 64%).

Following general procedure C with [(R)-2-(2-nitro-phenylamino)-1-phenyl-ethyl]-carbamic acid tert-butyl ester then general procedure A with the resulting amine and [(R)-3-(4-oxo-piperidin-1-yl)-butyl]-carbamic acid tert-butyl ester afforded the desired diamine. The diamine was treated with triphosgene under standard conditions to afford (3-{4-[(R)-3-(2-nitro-phenyl)-2-oxo-5-phenyl-imidazolidin-1-yl]-piperidin-1-yl}-butyl)-carbamic acid tert-butyl ester.

To a solution of (3-{4-[(R)-3-(2-nitro-phenyl)-2-oxo-5-phenyl-imidazolidin-1-yl]-piperidin-1-yl}-butyl)-carbamic acid tert-butyl ester (180 mg, 0.334 mmol) in CH$_3$OH (3 ml) was added Pd/C (20 mg, 50%). The mixture was hydrogenated under H$_2$ (2 atm.) for 10 min. Filtration and concentration gave (3-{4-[(R)-3-(2-amino-phenyl)-2-oxo-5-phenyl-imidazolidin-1-yl]-piperidin-1-yl}-butyl)-carbamic acid tert-butyl ester (160 mg, 94%). Treatment with TFA (1 ml) and CH$_2$Cl$_2$ (1 ml) according to general procedure C gave (R)-3-[1-(3-amino-1-methyl-propyl)-piperidin-4-yl]-1-(2-amino-phenyl)-4-phenyl-imidazolidin-2-one (114 mg, 94%).

Following general procedure E: a solution of (R)-3-[1-(3-amino-1-methyl-propyl)-piperidin-4-yl]-1-(2-amino-phenyl)-4-phenyl-imidazolidin-2-one (57 mg, 0.14 mmol), 6-chloro-2,4-dimethylnicotinic acid (34 mg, 0.30 mmol), EDCI (33 mg, 0.14 mmol), HOBT (19 mg, 0.14 mmol), and NEt$_3$ (0.06 ml, 0.40 mmol) in CH$_2$Cl$_2$ (2.0 ml) was stirred overnight. Purification of the crude product by column chromatography on silica gel (CH$_2$Cl$_2$/MeOH, 9:1) afforded COMPOUND 299 (51 mg, 63%) as a white foam (mixture of rotamers). $^1$H NMR (CDCl$_3$) δ 0.80-1.25 (m, 4H), 1.26-2.20 (m, 6H), 2.28-2.80 (m, 9H), 3.10-4.49 (m, 7H), 6.71-6.78 (m, 2H), 6.99-7.12 (m, 3H), 7.27-7.45 (m, 5H), 8.15 (s, 0.44H), 6.30 (s, 0.56H); ES-MS m/z 575 (M+H).

Example 300

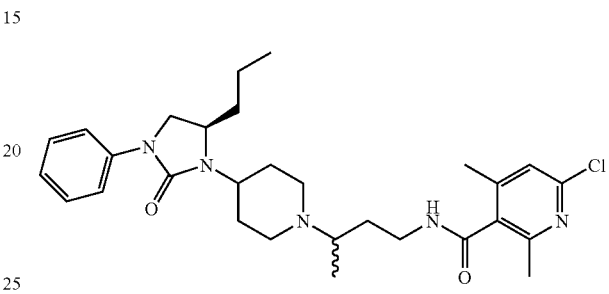

Compound 300

6-Chloro-2,4-dimethyl-N-{3-[4-((R)-2-oxo-3-phenyl-5-propyl-imidazolidin-1-yl)-piperidin-1-yl]-butyl}-nicotinamide A solution of D-norvaline (2.05 g, 17.5 mmol) and Boc$_2$O (3.55 g, 16.3 mmol) in 1M NaOH (25 ml) and t-BuOH (25 ml) was stirred at room temperature for 3.5 hours. The organic solvent was removed under reduced pressure, the remaining aqueous solution was adjusted to pH 2 by the addition of 4M HCl and the mixture was extracted with CHCl$_3$ (30 ml×3). The combined organic solution was dried (Na$_2$SO$_4$), filtered and concentrated under reduced pressure, giving crude (R)-2-tert-butoxycarbonylamino-pentanoic acid as a colorless oil (3.55 g, 100%).

To a 0° C. solution of the crude carboxylic acid (652 mg, 3.00 mmol) and NMM (0.50 ml, 4.5 mmol) in THF (12 ml) was added isobutyl chloroformate (0.45 ml, 3.5 mmol) and the resulting mixture was stirred at 0° C. for 5 minutes. A solution of aniline (0.45 ml, 4.9 mmol) in THF (3 ml) was then added dropwise. The reaction was warmed to room temperature and stirred for 66 hours. The reaction was diluted with 1M HCl (30 ml) and was extracted with Et$_2$O (25 ml×3). The organic solution was washed with brine (50 ml), was dried (Na$_2$SO$_4$), filtered and concentrated under reduced pressure, giving crude ((R)-1-phenylcarbamoyl-butyl)-carbamic acid tert-butyl ester as an oily, light yellow foam.

A solution of the crude tert-butyl carbamate (3.00 mmol) and TFA (3.0 ml) in CH$_2$Cl$_2$ (15 ml) was stirred at room temperature for 55 minutes. The reaction was made basic with 1M NaOH (50 ml) and was extracted with CHCl$_3$ (25 ml×3). The combined organic solution was dried (Na$_2$SO$_4$), filtered and concentrated under reduced pressure. Purification by flash column chromatography on silica (CH$_2$Cl$_2$/MeOH, 9:1) gave (R)-2-amino-pentanoic acid phenylamide as a yellow oil (265 mg, 46%). $^1$H NMR (CDCl$_3$) δ 0.97 (t, 3H, J=7.0 Hz), 1.37-1.70 (m, 5H), 1.86-1.99 (m, 1H), 3.46-3.55 (m, 1H), 7.09 (t, 1H, J=7.3 Hz), 7.32 (t, 2H, J=7.5 Hz), 7.60 (d, 2H, J=7.9 Hz), 9.48 (br s, 1H).

A solution of the amide (265 mg, 1.38 mmol) and BH₃.THF (1.0M in THF, 5.0 ml, 5.0 mmol) in THF (5.0 ml) was stirred at reflux under nitrogen for 15.5 hours. The reaction was cooled, quenched by the careful addition of 6M HCl (8 ml) and the mixture was stirred at 65° C. for another 3 hours. Once cooled, the reaction was made basic with 1.7M NaOH (30 ml) and was extracted with CH₂Cl₂ (25 ml×3). The organic solution was dried (Na₂SO₄), filtered and concentrated under reduced pressure. Purification by flash column chromatography on silica (CH₂Cl₂/MeOH/NH₄OH, 29:1:0.15, increased to 19:1:0.2) gave (R) —N¹-phenyl-pentane-1,2-diamine as a yellow oil (204 mg, 83%). ¹H NMR (CDCl₃) δ 0.95 (t, 3H, J=6.6 Hz), 1.25-1.54 (m, 6H), 2.81-2.90 (m, 1H), 2.95-3.04 (m, 1H), 3.15-3.24 (m, 1H), 4.12 (br s, 1H), 6.63 (d, 2H, J=7.9 Hz), 6.69 (t, 1H, J=7.5 Hz), 7.17 (t, 2H, J=7.7 Hz).

Following general procedure A: the amine (204 mg, 1.14 mmol), 1-Boc-4-piperidone (232 mg, 1.16 mmol) and NaBH(OAc)₃ (345 mg, 1.63 mmol) in CH₂Cl₂ (7.5 ml) was stirred at room temperature for 17.5 hours. Standard workup gave crude 4-((R)-1-phenylaminomethyl-butylamino)-piperidine-1-carboxylic acid tert-butyl ester as a yellow oil (460 mg).

To a 0° C. solution of the secondary amine (1.14 mmol) and pyridine (0.20 ml, 2.5 mmol) in CH₂Cl₂ (12 ml) was added triphosgene (174 mg, 0.59 mmol) and the resulting yellow solution was stirred at 0° C. for 60 minutes. The reaction was diluted with 0.5M HCl (30 ml) and extracted with CH₂Cl₂ (25 ml×2). The organic solution was dried (Na₂SO₄), filtered and concentrated under reduced pressure. Purification by flash column chromatography on silica (CH₂Cl₂/Et₂O, 14:1, increased to 9:1) gave 4-((R)-2-oxo-3-phenyl-5-propyl-imidazolidin-1-yl)-piperidine-1-carboxylic acid tert-butyl ester as an oily, white foam (405 mg, 92%). ¹H NMR (CDCl₃) δ 0.96 (t, 3H, J=7.2 Hz), 1.23-1.58 (m, 3H), 1.46 (s, 9H), 1.65-1.97 (m, 5H), 2.68-2.83 (m, 2H), 3.42 (dd, 1H, J=8.7, 5.2 Hz), 3.68-3.86 (m, 2H), 3.86 (t, 1H, J=9.0 Hz), 4.11-4.31 (m, 2H), 7.00 (t, 1H, J=7.3 Hz), 7.31 (t, 2H, J=8.0 Hz), 7.51 (d, 2H, J=8.0 Hz).

Following general procedure C, the tert-butyl carbamate (405 mg, 1.05 mmol) gave the crude piperidine as a yellow oil (311 mg, quantitative).

Following general procedure B: a solution of (R)-1-phenyl-3-piperidin-4-yl-4-propyl-imidazolidin-2-one (152 mg, 0.53 mmol), 2-(3-oxo-butyl)-isoindole-1,3-dione (230 mg, 1.06 mmol), NaBH₃CN (108 mg, 1.72 mmol) and glacial AcOH (8 drops) in MeOH (2.5 ml) was stirred at 60° C. for 16.5 hours. Standard workup and purification by flash column chromatography on silica (CH₂Cl₂/MeOH, 29:1) gave 2-{3-[4-((R)-2-oxo-3-phenyl-5-propyl-imidazolidin-1-yl)-piperidin-1-yl]-butyl}-isoindole-1,3-dione, contaminated with alcohol resulting from reduction of excess ketone (302 mg).

Following general procedure D, the phthalimide gave the primary amine as a light yellow oil (92.3 mg, 49%). ¹H NMR (CDCl₃) δ 0.96 (t, 3H, J=7.2 Hz), 0.96 and 0.97 (d, 3H, J=6.6 Hz), 1.23-2.04 (m, 12H), 2.17-2.28 (m, 1H), 2.41-2.52 (m, 1H), 2.67-2.91 (m, 5H), 3.42 (dd, 1H, J=8.7, 4.8 Hz), 3.63-3.80 (m, 2H), 3.87 and 3.88 (t, 1H, J=9.0 Hz), 7.00 (t, 1H, J=7.1 Hz), 7.31 (t, 2H, J=8.0 Hz), 7.52 (d, 2H, J=7.8 Hz).

Following general procedure E: a solution of the primary amine (46.1 mg, 0.13 mmol), 6-chloro-2,4-dimethylnicotinic acid (30 mg, 0.16 mmol), EDCI (34 mg, 0.18 mmol), HOBT (25 mg, 0.18 mmol) and NMM (35 μL, 0.32 mmol) in DMF (0.85 ml) was stirred at room temperature for 15.5 hours. Standard workup and purification by flash column chromatography on silica (CH₂Cl₂/MeOH, 19:1, increased to 9:1) gave COMPOUND 300 as a yellow foam (56.2 mg, 83%). ¹H NMR (CDCl₃) δ 0.92 and 0.93 (t, 3H, J=6.8 Hz), 1.06 and 1.09 (d, 3H, J=7.1 Hz), 1.23-1.95 (m, 10H), 2.23-2.35 (m, 1H), 2.33 (s, 3H), 2.53 (s, 3H), 2.59-2.71 (m, 1H), 2.81-3.00 (m, 3H), 3.27-3.50 (m, 2H), 3.40 (dd, 1H, J=8.6, 4.4 Hz), 3.66-3.94 (m, 2H), 3.85 and 3.86 (t, 1H, J=8.5 Hz), 6.99-7.05 (m, 2H), 7.32 (t, 2H, J=8.1 Hz), 7.49 (d, 2H, J=8.0 Hz), 8.11 (br s, 1H); ES-MS m/z 526 (M+H), 528 (M+H+2). Anal. Calcd. for C₂₉H₄₀ClN₅O₂.0.2CH₂Cl₂: C, 64.58; H, 7.50; N, 12.89. Found: C, 64.59; H, 7.57; N, 12.83.

Example 301

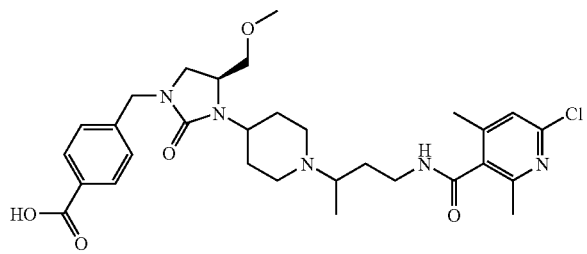

Compound 301

4-[(S)-3-(1-{3-[(6-Chloro-2,4-dimethyl-pyridine-3-carbonyl)-amino]-1-methyl-propyl}-piperidin-4-yl)-4-methoxymethyl-2-oxo-imidazolidin-1-ylmethyl]-benzoic acid methyl ester (R)-2-tert-Butoxycarbonylamino-3-hydroxy-propionic acid methyl ester (2.2 mg, 10 mmol) was dissolved in THF (20 ml). Imidazole (818 mg, 12 mmol) and TBDPS chloride (2.9 ml, 11 mmol) were added. The mixture was stirred at rt overnight. The mixture was then partitioned between CH₂Cl₂ and water (30 ml/30 ml). The organic layer was concentrated and the residue was purified by column chromatography (6/1, Hexanes/EtOAc) to give (R)-2-tert-butoxycarbonylamino-3-(tert-butyl-diphenyl-silanyloxy)-propionic acid methyl ester (3.3 g, 72%).

(R)-2-tert-Butoxycarbonylamino-3-(tert-butyl-diphenyl-silanyloxy)-propionic acid methyl ester (3.3 g, 7.2 mmol) was dissolved in ether (25 ml). The solution was cooled to 0° C. in an ice bath. LiBH₄ (2.32 g, 10 mmol) was added in small portions. The resultant mixture was stirred for 20 min at this temperature before warming to rt and was stirred for an additional 60 min. The mixture was then transferred dropwise to an aqueous HCl solution (2%, 10 ml). The aqueous layer was extracted with EtOAc (20 ml×2). The organic layer was dried over Na₂SO₄ and concentrated to give the desired alcohol (2.6 g, 81%).

The alcohol (2.6 g, 5.85 mmol) was subjected to general Mitsunobu reaction conditions using phthalimide (1.29 g, 8.5 mmol), DEAD (2.3 ml, 14.6 mmol) and Ph₃P (4.6 g, 17.4 mmol) in THF (60 ml). The reaction gave [(S)-2-(tert-butyl-diphenyl-silanyloxy)-1-(1,3-dioxo-1,3-dihydro-isoindol-2-ylmethyl)-ethyl]-carbamic acid tert-butyl ester (2.3 g, 63%).

[(S)-2-(tert-Butyl-diphenyl-silanyloxy)-1-(1,3-dioxo-1,3-dihydro-isoindol-2-ylmethyl)-ethyl]-carbamic acid tert-butyl ester (1.1 g, 1.92 mmol) was treated with hydrazine hydrate (0.5 ml, 9 mmol) in EtOH (5 ml) at rt over night to give [(S)-1-aminomethyl-2-(tert-butyl-diphenyl-silanyloxy)-ethyl]-carbamic acid tert-butyl ester (640 mg, 75%).

[(S)-1-Aminomethyl-2-(tert-butyl-diphenyl-silanyloxy)-ethyl]-carbamic acid tert-butyl ester (640 mg, 1.44 mmol)

was stirred with methyl 4-formylbenzoate (237 mg, 1.44 mmol) in CH$_3$OH (3 ml) at rt for 2 h. NaBH$_4$ (58 mg, 1.44 mmol) was added. The mixture was stirred at rt for 20 min. Several drops of saturated aqueous NH$_4$Cl were added. The mixture was then partitioned between CH$_2$Cl$_2$ and water (20 ml/20 ml). The organic layer was concentrated to give 4-{[(S)-2-tert-butoxycarbonylamino-3-(tert-butyl-diphenyl-silanyloxy)-propylamino]-methyl}-benzoic acid methyl ester (650 mg, 76%).

According to general procedure C, 4-{[(S)-2-tert-butoxy-carbonylamino-3-(tert-butyl-diphenyl-silanyloxy)-propylamino]-methyl}-benzoic acid methyl ester (650 mg, 1.1 mmol) was treated with TFA (2 ml) and CH$_2$Cl$_2$ (2 ml) to give the deprotected amine, which was reacted with 4-BOC piperidone (237 mg, 1.2 mmol) and NaHB(OAc)$_3$ (362 mg, 1.5 mmol) in CH$_2$Cl$_2$ (5 ml) according to general procedure A, to give 4-{(S)-2-(tert-butyl-diphenyl-silanyloxy)-1-[(4-methoxycarbonyl-benzylamino)-methyl]-ethylamino}-piperidine-1-carboxylic acid methyl ester (305 mg, 42% over 2 steps). This diamine was subjected to standard cyclization with triphosgene (68 mg, 0.9 mmol) and pyridine (0.1 ml, 1 mmol) in CH$_2$Cl$_2$ (2 ml) to give 4-[(S)-5-(tert-butyl-diphenyl-silanyloxymethyl)-3-(4-methoxycarbonyl-benzyl)-2-oxo-imidazolidin-1-yl]-piperidine-1-carboxylic acid methyl ester (380 mg, containing impurity).

4-[(S)-5-(tert-Butyl-diphenyl-silanyloxymethyl)-3-(4-methoxycarbonyl-benzyl)-2-oxo-imidazolidin-1-yl]-piperidine-1-carboxylic acid methyl ester (380 mg, containing impurity) was dissolved in THF (3 ml) and treated with TBAF (283 mg, 1.1 mmol) at rt for 1 h. The mixture was then partitioned between CH$_2$Cl$_2$ and water (10 ml/10 ml). The organic layer was dried over Na$_2$SO$_4$ and concentrated. The residue was purified by column chromatography (EtOAc) to give the intermediate alcohol (170 mg). This alcohol was dissolved in DMF (2 ml) and cooled in an ice bath. NaH (22 mg, 0.6 mmol, 60% in oil) was added and the mixture was stirred at rt for 10 min. MeI (0.05 ml, 0.8 mmol) was added and the mixture stirred over night and then concentrated. The residue was purified by column chromatography (EtOAc) to give 4-[(S)-3-(4-methoxycarbonyl-benzyl)-5-methoxymethyl-2-oxo-imidazolidin-1-yl]-piperidine-1-carboxylic acid methyl ester (87 mg, 49%).

According to general procedure C, 4-[(S)-3-(4-methoxycarbonyl-benzyl)-5-methoxymethyl-2-oxo-imidazolidin-1-yl]-piperidine-1-carboxylic acid methyl ester (87 mg, 0.18 mmol) was treated with TFA/CH$_2$Cl$_2$ (2 ml/2 ml). Following general procedure B, the resultant free amine and 2-(3-oxo-butyl)-isoindole-1,3-dione gave the desired product which was then subjected to deprotection according to general procedure D to give 4-{(S)-3-[1-(3-amino-1-methyl-propyl)-piperidin-4-yl]-4-methoxymethyl-2-oxo-imidazolidin-1-ylmethyl}-benzoic acid methyl ester (40 mg).

According to general procedure E, 4-{(S)-3-[1-(3-amino-1-methyl-propyl)-piperidin-4-yl]-4-methoxymethyl-2-oxo-imidazolidin-1-ylmethyl}-benzoic acid methyl ester (40 mg) and 6-chloro-2,4-dimethyl-nicotinic acid gave 4-[(S)-3-(1-{3-[(6-chloro-2,4-dimethyl-pyridine-3-carbonyl)-amino]-1-methyl-propyl}-piperidin-4-yl)-4-methoxymethyl-2-oxo-imidazolidin-1-ylmethyl]-benzoic acid methyl ester (32 mg, 60%).

4-[(S)-3-(1-{3-[(6-Chloro-2,4-dimethyl-pyridine-3-carbonyl)-amino]-1-methyl-propyl}-piperidin-4-yl)-4-methoxymethyl-2-oxo-imidazolidin-1-ylmethyl]-benzoic acid methyl ester (32 mg, 0.045 mmol) was dissolved in CH$_3$OH (1 ml). NaOH (0.05 ml, 10 N, 0.47 mmol) was added and the mixture was heated at 60° C. for 3 h. It was then concentrated to remove CH$_3$OH and water (2 ml) was added. The pH of the solution was adjusted to 6 using 1 N HCl solution. It was then concentrated to dryness and the residue was extracted with CH$_2$Cl$_2$/CH$_3$OH (4/1, 10 ml×3). The combined extracts were concentrated to give COMPOUND 301 as white solid (26 mg, 94%). $^1$H NMR (CD$_3$OD) δ 1.30-1.45 (m, 3H), 1.70-2.80 (m, 1H), 2.85-4.00 (m, 18H, CH$_3$OH signal), 4.10-4.45 (m, 2H), 7.30-7.40 (m, 2H), 7.95-8.00 (m, 2H); ES-MS m/z 586 (M+1).

Example 302

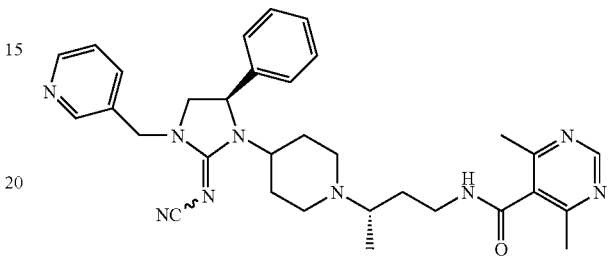

Compound 302

4,6-Dimethyl-pyrimidine-5-carboxylic acid {(S)-3-[4-((R)-2-cyanoimino-5-phenyl-3-pyridin-3-ylmethyl-imidazolidin-1-yl)-piperidin-1-yl]-butyl}-amide To a 0° C. solution of (R)-(−)-2-phenylglycinyl (3.03 g, 22.1 mmol) and NEt$_3$ (4.50 ml, 32.3 mmol) in THF (55 ml) was added Boc$_2$O (4.82 g, 22.1 mmol) and the resulting white suspension was stirred at 0° C. for 1 hour giving crude ((R)-2-hydroxy-1-phenyl-ethyl)-carbamic acid tert-butyl ester as a white powder (4.75 g, 91%) following an acidic work-up.

To a 0° C. solution of the alcohol (4.75 g, 20.0 mmol), phthalimide (3.32 g, 22.6 mmol) and PPh$_3$ (6.30 g, 24.0 mmol) in THF (130 ml) under nitrogen was added dropwise DEAD (3.3 ml, 21.0 mmol). The resulting light yellow solution was stirred at room temperature for 3 hours, and then the solvent was removed under reduced pressure, giving crude [(R)-2-(1,3-dioxo-1,3-dihydro-isoindol-2-yl)-1-phenyl-ethyl]-carbamic acid tert-butyl ester as a mixture with triphenylphosphine oxide.

A solution of the crude phthalimide and hydrazine hydrate (10.0 ml, 177 mmol) in EtOH (200 ml) was stirred at reflux for 1 hour. Once cooled, the mixture was concentrated under reduced pressure. The residue was suspended in 1.5M HCl (200 ml) and washed with CH$_2$Cl$_2$ (50 ml×3). The organic solution was extracted with 4M HCl (50 ml×2). The combined aqueous extracts were made basic with 10M NaOH (100 ml) and extracted with CH$_2$Cl$_2$ (50 ml×4). This organic solution was dried (Na$_2$SO$_4$), filtered and concentrated under reduced pressure. Purification gave ((R)-2-amino-1-phenyl-ethyl)-carbamic acid tert-butyl ester as an off-white solid (2.41 g, 51% over 2 steps).

A solution of 3-pyridinecarboxaldehyde (49 mg, 0.46 mmol) and ((R)-2-amino-1-phenyl-ethyl)-carbamic acid tert-butyl ester (108 mg, 0.457 mmol) in MeOH (4.6 ml) was stirred at room temperature for 1 hour. NaBH$_4$ (17 mg, 0.45 mmol) was added and the mixture stirred at room temperature for 50 minutes. Standard work up gave the crude carbamate. Using general procedure C with the substrate followed by general procedure A with the resulting amine and [(S)-3-(4- oxo-piperidin-1-yl)-butyl]-carbamic acid tert-butyl ester (161 mg, 0.595 mmol) afforded the desired diamine.

Using general procedure C, [3-(4-{1-phenyl-2-[(pyridin-3-ylmethyl)-amino]-ethylamino}-piperidin-1-yl)-butyl]-carbamic acid tert-butyl ester (80 mg, 0.166 mmol) and a mixture of $CH_2Cl_2$ and TFA (1:1, 1 ml) gave the desired amine (46 mg, 73%).

Using general procedure E, the amine above (46 mg, 0.12 mmol) and 4,6-dimethyl-pyrimidine-5-carboxylic acid (18 mg, 0.12 mmol) afforded the corresponding amide (32 mg, 52%).

The amide above (32 mg, 0.06 mmol) and dimethyl cyanoiminothiocarbonate (6 mg, 0.036 mmol) in methanol (1 ml) were heated at 60° C. for 18 h under $N_2$. Standard work-up and purification gave COMPOUND 302 as a cis and trans mixture. $^1H$ NMR ($CDCl_3$) δ 0.90-0.94 (m, 3H), 1.55-1.57 (m, 2H), 1.67-1.88 (m, 3H), 2.36-2.48 (m, 3H), 2.52 (s, 6H), 2.67-2.76 (m, 2H), 2.85-3.05 (m, 1H), 3.20-3.26 (m, 1H), 3.46-3.54 (m, 1H), 3.67-3.85 (m, 2H), 4.09-4.77 (m, 4H), 7.07-7.16 (m, 2H), 7.33-7.35 (m, 4H), 7.65 and 7.58 (two d, 1H, J=7.8 Hz), 7.85-7.91 (m, 1H), 8.46-8.55 (m, 2H), 8.94 and 8.97 (two s, 1H); $^{13}C$ NMR ($CDCl_3$) δ 13.46, 13.78, 22.40, 29.66, 30.10, 31.80, 32.06, 32.16, 32.41, 39.81, 39.89, 43.48, 43.83, 45.38, 46.03, 47.33, 51.85, 52.36, 52.51, 52.66, 53.83, 53.96, 54.75, 55.74, 57.00, 60.20, 60.36, 116.50, 124.01, 124.27, 125.94, 126.58, 128.58, 129.13, 129.27, 129.68, 131.26, 131.34, 133.03, 136.17, 136.35, 141.79, 149.41, 149.76, 150.09, 157.81, 158.48, 160.78, 163.53, 163.65, 166.42; ES-MS m/z 588.5 (M+Na).

Example 303

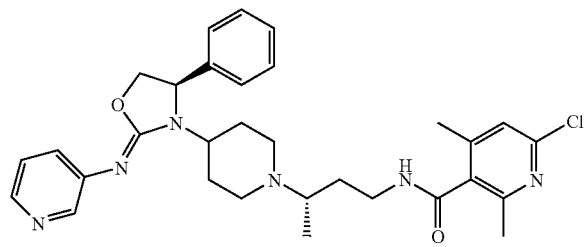

Compound 303

6-Chloro-2,4-dimethyl-N—((S)-3-{4-[(R)-4-phenyl-2-(pyridin-3-ylamino)-oxazolidin-3-yl]-piperidin-1-yl}-butyl)-nicotinamide Following general procedure A, [(S)-3-(4-oxo-piperidin-1-yl)-butyl]-carbamic acid tert-butyl ester (709 mg, 2.63 mmol) and (R)-(−)-2-phenylglycinyl (343 mg, 2.50 mmol) provided {3-[4-(2-hydroxy-1-phenyl-ethylamino)-piperidin-1-yl]-butyl}-carbamic acid tert-butyl ester (600 mg, 61%).

To a solution of above product (170 mg, 0.435 mmol) in $CH_2Cl_2$ (2 ml) was added pyridine-3-isocyanate (54.7 mg, 0.456 mmol) and the mixture was stirred at room temperature overnight. The mixture was concentrated under reduced pressure and purified by column chromatography on silica gel (95:5:1, $CH_2Cl_2$/MeOH/$NH_4OH$) to provide (3-{4-[1-(2-hy-droxy-1-phenyl-ethyl)-3-pyridin-3-yl-ureido]-piperidin-1-yl}-butyl)-carbamic acid tert-butyl ester (222 mg, 100%).

To a solution of above product (222 mg, 0.435 mmol) in $CH_2Cl_2$ (3 ml) and triethylamine (67, mg, 0.663 mmol) was added methanesulfonylchloride (53 mg, 0.464 mmol) and the mixture was stirred at room temperature for 3 h and then heated at reflux for 1 h. The mixture was concentrated under reduced pressure and purified by column chromatography on silica gel (95:5:1, $CH_2Cl_2$/MeOH/$NH_4OH$) to provide (3-{4-[4-phenyl-2-(pyridin-3-ylamino)-oxazolidin-3-yl]-piperidin-1-yl}-butyl)-carbamic acid tert-butyl ester (128 mg, 59%).

Following general procedure C, the above product gave {3-[1-(3-amino-1-methyl-propyl)-piperidin-4-yl]-4-phenyl-oxazolidin-2-ylidene}-pyridin-3-yl-amine (82.1 mg, 80%).

Following general procedure E, the above product (82.1 mg, 0.209 mmol) and 6-chloro-2,4-dimethyl-nicotinic acid HCl salt (48.6 mg, 0.219 mmol) gave COMPOUND 303 (102 mg, 87%). $^1H$ NMR ($CDCl_3$) δ 0.88-1.01 (m, 2H), 0.93 (d, 3H, J=6.6 Hz), 1.42 (d, 1H, J=12.3 Hz), 1.49-1.55 (m, 1H), 1.91 (d, 1H, J=12.0 Hz), 2.20 (t, 1H, J=11.1 Hz), 2.32 (s, 3H), 2.39 (t, 1H, J=11.1 Hz), 2.53 (s, 3H), 2.56 (m, 1H), 2.72-2.81 (m, 2H), 3.14-3.22 (m, 1H), 3.81-3.90 (m, 2H), 4.05 (dd, 1H, J=8.4, 3.9 Hz), 4.24 (dd, 1H, J=8.4, 3.9 Hz), 4.53 (t, 1H, J=8.4 Hz), 7.07 (s, 1H), 7.12-7.16 (m, 1H), 7.26-7.46 (m, 6H), 8.16 (br s, 1H), 8.29 (d, 1H, J=6.0 Hz), 8.33 (br s, 1H); $^{13}C$ NMR ($CDCl_3$) δ 13.57, 19.18, 22.53, 29.11, 31.79, 31.94, 39.84, 43.72, 52.03, 53.11, 58.15, 60.51, 73.92, 122.92, 123.52, 126.45, 128.87, 129.50, 130.59, 133.28, 142.09, 143.19, 144.36, 146.17, 148.23, 150.38, 154.14, 155.75, 167.26; ES-MS m/z 562 (M+H). Anal Calcd. for $C_{31}H_{37}N_6ClO_2 \cdot 0.2CH_2Cl_2$: C, 64.82; H, 6.52; N, 14.54. Found: C, 64.71; H, 6.70; N, 14.59.

Example 304

Cell Fusion Assay

The assay measures the ability of a test compound to inhibit gp120 and CD4/CCR5-dependent cell-cell fusion. The assay uses two cell lines, 1) CHO-tat cell line that expresses the viral gp120 from a R5 using virus (JR-FL) and the HIV tat proteins, 2) P4-CCR5 cell line that expresses human CD4 and CCR5 on the surface and carries a β-galactosidase construct under the control of the retroviral promoter LTR. Once fusion of these two cell lines occurs, the tat protein from the CHO cell line trans-activates the reporter gene β-galactosidase in the P4-CCR5 cell line. In a 96 well format, $1 \times 10^4$ cells of each cell line are plated per well in the presence or absence of test compound. The cells are then incubated at 37° C., 5% $CO_2$ for 18-24 hours. The β-galactosidase activity in each well is measured by the addition of a luminescence substrate (Gal-Screen substrate, Applied Biosystems) and luminescence monitored with a Victor 2 plate reader (Wallac). The ability of test compounds to inhibit fusion is indicated by a decrease in β-galactosidase activity. Results are reported as the concentration of test compound required to inhibit 50% of the β-galactosidase activity in the test controls.

When tested in the assay described above, many compounds of the invention exhibited $IC_{50}$'s in the range of 0.01 nM to 100 nM.

Example 305

Assay for Inhibition of RANTES Binding to HEK293F.CCR5 Cells

For the competition binding studies, a concentration range of antagonist was incubated for 45 minutes at room temperature in binding buffer (50 mM HEPES, 5 mM mgCl$_2$, 1 mM CaCl$_2$, 0.2% BSA pH 7.4) with 8 μg of HEK293F.CCR5 cell membrane and 50 pM $^{125}$I-RANTES (Perkin Elmer, 81400 GBq/mmol) in Milipore GF-B filter plates. Unbound $^{125}$I-RANTES was removed by washing with cold 50 mM HEPES, 0.5 M NaCl pH 7.4. Compounds were tested at a concentration range of 10000-0.6 nM. The 50% inhibitory concentration (IC$_{50}$ value) was defined as the concentration of test compound required to inhibit RANTES binding by 50% relative to untested controls.

When tested in the assay described above, many of the compounds of the invention exhibited IC$_{50}$'s in the range of 1 nM to 500 nM.

Example 306

Assay for Inhibition of HIV-1 Using PBMC and R5

Performed as described in literature (Inhibition of T-tropic HIV strains by selective antagonization of the chemokine receptor CXCR4. 1997—D. Schols, S. Struyf, J. Van Damme, J. A. Esté, G. Henson & E. De Clercq. J. Exp. Med. 186, 1383-1388.)

The method were as follows:

PBMC from healthy donors were isolated by density gradient centrifugation and stimulated with PHA at 1 μg/ml (Sigma Chemical Co., Bornem, Belgium) for 3 days at 37° C. The activated cells (PHA-stimulated blasts) were washed three times with PBS, and viral infections were performed. The cells were seeded in 48-well plates (5×10$^5$ cells per well in 200 uL culture medium) and pre-incubated for 15 min with compounds at different concentrations. Then 500 pg p24 viral Ag/well of CCR5-using viruses was added. The HIV-1 R5 strains BaL, SF-162, ADA, and JR-FL were all obtained through the Medical Research Council AIDS reagent project (Herts, UK).

HIV-infected or mock-infected PHA-stimulated blasts were then further cultured in the presence of 25 U/ml of IL-2 and supernatant was collected at days 8-10, and HIV-1 core antigen in the culture supernatant was analyzed by the p24 Ag ELISA kit from DuPont-Merck Pharmaceutical Co. (Wilmington, Del.).

When tested in the assay described above, many compounds of the invention exhibited IC$_{50}$'s in the range of 0.01 nM to 50 μM.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A compound having the formula 1:

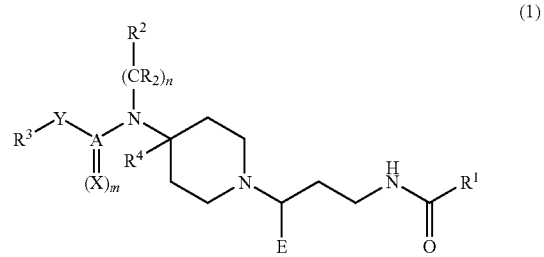

and pharmaceutically acceptable salts thereof, wherein A is carbon or sulfur;

X is oxygen, sulfur, NR$^2$, NOR$^2$, NCN, NSO$_2$R$^2$, NAc, NNO$_2$, CRNO$_2$, NCOR$^2$, C(CN)$_2$ or CRCN, provided X is oxygen if A is sulfur;

Y is a bond, O(CR$_2$)$_p$, S(CR$_2$)$_p$, NR(CR$_2$)$_p$ or (CR$_2$)$_p$ wherein one carbon in (CR$_2$)$_p$ may optionally be substituted and/or replaced with N, O or S;

n and p are independently 0 to 6;

m is 1 to 2, provided m is 1 if A is carbon;

E is H or methyl;

R$^1$ is an optionally substituted aryl or heteroaryl;

R$^2$ is H, an optionally substituted alkyl, a carbocyclic ring, a heterocyclic ring, an aryl, or a heteroaryl; and R$^3$ is H; an optionally substituted alkyl, alkenyl or alkynyl; hydroxy, alkoxy, cyano, amino, amido, carboxyl, CO$_2$R$^2$, S═(O)$_p$R$^2$, CR═N—OR, O(CR$_2$)CN, NR—COR$^2$, SR$^2$; a carbocyclic ring, a heterocyclic ring, an aryl, or a heteroaryl;

R and R$^4$ are independently H, C$_{1-6}$ alkyl, or C$_{3-6}$ cycloalkyl;

wherein in each said optionally substituted alkyl, alkenyl or alkynyl, a carbon may be optionally substituted with halo, N, O, or S, and/or replaced with N, O or S; and each carbocyclic ring, heterocyclic ring, aryl or heteroaryl may be optionally substituted and/or fused with a carbocyclic, aryl, heterocyclic, or heteroaryl ring.

2. The compound of claim 1, wherein R$^1$ is phenyl, pyrimidinyl, pyridinyl, pyridine N-oxide, thienyl, isoxazolyl or pyrazolyl, each of which is optionally substituted by one or more halo, cyano, alkyl, alkoxy, amine, amide, cycloalkyl, heterocyclyl, aryl, heteroaryl, or N-oxide.

3. The compound of claim 1, wherein R$^2$ is H, an optionally substituted alkyl, cycloalkyl, aryl or heteroaryl, each of which is optionally linked to one or more C$_{1-6}$ alkyl, alkoxy, trifluoromethyl, carboxylalkyl, cyano, halo, cycloalkyl, heterocyclyl, aryl, heteroaryl, or N-oxide.

4. The compound of claim 3, wherein R$^2$ is phenyl, pyrimidinyl, pyridinyl, thiazolyl, furanyl, thienyl, or imidazolyl.

5. The compound of claim 1, wherein R$^3$ is H, OH, cyano, NR$_2$, SR, SOR, SO$_2$R, CO$_2$R, CONR$_2$, or an optionally substituted alkyl or alkoxy, wherein R is independently H or C$_{1-6}$ alkyl; or R$^3$ may be a carbocyclic ring, a heterocyclic ring, an aryl, or a heteroaryl, each of which may be optionally substituted with halo, cyano, alkyl, alkoxy, cycloalkyl, heterocyclyl, aryl, heteroaryl, or N-oxide and/or fused with a carbocyclic, aryl, heterocyclic, or heteroaryl ring.

6. The compound of claim 5, wherein R$^3$ is cyclohexyl, tetrahydropyran, morpholine, phenyl optionally fused with a 5-6 membered heterocyclic ring, pyridinyl, thienyl, C$_{1-6}$ straight or branched alkyl, bicyclo[4.2.0]octa-1,3,5-triene, indolyl, benzodioxolyl, dihydrobenzofuranyl, dihydroisobenzofuranyl, benzofuranyl, dihydrobenzodioxinyl, pyrrolidin-2-one, tetrazole, imidazole, dioxolane, or isoxazole.

7. The compound of claim 1, where $R^4$ is hydrogen.

8. The compound of claim 1, wherein n is 1.

9. The compound of claim 1, wherein n=1 and $R^2$ is unsubstituted thiophenyl.

10. The compound of claim 1, wherein $R^1$ is optionally substituted pyridyl.

11. The compound of claim 10, wherein said optional substituents comprise halo.

12. A pharmaceutical composition comprising the compound of claim 1 and a pharmaceutically acceptable carrier.

13. The compound of claim 1, wherein said compound is selected from the group consisting of:

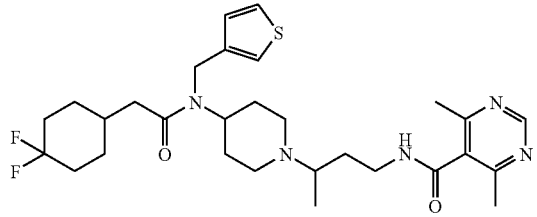

4,6-Dimethylpyrimidine-5-carboxylic acid
[3-(4-{[2-(4,4-difluorocyclohexyl)-acetyl]-
thiophen-3-ylmethylamino}-piperidin-1-yl)-
butyl]-amide

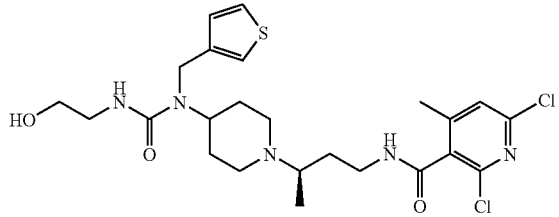

2,6-Dichloro-N-((R)-3-{4-[3-(2-hydroxy-
ethyl)-1-thiophen-3-ylmethyl-ureido]-
piperidin-1-yl}-butyl)-4-methyl-nicotinamide

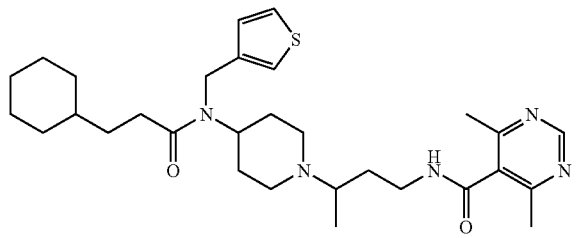

4,6-Dimethyl-pyrimidine-5-carboxylic acid
(3-{4-[(3-cyclohexyl-propionyl)-thiophen-3-
ylmethyl-amino]-piperidin-1-yl}-butyl)-
amide

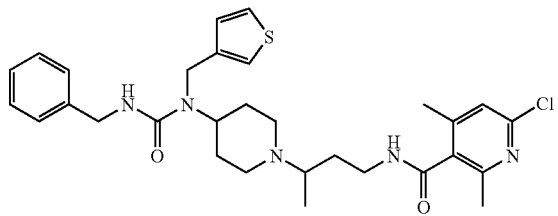

N-{3-[4-(3-Benzyl-1-thiophen-3-ylmethyl-
ureido)-piperidin-1-yl]-butyl}-6-chloro-2,4-
dimethyl-nicotinamide

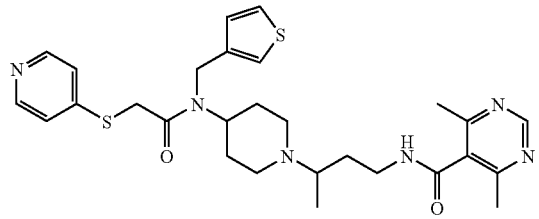

4,6-Dimethyl-pyrimidine-5-carboxylic acid
(3-{4-{[2-(pyridin-4-ylsulfanyl)-acetyl]-
thiophen-3-ylmethyl-amino}-piperidin-1-yl}-
butyl]-amide

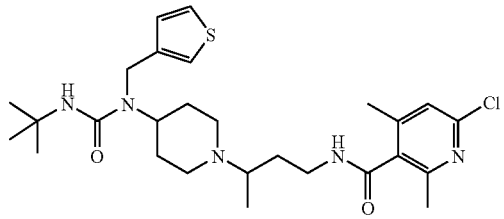

N-{3-[4-(3-tert-Butyl-1-thiophen-3-ylmethyl-
ureido)-piperidin-1-yl]-butyl}-6-chloro-2,4-
dimethyl-nicotinamide

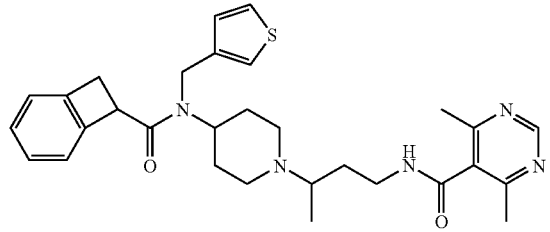

4,6-Dimethyl-pyrimidine-5-carboxylic acid
(3-{4-[(bicyclo[4.2.0]octa-1(6),2,4-triene-7-
carbonyl)-thiophen-3-ylmethyl-amino]-
piperidin-1-yl}-butyl)-amide

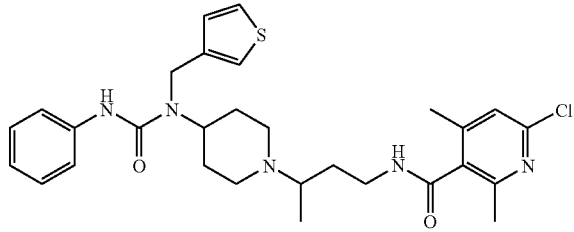

6-Chloro-2,4-dimethyl-N-{3-[4-(3-phenyl-1-
thiophen-3-ylmethyl-ureido)-piperidin-1-yl]-
butyl}-nicotinamide -continued

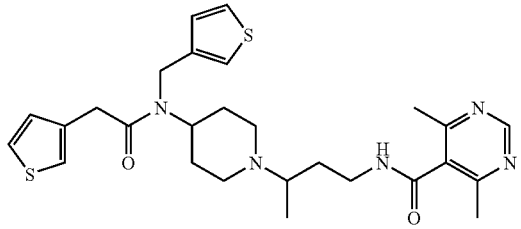

4,6-Dimethyl-pyrimidine-5-carboxylic acid (3-{4-[(2-thiophen-3-yl-acetyl)-thiophen-3-ylmethyl-amino]-piperidin-1-yl}-butyl)-amide

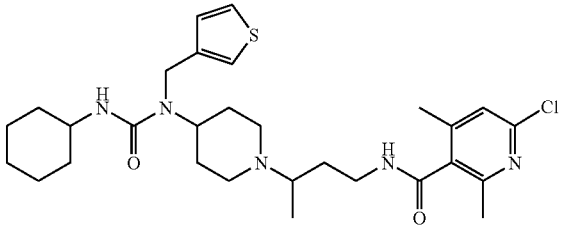

6-Chloro-N-{3-[4-(3-cyclohexyl-1-thiophen-3-ylmethyl-ureido)-piperidin-1-yl]-butyl}-2,4-dimethyl-nicotinamide

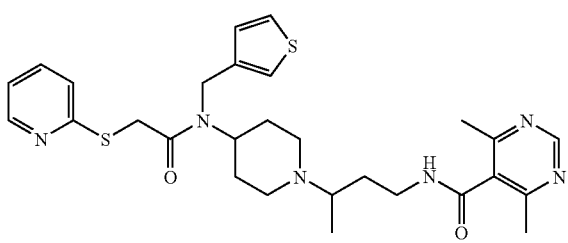

4,6-Dimethyl-pyrimidine-5-carboxylic acid [3-(4-{[2-(pyridin-2-ylsulfanyl)-acetyl]-thiophen-3-ylmethyl-amino}-piperidin-1-yl)-butyl]-amide

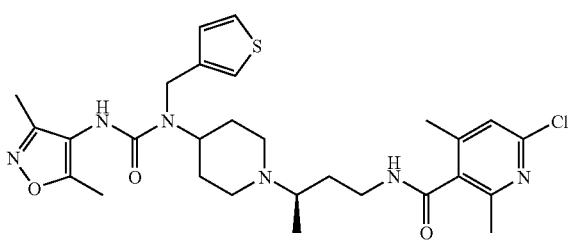

6-Chloro-N-((R)-3-{4-[3-(3,5-dimethyl-isoxazol-4-yl)-1-thiophen-3-ylmethyl-ureido]-piperidin-1-yl}-butyl)-2,4-dimethyl-nicotinamide

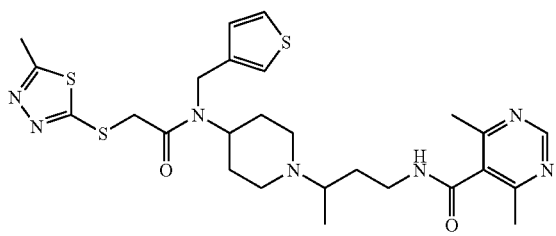

4,6-Dimethyl-pyrimidine-5-carboxylic acid [3-(4-{[2-(5-methyl-[1,3,4]thiadiazol-2-ylsulfanyl)-acetyl]-thiophen-3-ylmethyl-amino}-piperidin-1-yl)-butyl]-amide

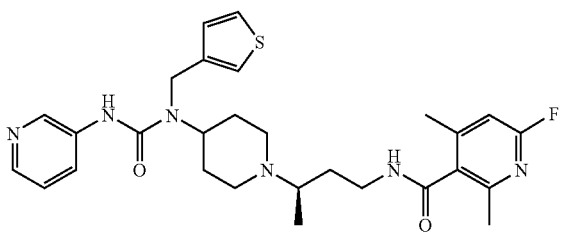

6-Fluoro-2,4-dimethyl-N-{(R)-3-[4-(3-pyridin-3-yl-1-thiophen-3-ylmethyl-ureido)-piperidin-1-yl]-butyl}-nicotinamide

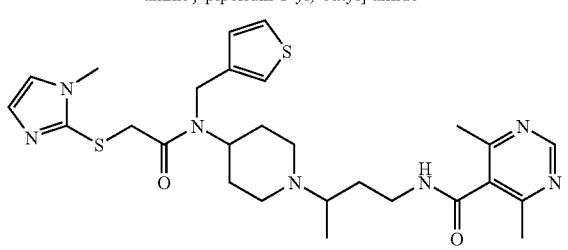

4,6-Dimethyl-pyrimidine-5-carboxylic acid [3-(4-{[2-(1-methyl-1H-imidazol-2-ylsulfanyl)-acetyl]-thiophen-3-ylmethyl-amino}-piperidin-1-yl)-butyl]-amide

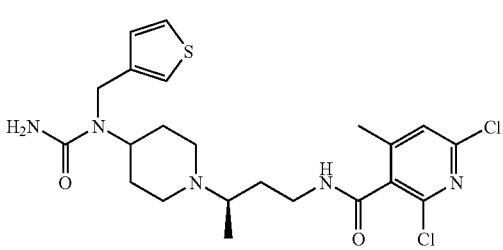

2,6-Dichloro-4-methyl-N-{(R)-3-[4-(1-thiophen-3-ylmethyl-ureido)-piperidin-1-yl]-butyl}-nicotinamide

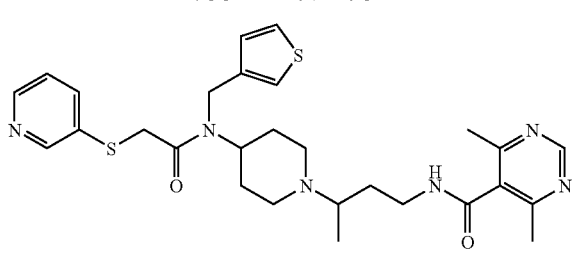

4,6-Dimethyl-pyrimidine-5-carboxylic acid [3-(4-{[2-(pyridin-3-ylsulfanyl)-acetyl]-thiophen-3-ylmethyl-amino}-piperidin-1-yl)-butyl]-amide

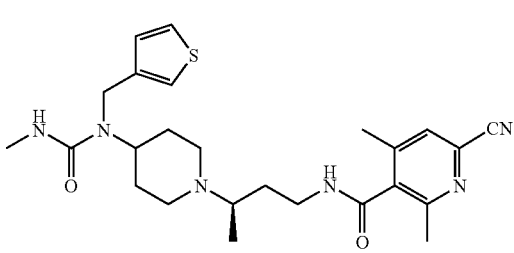

6-Cyano-2,4-dimethyl-N-{(R)-3-[4-(3-methyl-1-thiophen-3-ylmethyl-ureido)-piperidin-1-yl]-butyl}-nicotinamide

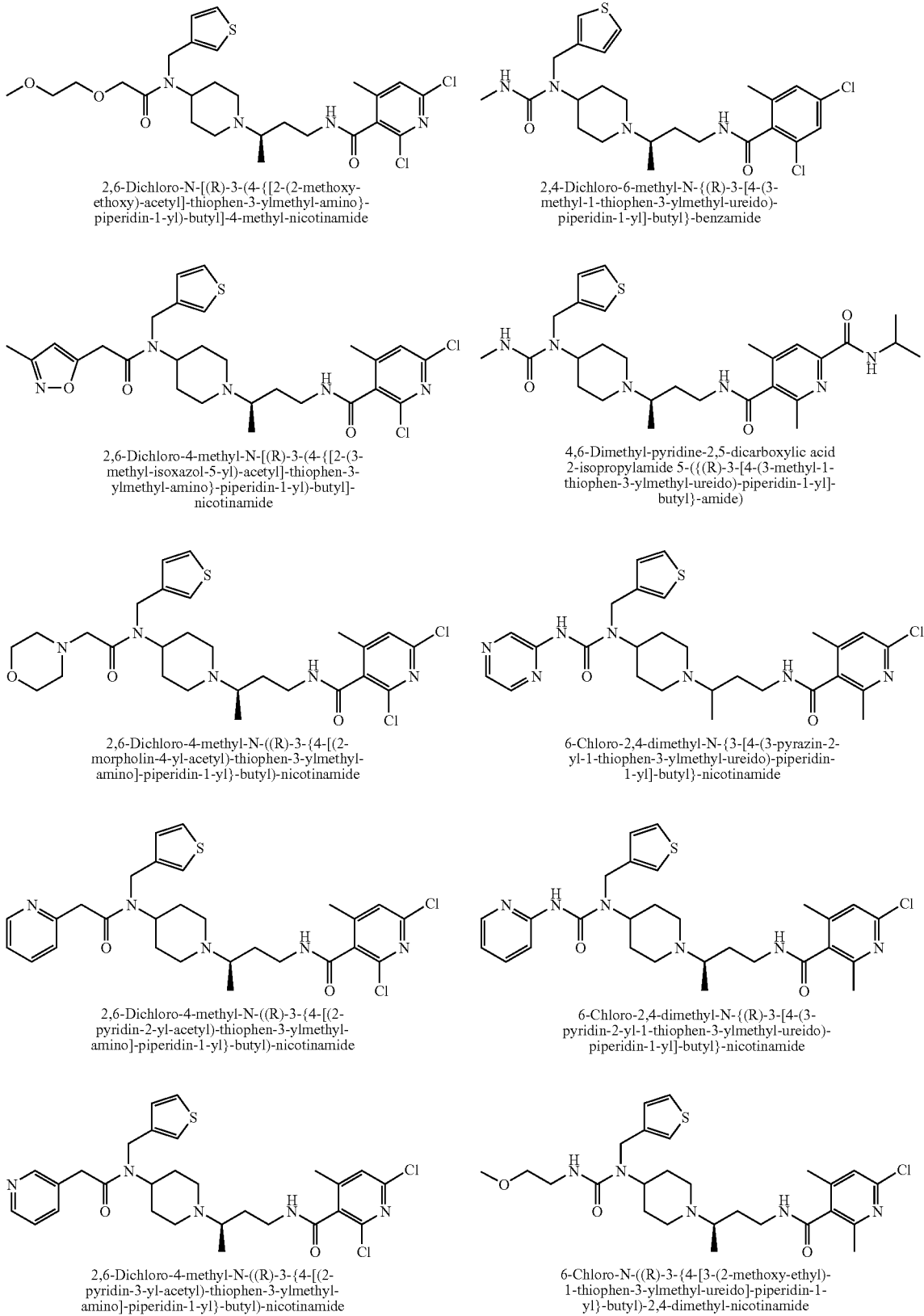

-continued

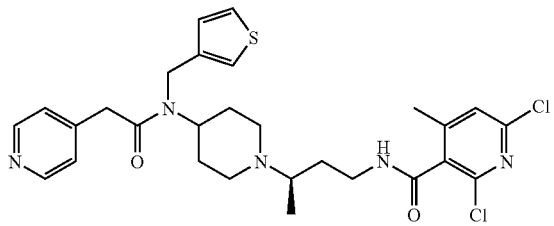

2,6-Dichloro-4-methyl-N-((R)-3-{4-[(2-pyridin-4-yl-acetyl)-thiophen-3-ylmethyl-amino]-piperidin-1-yl}-butyl)-nicotinamide

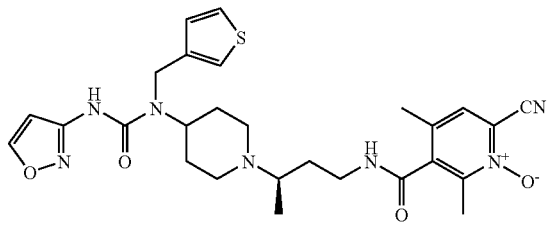

6-Cyano-N-{(R)-3-[4-(3-isoxazol-3-yl-1-thiophen-3-ylmethyl-ureido)-piperidin-1-yl]-butyl}-2,4-dimethyl-1-oxy-nicotinamide

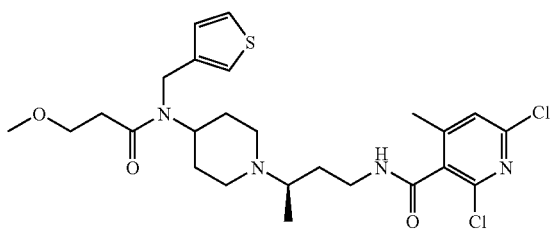

2,6-Dichloro-N-((R)-3-{4-[(3-methoxy-propionyl)-thiophen-3-ylmethyl-amino]-piperidin-1-yl}-butyl)-4-methyl-nicotinamide

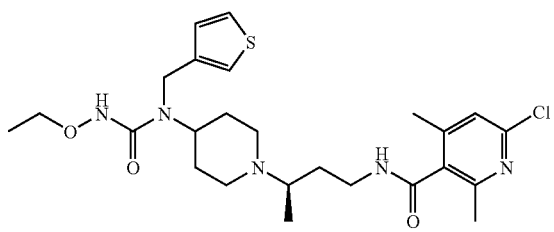

6-Chloro-2,4-dimethyl-N-{(R)-3-[4-(3-ethoxy-1-thiophen-3-ylmethyl-ureido)-piperidin-1-yl]-butyl}-nicotinamide

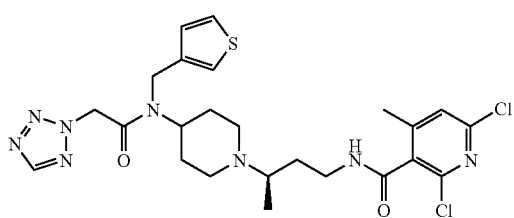

2,6-Dichloro-4-methyl-N-((R)-3-{4-[(2-tetrazol-2-yl-acetyl)-thiophen-3-ylmethyl-amino]-piperidin-1-yl}-butyl)-nicotinamide

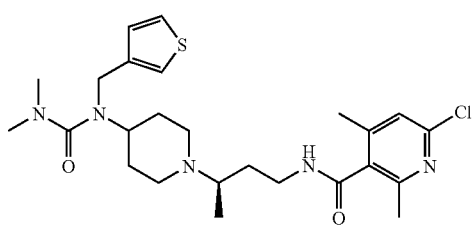

6-Chloro-N-{(R)-3-[4-(3,3-dimethyl-1-thiophen-3-ylmethyl-ureido)-piperidin-1-yl]-butyl}-2,4-dimethyl-nicotinamide

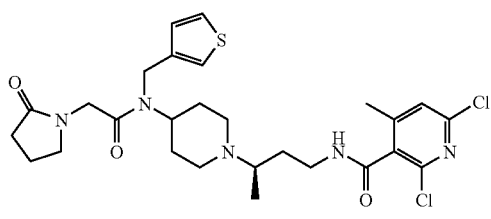

2,6-Dichloro-4-methyl-N-[(R)-3-(4-{[2-(2-oxo-pyrrolidin-1-yl)-acetyl]-thiophen-3-ylmethyl-amino}-piperidin-1-yl)-butyl]-nicotinamide

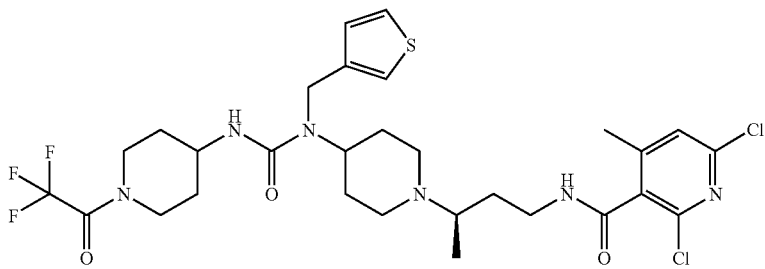

2,6-Dichloro-4-methyl-N-[(R)-3-(4-{1-thiophen-3-ylmethyl-3-[1-(2,2,2-trifluoro-acetyl)-piperidin-4-yl]-ureido}-piperidin-1-yl)-butyl]-nicotinamide

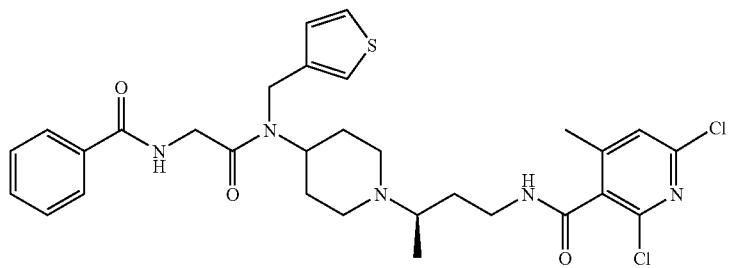

N-((R)-3-{4-[(2-Benzoylamino-acetyl)-
thiophen-3-ylmethyl-amino]-piperidin-1-yl}-
butyl)-2,6-dichloro-4-methyl-nicotinamide

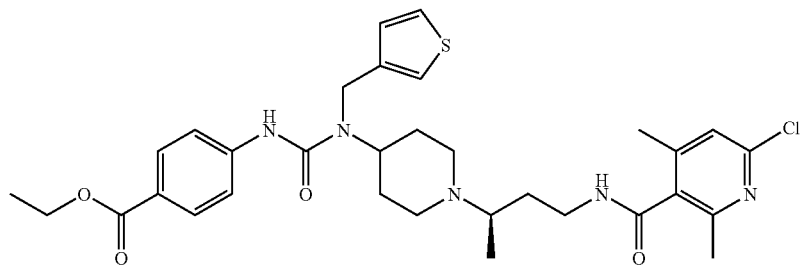

4-[3-(1-{(R)-3-[(6-Chloro-2,4-dimethyl-
pyridine-3-carbonyl)-amino]-1-methyl-
propyl}-piperidin-4-yl)-3-thiophen-3-
ylmethyl-ureido]-benzoic acid ethyl ester

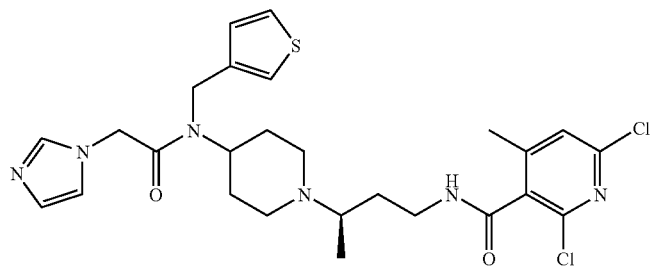

2,6-Dichloro-N-((R)-3-{4-[(2-imidazol-1-yl-
acetyl)-thiophen-3-ylmethyl-amino]-
piperidin-1-yl}-butyl)-4-methyl-nicotinamide

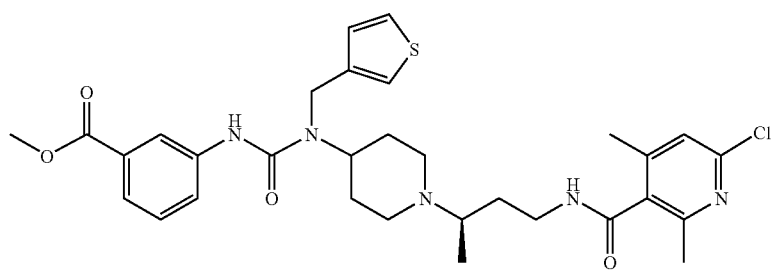

3-[3-(1-{(R)-3-[(6-Chloro-2,4-dimethyl-
pyridine-3-carbonyl)-amino]-1-methyl-
propyl}-piperidin-4-yl)-3-thiophen-3-
ylmethyl-ureido]-benzoic acid methyl ester

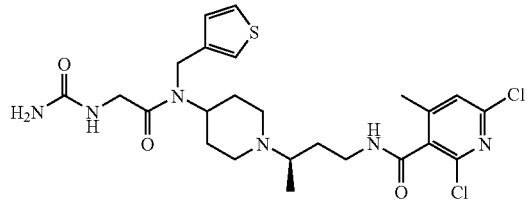

2,6-Dichloro-4-methyl-N-((R)-3-{4-
[thiophen-3-ylmethyl-(2-ureido-acetyl)-
amino]-piperidin-1-yl}-butyl)-nicotinamide

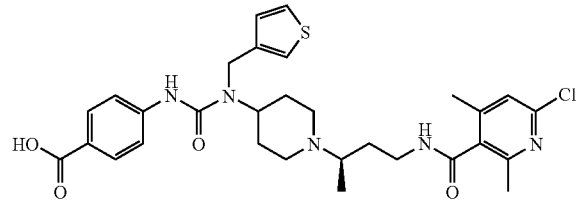

4-[3-(1-{(R)-3-[(6-chloro-2,4-dimethyl-
pyridine-3-carbonyl)-amino]-1-methyl-
propyl}-piperidin-4-yl)-3-thiophen-3-
ylmethyl-ureido]-benzoic acid -continued

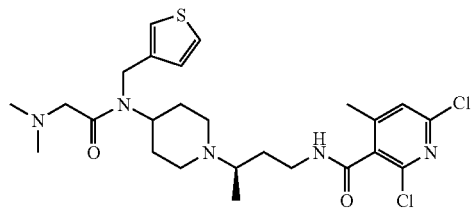

2,6-Dichloro-N-((R)-3-{4-[(2-dimethylamino-acetyl)-thiophen-3-ylmethyl-amino]-piperidin-1-yl}-butyl)-4-methyl-nicotinamide

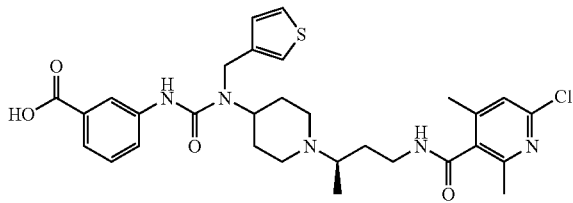

3-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureido]-benzoic acid

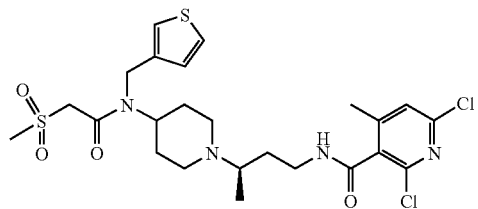

2,6-Dichloro-N-((R)-3-{4-[(2-methanesulfonyl-acetyl)-thiophen-3-ylmethyl-amino]-piperidin-1-yl}-butyl)-4-methyl-nicotinamide

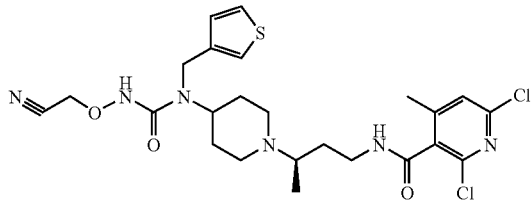

2,6-Dichloro-4-methyl-N-{(R)-3-[4-(3-(cyanomethoxy)-1-thiophen-3-ylmethyl-ureido)-piperidin-1-yl]-butyl}-nicotinamide

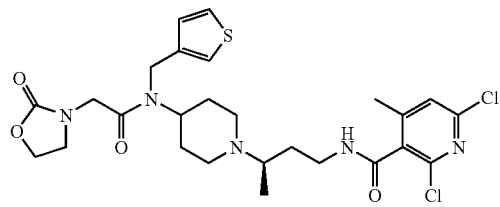

2,6-Dichloro-4-methyl-N-[(R)-3-(4-{[2-(2-oxo-oxazolidin-3-yl)-acetyl]-thiophen-3-ylmethyl-amino}-piperidin-1-yl)-butyl]-nicotinamide

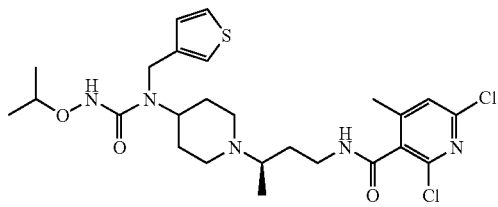

2,6-Dichloro-N-{(R)-3-[4-(3-isopropoxy-1-thiophen-3-ylmethyl-ureido)-piperidin-1-yl]-butyl}-4-methyl-nicotinamide

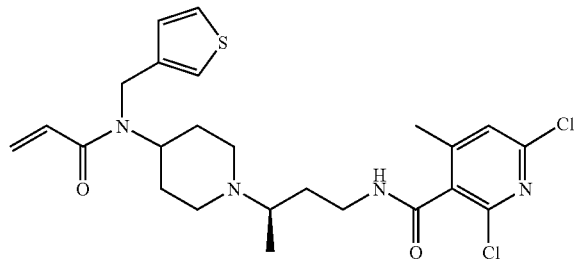

N-{(R)-3-[4-(Acryloyl-thiophen-3-ylmethyl-amino)-piperidin-1-yl]-butyl}-2,6-dichloro-4-methyl-nicotinamide

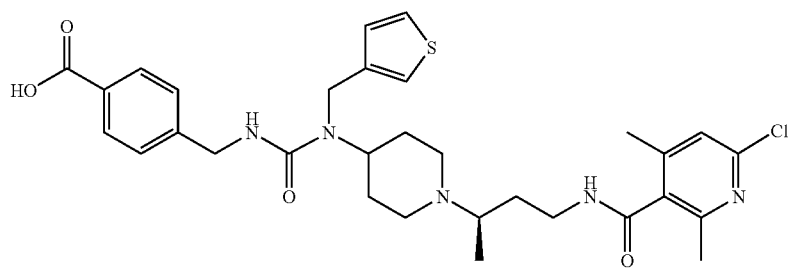

4-[3-(1-{(R)-3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid

353

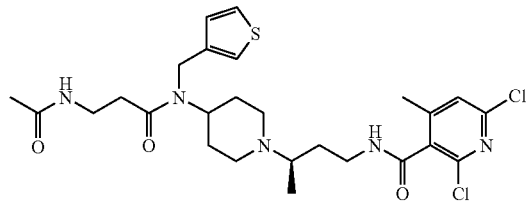

N-((R)-3-{4-[(3-Acetylamino-propionyl)-thiophen-3-ylmethyl-amino]-piperidin-1-yl}-butyl)-2,6-dichloro-4-methyl-nicotinamide

354

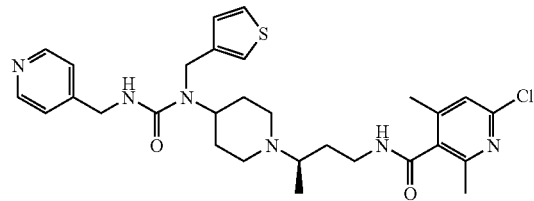

6-Chloro-2,4-dimethyl-N-{(R)-3-[4-(3-pyridin-4-ylmethyl-1-thiophen-3-ylmethyl-ureido)-piperidin-1-yl]-butyl}-nicotinamide

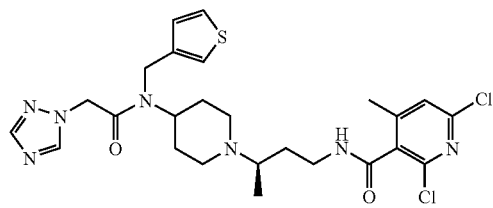

2,6-Dichloro-4-methyl-N-((R)-3-{4-[thiophen-3-ylmethyl-(2-[1,2,4]triazol-1-yl-acetyl)-amino]-piperidin-1-yl}-butyl)-nicotinamide

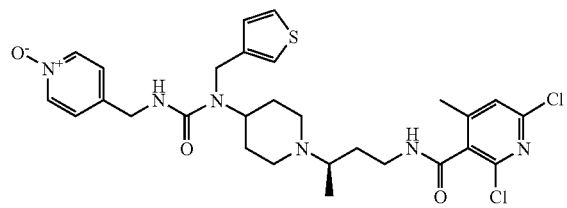

6-Chloro-2,4-dimethyl-N-((R)-3-{4-[3-(1-oxy-pyridin-4-ylmethyl)-1-thiophen-3-ylmethyl-ureido]-piperidin-1-yl}-butyl)-nicotinamide

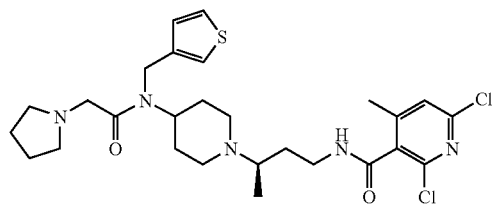

2,6-Dichloro-4-methyl-N-((R)-3-{4-[(2-pyrrolidin-1-yl-acetyl)-thiophen-3-ylmethyl-amino]-piperidin-1-yl}-butyl)-nicotinamide

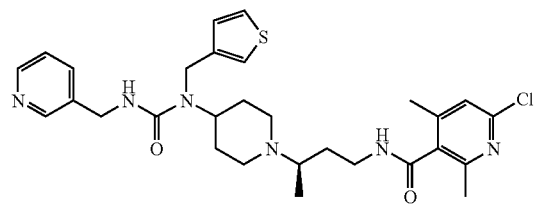

6-Chloro-2,4-dimethyl-N-{(R)-3-[4-(3-pyridin-3-ylmethyl-1-thiophen-3-ylmethyl-ureido)-piperidin-1-yl]-butyl}-nicotinamide

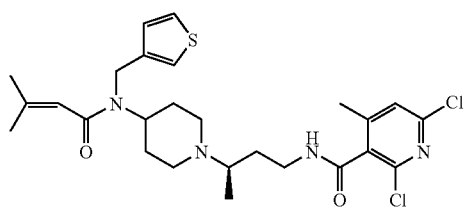

2,6-Dichloro-4-methyl-N-((R)-3-{4-[(3-methyl-but-2-enoyl)-thiophen-3-ylmethyl-amino]-piperidin-1-yl}-butyl)-nicotinamide

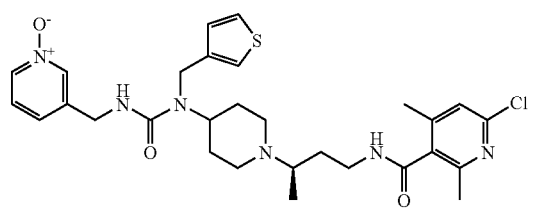

6-Chloro-2,4-dimethyl-N-((R)-3-{4-[3-(1-oxy-pyridin-3-ylmethyl)-1-thiophen-3-ylmethyl-ureido]-piperidin-1-yl}-butyl)-nicotinamide

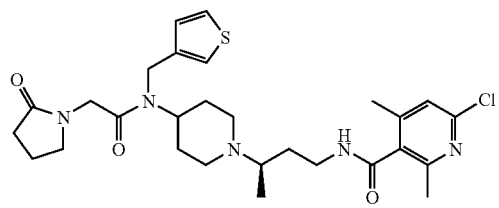

6-Chloro-2,4-dimethyl-N-[(R)-3-(4-{[2-(2-oxy-pyrrolidin-1-yl)-acetyl]-thiophen-3-ylmethyl-amino}-piperidin-1-yl)-butyl]-nicotinamide

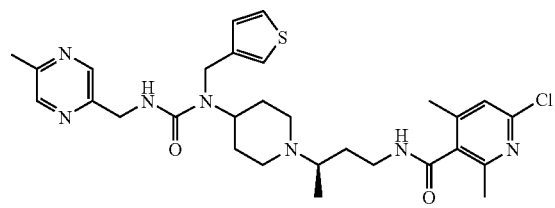

6-Chloro-2,4-dimethyl-N-((R)-3-{4-[3-(5-methyl-pyrazin-2-ylmethyl)-1-thiophen-3-ylmethyl-ureido]-piperidin-1-yl}-butyl)-nicotinamide

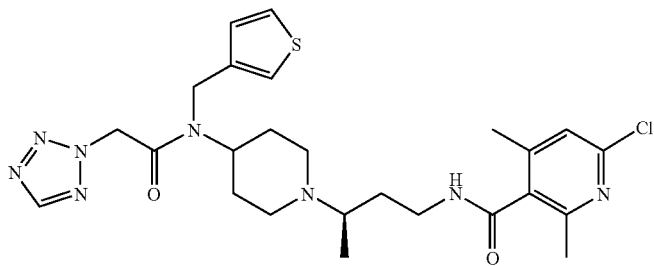

6-Chloro-2,4-dimethyl-N-((R)-3-{4-[(2-tetrazol-2-yl-acetyl)-thiophen-3-ylmethyl-amino]-piperidin-1-yl}-butyl)-nicotinamide

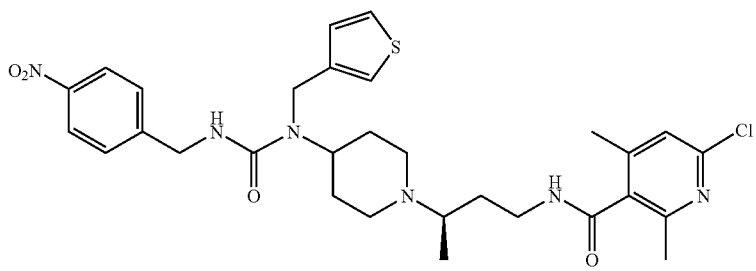

6-Chloro-2,4-dimethyl-N-((R)-3-{4-[3-(4-nitro-benzyl)-1-thiophen-3-ylmethyl-ureido]-piperidin-1-yl}-butyl)-nicotinamide

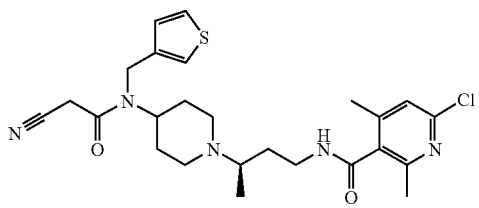

6-Chloro-N-((R)-3-{4-[(2-cyano-acetyl)-thiophen-3-ylmethyl-amino]-piperidin-1-yl}-butyl)-2,4-dimethyl-nicotinamide

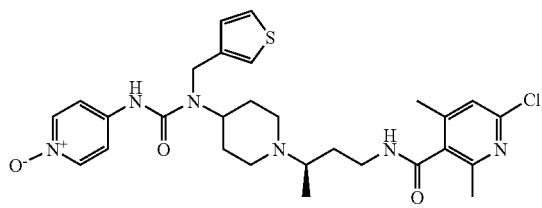

6-Chloro-2,4-dimethyl-N-((R)-3-{4-[3-(1-oxy-pyridin-4-yl)-1-thiophen-3-ylmethyl-ureido]-piperidin-1-yl}-butyl)-nicotinamide

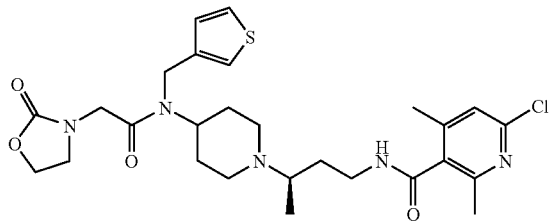

6-Chloro-2,4-dimethyl-N-[(R)-3-(4-{[2-(2-oxy-oxazolidin-3-yl)-acetyl]-thiophen-3-ylmethyl-amino}-piperidin-1-yl)-butyl]-nicotinamide

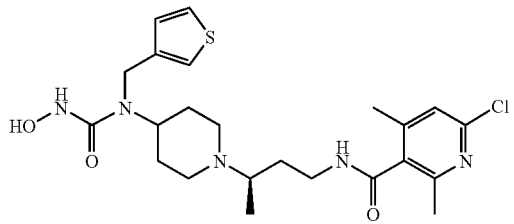

6-Chloro-N-{(R)-3-[4-(3-hydroxy-1-thiophen-3-ylmethyl-ureido)-piperidin-1-yl]-butyl}-2,4-dimethyl-nicotinamide

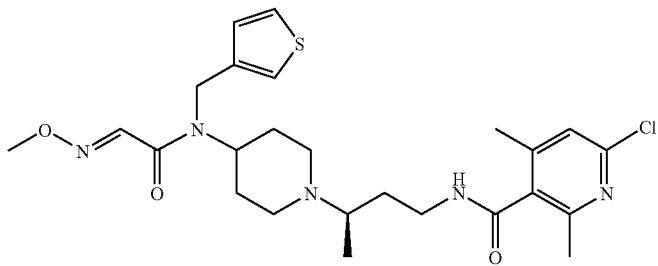

6-Chloro-N-((R)-3-{4-[(2-methoxyimino-acetyl)-thiophen-3-ylmethyl-amino]-piperidin-1-yl}-butyl)-2,4-dimethyl-nicotinamide

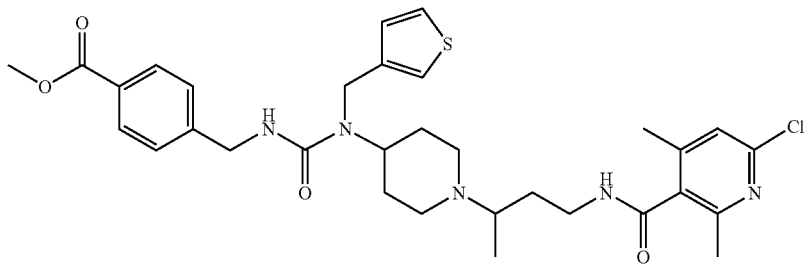

4-[3-(1-{3-[(6-Chloro-2,4-dimethyl-pyridine-3-carbonyl)-amino]-1-methyl-propyl}-piperidin-4-yl)-3-thiophen-3-ylmethyl-ureidomethyl]-benzoic acid methyl ester

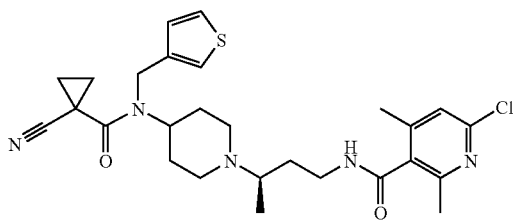

6-Chloro-N-((R)-3-{4-[(1-cyano-cyclopropanecarbonyl)-thiophen-3-ylmethyl-amino]-piperidin-1-yl}-butyl)-2,4-dimethyl-nicotinamide

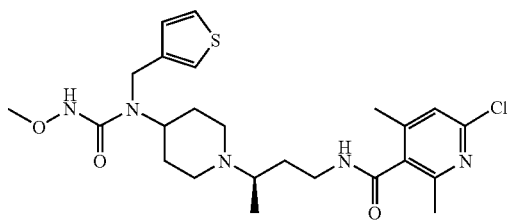

6-Chloro-N-{(R)-3-[4-(3-methoxy-1-thiophen-3-ylmethyl-ureido)-piperidin-1-yl]-butyl}-2,4-dimethyl-nicotinamide

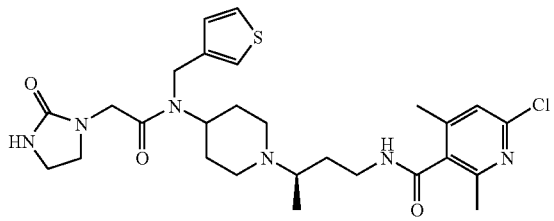

6-Chloro-2,4-dimethyl-N-[(R)-3-(4-{[2-(2-oxo-imidazolidin-1-yl)-acetyl]-thiophen-3-ylmethyl-amino}-piperidin-1-yl)-butyl]-nicotinamide

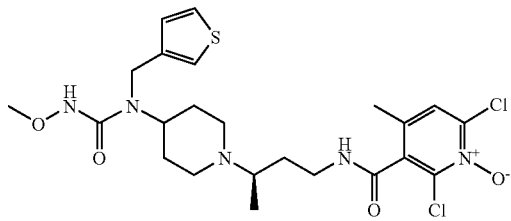

2,6-Dichloro-4-methyl-N-{(R)-3-[4-(3-methoxy-1-thiophen-3-ylmethyl-ureido)-piperidin-1-yl]-butyl}-nicotinamide-N-oxide

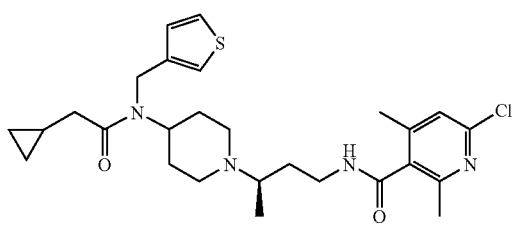

6-Chloro-N-((R)-3-{4-[(2-cyclopropyl-acetyl)-thiophen-3-ylmethyl-amino]-piperidin-1-yl}-butyl)-2,4-dimethyl-nicotinamide

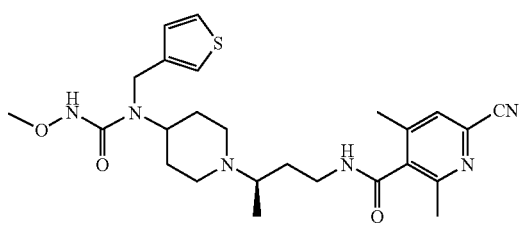

6-Cyano-2,4-dimethyl-N-{(R)-3-[4-(3-methoxy-1-thiophen-3-ylmethyl-ureido)-piperidin-1-yl]-butyl}-nicotinamide

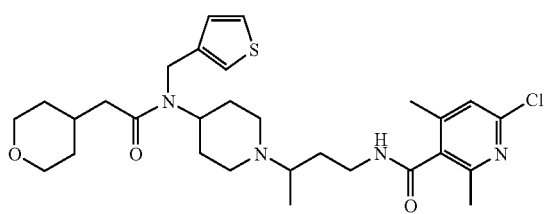

N-(3-{4-[(Thiophen-3-ylmethyl)-2-(tetrahydro-pyran-4-yl)-acetyl-amino]-piperidin-1-yl}-butyl)-6-chloro-2,4-dimethyl-nicotinamide

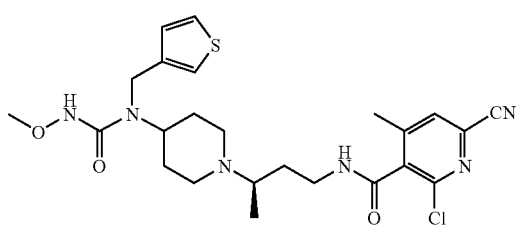

2-Chloro-6-cyano-4-methyl-N-{(R)-3-[4-(3-methoxy-1-thiophen-3-ylmethyl-ureido)-piperidin-1-yl]-butyl}-nicotinamide

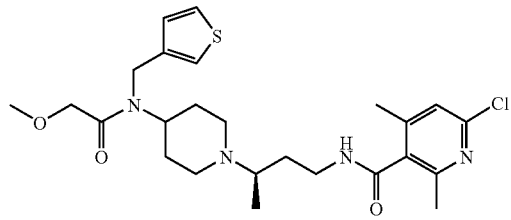

6-Chloro-N-((R)-3-{4-[2-methoxy-acetyl)-
thiophen-3-ylmethyl-amino]-piperidin-1-yl}-
butyl)-2,4-dimethyl-nicotinamide

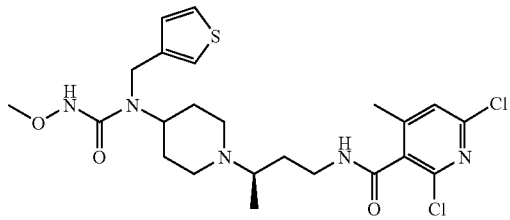

2,6-Dichloro-N-{(R)-3-[4-(3-methoxy-1-
thiophen-3-ylmethyl-ureido)-piperidin-1-yl]-
butyl}-4-methyl-nicotinamide

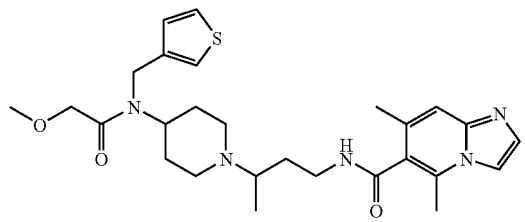

5,7-Dimethyl-imidazo[1,2-a]pyridine-6-
carboxylic acid (3-{4-[(2-methoxy-acetyl)-
thiophen-3-ylmethyl-amino]-piperidin-1-yl}-
butyl)-amide

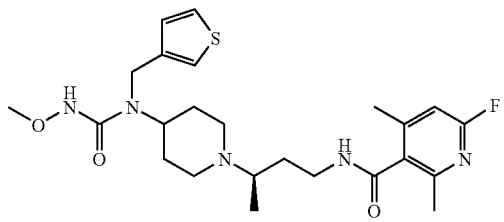

2,4-Dimethyl-6-fluoro-N-{(R)-3-[4-(3-
methoxy-1-thiophen-3-ylmethyl-ureido)-
piperidin-1-yl]-butyl}-nicotinamide

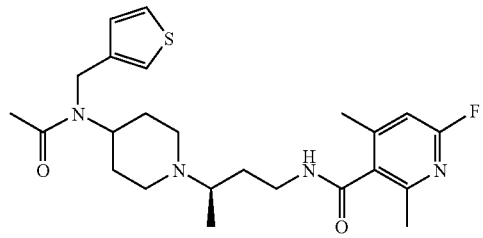

N-{(R)-3-[4-(Acetyl-thiophen-3-ylmethyl-
amino)-piperidin-1-yl]-butyl}-6-fluoro-2,4-
dimethyl-nicotinamide

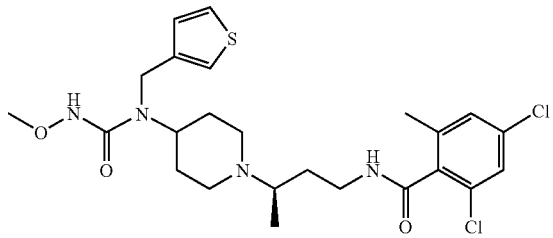

2,6-Dichloro-4-methyl-N-{(R)-3-[4-(3-
methoxy-1-thiophen-3-ylmethyl-ureido)-
piperidin-1-yl]-butyl}-benzamide

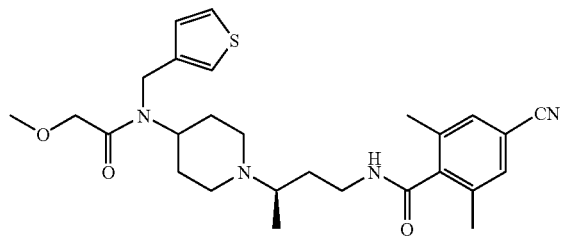

4-Cyano-N-((R)-3-{4-[(2-methoxy-acetyl)-
thiophen-3-ylmethyl-amino]-piperidin-1-yl}-
butyl)-2,6-dimethyl-benzamide

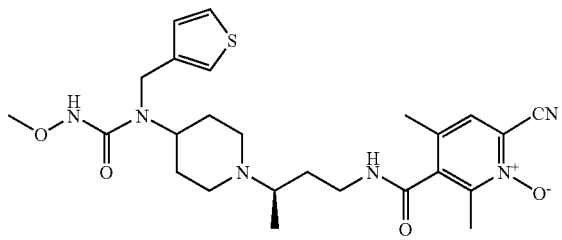

6-Cyano-2,4-dimethyl-N-{(R)-3-[4-(3-
methoxy-1-thiophen-3-ylmethyl-ureido)-
piperidin-1-yl]-butyl}-nicotinamide-N-oxide

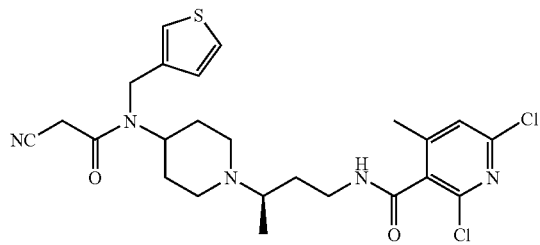

2,6-Dichloro-N-((R)-3-{4-[(2-cyano-acetyl)-
thiophen-3-ylmethyl-amino]-piperidin-1-yl}-
butyl)-4-methyl-nicotinamide

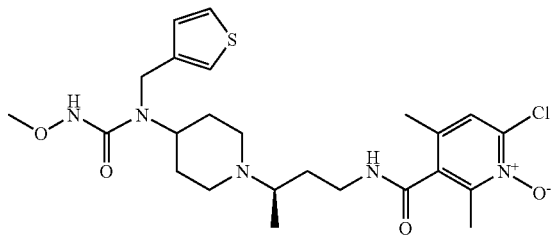

6-Chloro-2,4-dimethyl-N-{(R)-3-[4-(3-
methoxy-1-thiophen-3-ylmethyl-ureido)-
piperidin-1-yl]-butyl}-nicotinamide-N-oxide

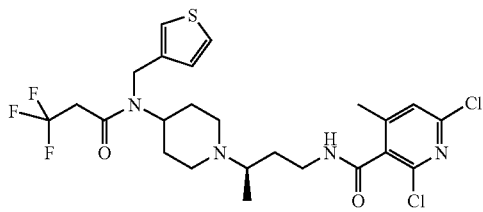

2,6-Dichloro-4-methyl-N-((R)-3-{4-
[thiophen-3-ylmethyl-(3,3,3-trifluoro-
propionyl)-amino]-piperidin-1-yl}-butyl)-
nicotinamide

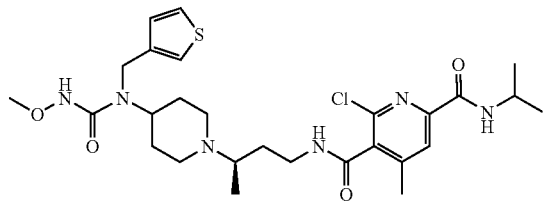

6-Chloro-4-methyl-pyridine-2,5-dicarboxylic
acid 2-isopropylamide 5-({(R)-3-[4-(3-
methoxy-1-thiophen-3-ylmethyl-ureido)-
piperidin-1-yl]-butyl}-amide)

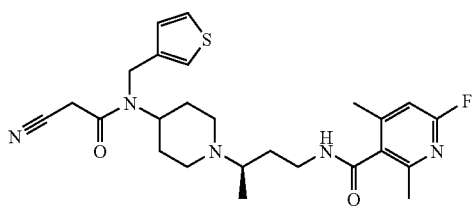

N-((R)-3-{4-[(2-Cyano-acetyl)-thiophen-3-
ylmethyl-amino]-piperidin-1-yl}-butyl)-6-
fluoro-2,4-dimethyl-nicotinamide

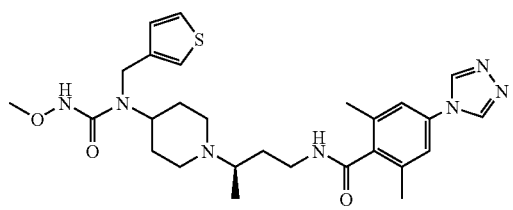

N-{(R)-3-[4-(3-methoxy-1-thiophen-3-
ylmethyl-ureido)-piperidin-1-yl]-butyl}-2,6-
dimethyl-4-1,2,4-triazol-4-yl-benazmide

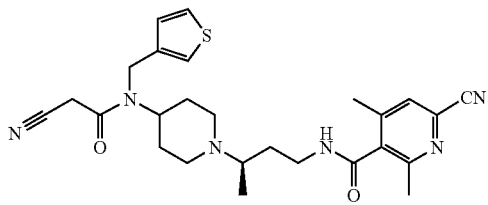

6-Cyano-N-((R)-3-{4-[(2-cyano-acetyl)-
thiophen-3-ylmethyl-amino]-piperidin-1-yl}-
butyl)-2,4-dimethyl-nicotinamide

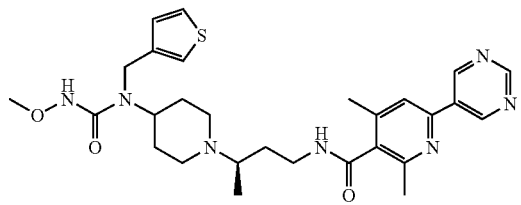

N-{(R)-3-[4-(3-methoxy-1-thiophen-3-
ylmethyl-ureido)-piperidin-1-yl]-butyl}-2,4-
dimethyl-6-pyrimidin-5-yl-nicotinamide

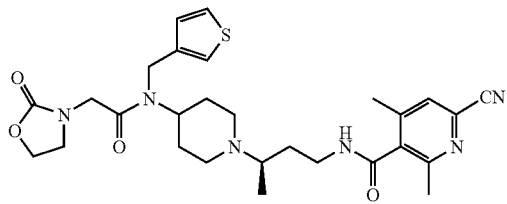

6-Cyano-2,4-dimethyl-N-[(R)-3-(4-{[2-(2-
oxo-oxazolidin-3-yl)-acetyl]-thiophen-3-
ylmethyl-amino}-piperidin-1-yl)-butyl]-
nicotinamide

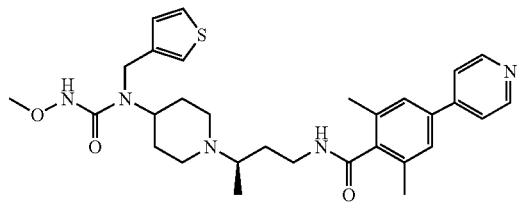

N-{(R)-3-[4-(3-methoxyl-1-thiophen-3-
ylmethyl-ureido)-piperidin-1-yl]-butyl}-2,6-
dimethyl-4-pyridin-4-yl-benzamide

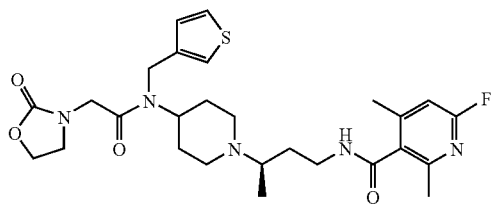

6-Fluoro-2,4-dimethyl-N-[(R)-3-(4-{[2-(2-
oxo-oxazolidin-3-yl)-acetyl]-thiophen-3-
ylmethyl-amino}-piperidin-1-yl)-butyl]-
nicotinamide

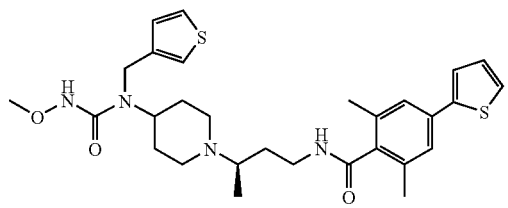

N-{(R)-3-[4-(3-methoxyl-1-thiophen-3-
ylmethyl-ureido)-piperidin-1-yl]-butyl}-2,6-
dimethyl-4-thiophen-2-yl-benzamide

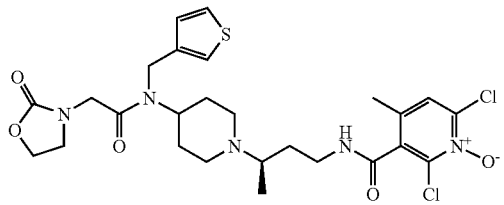

2,6-Dichloro-4-methyl-N-[(R)-3-(4-{[2-(2-oxo-oxazolidin-3-yl)-acetyl]-thiophen-3-ylmethyl-amino}-piperidin-1-yl)-butyl]-nicotinamide-N-oxide

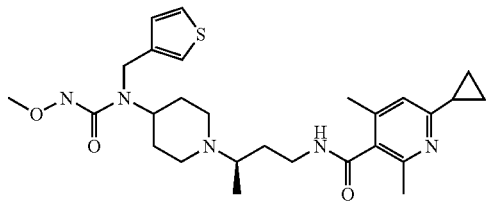

6-Cyclopropyl-N-{(R)-3-[4-(3-ethyl-1-thiophen-3-ylmethyl-ureido)-piperidin-1-yl]-butyl}-2,4-dimethyl-nicotinamide

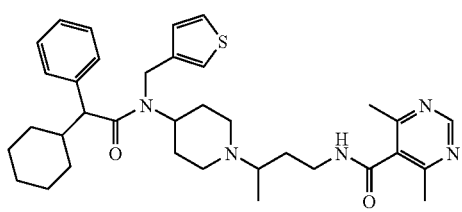

4,6-Dimethyl-pyrimidine-5-carboxylic acid (3-{4-[(2-cyclohexyl-2-phenyl-acetyl)-thiophen-3-ylmethyl-amino]-piperidin-1-yl}-butyl)-amide

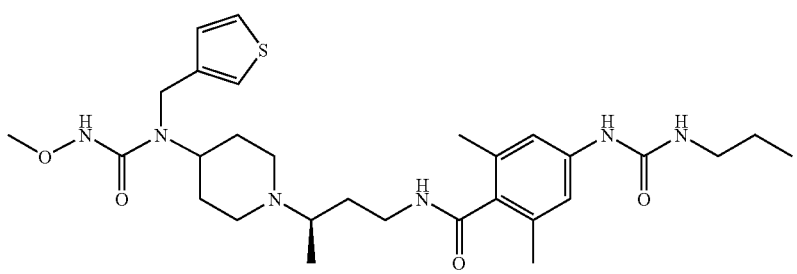

2,6-Dimethyl-N-{(R)-3-[4-(3-methoxy-1-thiophen-3-ylmethyl-ureido)-piperidin-1-yl]-butyl}-4-(3-propyl-ureido)-benzamide

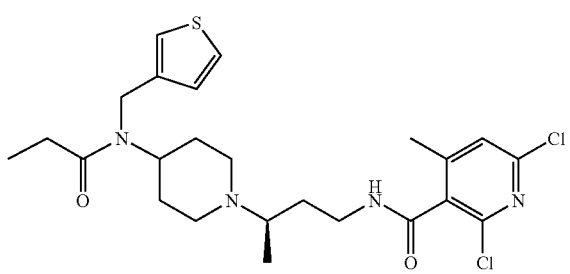

2,6-Dichloro-4-methyl-N-{(R)-3-[4-(propionyl-thiophen-3-ylmethyl-amino)-piperidin-1-yl]-butyl}-nicotinamide

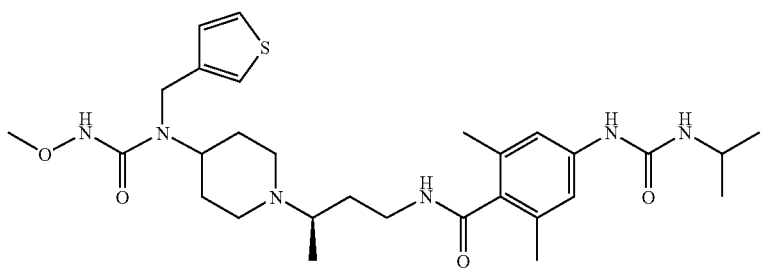

4-(3-Isopropyl-ureido)-2,6-dimethyl-N-{(R)-3-[4-(3-methoxy-1-thiophen-3-ylmethyl-ureido)-piperidin-1-yl]-butyl}-benzamide

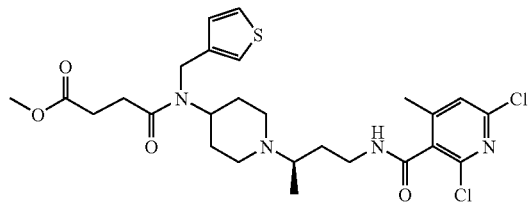

N-(1-{(R)-3-[(2,6-Dichloro-4-methyl-pyridine-3-carbonyl)-amino]-1-methyl-propyl}-piperidin-4-yl)-N-thiophen-3-ylmethyl-succinamic acid methyl ester

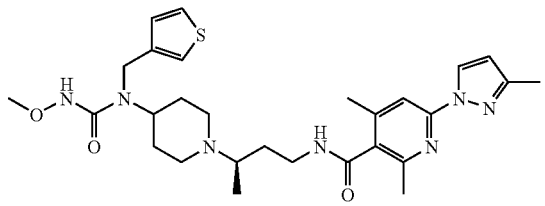

N-{(R)-3-[4-(3-methoxy-1-thiophen-3-ylmethyl-ureido)-piperidin-1-yl]-butyl}-2,4-dimethyl-6-(3-methyl-pyrazol-1-yl)-nicotinamide

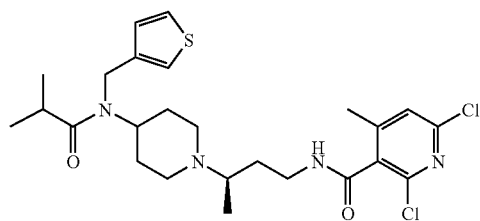

2,6-Dichloro-N-{(R)-3-[4-(isobutyryl-thiophen-3-ylmethyl-amino)-piperidin-1-yl]-butyl}-4-methyl-nicotinamide

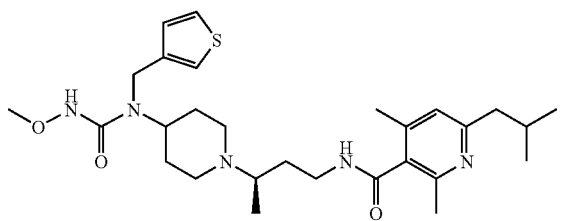

N-{(R)-3-[4-(3-methoxy-1-thiophen-3-ylmethyl-ureido)-piperidin-1-yl]-butyl}-6-isobutyl-2,4-dimethyl-nicotinamide

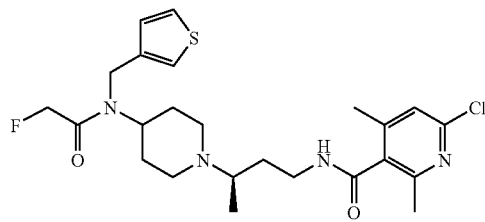

6-Chloro-N-((R)-3-{4-[(2-fluoro-acetyl)-thiophen-3-ylmethyl-amino]-piperidin-1-yl}-butyl)-2,4-dimethyl-nicotinamide

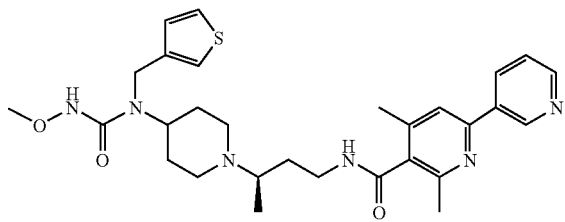

4,6-Dimethyl-[2,3']bipyridinyl-5-carboxylic acid {(R)-3-[4-(3-methoxyl-1-thiophen-3-ylmethyl-ureido)-piperidin-1-yl]-butyl}-amide

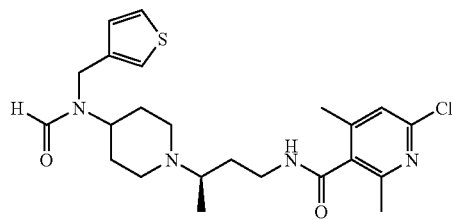

6-Chloro-N-{(R)-3-[4-(formyl-thiophen-3-ylmethyl-amino)-piperidin-1-yl]-butyl}-2,4-dimethyl-nicotinamide

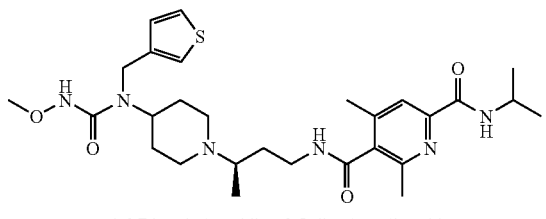

4,6-Dimethyl-pyridine-2,5-dicarboxylic acid 2-isopropylamide 5-({(R)-3-[4-(3-methoxy-1-thiophen-3-ylmethyl-ureido)-piperidin-1-yl]-butyl}-amide)

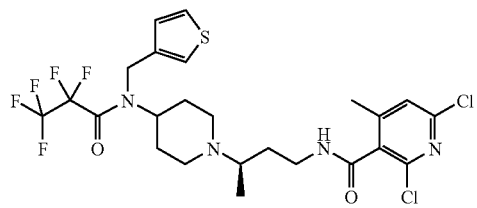

2,6-Dichloro-4-methyl-N-((R)-3-{4-[(2,2,3,3,3-pentafluoro-propionyl)-thiophen-3-ylmethyl-amino]-piperidin-1-yl}-butyl)-nicotinamide

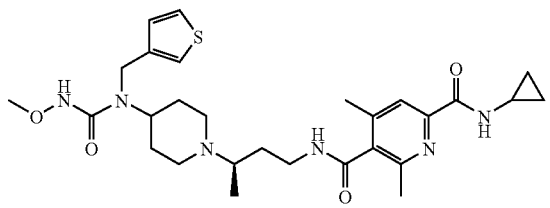

4,6-Dimethyl-pyridine-2,5-dicarboxylic acid 2-cyclopropylamide 5-({(R)-3-[4-(3-methoxy-1-thiophen-3-ylmethyl-ureido)-piperidin-1-yl]-butyl}-amide)

-continued

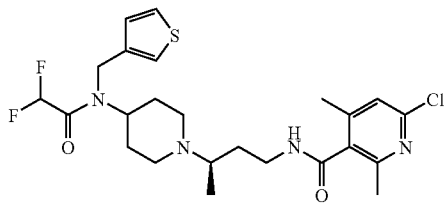

6-Chloro-N-((R)-3-{4-[(2,2-difluoro-acetyl)-
thiophen-3-ylmethyl-amino]-piperidin-1-yl}-
butyl)-2,4-dimethyl-nicotinamide

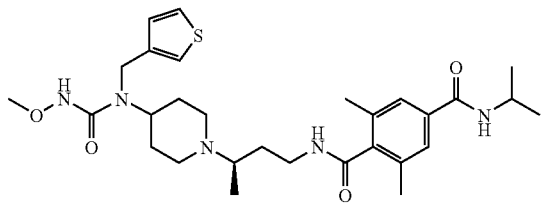

N-{(R)-3-[4-(3-methoxy-1-thiophen-3-
ylmethyl-ureido)-piperidin-1-yl]-butyl}-N'-
isopropyl-2,6-dimethyl-terephthalamide

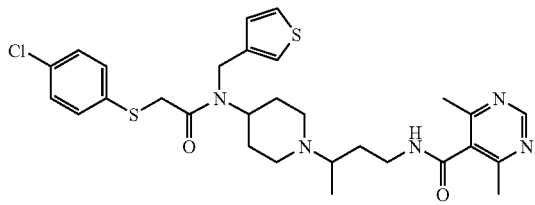

4,6-Dimethyl-pyrimidine-5-carboxylic acid
[3-(4-{[2-(4-chloro-phenylsulfanyl)-acetyl]-
thiophen-3-ylmethyl-amino}-piperidin-1-yl)-
butyl]-amide

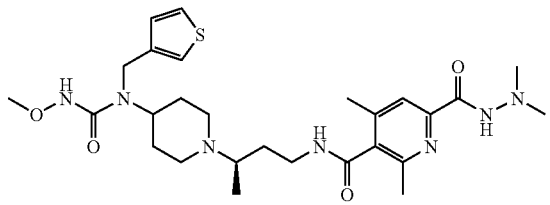

6-(N',N'-Dimethyl-hydrazinocarbonyl)-2,4-
dimethyl-N-{(R)-3-[4-(3-methoxy-1-
thiophen-3-ylmethyl-ureido)-piperidin-1-yl]-
butyl}-nicotinamide

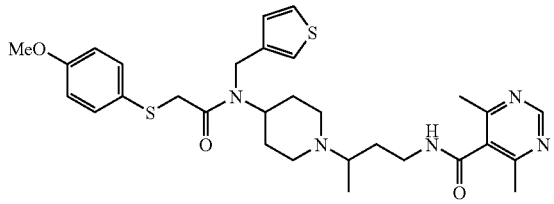

4,6-Dimethyl-pyrimidine-5-carboxylic acid
[3-(4-{[2-(4-methoxy-phenylsulfanyl)-
acetyl]-thiophen-3-ylmethyl-amino}-
piperidin-1-yl)-butyl]-amide

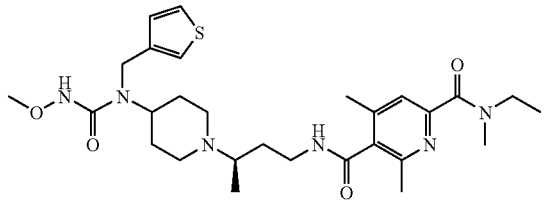

4,6-Dimethyl-pyridine-2,5-dicarboxylic acid
2-(ethyl-methyl-amide) 5-({(R)-3-[4-(3-
methoxy-1-thiophen-3-ylmethyl-ureido)-
piperidin-1-yl]-butyl}-amide)

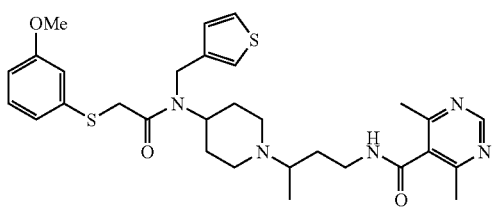

4,6-Dimethyl-pyrimidine-5-carboxylic acid
[3-(4-{[2-(3-methoxy-phenylsulfanyl)-
acetyl]-thiophen-3-ylmethyl-amino}-
piperidin-1-yl)-butyl]-amide

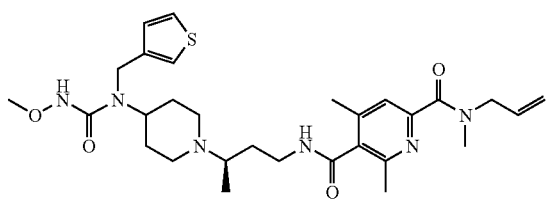

4,6-Dimethyl-pyridine-2,5-dicarboxylic acid
2-(allyl-methyl-amide) 5-({(R)-3-[4-(3-
methoxy-1-thiophen-3-ylmethyl-ureido)-
piperidin-1-yl]-butyl}-amide)

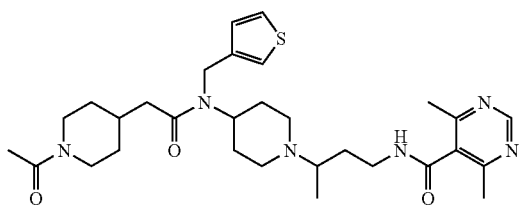

4,6-Dimethyl-pyrimidine-5-carboxylic acid
[3-(4-{[2-(1-acetyl-piperidin-4-yl)-acetyl]-
thiophen-3-ylmethyl-amino}-piperidin-1-yl)-
butyl]-amide

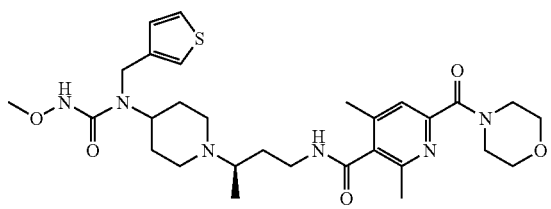

2,4-Dimethyl-6-(morpholine-4-carbonyl)-N-
{(R)-3-[4-(3-methoxy-1-thiophen-3-
ylmethyl-ureido)-piperidin-1-yl]-butyl}-
nicotinamide -continued

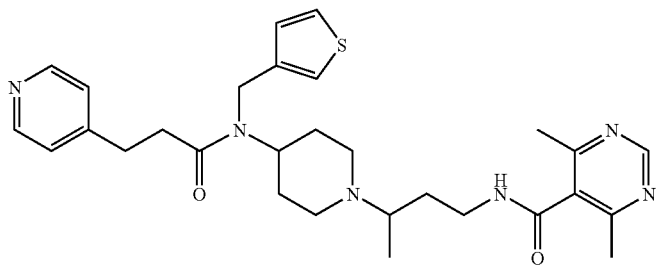

4,6-Dimethyl-pyrimidine-5-carboxylic acid
(3-{4-[(3-pyridin-4-yl-propionyl)-thiophen-
3-ylmethyl-amino]-piperidin-1-yl}-butyl)-
amide

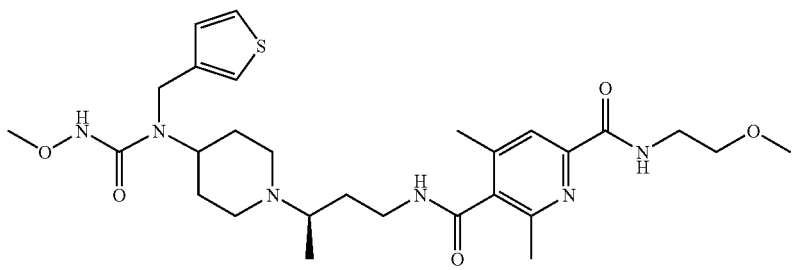

4,6-Dimethyl-pyridine-2,5-dicarboxylic acid
2-[(2-methoxy-ethyl)-amide] 5-({(R)-3-[4-(3-
methoxy-1-thiophen-3-ylmethyl-ureido)-
piperidin-1-yl]-butyl}-amide)

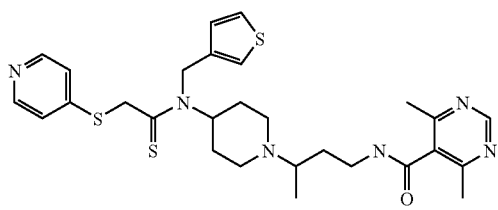

4,6-Dimethyl-pyrimidine-5-carboxylic acid
[3-(4-{[2-(pyridin-4-ylsulfanyl)-thioacetyl]-
thiophen-3-ylmethyl-amino}-piperidin-1-yl)-
butyl]-amide

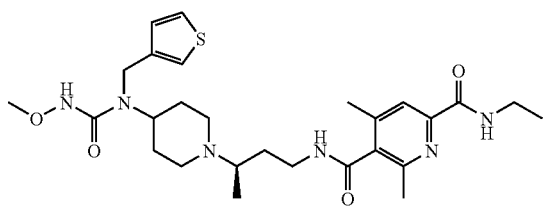

4,6-Dimethyl-pyridine-2,5-dicarboxylic acid
2-ethylamide 5-({(R)-3-[4-(3-methoxy-1-
thiophen-3-ylmethyl-ureido)-piperidin-1-yl]-
butyl}-amide)

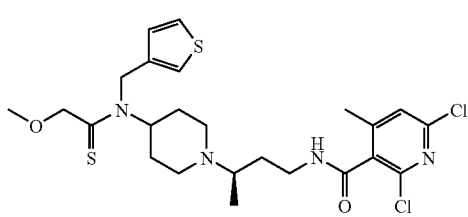

2,6-Dichloro-N-((R)-3-{4-[(2-methoxy-
thioacetyl)-thiophen-3-ylmethyl-amino]-
piperidin-1-yl}-butyl)-4-methyl-nicotinamide

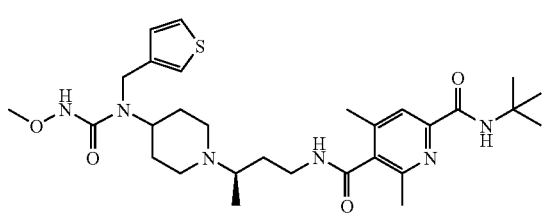

4,6-Dimethyl-pyridine-2,5-dicarboxylic acid
2-tert-butylamide 5-({(R)-3-[4-(3-methoxy-1-
thiophen-3-ylmethyl-ureido)-piperidin-1-yl]-
butyl}-amide)

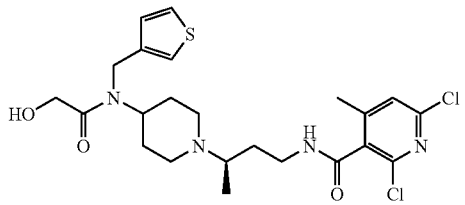

2,6-Dichloro-N-((R)-3-{4-[(2-hydroxy-
acetyl)-thiophen-3-ylmethyl-amino]-
piperidin-1-yl}-butyl)-4-methyl-nicotinamide

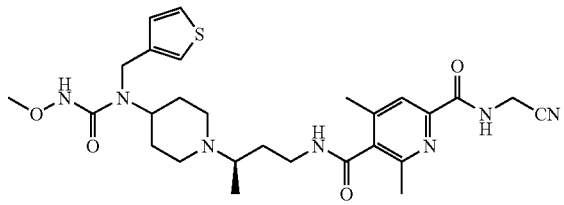

4,6-Dimethyl-pyridine-2,5-dicarboxylic acid
2-cyanomethyl 5-({(R)-3-[4-(3-methoxy-1-
thiophen-3-ylmethyl-ureido)-piperidin-1-yl]-
butyl}-amide)

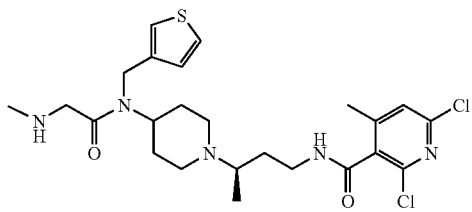

2,6-Dichloro-4-methyl-N-((R)-3-{4-[(2-
methylamino-acetyl)-thiophen-3-ylmethyl-
amino]-piperidin-1-yl}-butyl)-nicotinamide

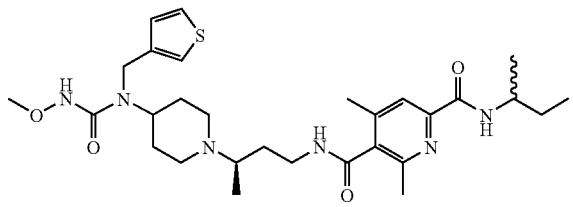

4,6-Dimethyl-pyridine-2,5-dicarboxylic acid
2-sec-butyl 5-({(R)-3-[4-(3-methoxy-1-
thiophen-3-ylmethyl-ureido)-piperidin-1-yl]-
butyl}-amide)

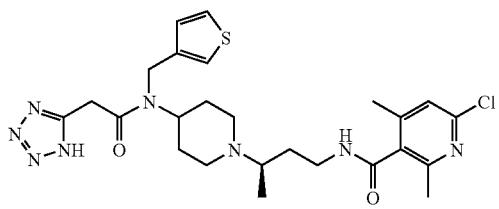

6-Chloro-2,4-dimethyl-N-((R)-3-{4-[(2-1H-
tetrazol-5-yl-acetyl)-thiophen-3-ylmethyl-
amino]-piperidin-1-yl}-butyl)-nicotinamide

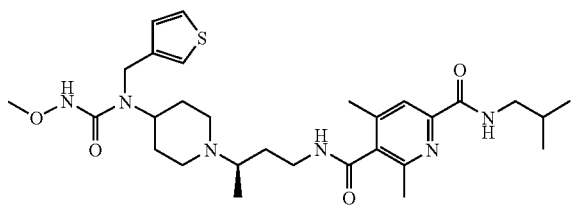

4,6-Dimethyl-pyridine-2,5-dicarboxylic acid
2-isobutyl 5-({(R)-3-[4-(3-methoxy-1-
thiophen-3-ylmethyl-ureido)-piperidin-1-yl]-
butyl}-amide)

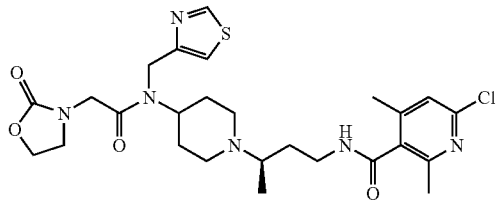

6-Chloro-2,4-dimethyl-N-[(R)-3-(4-{[2-(2-
oxo-oxazolidin-3-yl)-acetyl]-thiazol-4-
ylmethyl-amino}-piperidin-1-yl)-butyl]-
nicotinamide

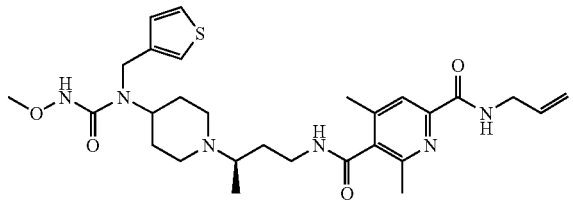

4,6-Dimethyl-pyridine-2,5-dicarboxylic acid
2-allyl 5-({(R)-3-[4-(3-methoxy-1-thiophen-
3-ylmethyl-ureido)-piperidin-1-yl]-butyl}-
amide)

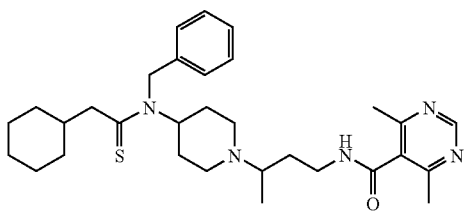

4,6-Dimethyl-pyrimidine-5-carboxylic acid
(3-{4-[benzyl-(2-cyclohexyl-thioacetyl)-
amino]-piperidin-1-yl}-butyl)-amide

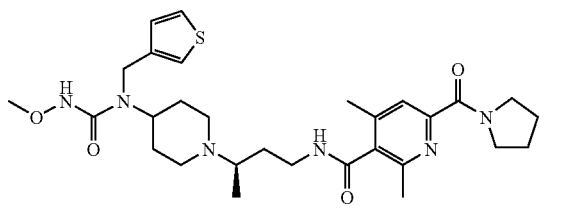

2,4-Dimethyl-N-{(R)-3-[4-(3-methyl-1-
thiophen-3-ylmethyl-ureido)-piperidin-1-yl]-
butyl}-6-(pyrrolidine-1-carbonyl)-
nicotinamide

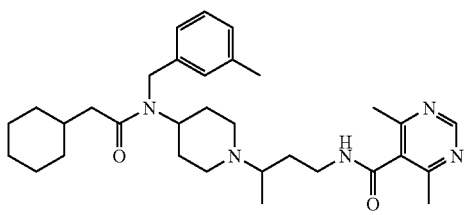

4,6-Dimethyl-pyrimidine-5-carboxylic acid
(3-{4-[(2-cyclohexyl-acetyl)-(3-methyl-
benzyl)-amino]-piperidin-1-yl}-butyl)-amide

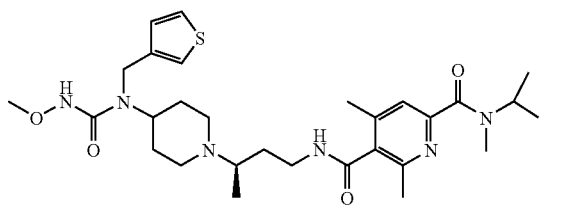

4,6-Dimethyl-pyridine-2,5-dicarboxylic acid
2-(isopropyl-methyl-amide) 5-({(R)-3-[4-(3-
methoxy-1-thiophen-3-ylmethyl-ureido)-
piperidin-1-yl]-butyl}-amide)

-continued

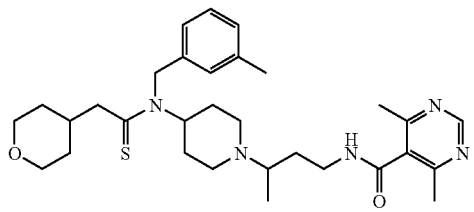

4,6-Dimethyl-pyrimidine-5-carboxylic acid
(3-{4-[(3-methylbenzyl)-(2-tetrahydropyran-
4-yl-thioacetyl)-amino]-piperidin-1-yl}-
butyl)-amide

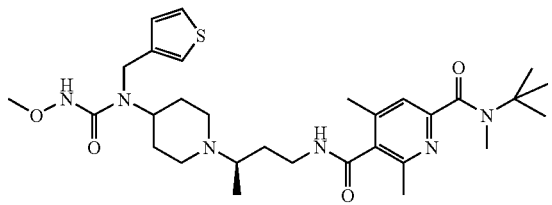

4,6-Dimethyl-pyridine-2,5-dicarboxylic acid
2-(methyl-tert-butyl-amide) 5-({(R)-3-[4-(3-
methoxy-1-thiophen-3-ylmethyl-ureido)-
piperidin-1-yl]-butyl}-amide)

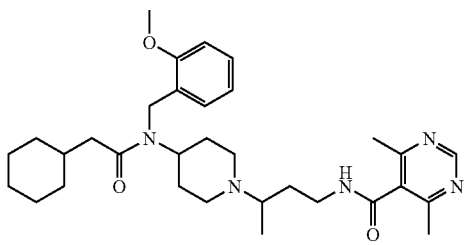

4,6-Dimethyl-pyrimidine-5-carboxylic acid
(3-{4-[(2-cyclohexyl-acetyl)-(2-methoxy-
benzyl)-amino]-piperidin-1-yl}-butyl)-amide

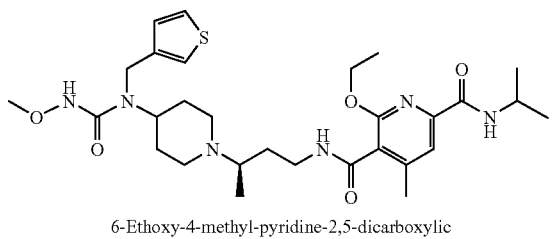

6-Ethoxy-4-methyl-pyridine-2,5-dicarboxylic
acid 2-isopropylamide 5-({(R)-3-[4-(3-
methoxy-1-thiophen-3-ylmethyl-ureido)-
piperidin-1-yl]-butyl}-amide)

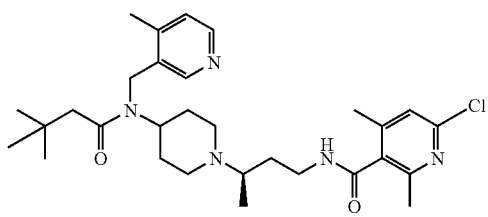

6-Chloro-N-((R)-3-{4-[(3,3-dimethyl-
butyryl)-(4-methyl-pyridin-3-ylmethyl)-
amino]-piperidin-1-yl}-butyl)-2,4-dimethyl-
nicotinamide

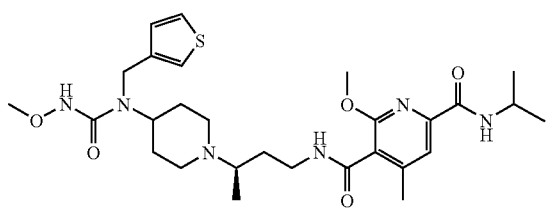

6-Methoxy-4-methyl-pyridine-2,5-
dicarboxylic acid 2-isopropylamide 5-({(R)-
3-[4-(3-methoxy-1-thiophen-3-ylmethyl-
ureido)-piperidin-1-yl]-butyl}-amide)

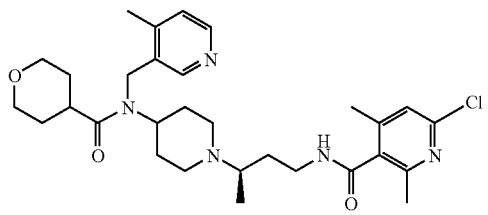

6-Chloro-2,4-dimethyl-N-((R)-3-{4-[(4-
methyl-pyridin-3-ylmethyl)-(tetrahydro-
pyran-4-carbonyl)-amino]-piperidin-1-y}-
butyl)-nicotinamide

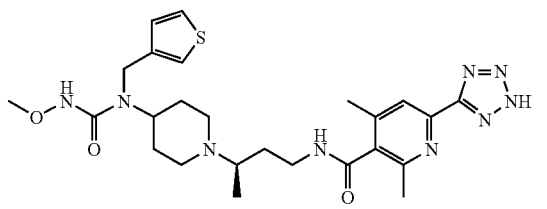

2,4-Dimethyl-N-{(R)-3-[4-(3-methoxy-1-
thiophen-3-ylmethyl-ureido)-piperidin-1-yl]-
butyl}-6-(2H-tetrazol-5-yl)-nicotinamide

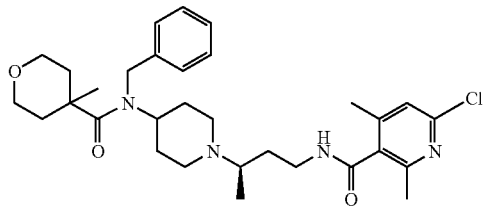

N-((R)-3-{4-[Benzyl-(4-methyl-tetrahydro-
pyran-4-carbonyl)-amino]-piperidin-1-yl}-
butyl)-6-chloro-2,4-dimethyl-nicotinamide

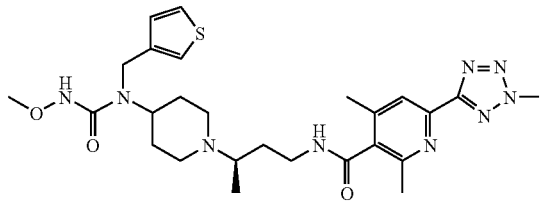

2,4-Dimethyl-6-(2-methyl-2H-tetrazol-5-yl)-
N-{(R)-3-[4-(3-methoxy-1-thiophen-3-
ylmethyl-ureido)-piperidin-1-yl]-butyl}-
nicotinamide

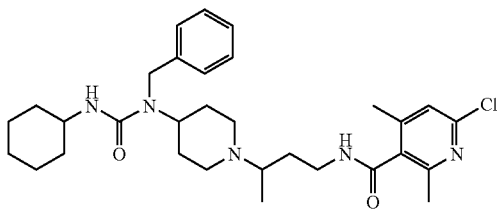

N-{3-[4-(1-Benzyl-3-cyclohexyl-ureido)-
piperidin-1-yl]-butyl}-6-chloro-2,4-dimethyl-
nicotinamide

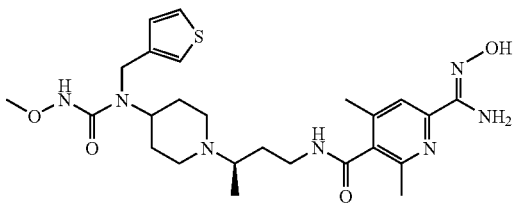

N-{(R)-3-[4-(3-methoxy-1-thiophen-3-
ylmethyl-ureido)-piperidin-1-yl]-butyl}-6-(N-
hydroxycarbamimidoyl)-2,4-dimethyl-
nicotinamide

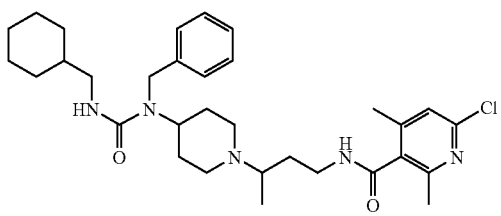

N-{3-[4-(1-Benzyl-3-cyclohexylmethyl-
ureido)-piperidin-1-yl]-butyl}-6-chloro-2,4-
dimethyl-nicotinamide

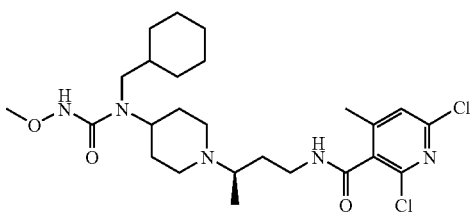

2,6-Dichloro-N-{(R)-3-[4-(1-
cyclohexylmethyl-3-methoxy-ureido)-
piperidin-1-yl]-butyl}-4-methyl-nicotinamide

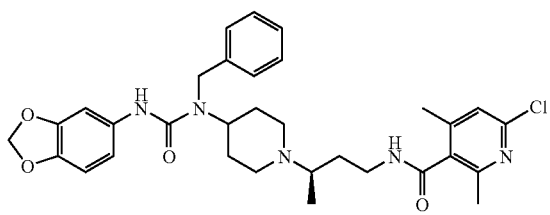

N-{3-[4-(3-Benzol[1,3]dioxol-5-yl-1-benzyl-
ureido)-piperidin-1-yl]-butyl}-6-chloro-2,4-
dimethyl-nicotinamide

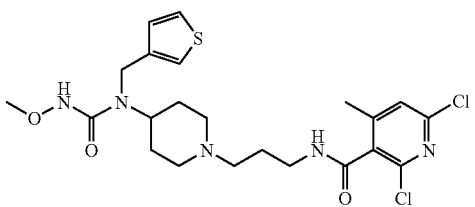

2,6-Dichloro-4-methyl-N-{3-[4-(3-methoxy-
1-thiophen-3-ylmethyl-ureido)-piperidin-1-
yl]-propyl}-nicotinamide

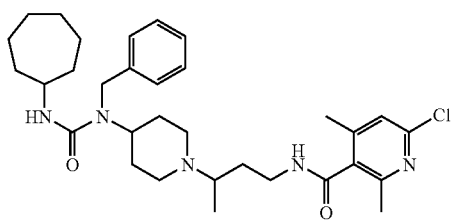

N-{3-[4-(1-Benzol-3-cycloheptyl-ureido)-
piperidin-1-yl]-butyl}-6-chloro-2,4-dimethyl-
nicotinamide

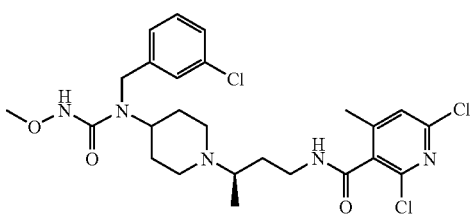

2,6-Dichloro-N-((R)-3-{4-[1-(3-chloro-
benzyl)-3-methoxy-ureido]-piperidin-1-yl}-
butyl)-4-methyl-nicotinamide

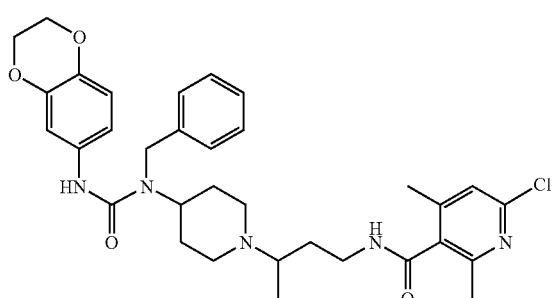

N-(3-{4-[1-Benzyl-3-(2,3-dihydro-
benzol[1,4]dioxin-6-yl)-ureido]-piperidin-1-
yl}-butyl)-6-chloro-2,4-dimethyl-
nicotinamide

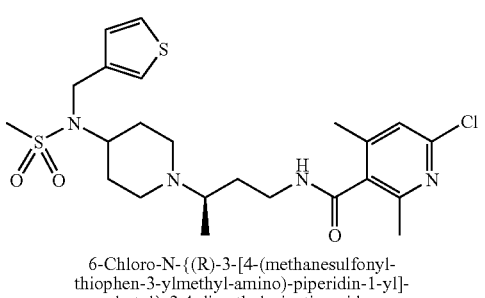

6-Chloro-N-{(R)-3-[4-(methanesulfonyl-
thiophen-3-ylmethyl-amino)-piperidin-1-yl]-
butyl}-2,4-dimethyl-nicotinamide -continued

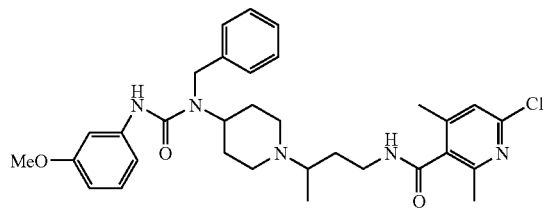

N-(3-{4-[1-Benzyl-3-(3-methoxy-phenyl)-ureido]-piperidin-1-yl}-butyl)-6-chloro-2,4-dimethyl-nicotinamide

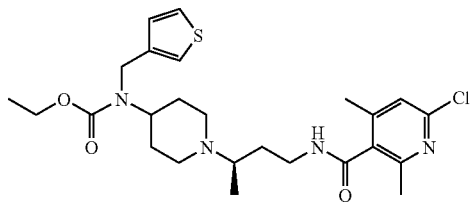

(1-(R)-{3-[(6-Chloro-2,4-dimethyl-pyridine-3-carbonyl)-amino]-1-methyl-propyl}-piperidin-4-yl)-thiophen-3-ylmethyl-carbamic acid ethyl ester

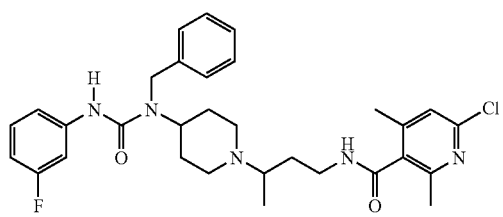

N-(3-{4-[1-Benzyl-3-(3-fluoro-phenyl)-ureido]-piperidin-1-yl}-butyl)-6-chloro-2,4-dimethyl-nicotinamide

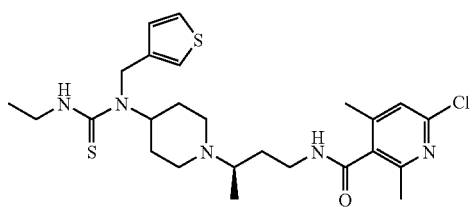

6-Chloro-N-{(R)-3-[4-(3-ethyl-1-thiophen-3-ylmethyl-thioureido)-piperidin-1-yl]-butyl}-2,4-dimethyl-nicotinamide

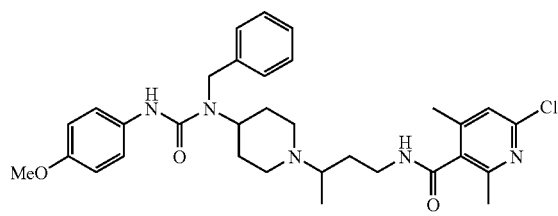

N-(3-{4-[1-Benzyl-3-(4-methoxy-phenyl)-ureido]-piperidin-1-yl}-butyl)-6-chloro-2,4-dimethyl-nicotinamide

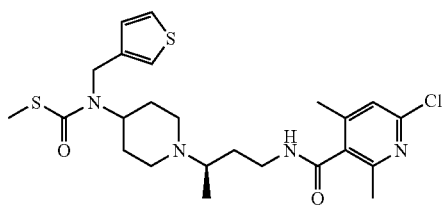

(1-{(R)-3-[(6-Chloro-2,4-dimethyl-pyridine-3-carbonyl)-amino]-1-methyl-propyl}-piperidin-4-yl)-thiophen-3-ylmethyl-thiocarbamic acid S-methyl ester

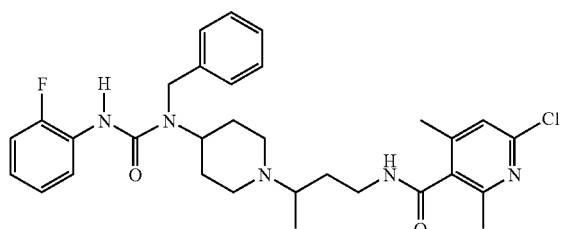

N-(3-{4-[1-Benzyl-3-(2-fluoro-phenyl)-ureido]-piperidin-1-yl}-butyl)-6-chloro-2,4-dimethyl-nicotinamide

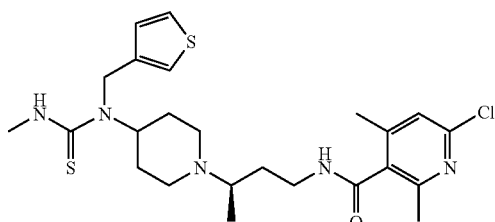

6-Chloro-2,4-dimethyl-N-{(R)-3-[4-(3-methyl-1-thiophen-3-ylmethyl-thioureido)-piperidin-1-yl]-butyl}-nicotinamide

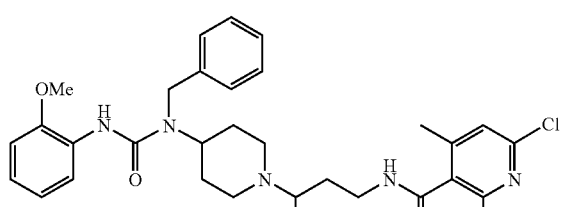

N-(3-{4-[1-Benzyl-3-(2-methoxy-phenyl)-ureido]-piperidin-1-yl}-butyl)-6-chloro-2,4-dimethyl-nicotinamide

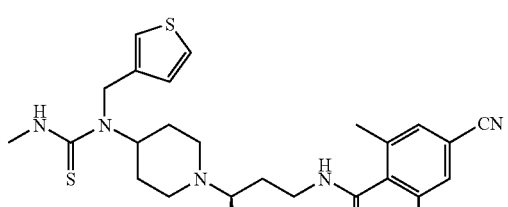

4-Cyano-2,6-dimethyl-N-{(R)-3-[4-(3-methyl-1-thiophen-3-ylmethyl-thioureido)-piperidin-1-yl]-butyl}-benzamide

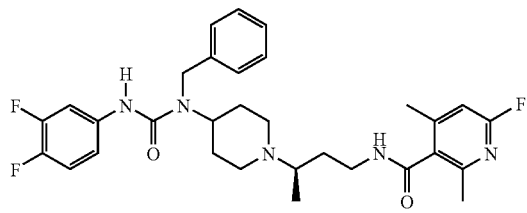

N-((R)-3-{4-[1-Benzyl-3-(3,4-difluoro-
phenyl)-ureido]-piperidin-1-yl}-butyl)-6-
fluoro-2,4-dimethyl-nicotinamide

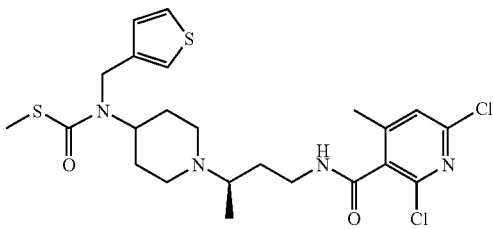

(1-{(R)-3-[(2,6-Dichloro-4-methyl-pyridine-
3-carbonyl)-amino]-1-methyl-propyl}-
piperidin-4-yl)-thiophen-3-ylmethyl-
thiocarbamic acid S-methyl ester

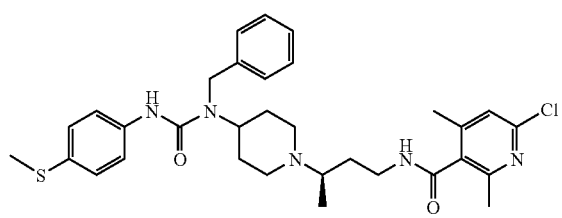

N-((R)-3-{4-[1-Benzyl-3-(4-methylsulfanyl-
phenyl)-ureido]-piperidin-1-yl}-butyl)-6-
chloro-2,4-dimethyl-nicotinamide

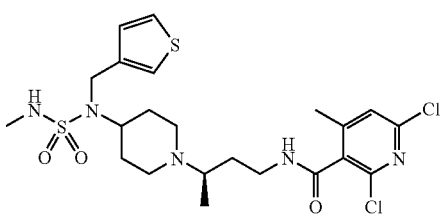

2,6-Dichloro-4-methyl-N-{(R)-3-[4-(3-
methyl-1-thiophen-3-ylmethyl-sulfonamido)-
piperidin-1-yl]-butyl}-nicotinamide

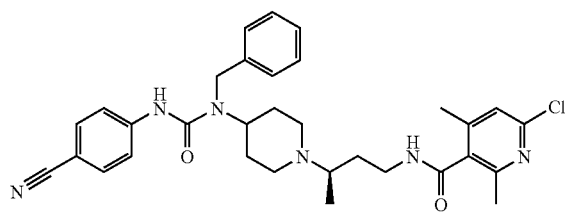

N-((R)-3-{4-[1-Benzyl-3-(4-cyano-phenyl)-
ureido]-piperidin-1-yl}-butyl)-6-chloro-2,4-
dimethyl-nicotinamide

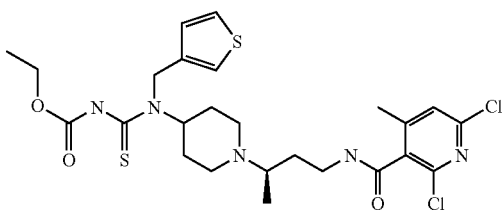

2,6-Dichloro-4-methyl-N-{(R)-3-[4-(3-
formyl ethyl ester-1-thiophen-3-ylmethyl-
thioureido)-piperidin-1-yl]-butyl}-
nicotinamide

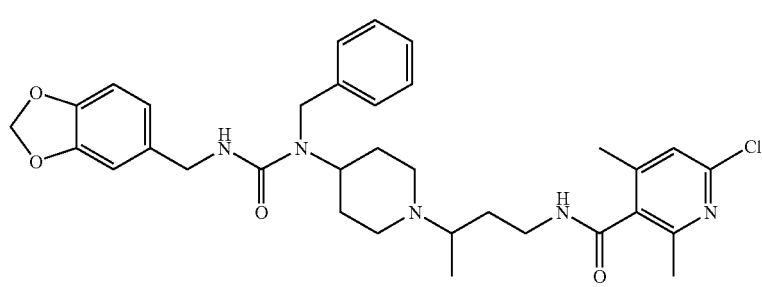

N-{3-[4-(3-1,3-Benzodioxol-5-ylmethyl-1-
benzyl-ureido)-piperidin-1-yl]-butyl}-6-
chloro-2,4-dimethyl-nicotinamide

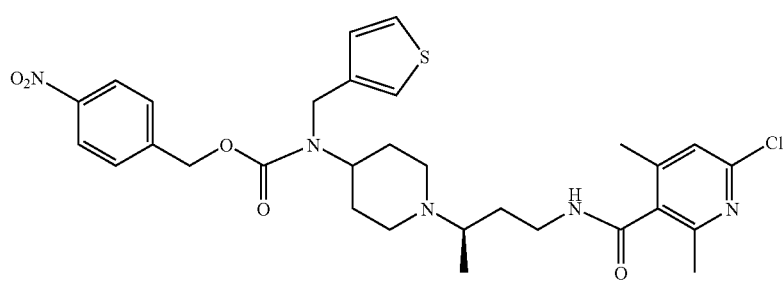

(1-{(R)-3-[(6-Chloro-2,4-dimethyl-pyridine-
3-carbonyl)-amino]-1-methyl-propyl}-
piperidin-4-yl)-thiophen-3-ylmethyl-
carbamic acid 4-nitro-benzyl ester -continued

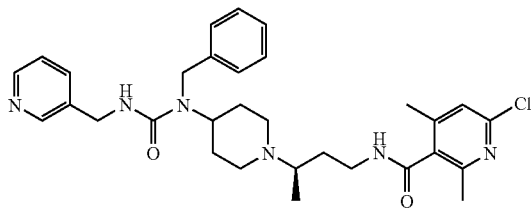

N-{(R)-3-[4-(1-Benzyl-3-pyridin-4-yl-
ureido)-piperidin-1-yl]-butyl}-6-chloro-2,4-
dimethyl-nicotinamide

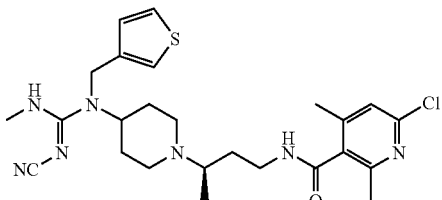

6-Chloro-2,4-dimethyl-N-{(R)-3-[4-(N'-
methyl-N-thiophen-3-ylmethyl-N''-
cyanoguanidino)-piperidin-1-yl]-butyl}-
nicotinamide

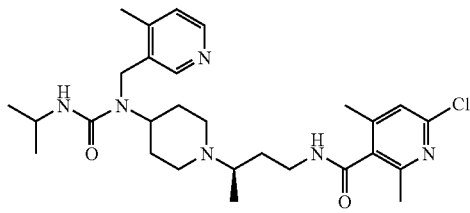

6-Chloro-N-((R)-3-{4-[3-isopropyl-1-(4-
methyl-pyridin-3-ylmethyl)-ureido]-
piperidin-1-yl}-butyl)-2,4-dimethyl-
nicotinamide

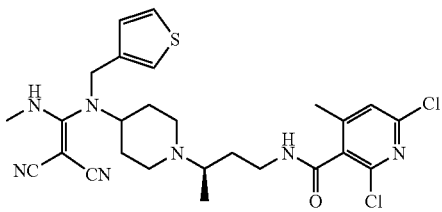

2,6-Dichloro-N-((R)-3-{4-[(2,2-dicyano-1-
methylamino-vinyl)-thiophen-3-ylmethyl-
amino]-piperidin-1-yl}-butyl)-4-methyl-
nicotinamide

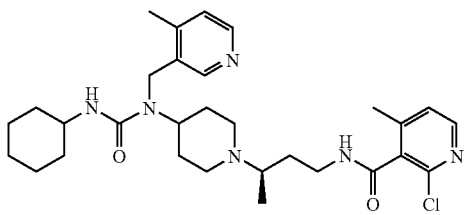

2-Chloro-N-((R)-3-{4-[3-cyclohexyl-1-(4-
methyl-pyridin-3-ylmethyl)-ureido]-
piperidin-1-yl}-butyl)-4-methyl-nicotinamide

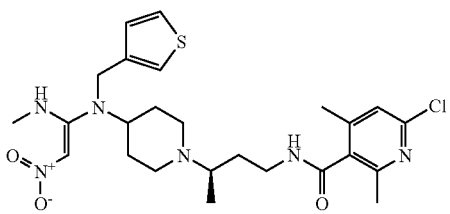

6-Chloro-2,4-dimethyl-N-((R)-3-{4-[(1-
methylamino-2-nitro-vinyl)-thiophen-3-
ylmethyl-amino]-piperidin-1-yl}-butyl)-
nicotinamide

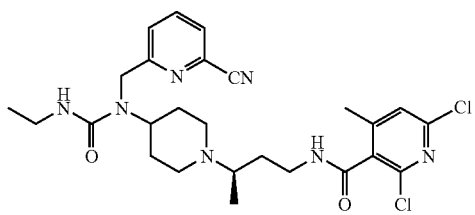

2,6-Dichloro-N-((R)-3-{4-[1-(6-cyano-
pyridin-2-ylmethyl)-3-ethyl-ureido]-
piperidin-1-yl}-butyl)-4-methyl-nicotinamide

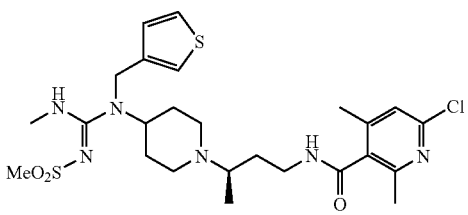

6-Chloro-2,4-dimethyl-N-{(R)-3-[4-(N'-
methyl-N-thiophen-3-ylmethyl-N''-
methanesulfonylguanidino)-piperidin-1-yl]-
butyl}-nicotinamide

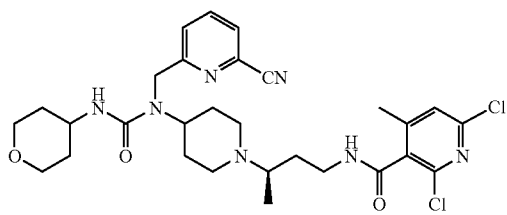

2,6-Dichloro-N-((R)-3-{4-[1-(6-cyano-
pyridin-2-ylmethyl)-3-(tetrahydro-pyran-4-
yl)-ureido]-piperidin-1-yl}-butyl)-4-methyl-
nicotinamide

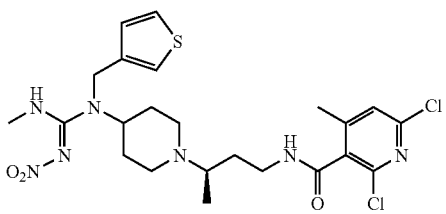

2,6-Dichloro-4-methyl-N-{(R)-3-[4-(N'-
methyl-N-thiophen-3-ylmethyl-N''-
nitroguanidino)-piperidin-1-yl]-butyl}-
nicotinamide

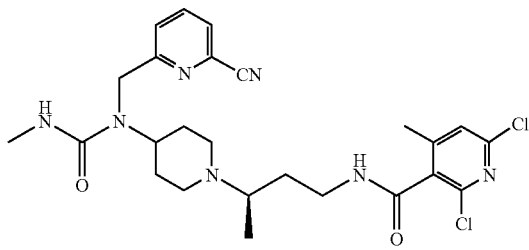

2,6-Dichloro-N-((R)-3-{4-[1-(6-cyano-pyridin-2-ylmethyl)-3-methyl-ureido]-piperidin-1-yl}-butyl)-4-methyl-nicotinamide

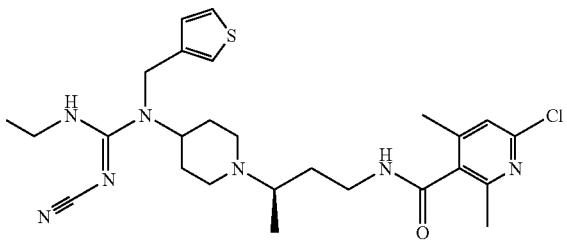

6-Chloro-N-{(R)-3-[4-(N'-ethyl-N-thiophen-3-ylmethyl-cyanoguanidino)-piperidin-1-yl]-butyl}-2,4-dimethyl-nicotinamide

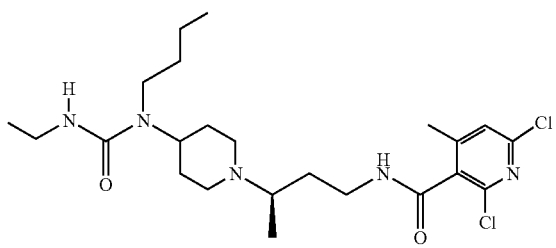

N-{(R)-3-[4-(1-Butyl-3-ethyl-ureido)-piperidin-1-yl]-butyl}-2,6-dichloro-4-methyl-nicotinamide

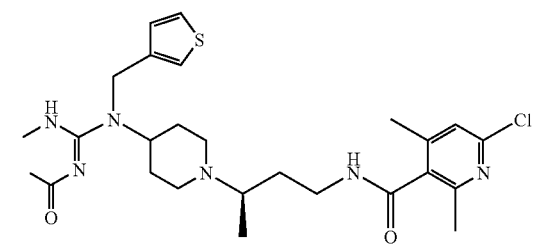

6-Chloro-2,4-dimethyl-N-{(R)-3-[4-(N'-methyl-N-thiophen-3-ylmethyl-N''-acetylguanidino)-piperidin-1-yl]-butyl}-nicotinamide

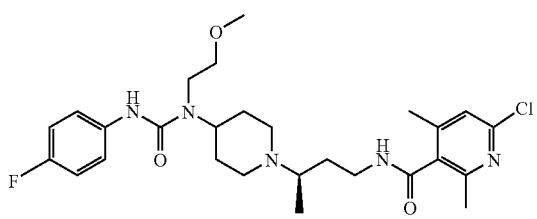

6-Chloro-N-((R)-3-{4-[3-(4-fluoro-phenyl)-1-(2-methoxy-ethyl)-ureido]-piperidin-1-yl}-butyl)-2,4-dimethyl-nicotinamide

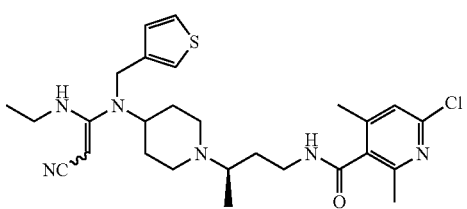

6-Chloro-N-((R)-3-{4-[(2-cyano-1-ethylamino-vinyl)-thiophen-3-ylmethyl-amino]-piperidin-1-yl}-butyl)-2,4-dimethyl-nicotinamide

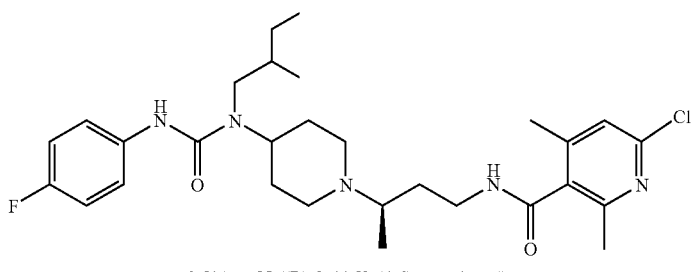

6-Chloro-N-((R)-3-{4-[3-(4-fluoro-phenyl)-1-(2-methyl-butyl)-ureido]-piperidin-1-yl}-butyl)-2,4-dimethyl-nicotinamide

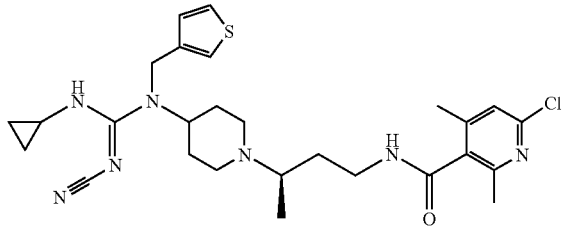

6-Chloro-N-{(R)-3-{4-(N'-cyclopropyl-N-thiophen-3-ylmethyl-cyanoguanidino)-piperidin-1-yl}-butyl}-2,4-dimethyl-nicotinamide

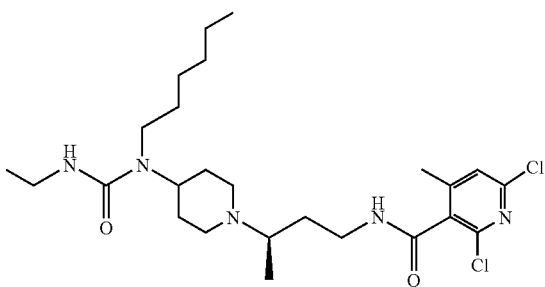

2,6-Dichloro-N-{(R)-3-[4-(3-ethyl-1-hexyl-ureido)-piperidin-1-yl]-butyl}-4-methyl-nicotinamide -continued

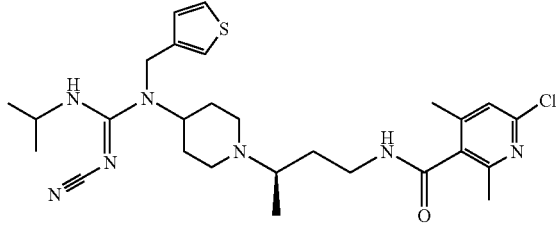

6-Chloro-N-{(R)-3-[4-(N'-isopropyl-N-thiophen-3-ylmethyl-cyanoguanidino)-piperidin-1-yl]-butyl}-2,4-dimethyl-nicotinamide

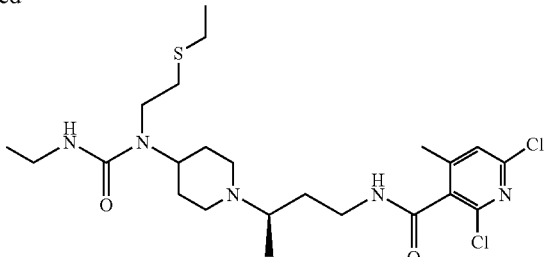

2,6-Dichloro-N-((R)-3-{4-[3-ethyl-1-(2-ethylsulfanyl-ethyl)-ureido]-piperidin-1-yl}-butyl)-4-methyl-nicotinamide

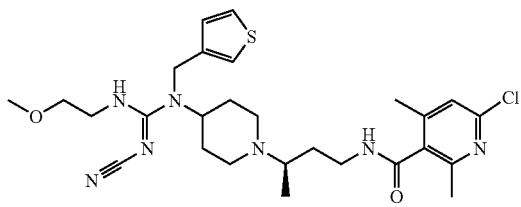

6-Chloro-N-((R)-3-{4-[N'-(2-methoxy-ethyl)-N-thiophen-3-ylmethyl-cyanoguanidino]-piperidin-1-yl}-butyl)-2,4-dimethyl-nicotinamide

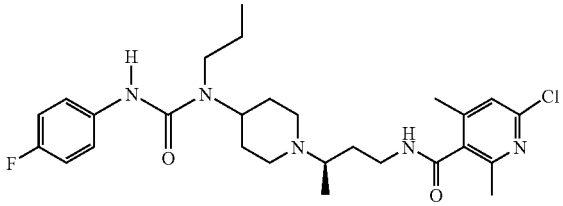

6-Chloro-N-((R)-3-{4-[3-(4-fluoro-phenyl)-1-propyl-ureido]-piperidin-1-yl}-butyl)-2,4-dimethyl-nicotinamide

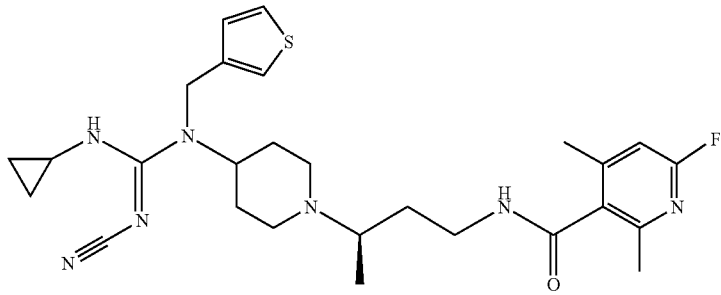

N-{(R)-3-[4-(N'-Cyclopropyl-N-thiophen-3-ylmethyl-cyanoguanidino)-piperidin-1-yl]-butyl}-6-fluoro-2,4-dimethyl-nicotinamide

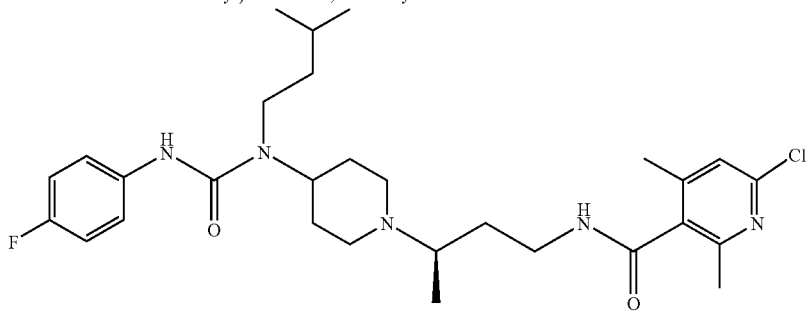

6-Chloro-N-((R)-3-{4-[3-(4-fluoro-phenyl)-1-(3-methyl-butyl)-ureido]-piperidin-1-yl}-butyl)-2,4-dimethyl-nicotinamide

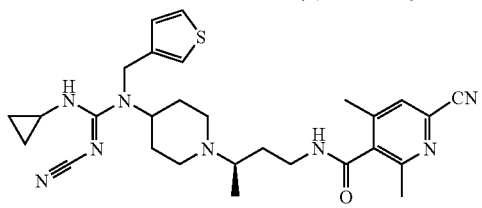

6-Cyano-N-{(R)-3-[4-(N'-cyclopropyl-N-thiophen-3-ylmethyl-cyanoguanidino)-piperidin-1-yl]-butyl}-2,4-dimethyl-nicotinamide

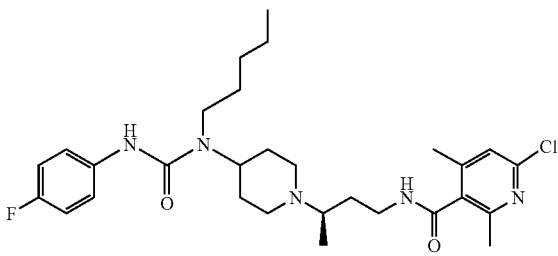

6-Chloro-N-((R)-3-{4-[3-(4-fluoro-phenyl)-1-pentyl-ureido]-piperidin-1-yl}-butyl)-2,4-dimethyl-nicotinamide -continued

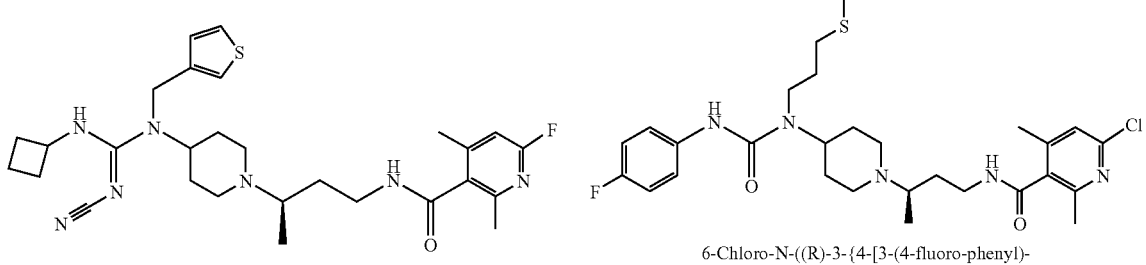

N-{(R)-3-[4-(N'-Cyclobutyl-N-thiophen-3-ylmethyl-cyanoguanidino)-piperidin-1-yl]-butyl}-6-fluoro-2,4-dimethyl-nicotinamide

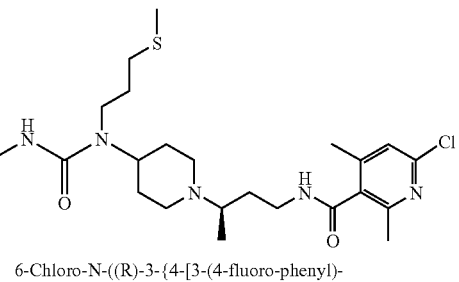

6-Chloro-N-((R)-3-{4-[3-(4-fluoro-phenyl)-1-(3methyl sulfanyl-propyl)-ureido]-piperidin-1-yl}-butyl)-2,4-dimethyl nicotinamide

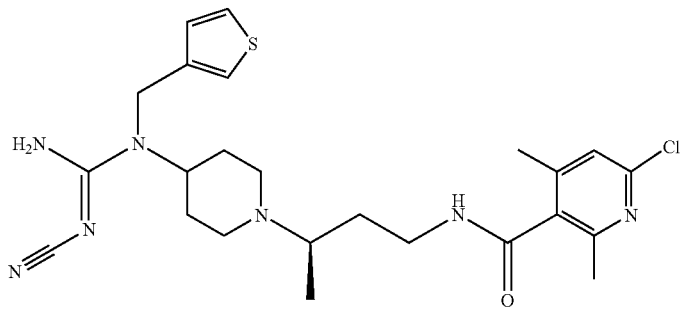

6-Chloro-2,4-dimethyl-N-{(R)-3-[4-(N-thiophen-3-ylmethyl-N''-cyanoguandino)-piperidin-1-yl]-butyl}-nicotinamide

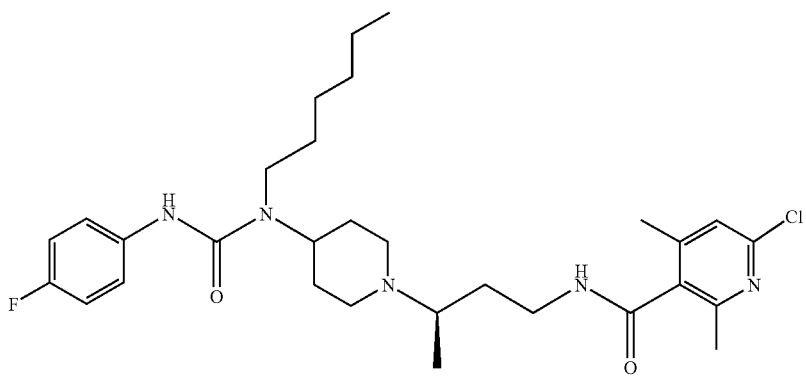

6-Chloro-N-((R)-3-{4-[3-(4-fluoro-phenyl)-1-hexyl-ureido]-piperidin-1-yl}-butyl)-2,4-dimethyl-nicotinamide

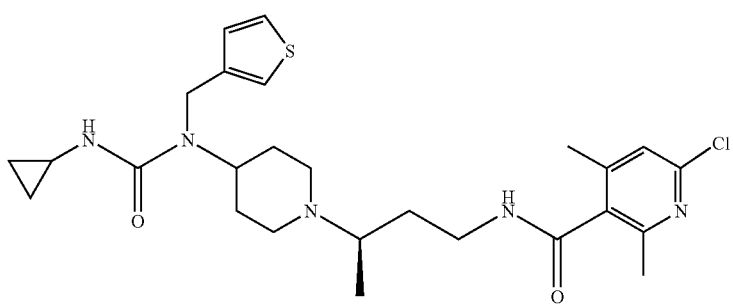

6-Chloro-N-{(R)-3-[4-(3-cyclopropyl-1-thiophen-3-ylmethyl-ureido)-piperidin-1-yl]-butyl}-2,4-dimethyl-nicotinamide

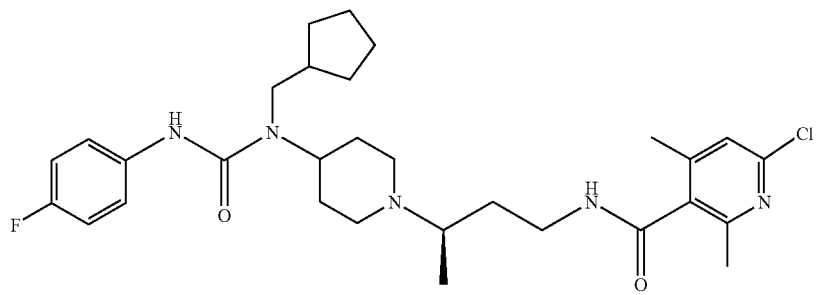

6-Chloro-N-((R)-3-{4-[1-cyclopentylmethyl-
3-(4-fluoro-phenyl)-ureido]-piperidin-1-yl}-
butyl)-2,4-dimethyl-nicotinamide

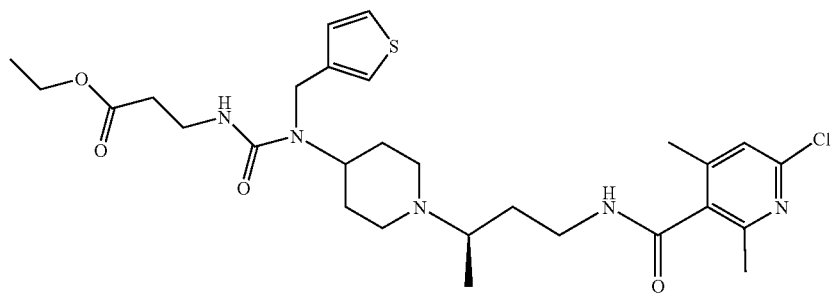

3-[3-(1-{(R)-3-[(6-Chloro-2,4-dimethyl-
pyridine-3-carbonyl)-amino]-1-methyl-
propyl}-piperidin-4-yl)-3-thiophen-3-
ylmethyl-ureido]-propionic acid ethyl ester

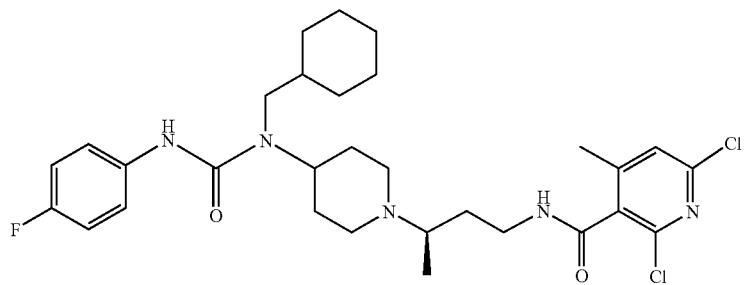

2,6-Dichloro-N-((R)-3-{4-[1-
cyclohexylmethyl-3-(4-fluoro-phenyl)-
ureido]-piperidin-1-yl}-butyl)-4-methyl-
nicotinamide

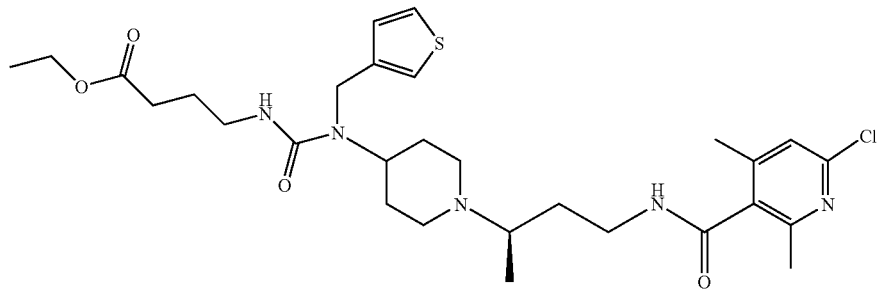

4-[3-(1-{(R)-3-[(6-Chloro-2,4-dimethyl-
pyridine-3-carbonyl)-amino]-1-methyl-
propyl}-piperidin-4-yl)-3-thiophen-3-
ylmethyl-ureido]-butyric acid ethyl ester

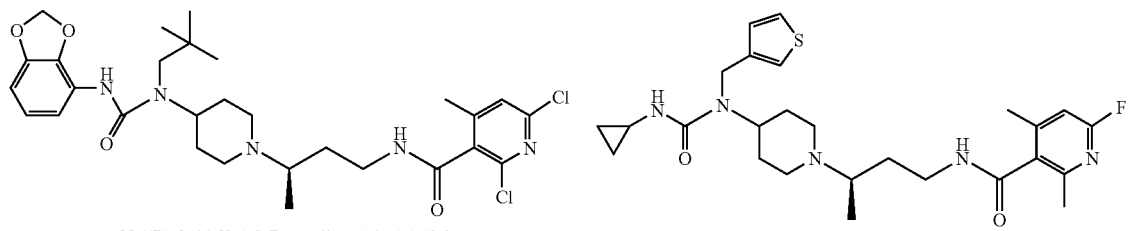

N-((R)-3-{4-[3-1,3-Benzodioxol-4-yl-1-(2,2-dimethyl-propyl)-ureido]-piperidin-1-yl}-butyl)-6-chloro-2,4-dimethyl-nicotinamide N-{(R)-3-[4-(3-Cyclopropyl-1-thiophen-3-ylmethyl-ureido)-piperidin-1-yl]-butyl}-6-fluoro-2,4-dimethyl-nicotinamide

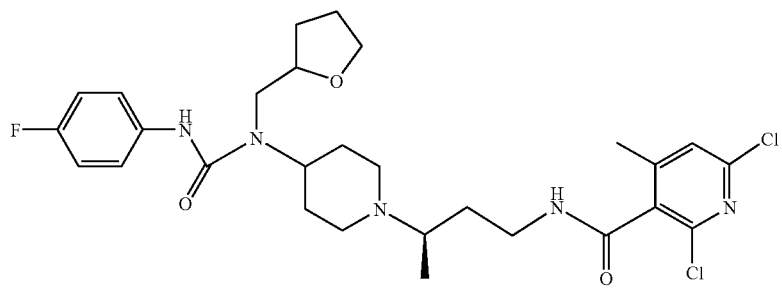

6-Chloro-N-((R)-3-{4-[3-(4-fluoro-phenyl)-1-(tetrahydro-furan-2-ylmethyl)-ureido]-piperidin-1-yl}-butyl)-2,4-dimethyl-nicotinamide

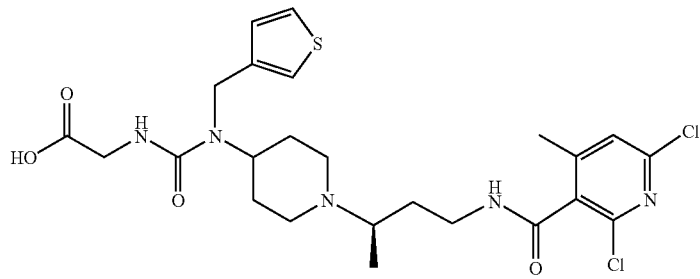

[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid

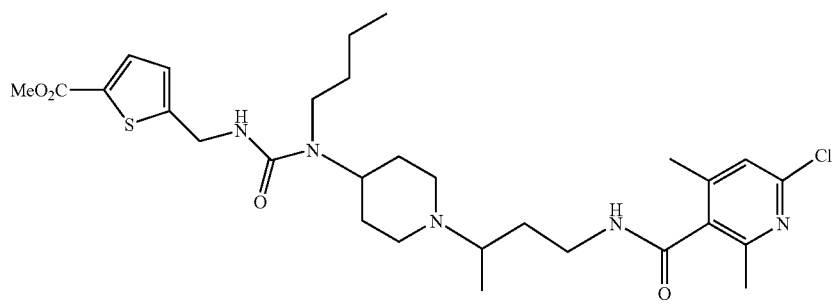

5-[3-Butyl-3-(1-{3-[(6-chloro-2,4-dimethyl-pyridine-3-carbonyl)-amino]-1-methyl-propyl}-piperidin-4-yl)-ureidomethyl]-thiophene-2-carboxylic acid methyl ester

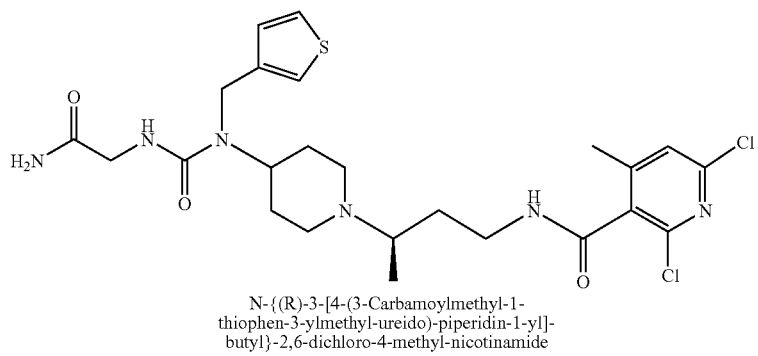

N-{(R)-3-[4-(3-Carbamoylmethyl-1-
thiophen-3-ylmethyl-ureido)-piperidin-1-yl]-
butyl}-2,6-dichloro-4-methyl-nicotinamide

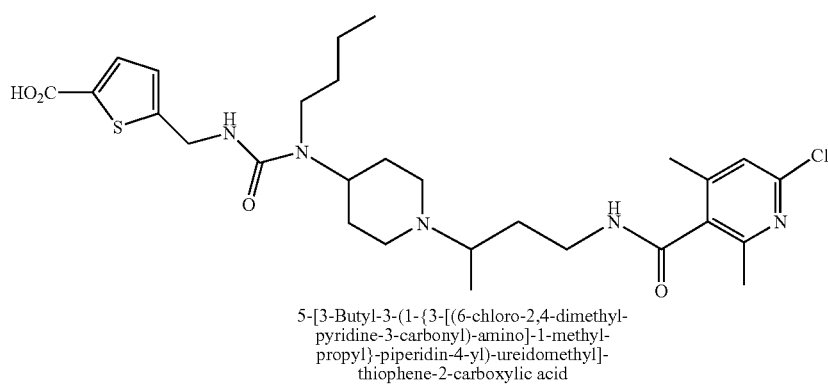

5-[3-Butyl-3-(1-{3-[(6-chloro-2,4-dimethyl-
pyridine-3-carbonyl)-amino]-1-methyl-
propyl}-piperidin-4-yl)-ureidomethyl]-
thiophene-2-carboxylic acid

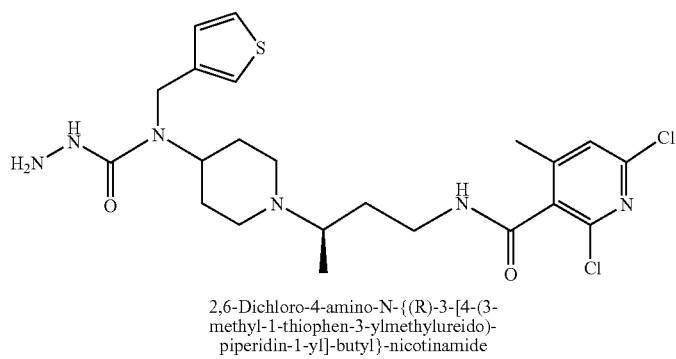

2,6-Dichloro-4-amino-N-{(R)-3-[4-(3-
methyl-1-thiophen-3-ylmethylureido)-
piperidin-1-yl]-butyl}-nicotinamide

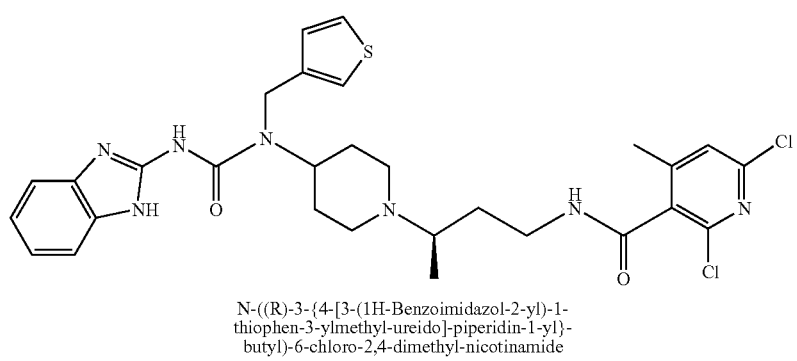

N-((R)-3-{4-[3-(1H-Benzoimidazol-2-yl)-1-
thiophen-3-ylmethyl-ureido]-piperidin-1-yl}-
butyl)-6-chloro-2,4-dimethyl-nicotinamide

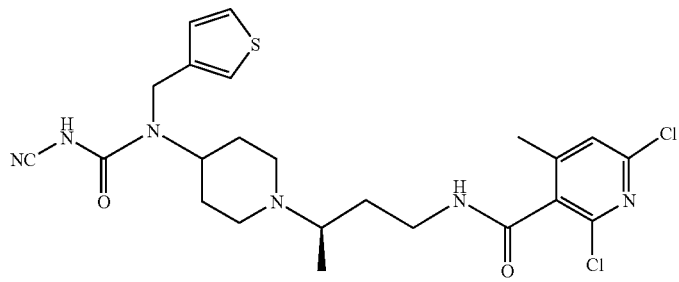

2,6-Dichloro-4-methyl-N-{(R)-3-[4-(3-
cyano-1-thiophen-3-ylmethyl-ureido)-
piperidin-1-yl]-butyl}-nicotinamide

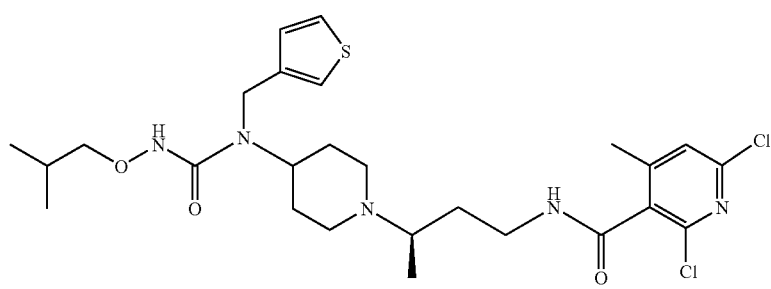

2,6-Dichloro-4-isobutoxy-N-{(R)-3-[4-(3-
methyl-1-thiophen-3-ylmethyl-ureido)-
piperidin-1-yl]-butyl}-nicotinamide

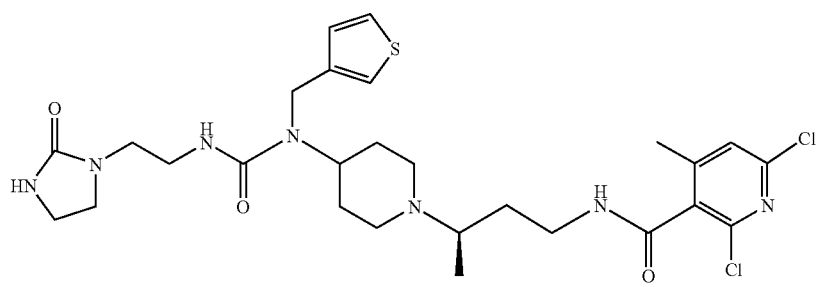

2,6-Dichloro-4-methyl-N-[(R)-3-(4-{3-[2-(2-
oxo-imidazolidin-1-yl)-ethyl]-1-thiophen-3-
ylmethyl-ureido}-piperidin-1-yl)-butyl]-
nicotinamide

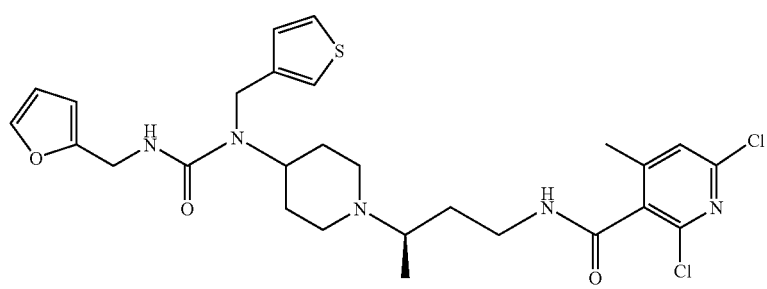

2,6-Dichloro-N-{(R)-3-[4-(3-furan-2-
ylmethyl-1-thiophen-3-ylmethyl-ureido)-
piperidin-1-yl]-butyl}-4-methyl-nicotinamide

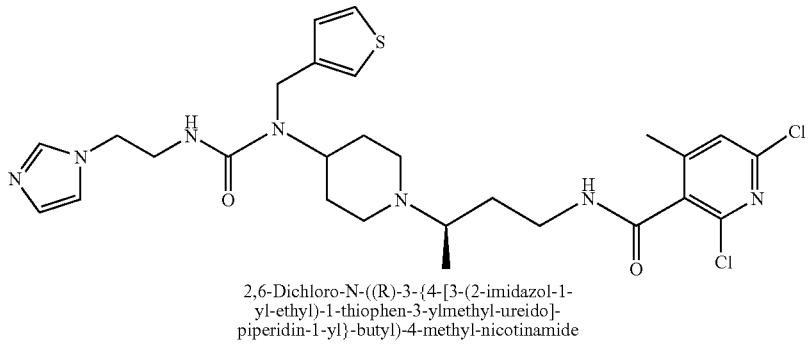

2,6-Dichloro-N-((R)-3-{4-[3-(2-imidazol-1-yl-ethyl)-1-thiophen-3-ylmethyl-ureido]-piperidin-1-yl}-butyl)-4-methyl-nicotinamide

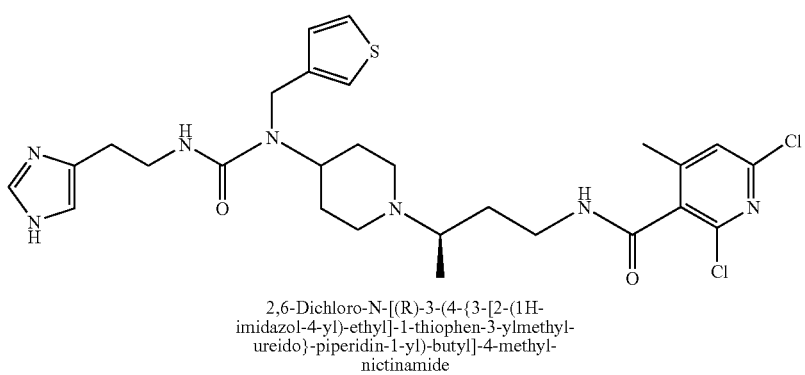

2,6-Dichloro-N-[(R)-3-(4-{3-[2-(1H-imidazol-4-yl)-ethyl]-1-thiophen-3-ylmethyl-ureido}-piperidin-1-yl)-butyl]-4-methyl-nictinamide

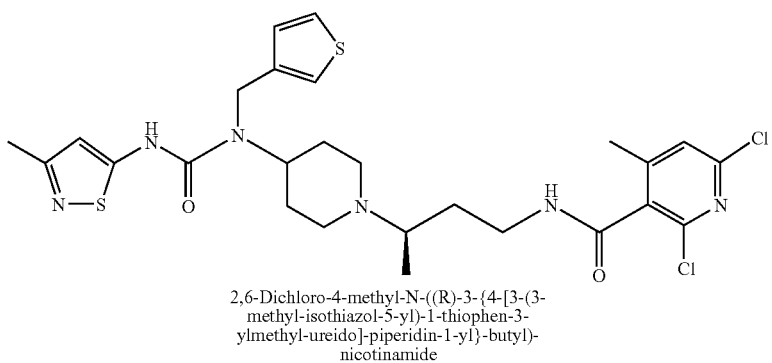

2,6-Dichloro-4-methyl-N-((R)-3-{4-[3-(3-methyl-isothiazol-5-yl)-1-thiophen-3-ylmethyl-ureido]-piperidin-1-yl}-butyl)-nicotinamide

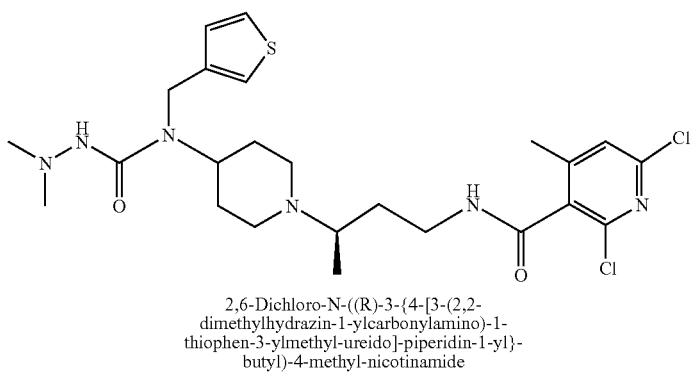

2,6-Dichloro-N-((R)-3-{4-[3-(2,2-dimethylhydrazin-1-ylcarbonylamino)-1-thiophen-3-ylmethyl-ureido]-piperidin-1-yl}-butyl)-4-methyl-nicotinamide

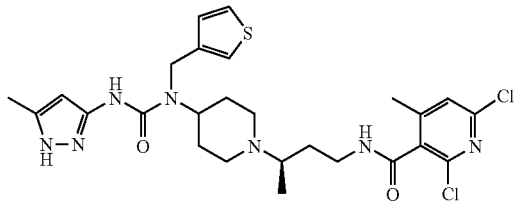

2,6-Dichloro-4-methyl-N-((R)-3-{4-[3-(5-methyl-1H-pyrazol-3-yl)-1-thiophen-3-ylmethyl-ureido]-piperidin-1-yl}-butyl)-nicotinamide

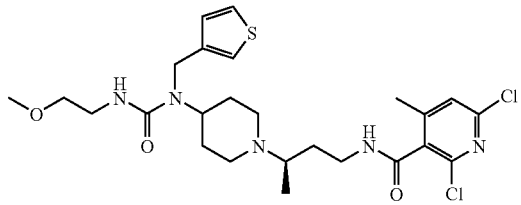

2,6-Dichloro-N-((R)-3-{4-[3-(2-methoxy-ethyl)-1-thiophen-3-ylmethyl-ureido]-piperidin-1-yl}-butyl)-4-methyl-nicotinamide

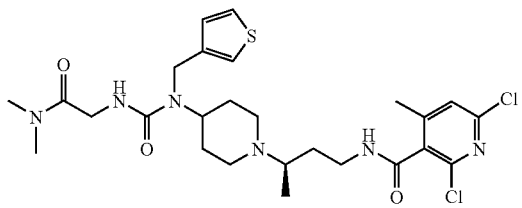

2,6-Dichloro-N-{(R)-3-[4-(3-dimethylcarbamoylmethyl-1-thiophen-3-ylmethyl-ureido)-piperidin-1-yl]-butyl}-4-methyl-nicotinamide

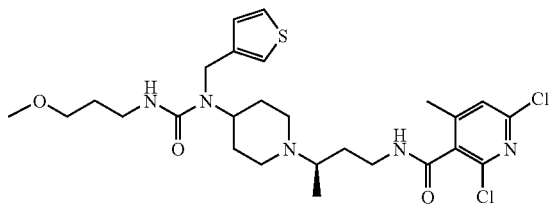

2,6-Dichloro-N-((R)-3-{4-[3-(3-methoxy-propyl)-1-thiophen-3-ylmethyl-ureido]-piperidin-1-yl}-butyl)-4-methyl-nicotinamide

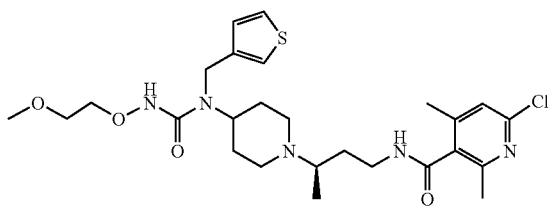

6-Chloro-N-((R)-3-{4-[3-methoxyethoxy)-1-thiophen-3-ylmethyl-ureido]-piperidin-1-yl}-butyl)-2,4-dimethyl-nicotinamide

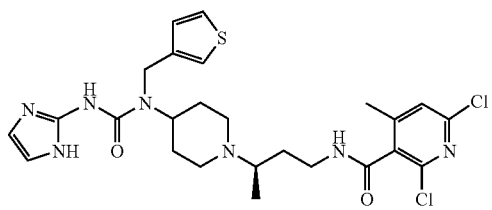

2,6-Dichloro-N-((R)-3-{4-[3-(1H-imidazol-2-yl)-1-thiophen-3-ylmethyl-ureido]-piperidin-1-yl}-butyl)-4-methyl-nicotinamide

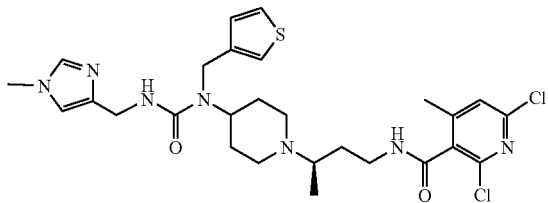

2,6-Dichloro-4-methyl-N-((R)-3-{4-[3-(1-methyl-1H-inidazol-4-ylmethyl)-1-thiophen-3-ylmethyl-ureido]-piperidin-1-yl}-butyl)-nicotinamide

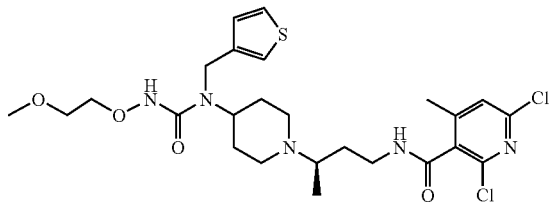

2,6-Dichloro-N-{(R)-3-[4-(3-(2-methoxyethoxy)-1-thiophen-3-ylmethyl-ureido)-piperidin-1-yl]-butyl}-4-methyl-nicotinamide

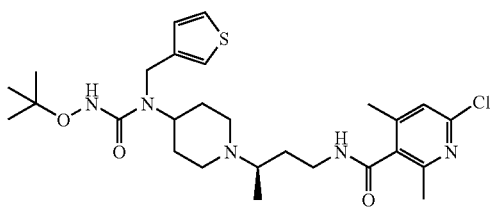

6-Chloro-N-{(R)-3-[4-(3-t-butoxy-1-thiophen-3-ylmethyl-ureido)-piperidin-1-yl]-butyl}-2,4-dimethyl-nicotinamide

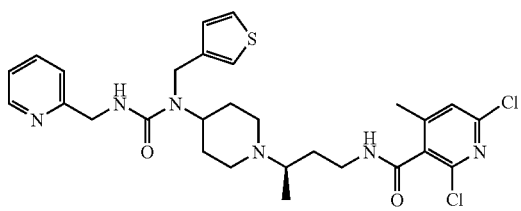

2,6-Dichloro-4-methyl-N-{(R)-3-[4-(3-pyridin-2-ylmethyl-1-thiophen-3-ylmethyl-ureido)-piperidin-1-yl]-butyl}-nicotinamide -continued

| 401 | 402 |
|---|---|
| 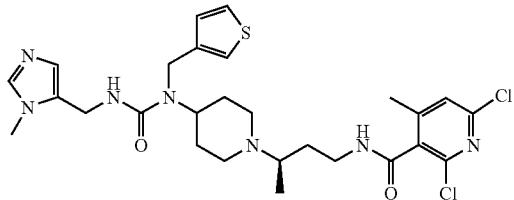 2,6-Dichloro-4-methyl-N-((R)-3-{4-[3-(3-methyl-3H-imidazol-4-ylmethyl)-1-thiophen-3-ylmethyl-ureido]-piperidin-1-yl}-butyl)-nicotinamide | 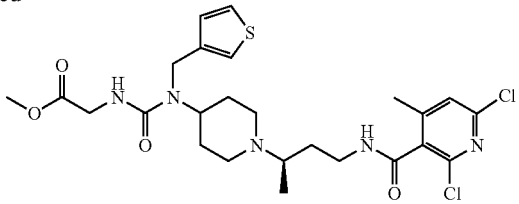 [3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-acetic acid methyl ester |
| 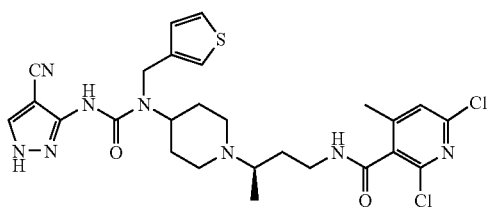 2,6-Dichloro-N-((R)-3-{4-[3-(4-cyano-1H-pyrazol-3-yl)-1-thiophen-3-ylmethyl-ureido]-piperidin-1-yl}-butyl)-4-methyl-nicotinamide | 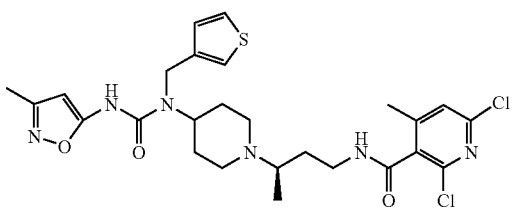 2,6-Dichloro-4-methyl-N-((R)-3-{4-[3-(3-methyl-isoxazol-5-yl)-1-thiophen-3-ylmethyl-ureido]-piperidin-1-yl}-butyl)-nicotinamide |
| 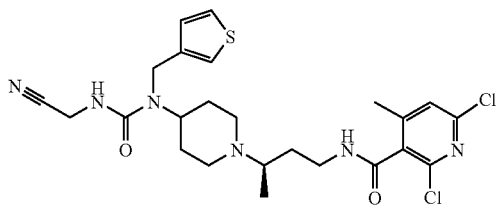 2,6-Dichloro-N-{(R)-3-[4-(3-cyanomethyl-1-thiophen-3-ylmethyl-ureido]-piperidin-1-yl]-butyl}-4-methyl-nicotinamide | 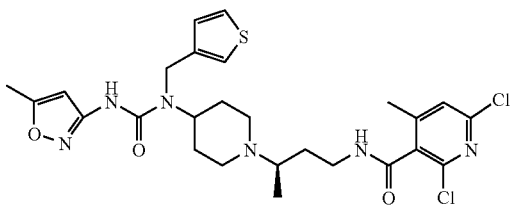 2,6-Dichloro-4-methyl-N-((R)-3-{4-[3-(5-methyl-isoxazol-3-yl)-1-thiophen-3-ylmethyl-ureido]-piperidin-1-yl}-butyl)-nicotinamide |
| 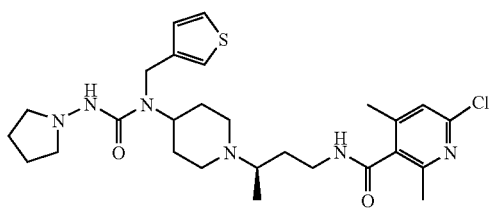 6-Chloro-2,4-dimethyl-N-{(R)-3-[4-(3-pyrrolidin-1-yl-1-thiophen-3-ylmethyl-ureido)-piperidin-1-yl]-butyl}-nicotinamide | 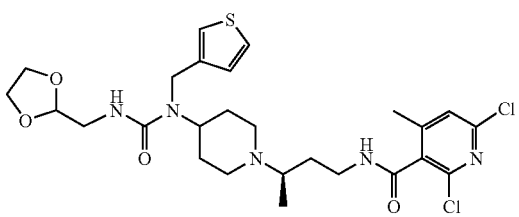 2,6-Dichloro-N-{(R)-3-[4-(3-1,3-dioxolan-2-ylmethyl-1-thiophen-3-ylmethyl-ureido)-piperidin-1-yl]-butyl}-4-methyl-nicotinamide |
| 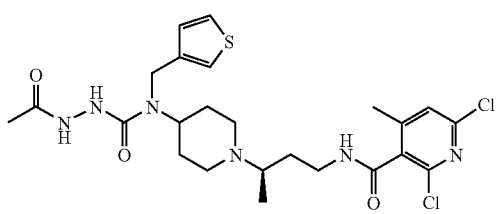 2,6-Dichloro-4-methyl-N-{(R)-[4-(3-acetamido-1-thiophen-3-ylmethyl-ureido)-piperidin-1-yl]-butyl}-nicotinamide | 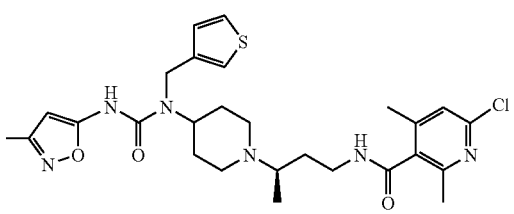 6-Chloro-2,4-dimethyl-N-((R)-3-{4-[3-(3-methyl-isoxazol-5-yl)-1-thiophen-3-ylmethyl-ureido]-piperidin-1-yl}-butyl)-nicotinamide |

-continued

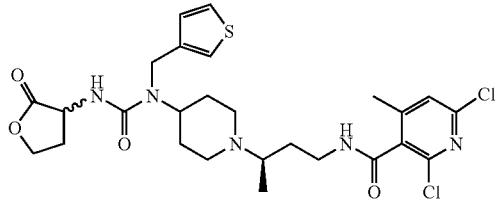

2,6-Dichloro-4-methyl-N-((R)-3-{4-[3-(2-oxo-tetrahydro-furan-3-yl)-1-thiophen-3-ylmethyl-ureido]-piperidin-1-yl}-butyl)-nicotinamide 2,6-Dichloro-4-methyl-N-{(R)-3-[4-(1-thiophen-3-ylmethyl-3-[1,2,4]triazol-4-yl-ureido)-piperidin-1-yl]-butyl}-nicotinamide

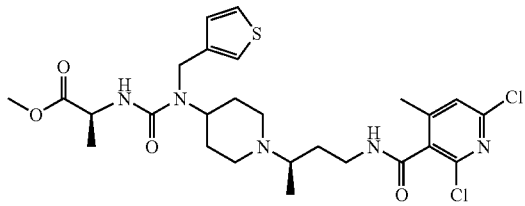

(S)-2-[3-(1-{(R)-3-[(2,6-Dichloro-4-methyl-pyridine-3-carbonyl)-amino]-1-methyl-propyl}-piperidin-4-yl)-3-thiophen-3-ylmethyl-ureido]-propionic acid methyl ester 2,6-Dichloro-4-methyl-N-((R)-3-{4-[1-thiophen-3-ylmethyl-3-(1H-[1,2,4]triazol-3-yl)-ureido]-piperidin-1-yl}-butyl)-nicotinamide

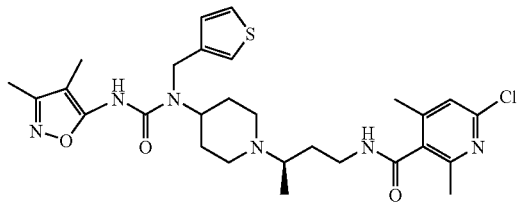

6-Chloro-N-((R)-3-{4-[3-(3,4-dimethyl-isoxazol-5-yl)-1-thiophen-3-ylmethyl-ureido]-piperidin-1-yl}-butyl)-2,4-dimethyl-nicotinamide 2,6-Dichloro-4-methyl-N-{(R)-3-[4-(3-morpholin-4-yl-1-thiophen-3-ylmethyl-ureido)-piperidin-1-yl]-butyl}-nicotinamide

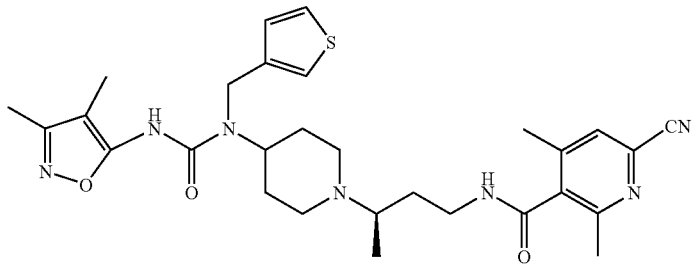

6-Cyano-N-((R)-3-{4-[3-(3,4-dimethyl-isoxazol-5-yl)-1-thiophen-3-ylmethyl-ureido]-piperidin-1-yl}-butyl)-2,4-dimethyl-nicotinamide; and

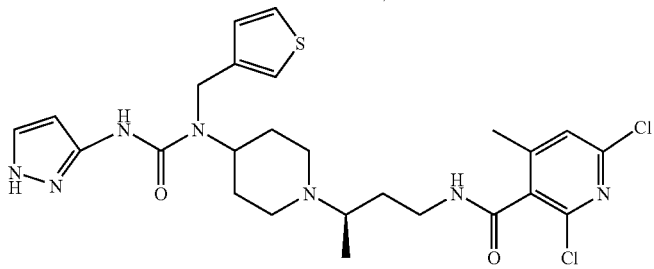

2,6-Dichloro-4-methyl-N-((R)-3-{4-[3-(1H-pyrazol-3-yl)-1-thiophen-3-ylmethyl-ureido]-piperidin-1-yl}-butyl)-nicotinamide and pharmaceutically acceptable salts thereof.

14. A pharmaceutical composition comprising a compound of claim 13 or a pharmaceutically acceptable salt thereof and a pharmaceutically acceptable carrier.

* * * * *